(12) United States Patent
Zeng et al.

(10) Patent No.: US 11,302,872 B2
(45) Date of Patent: Apr. 12, 2022

(54) ORGANIC ELECTROLUMINESCENT MATERIALS AND DEVICES

(71) Applicant: Universal Display Corporation, Ewing, NJ (US)

(72) Inventors: Lichang Zeng, Lawrenceville, NJ (US); Vadim Adamovich, Yardley, PA (US); Alexey Borisovich Dyatkin, Ambler, PA (US); Walter Yeager, Yardley, PA (US); Chuanjun Xia, Lawrenceville, NJ (US); Zhiqiang Ji, Hillsborough, NJ (US); Michael S. Weaver, Princeton, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 71 days.

(21) Appl. No.: 15/239,877

(22) Filed: Aug. 18, 2016

(65) Prior Publication Data

US 2017/0069848 A1   Mar. 9, 2017

Related U.S. Application Data

(60) Provisional application No. 62/240,256, filed on Oct. 12, 2015, provisional application No. 62/216,113, filed on Sep. 9, 2015.

(51) Int. Cl.
| | | |
|---|---|---|
| *H01L 51/54* | (2006.01) |
| *H01L 51/00* | (2006.01) |
| *C07D 487/04* | (2006.01) |
| *C07F 15/00* | (2006.01) |
| *C09K 11/02* | (2006.01) |
| *C09K 11/06* | (2006.01) |
| *H01L 51/50* | (2006.01) |
| *H01L 51/56* | (2006.01) |

(52) U.S. Cl.
CPC ........ *H01L 51/0067* (2013.01); *C07D 487/04* (2013.01); *C07F 15/0033* (2013.01); *C09K 11/025* (2013.01); *C09K 11/06* (2013.01); *H01L 51/0072* (2013.01); *H01L 51/0085* (2013.01); *C09K 2211/185* (2013.01); *H01L 51/0005* (2013.01); *H01L 51/0097* (2013.01); *H01L 51/5004* (2013.01); *H01L 51/506* (2013.01); *H01L 51/5016* (2013.01); *H01L 51/5076* (2013.01); *H01L 51/5096* (2013.01); *H01L 51/56* (2013.01)

(58) Field of Classification Search
CPC .. C07D 209/82; C07D 487/00; C07D 487/02; C07D 487/04; C07F 15/00; C07F 15/0033; C09K 11/025; C09K 11/06; C09K 2211/00; C09K 2211/10; C09K 2211/1007; C09K 2211/1018; C09K 2211/1022; C09K 2211/1025; C09K 2211/1029; C09K 2211/1033; C09K 2211/1037; C09K 2211/1044; C09K 2211/185; H01L 51/0032; H01L 51/005; H01L 51/0005; H01L 51/0072; H01L 51/0073; H01L 51/0074; H01L 51/0085; H01L 51/0067; H01L 51/50; H01L 51/5004; H01L 51/506; H01L 51/5076; H01L 51/5012; H01L 51/5016; H01L 51/0097; H01L 51/56; H01L 51/5096

USPC ....... 428/690, 691, 917, 411.4, 336; 427/58, 427/66; 313/500–512; 257/40, 88–104, 257/E51.001–E51.052; 252/301.16–301.35

See application file for complete search history.

(56) References Cited

U.S. PATENT DOCUMENTS

| | | |
|---|---|---|
| 4,769,292 A | 9/1988 | Tang et al. |
| 5,061,569 A | 10/1991 | VanSlyke et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Machine translation of JP2012-140365. (Year: 2012).*

(Continued)

*Primary Examiner* — Andrew K Bohaty
(74) *Attorney, Agent, or Firm* — Duane Morris LLP

(57) ABSTRACT

A composition of matter that includes a novel combination of host compounds containing indol-fused hosts and emissive dopants containing benzofuran or azabenzofuran ligand is disclosed,

17 Claims, 2 Drawing Sheets

(56) References Cited

U.S. PATENT DOCUMENTS

| | | |
|---|---|---|
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0016907 A1* | 1/2004 | Shi ............... H01L 51/0008 252/301.16 |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2009/0295276 A1* | 12/2009 | Asari ............... C09K 11/06 313/504 |
| 2010/0187977 A1* | 7/2010 | Kai ............... C07D 487/04 313/504 |
| 2010/0244004 A1* | 9/2010 | Xia ............... C07F 15/0033 257/40 |
| 2012/0068170 A1* | 3/2012 | Pflumm ............... C07D 209/82 257/40 |
| 2013/0112952 A1* | 5/2013 | Adamovich ........ H01L 51/0054 257/40 |
| 2014/0054564 A1* | 2/2014 | Kim ............... C07B 59/00 257/40 |
| 2014/0061609 A1* | 3/2014 | Kim ............... C09K 11/06 257/40 |
| 2014/0131676 A1* | 5/2014 | Beers ............... H01L 51/0085 257/40 |
| 2014/0275530 A1* | 9/2014 | Jatsch ............... H01L 51/0074 544/180 |
| 2014/0332793 A1* | 11/2014 | Park ............... H01L 51/0061 257/40 |
| 2014/0364625 A1* | 12/2014 | Ahn ............... C07D 405/04 548/418 |
| 2015/0115205 A1 | 4/2015 | Kang et al. |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| JP | 2012140365 A * | 7/2012 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 04107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072092 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2011136755 | 11/2011 |
| WO | WO-2013056776 A1 * | 4/2013 ........ C07D 409/04 |
| WO | WO-2013108997 A1 * | 7/2013 ........ H01L 51/0071 |

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

(56) References Cited

OTHER PUBLICATIONS

Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 1:15-20(2000).
Hamada, Yuji et al., "High Luminance in Organic Electroluminescent Devices with Bis(10-hydroxybenzo[h]quinolinato)beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164(2002).
Lamansky, Sergey et al., "Synthesis and Characterization of Phosphorescent Cyclometalated Iridium Complexes," Inorg Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based On Silole Derivatives And Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91:209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes Of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

ORGANIC ELECTROLUMINESCENT MATERIALS AND DEVICES

CROSS-REFERENCE TO RELATED APPLICATIONS

This application claims priority under 35 U.S.C. § 119(e) to U.S. Provisional Applications Ser. No. 62/216,113, filed Sep. 9, 2015 and 62/240,256, filed Oct. 12, 2015, the entire contents of which is incorporated herein by reference.

PARTIES TO A JOINT RESEARCH AGREEMENT

The claimed invention was made by, on behalf of and/or in connection with one or more of the following parties to a joint university corporation research agreement: The Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD

The present invention relates to compositions of matter that comprise a novel combination of host compounds containing indol-fused hosts and emissive dopants containing benzofuran or azabenzofuran ligand.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CV coordinates, which are well known to the art.

One example of a green emissive molecule is tris(2-phenylpyridine) iridium, denoted Ir(ppy)$_3$, which has the following structure:

In this, and later figures herein, we depict e dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is nota polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules, As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form, A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

In the state of the art OLED devices, the emissive layer (EML) may consist of three or more components. In one example, the EML can consist of two host-type compounds and an emitter combination (e.g. a hole transporting cohost (h-host), an electron transporting cohost (e-host), and a compound capable of functioning as an emitter in an OLED at room temperature). In another example, the EML can consist of one host-type compound and two emitter-type compounds (e.g., a host compound and two compounds each capable of functioning as an emitter in an OLED at room temperature). Conventionally, in order to fabricate such EMU having three or more components using vacuum thermal evaporation (VTE) process, three or more evaporation sources are required, one for each of the components. Because the concentration of the components are important for the device performance, typically, the rate of deposition of each component is measured individually during the deposition process. This makes the VTE process complicated and costly compared to a standard two-component EML with a single host and an emitter, which requires only two evaporation sources.

Premixing two or more materials and evaporating them from one VTE sublimation crucible can reduce the number of VTE evaporation sources and simplify the fabrication process. In order for materials to be premixable into an evaporation source, they should co-evaporate and deposit uniformly without changing the ratio. The ratio of the components in the mixture should be the same as the ratio of the components in the evaporation deposited films from these premixed materials. Therefore, the concentration of the two components in the deposited film is controlled by their concentration in the premixed evaporation source. Variations in the film's composition may adversely affect the device performance. In order to obtain a stable co-evaporation from a mixture of compounds under vacuum, one would assume that the materials must have the same evaporation temperature under the same condition. However, this may not be the only parameter one has to consider. When two compounds are mixed together, they may interact with each other and the evaporation property of the mixture may differ from their individual properties. On the other hand, materials with slightly different evaporation temperatures may form a stable co-evaporation mixture. Therefore, it is extremely difficult to achieve a stable co-evaporation mixture. So far, there have been very few stable co-evaporation mixture examples. "Evaporation temperature" of a material is measured in a vacuum deposition tool at a constant pressure, normally between $1\times10^{-7}$ Torr to $1\times10^{-8}$ Torr, at a 2 Å/sec deposition rate on a surface positioned at a set distance away from the evaporation source of the material being evaporated, e.g. sublimation crucible in a VTE tool. The various measured values such as temperature, pressure, deposition rate, etc. disclosed herein are expected to have nominal variations because of the expected tolerances in the measurements that produced these quantitative values as understood by one of ordinary skill in the art.

Many factors other than temperature can contribute to the ability to achieve stable co-evaporation, such as the miscibility of the different materials and the phase transition temperatures of the different materials. The inventors found that when two materials have similar evaporation temperatures, and similar mass loss rate or similar vapor pressures, the two materials can co-evaporate consistently. "Mass loss rate" of a material is defined as the percentage of mass lost over time ("percentage/minute" or "%/min") and is determined by measuring the time it takes to lose the first 10% of the mass of a sample of the material as measured by thermal gravity analysis (TGA) under a given experimental condition at a given constant temperature for a given material after the a steady evaporation state is reached. The given constant temperature is one temperature point that is chosen so that the value of mass loss rate is between about 0.05 to 0.50%/min. One of ordinary skill in this field should appreciate that in order to compare two parameters, the experimental condition should be consistent. The method of measuring mass loss rate and vapor pressure is well known in the art and can be found, for example, in Bull. et al. Mater. Sci. 2011, 34, 7.

A proper combination of host materials and emissive dopant in the emissive layer is important to achieve excellent performance of OLEDs. When an indo-fused compound is used as host and metal complex with benzofuran or azabenzofuran ligand is used as emissive dopant, the OLED device exhibits an unexpectedly high efficiency and long lifetime.

SUMMARY

According to an embodiment, a composition of material comprising a mixture of a first compound and a second compound is disclosed. The first compound has the structure of Formula I

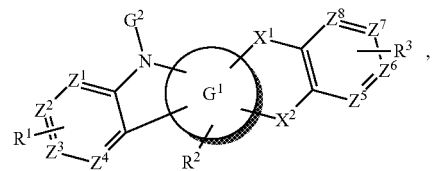

wherein $G^1$ is a six-member aromatic ring;
wherein $X^1$ and $X^2$ are each independently selected from the group consisting of direct bond, $CR^4R^5$, $NR^6$, O, S and Se;
wherein at least one of $X^1$ and $X^2$ is not a direct bond;
wherein $Z^1$ to $Z^8$ are each independently selected from the group consisting of nitrogen and carbon;

wherein $R^1$ to $R^3$ each independently represent mono to the possible maximum number of substitution, or no substitution;

wherein $G^2$, $R^1$, $R^2$, $R^3$, $R^4$, $R^5$ and $R^6$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein any two adjacent substituents can optionally join or fuse into a ring;

wherein the second compound has a formula $Ir(L_A)_n(L_B)_{3-n}$, having the structure according to Formula II:

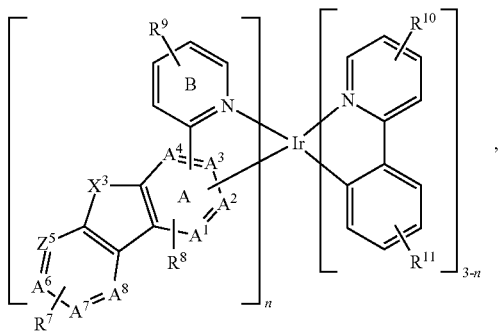

wherein each $A^1$, $A^2$, $A^3$, $A^4$, $A^5$, $A^6$, $A^7$, and $A^8$ comprise carbon or nitrogen;

wherein ring B is bonded to ring A through a C—C bond;

wherein the iridium is bonded to ring A through a Ir—C bond;

wherein $X^3$ is selected from a group consisting of O, S and Se;

wherein $R^7$ to $R^{11}$ each independently represent mono to the possible maximum number of substitution, or no substitution;

wherein $R^7$ to $R^{11}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

wherein any two adjacent substituents can optionally join or fuse into a ring; and wherein n is an integer from 1 to 3.

According to another embodiment, an organic light emitting diode/device (OLED) is also provided. The OLED can include an anode; a cathode; and an organic layer, disposed between the anode and the cathode, comprising a composition of materials comprising a mixture of a first compound and a second compound, wherein the first compound has the structure of Formula I

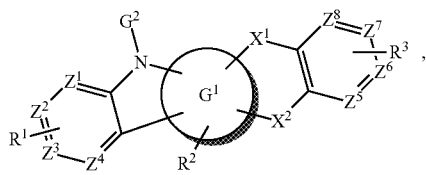

wherein $G^1$ is a six-member aromatic ring;

wherein $X^1$ and $X^2$ are each independently selected from the group consisting of direct bond, $CR^4R^5$, $NR^6$, O, S and Se;

wherein at least one of $X^1$ and $X^2$ is not a direct bond;

wherein $Z^1$ to $Z^8$ are each independently selected from the group consisting of nitrogen and carbon;

wherein $R^1$ to $R^3$ each independently represent mono to the possible maximum number of substitution, or no substitution;

wherein $G^2$, $R^1$, $R^2$, $R^3$, $R^4$, $R^5$ and $R^6$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein any two adjacent substituents can optionally join or fuse into a ring;

wherein the second compound has a formula $Ir(L_A)_n(L_B)_{3-n}$, and having the structure according to Formula II

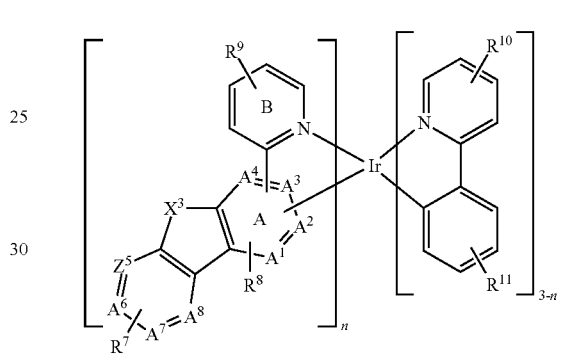

wherein each $A^1$, $A^2$, $A^3$, $A^4$, $A^5$, $A^6$, $A^7$, and $A^8$ comprise carbon or nitrogen;

wherein ring B is bonded to ring A through a C—C bond;

wherein the iridium is bonded to ring A through a Ir—C bond;

wherein $X^3$ is selected from a group consisting of O, S and Se;

wherein $R^7$ to $R^{11}$ each independently represent mono to the possible maximum number of substitution, or no substitution;

wherein $R^7$ to $R^{11}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, sulfanyl, sulfonyl, phosphino, and combinations thereof; and wherein any two adjacent substituents can optionally join or fuse into a ring; and wherein n is an integer from 1 to 3.

According to yet another embodiment, a method for fabricating an OLED is disclosed. The method comprises:

providing a substrate having a first electrode disposed thereon;

depositing a first organic layer over the first electrode by evaporating a mixture of a first compound and a second compound in a vacuum deposition tool at a constant pressure between $1\times10^{-6}$ Torr to $1\times10^{-9}$ Torr, at a 2 Å/sec deposition rate on a surface position at a predefined distance away from the mixture being evaporated; and depositing a second electrode over the first organic layer;

wherein the first compound has the structure of Formula I

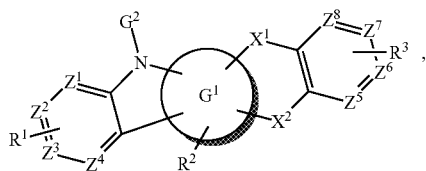

wherein $G^1$ is a six-member aromatic ring;

wherein $X^1$ and $X^2$ are each independently selected from the group consisting of direct bond, $CR^4R^5$, $NR^6$, O, S and Se;

wherein at least one of $X^1$ and $X^2$ is not a direct bond;

wherein $Z^1$ to $Z^8$ are each independently selected from the group consisting of nitrogen and carbon;

wherein $R^1$ to $R^3$ each independently represent mono to the possible maximum number of substitution, or no substitution;

wherein $G^2$, $R^1$, $R^2$, $R^3$, $R^4$, $R^5$ and $R^6$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein any two adjacent substituents can optionally join or fuse into a ring;

wherein the second compound has a formula $Ir(L_A)_n(L_B)_{3-n}$, and having the structure according to Formula II

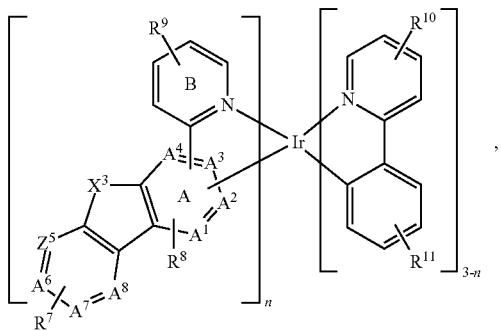

wherein each $A^1$, $A^2$, $A^3$, $A^4$, $A^5$, $A^6$, $A^7$, and $A^8$ comprise carbon or nitrogen;

wherein ring B is bonded to ring A through a C—C bond;

wherein the iridium is bonded to ring A through a Ir—C bond;

wherein $X^3$ is selected from a group consisting of O, S and Se;

wherein $R^7$ to $R^{11}$ each independently represent mono to the possible maximum number of substitution, or no substitution;

wherein $R^7$ to are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein any two adjacent substituents can optionally join or fuse into a ring; and wherein n is an integer from 1 to 3.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
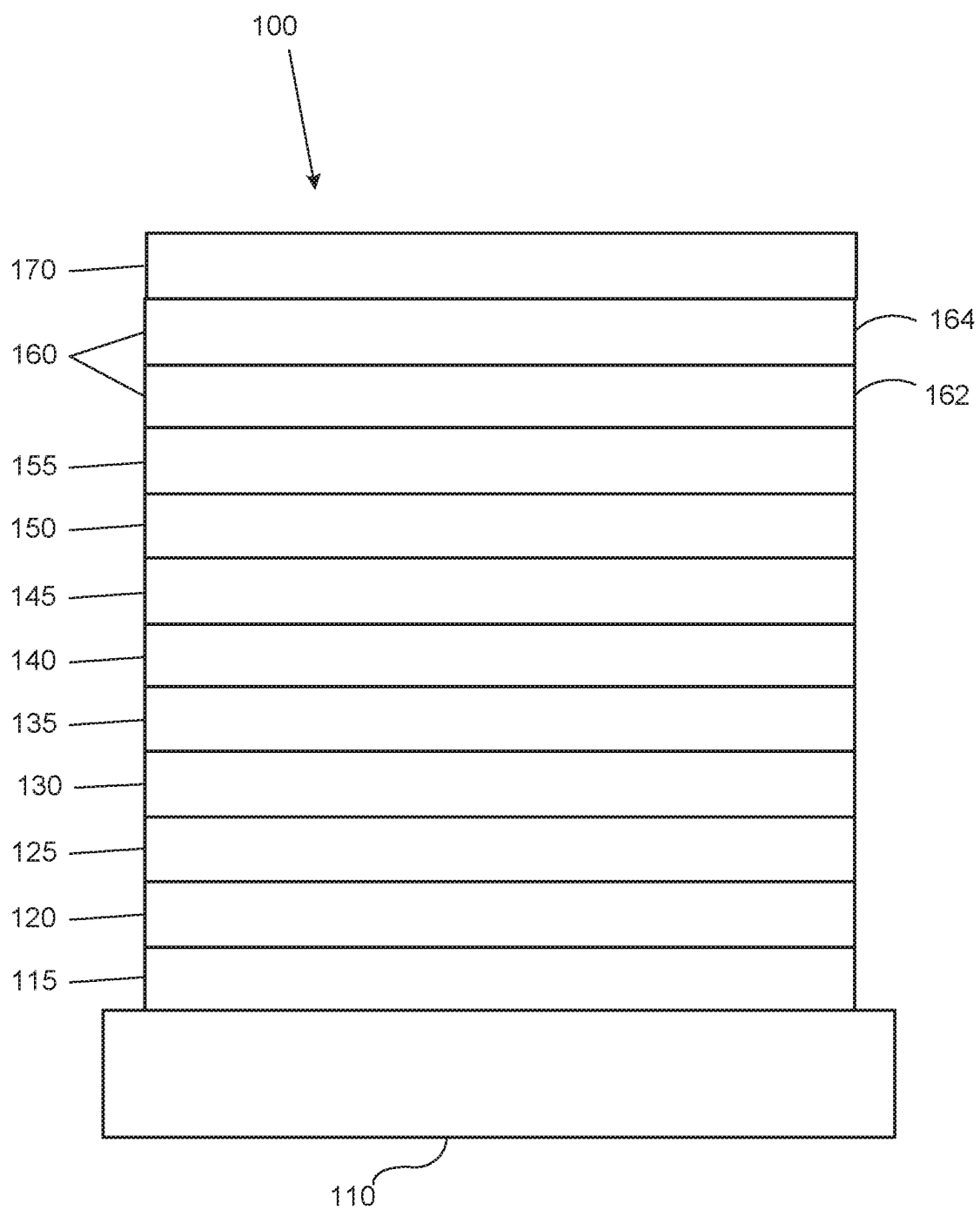
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
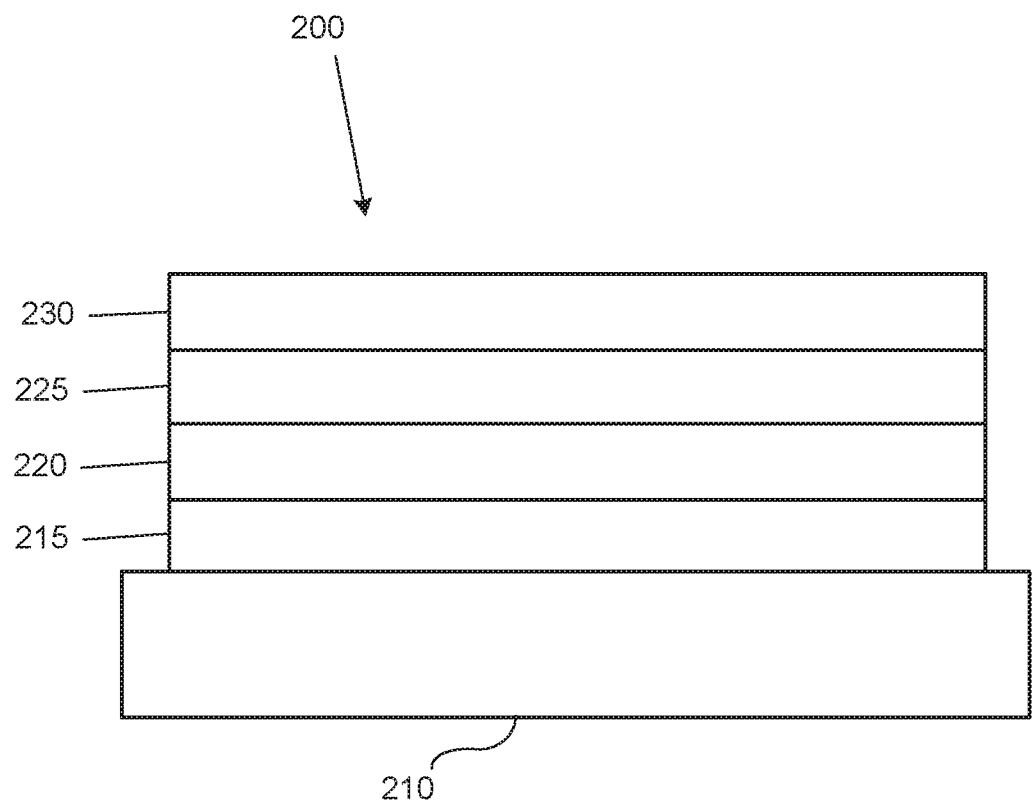
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors, Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJP. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can he utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules or units) incorporated therein. Such consumer products would include any kind of products that include one or more light source(s)and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), wearable device, laptop computers, digital cameras, camcorders, viewfinders, micro-displays, 3-D displays, vehicles, a large area wall, theater or stadium screen, or a sign. Various control mechanisms may he used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine, The term "alkyl" as used herein contemplates both straight and branched chain alkyl radicals. Preferred alkyl groups are those containing from one to fifteen carbon atoms and includes methyl, ethyl, propyl, 1-methylethyl, butyl, 1-methylpropyl. 2-methylpropyl, pentyl, 1-methylbutyl, 2-methyl butyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" as used herein contemplates cyclic alkyl radicals. Preferred cycloalkyl groups are those containing 3 to 10 ring carbon atoms and includes cyclopropyl, cyclopentyl, cyclohexyl, adamantyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 to 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" as used herein contemplates single-ring hetero-aromatic groups that may include from one to five heteroatoms. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azabotine, 1,3-azaborine, 1,4-azaborine, borazine, and aza-analogs thereof. Additionally, the heteroaryl group may be optionally substituted.

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, heteroalkyl, arylalkyl, alkoxy, aryloxy, amino, cyclic amino, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxalline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

A novel combination of host compounds containing indol-fused hosts and emissive dopants containing benzofuran or azabenzofuran ligand is disclosed. It was found that this combination of host and dopant provides outstanding performance compared to other compounds reported in the literature.

According to an aspect of the present disclosure, a composition of material comprising a mixture of a first compound and a second compound is described. The first compound has the structure of Formula I

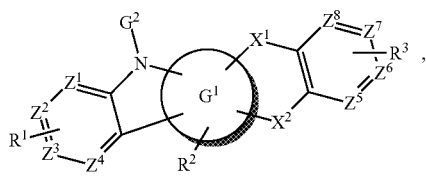

wherein $G^1$ is a six-member aromatic ring;

wherein $X^1$ and $X^2$ are each independently selected from the group consisting of direct bond, $CR^4R^5$, $NR^6$, O, S and Se;

wherein at least one of $X^1$ and $X^2$ is not a direct bond;

wherein $Z^1$ to $Z^8$ are each independently selected from the group consisting of nitrogen and carbon;

wherein $R^1$ to $R^3$ each independently represent mono to the possible maximum number of substitution, or no substitution;

wherein $G^2$, $R^1$, $R^2$, $R^3$, $R^4$, $R^5$ and $R^6$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein any two adjacent substituents can optionally join or fuse into a ring;

wherein the second compound has a formula $Ir(L_A)_n(L_B)_{3-n}$, and having the structure according to Formula II

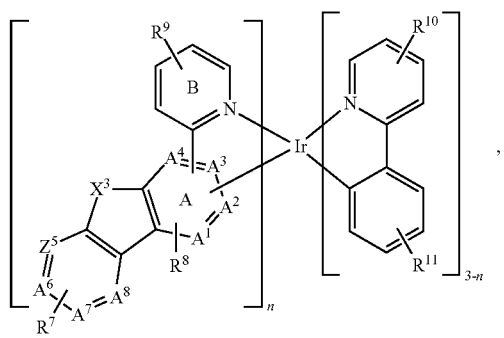

wherein each $A^1$, $A^2$, $A^3$, $A^4$, $A^5$, $A^6$, $A^7$, and $A^8$ comprise carbon or nitrogen;

wherein ring B is bonded to ring A through a C—C bond;

wherein the iridium is bonded to ring A through a Ir—C bond;

wherein $X^3$ is selected from a group consisting of O, S and Se;

wherein $R^7$ to $R^{11}$ each independently represent mono to the possible maximum number of substitution, or no substitution;

wherein $R^7$ to $R^{11}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfifsnyl, sulfonyl, phosphino, and combinations thereof;

wherein any two adjacent substituents can optionally join or fuse into a ring; and wherein n is an integer from 1 to 3.

In some embodiments of the composition of material, $X^1$ is $NR^6$, $X^2$ is direct bond. In some embodiments of the composition of material, at least one of $G^2$ and $R^6$ comprises a triazine group. In some embodiments of the composition of material, $G^2$ is aryl or heteroaryl group which can be further substituted. In some embodiments of the composition of material, $G^2$ is selected from the group consisting of phenyl, biphenyl, terphenyl, dibenzofuran, dibenzothiophene, dibenzoselenophene, fluorene, triphenylene, and combinations thereof. In some embodiments of the composition of material, $G^2$ is selected from the group consisting of pyridine, pyrimidine, pyrazine, triazine, quinoline, isoquinoline, quinazoline, phenanthroline, azadibenzofuran, azadibenzothiophene, azadibenzoselenophene, azafluorene, azatriphenylene, and combinations thereof. In some embodiments of the composition of material, $Z^1$ to $Z^8$ are each a carbon.

In some embodiments of the composition of material, the first compound is selected from the group consisting of:

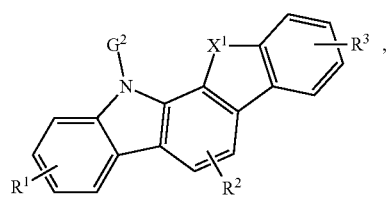

-continued
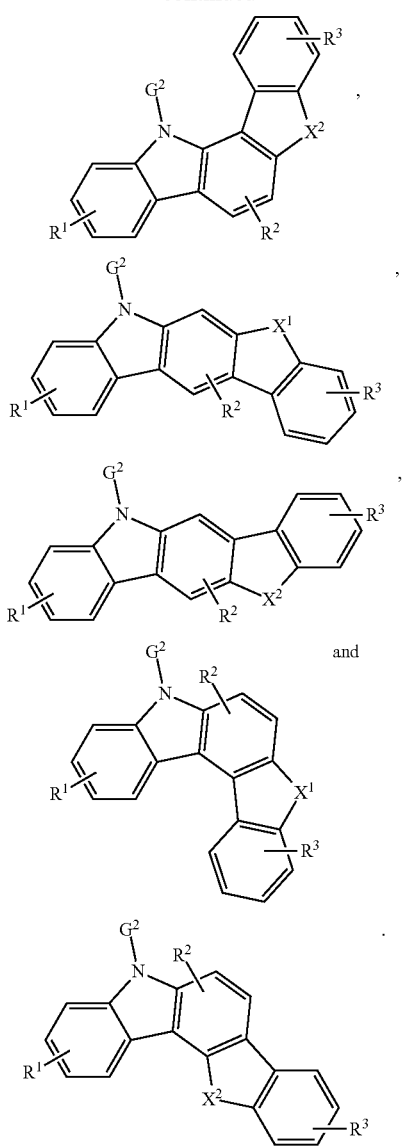
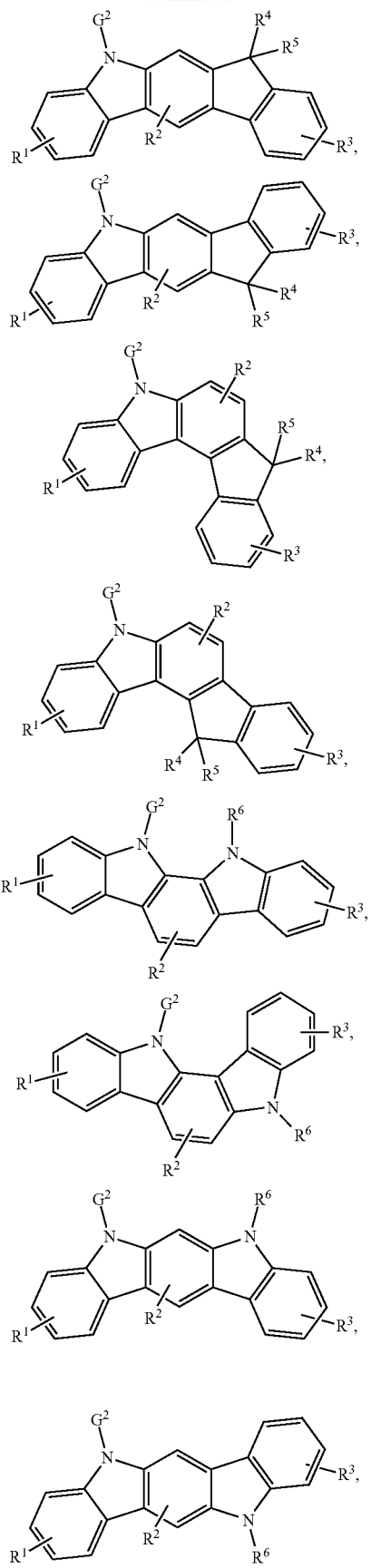
In some embodiments of the composition of the first compound is selected from the group consisting of:
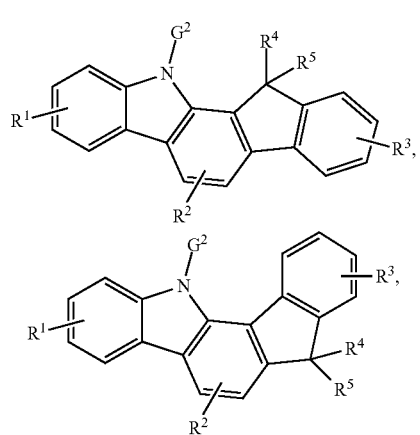
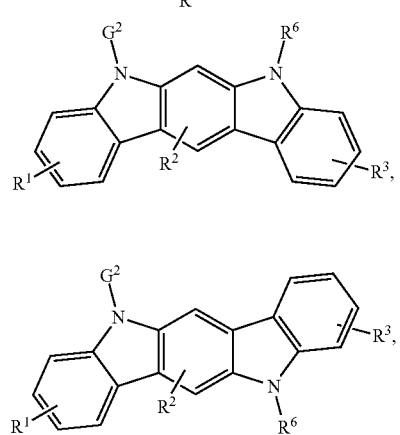

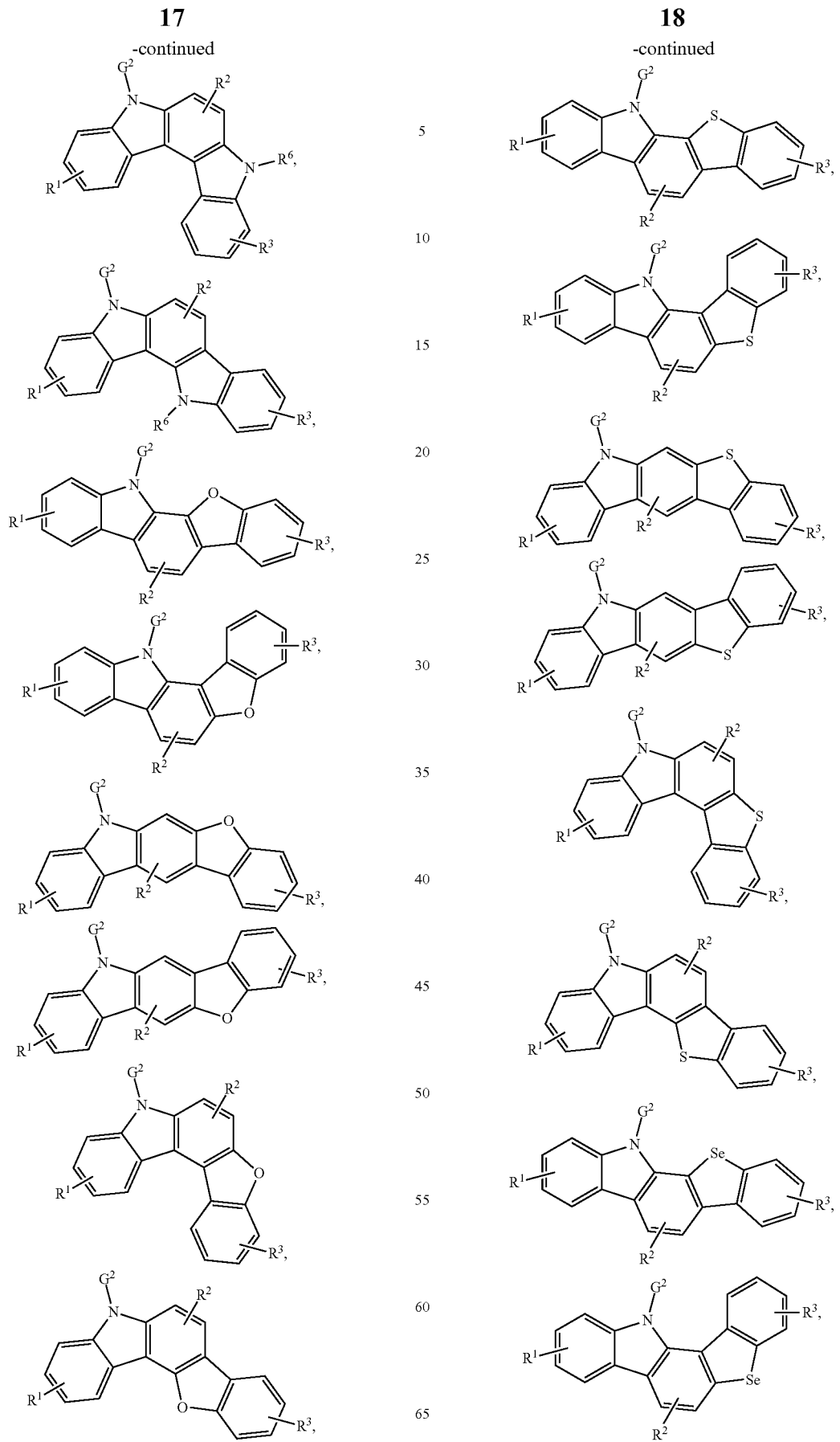

-continued

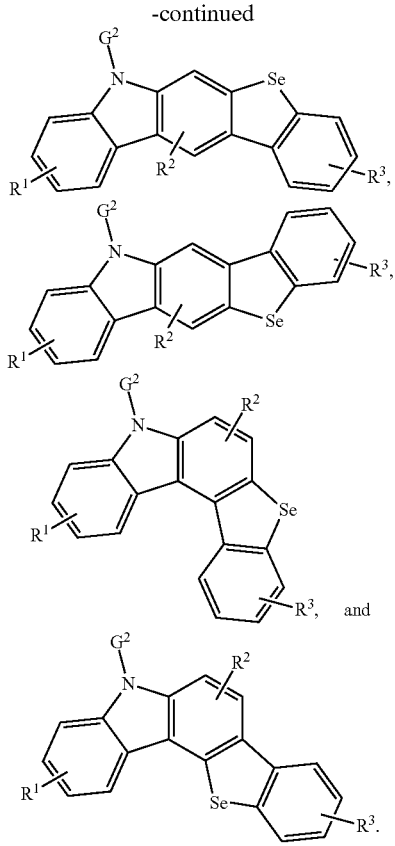

In some embodiments of the composition of material, n in Formula II is 1.

In some embodiments of the composition of material, $A^1$ to $A^8$ in Formula II are carbon. In some embodiments, at least one of $A^1$ to $A^8$ is nitrogen.

In some embodiments of the composition of material, the second compound has the formula:

Formula III

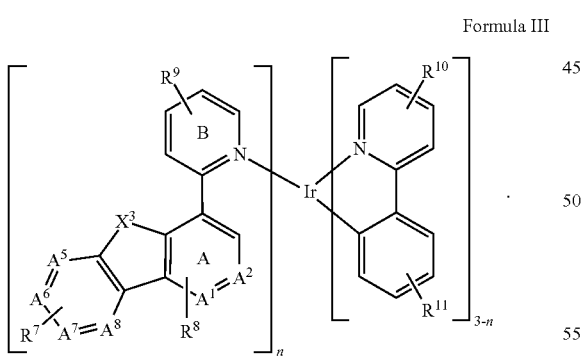

In some embodiments of the composition of material, $X^3$ in Formula II is O.

In some embodiments of the composition of material, $R^7$ to $R^{11}$ in Formula II are each independently selected from the group consisting of hydrogen, deuterium, alkyl, cycloalkyl, and combinations thereof.

In some embodiments, $R^9$ in Formula II is alkyl or cycloalkyl. In some embodiments, $R^9$ in Formula II is selected from the group consisting of aryl, substituted aryl, heteroaryl, and substituted heteroaryl.

In some embodiments of the composition of material, the second compound has $L_A$ selected from the group consisting of:

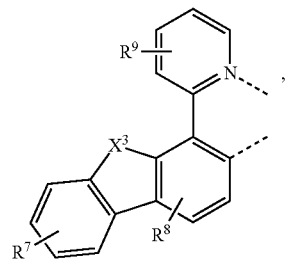

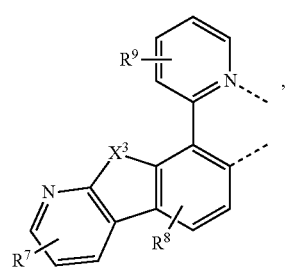

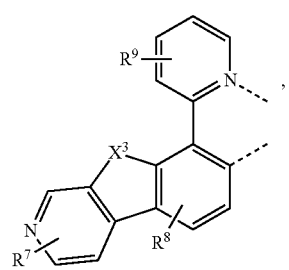

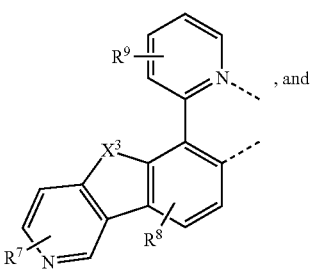

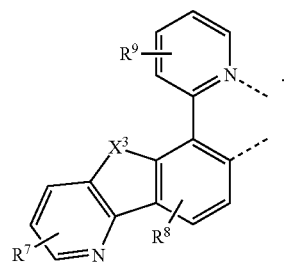

In some embodiments of the composition of material, the first compound is selected from the group consisting of:

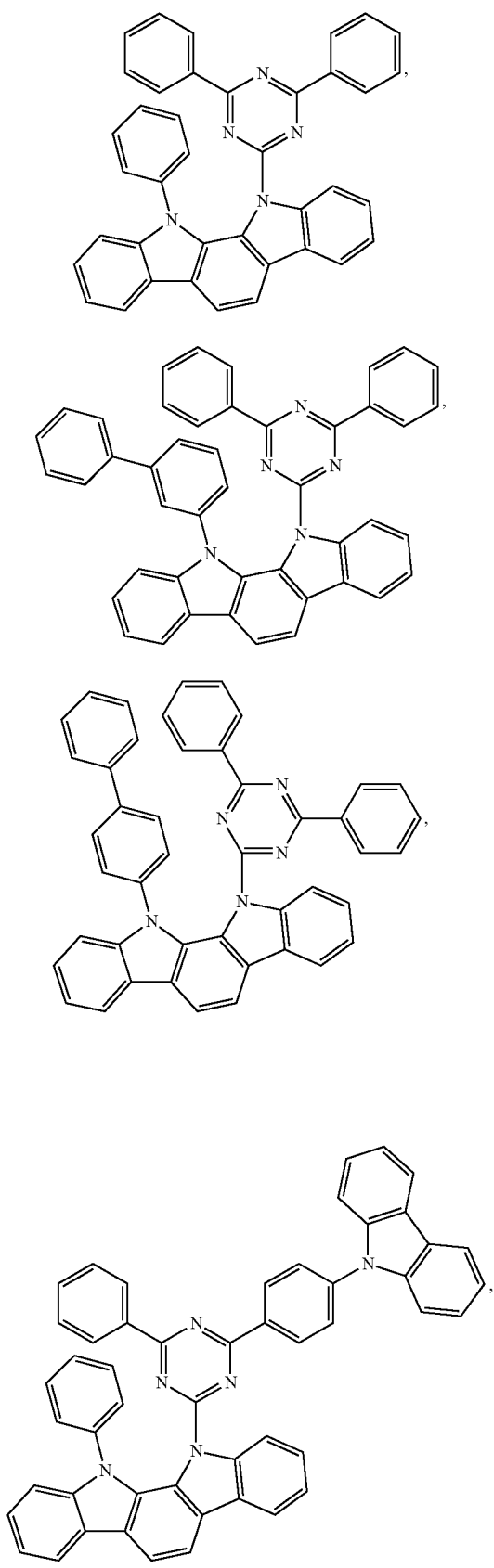
A1
A2
A3
A4
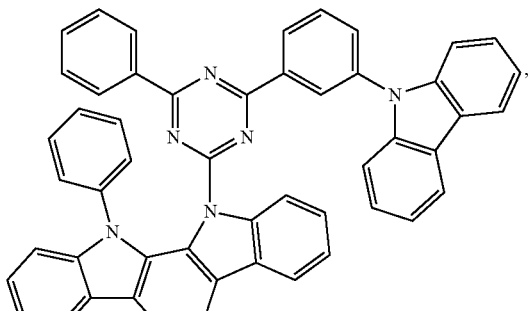
A5
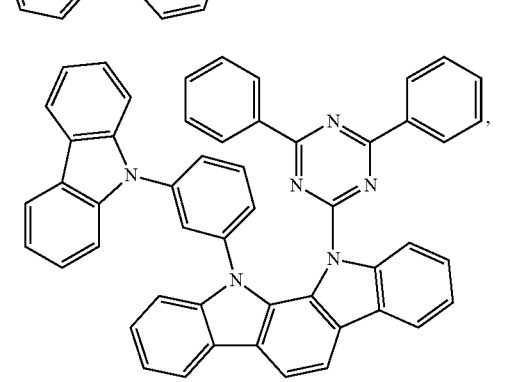
A6
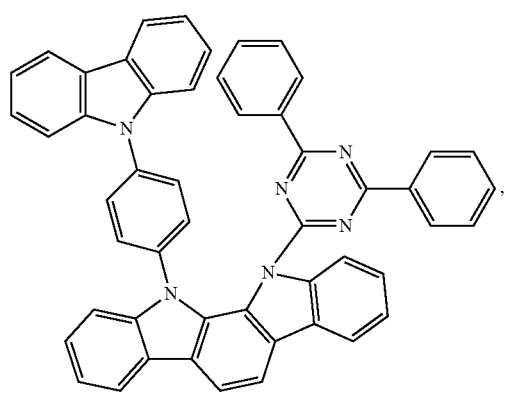
A7
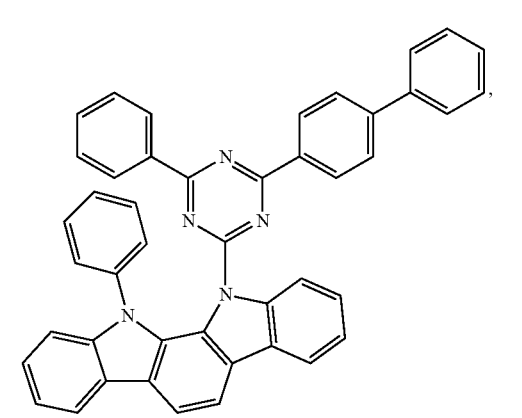
A8

A9
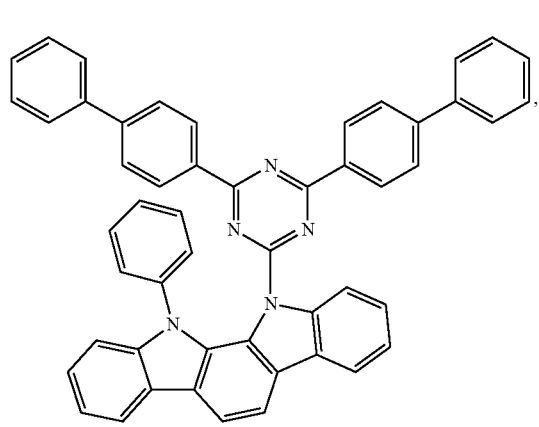
A10
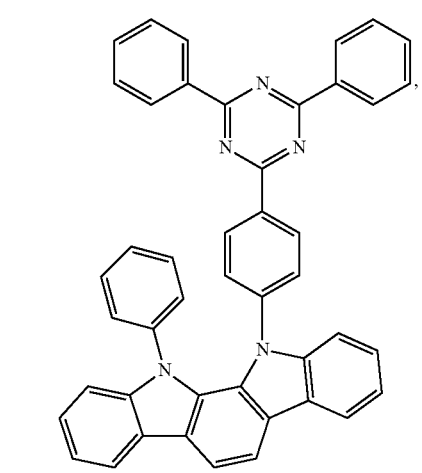
A11
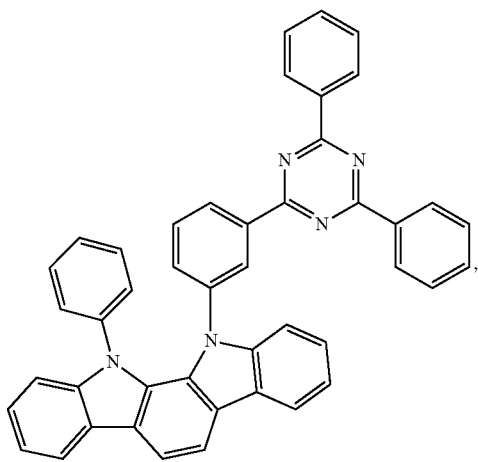
A12
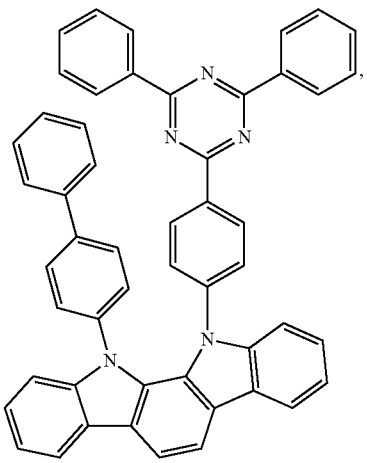
A13
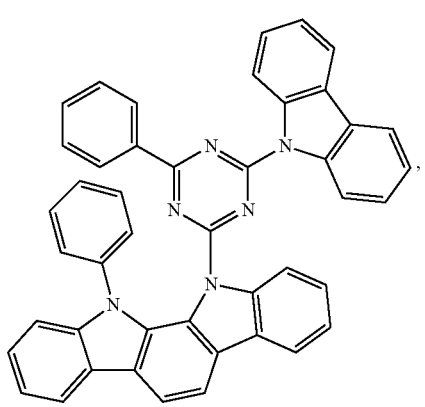
A14
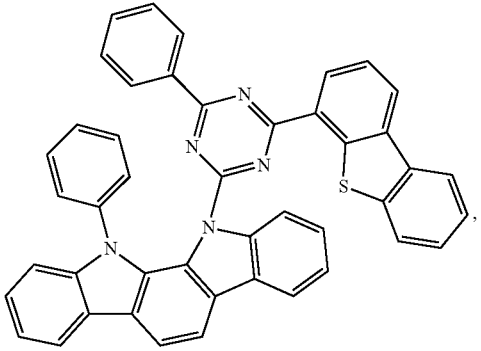
A15
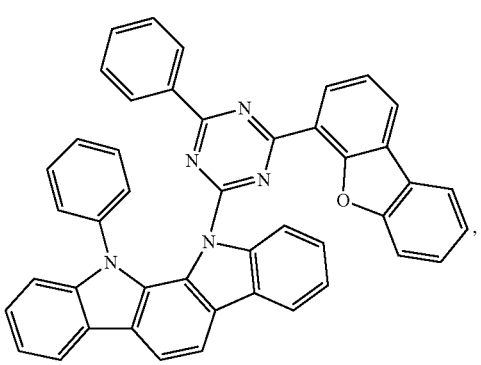

A16
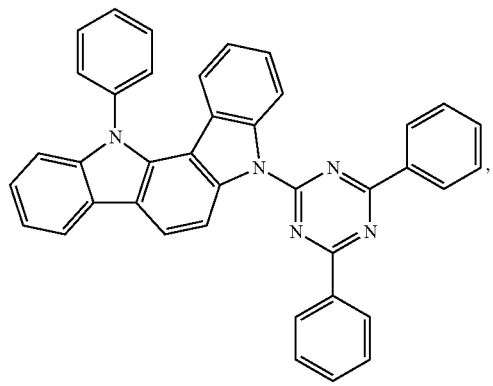
A17
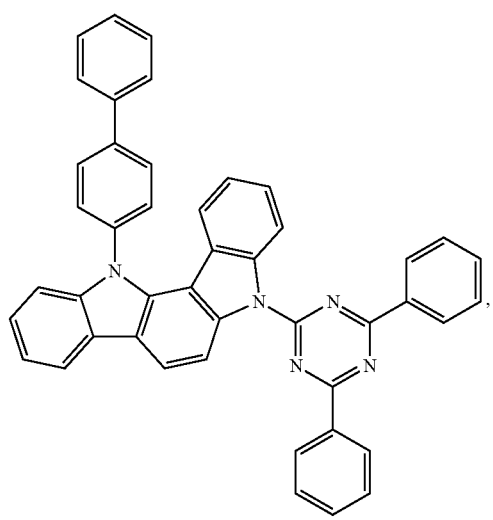
A18
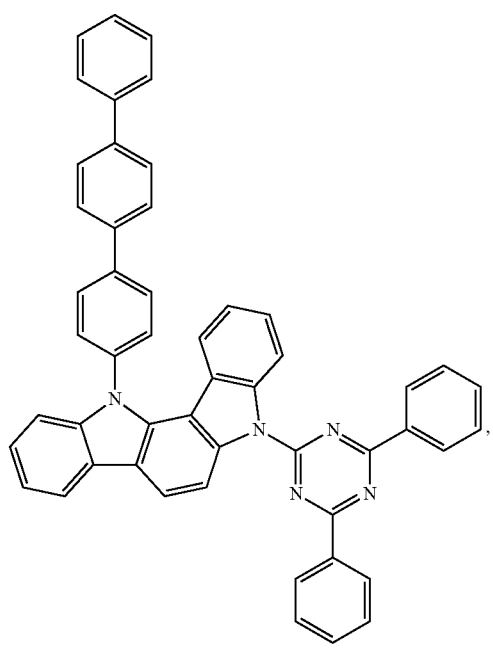
A19
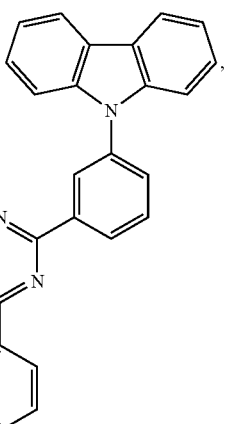
A20
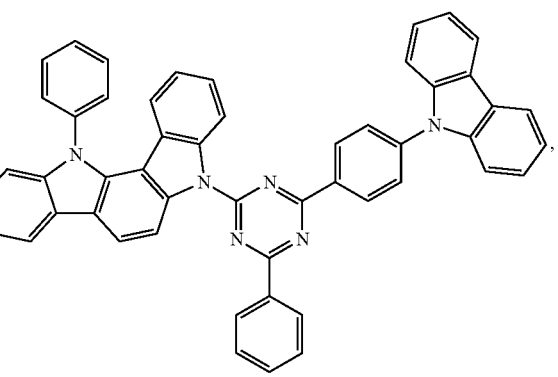
A21
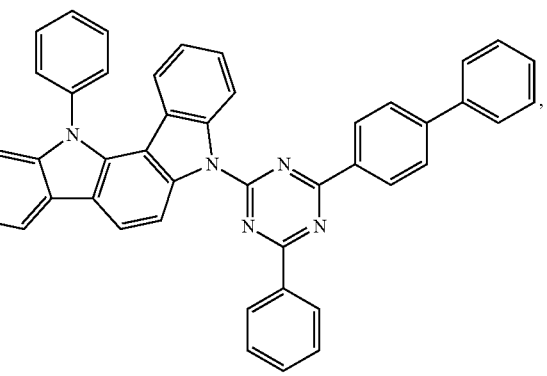
A22
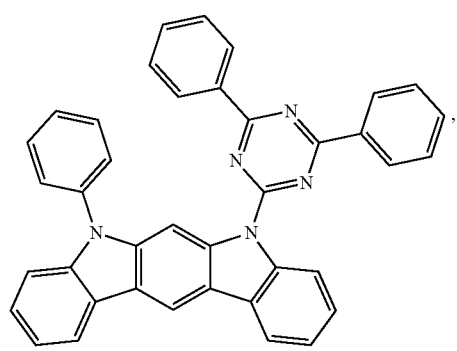

-continued
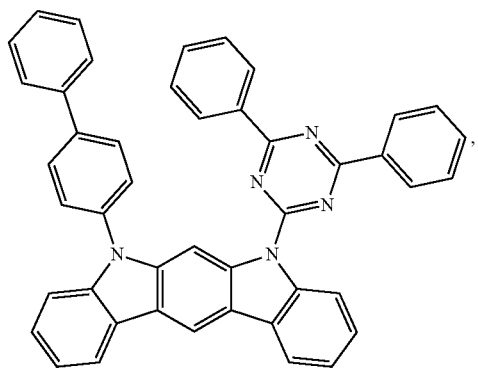
A23
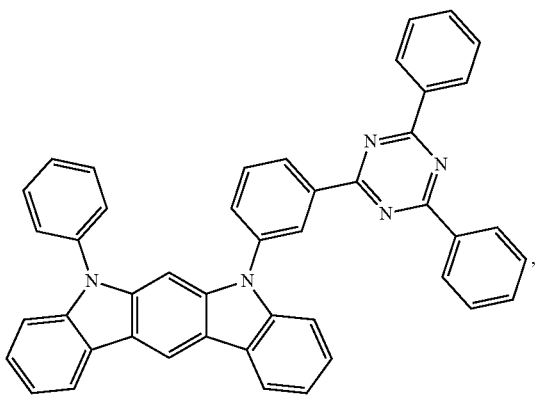
A26
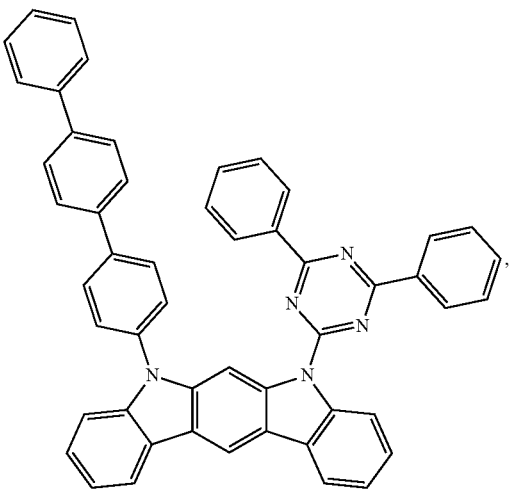
A24
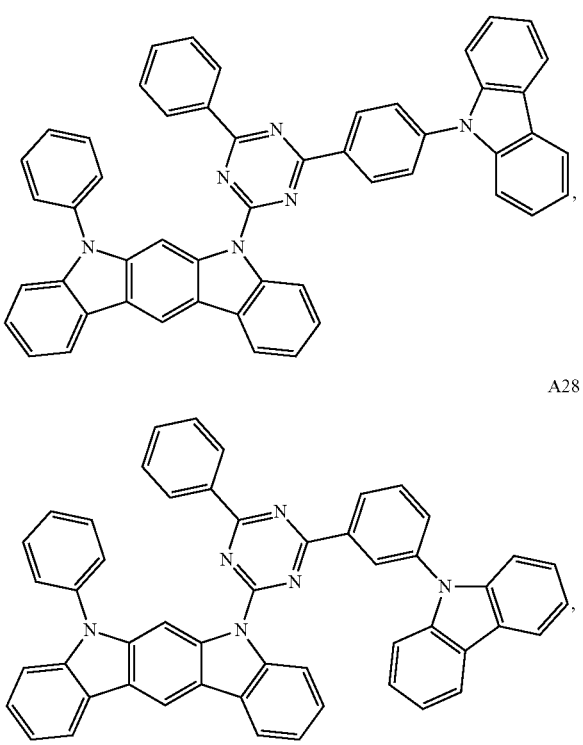
A27
A28
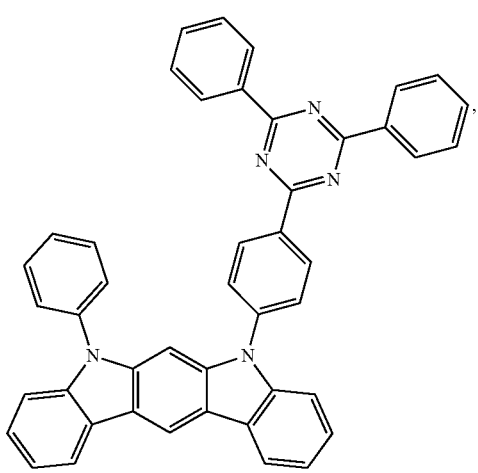
A25
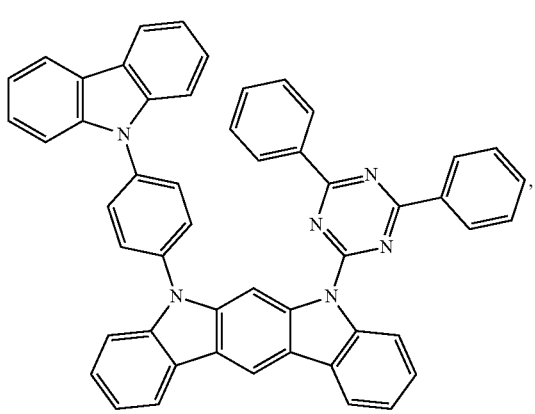
A29

A30
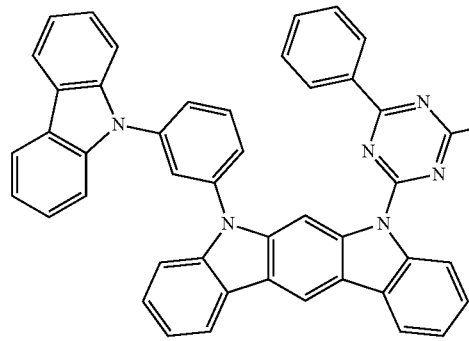
A31
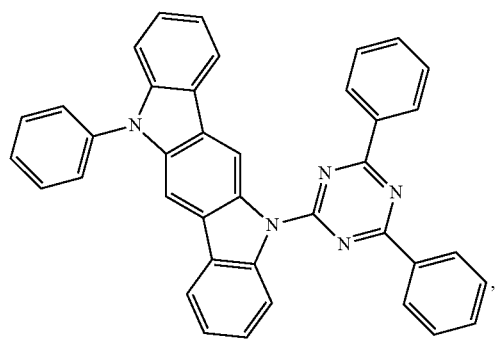
A32
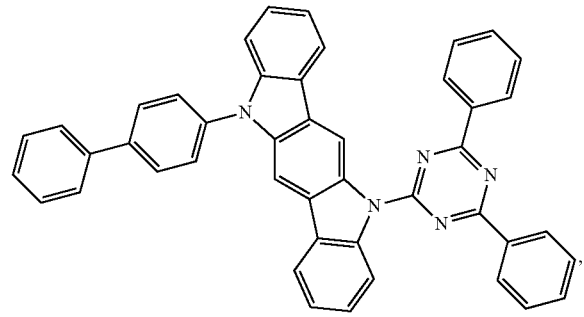
A33
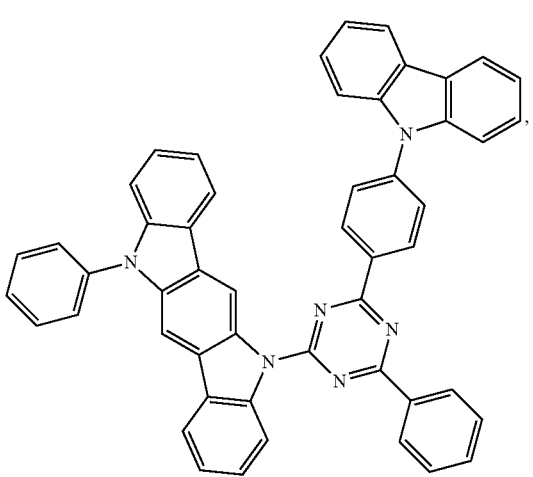
A34
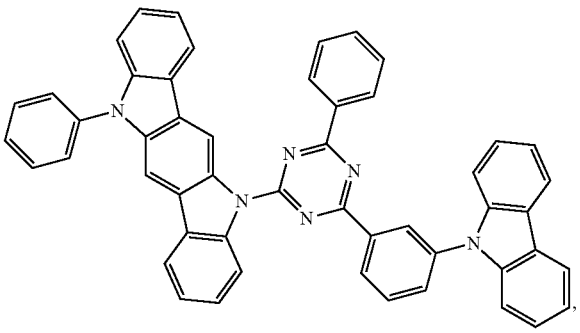
A35
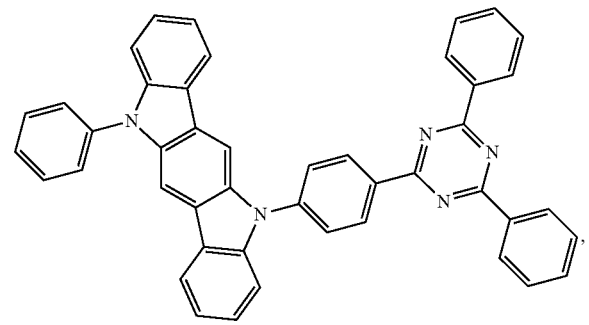
A36
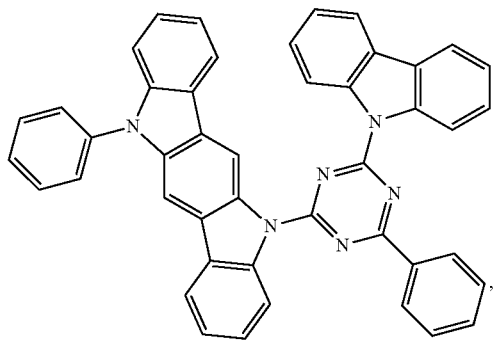
A37
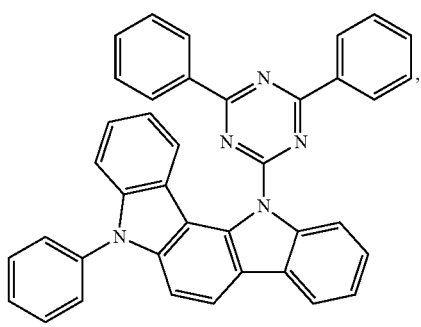

-continued
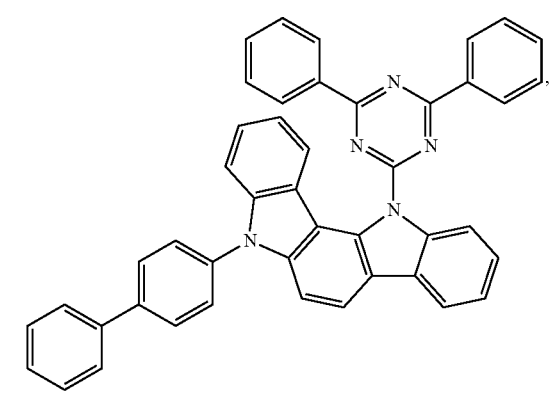
A38
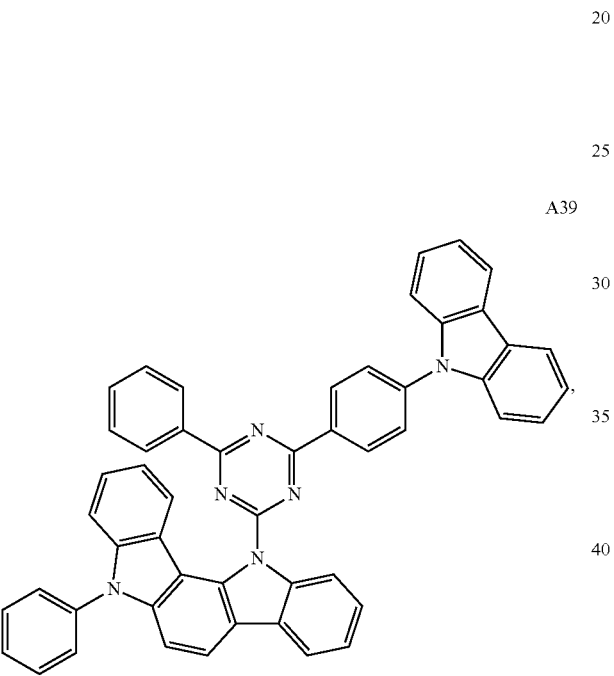
A39
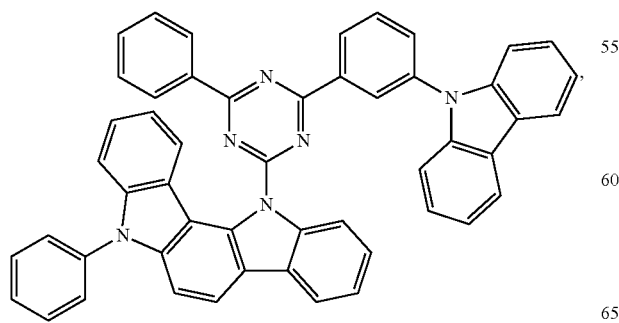
A40
-continued
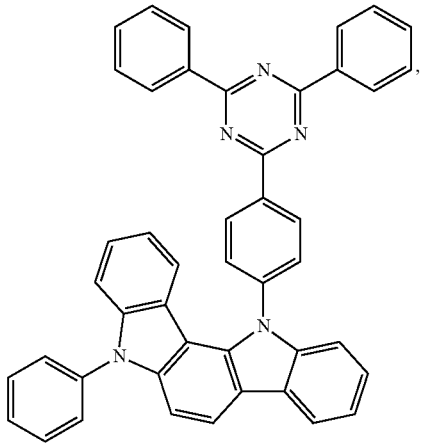
A41
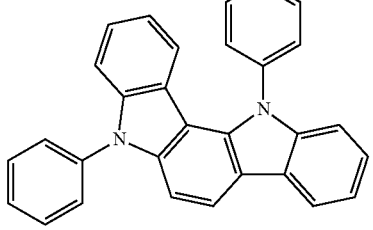
A42
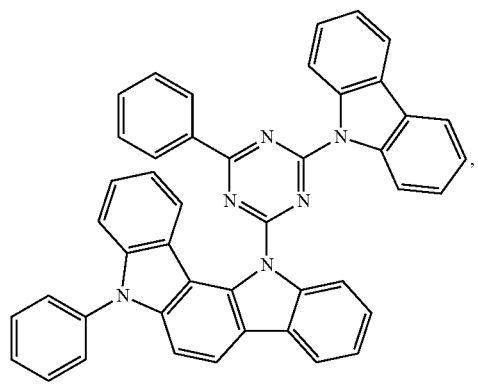
B1
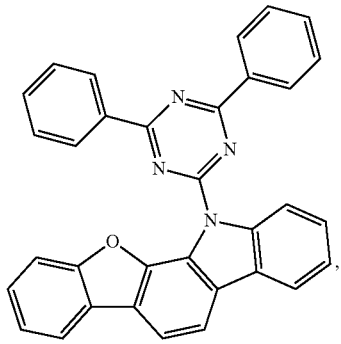
B2

B3
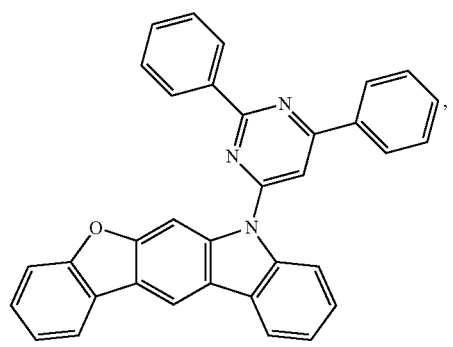
B4
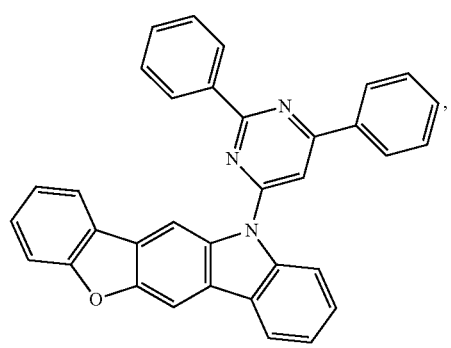
B5
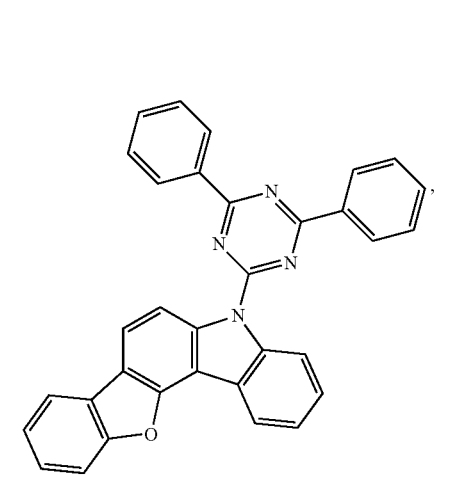
B6
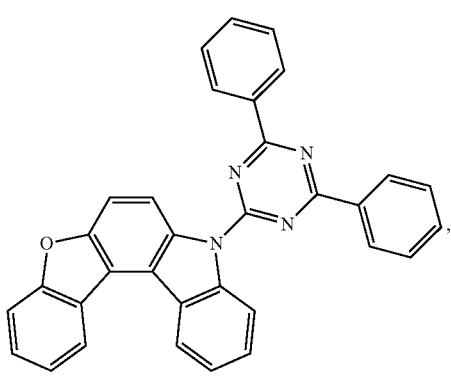
B7
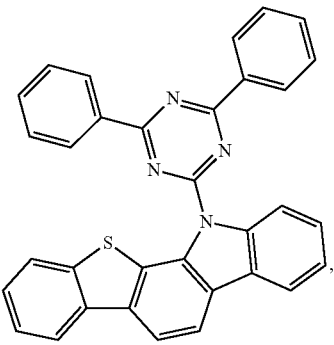
B8
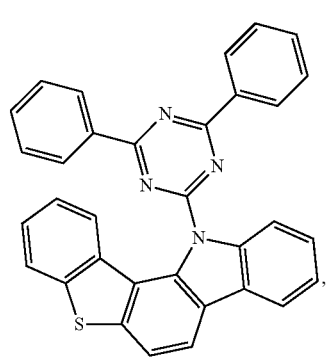
B9
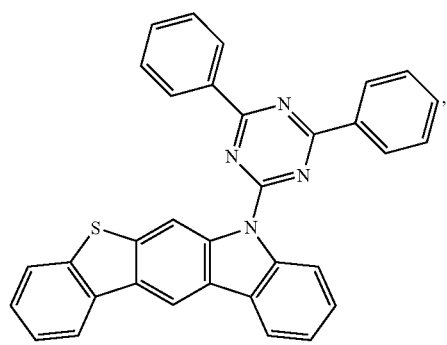
B10
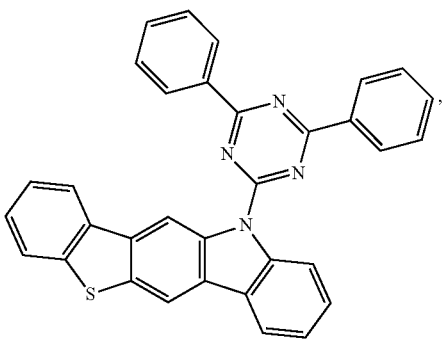

-continued
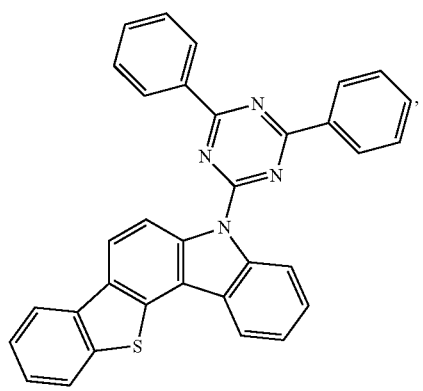
B11
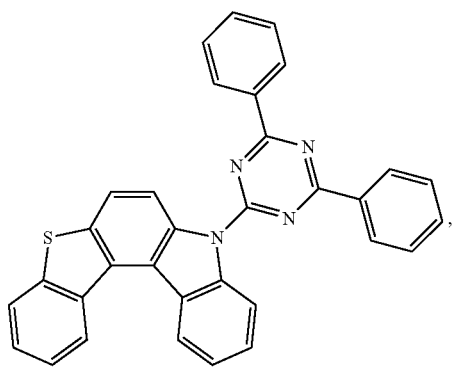
B12
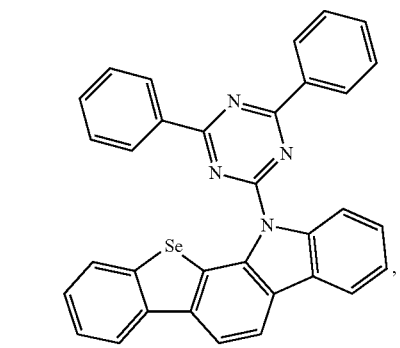
B13
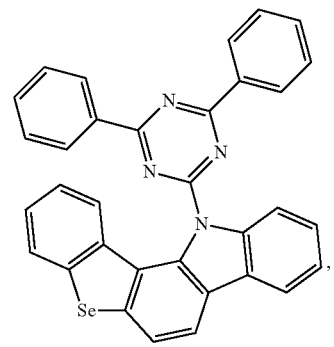
B14
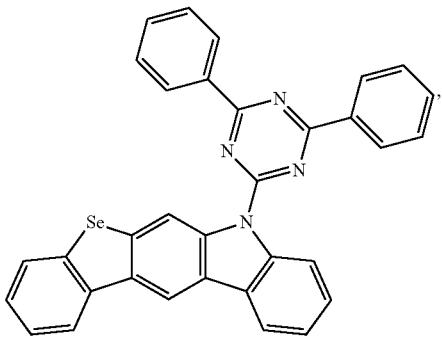
B15
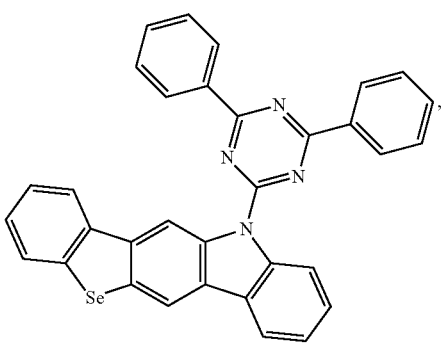
B16
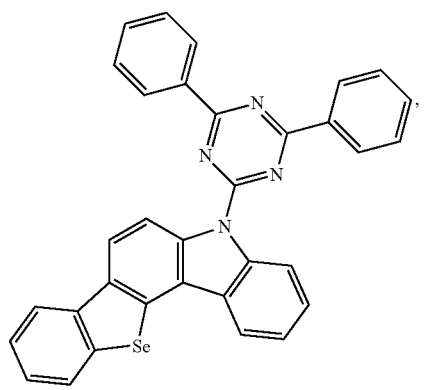
B17
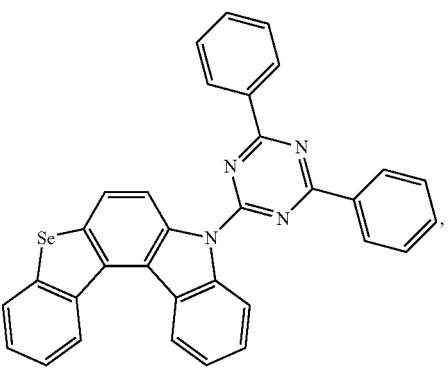
B18

-continued
B19
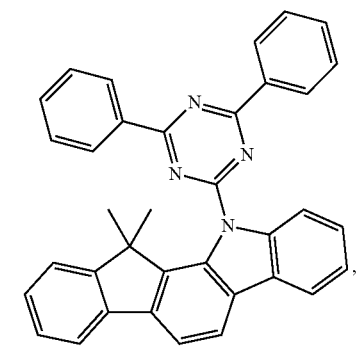
B20
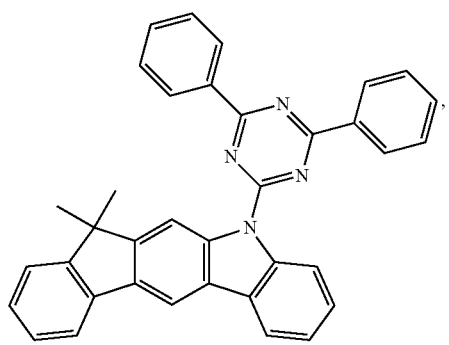
B21
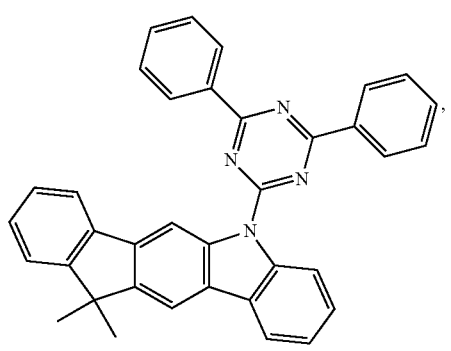
B22
-continued
B23
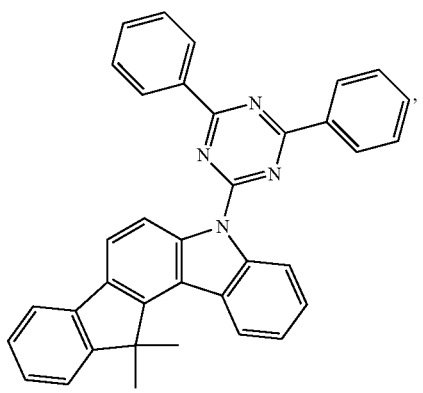
B24
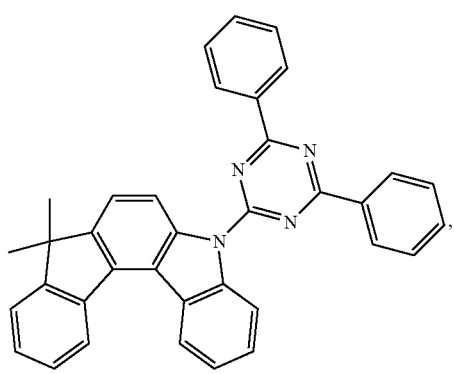
B25
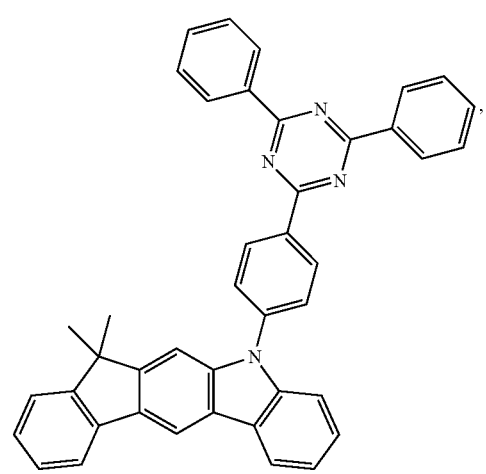

B26 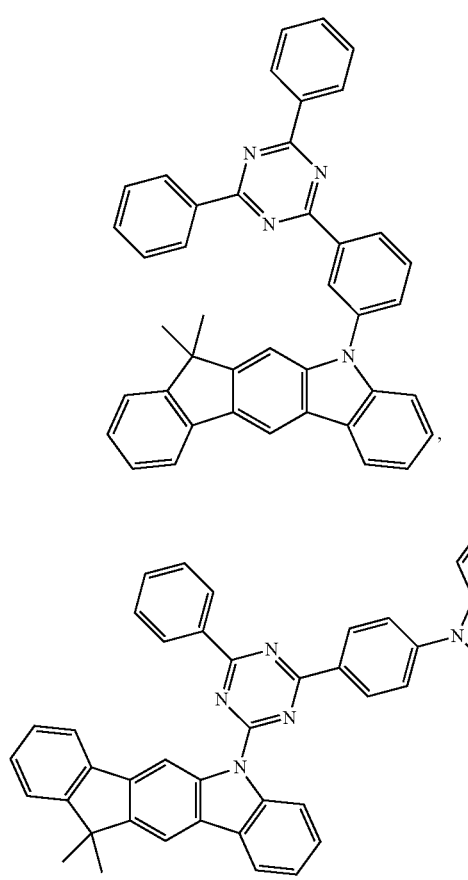
B27
C1
C2 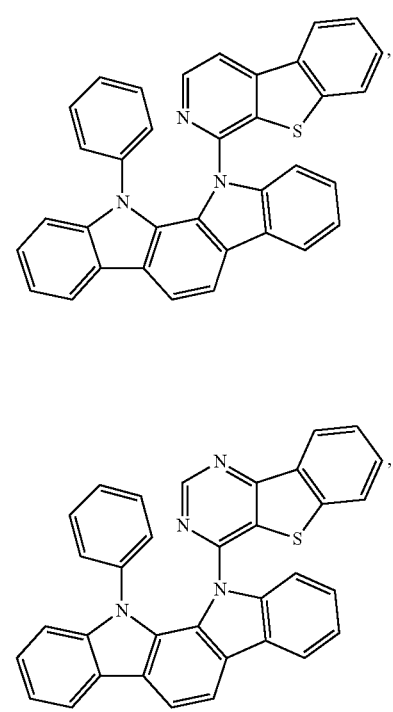
C3 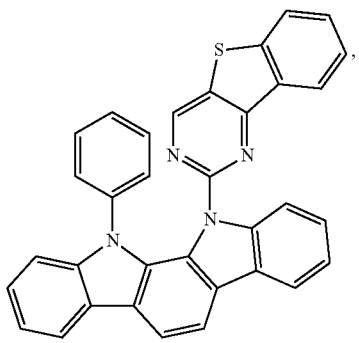
C4 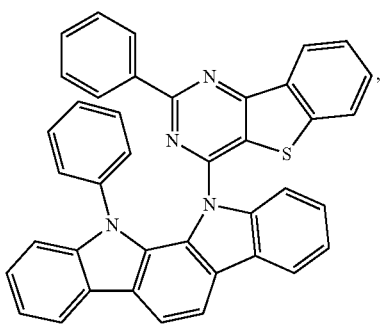
C5 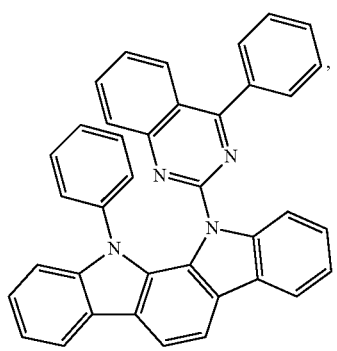
C6 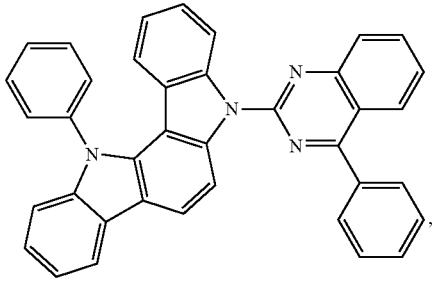
C7 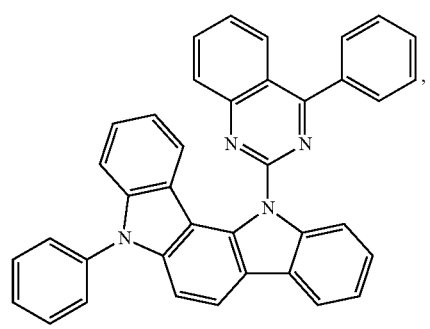

C8
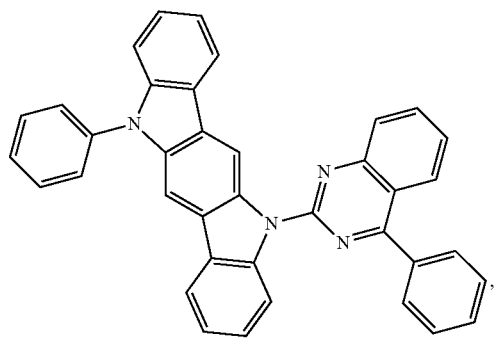
C9
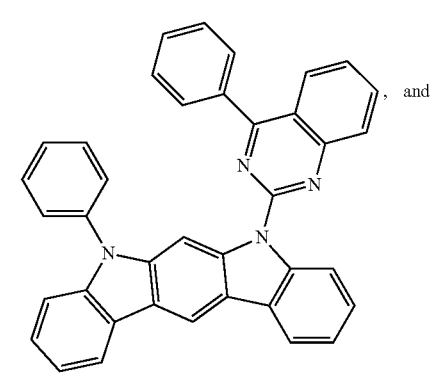, and
C10
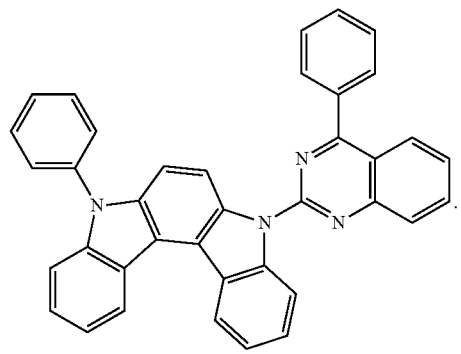
In some embodiments of the composition of material, the first compound is selected from the group consisting of:
HA1
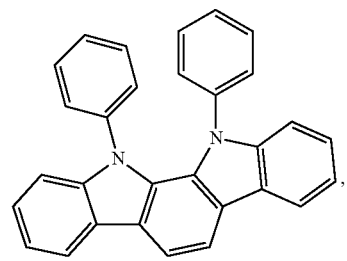
HA2
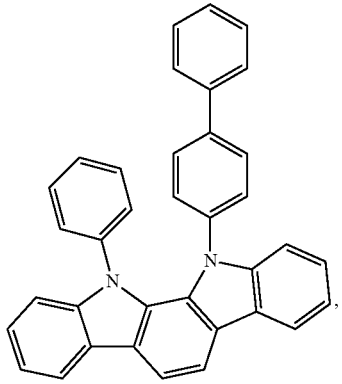
HA3
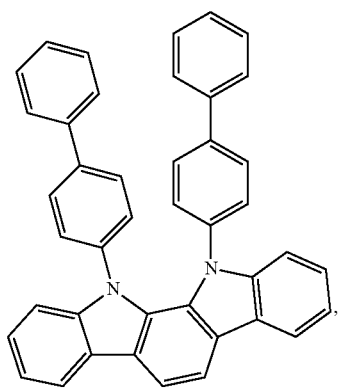
HA4
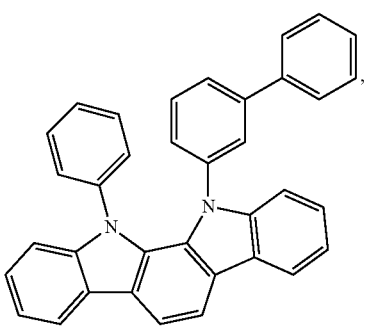
HA5
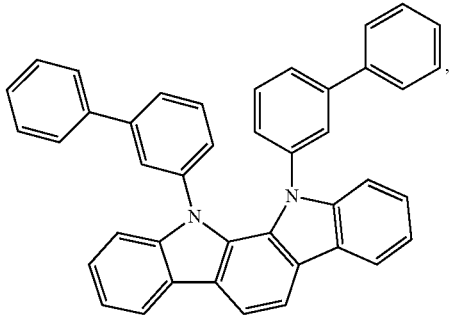

-continued
HA6
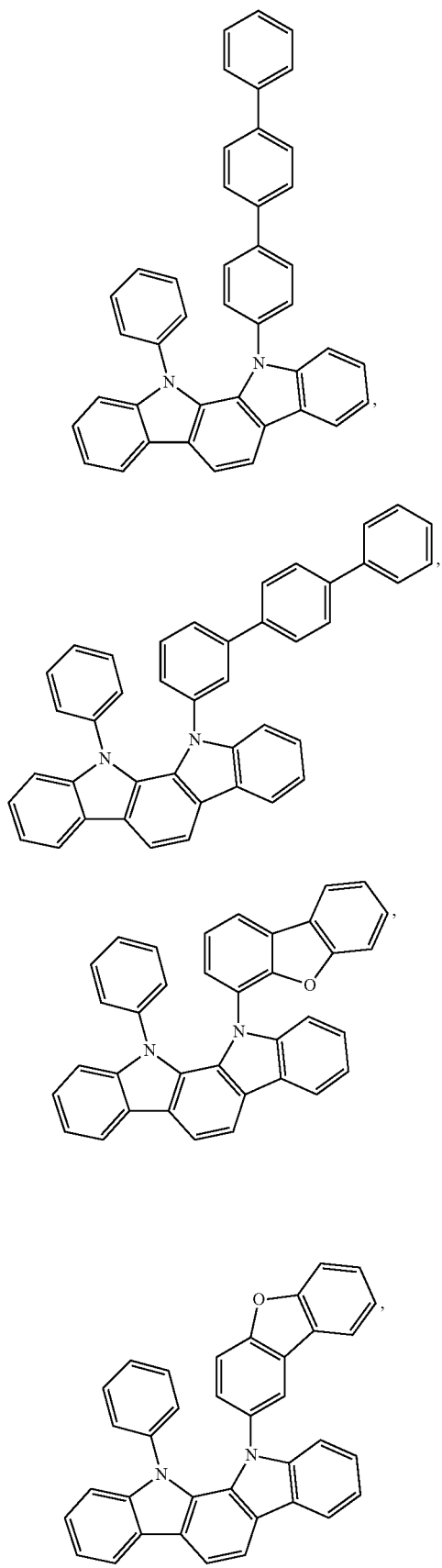
HA7
HA8
HA9
HA10
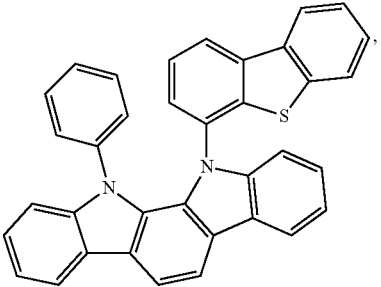
HA11
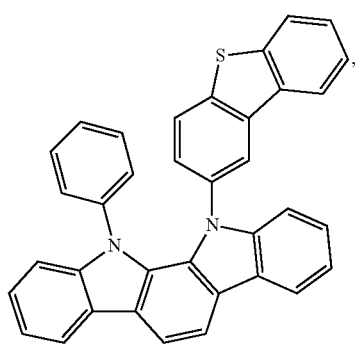
HA12
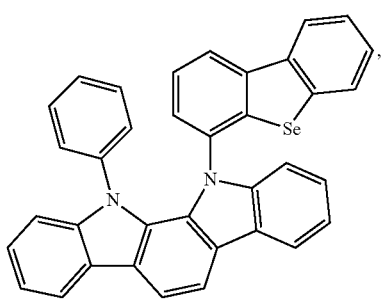
HA13
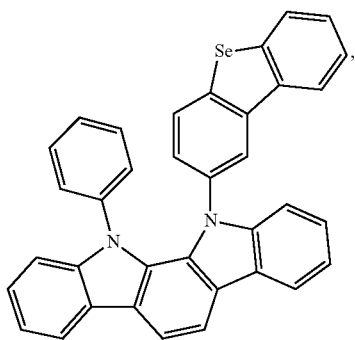

HA14
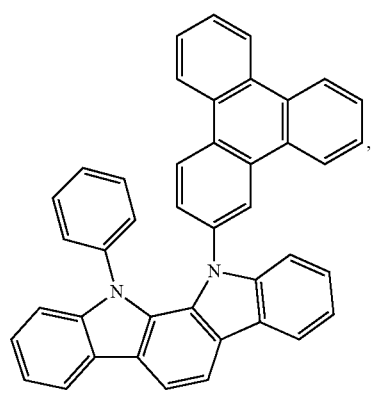
HA15
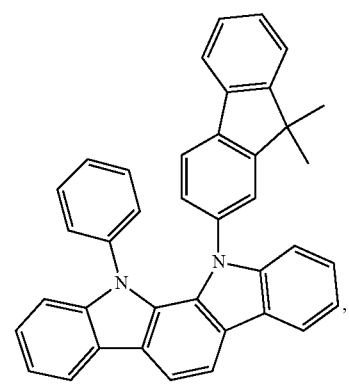
HA16
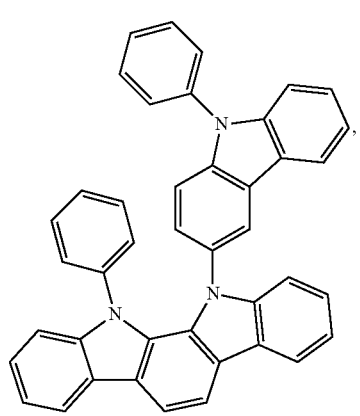
HA17
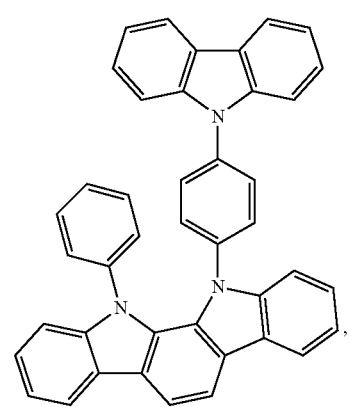
HA18
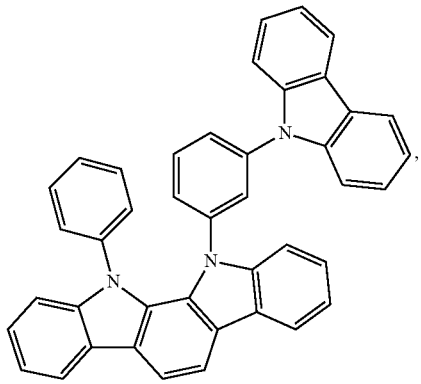
HA19
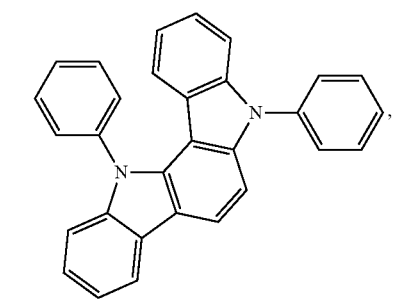
HA20
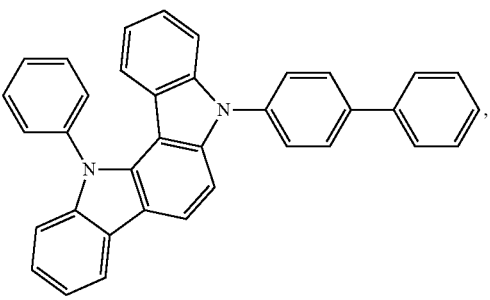
HA21
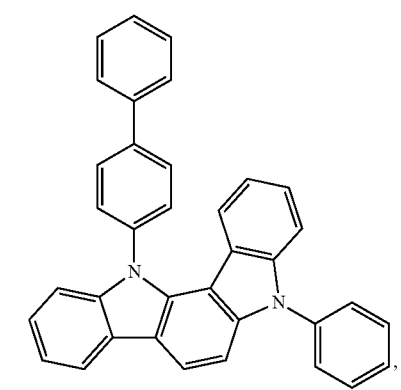

HA22
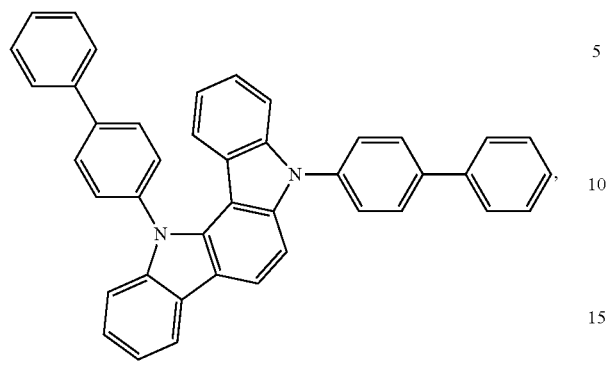
HA26
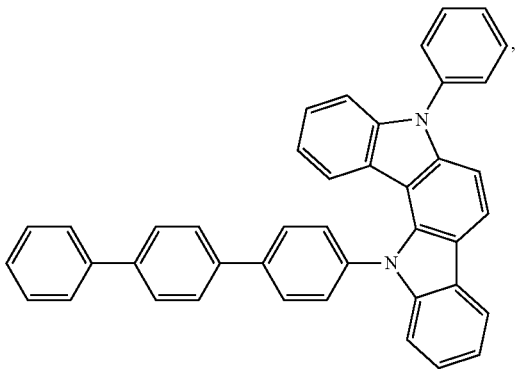
HA23
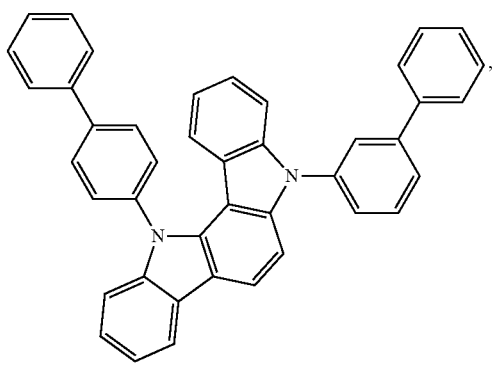
HA27
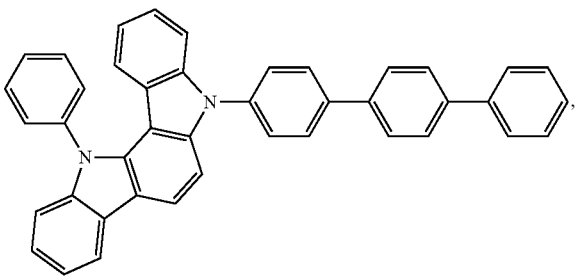
HA24
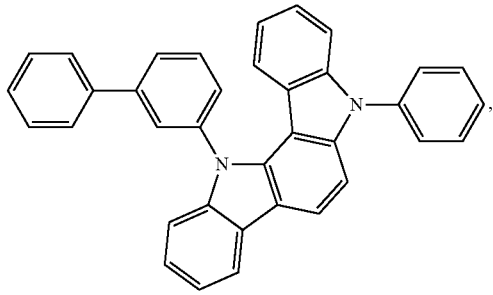
HA28
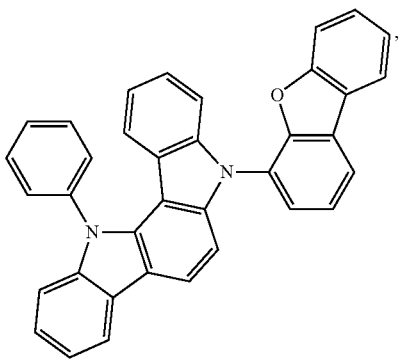
HA25
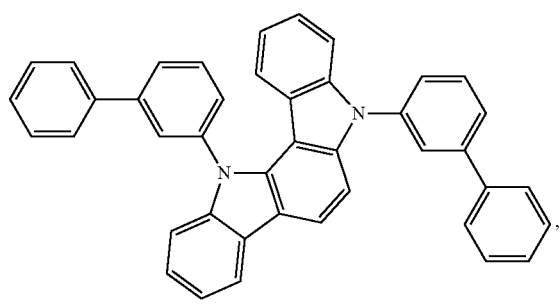
HA29
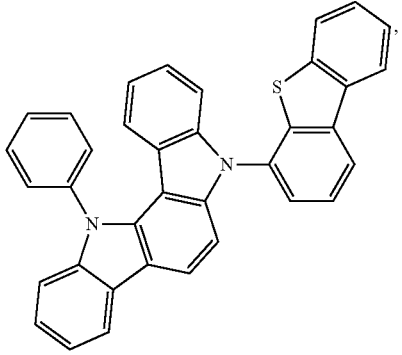

HA30
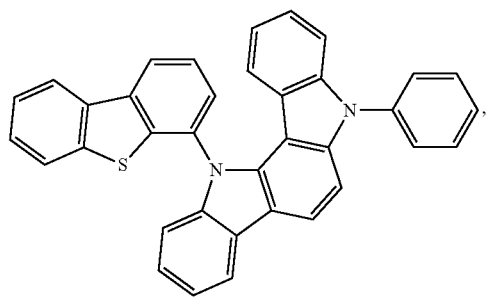
HA34
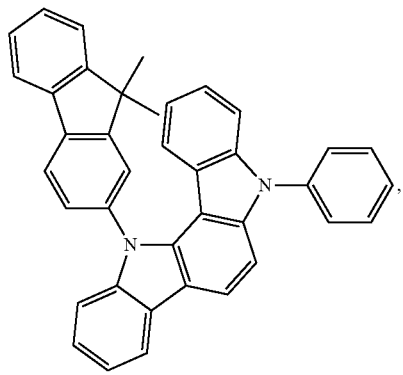
HA31
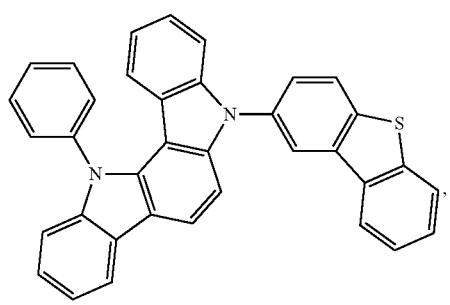
HA35
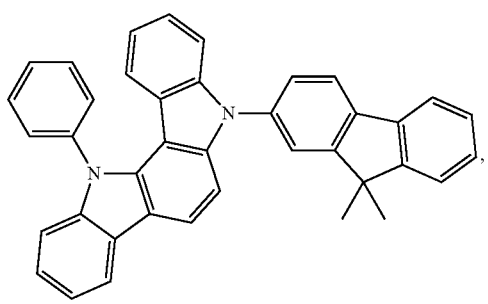
HA32
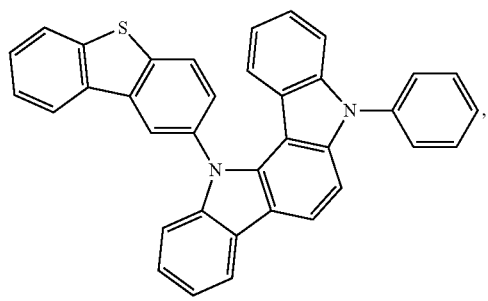
HA36
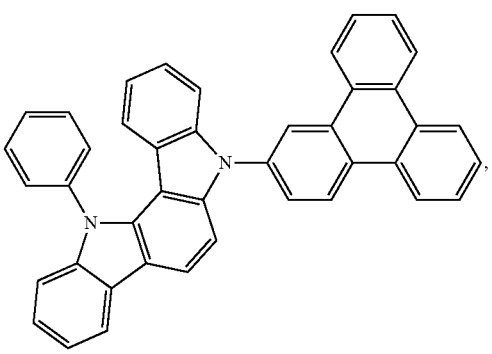
HA33
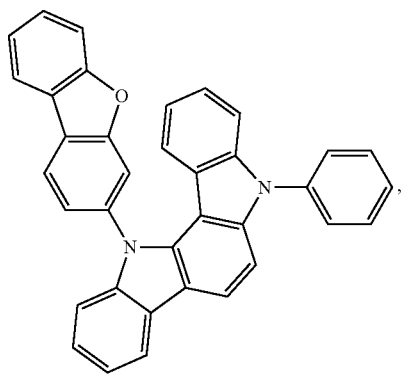
HA37
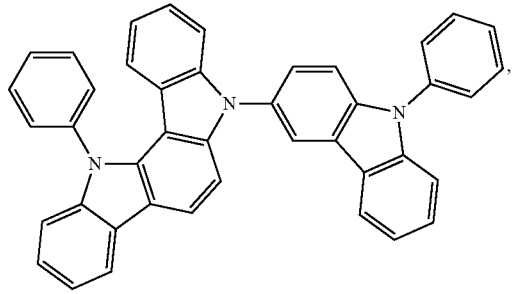

HA38
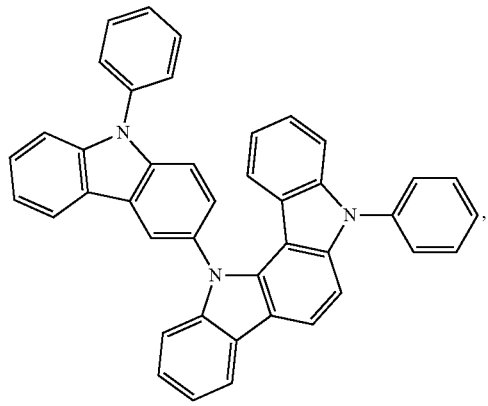
HA39
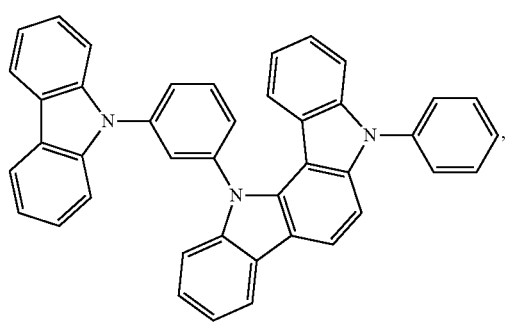
HA40
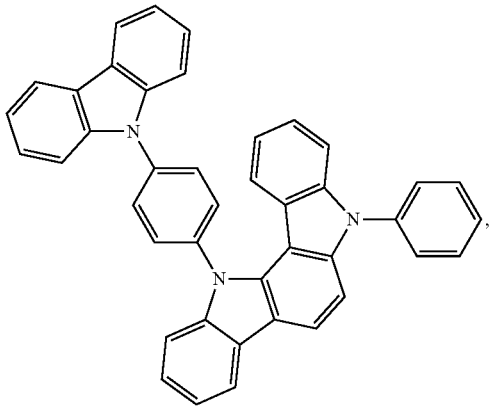
HA41
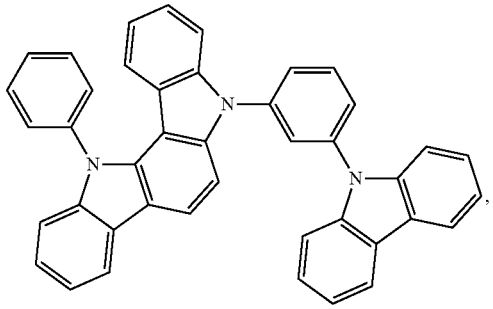
HA42
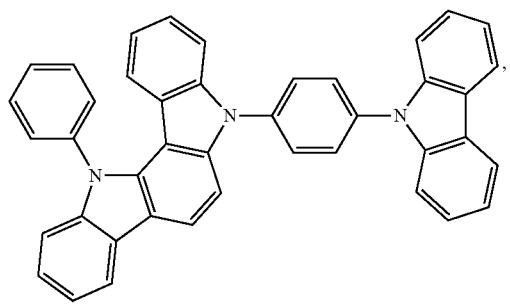
HA43
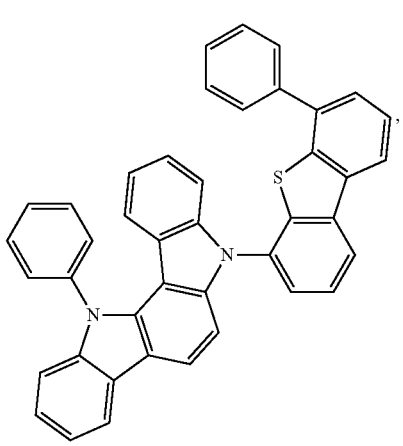
HA44
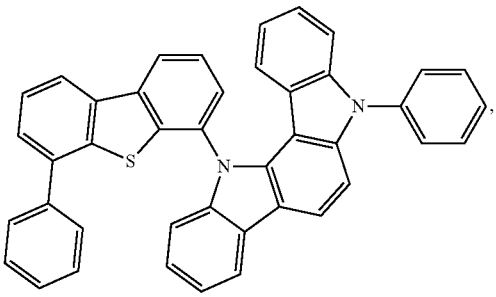
HA45
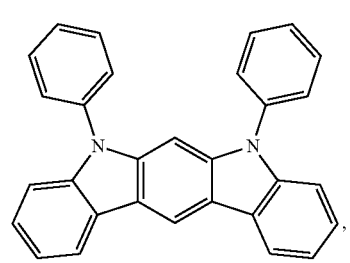

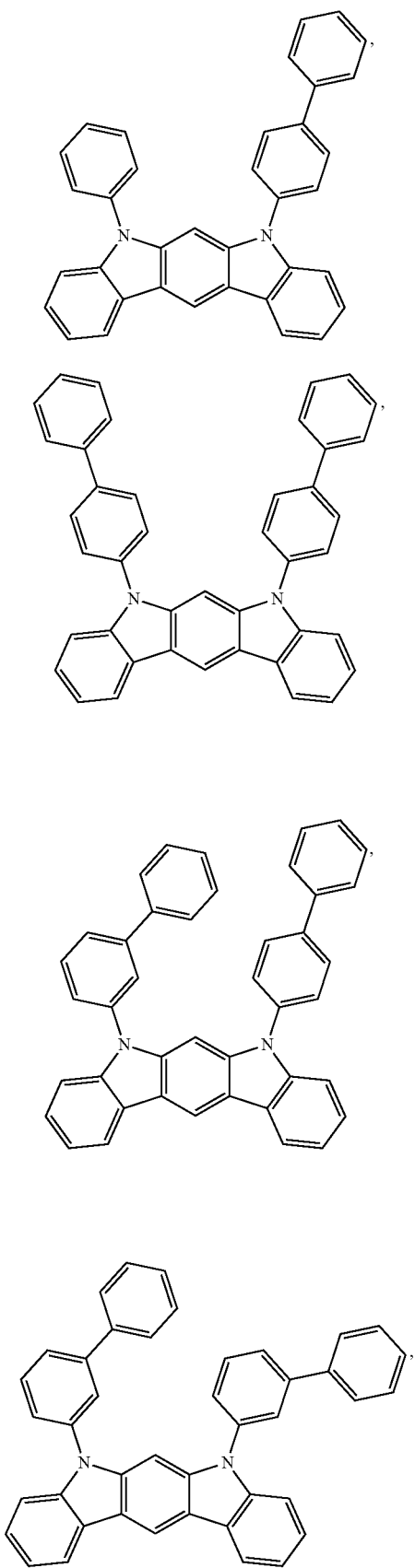
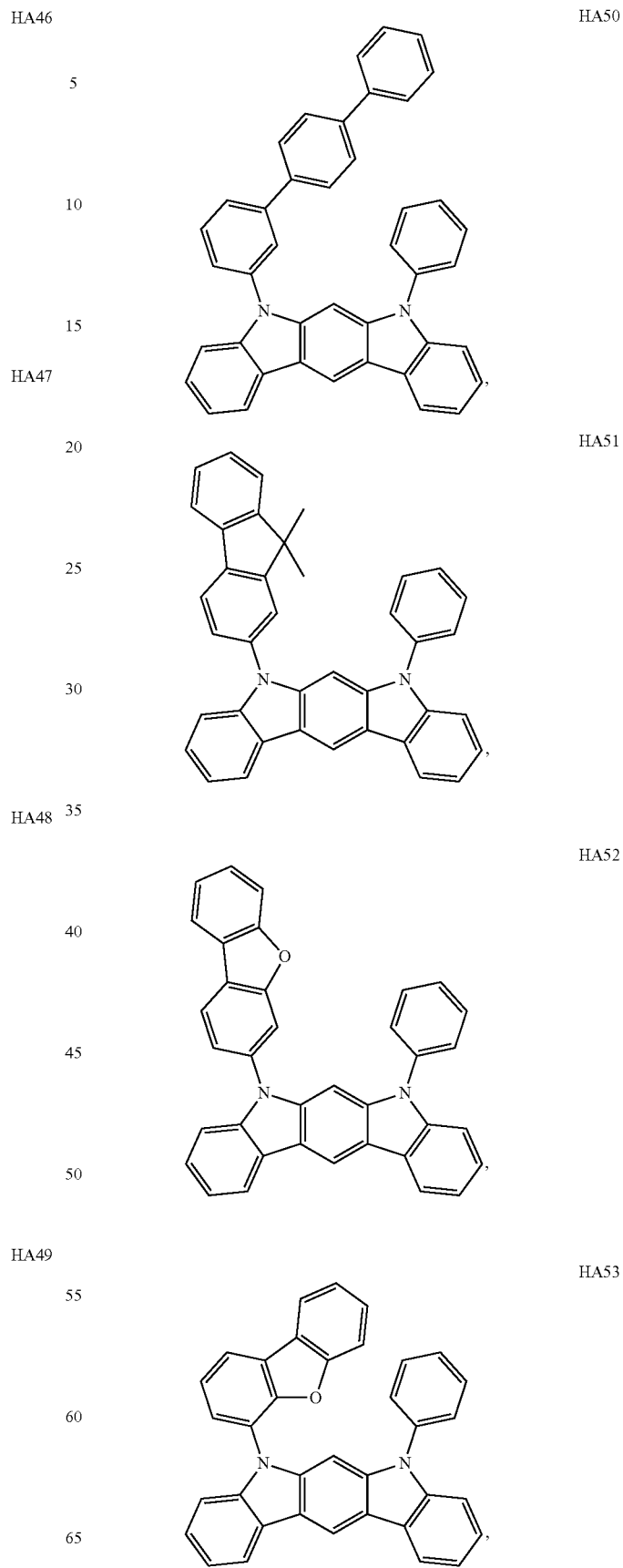

HA54
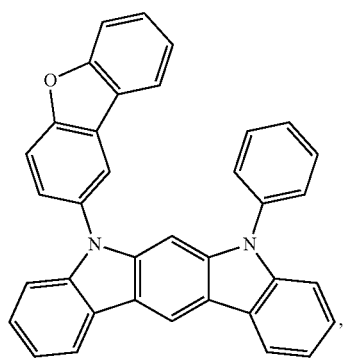
HA55
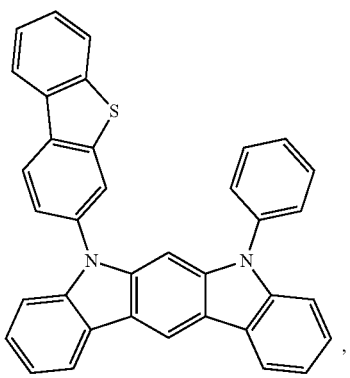
HA56
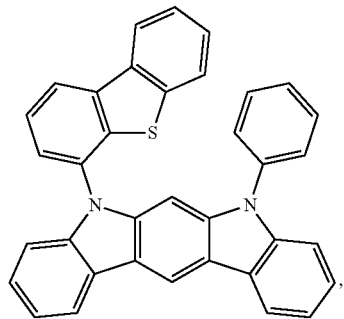
HA57
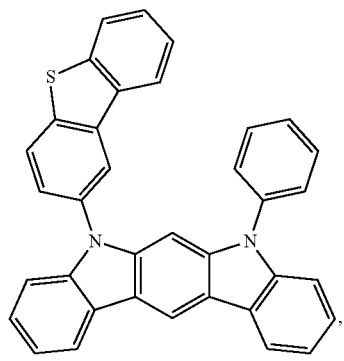
HA58
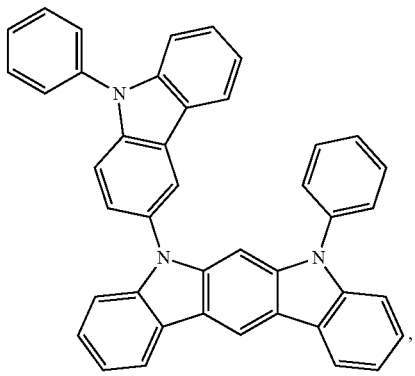
HA59
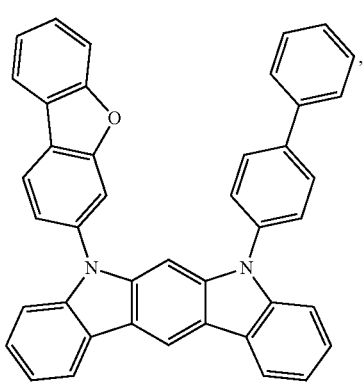
HA60
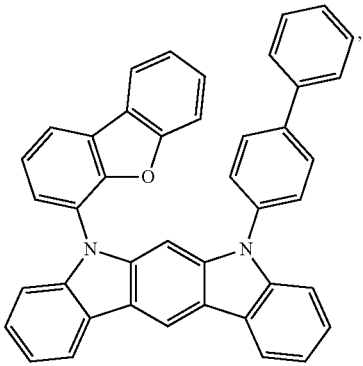
HA61
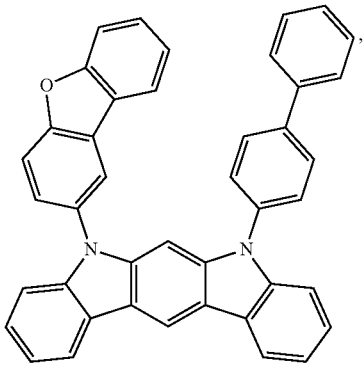

HA62
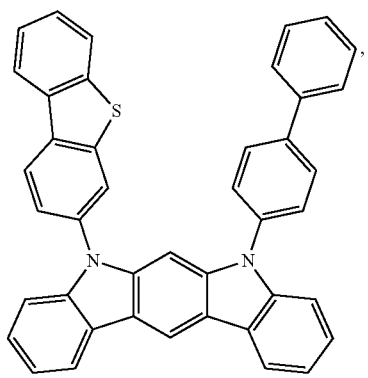
HA63
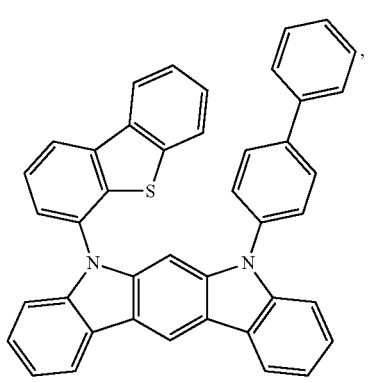
HA64
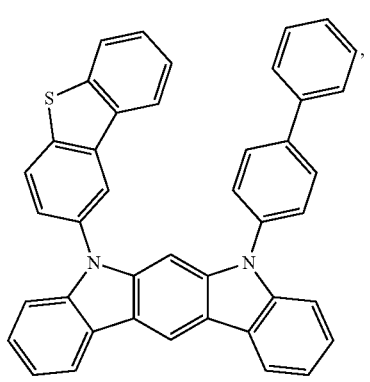
HA65
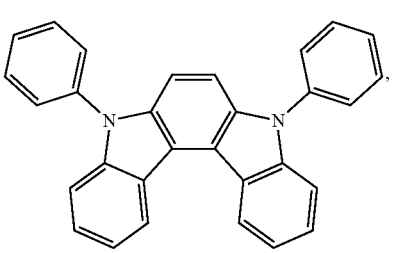
HA66
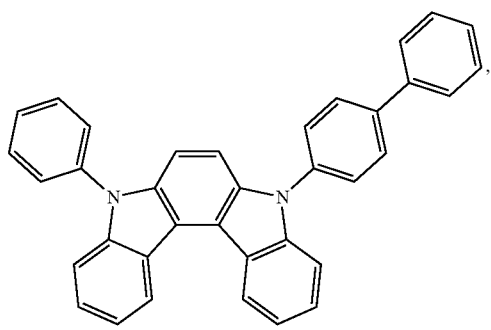
HA67
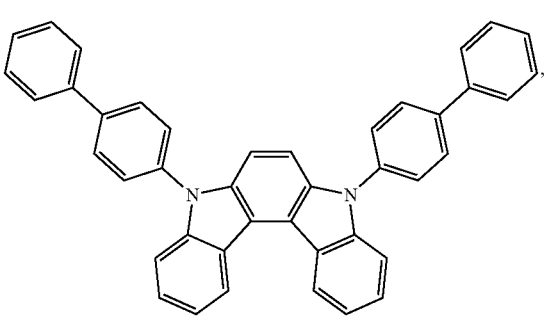
HA68
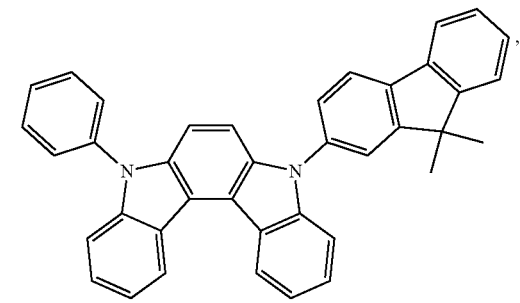
HA69
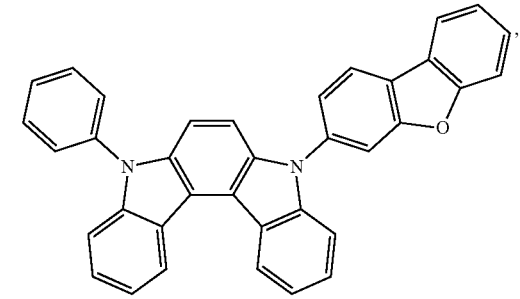

HA70
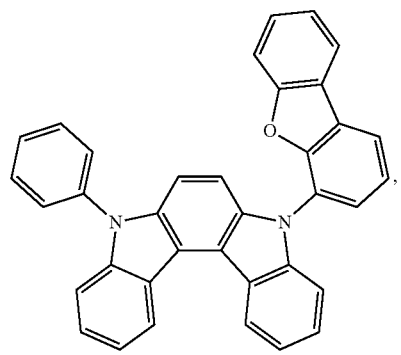
HA71
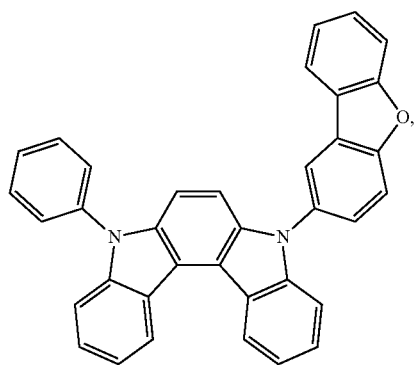
HA72
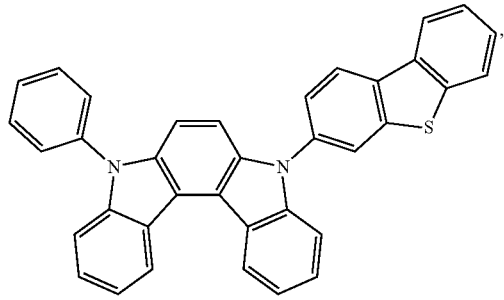
HA73
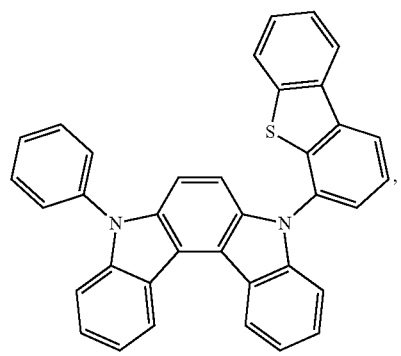
HA74
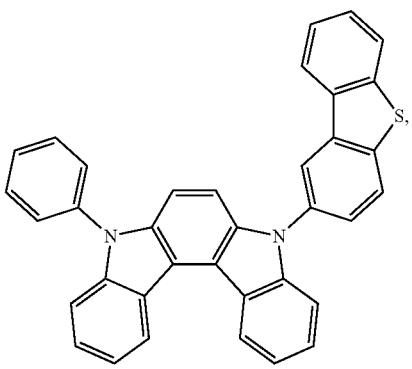
HA75
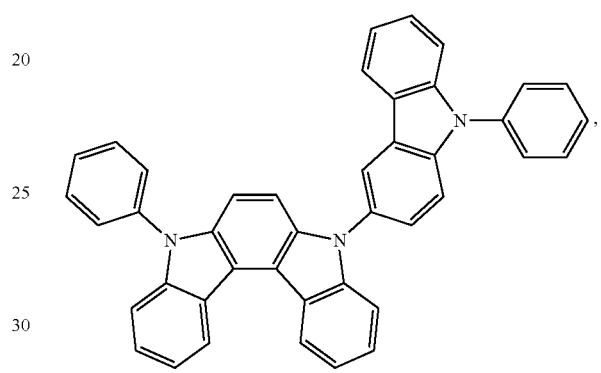
HA76
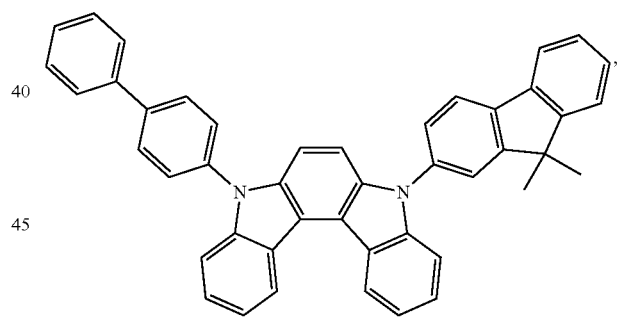
HA77
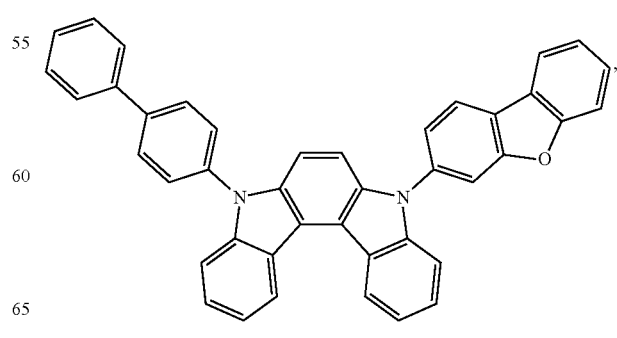

HA78
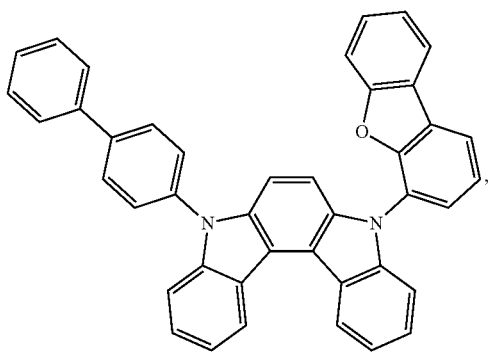
HA82
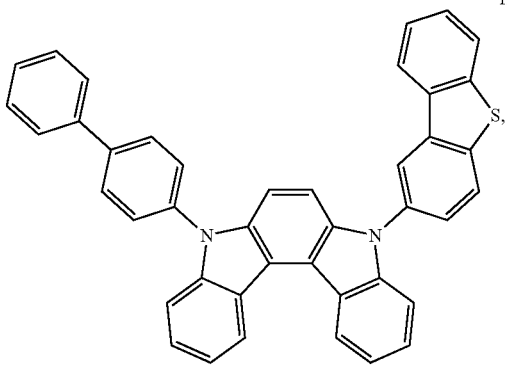
HA79
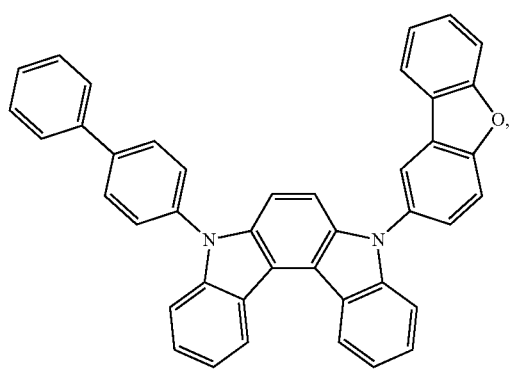
HA83
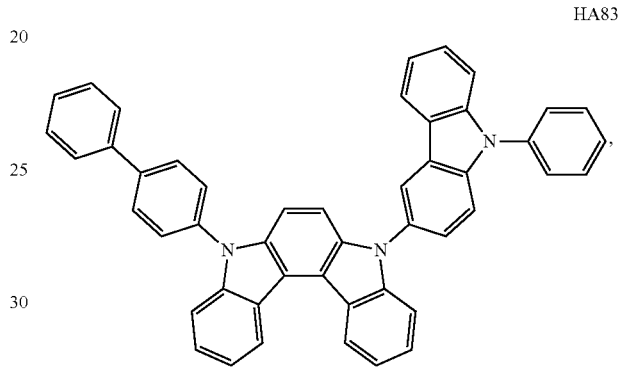
HA80
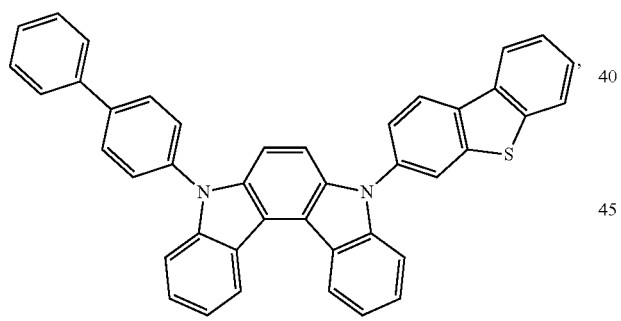
HA84
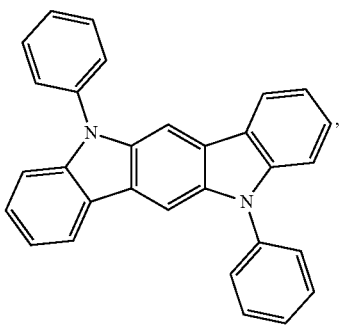
HA81
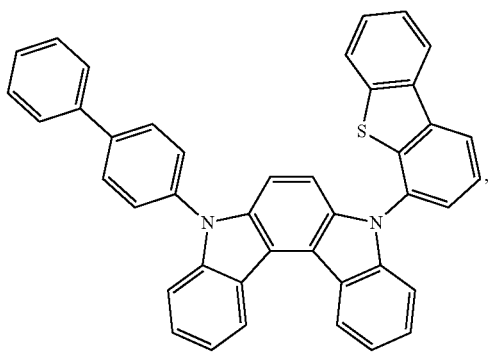
HA85
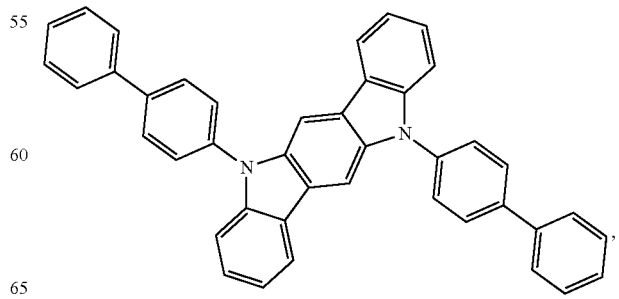

HA86 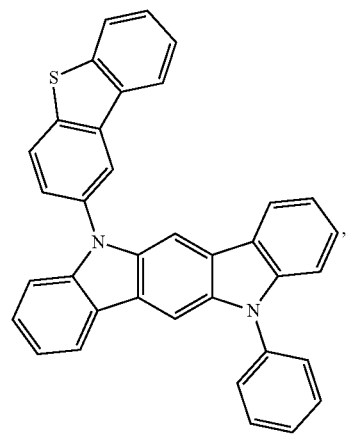
HA90 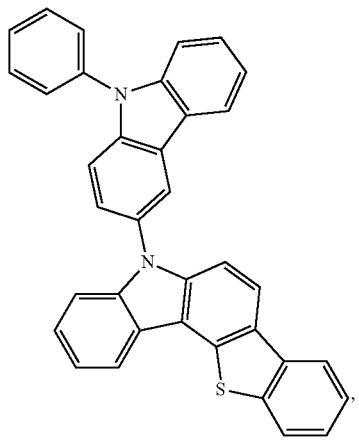
HA87 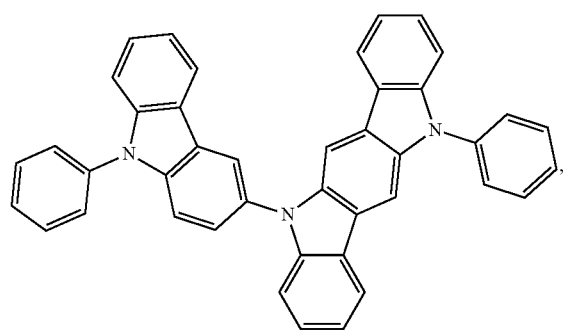
HA91 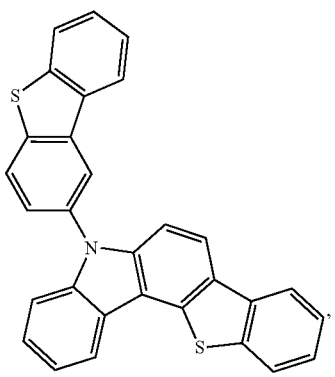
HA88 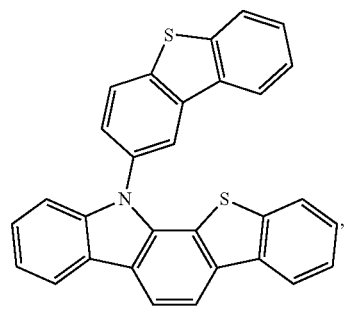
HA92 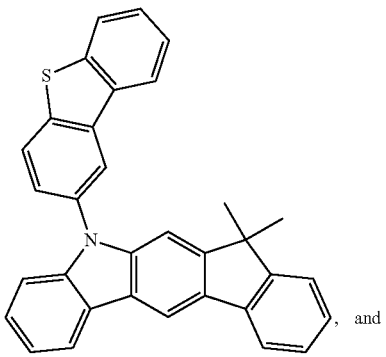, and
HA89 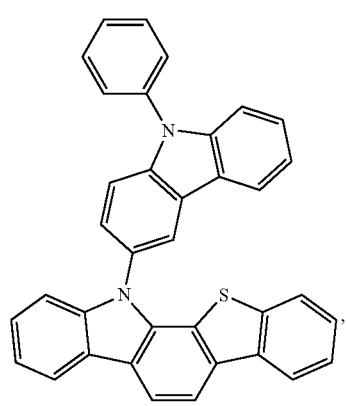
HA93 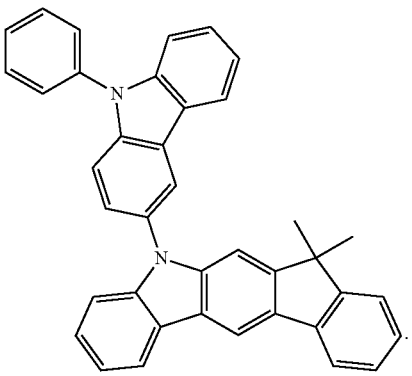.
In some embodiments of the composition of material, the second compound is selected from the group consisting of:

D1 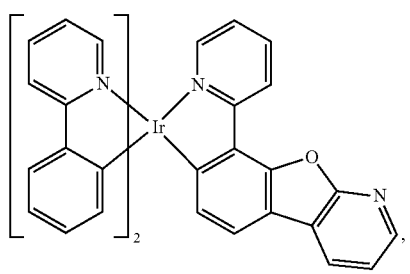
D2 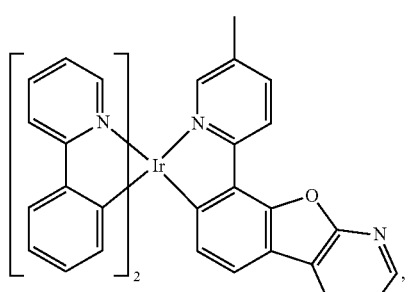
D3 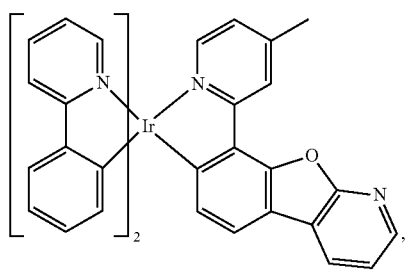
D4 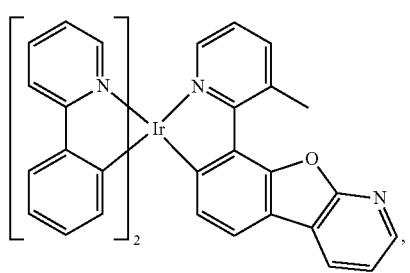
D5 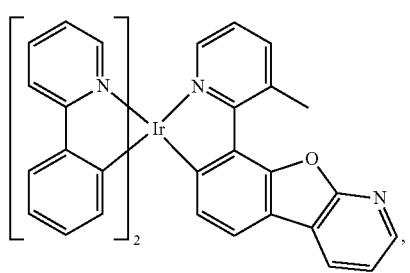
-continued
D6 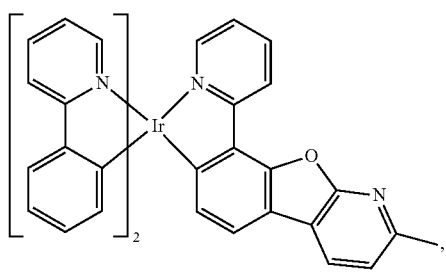
D7 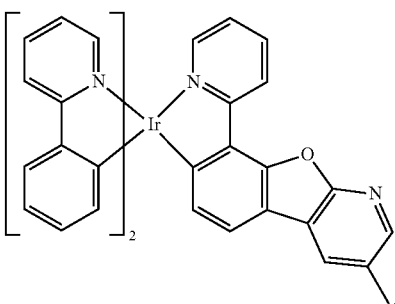
D8 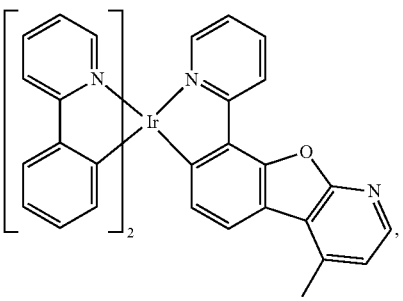
D9 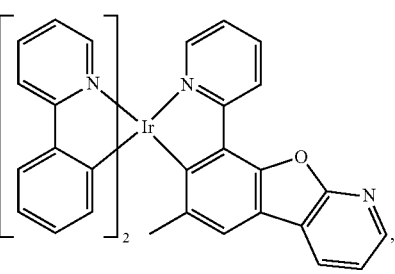
D10 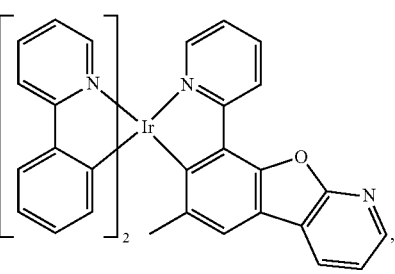

D11 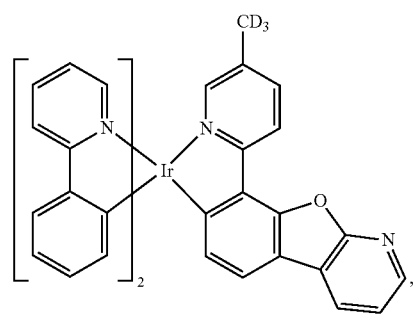
D12 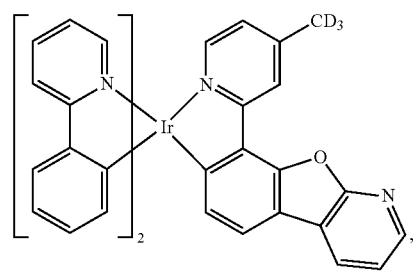
D13 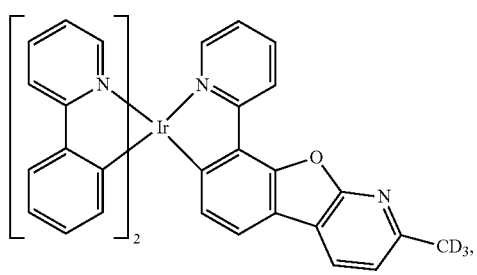
D14 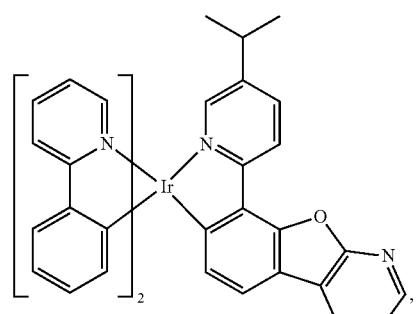
D15 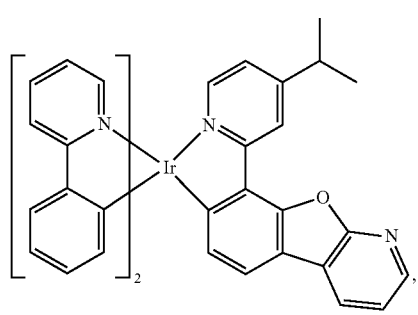
D16 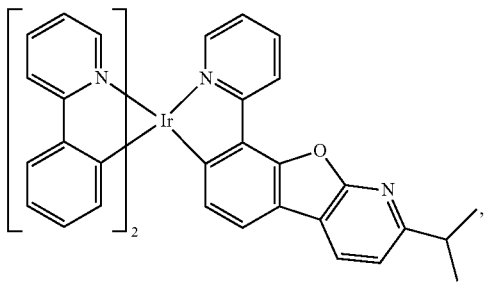
D17 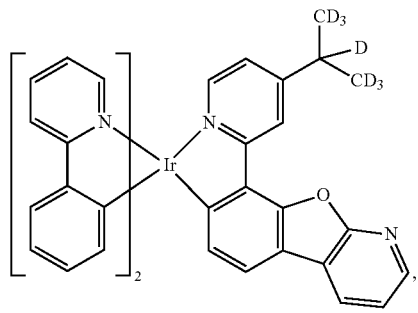
D18 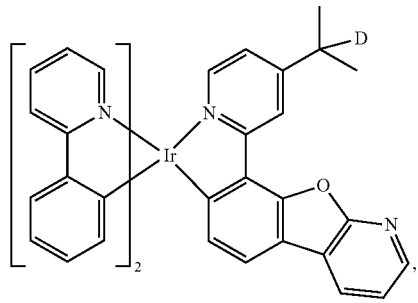
D19 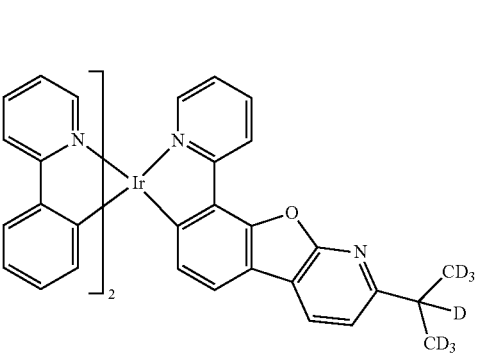
D20 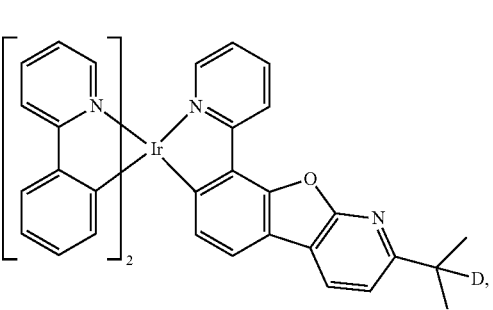

D21 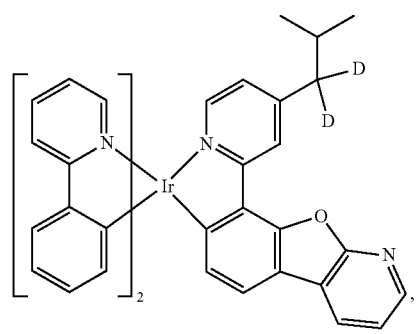
D22 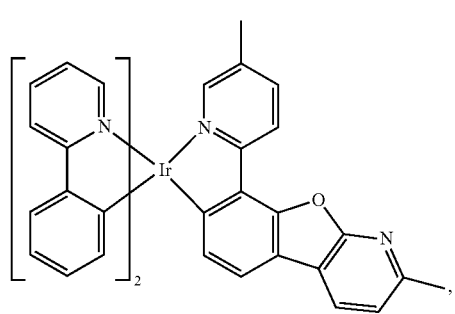
D23 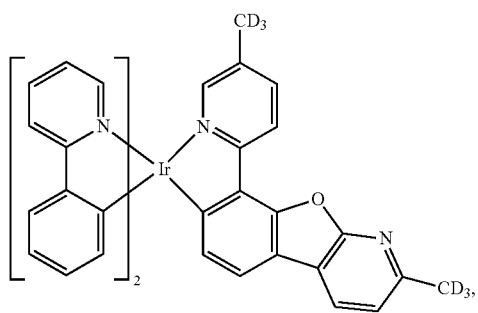
D24 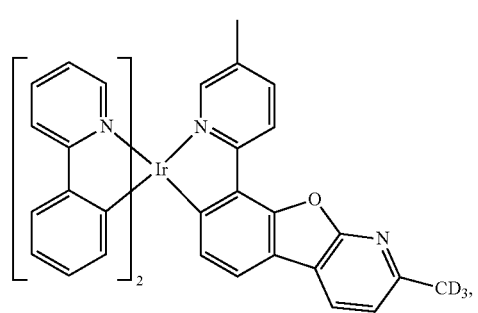
D25 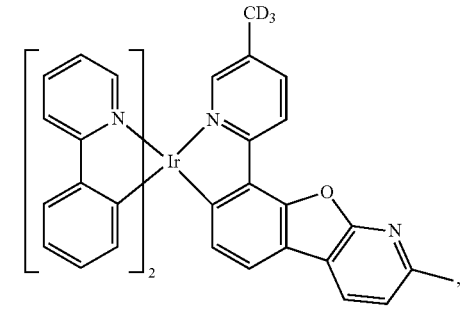
D26 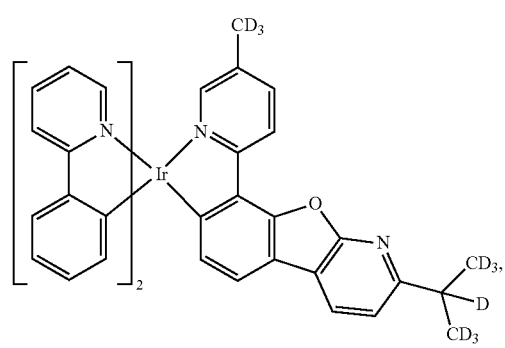
D27 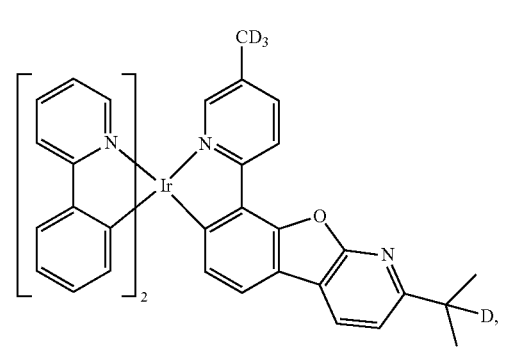
D28 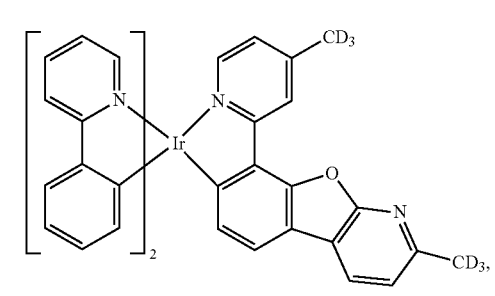
D29 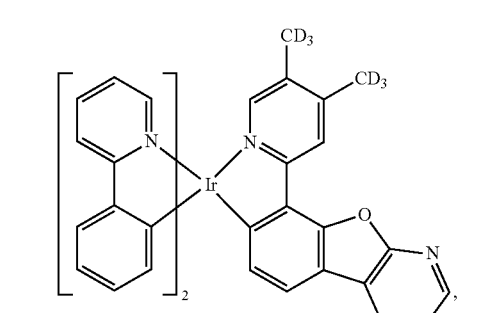
D30 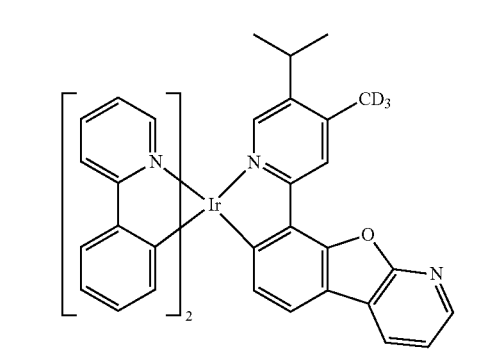

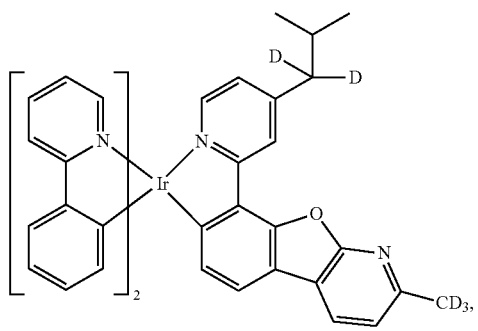
D31
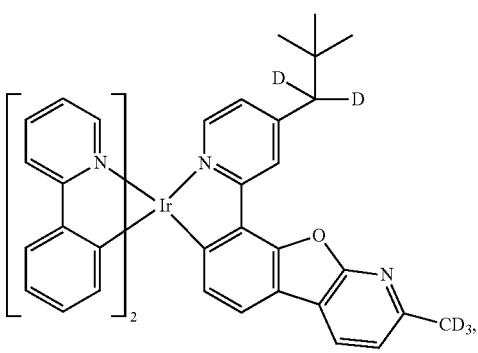
D32
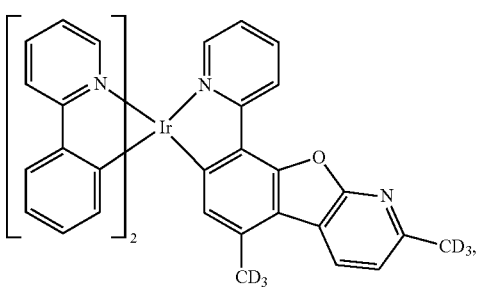
D33
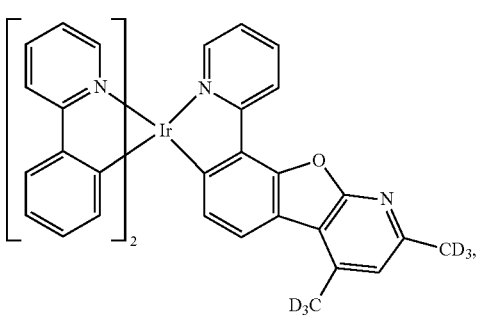
D34
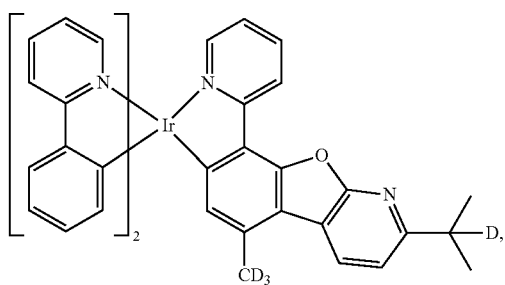
D35
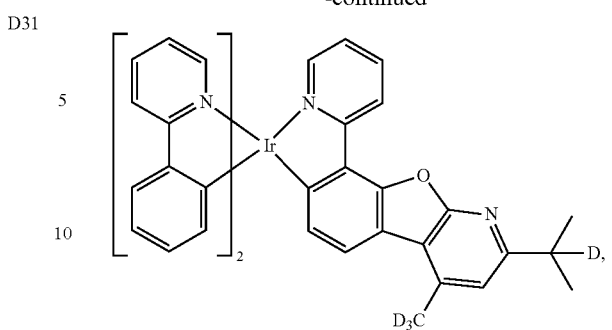
D36
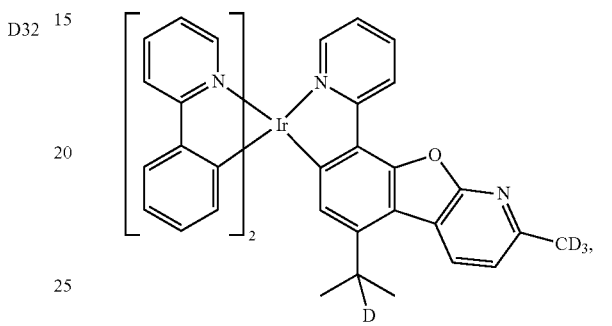
D37
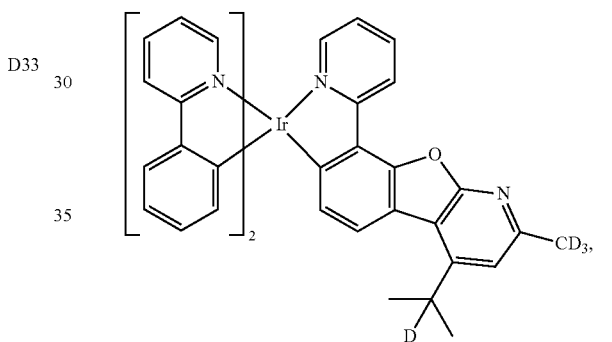
D38
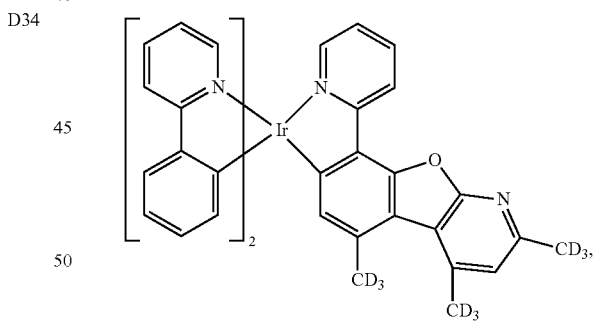
D39
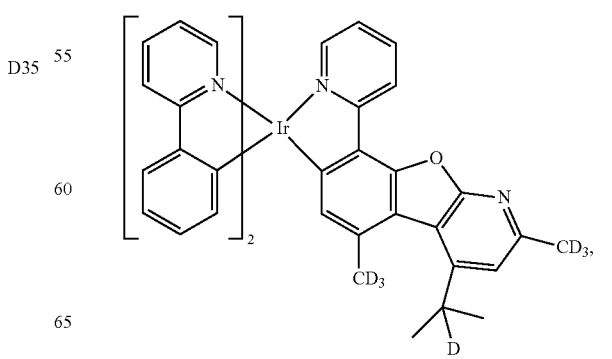
D40

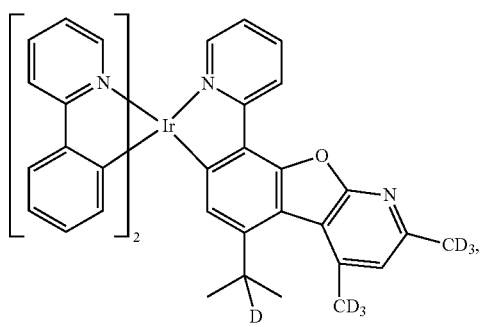
D41
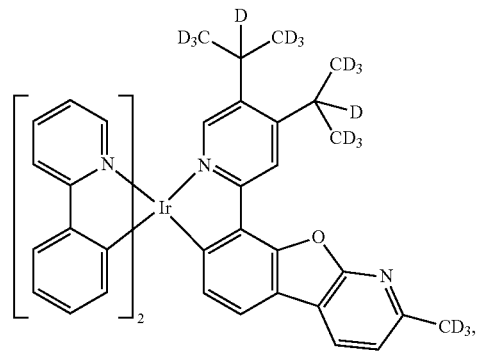
D45
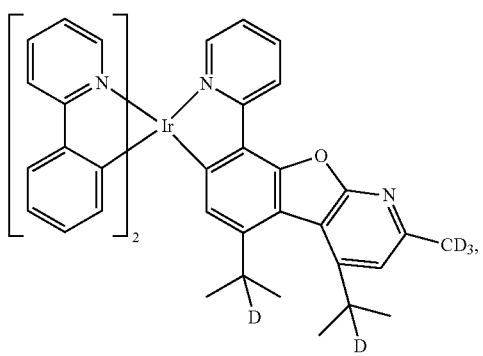
D42
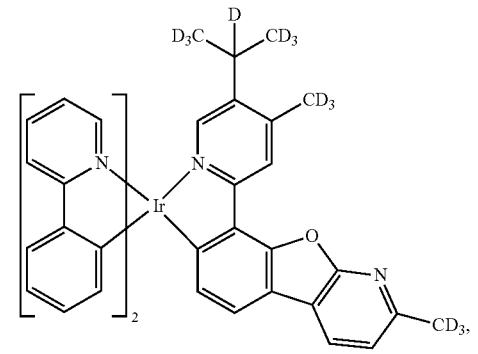
D46
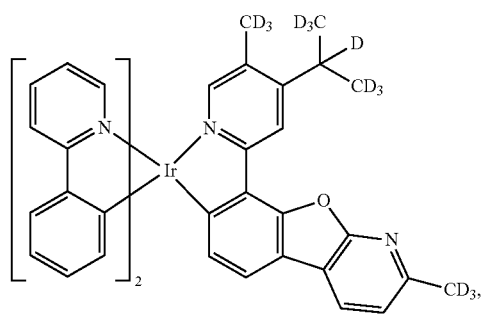
D43
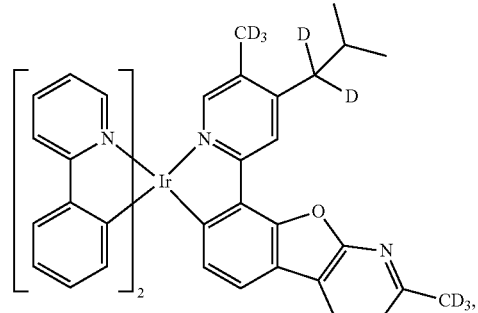
D47
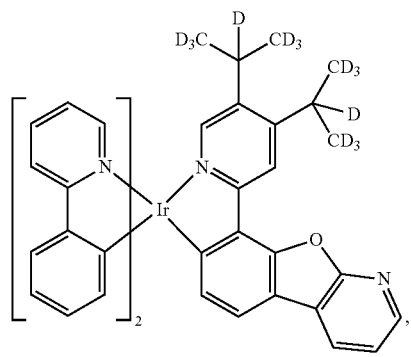
D44
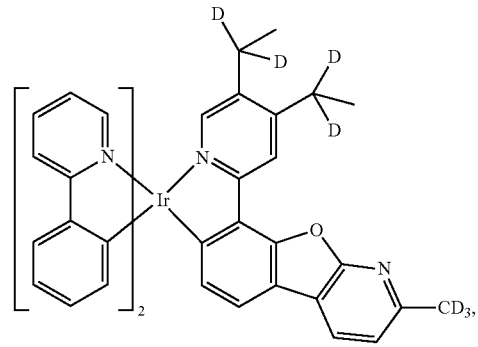
D48

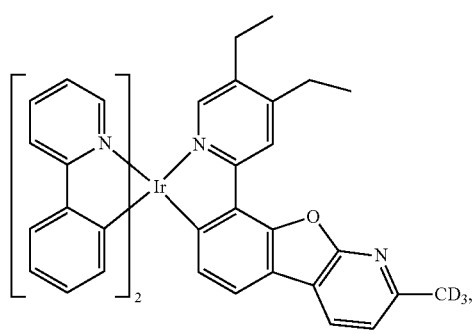
D49
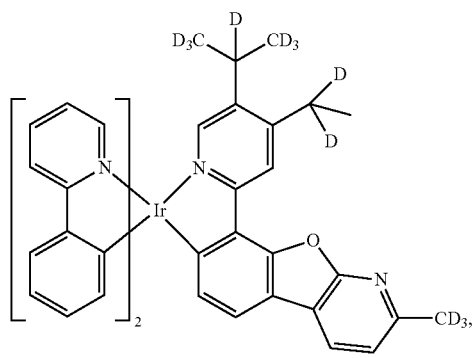
D50
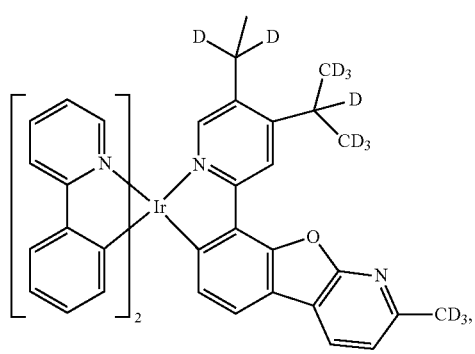
D51
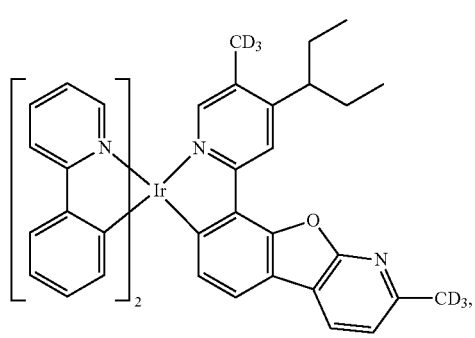
D52
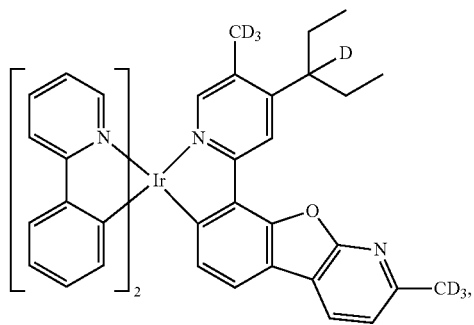
D53
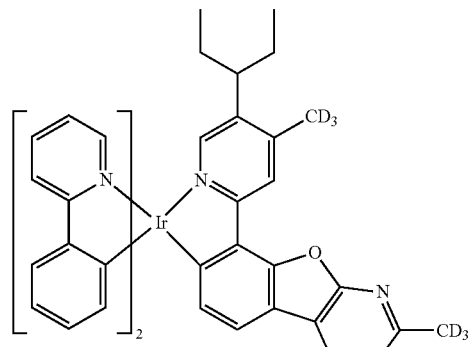
D54
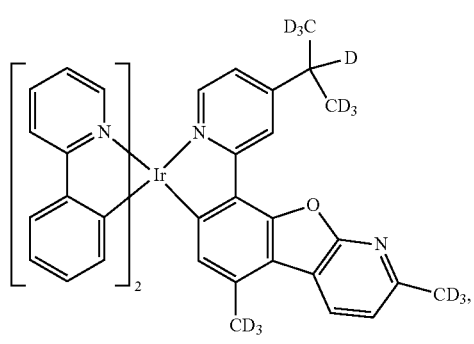
D55
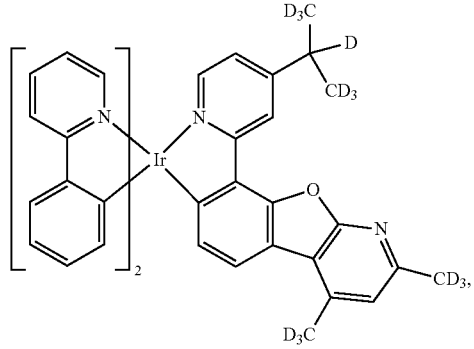
D56

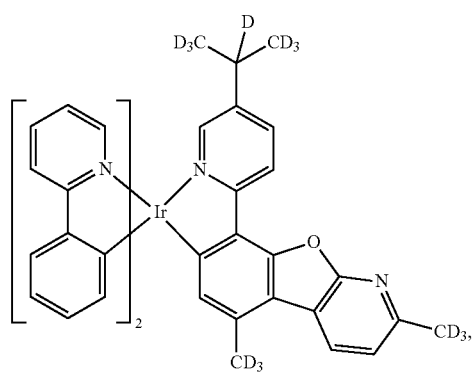
D57
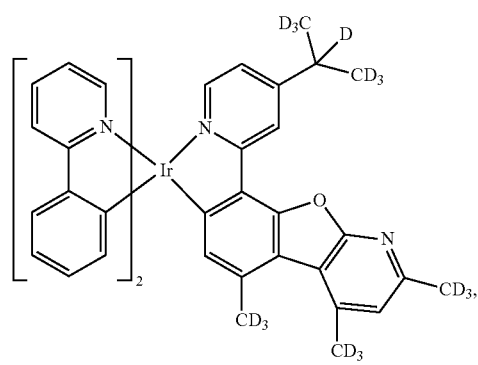
D61
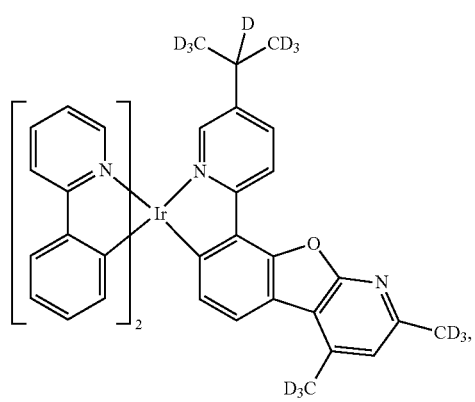
D58
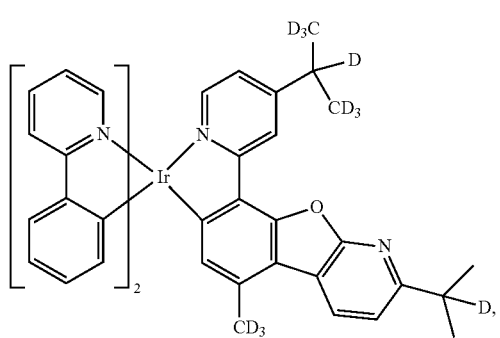
D62
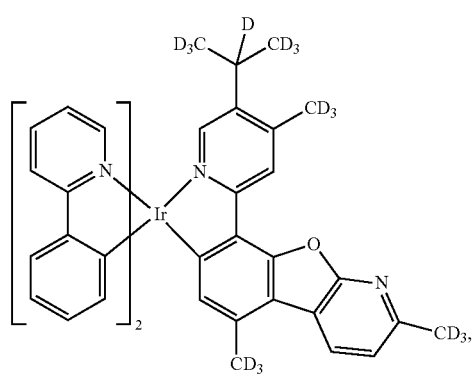
D59
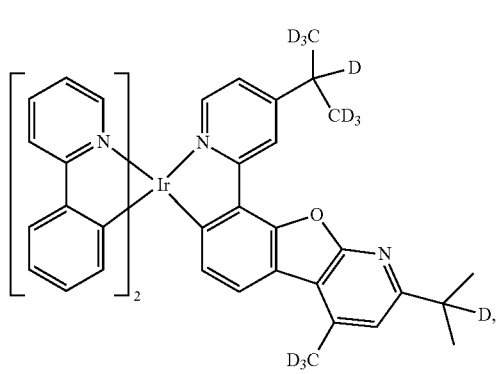
D63
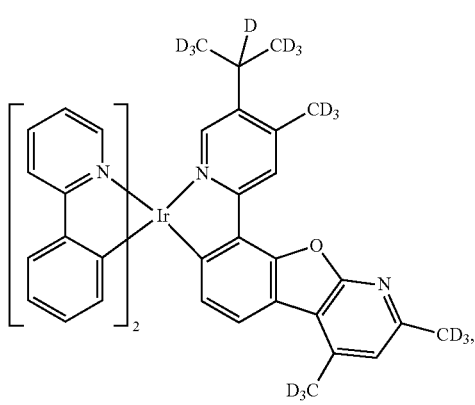
D60
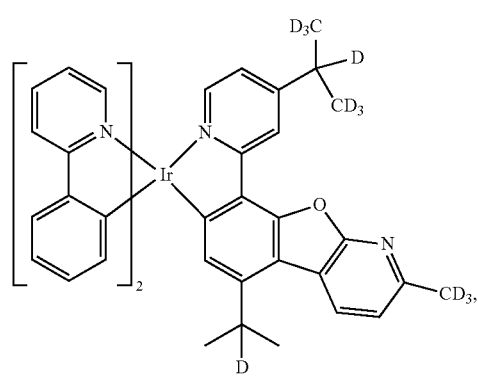
D64

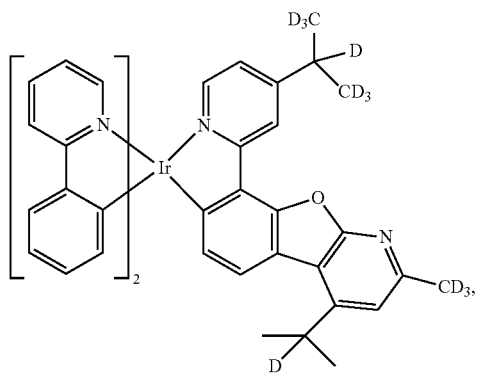 D65
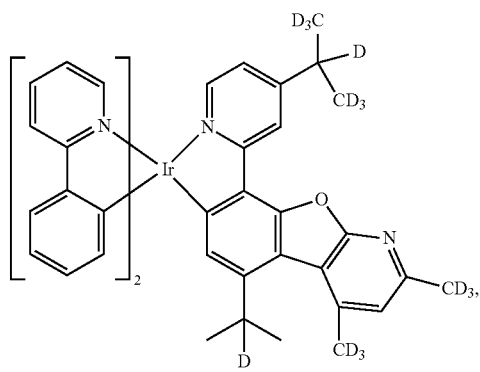 D69
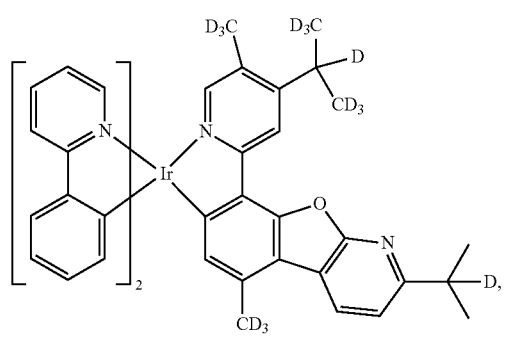 D66
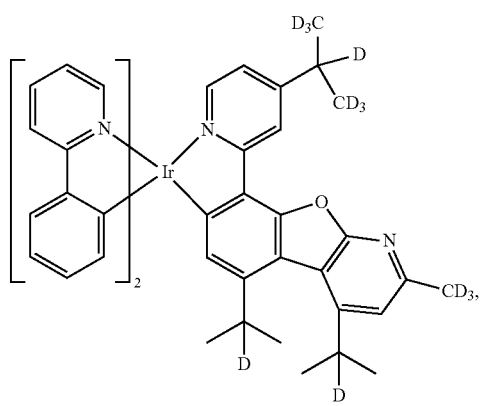 D70
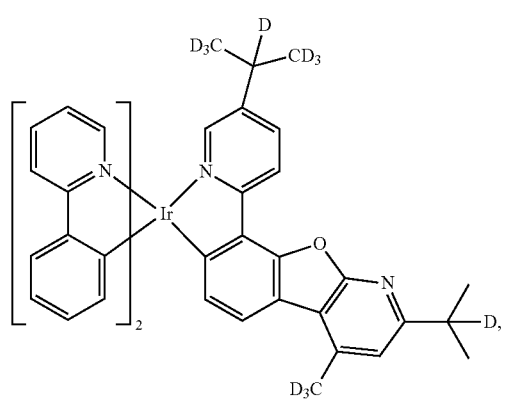 D67
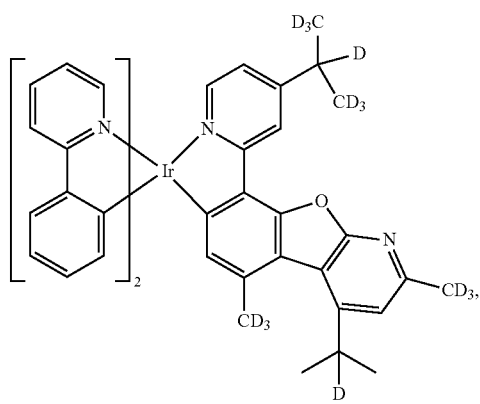 D71
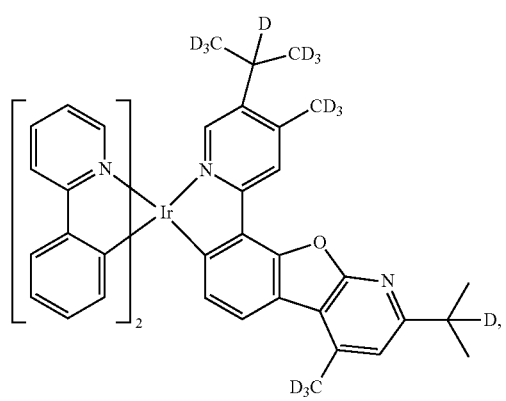 D68
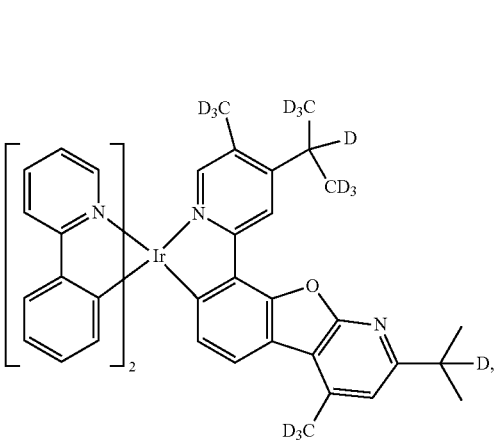 D72

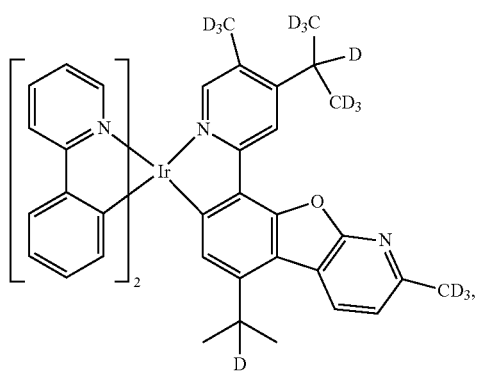
D73
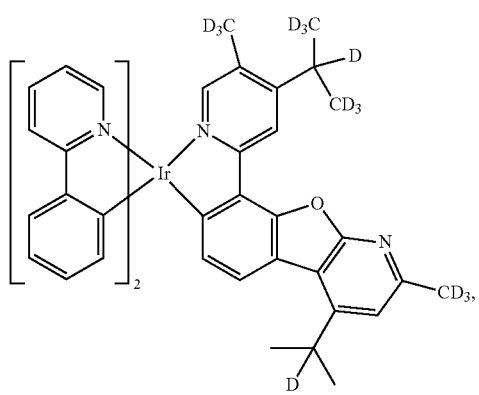
D74
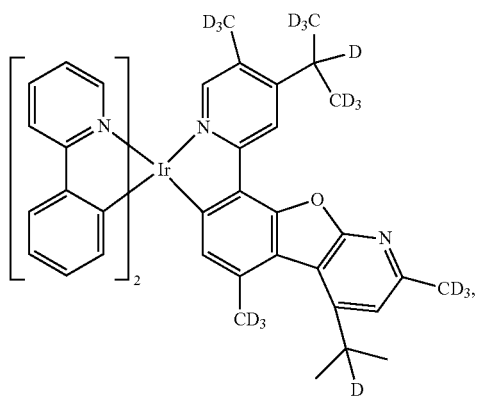
D75
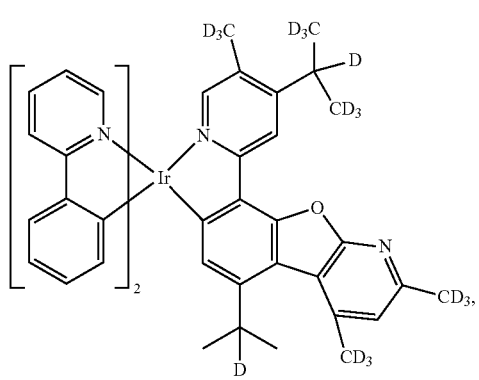
D76

D77
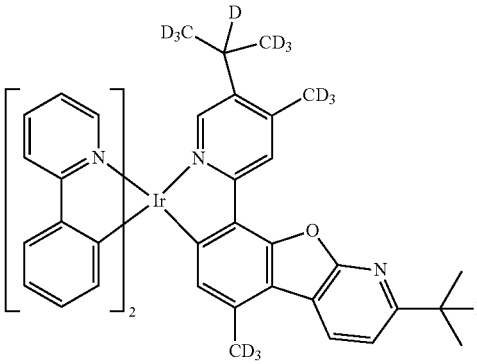
D78
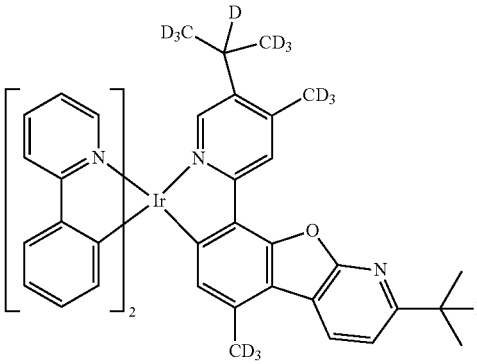
D79
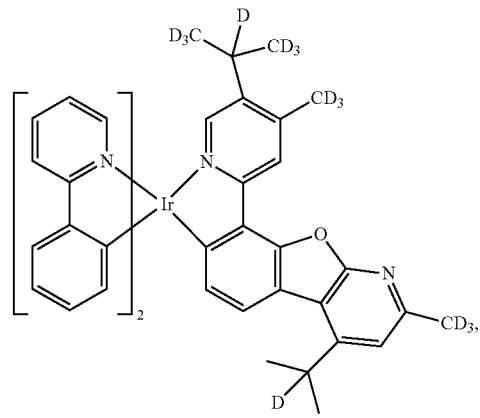
D80

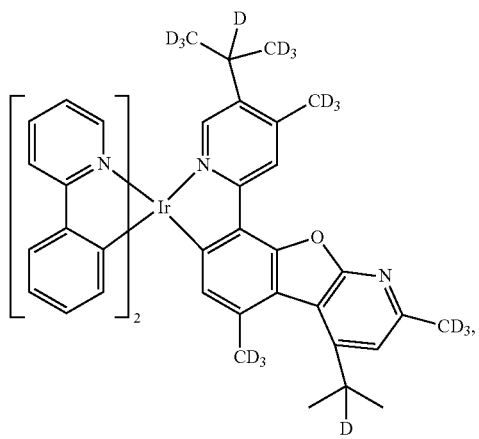
D81
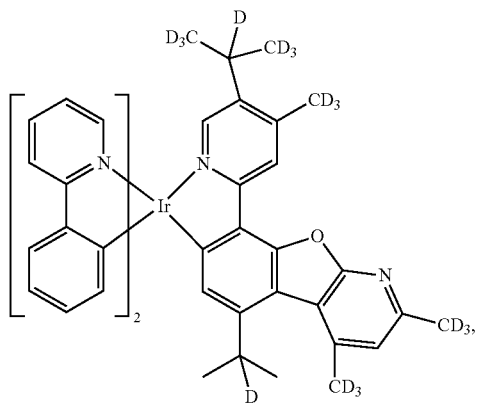
D82
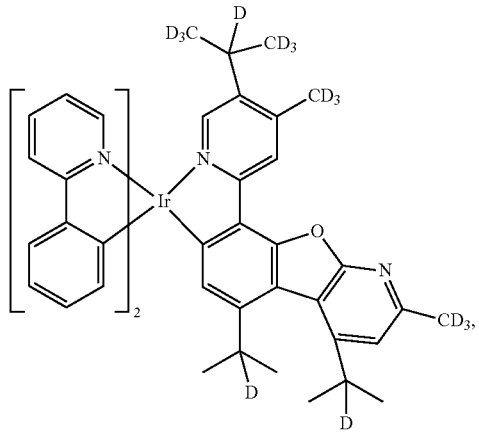
D83
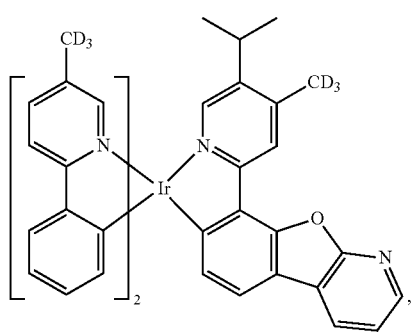
D84
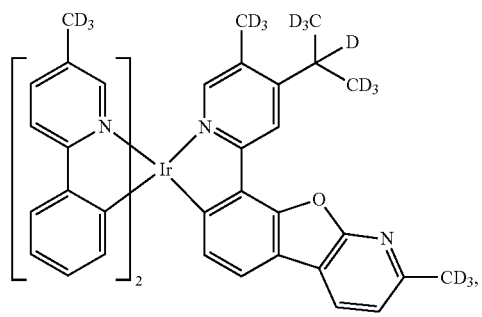
D85
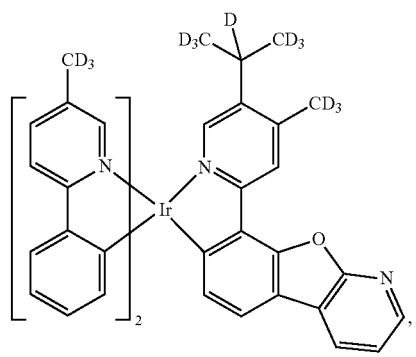
D86
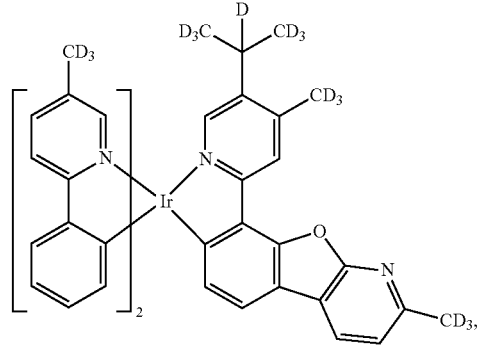
D87
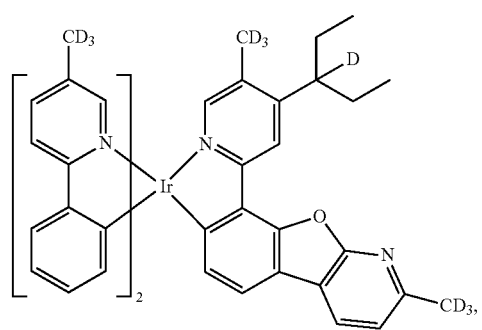
D88

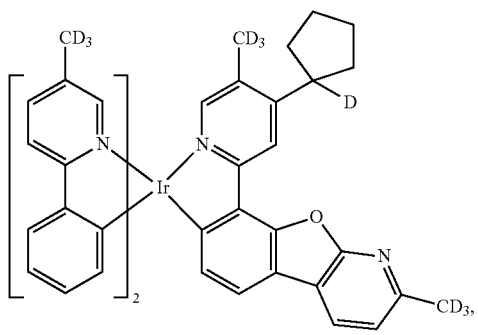
D89
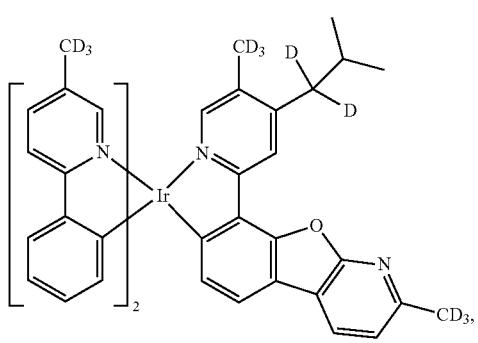
D90
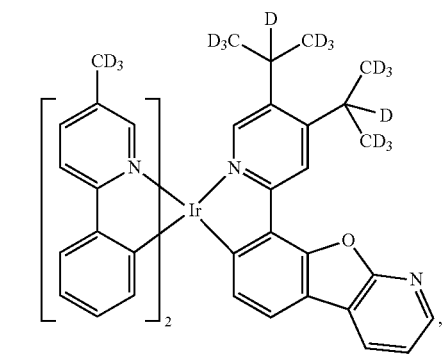
D91
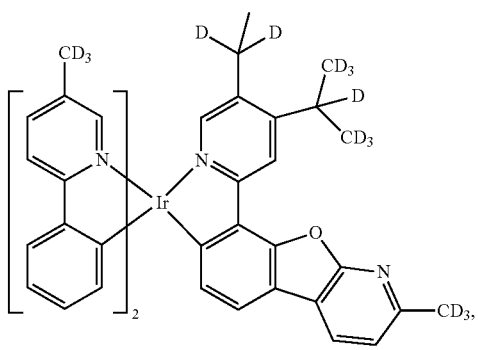
D92
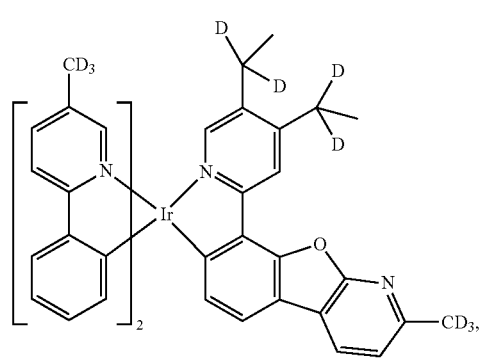
D93
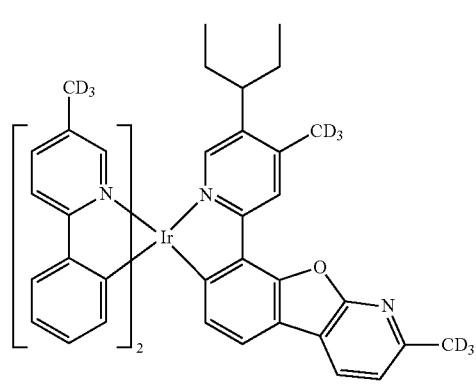
D94
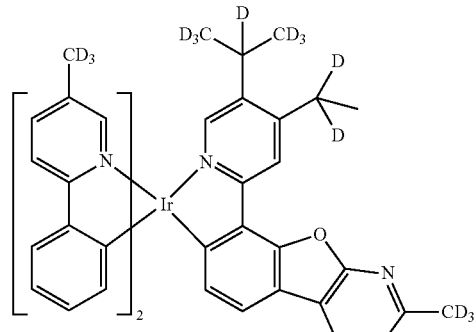
D95
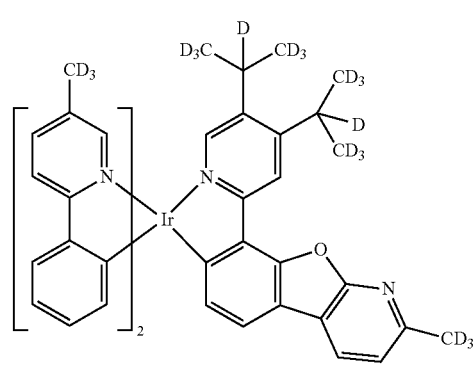
D96

-continued
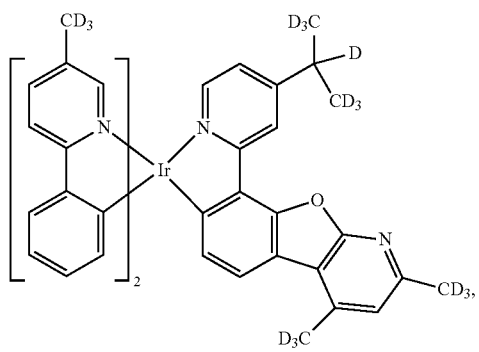
D97
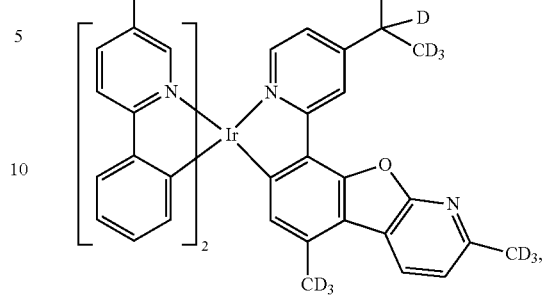
D101
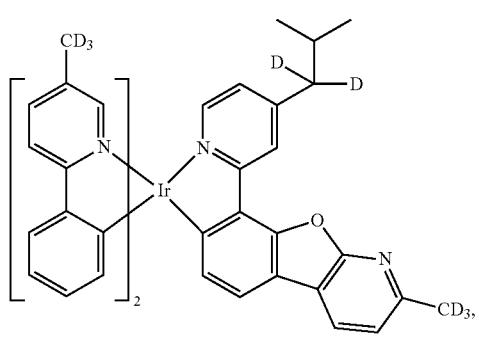
D98
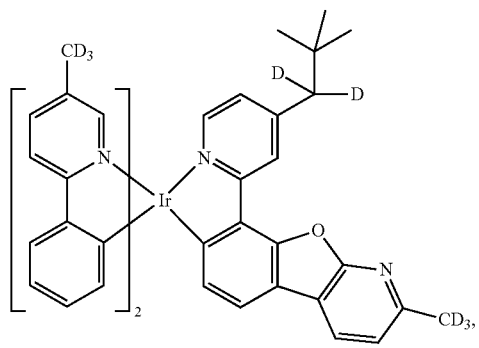
D102
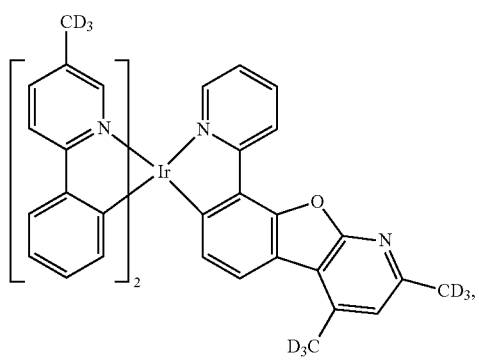
D99
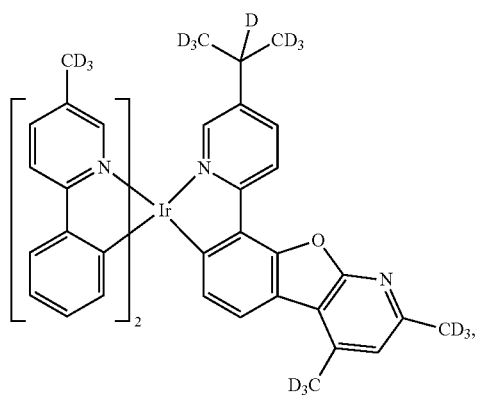
D103
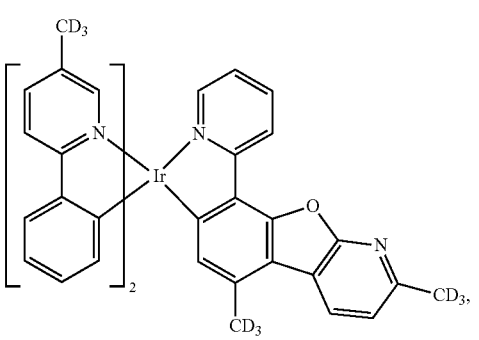
D100
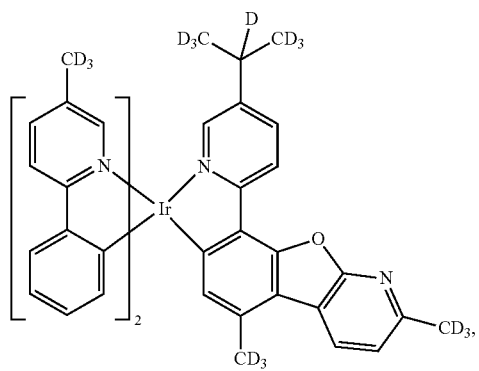
D104

D105 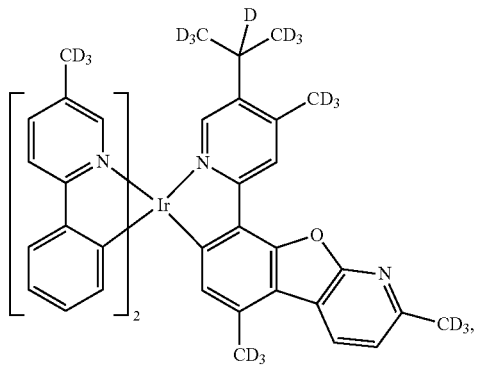
D106 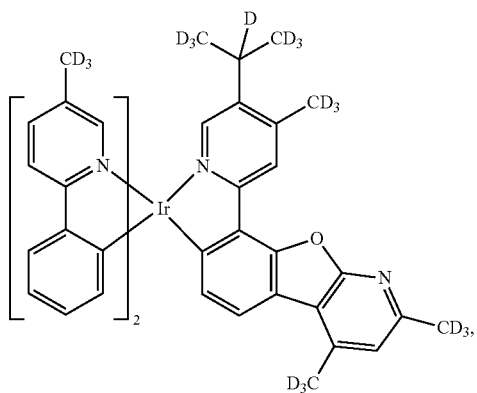
D107 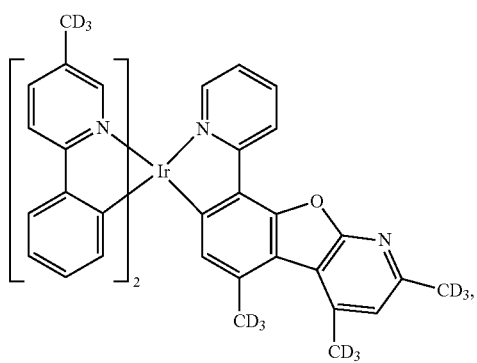
D108 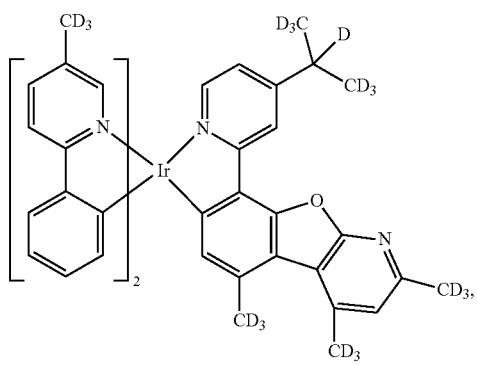
D109 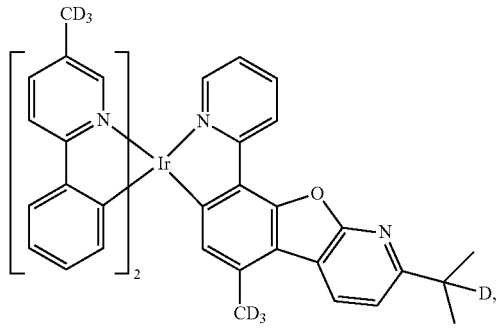
D110 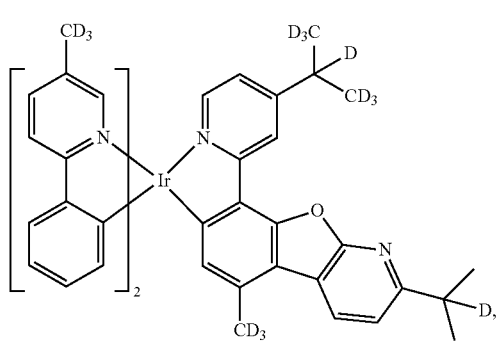
D111 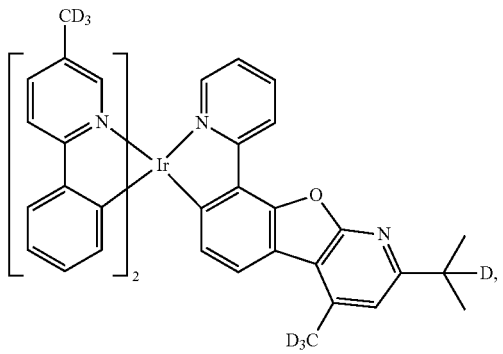
D112 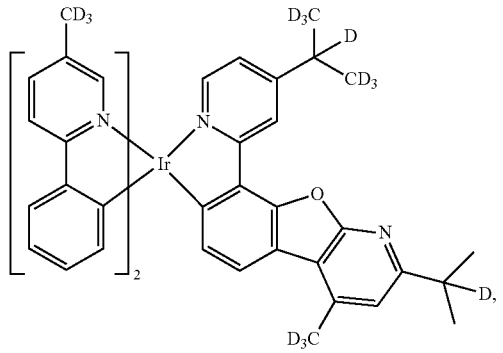

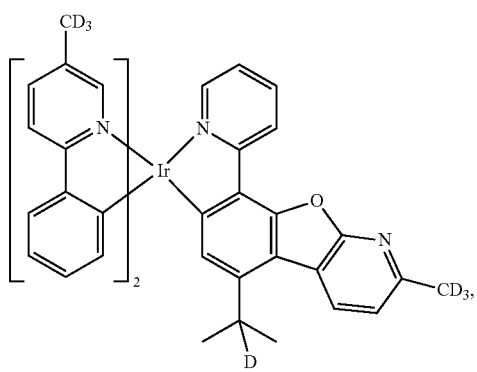
D113
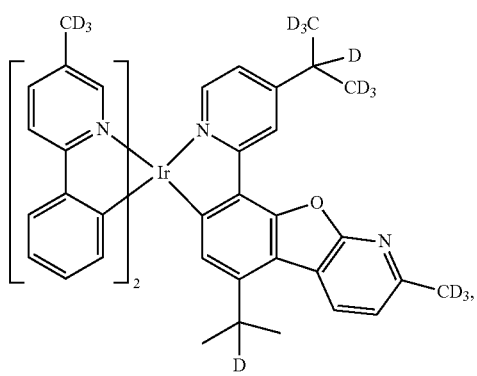
D114
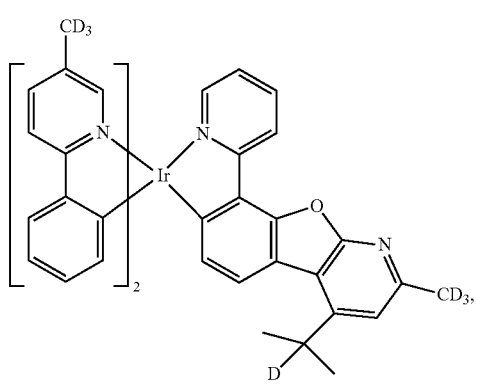
D115
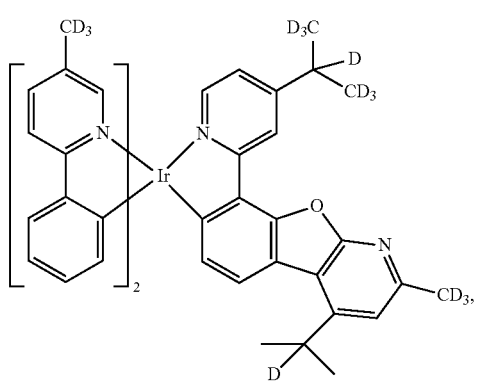
D116
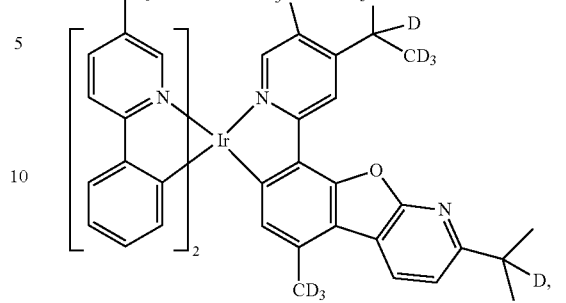
D117
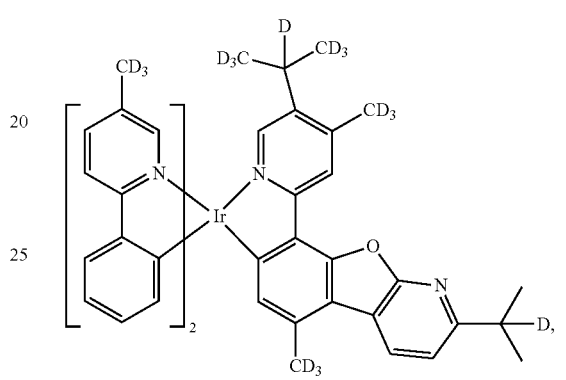
D118
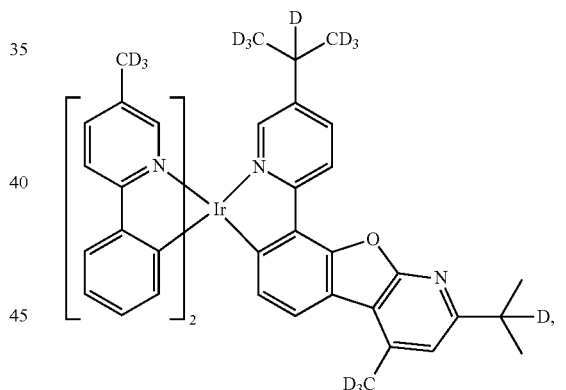
D119
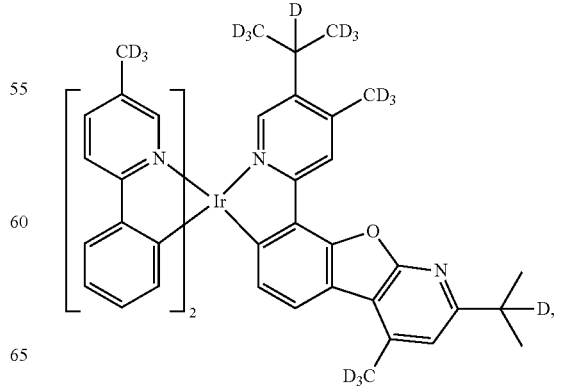
D120

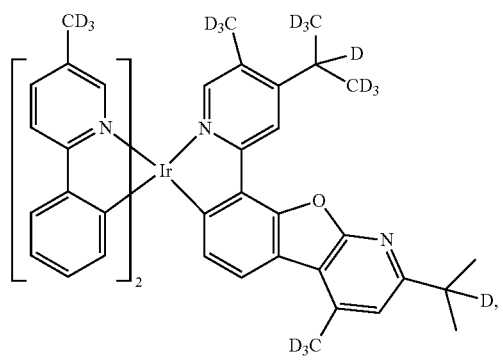
D121
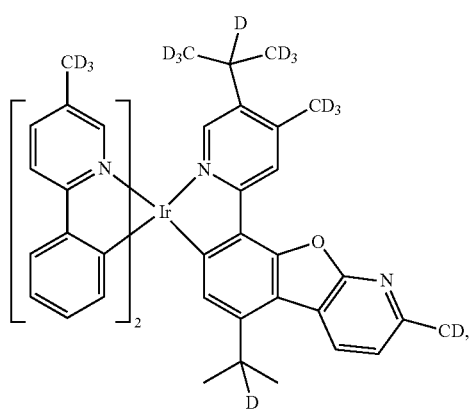
D122
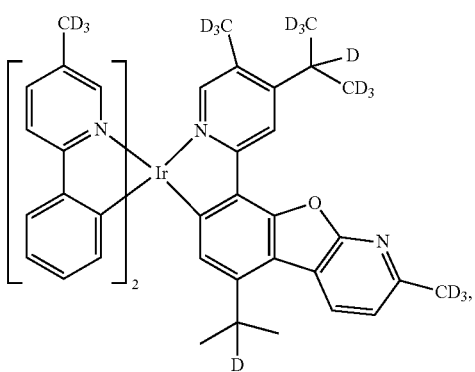
D123
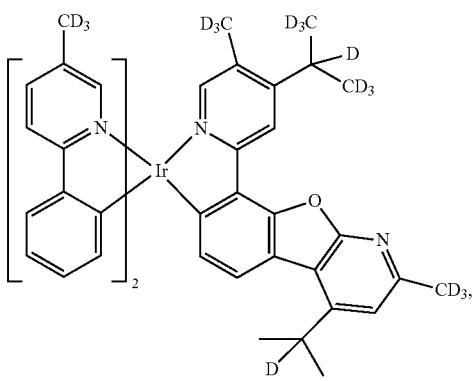
D124
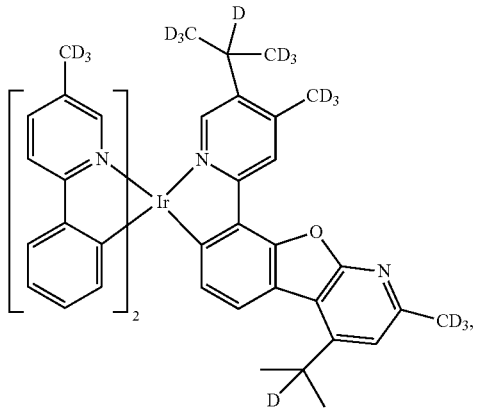
D125
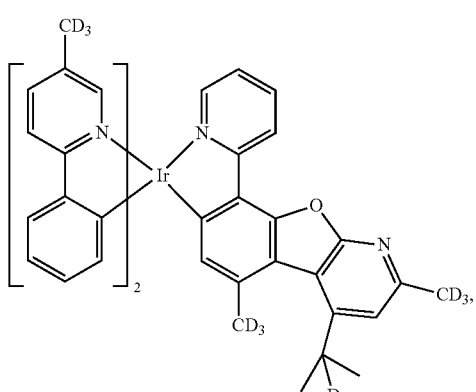
D126
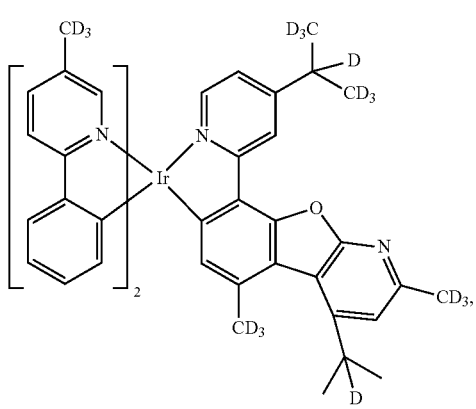
D127
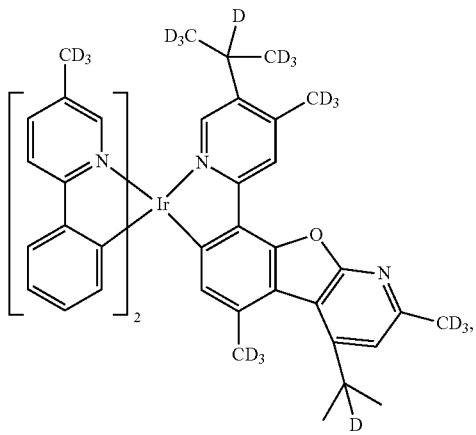
D128

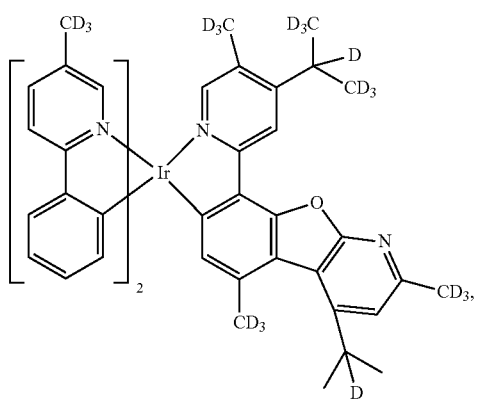
D129
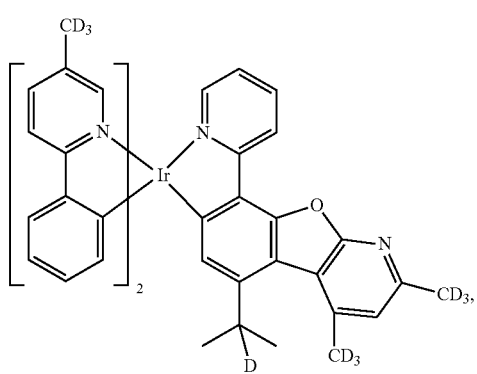
D130
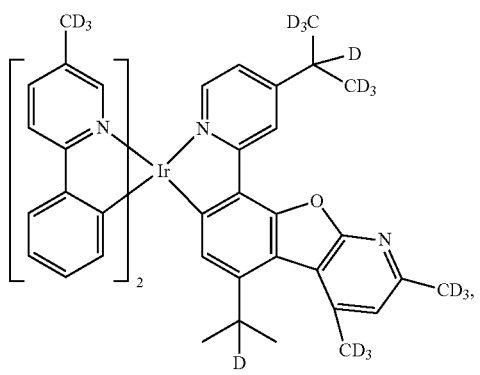
D131
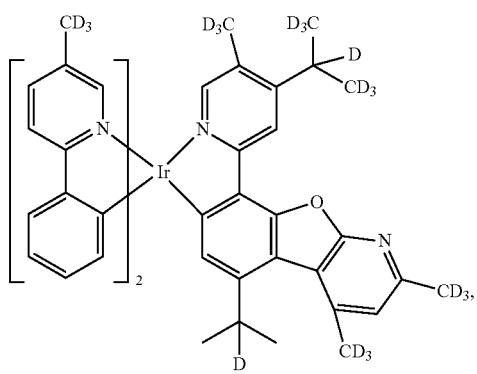
D132
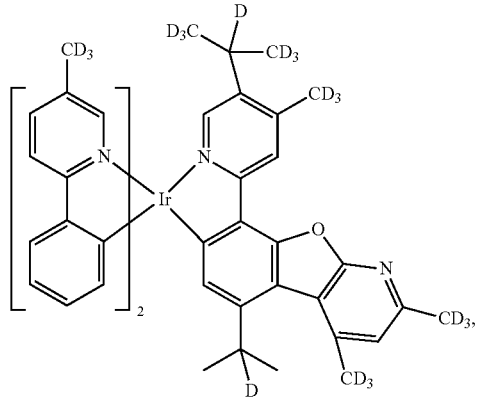
D133
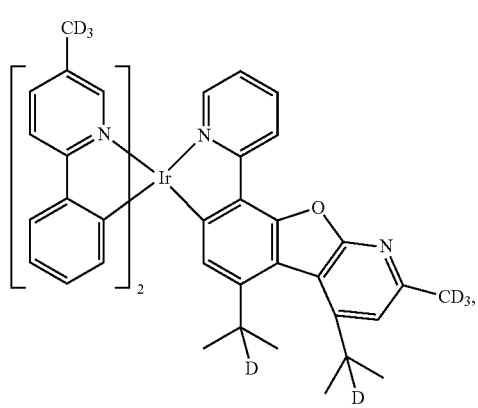
D134
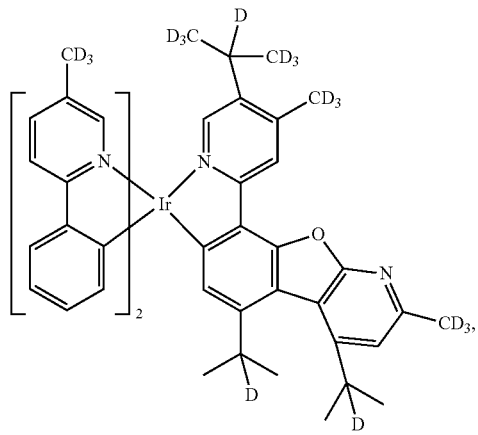
D135
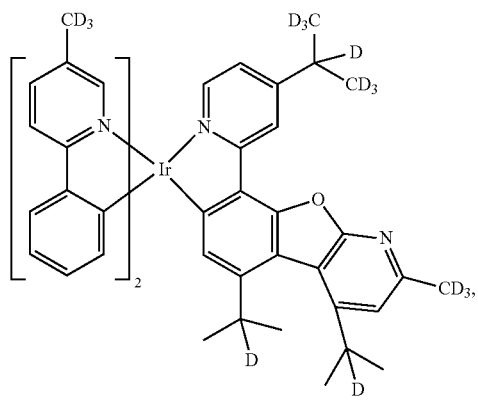
D136

D137
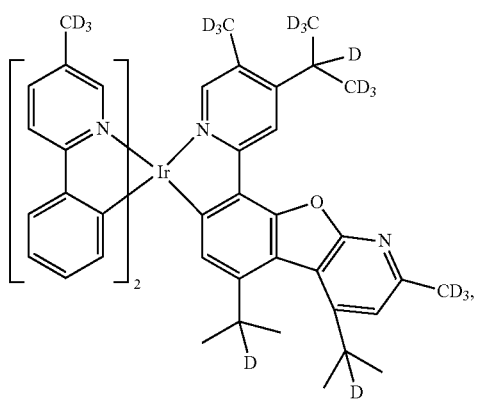
D138
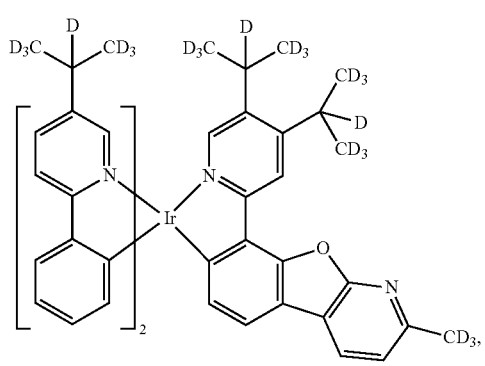
D139
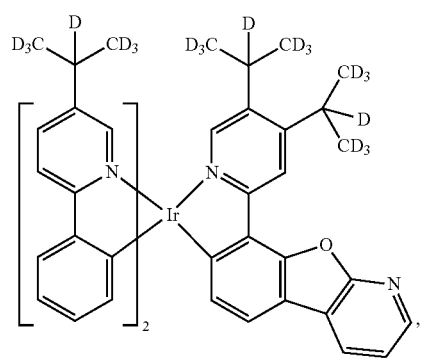
D140
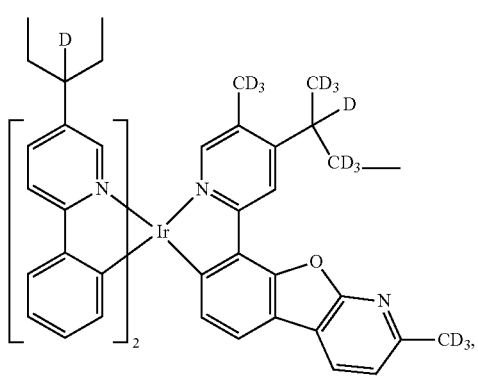
D141
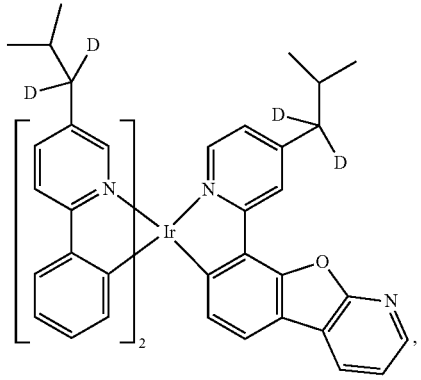
D142
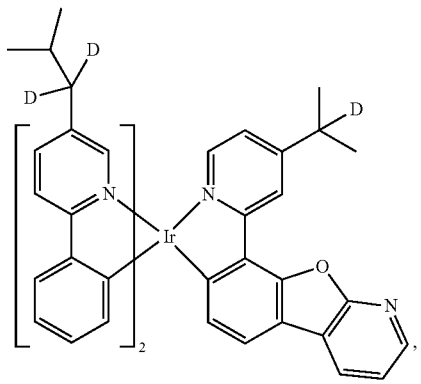
D143
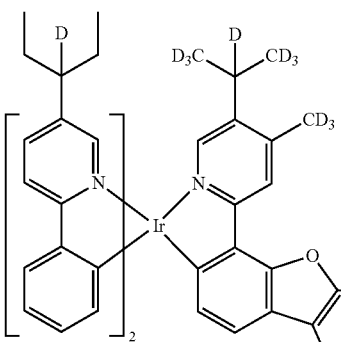
D144
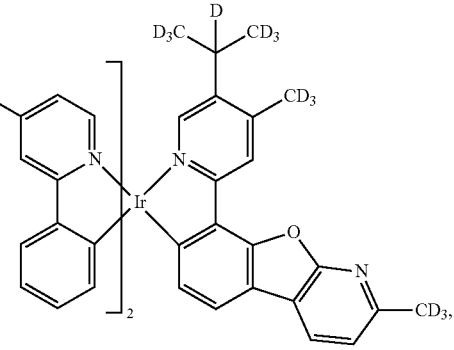

-continued
D145
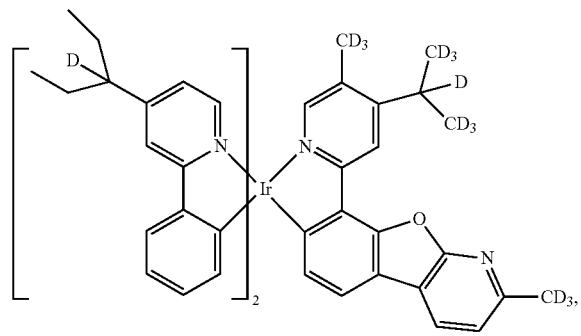
D146
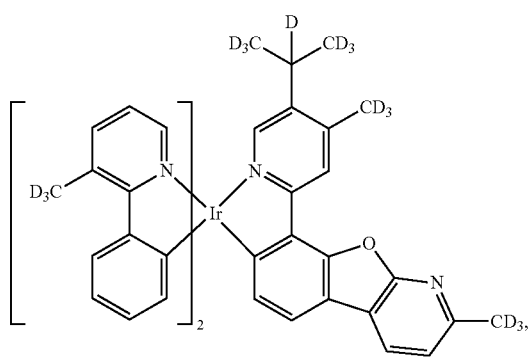
D147
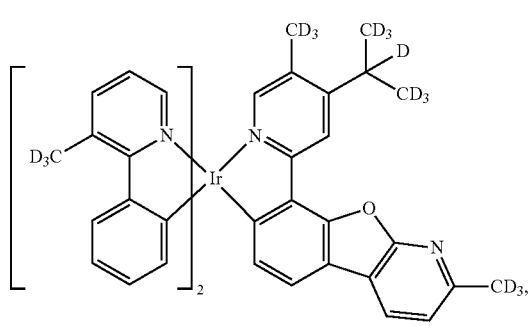
D148
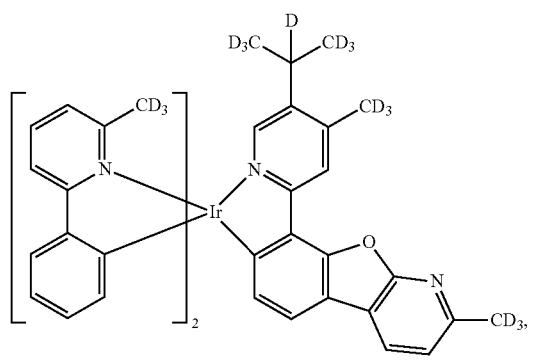
D149
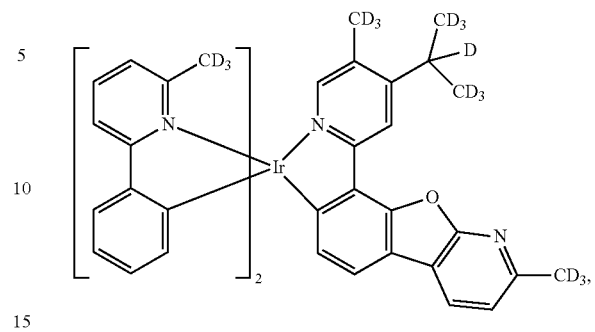
D150
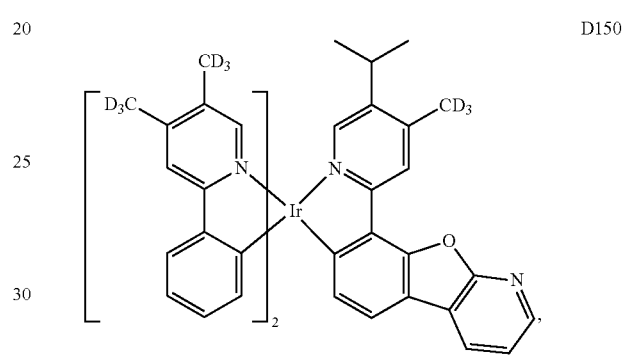
D151
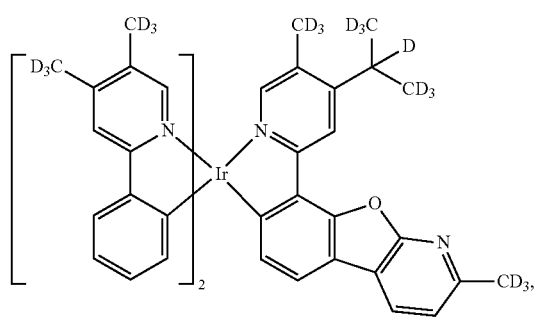
D152
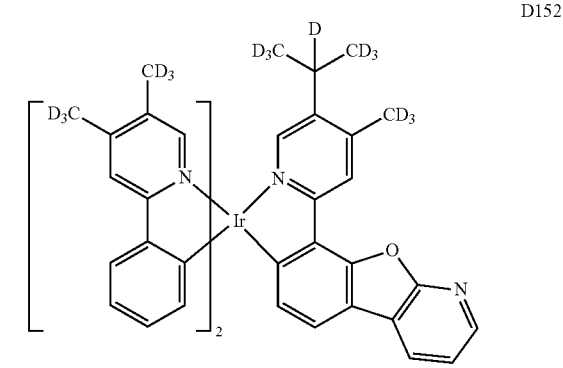

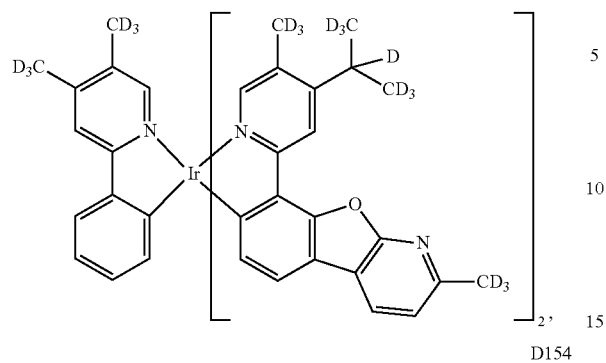
D153
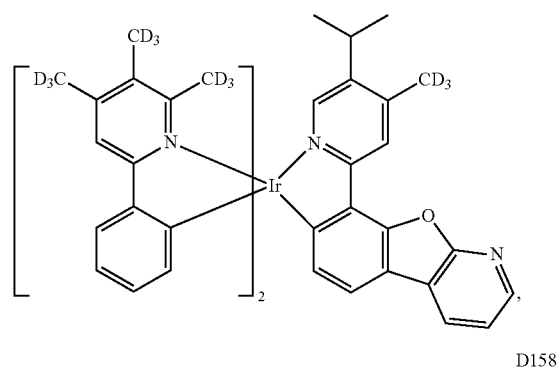
D157
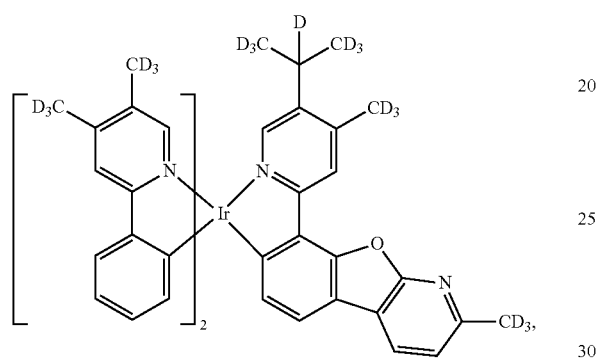
D154
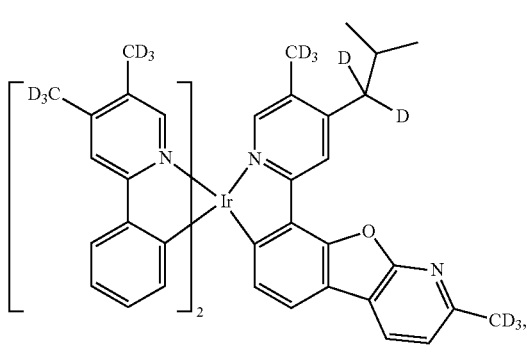
D158
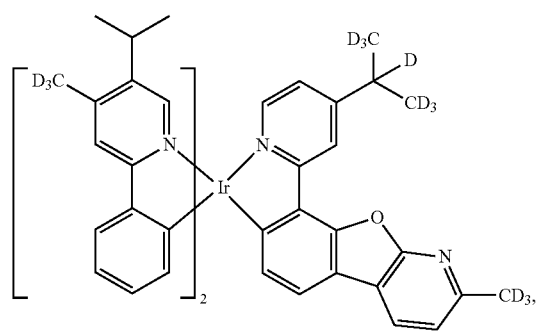
D155
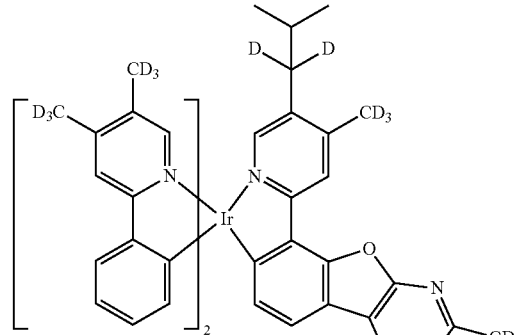
D159
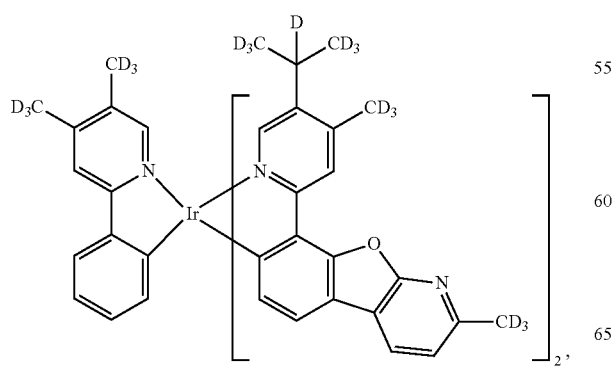
D156
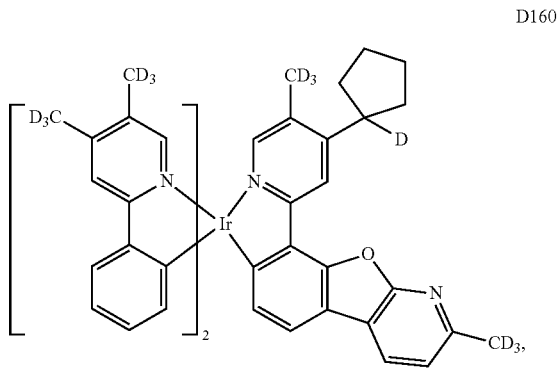
D160

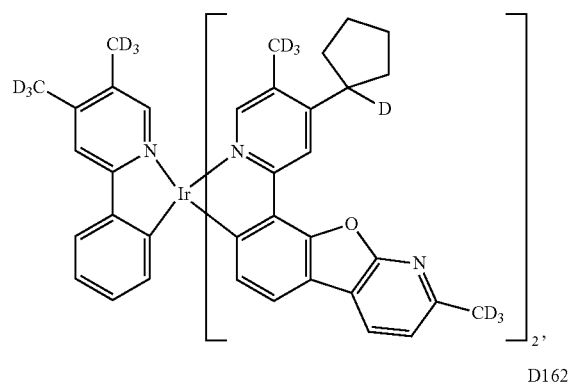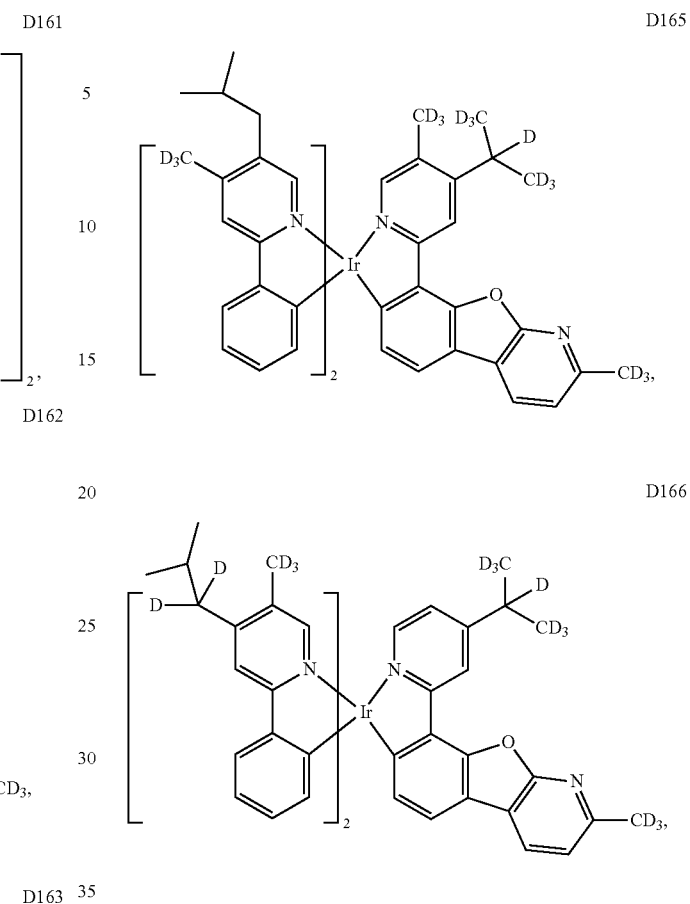

D169, D170, D171, D172, D173, D174, D175, D176

D177
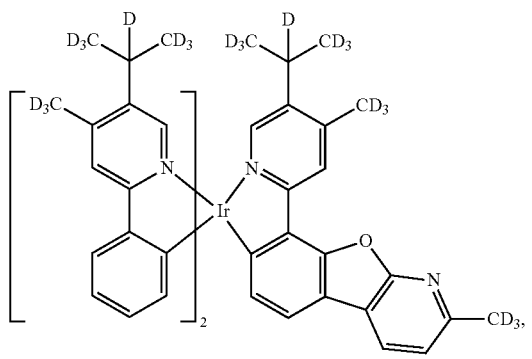
D178
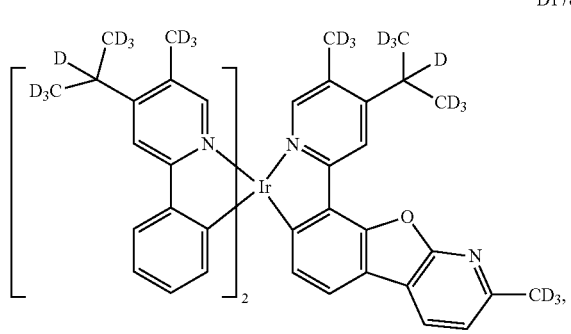
D179
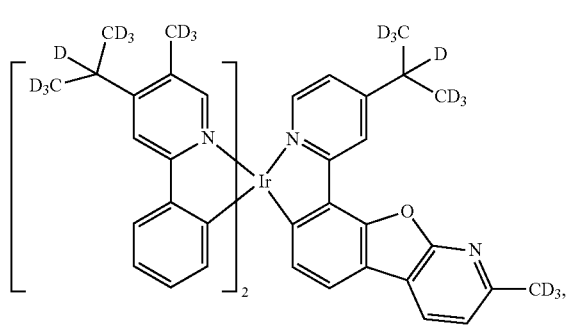
D180
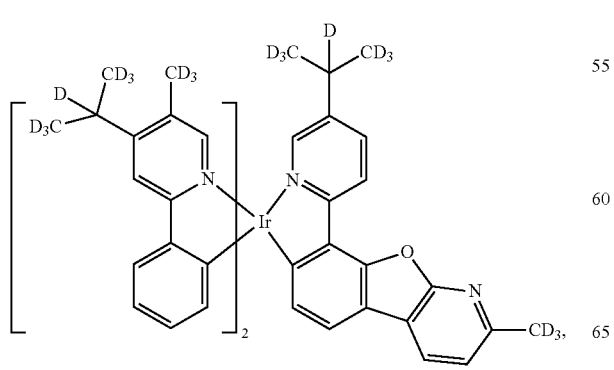
D181
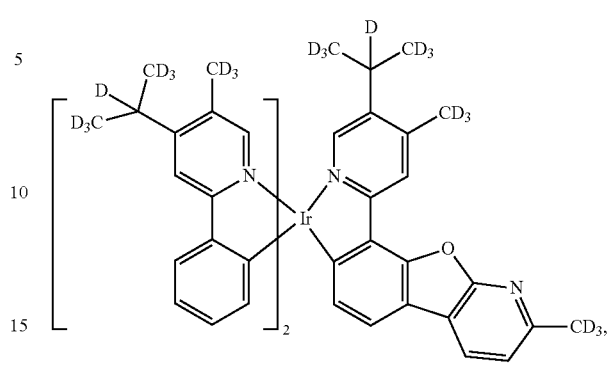
D182
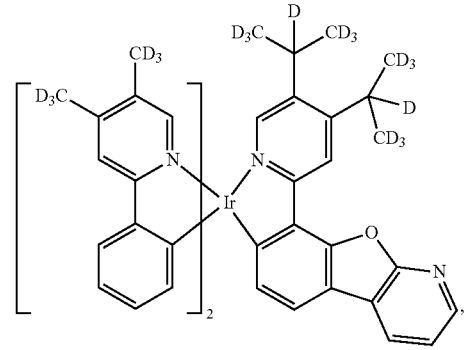
D183
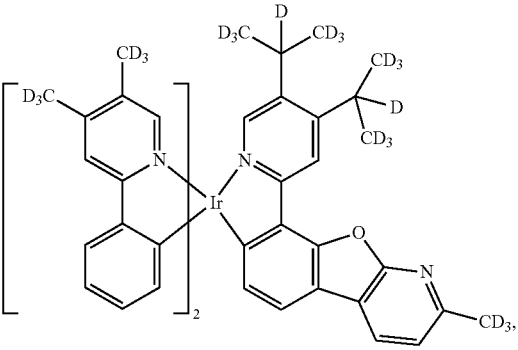
D184
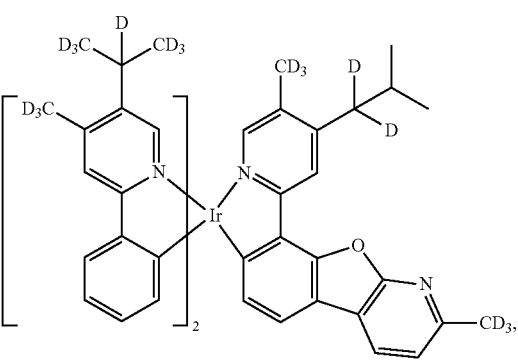

D185
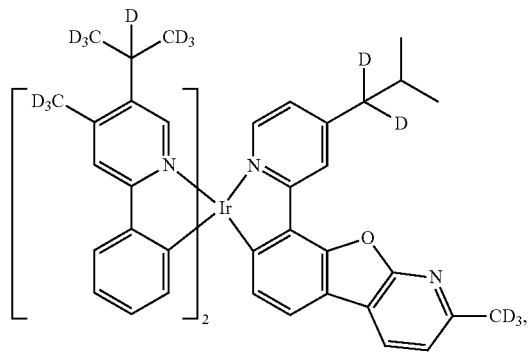
D186
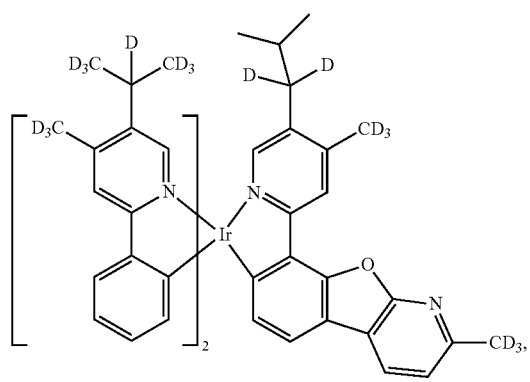
D187
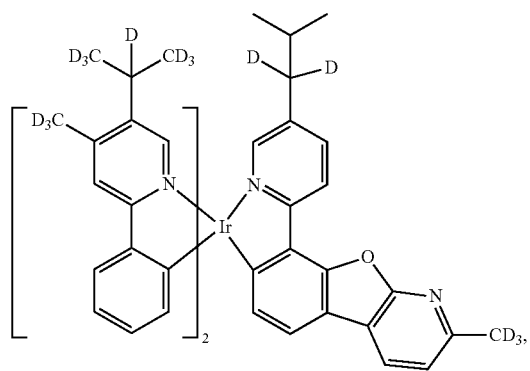
D188
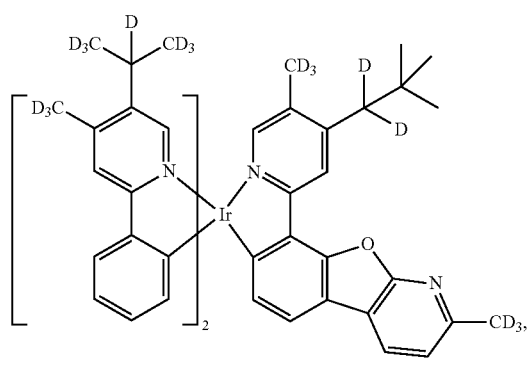
D189
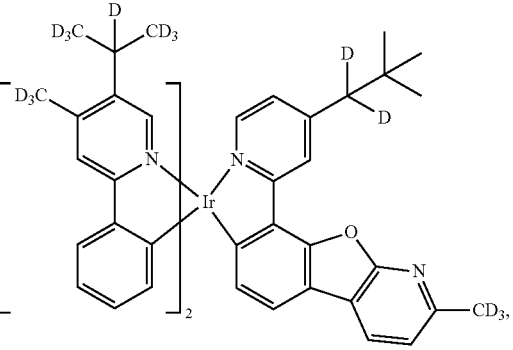
D190
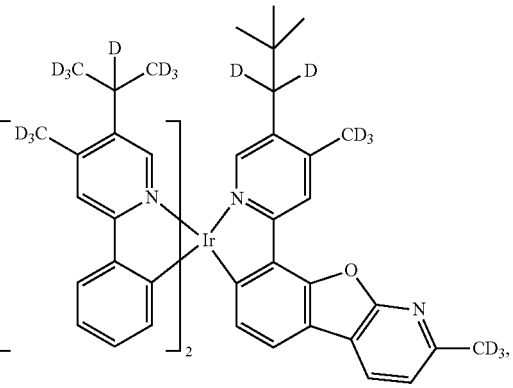
D191
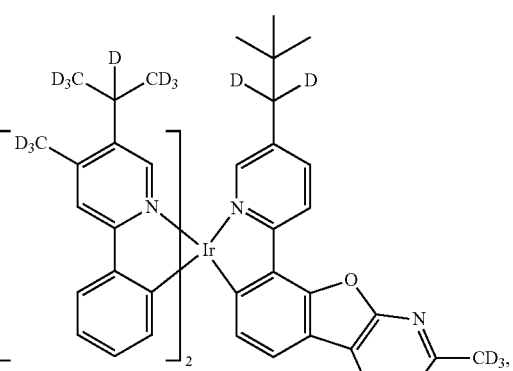
D192
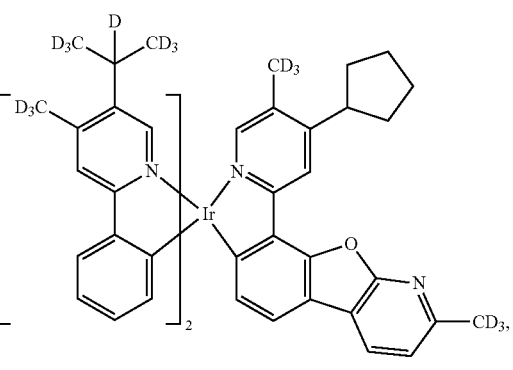

-continued
D193
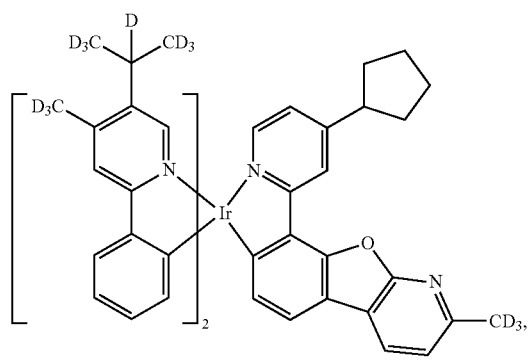
D194
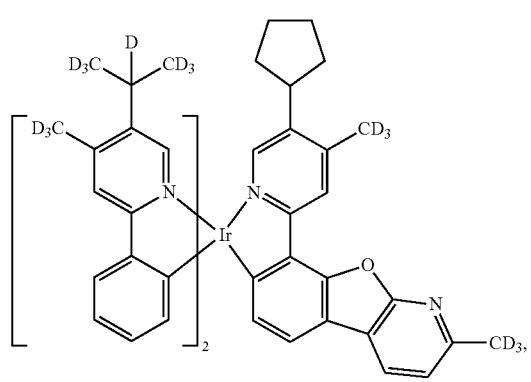
D195
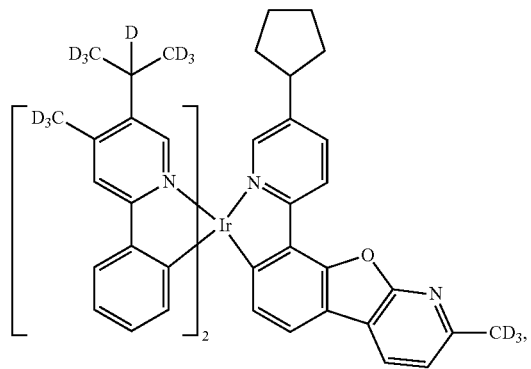
D196
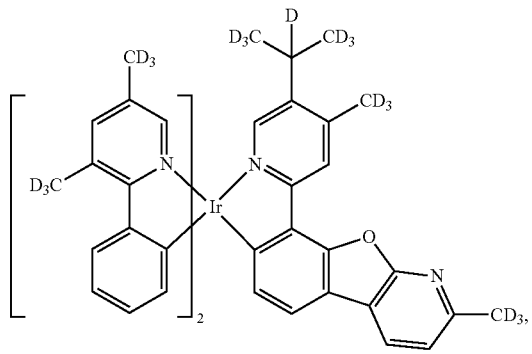
-continued
D197
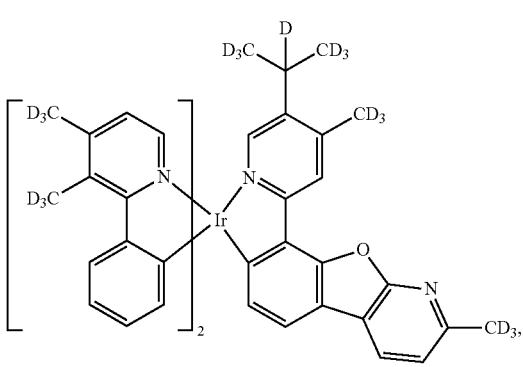
D198
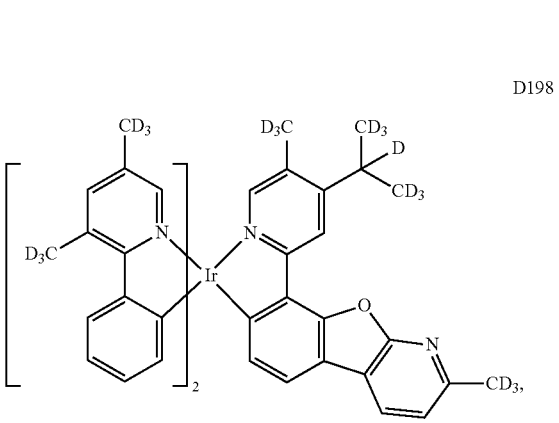
D199
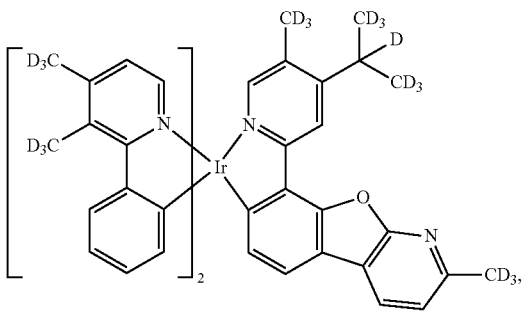
D200
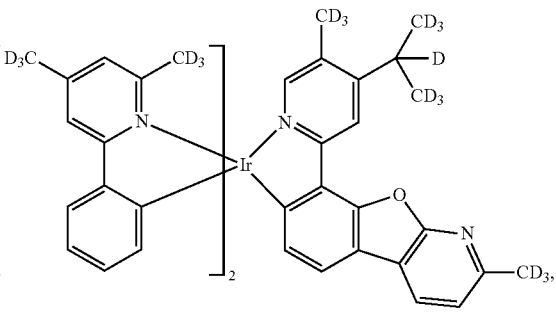

D201
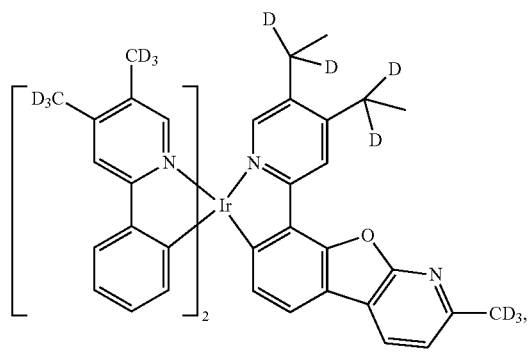
D202
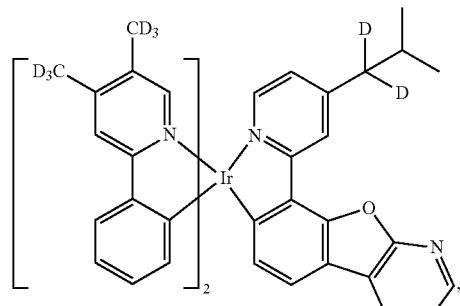
D203
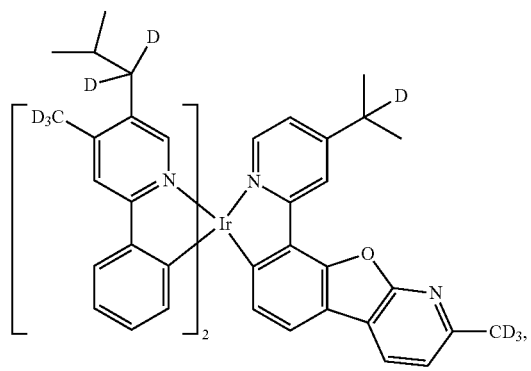
D204
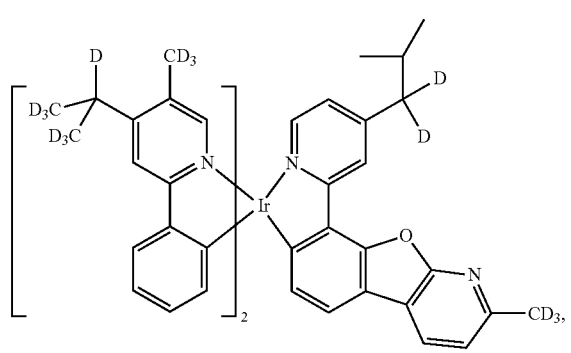
D205
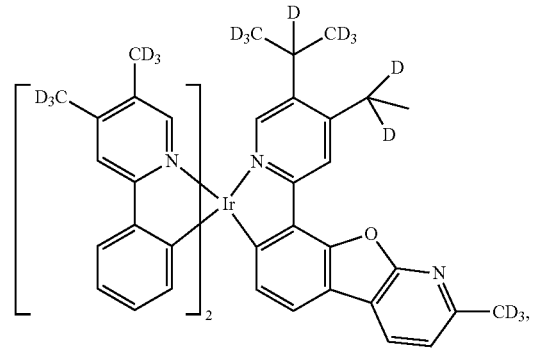
D206
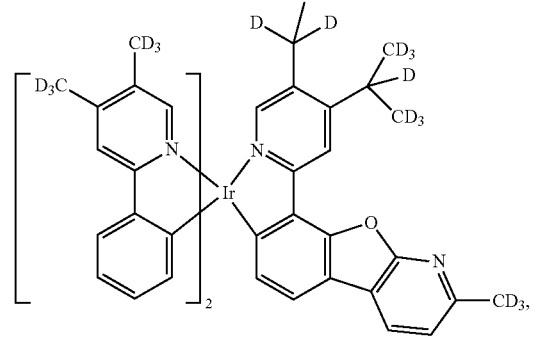
D207
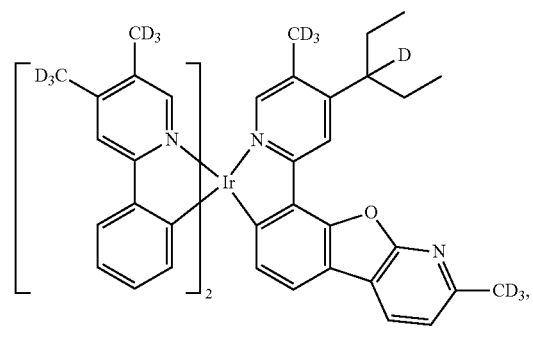
D208
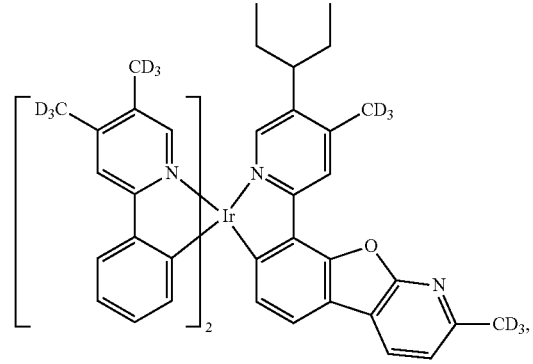

D209
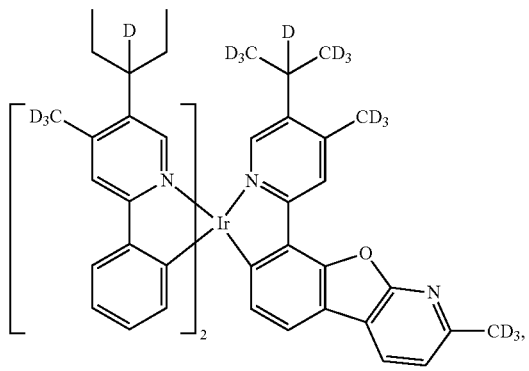
D210
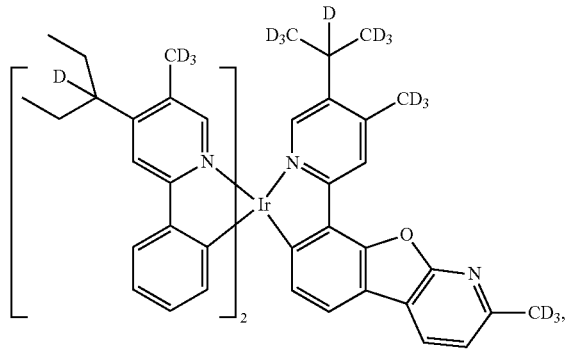
D211
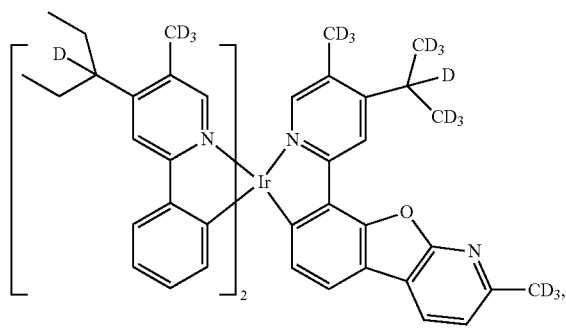
D212
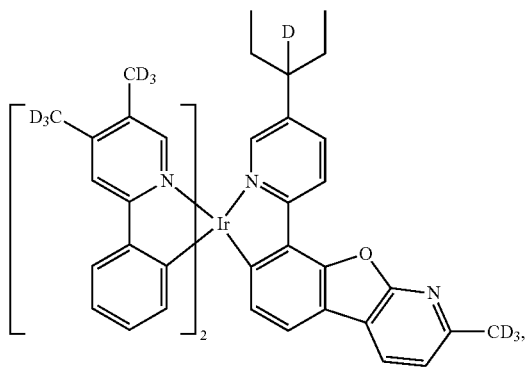
D213
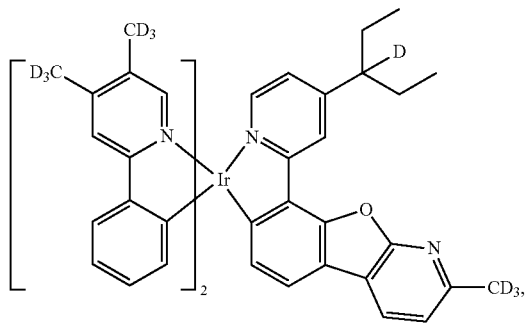
D214
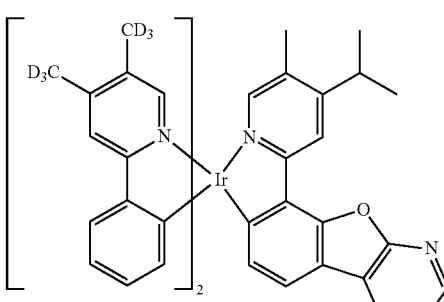
D215
D216
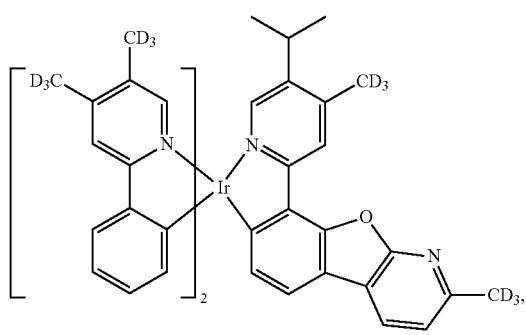

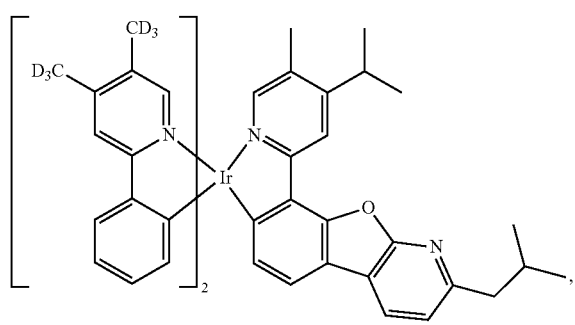
D217
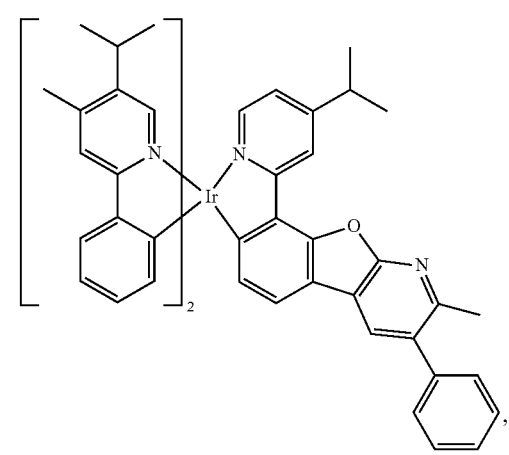
D221
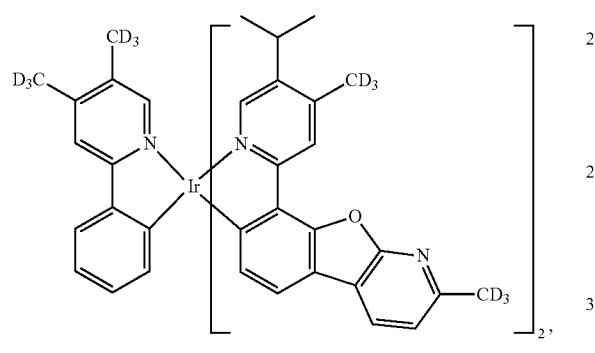
D218
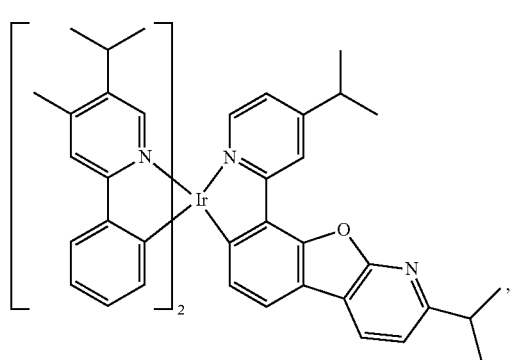
D222
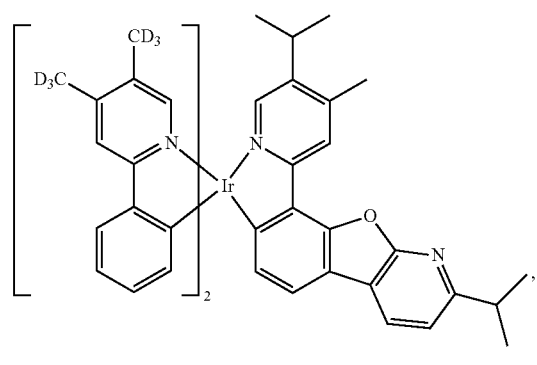
D219
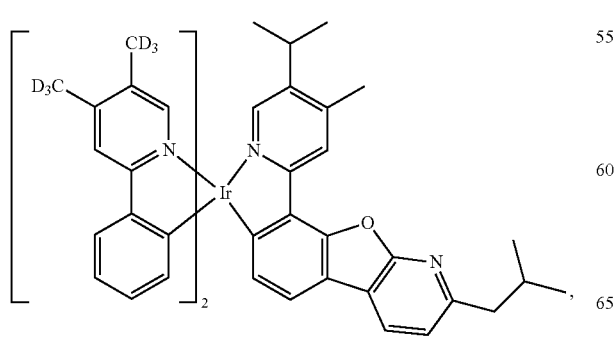
D220
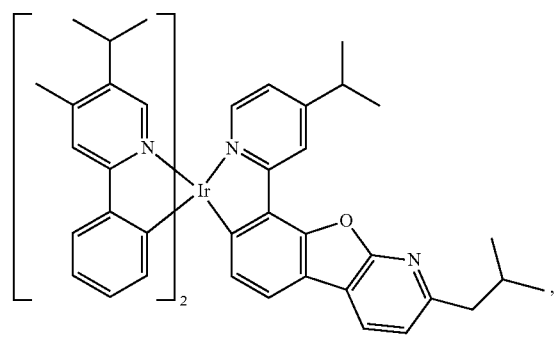
D223
D224

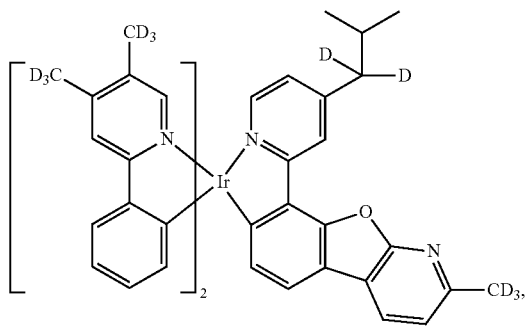
D225
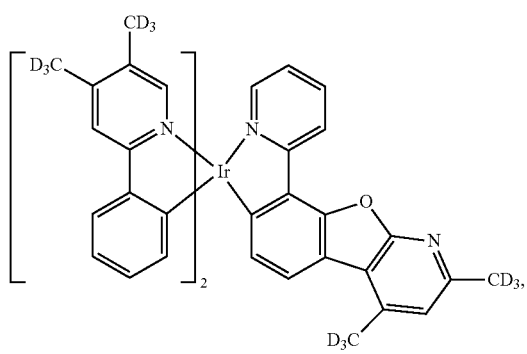
D229
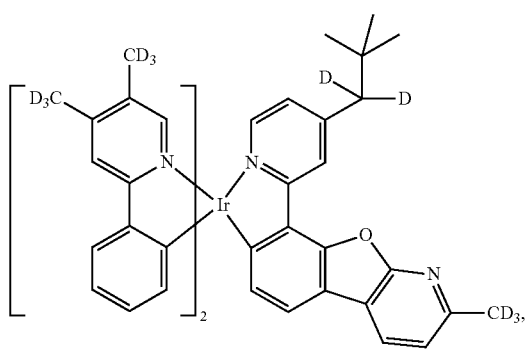
D226
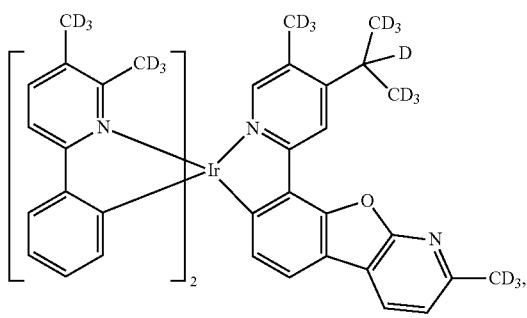
D230
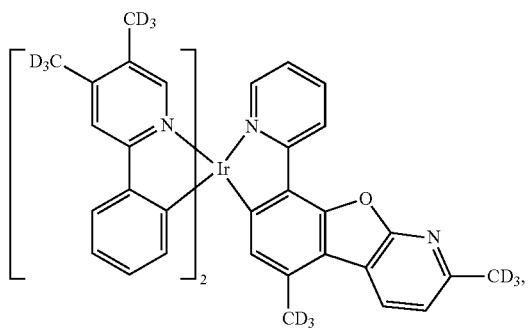
D227
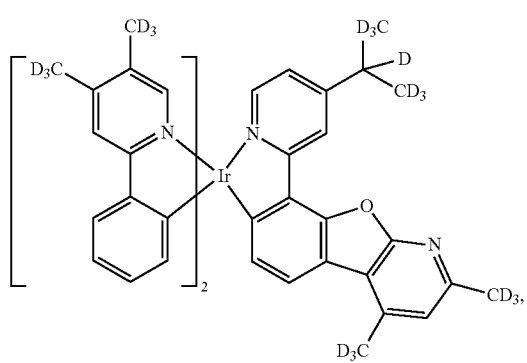
D231
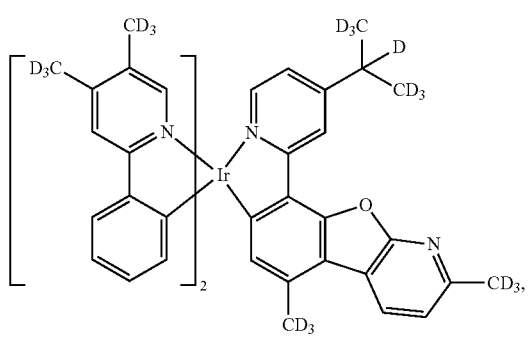
D228
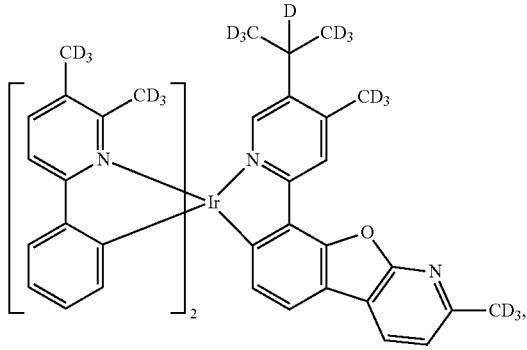
D232

D233 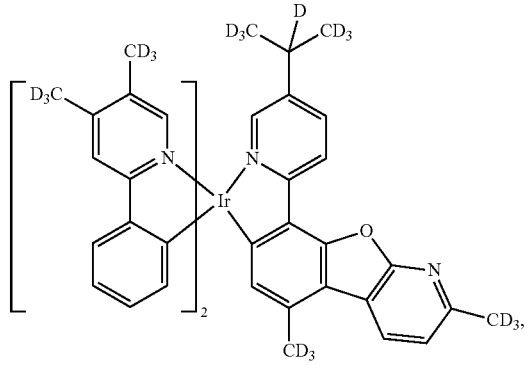
D234 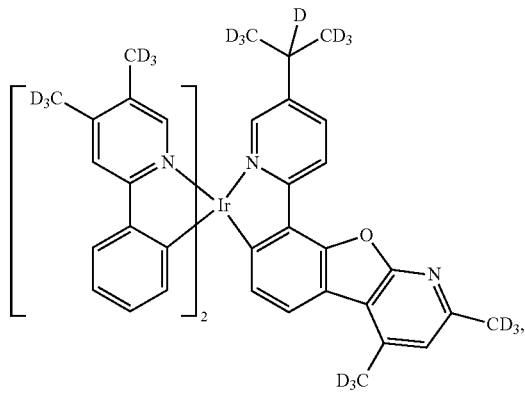
D235 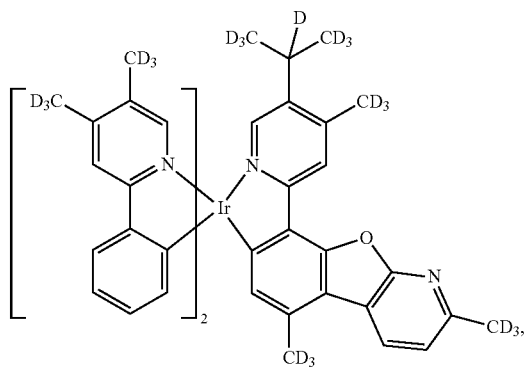
D236 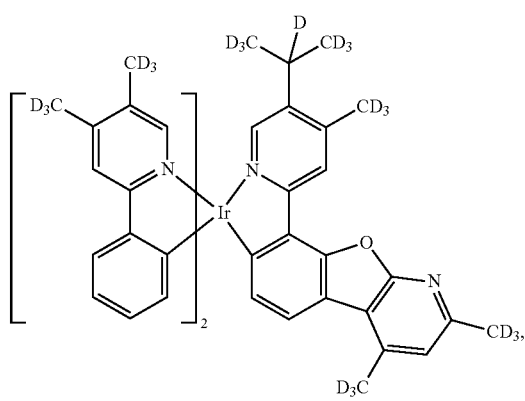
D237 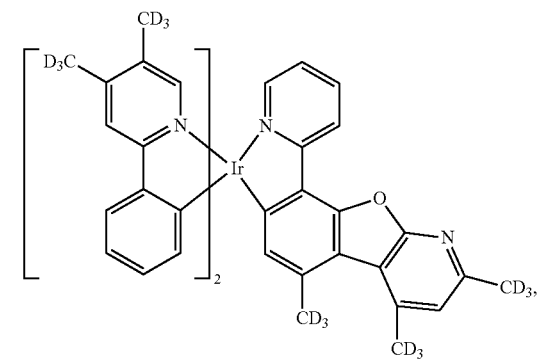
D238 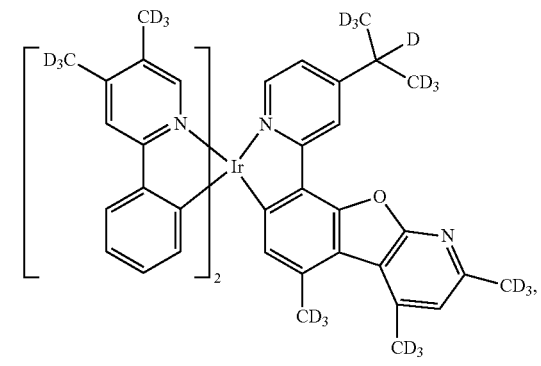
D239 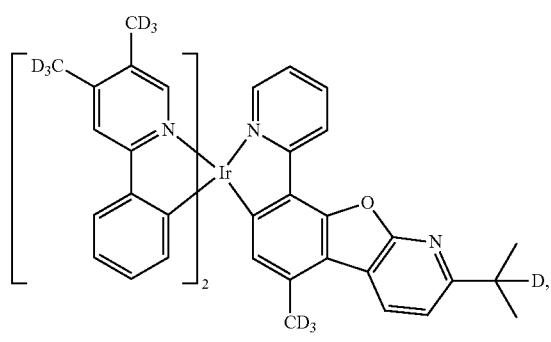
D240 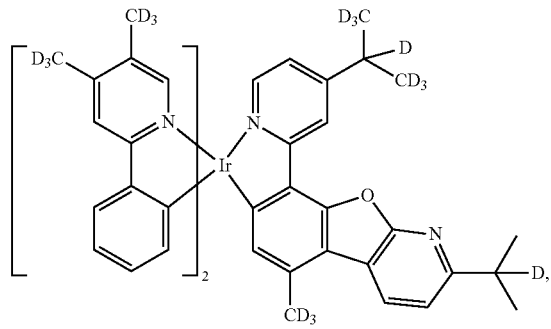

D241
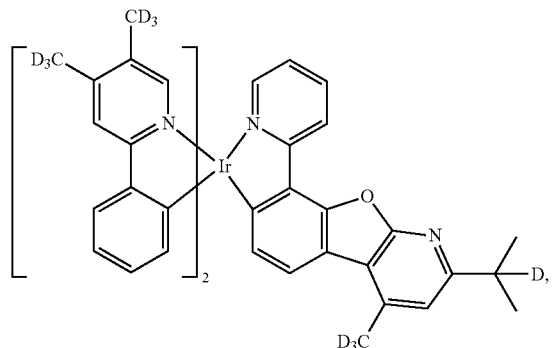
D242
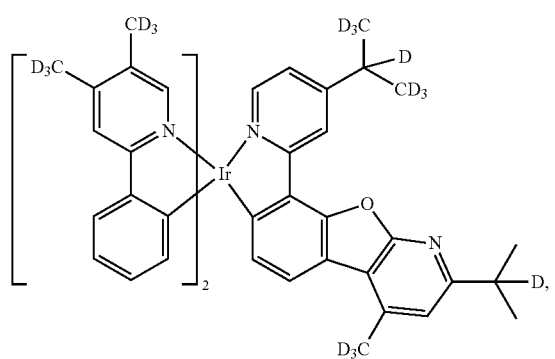
D243
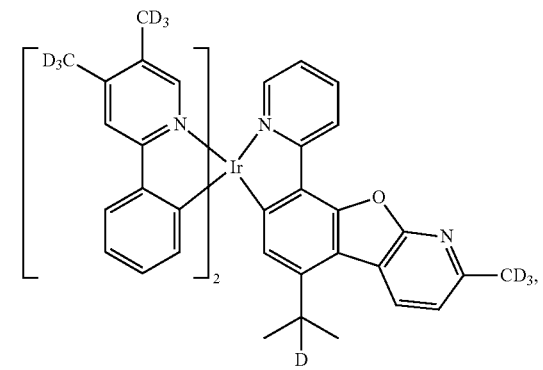
D244
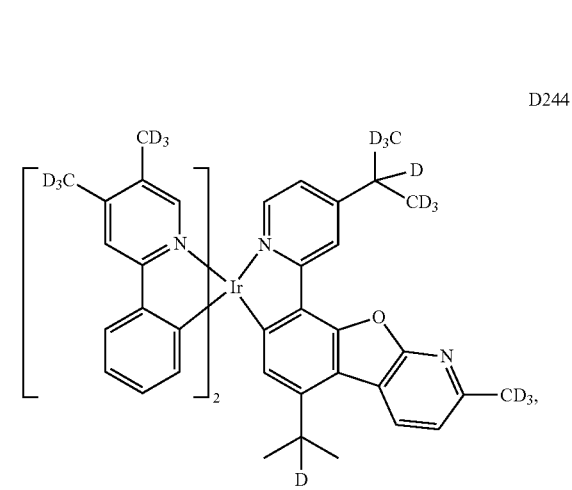
D245
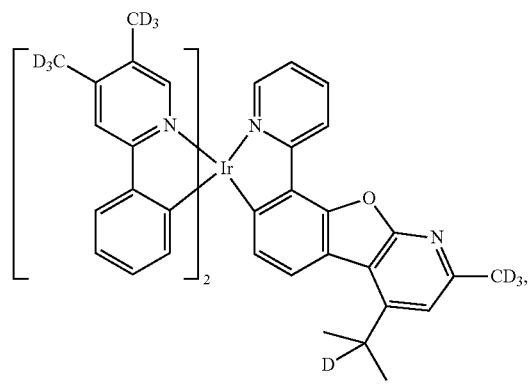
D246
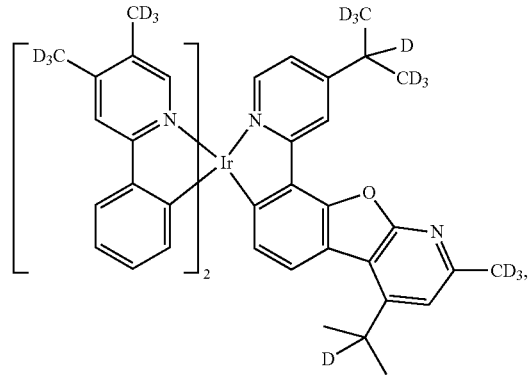
D247
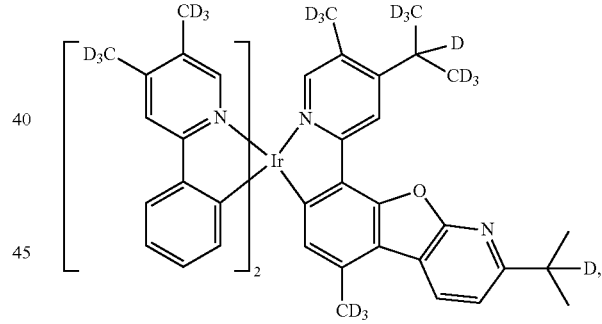
D248
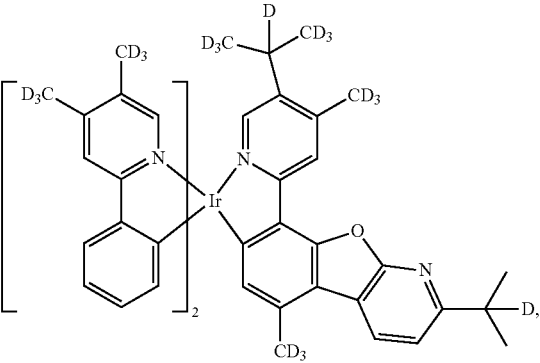

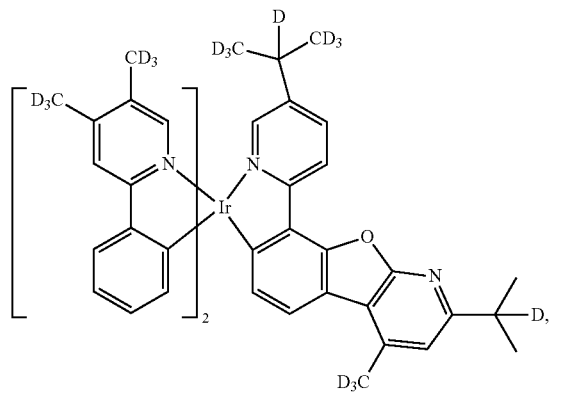
D249
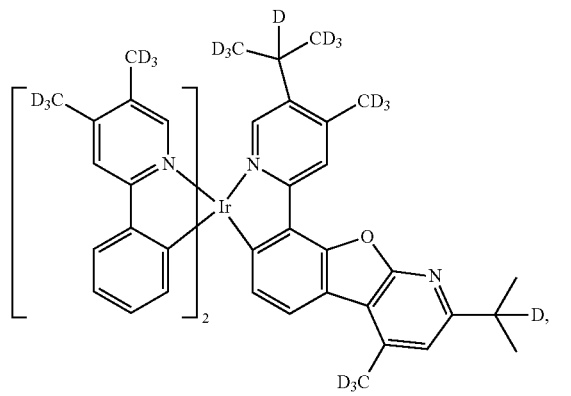
D250
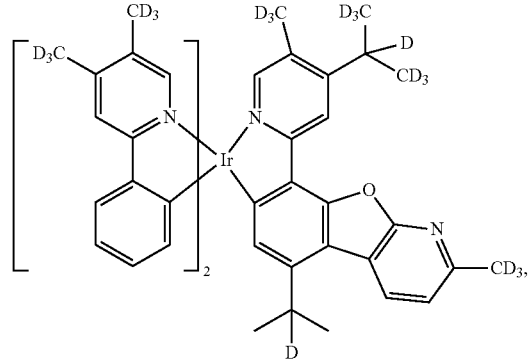
D253
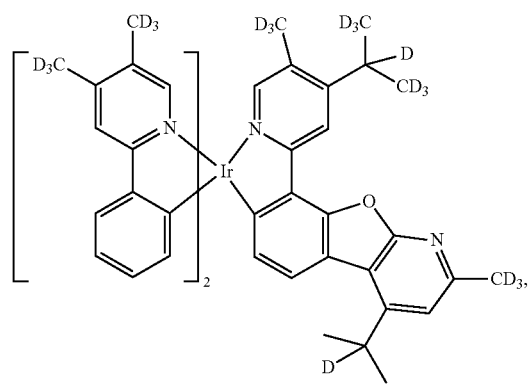
D254
D251
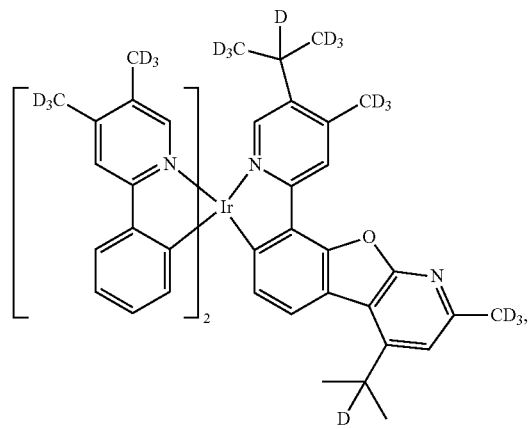
D255
D252
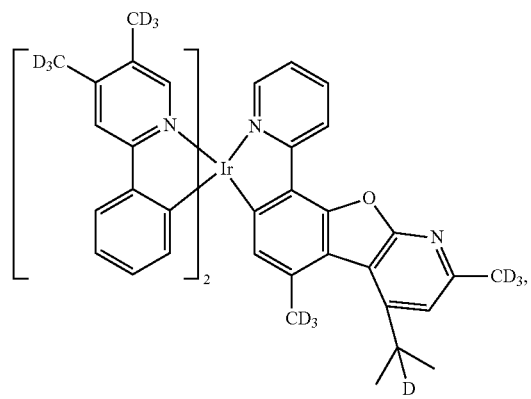
D256

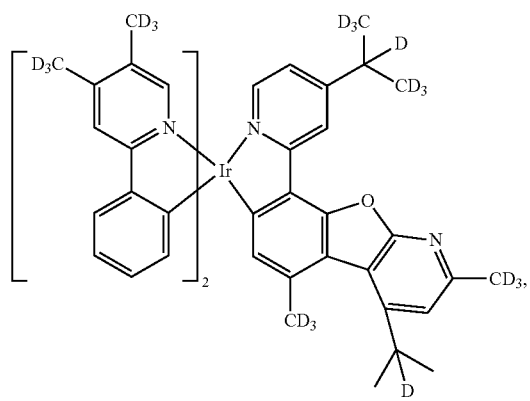
D257
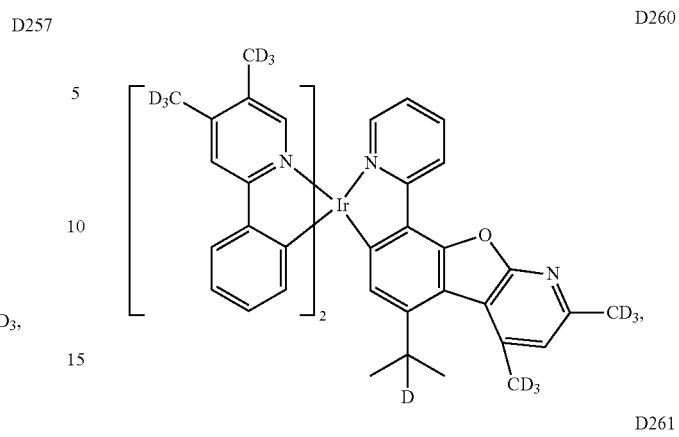
D260
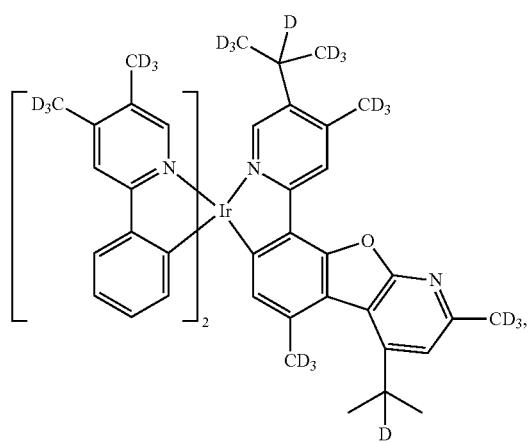
D258
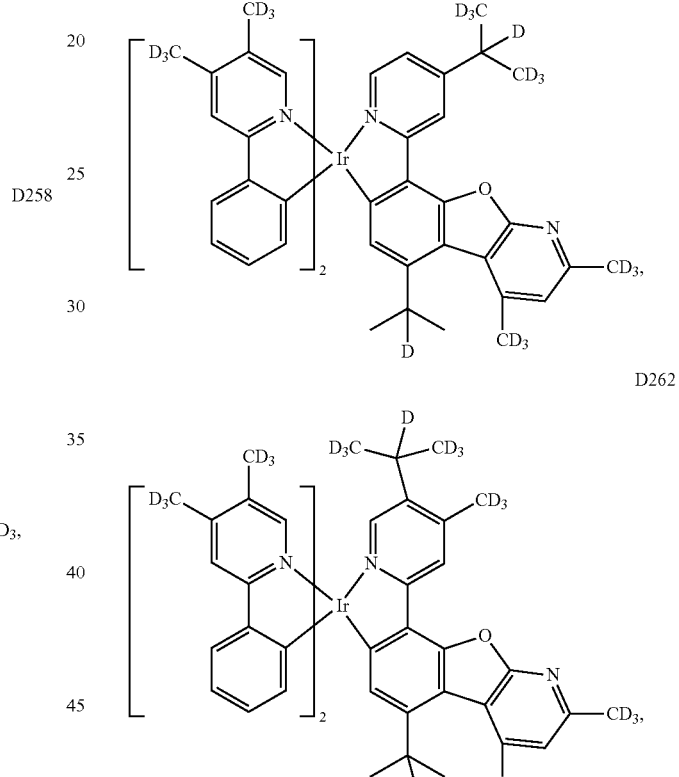
D261
D262
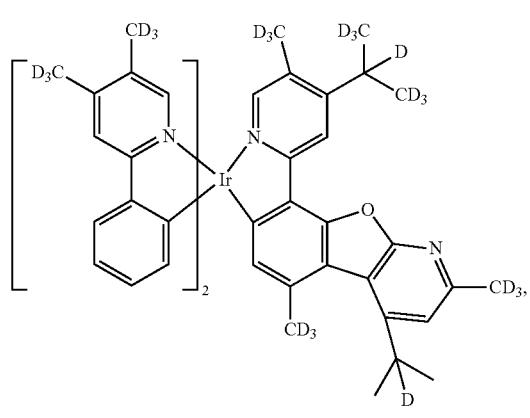
D259
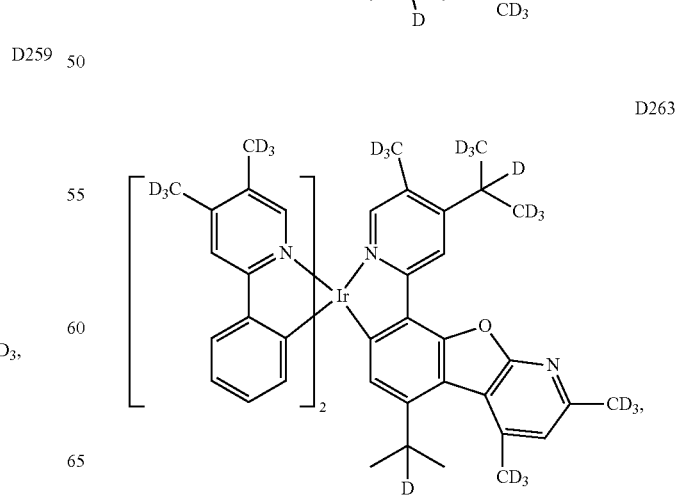
D263

D264
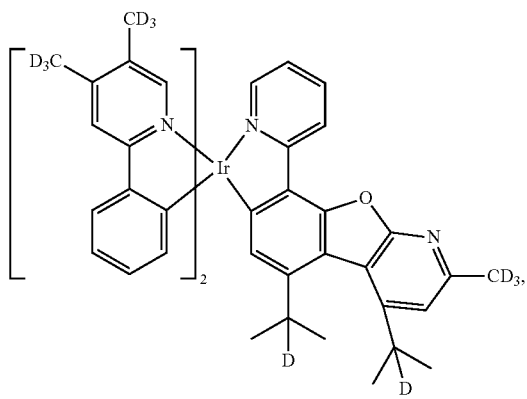
D265
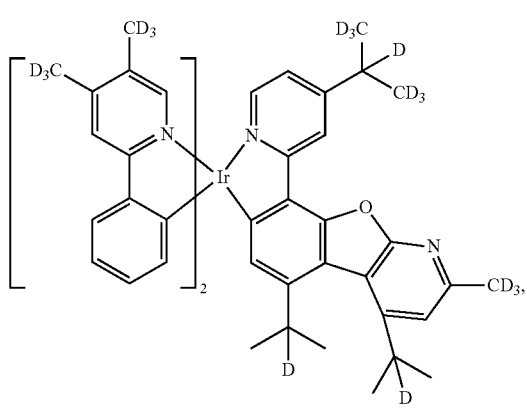
D266
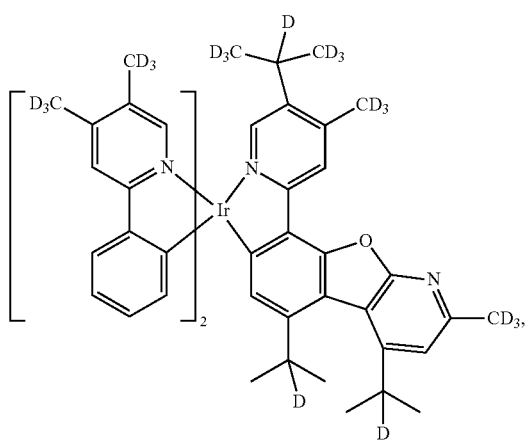
D267
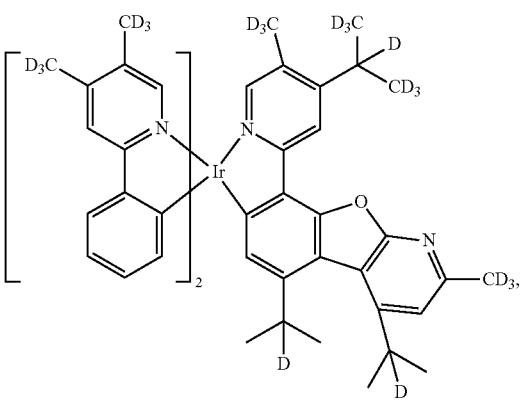
D268
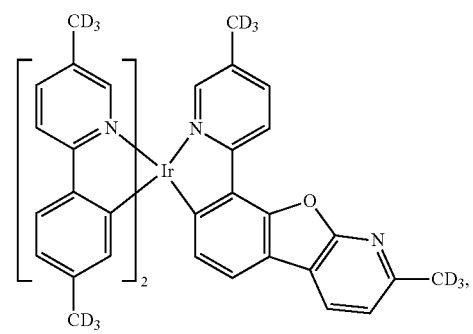
D269
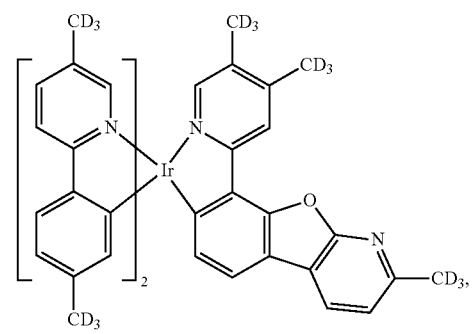
D270
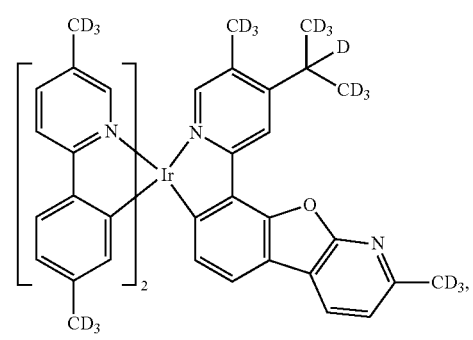

-continued
D271
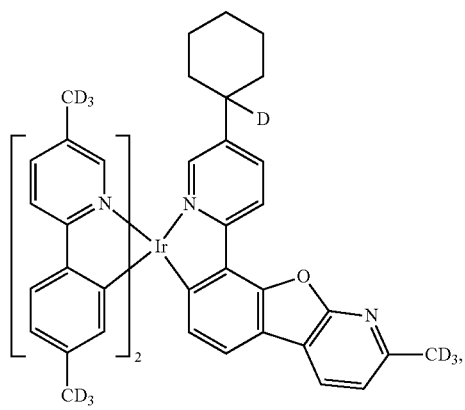
D272
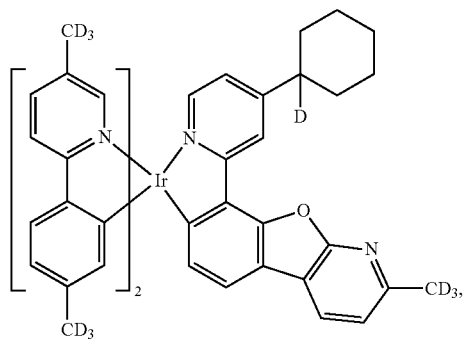
D273
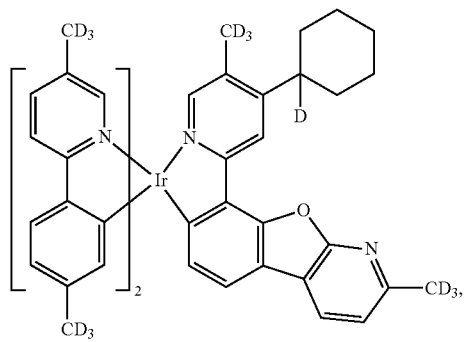
D274
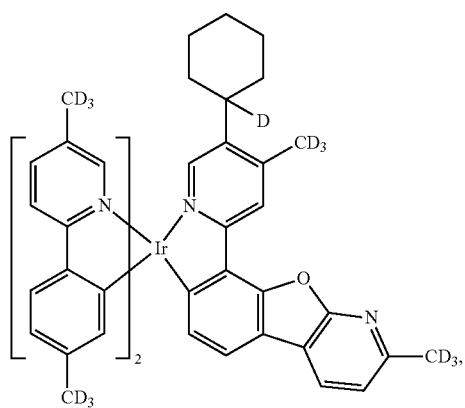
-continued
D275
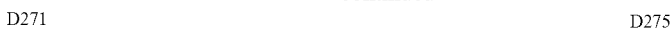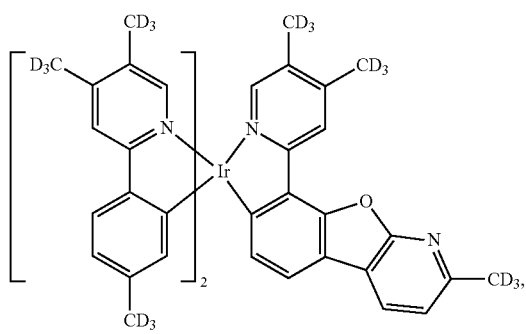
D276
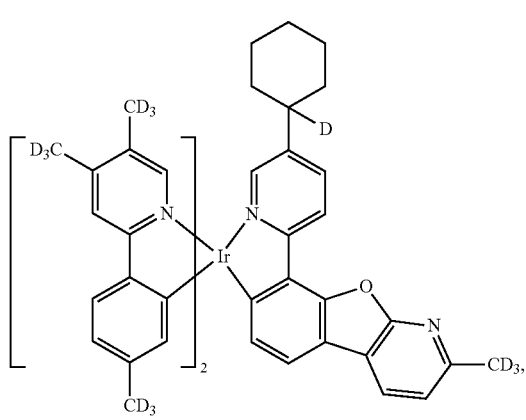
D277
D278
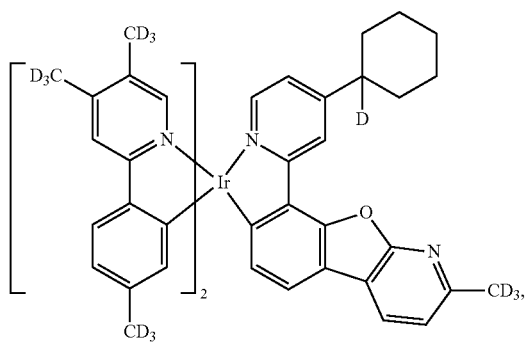

E1 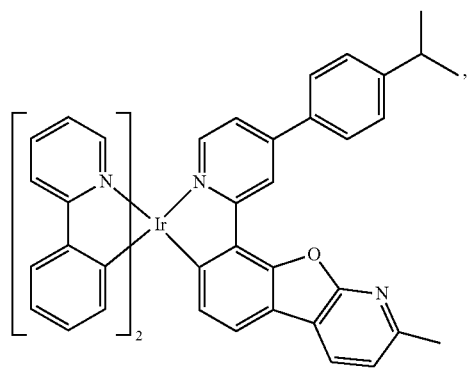
E2 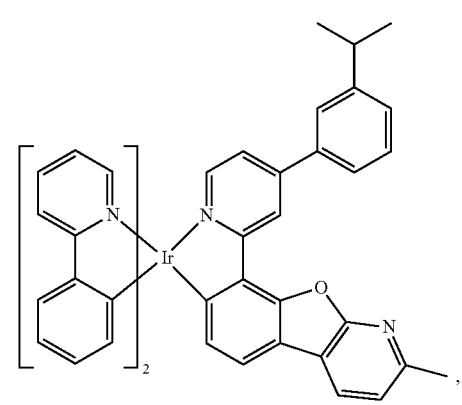
E3 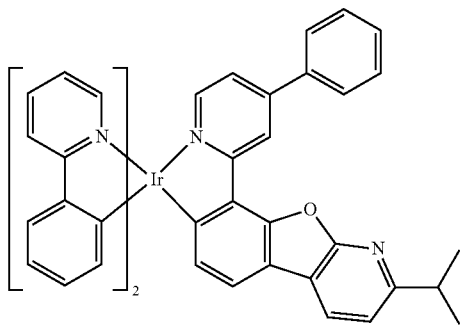
E4 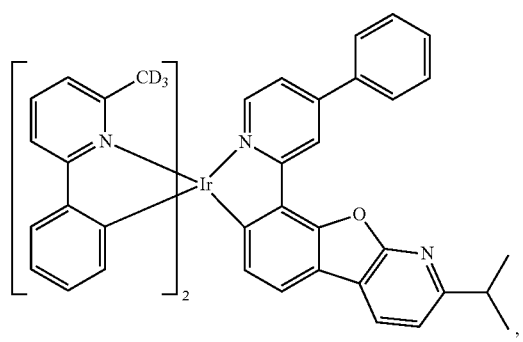
E5 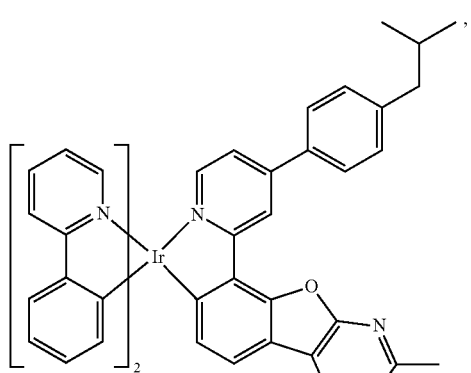
E6 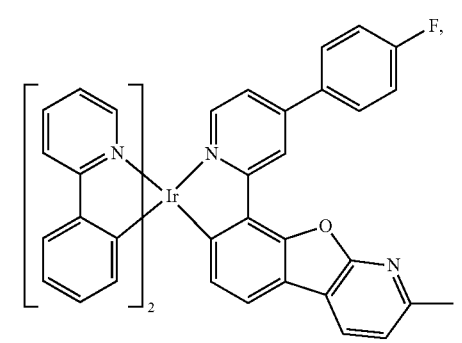
E7 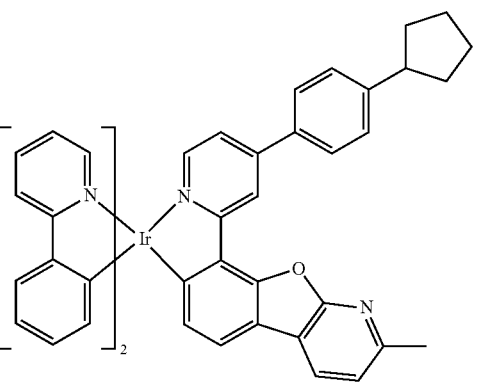
E8 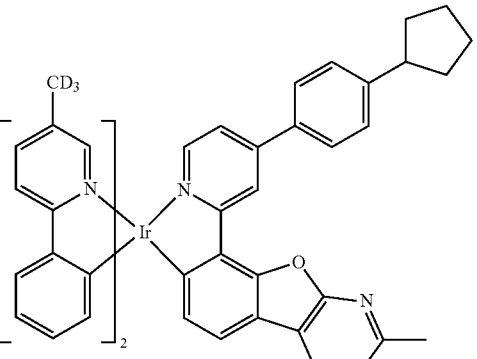

E9
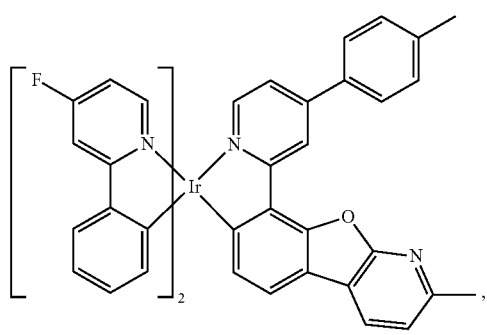
E10
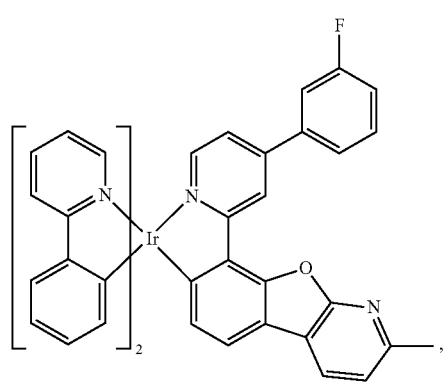
E11
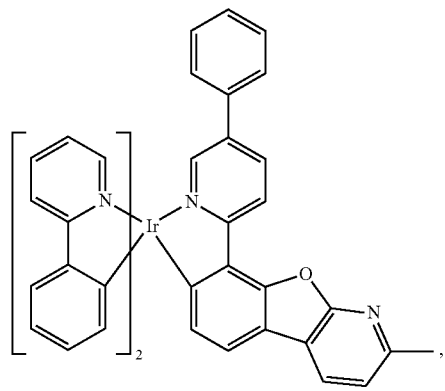
E12
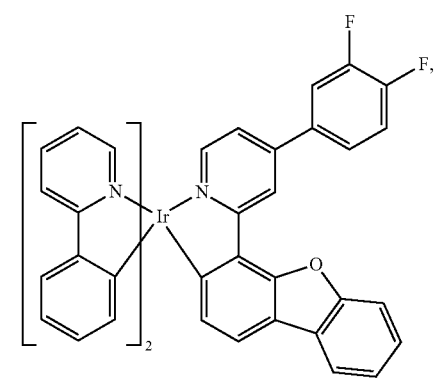
E13
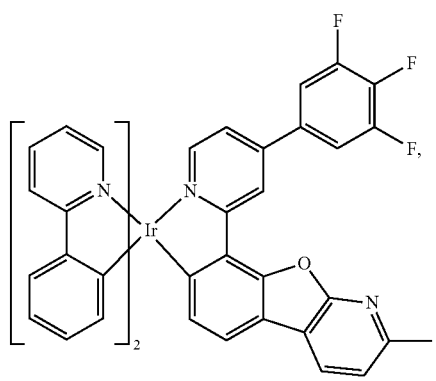
E14
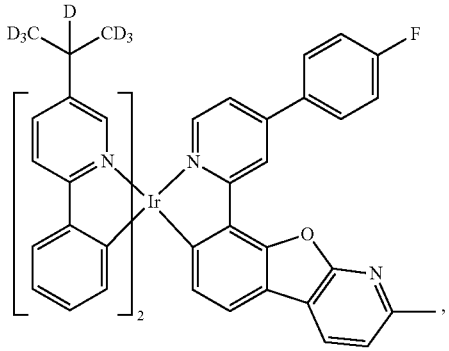
E15
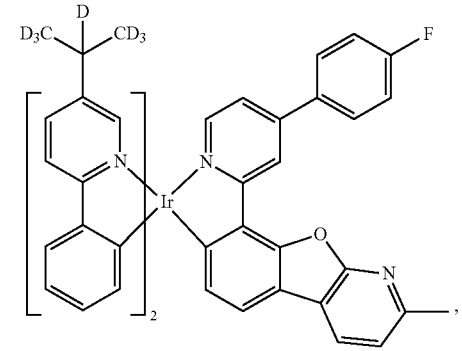
E16
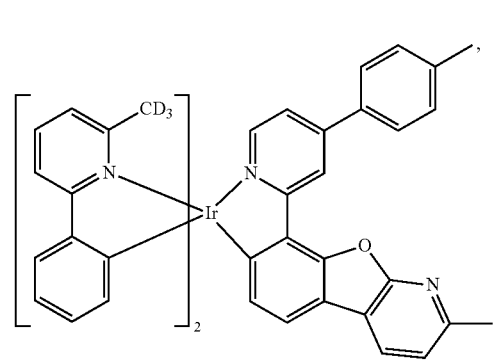

E17 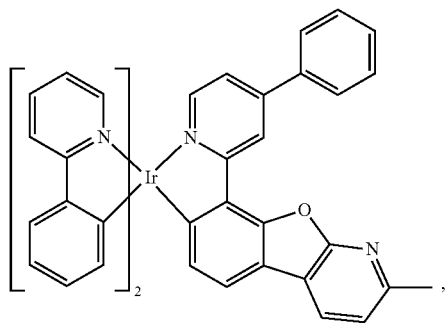
E18 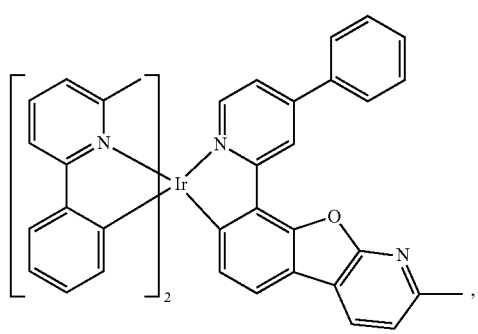
E19 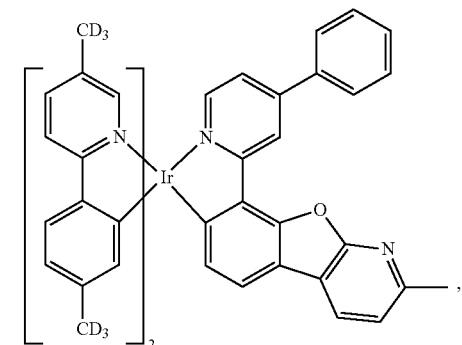
E20 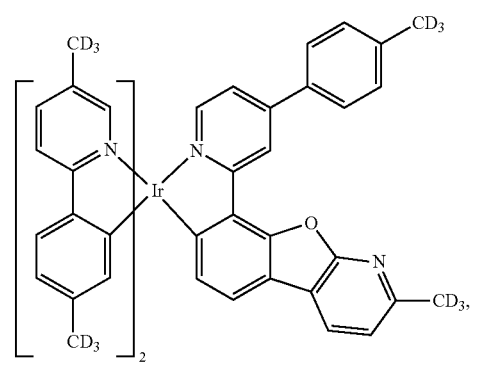
E21 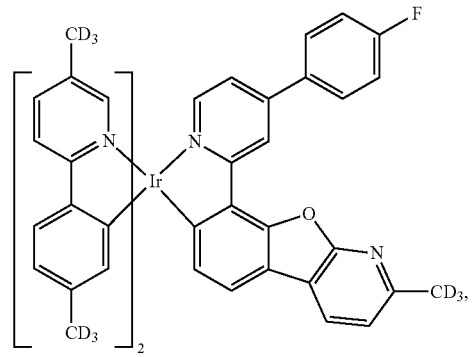
E19 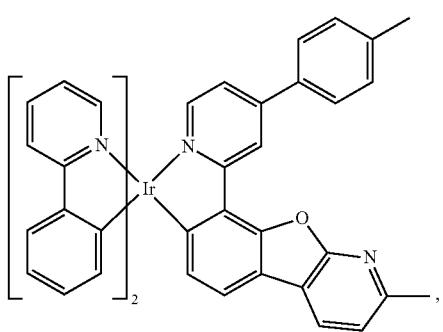
F1 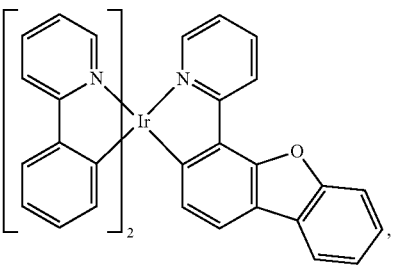
F2 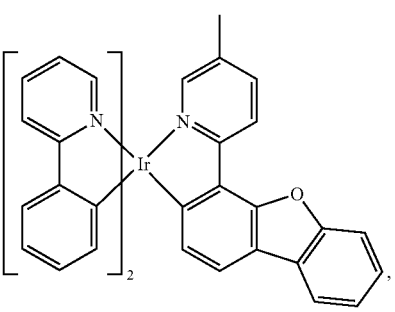
F3 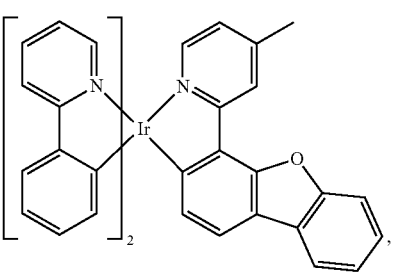

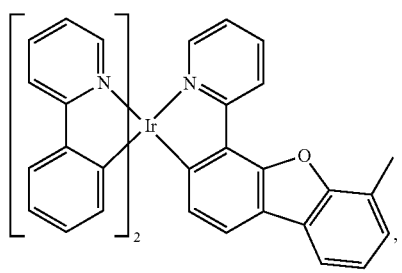 F4
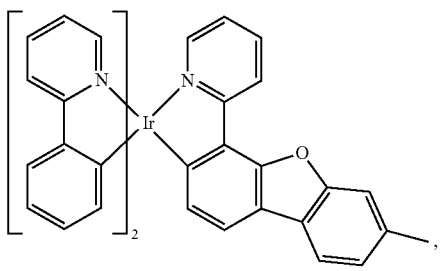 F5
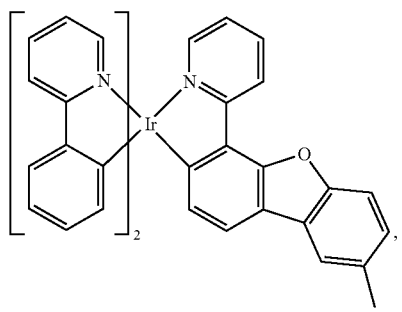 F6
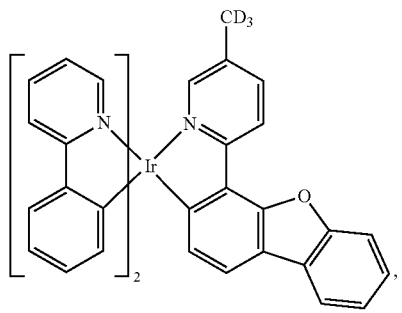 F7
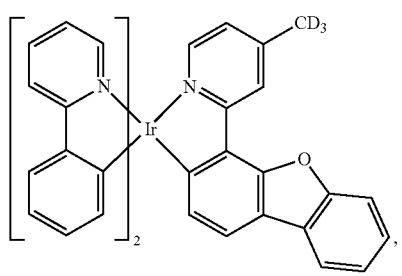 F8
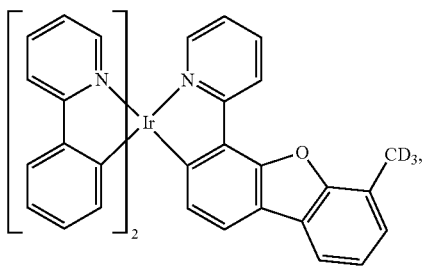 F9
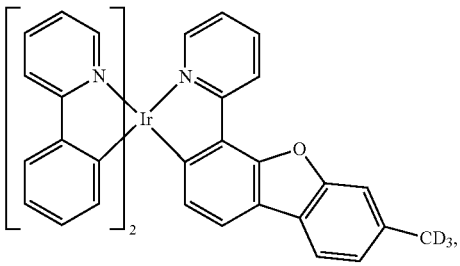 F10
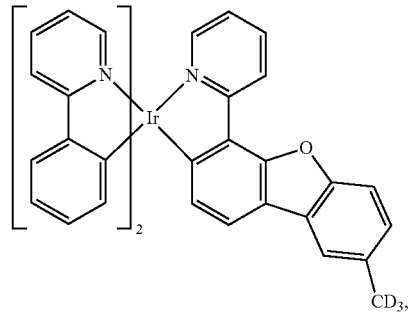 F11
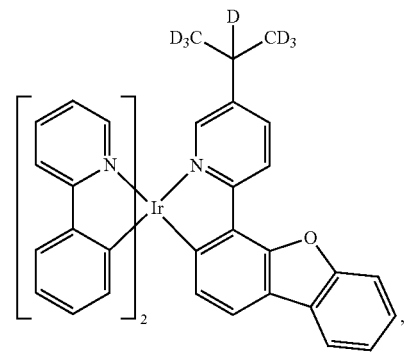 F12
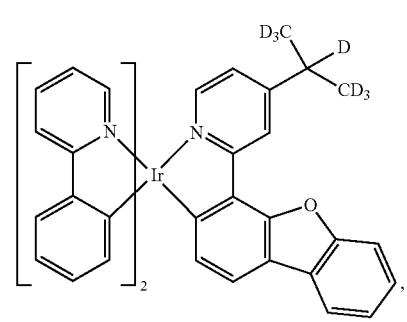 F13

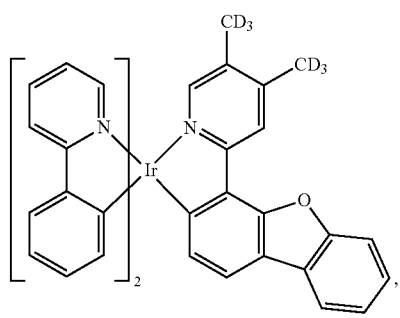
F14
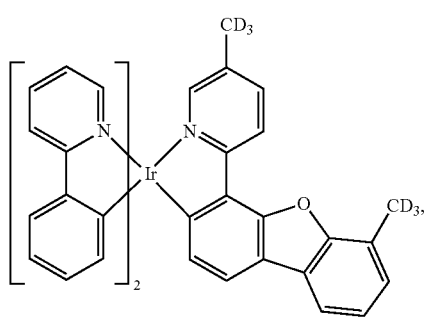
F15
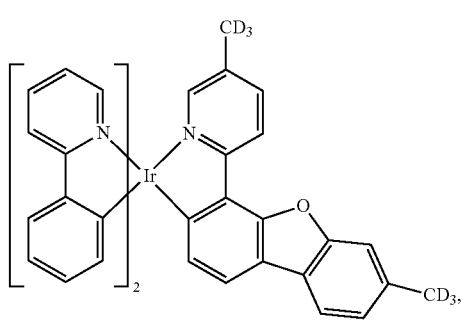
F16
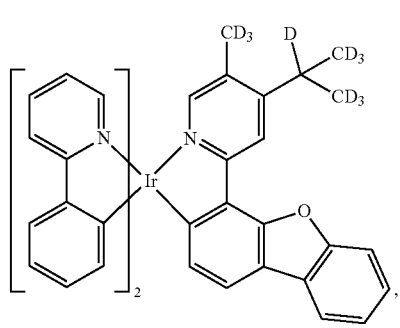
F17
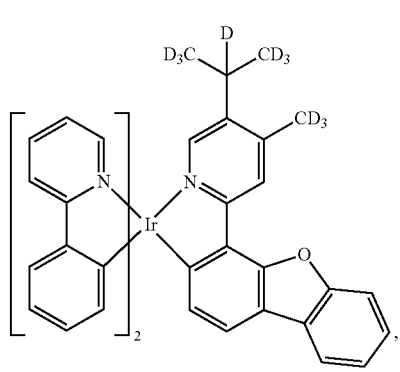
F18
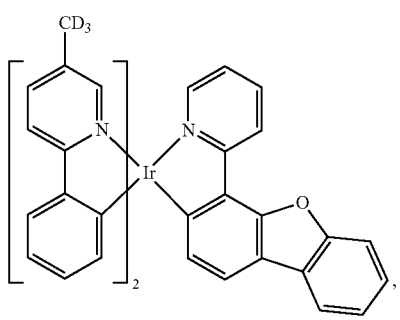
F19
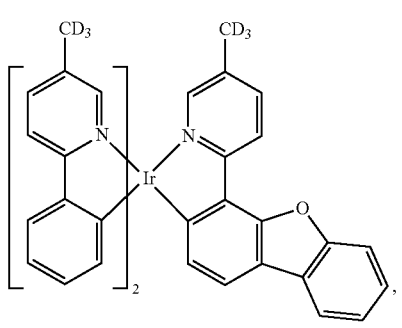
F20
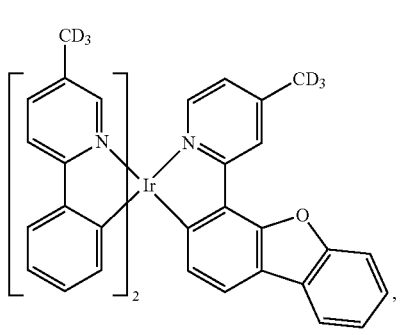
F21
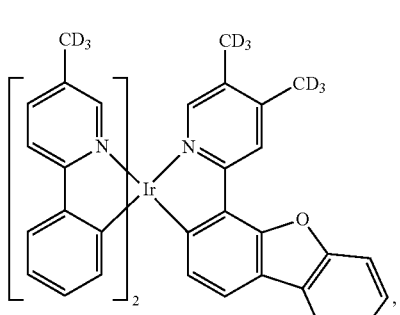
F22
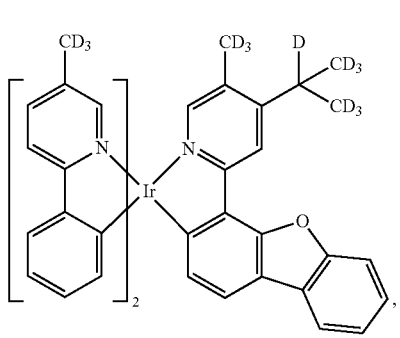
F23

F24
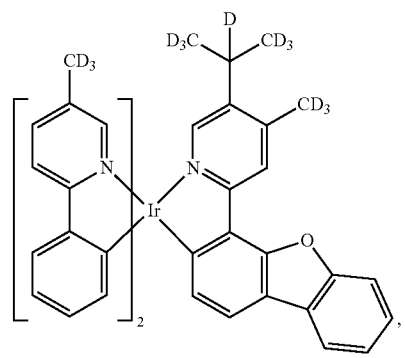
F25
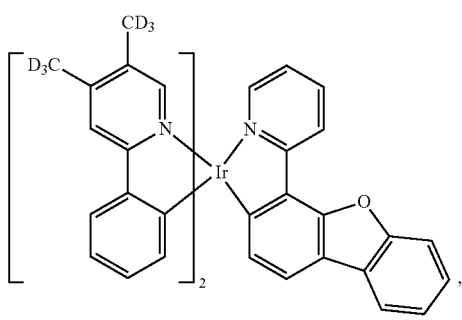
F26
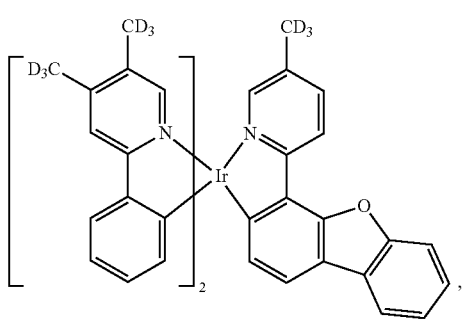
F27
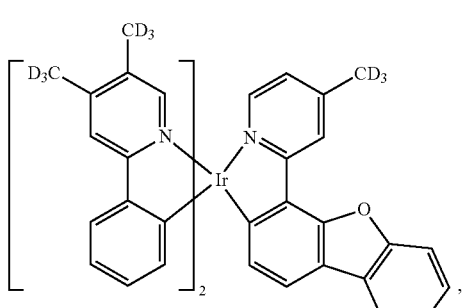
F28
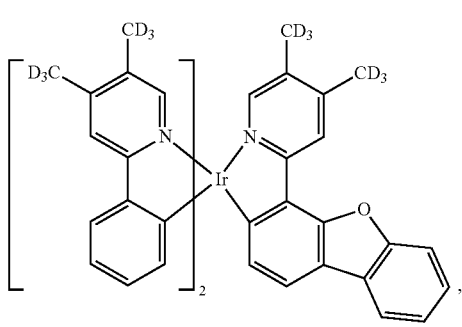
F29
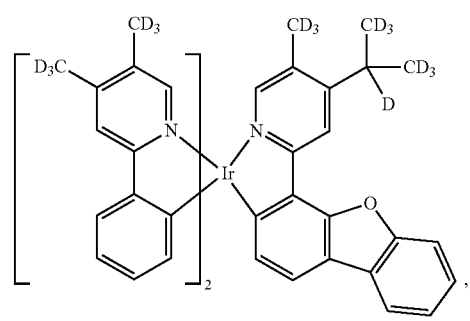
F30
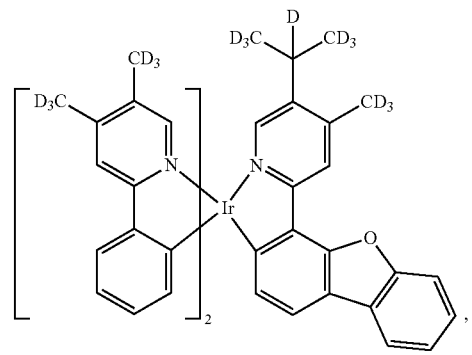
F31
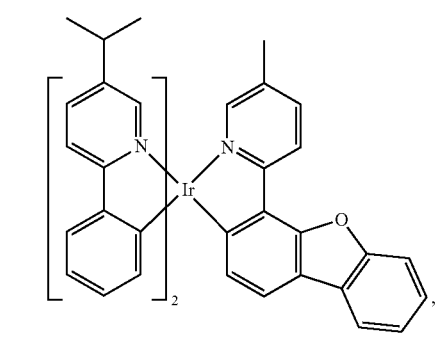
F32
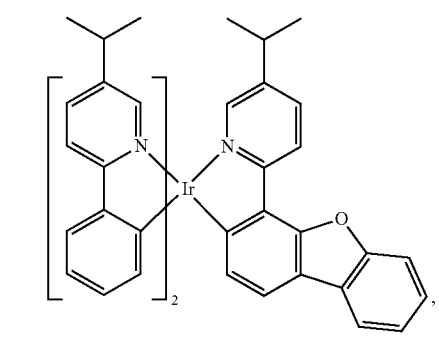

-continued

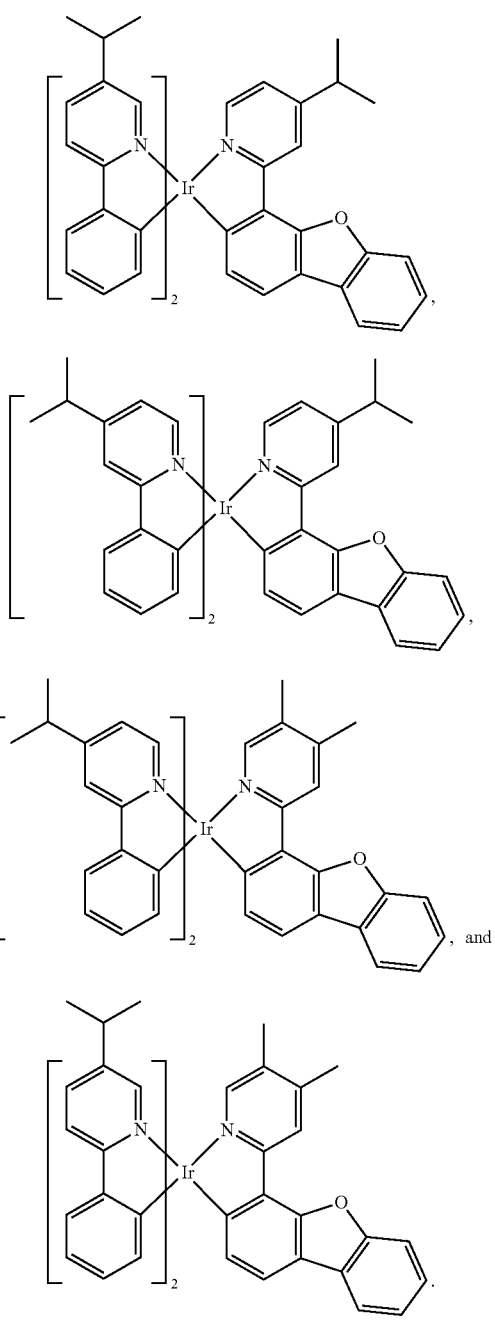

In some embodiments of the composition of material, the mixture of the first compound and the second compound is selected from the group consisting of (Compound A1, Compound D1), (Compound A1, Compound D3), (Compound A1, Compound D4), (Compound A1, Compound D6), (Compound A1, Compound D11), (Compound A1, Compound D12), (Compound A1, Compound D13), (Compound A1, Compound D17), (Compound A1, Compound D18), (Compound A1, Compound D19), (Compound A1, Compound D23), (Compound A1, Compound D28), (Compound A1, Compound D29), (Compound A1, Compound D85), (Compound A1, Compound D87), (Compound A1, Compound D154), (Compound A1, Compound D162), (Compound A1, Compound E3), (Compound A1, Compound :E6), (Compound A1, Compound E8), (Compound A1, Compound E15), (Compound A1, Compound F10), (Compound A1, Compound F12), (Compound A1, Compound F27), (Compound A1, Compound F36), (Compound A3, Compound D1), (Compound A4, Compound D3), (Compound A5, Compound D4), (Compound A6, Compound D6), (Compound A7, Compound D11), (Compound A12, Compound D12), (Compound A3, Compound D13), (Compound A4, Compound D13), (Compound A5, Compound D13), (Compound A6, Compound D13), (Compound A7, Compound D13), (Compound B21, Compound D13), (Compound B25, Compound D13), (Compound C2, Compound D18), (Compound C3, Compound D19), (Compound C4, Compound D23), (Compound HA20, Compound D13), (Compound HA21, Compound D85), (Compound HA26, Compound D151), (Compound HA30, Compound 87), (Compound HA31, Compound D26), (Compound HA33, Compound D13), (Compound HA34, Compound D85), (Compound HA38, Compound D28), (Compound HA47, Compound D162), (Compound HA52, Compound D85), (Compound HA68, Compound D151), (Compound HA90, Compound D13), (Compound HA91, Compound D6), (Compound HA92, Compound D154) and Compound HA93, Compound E15).

In some embodiments of the mixture comprising a first compound and a second compound, the first compound has an evaporation temperature T1 of 150 to 350° C.; wherein the second compound has an evaporation temperature T2 of 150 to 350° C.; wherein absolute value of T1-T2 is less than 20° C.; wherein the first compound has a concentration C1 in said mixture and a concentration C2 in a film formed by evaporating the mixture in a vacuum deposition tool at a constant pressure between $1\times10^{-6}$ Torr to $1\times10^{-9}$ Torr, at a 2 Å/sec deposition rate on a surface positione at a predefined distance away from the mixture being evaporated; and wherein absolute value of (C1-C2)/C1 is less than 5%.

In some embodiments of the mixture, the first compound has a vapor pressure of P1 at T1 at 1 atm, the second compound has a vapor pressure of P2 at T2 at 1 atm; and wherein the ratio of P1/P2 is within the range of 0.90 to 1.10.

In some embodiments of the mixture, the first compound has a first mass loss rate and the second compound has a second mass loss rate, wherein the ratio between the first mass loss rate and the second mass loss rate is within the range of 0.90 to 1.10.

In some embodiments of the mixture, the first compound and the second compound each has a purity in excess of 99% as determined by high pressure liquid chromatography.

In some embodiments, the mixture further comprises a third compound, wherein the third compound has a different chemical structure than the first and second compounds, wherein the third compound has an evaporation temperature T3 of 150 to 350° C., and wherein absolute value of T1-T3 is less than 20° C.

In some embodiments, the mixture further comprises a third compound, wherein the third compound has a different chemical structure than the first and second compounds, wherein the third compound has a third mass loss rate and the ratio between the first mass loss rate and third mass loss rate is within the range of 0.90 to 1.10.

In some embodiments, the composition of material comprising the mixture is in liquid form at a temperature less than T1 and T2.

According to another aspect of the present disclosure, an OLED is disclosed, wherein the OLED comprises an anode; a cathode; and an organic layer disposed between the anode and the cathode. The organic layer comprises a composition of material comprising a mixture of a first compound and a second compound, wherein the first compound has the structure of Formula I

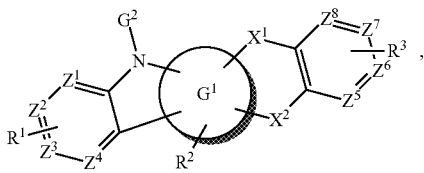

wherein $G^1$ is a six-member aromatic ring;
wherein $X^1$ and $X^2$ are each independently selected from the group consisting of direct bond, $CR^4R^5$, $NR^6$, O, S and Se;
wherein at least one of $X^1$ and $X^2$ is not a direct bond;
wherein $Z^1$ to $Z^8$ are each independently selected from the group consisting of nitrogen and carbon;
wherein $R^1$ to $R^3$ each independently represent mono to the possible maximum number of substitution, or no substitution;
wherein $G^2$, $R^1$, $R^2$, $R^3$, $R^4$, $R^5$ and $R^6$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, suifinyl, sulfonyl, phosphino, and combinations thereof, and wherein any two adjacent substituents can optionally join or fuse into a ring;
wherein the second compound has a formula $Ir(L_A)_n(L_B)_{3-n}$, and having a structure according to Formula II

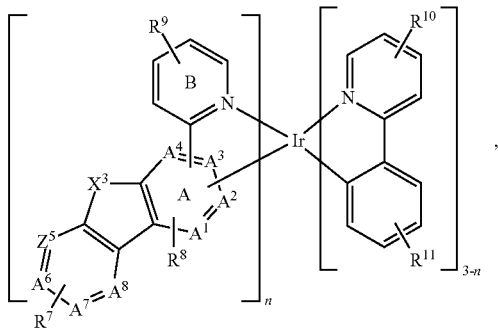

wherein each $A^1$, $A^2$, $A^3$, $A^4$, $A^5$, $A^6$, $A^7$, and $A^8$ comprise carbon or nitrogen;
wherein ring B is bonded to ring A through a C—C bond;
wherein the iridium is bonded to ring A through a Ir—C bond;
wherein $X^3$ is selected from a group consisting of O, S and Se;
wherein $R^7$ to $R^{11}$ each independently represent mono to the possible maximum number of substitution, or no substitution;
wherein $R^7$ to $R^{11}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein any two adjacent substituents can optionally join or fuse into a ring; and wherein n is an integer from 1 to 3.

In some embodiments of the OLED, the organic layer is an emissive layer. In some embodiments of the OLED, the OLED is incorporated into a device selected from the group consisting of a consumer product, an electronic component module, and a lighting panel.

According to another aspect of the present disclosure, a method for fabricating an organic light emitting device is disclosed. The method comprising: providing a substrate having a first electrode disposed thereon; depositing a first organic layer over the first electrode by evaporating a mixture of a first compound and a second compound in a vacuum deposition tool at a constant pressure between $1 \times 10^{-6}$ Torr to $1 \times 10^{-9}$ Torr, at a 2 Å/sec deposition rate on a surface position at a predefined distance away from the mixture being evaporated; and depositing a second electrode over the first organic layer;
wherein the first compound has the structure of Formula I

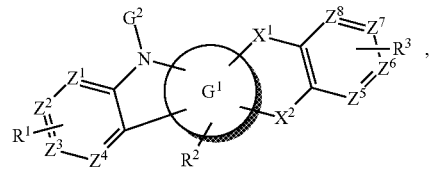

wherein $G^1$ is a six-member aromatic ring;
wherein $X^1$ and $X^2$ are each independently selected from the group consisting of direct bond, $CR^4R^5$, $NR^6$, O, S and Se;
wherein at least one of $X^1$ and $X^2$ is not a direct bond;
wherein $Z^1$ to $Z^8$ are each independently selected from the group consisting of nitrogen and carbon;
wherein $R^1$ to $R^3$ each independently represent mono to the possible maximum number of substitution, or no substitution;
wherein $G^2$, $R^1$, $R^2$, $R^3$, $R^4$, $R^5$ and $R^b$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein any two adjacent substituents can optionally join or fuse into a ring;
wherein the second compound has a formula $Ir(L_A)_n(L_B)_{3-n}$, and having a structure according to Formula II

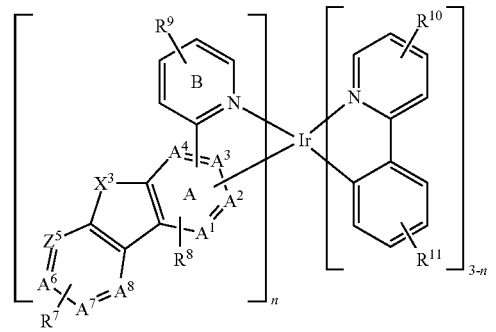

wherein each A¹, A², A³, A⁴, A⁵, A⁶, A⁷, and A⁸ comprise carbon or nitrogen;

wherein ring B is bonded to ring A through a C—C bond;

wherein the iridium is bonded to ling A through a Ir—C bond;

wherein X³ is selected from a group consisting of O, S and Se;

wherein R⁷ to R¹¹ each independently represent mono to the possible maximum number of substitution, or no substitution;

wherein R⁷ to R¹¹ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein any two adjacent substituents can optionally join or fuse into a ring; and wherein n is an integer from 1 to 3.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, 0820070160905, US20090167167, US2010288362, WO06081780, WO2009003455, WO2009008277, WO2009011327, WO2014009310, US2007252140, US2015060804 and US2012146012.

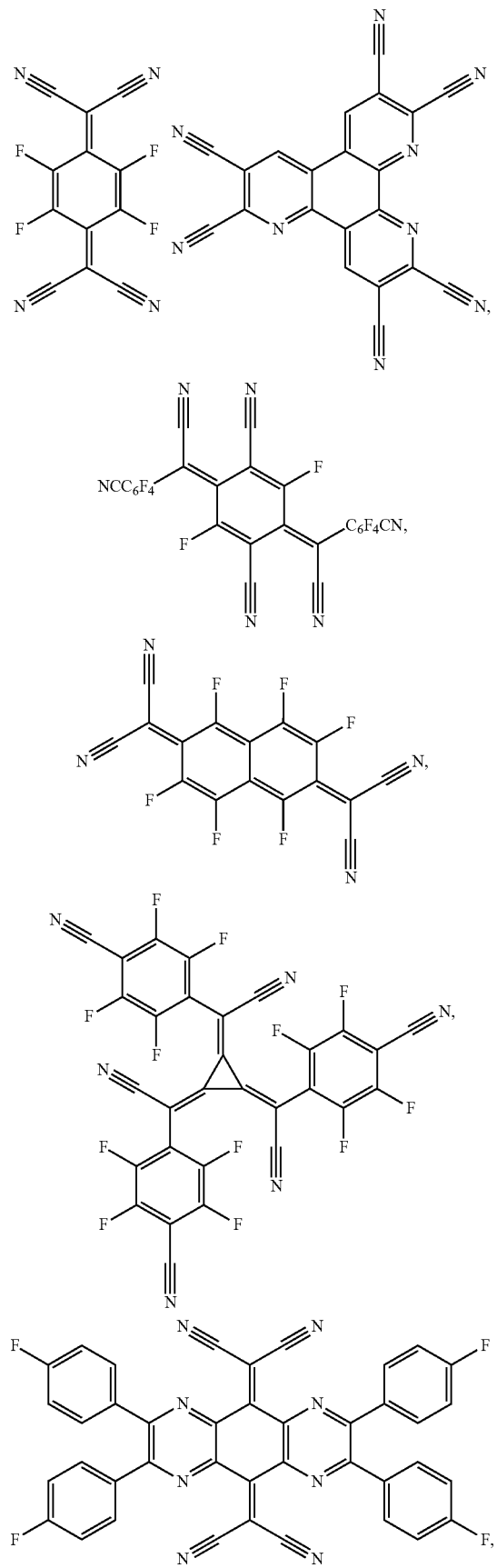

-continued

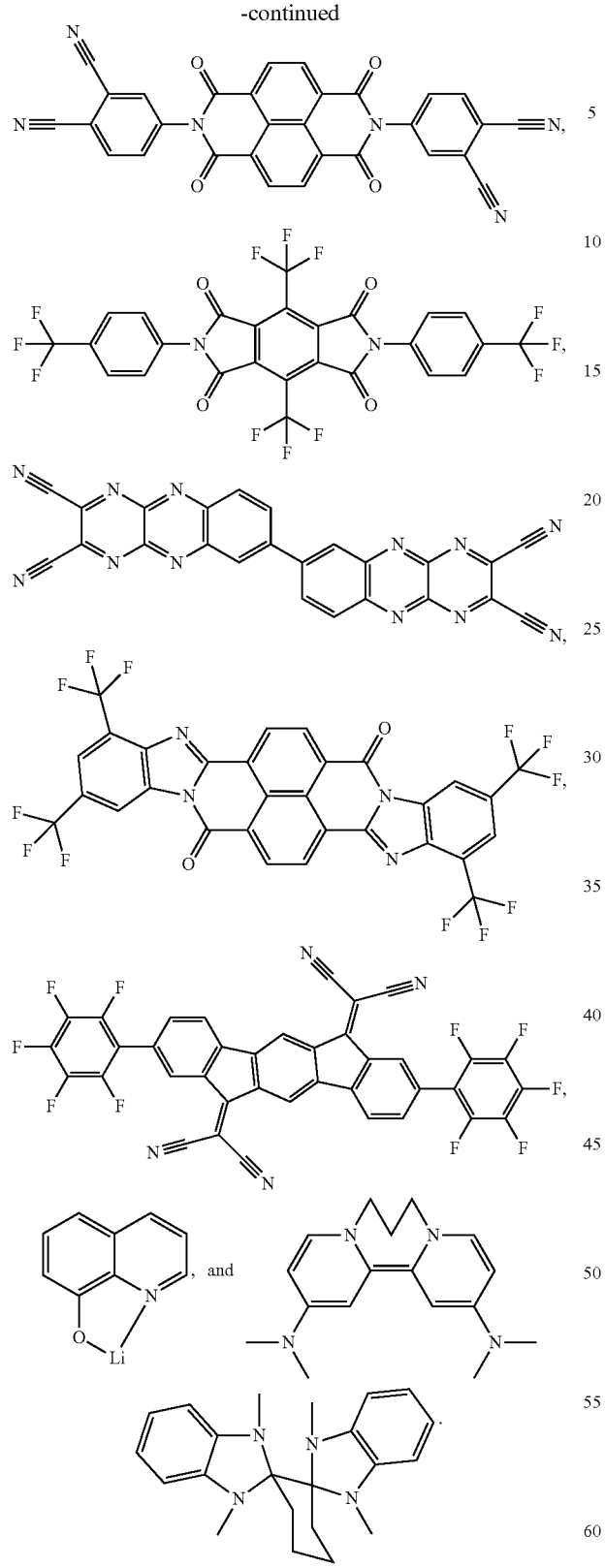

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but are not limited to the following general structures:

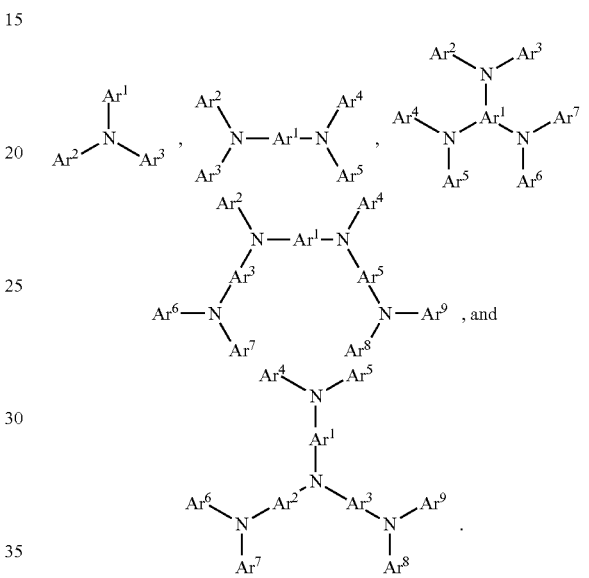

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrite, isonitrile, sulfanyl, sulfinyl, sulfonyl, phosphino, and combinations thereof.

In one aspect, $Ar^1$ to $Ar^9$ is independently selected from the group consisting of:

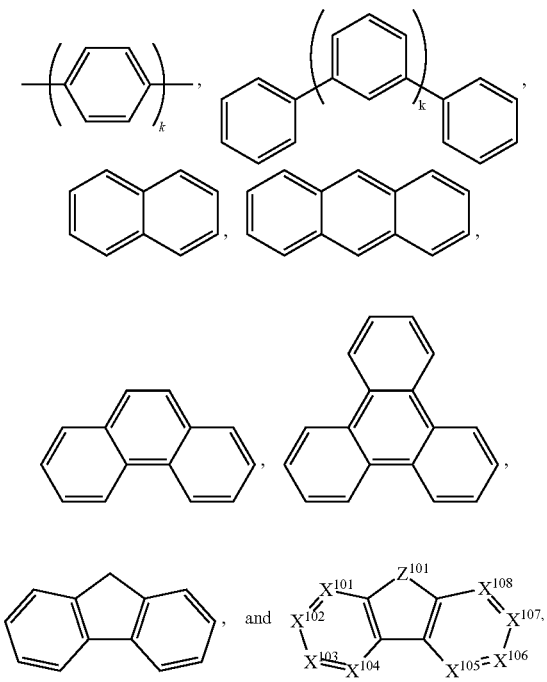

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in Hit or HTL include, but are not limited to the following general formula:

$$\left[ \begin{matrix} Y^{101} \\ Y^{102} \end{matrix} \right]_{k'} Met\text{-}(L^{101})_{k''}$$

wherein Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs, $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, US06517957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. No. 5,061,569, U.S. Pat. No. 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO02014104514, WO2014157018,

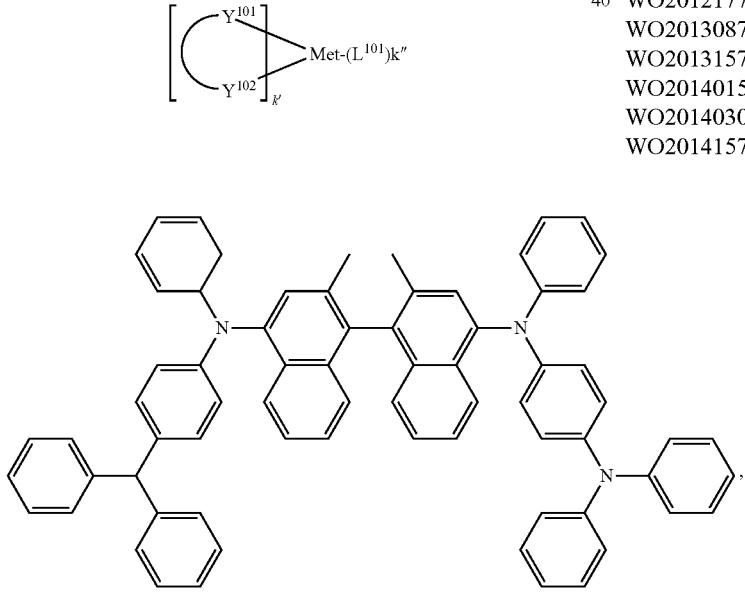

-continued
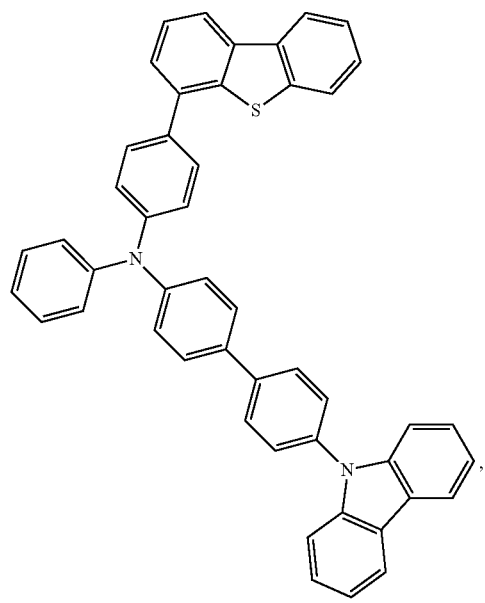
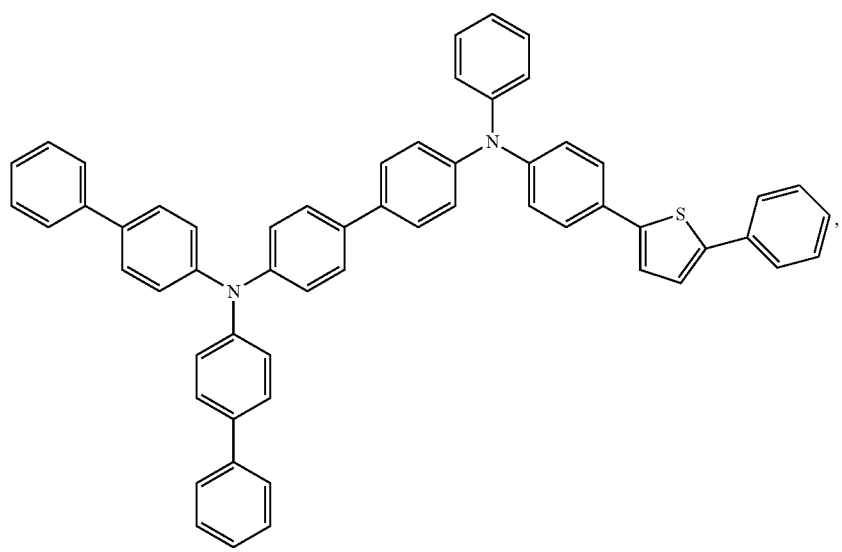
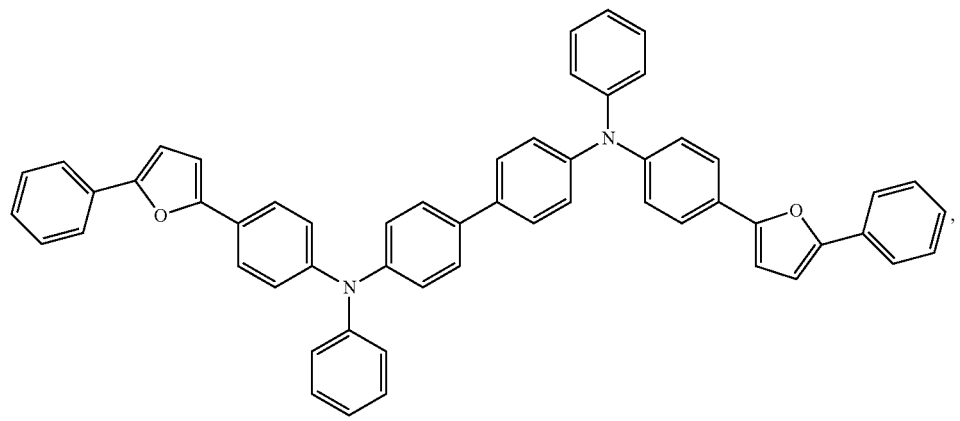

-continued
157
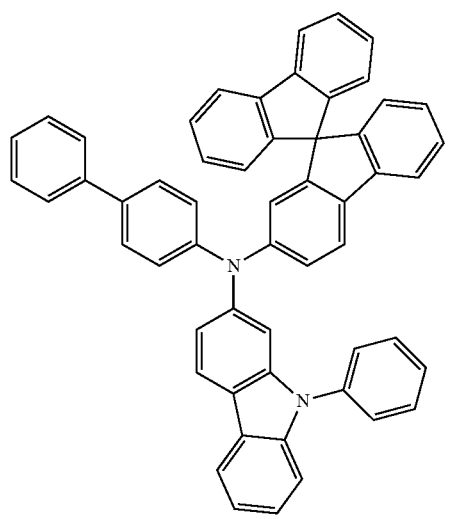
158
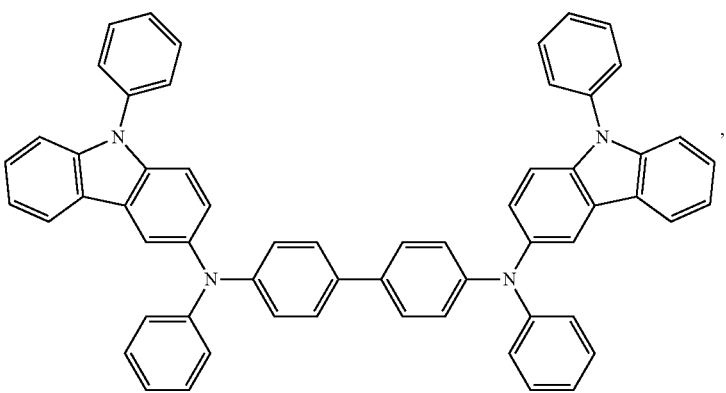
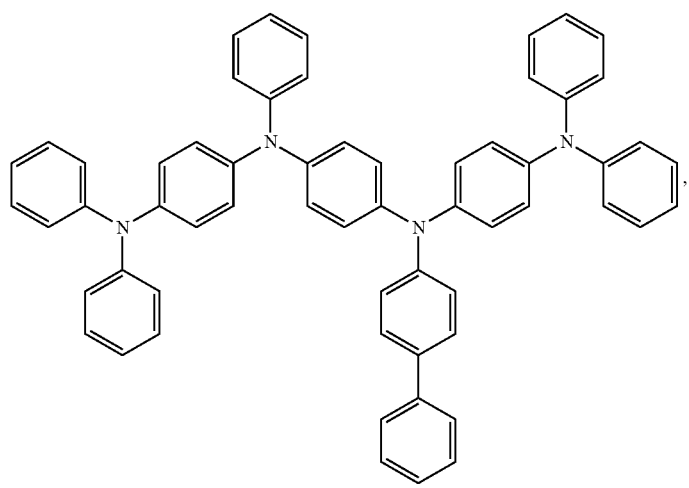
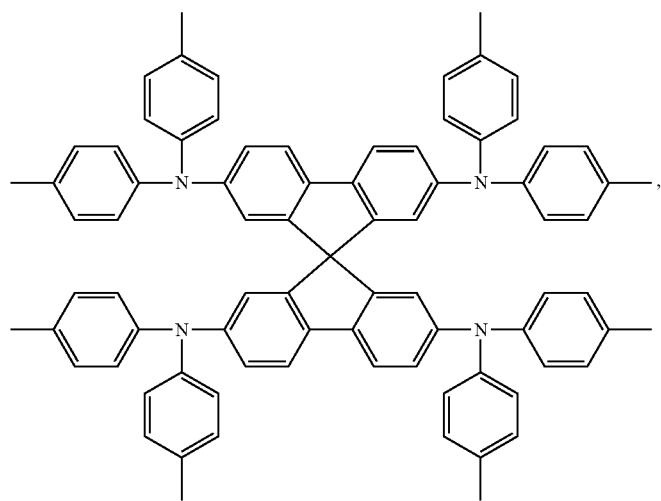

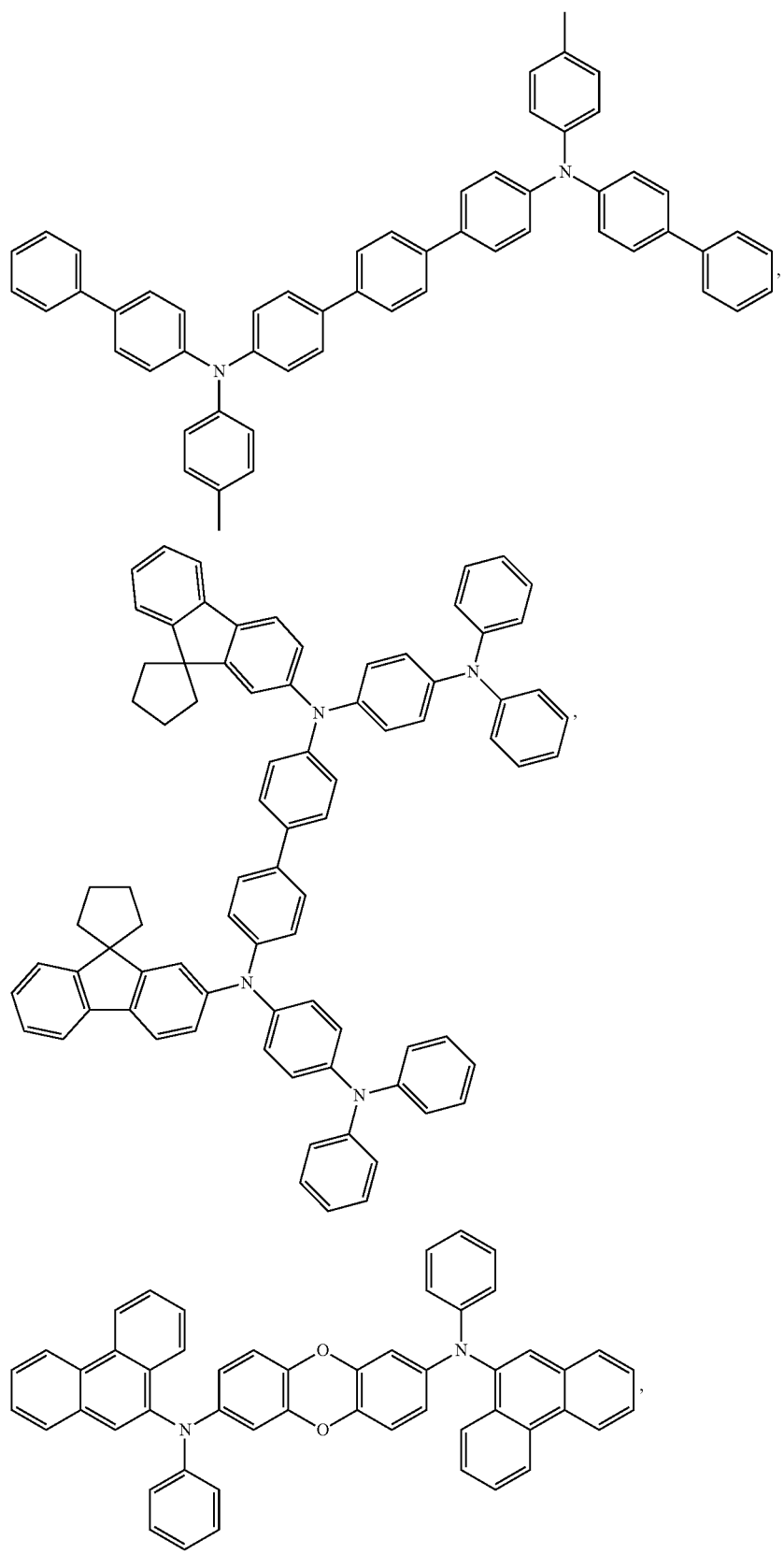

-continued
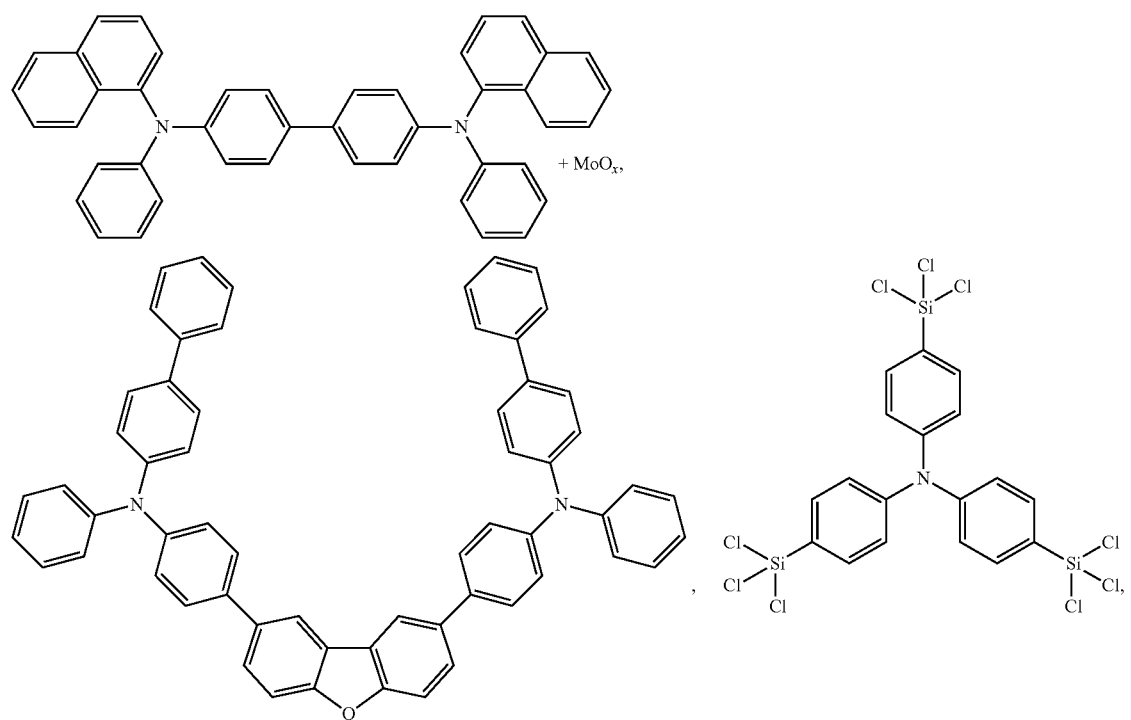
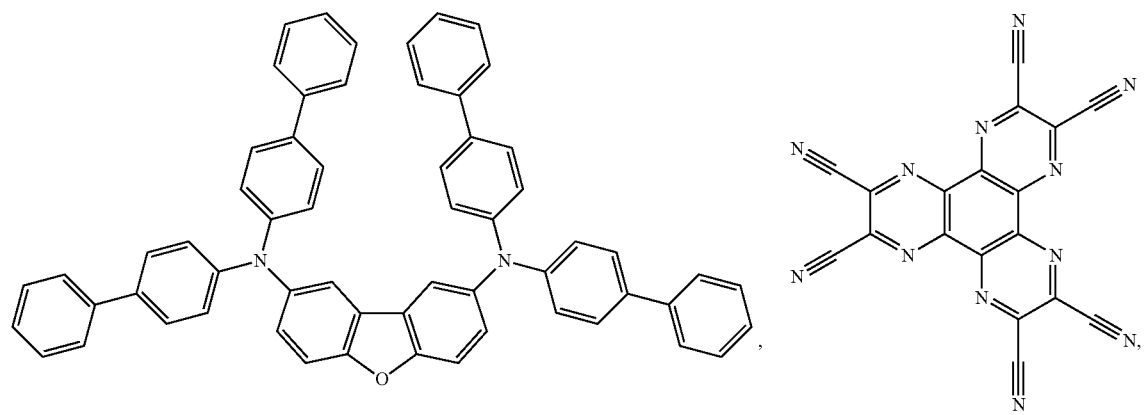
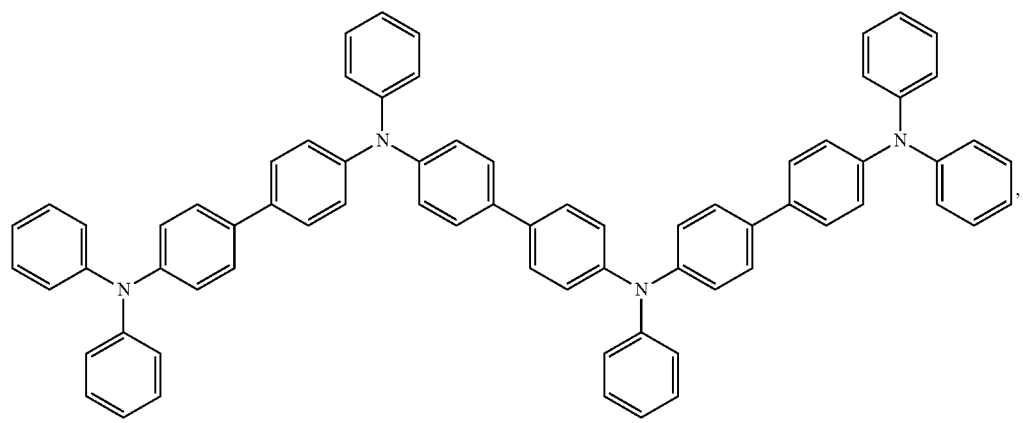

-continued
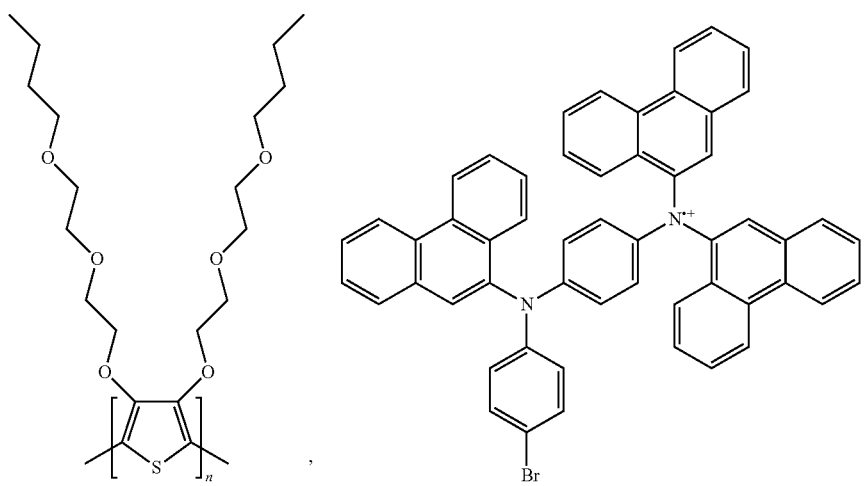
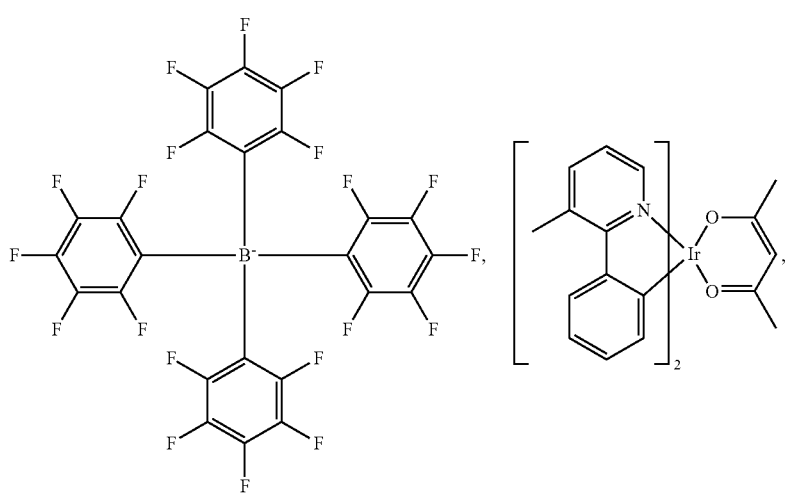
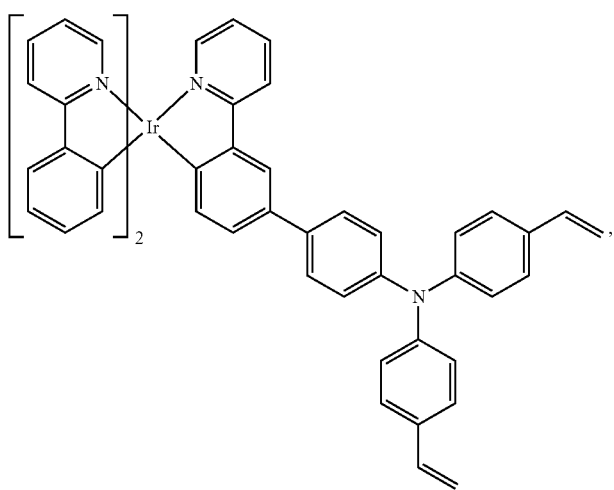

-continued
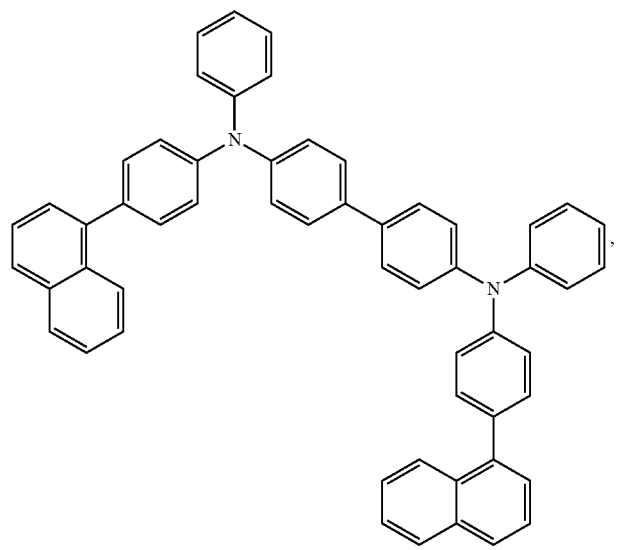
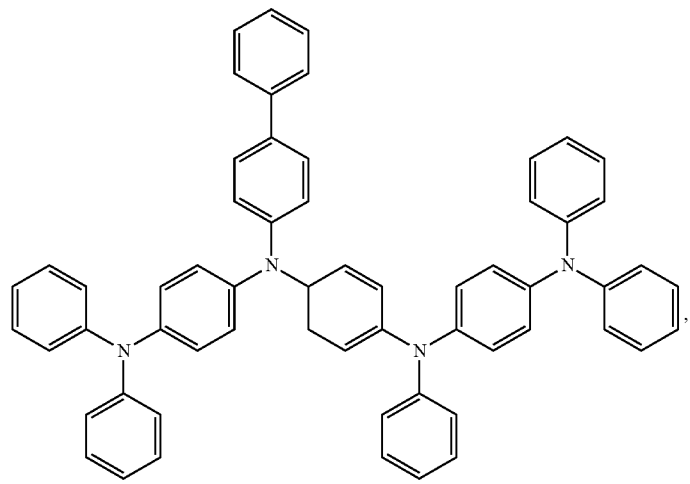
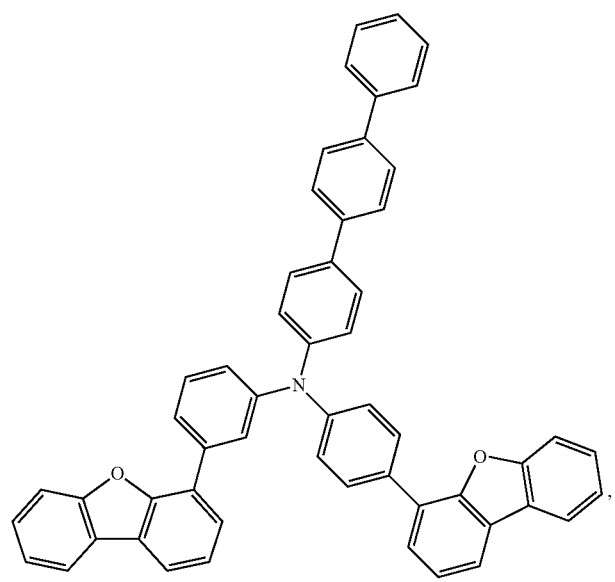

-continued
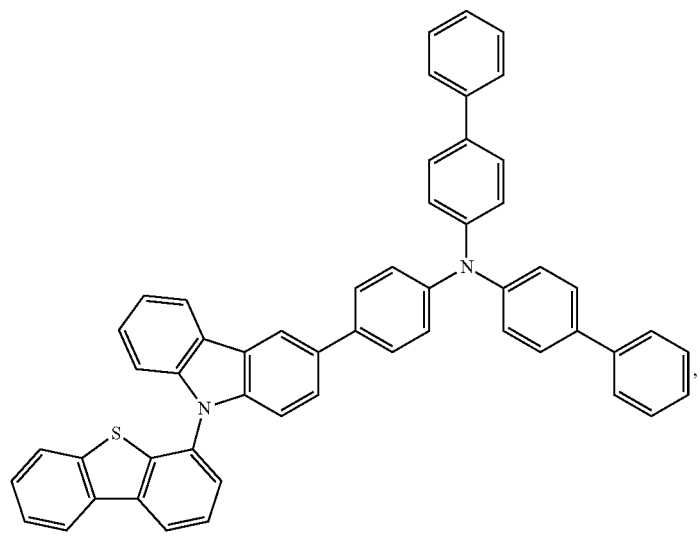
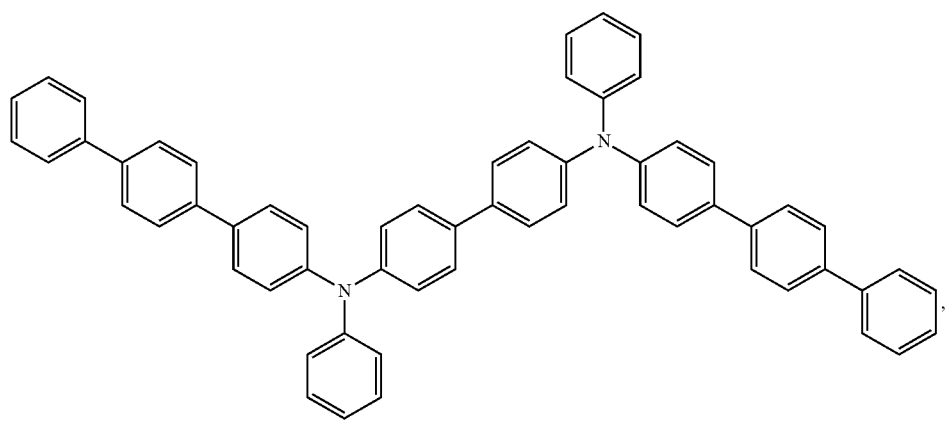
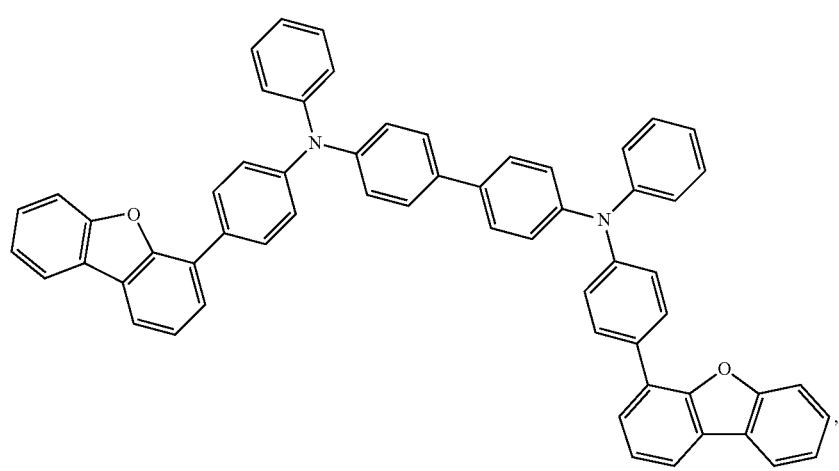

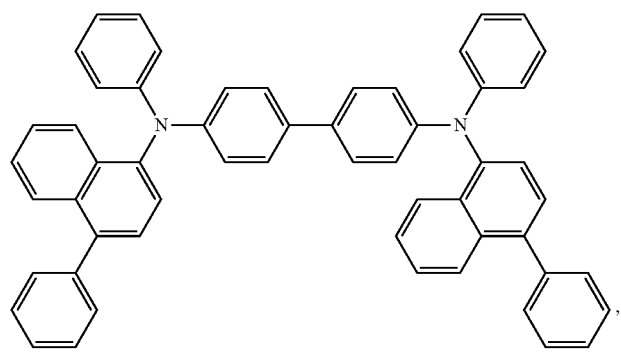
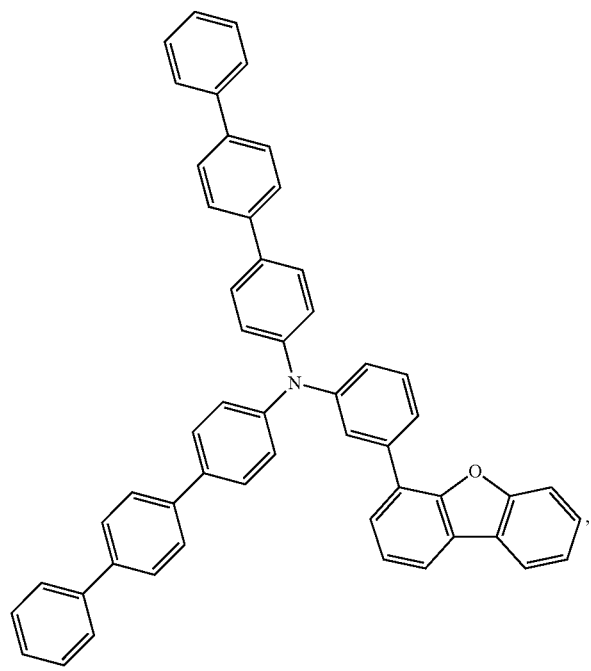
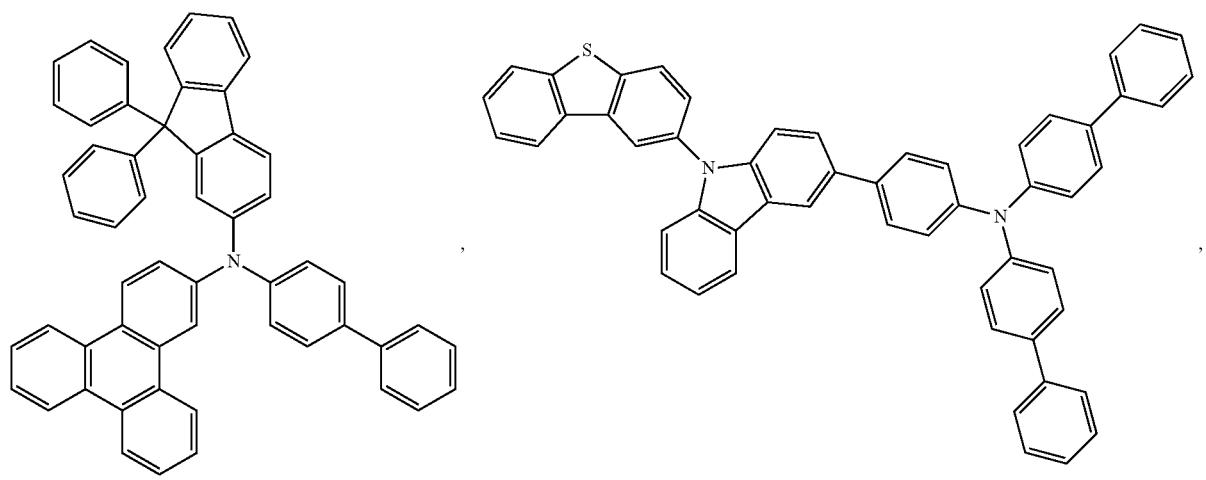

171 172
-continued
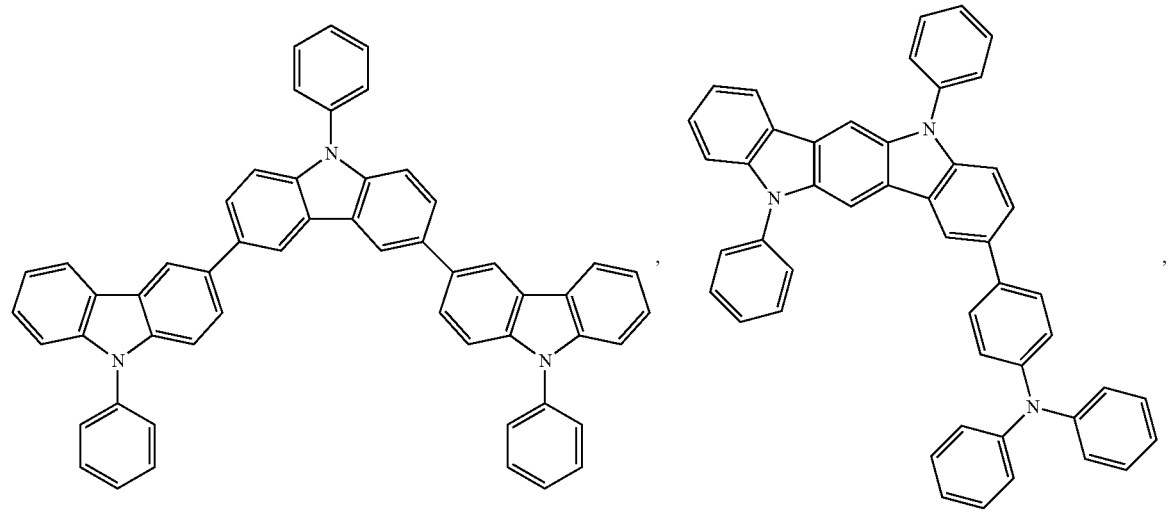
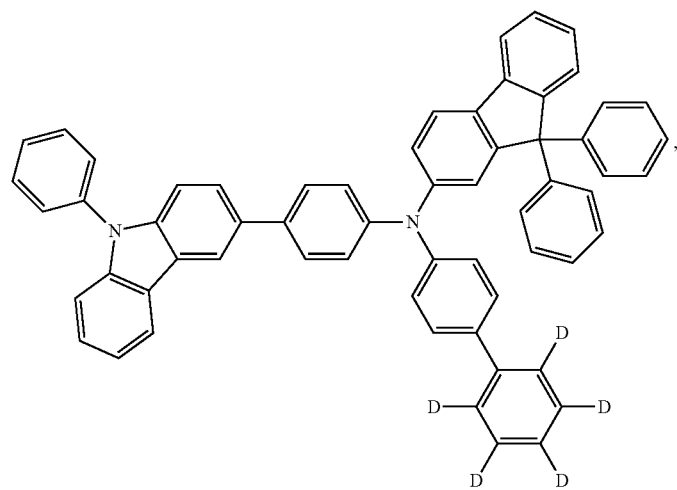
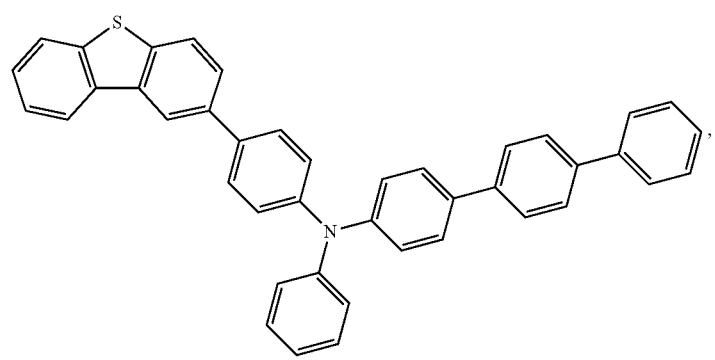

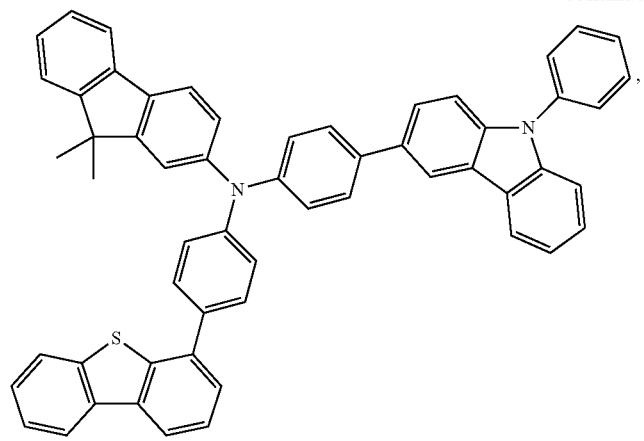
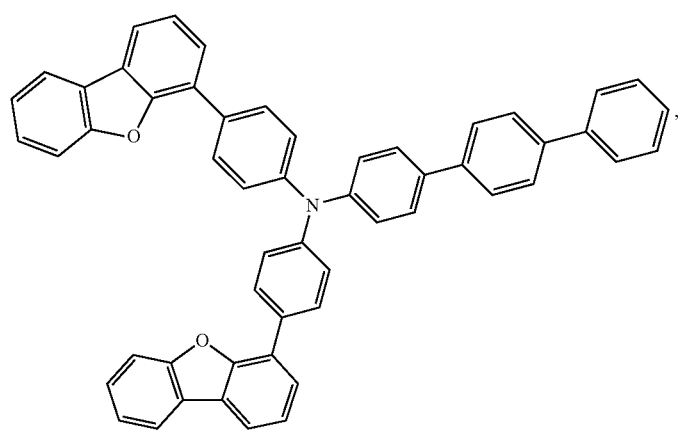
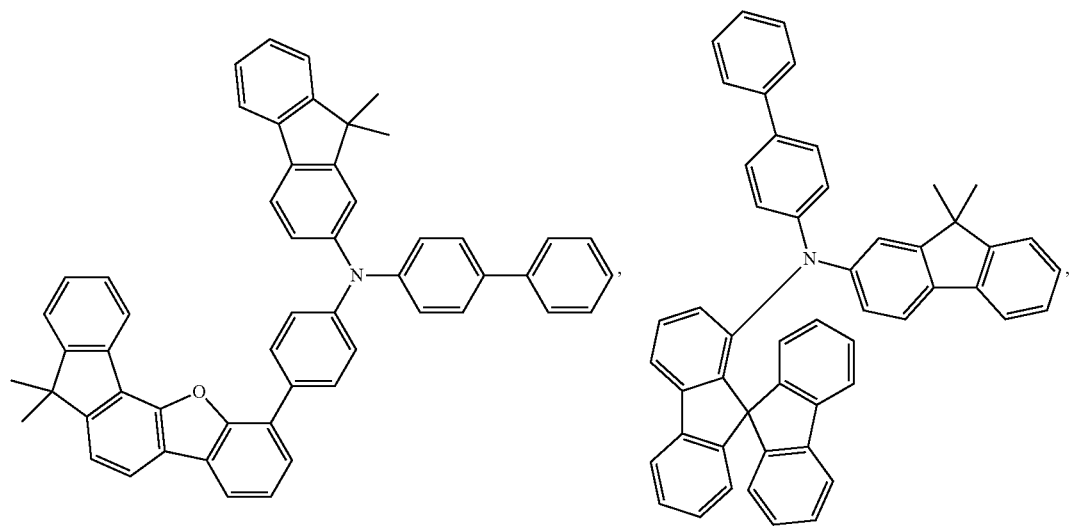

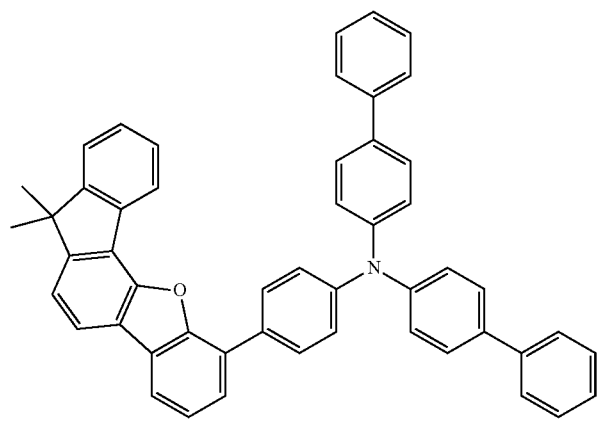
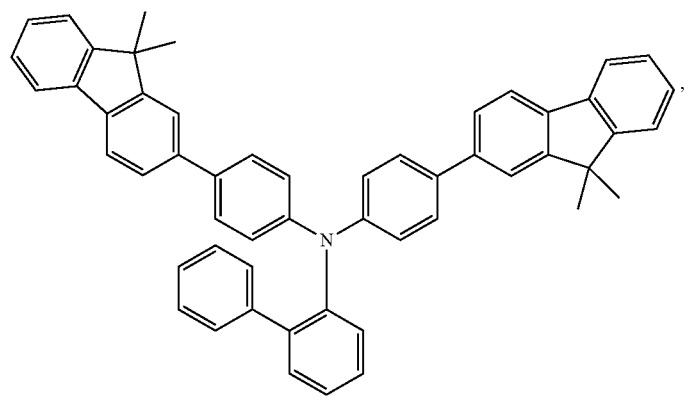
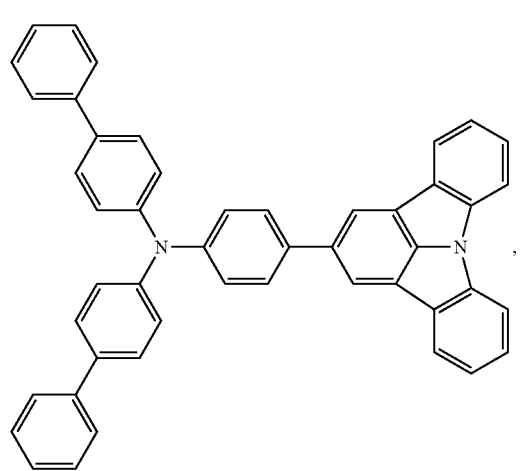

177 178
-continued
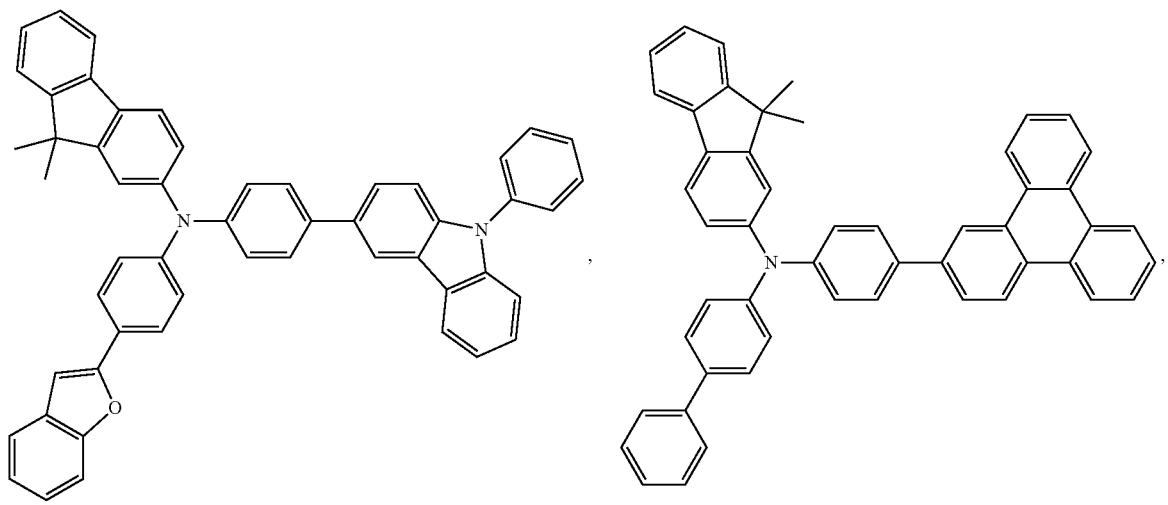
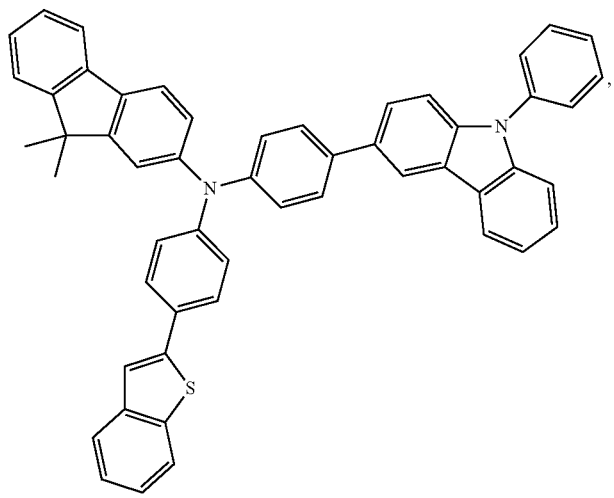
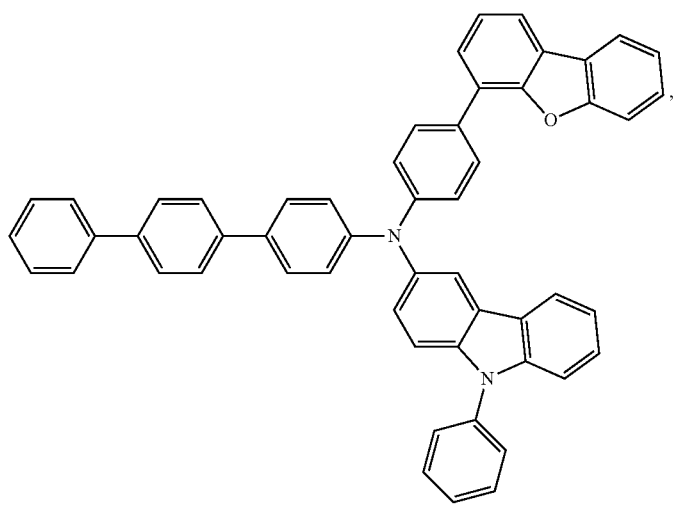

-continued
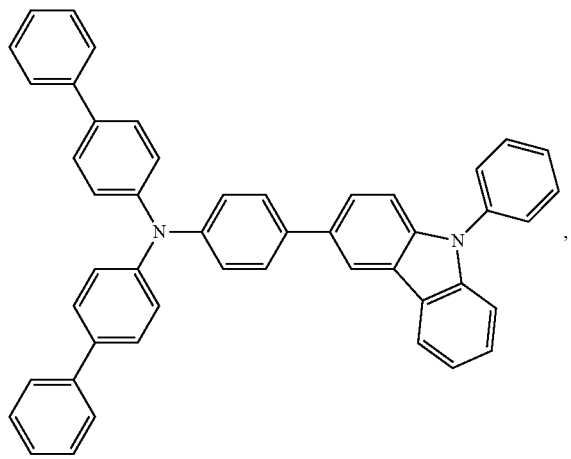
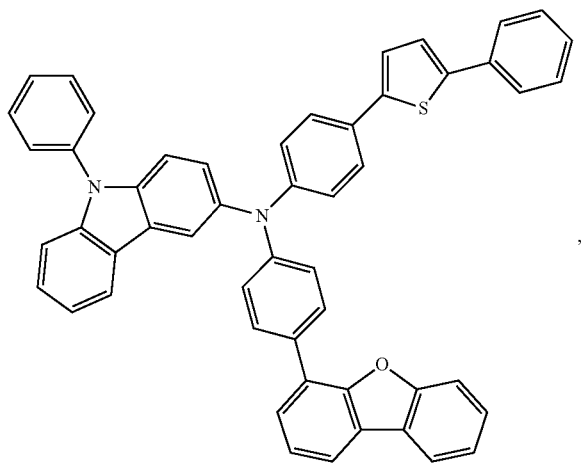
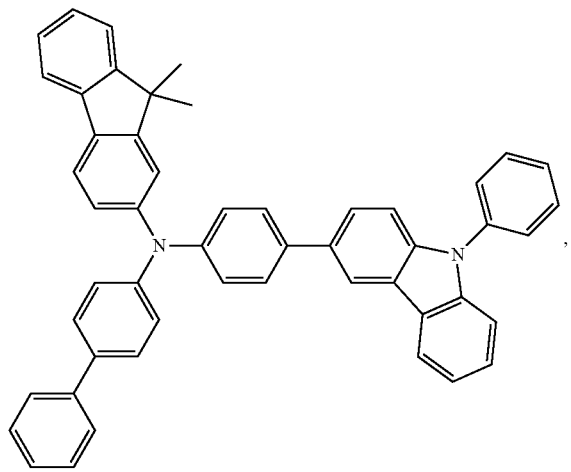
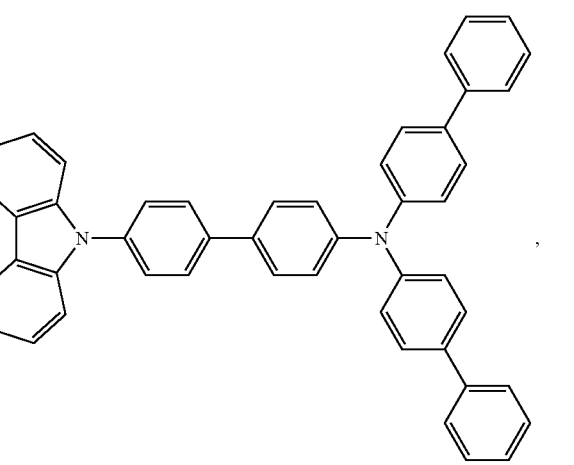
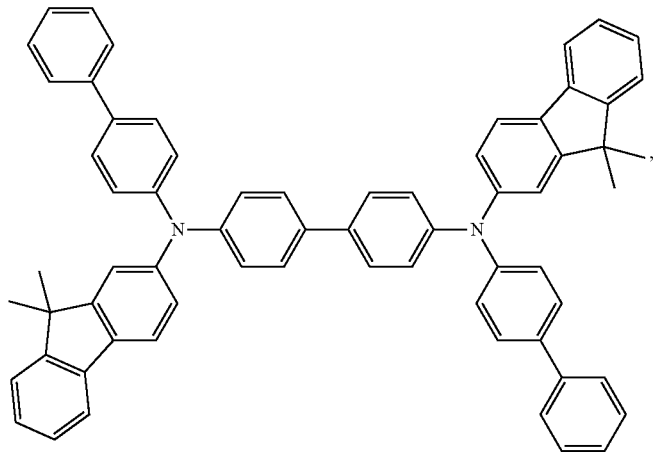

-continued
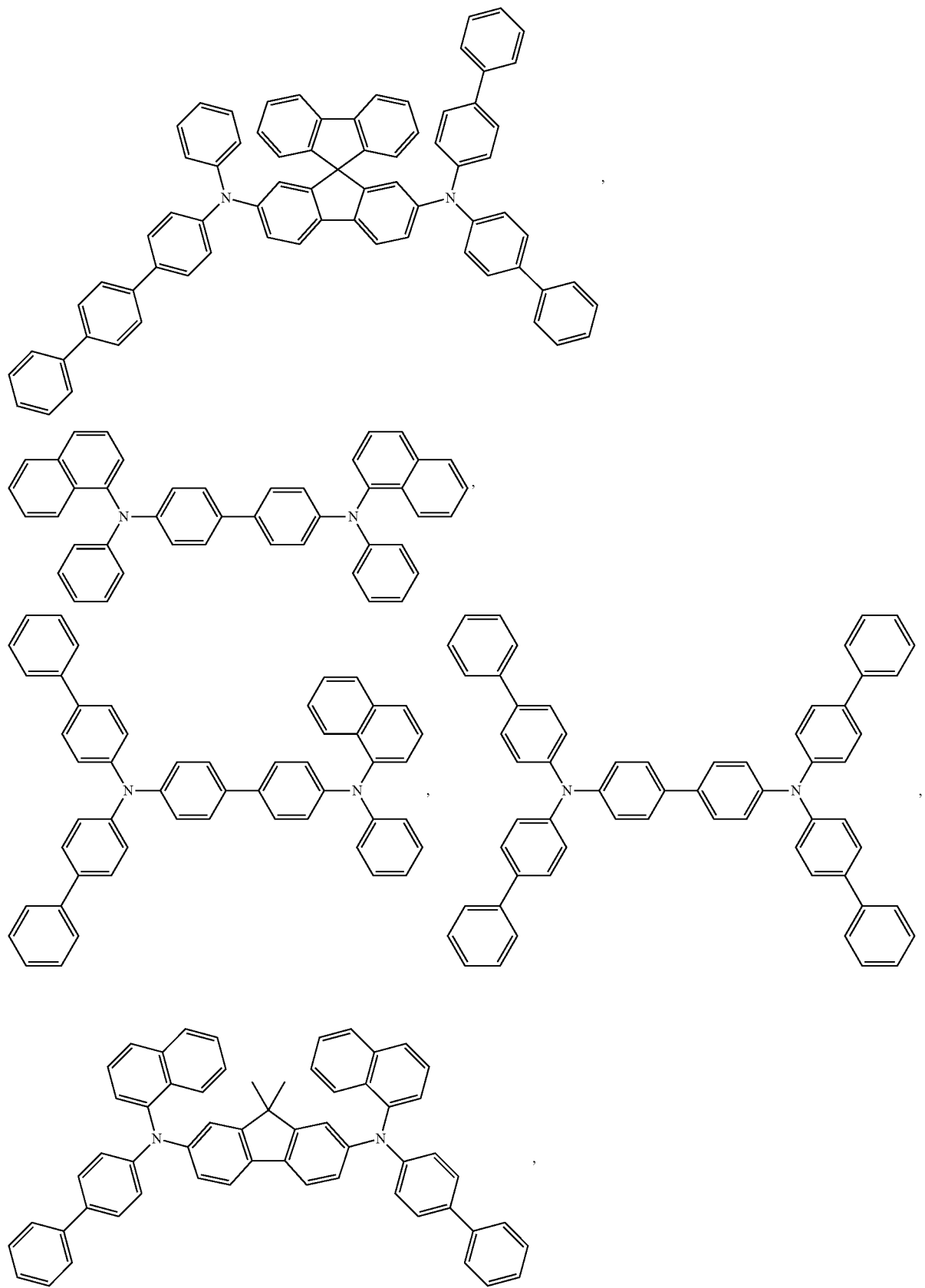

-continued
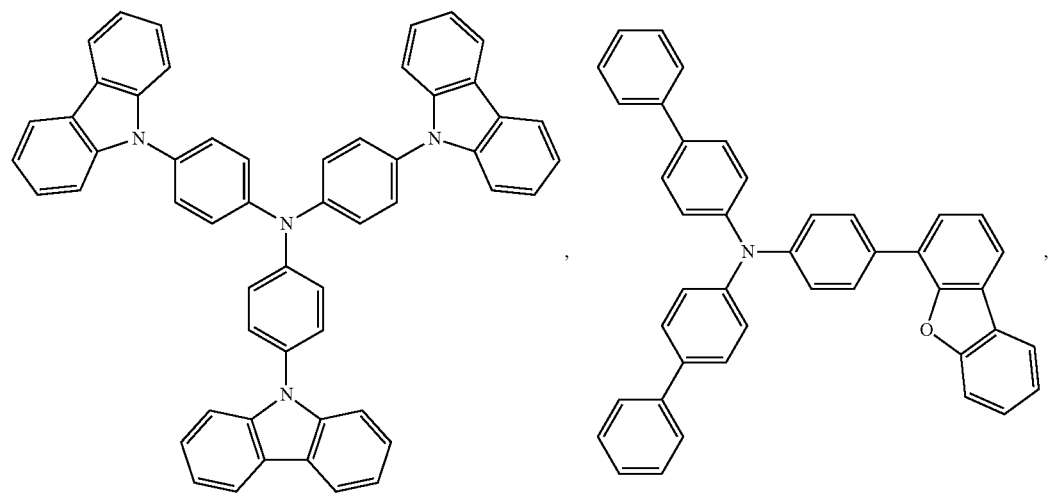
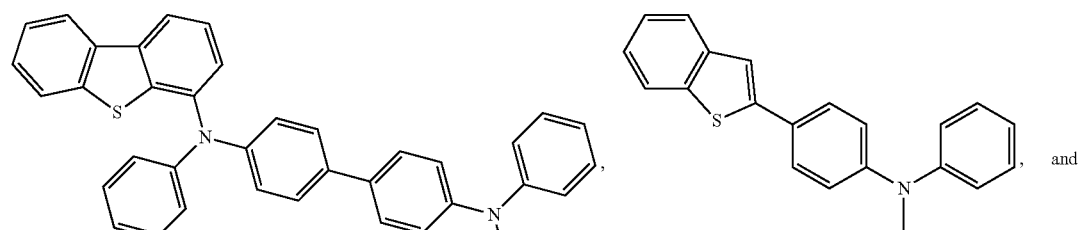
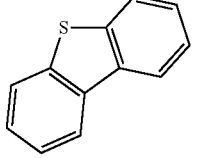 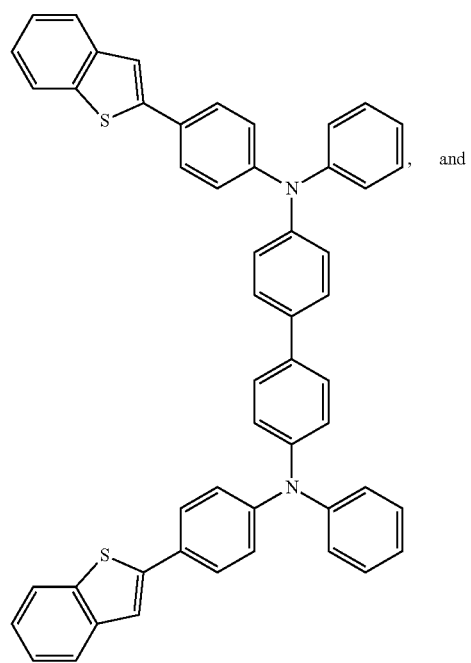
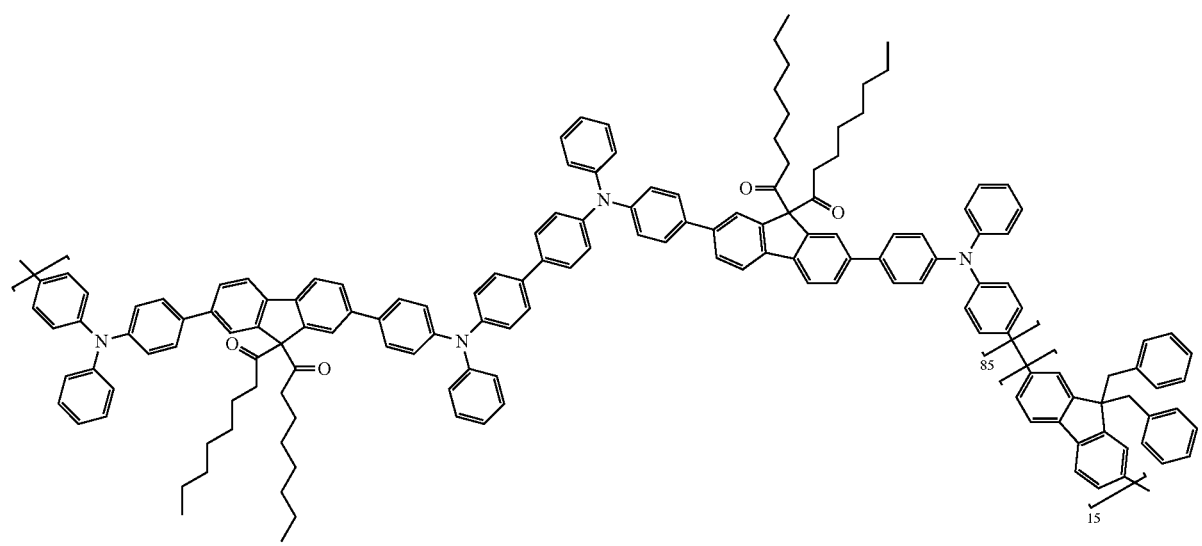

EBL:

An electron blocking layer (EBL) may be used to reduce the number of electrons and/or, excitons that leave the emissive layer. The presence of such a blocking layer in a device may result in substantially higher efficiencies, and or, longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and or higher triplet energy than one or more of the hosts closest to the EBL interface. In one aspect, the compound used in EBL contains the same molecule or the same functional groups used as one of the hosts described below.

Additional Hosts:

The light emitting layer of the organic EL device of the present invention preferably contains at least a metal complex as light emitting dopant material, and may contain one or more additional host materials using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred have the following general formula:

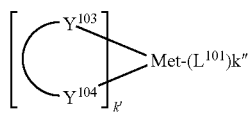

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

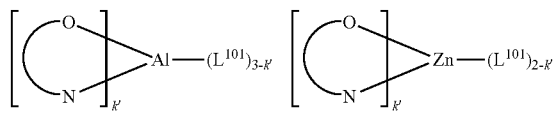

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of other organic compounds used as additional host are selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

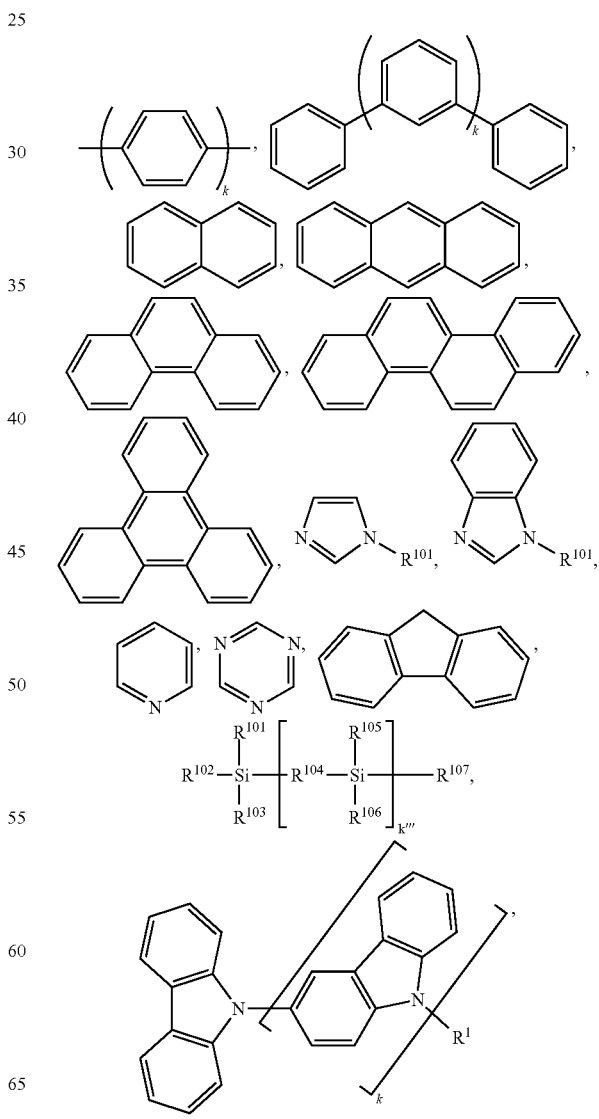

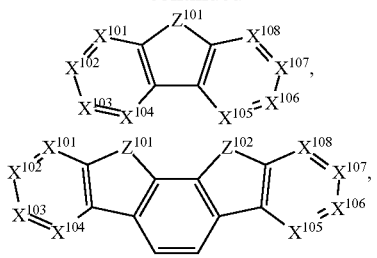

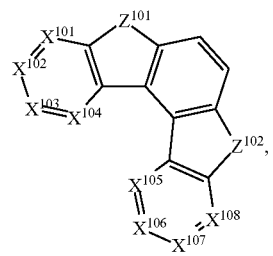

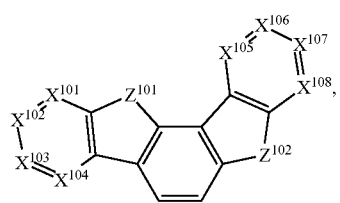

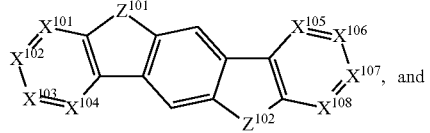

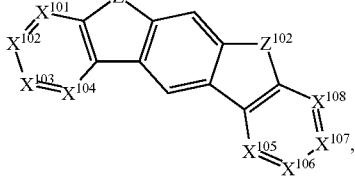

wherein $R^{101}$ to $R^{107}$ is independently selected from the group consisting of hydrogen, deuterium, halide, alkyl, cycloalkyl, heteroalkyl, alkoxy, aryloxy, amino, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k'" is an integer from 0 to 20. $X^{101}$ to $X^{108}$ to is selected from C (including CH) or N.

$Z^{101}$ and $Z^{102}$ is selected from $NR^{101}$, O, or S.

Non-limiting examples of the additional host materials that may be used in an MED in combination with the host compound disclosed herein are exemplified below together with references that disclose those materials: EP2034538, EP2034538A, EP2757608, JP2007254297. :KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472,

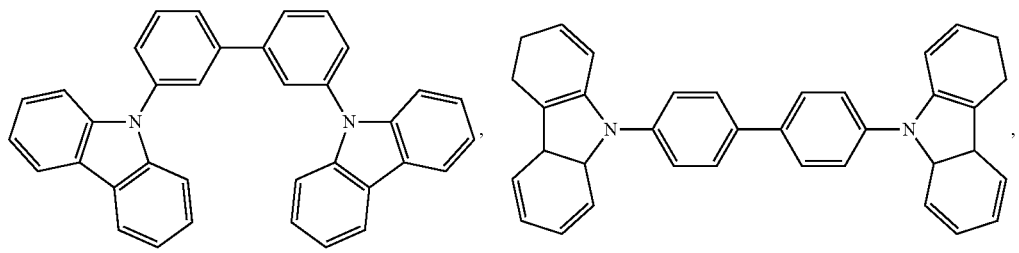

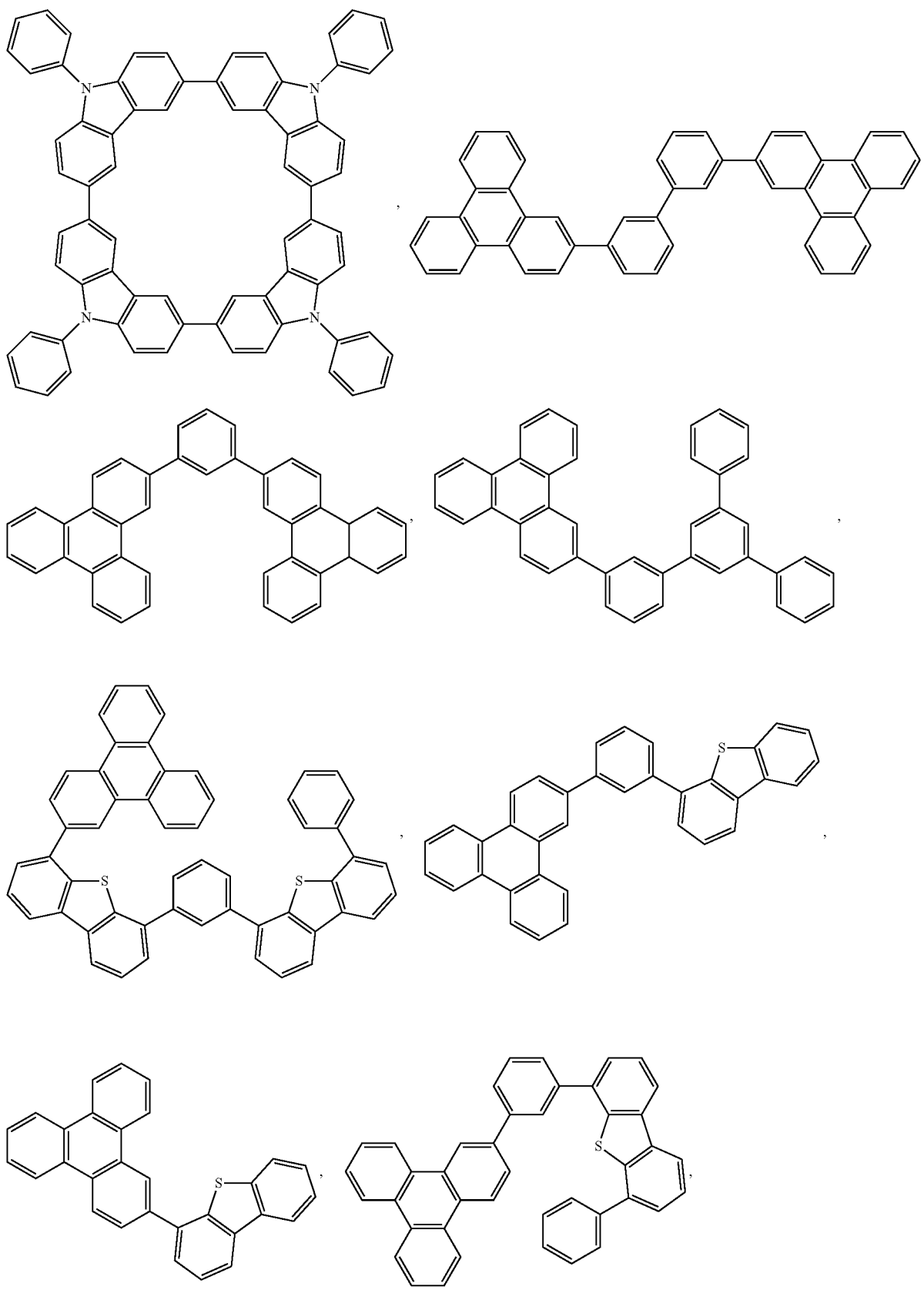

-continued
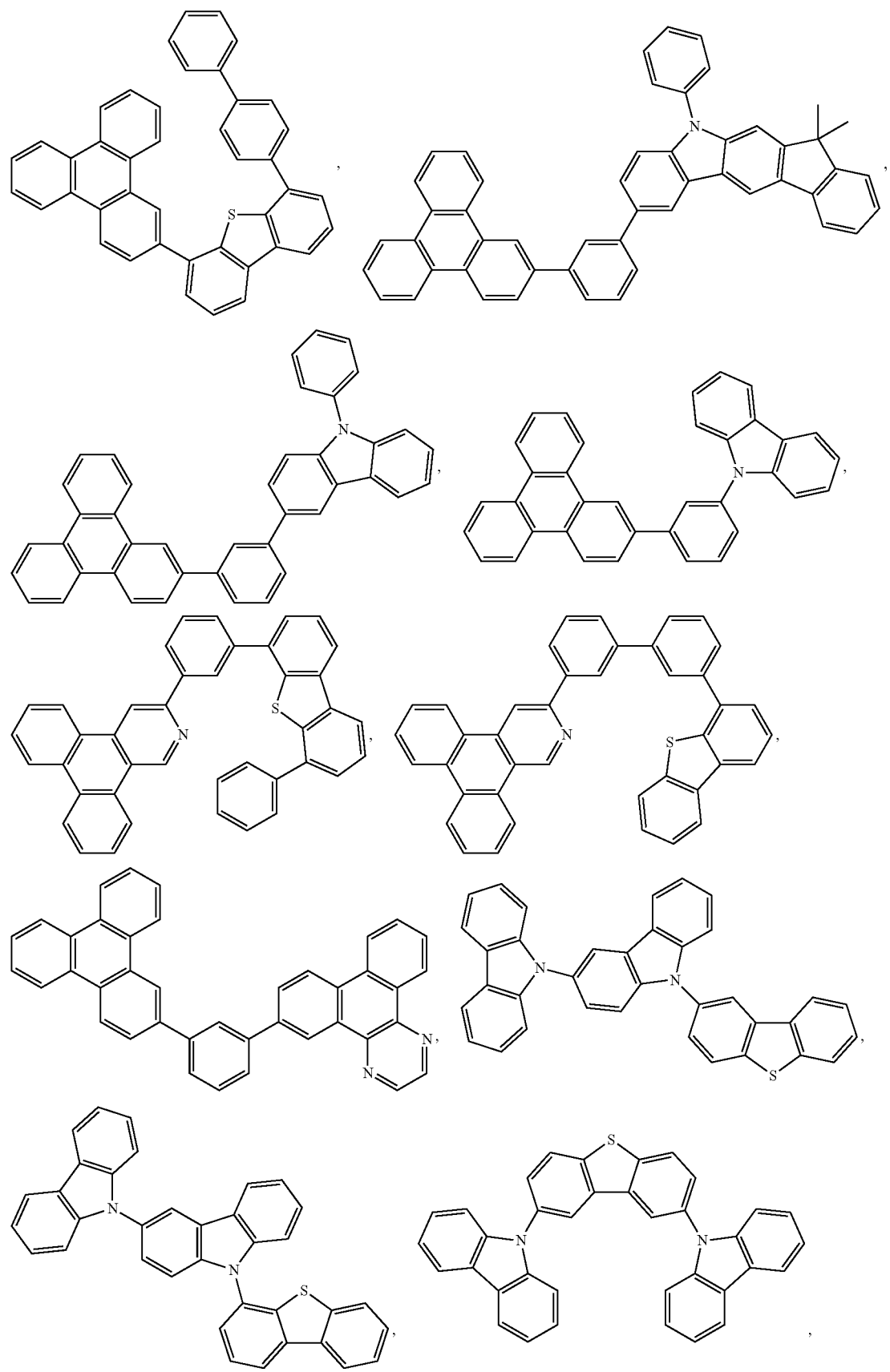

193 194
-continued
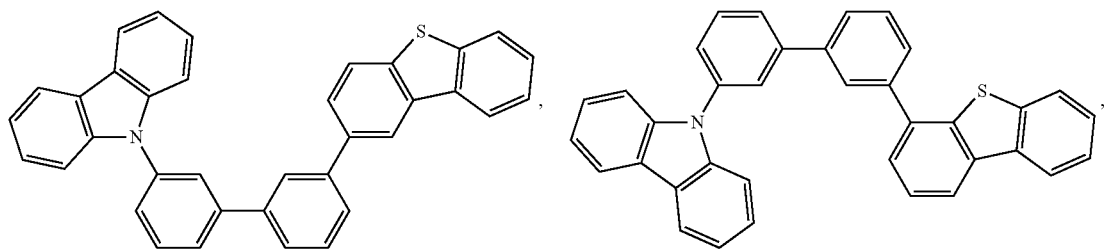
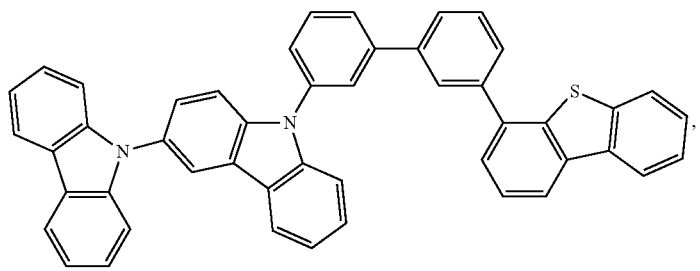
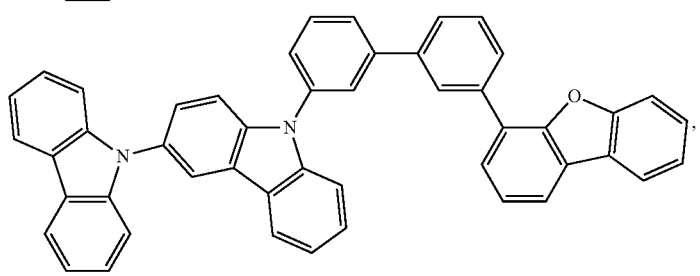
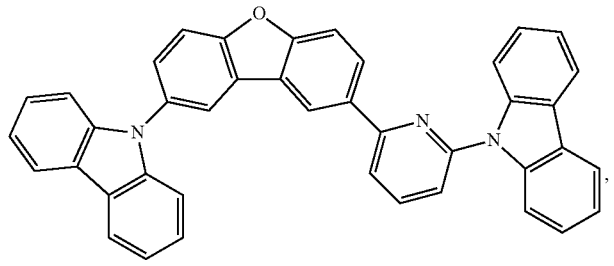
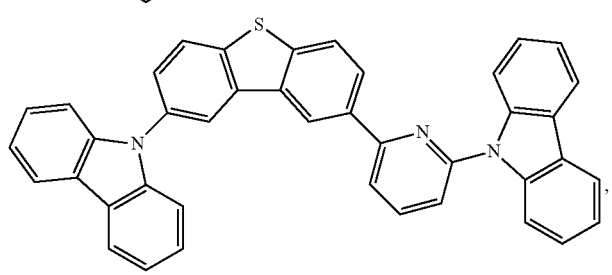
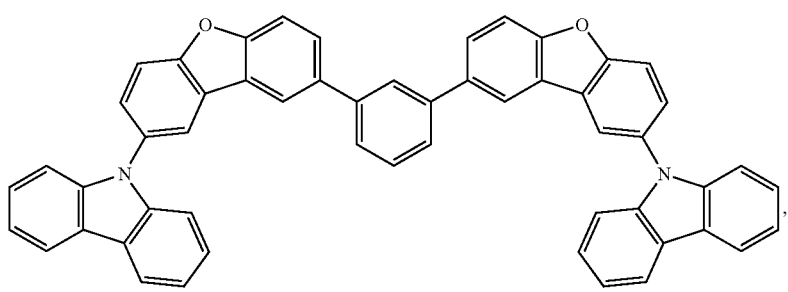

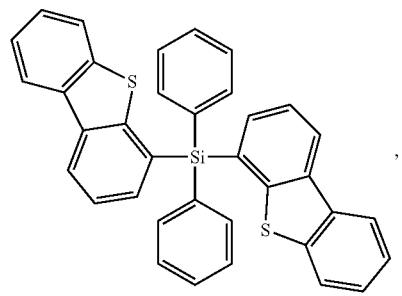
,
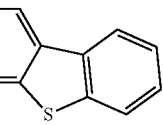
,
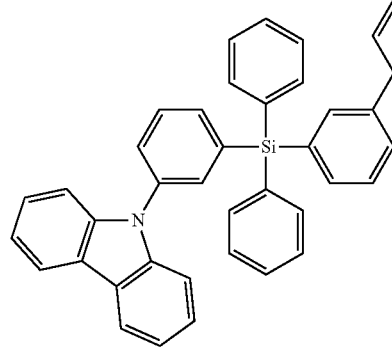
,
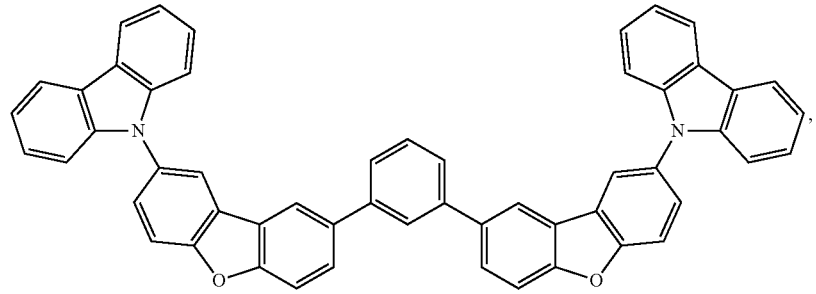
,
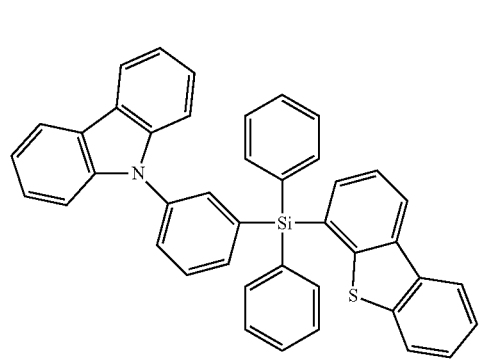
,
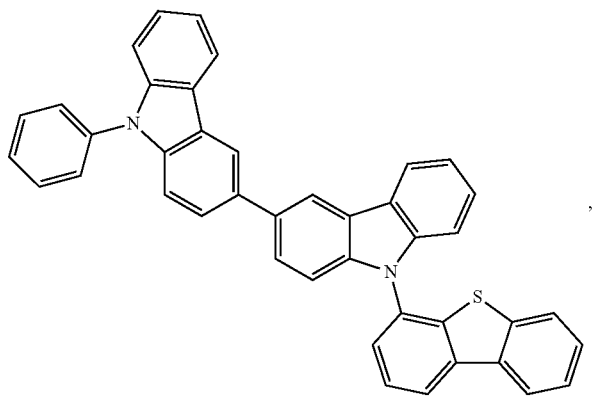
,
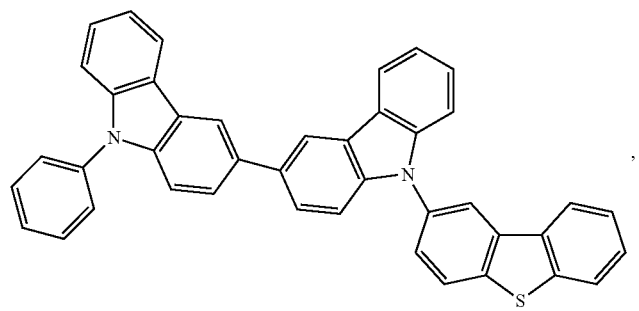
,

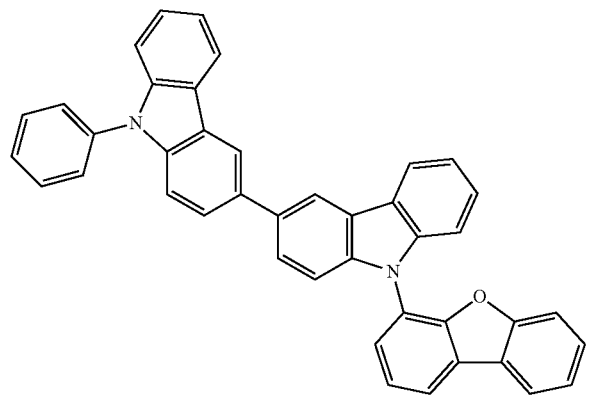
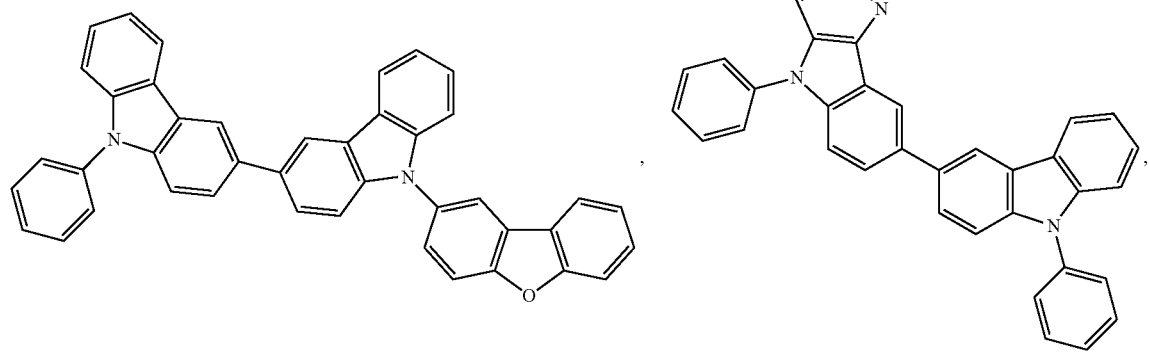
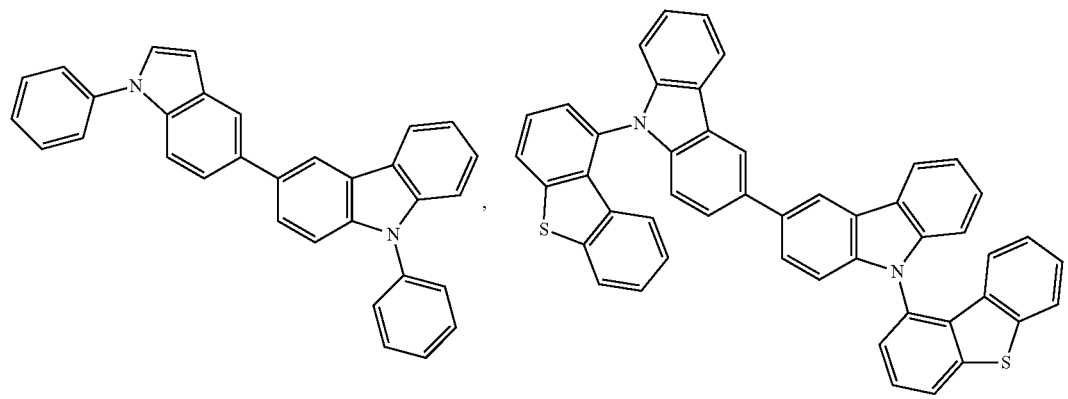
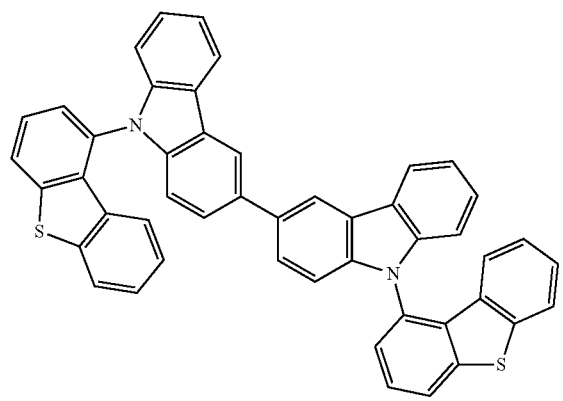

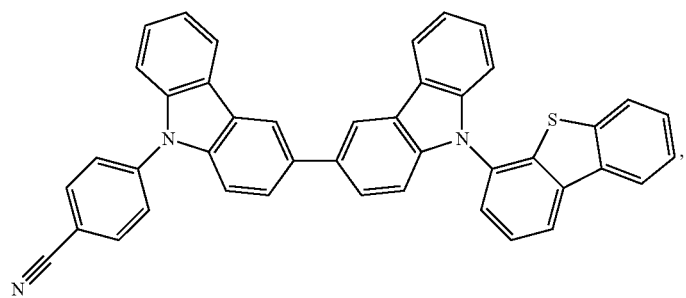
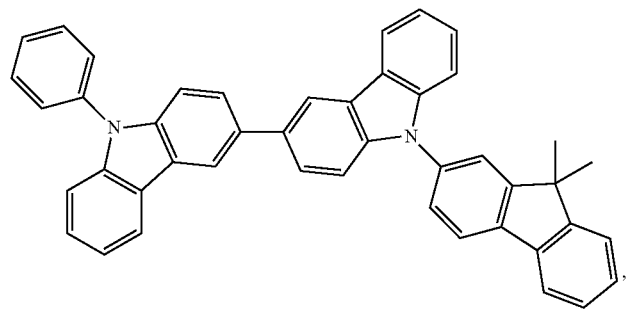
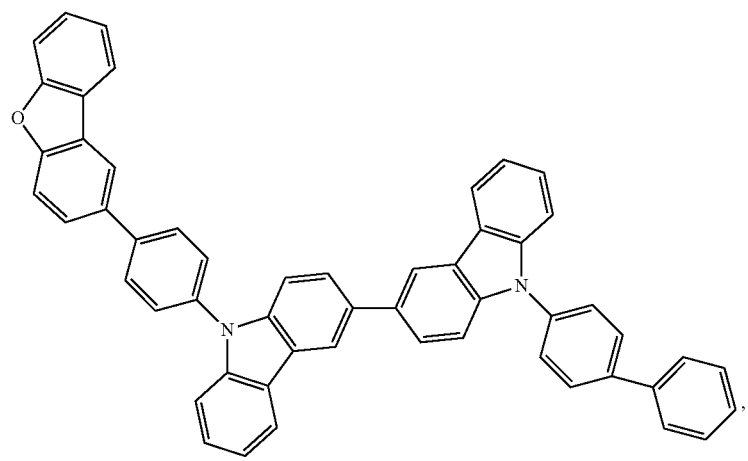
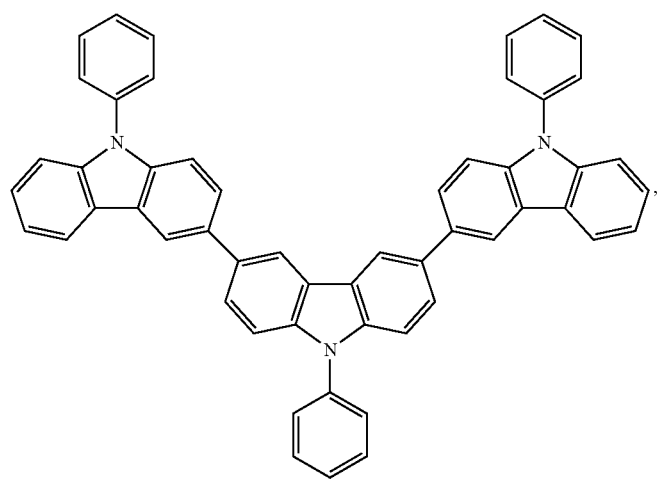

-continued
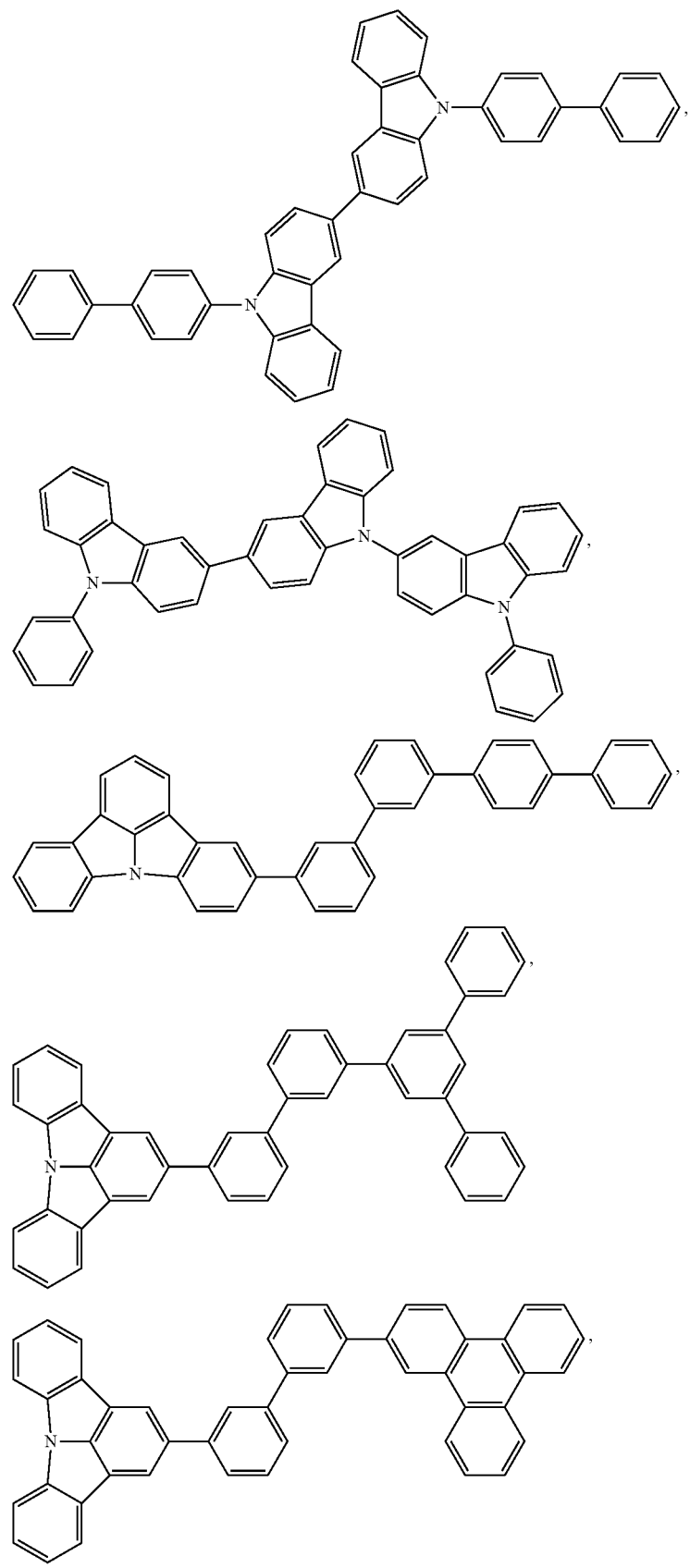

-continued
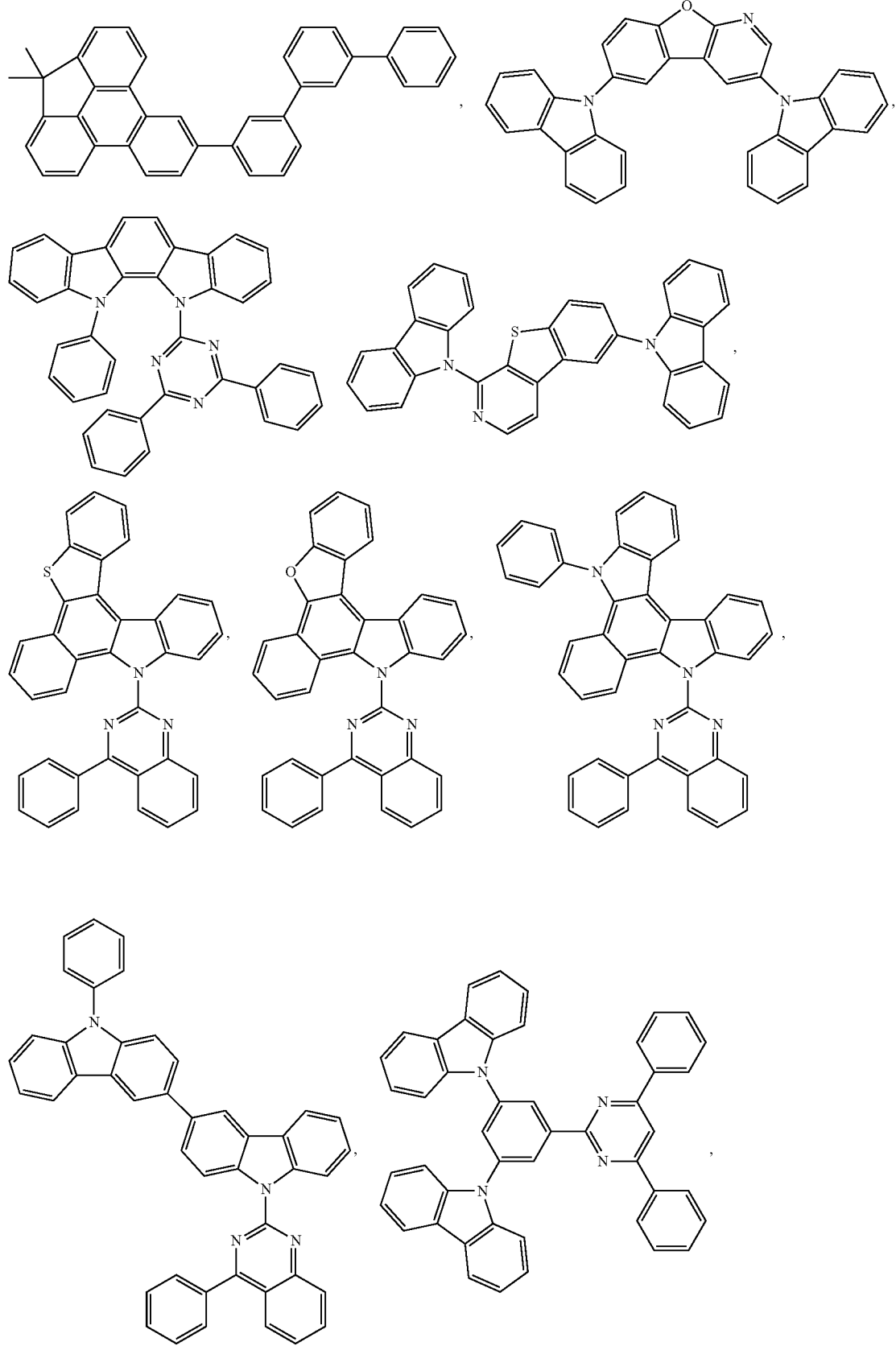

205
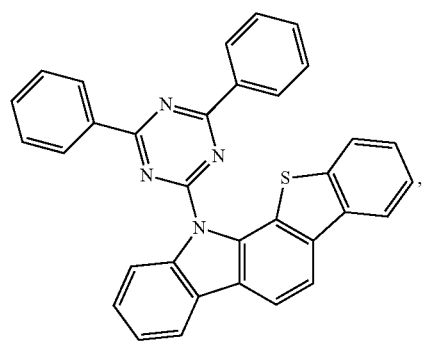
206
-continued
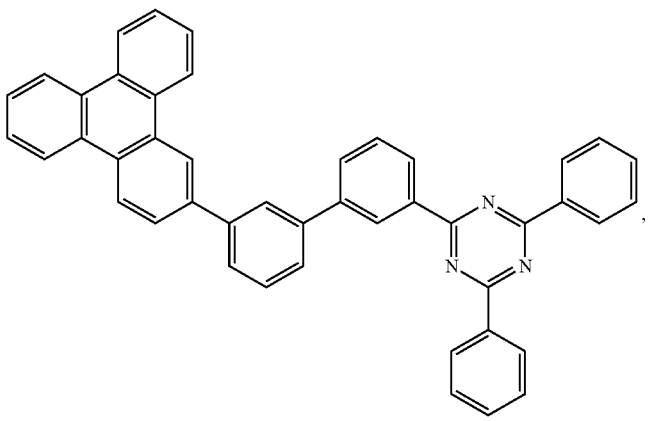
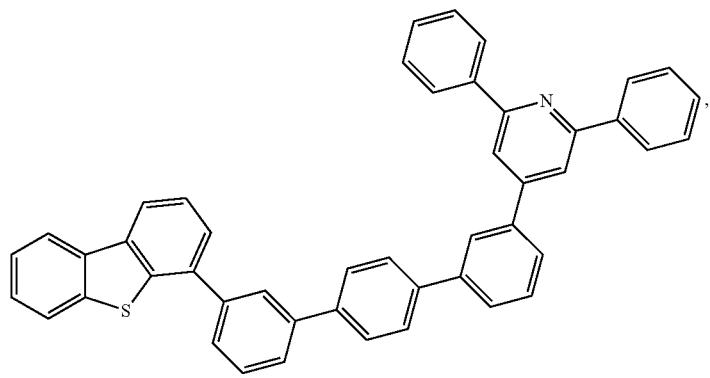
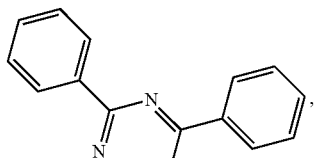
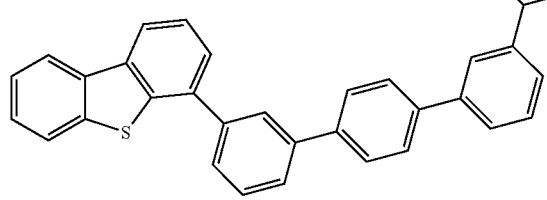
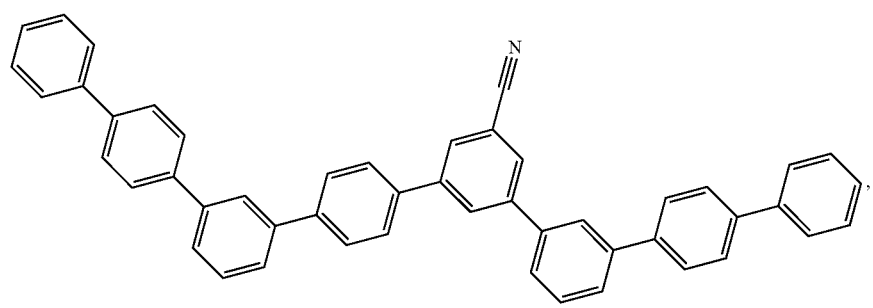

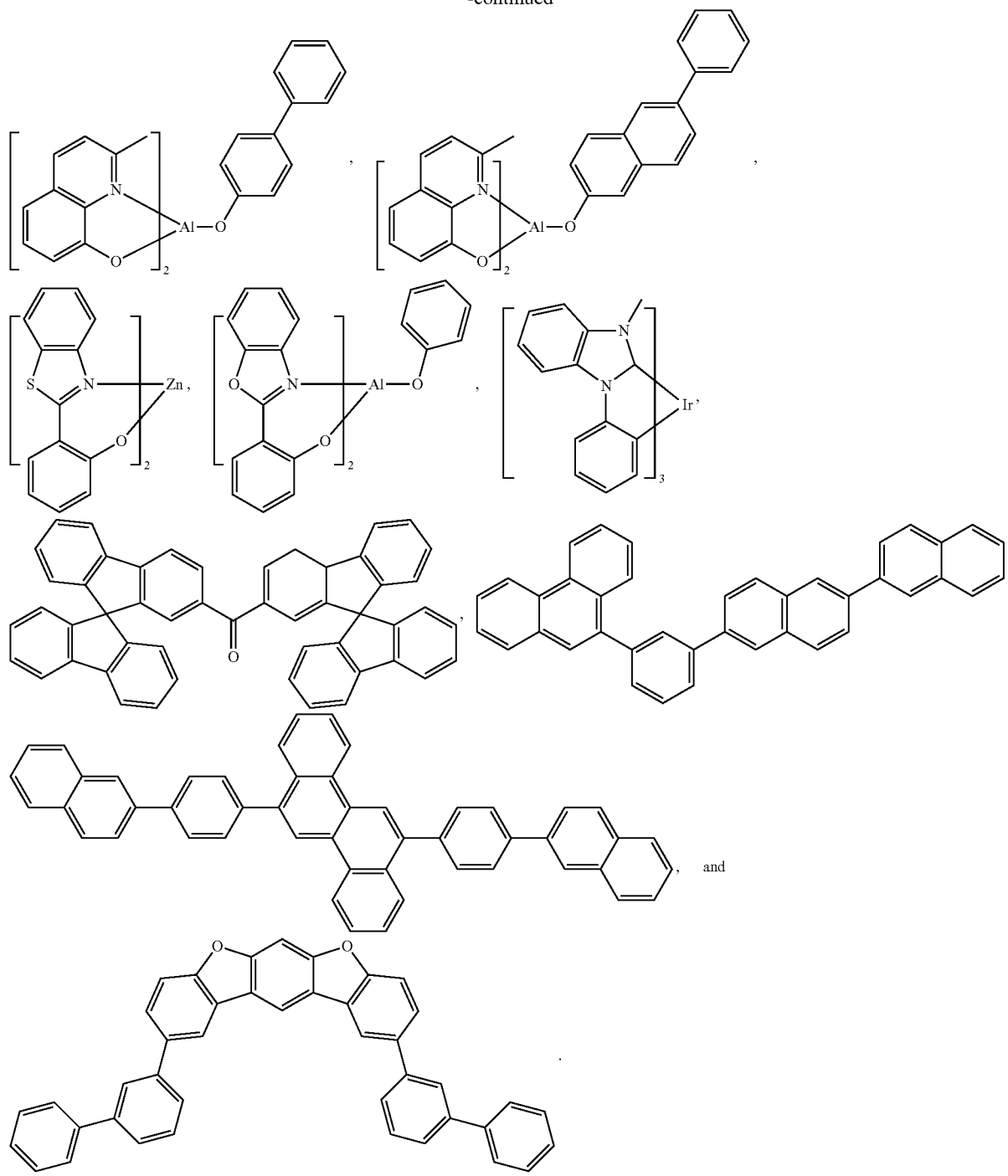

Emitter:

An emitter example is not particularly limited, and any compound may be used as long as the compound is typically used as an emitter material. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an MED in combination with materials disclosed herein are exemplified below together with references that disclose those materials: CN103694277, CN1696137, 0301238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, US06699599, US06916554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863; US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. No. 6,303,238, U.S. Pat. No. 6,413,656, U.S. Pat. No. 6,653,654, U.S. Pat. NO. 6,670,645, U.S. Pat. No. 6,687,266, U.S. Pat. No. 6,835,469, U.S. Pat. No. 6,921,915, U.S. Pat. No. 7,279,704, U.S. Pat. No. 7,332,232, U.S. Pat. No. 7,378,162, U.S. Pat. No. 7,534,505, U.S. Pat. No. 7,675,228, U.S. Pat. No. 7,728,137, U.S. Pat. No. 7,740,957, U.S. Pat. No. 7,759,489, U.S. Pat. No. 7,951,947, U.S. Pat. No. 8,067,099, U.S. Pat. No. 8,592,586, U.S. Pat. No. 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089. WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450, -continued

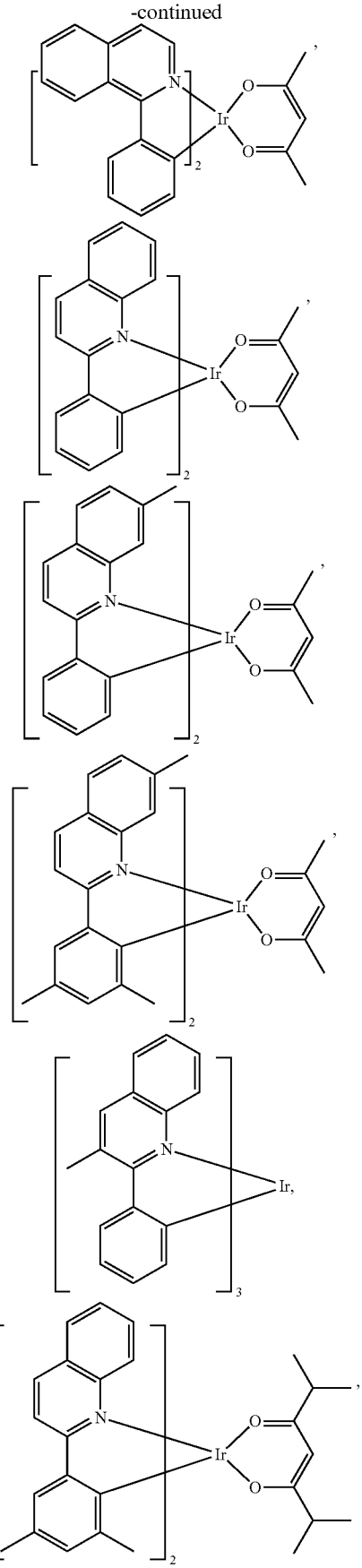

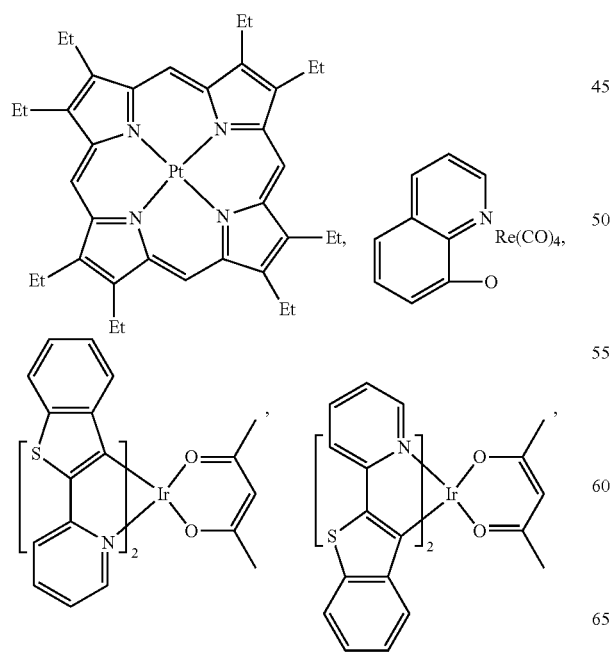

211
-continued
212
-continued
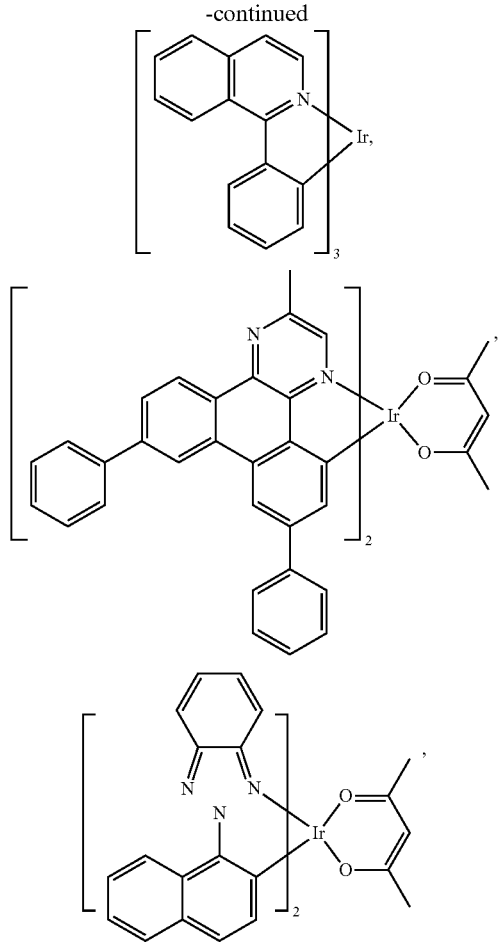
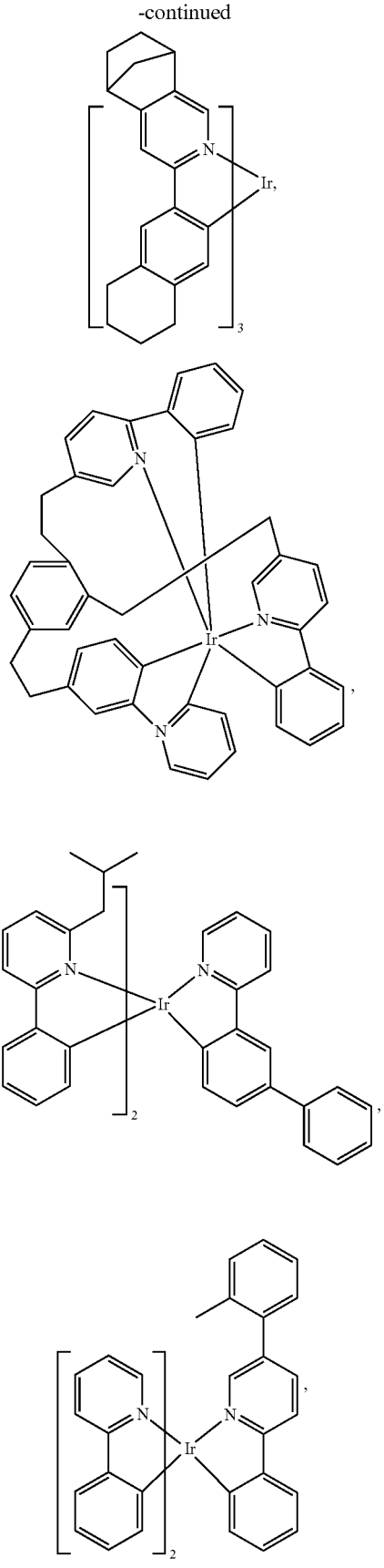

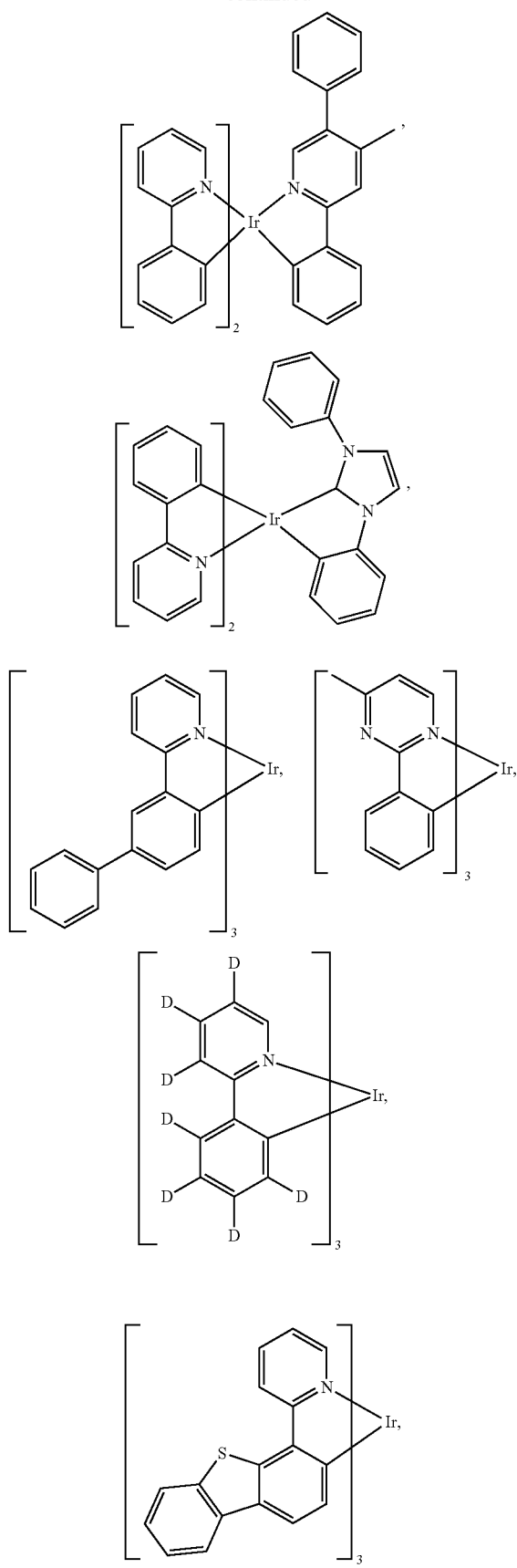
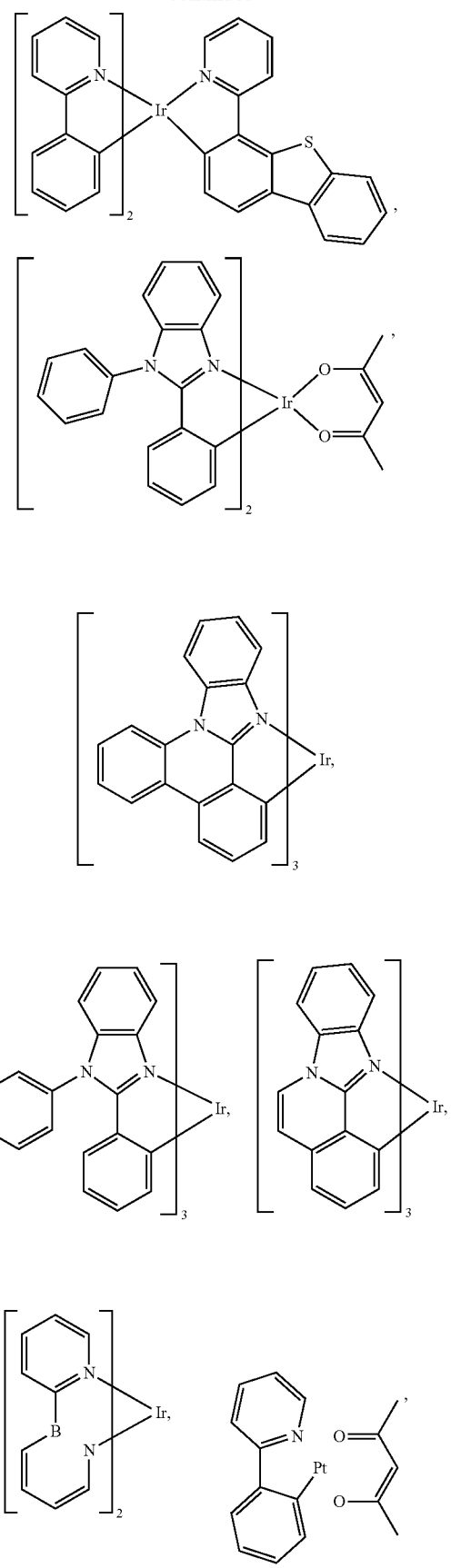

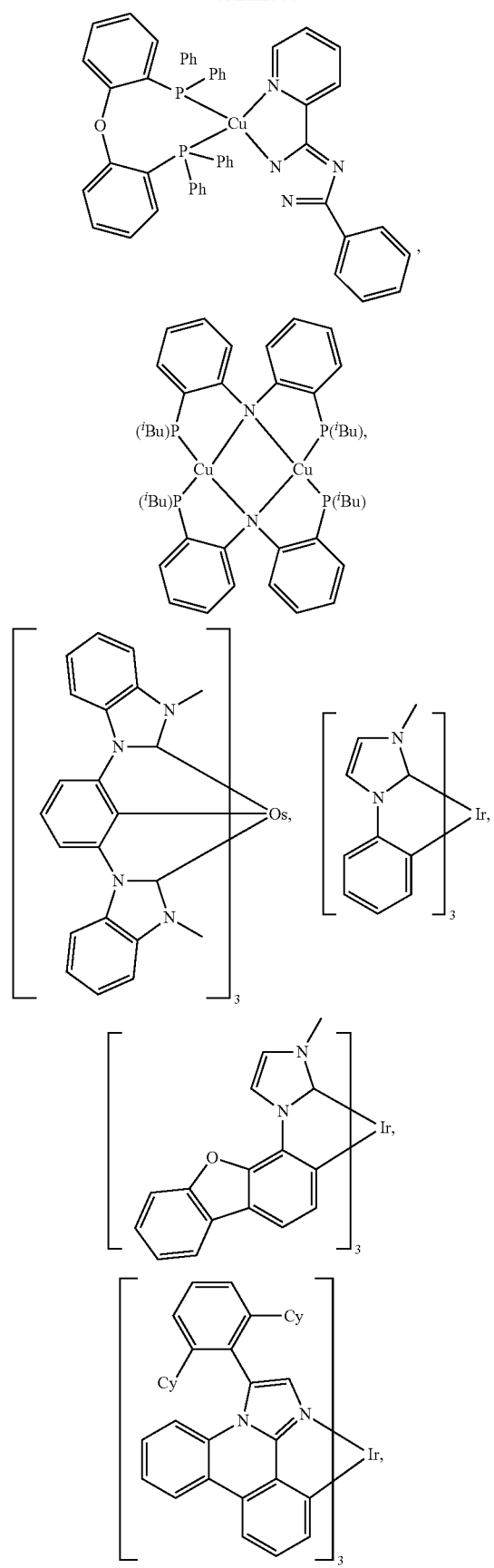
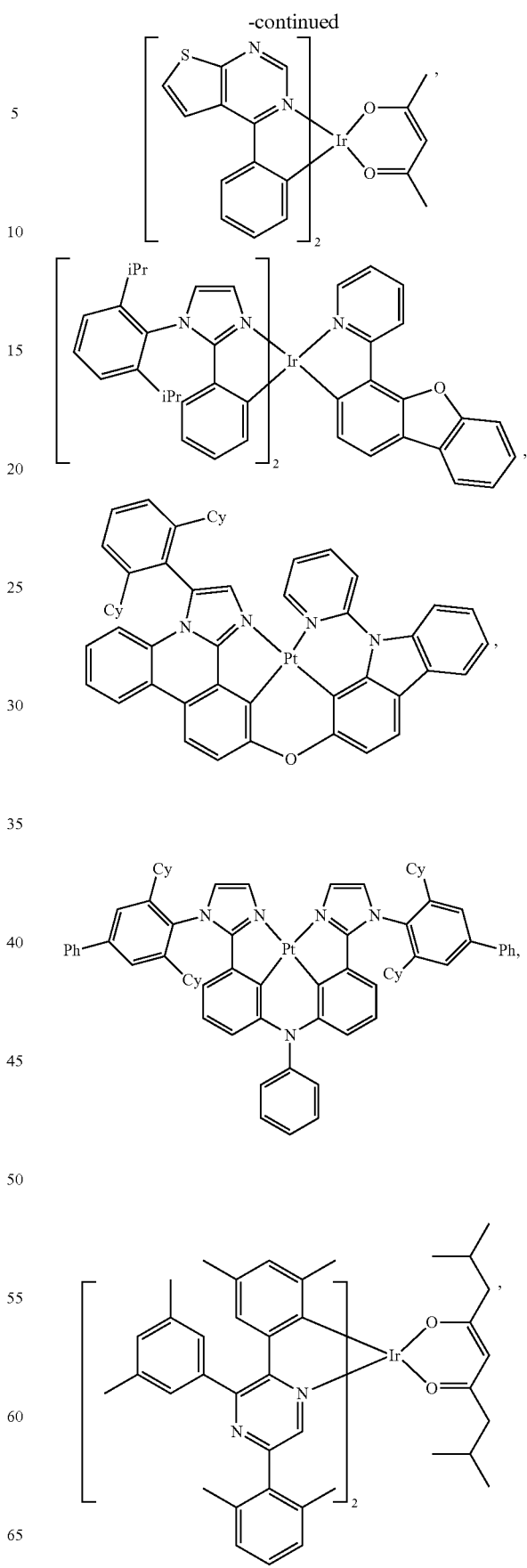

217
-continued
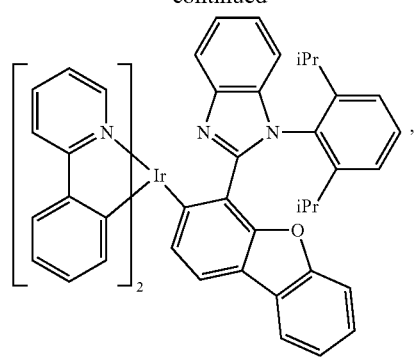
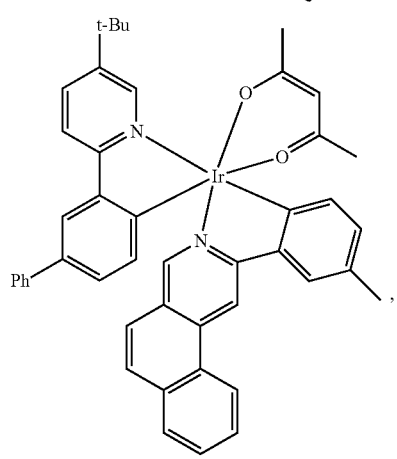
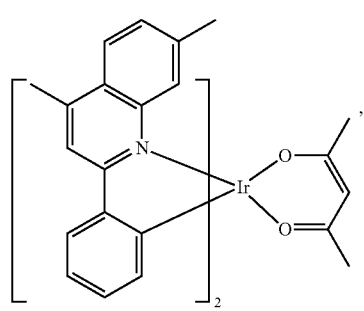
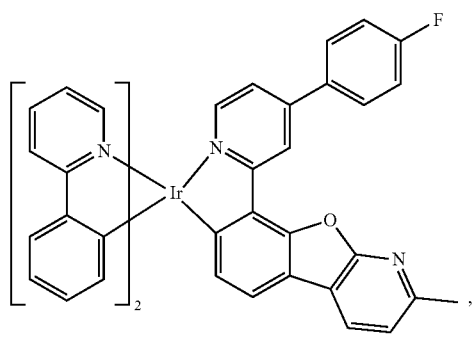
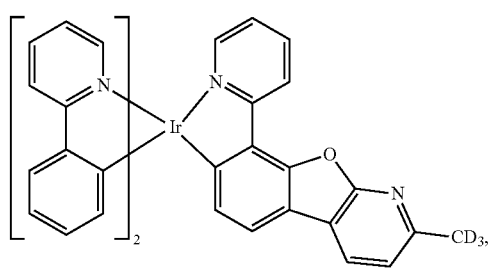
218
-continued
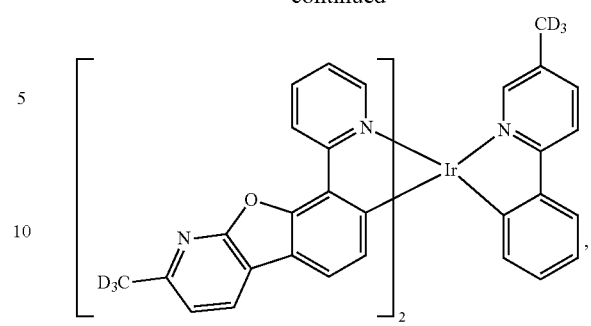
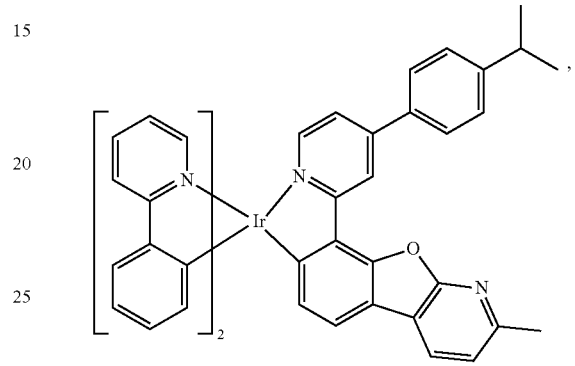
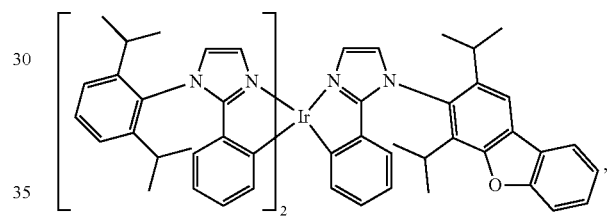
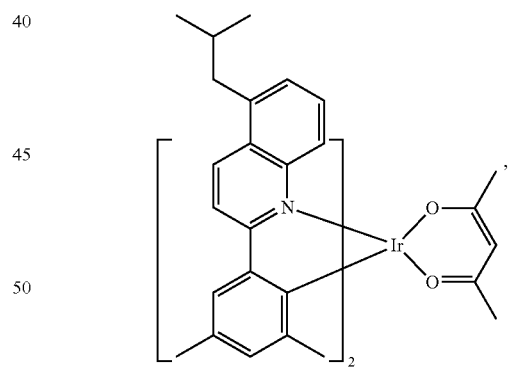
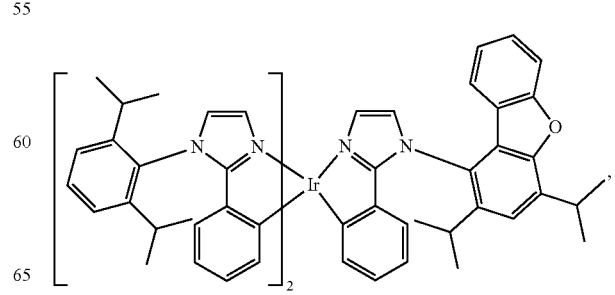

-continued
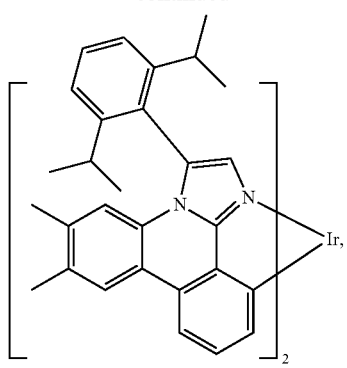
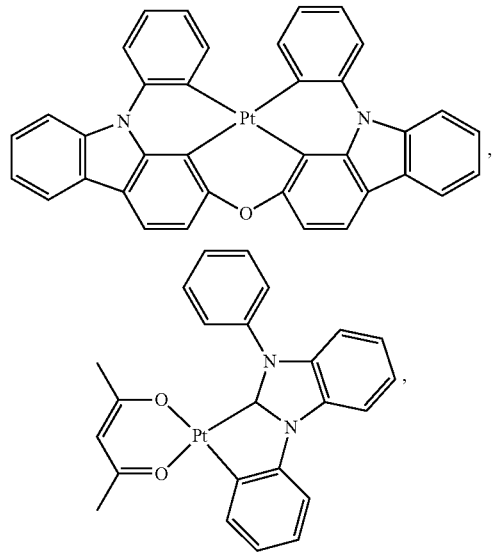
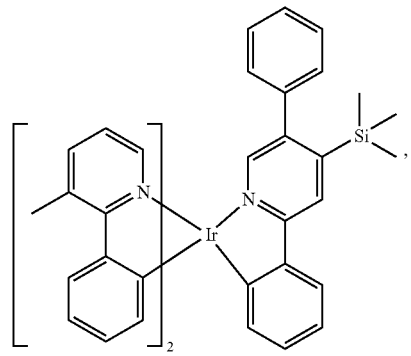
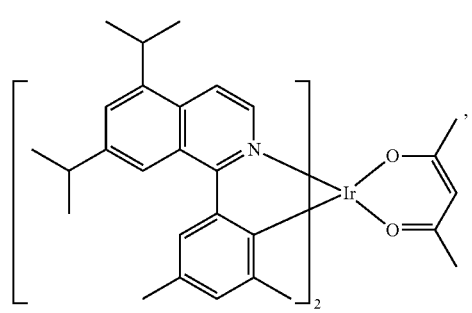
-continued
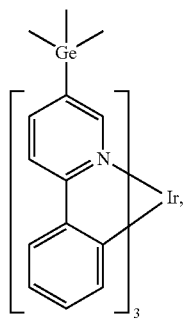
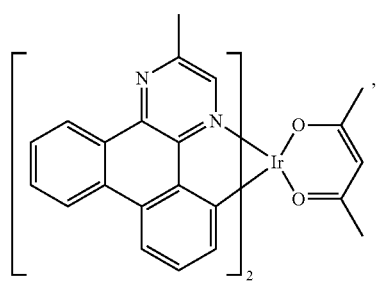
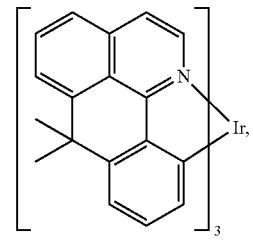

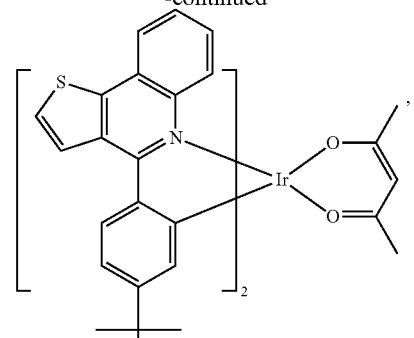
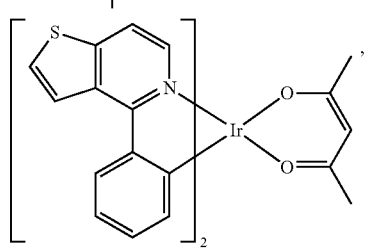
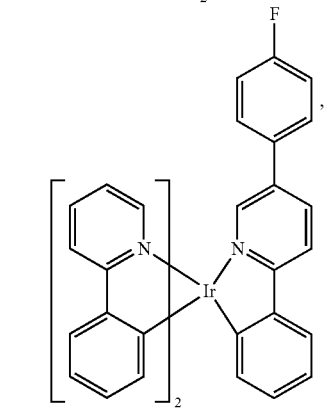
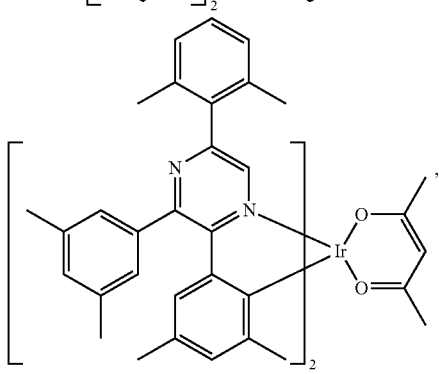
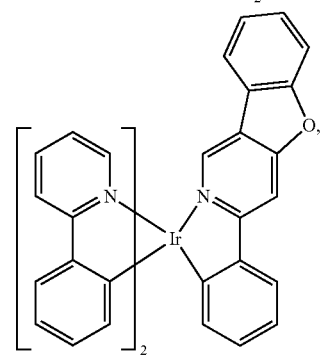
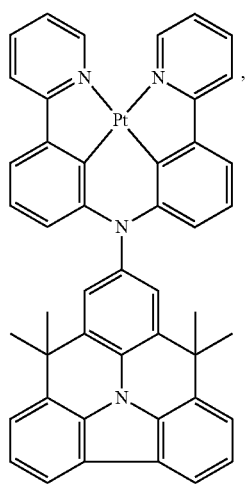
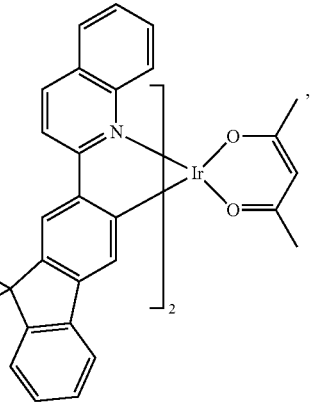
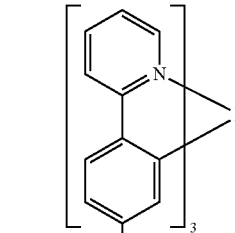
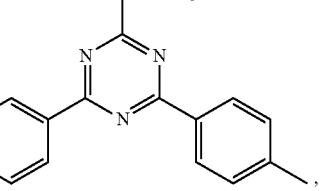
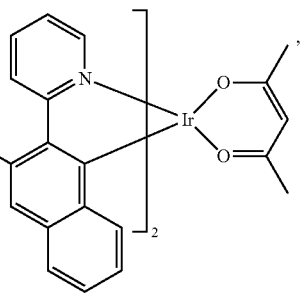

223
-continued
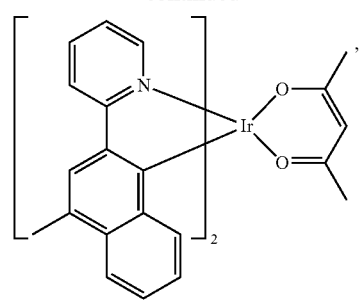
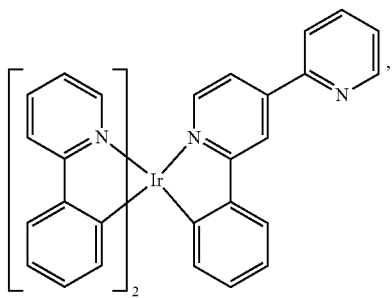
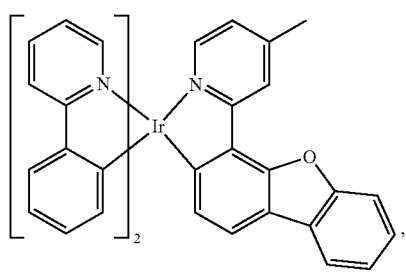
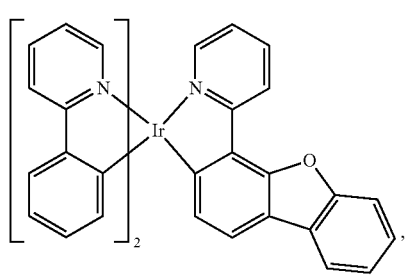
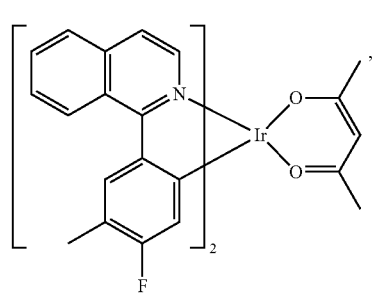
224
-continued
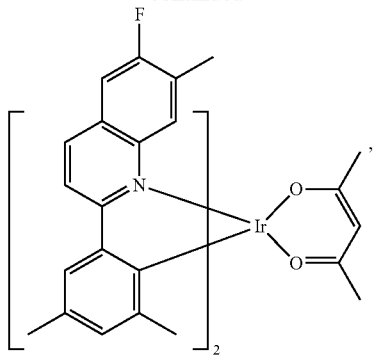
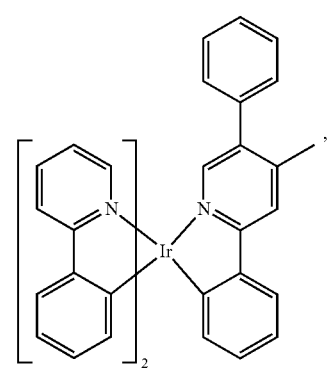
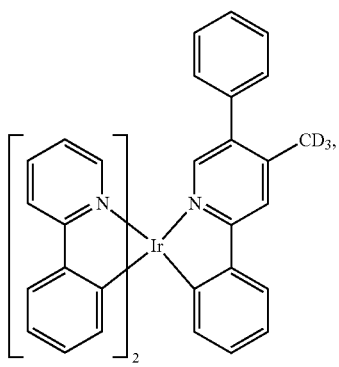
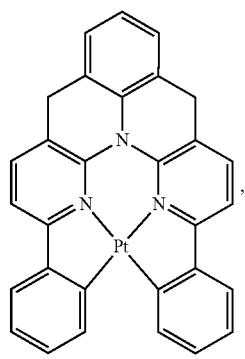

-continued
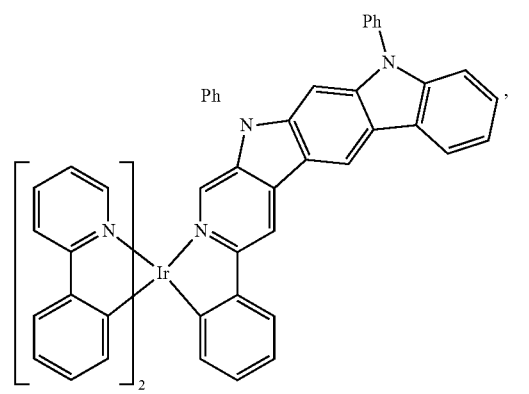
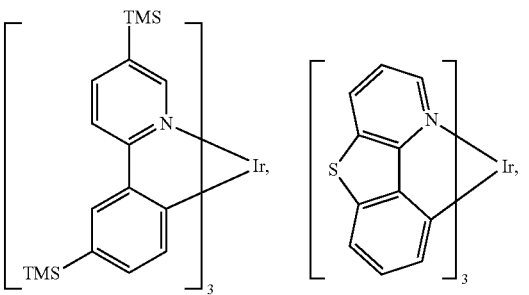
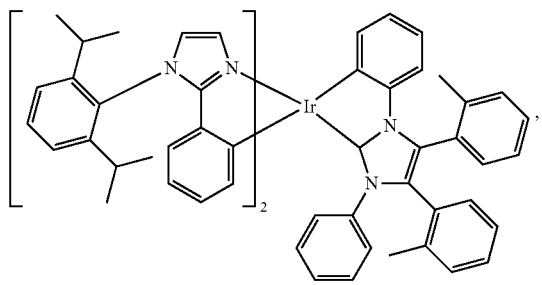
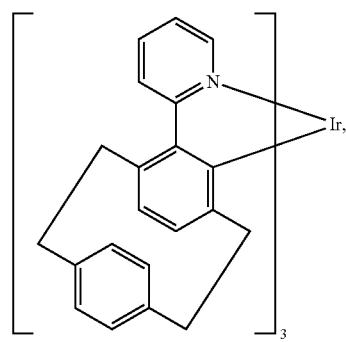
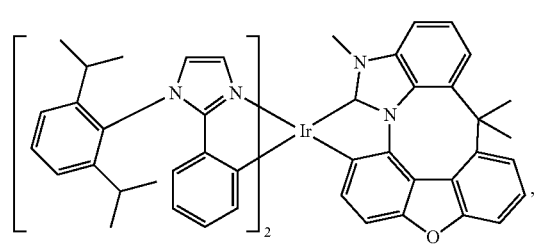
-continued
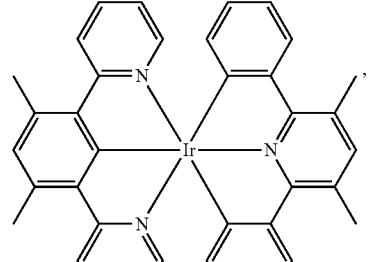
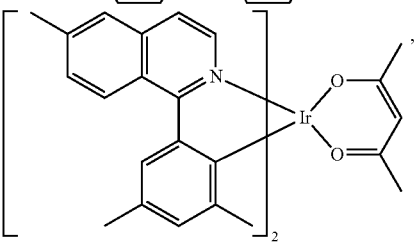
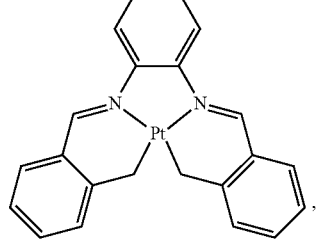
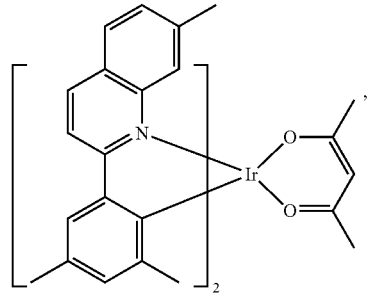
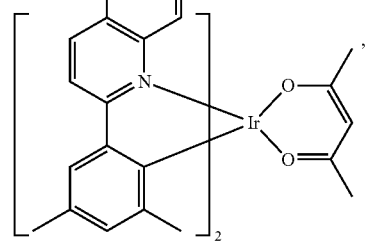
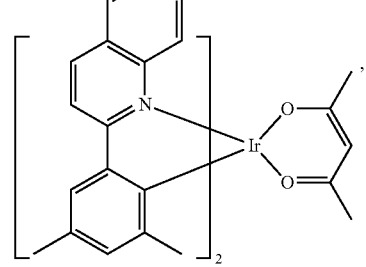

227
-continued
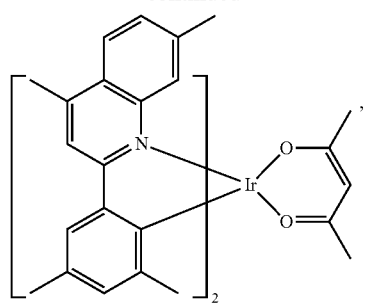
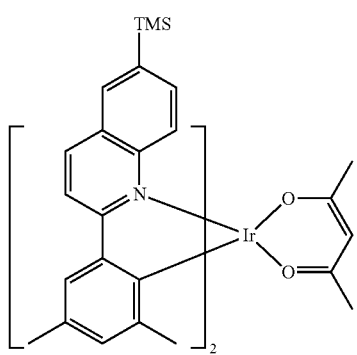
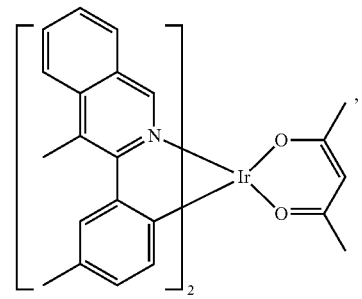
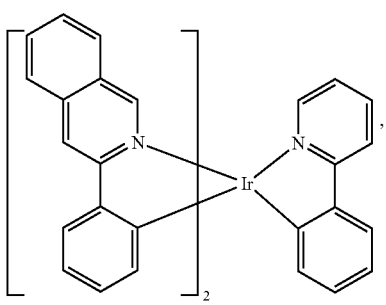
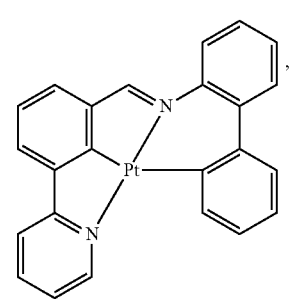
228
-continued
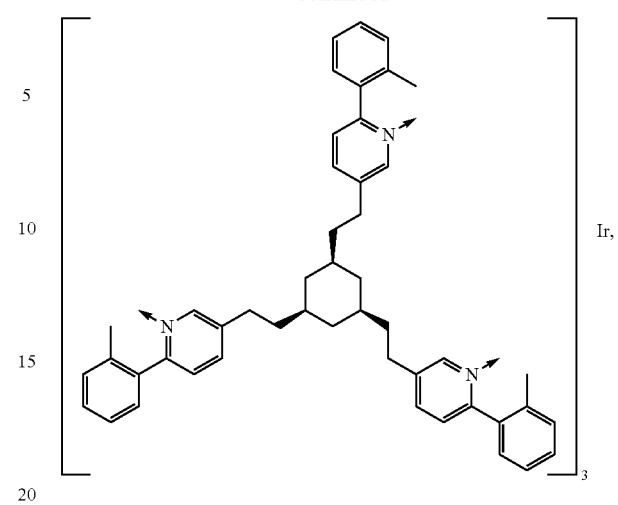
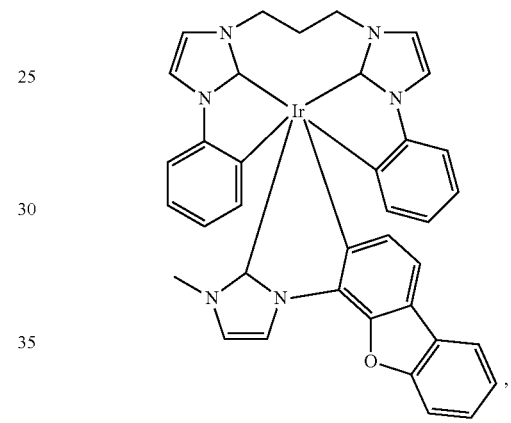
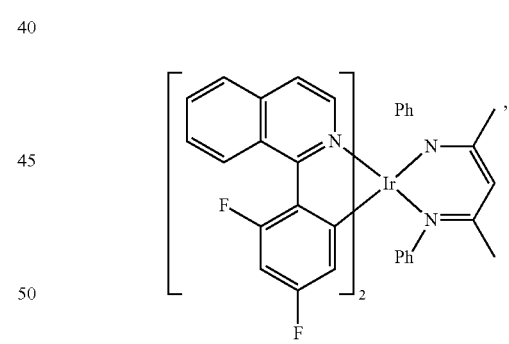
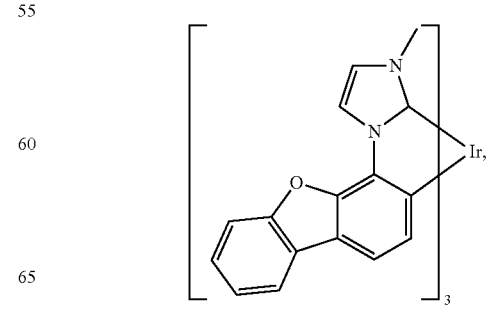

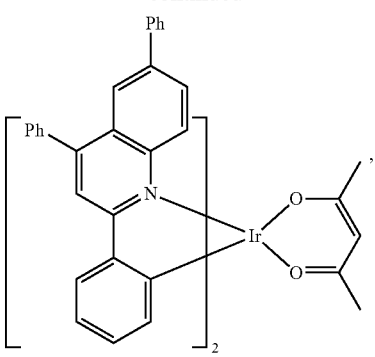
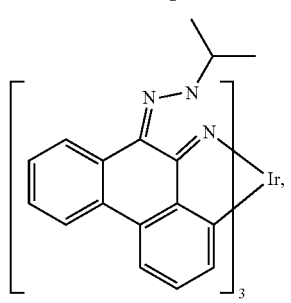
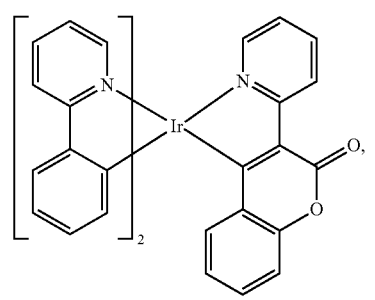
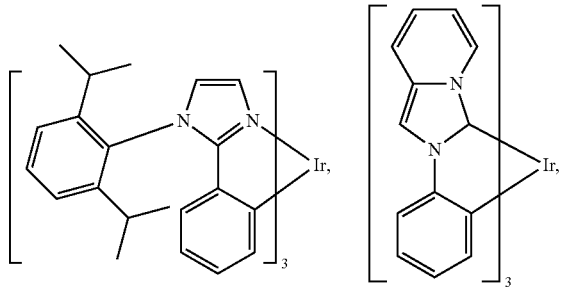
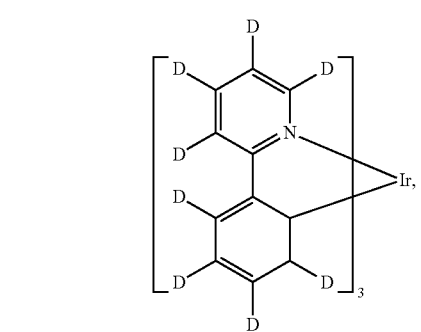
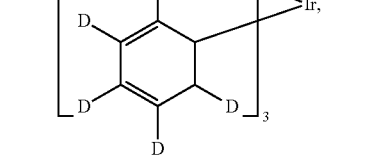
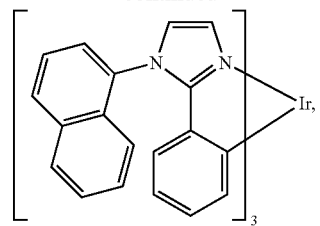
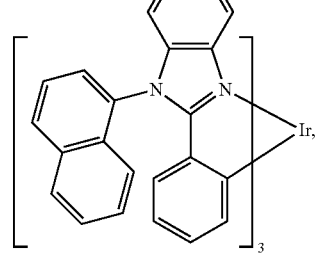
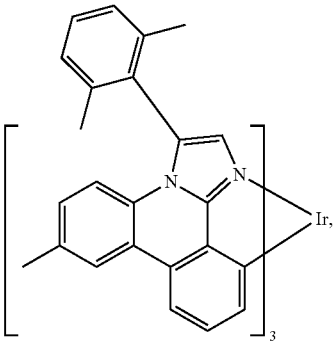
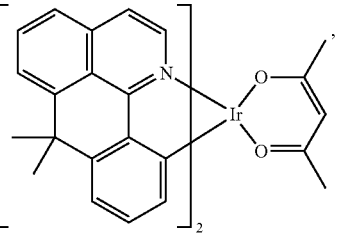
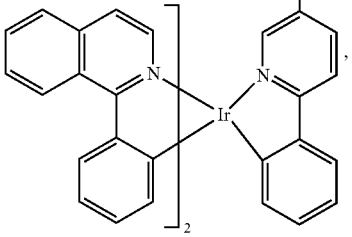
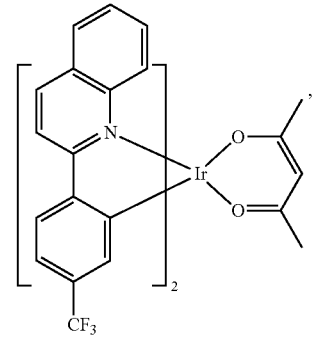

-continued

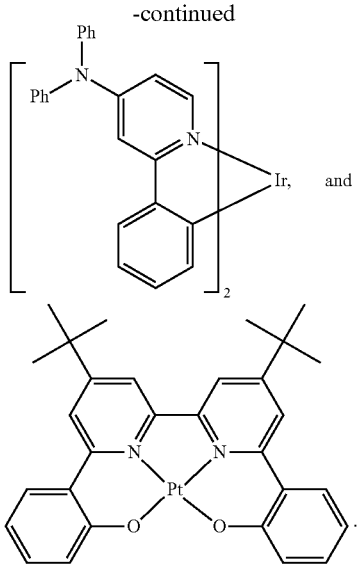

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED In some embodiments, the HBL material has a lower HOMO (further from the vacuum level) and or higher triplet energy than the emitter closest to the HBL interface. In some embodiments, the HBL material has a lower HOMO (further from the vacuum level) and or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

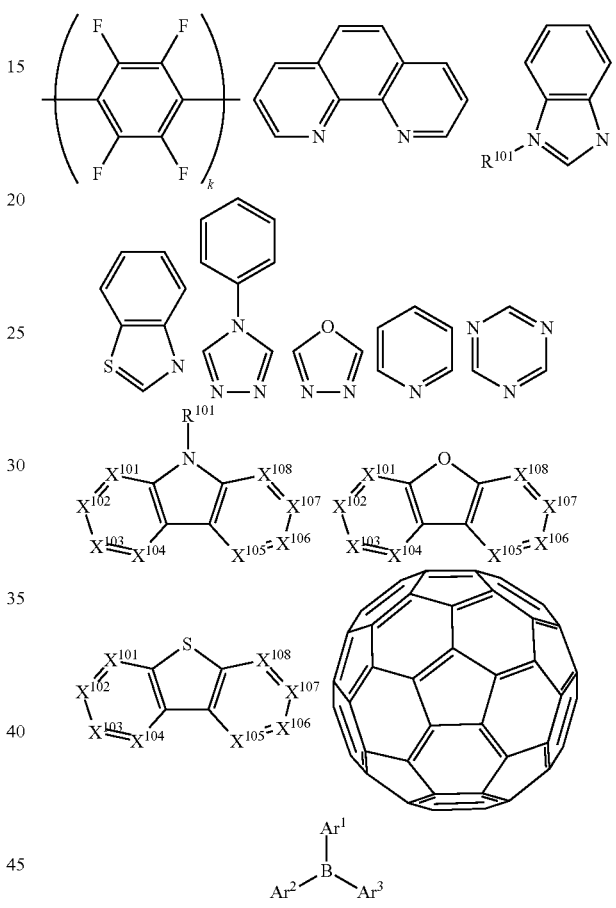

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above, $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL include, but are not limited to the following general formula:

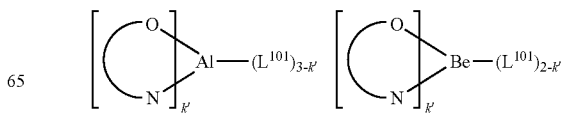

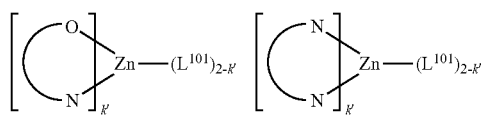

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL, materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. No. 6,656,612, U.S. Pat. No. 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

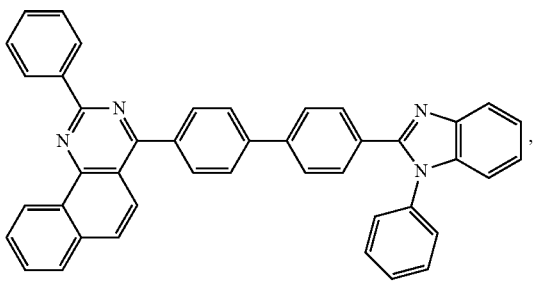

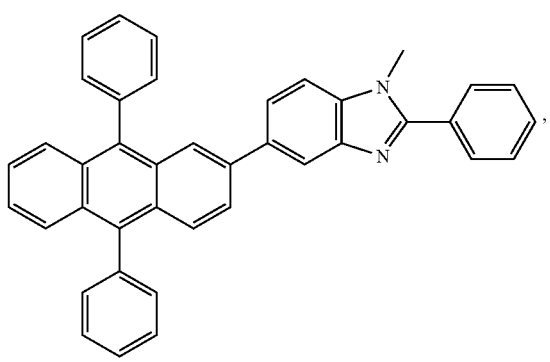

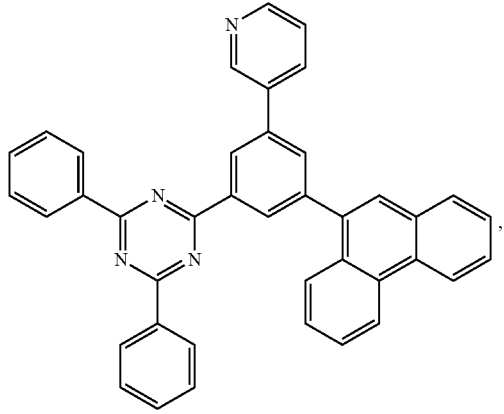

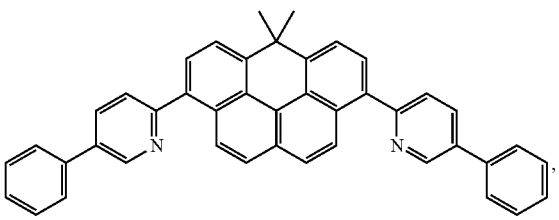

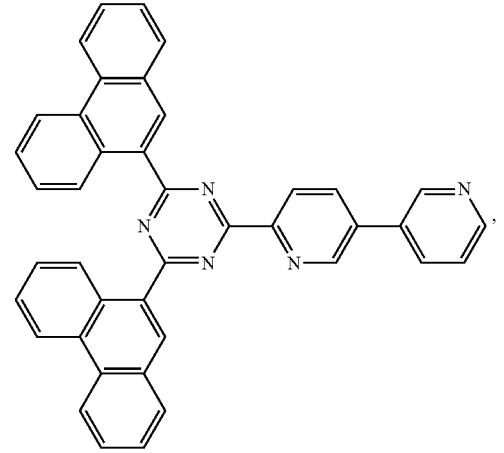

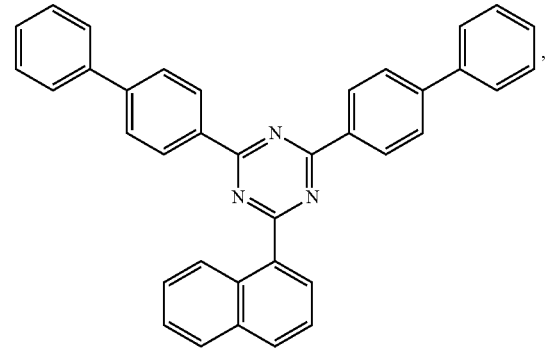

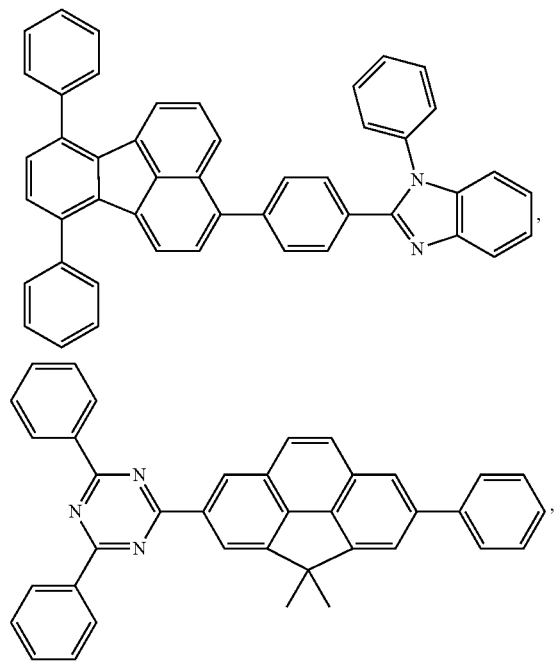
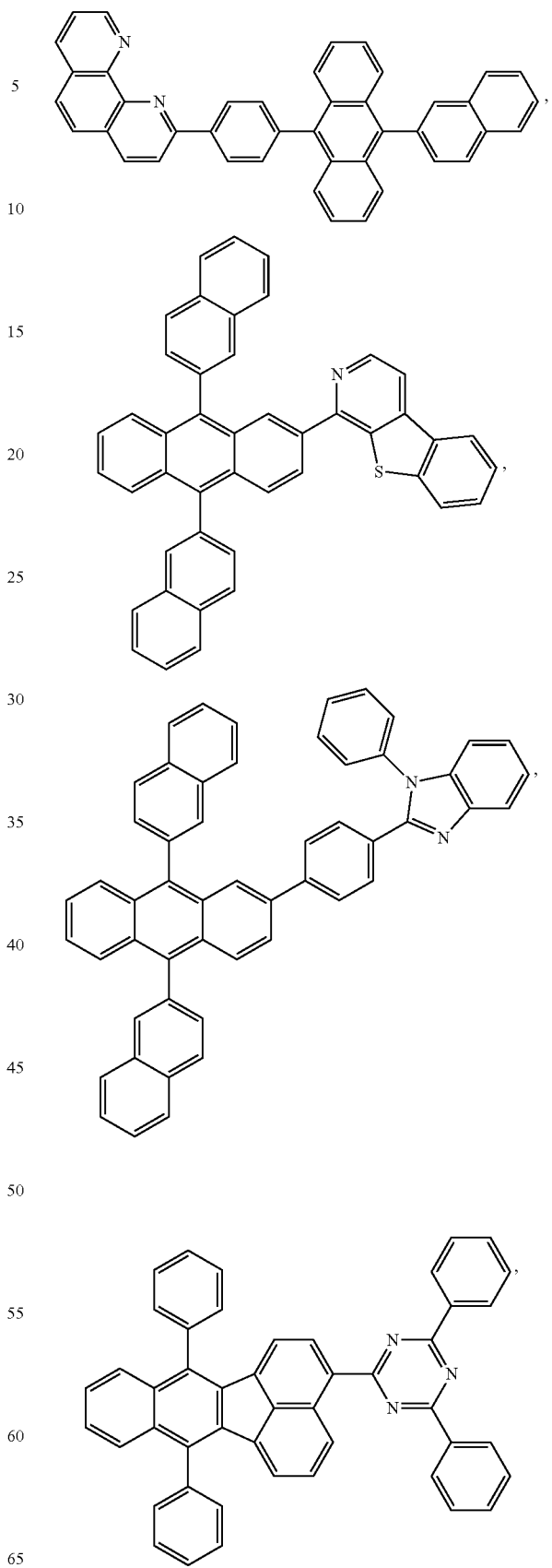

237
-continued
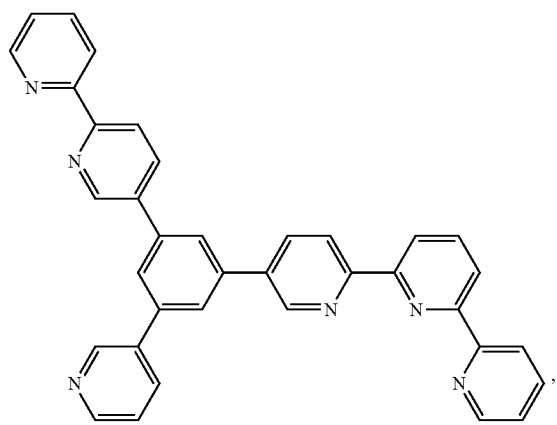
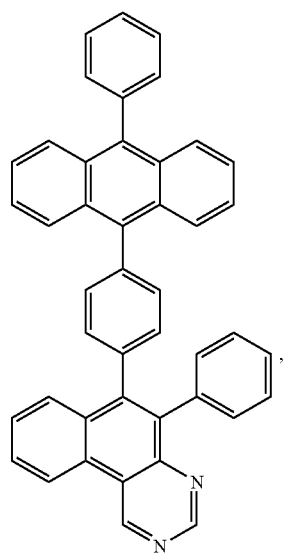
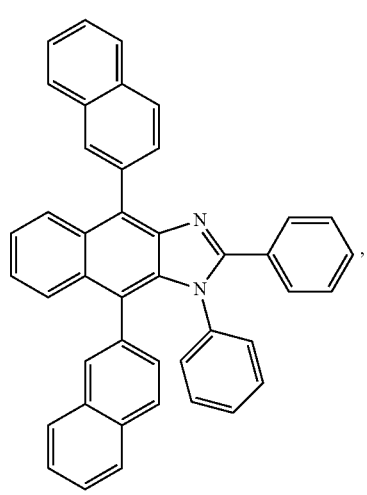
238
-continued
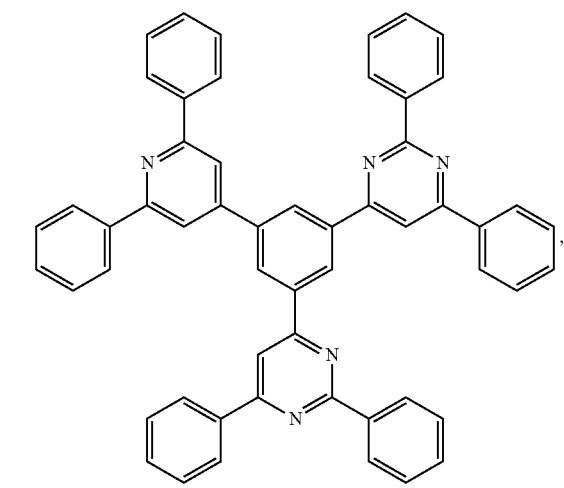
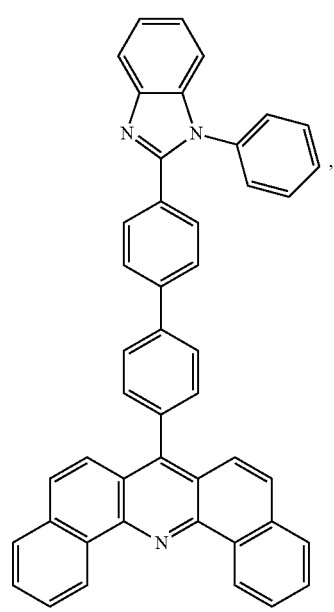
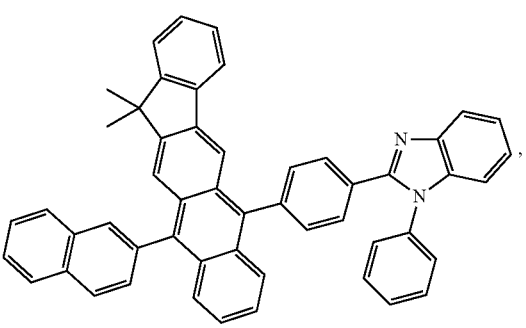

239
-continued
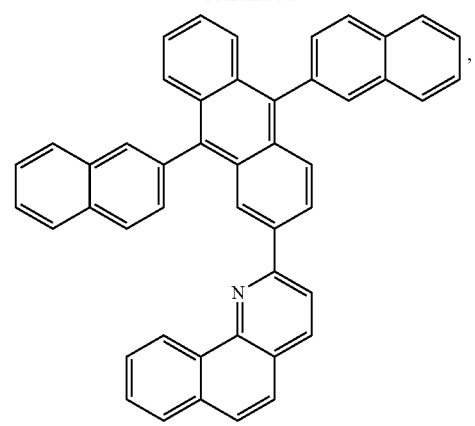
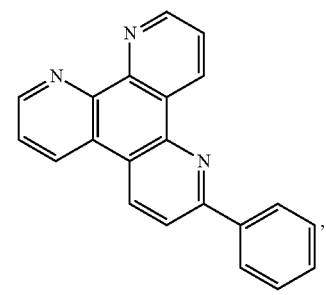
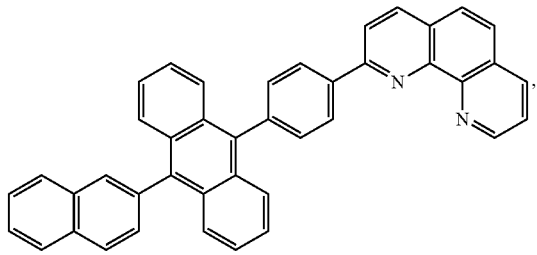
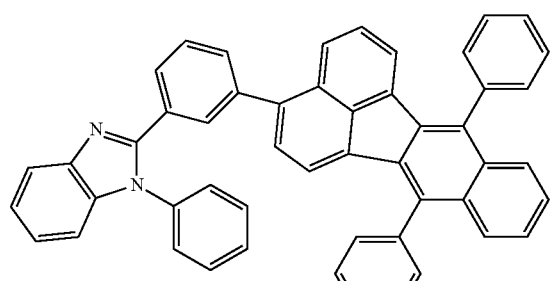
240
-continued
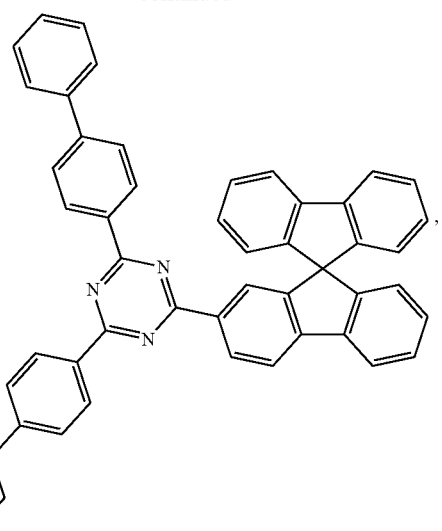
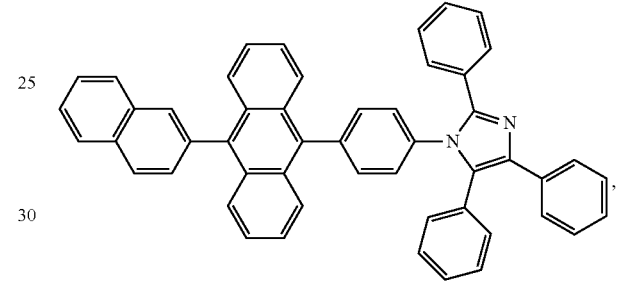
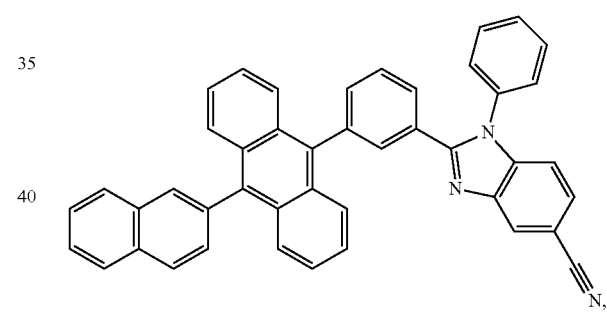
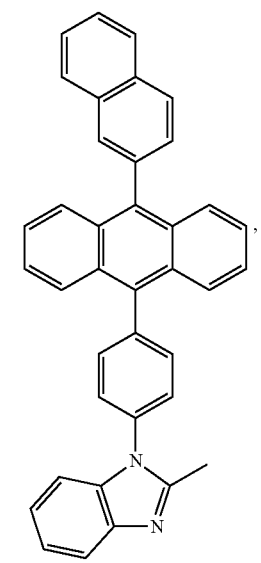

-continued

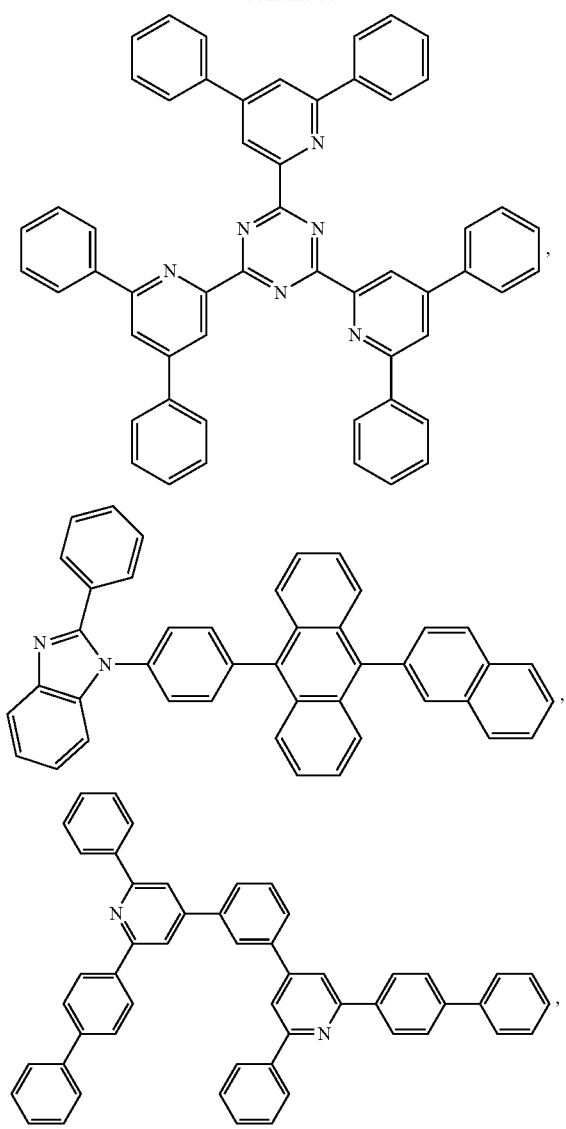

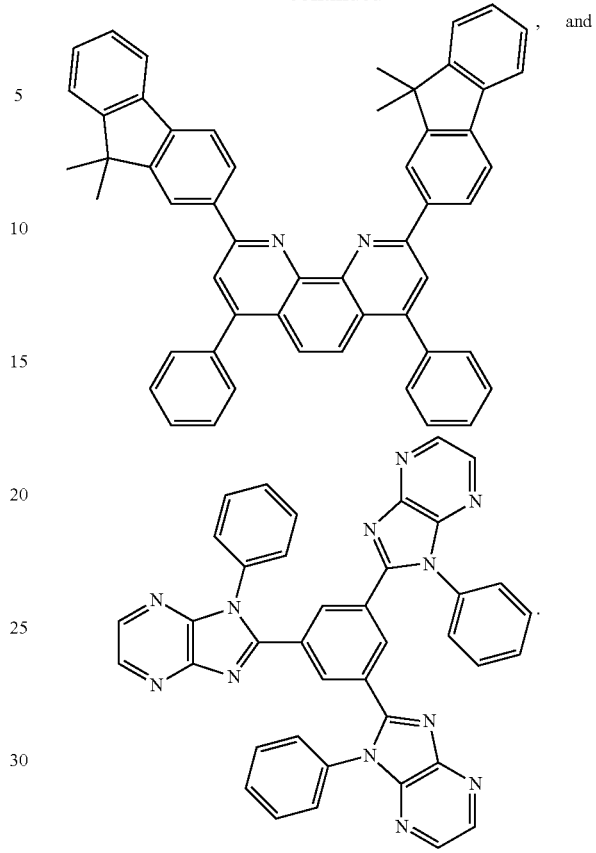

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated., partially deuterated, and fully deuterated versions thereof.

Experimental

All example devices were fabricated by high vacuum ($<10^{-7}$ Tour) thermal evaporation. The anode electrode was 750 Å of indium tin oxide (ITO). The cathode consisted of 10 Å of Liq (8-hydroxyquinoline lithium) followed by 1,000 Å of Al. All devices were encapsulated with a glass lid sealed with an epoxy resin in a nitrogen glove box (<1 ppm of $H_2O$ and $O_2$) immediately after fabrication, and a moisture getter was incorporated inside the package. The organic stack of the device examples consisted of sequentially, from the ITO surface, 100 Å of HATCN as the hole injection layer (HIL); 450 Å of HTM as a hole transporting layer (HTL);

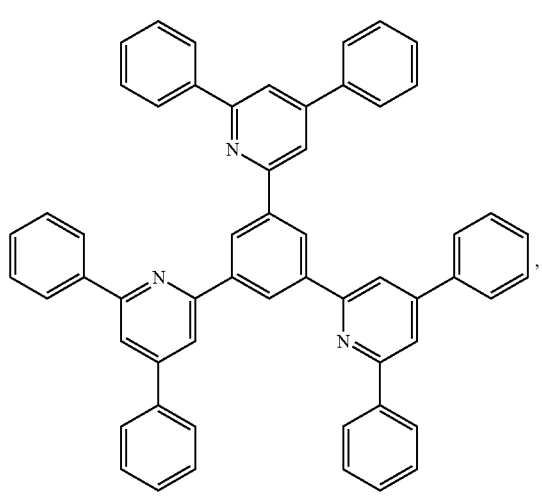

400 Å of an emissive layer (EML) containing H-host (HH1, HH2, or HA1) 50 weight %: E-host (A1) 40 weight %; and Green Emitter (GD) 10 weight %, and 350 Å of Liq (8-hydroxyquinoline lithium) doped with 40% of ETM as the ETL. The Comparative Example devices were the same as the device examples except that Comparative E-host CC-1 was used in the EML. Table 1 shows the device layer thickness and materials.

TABLE 1

Device layer materials and thicknesses

| Layer | Material | Thickness [Å] |
|---|---|---|
| Anode | ITO | 750 |
| HIL | HATCN | 100 |
| HTL | HTM | 450 |
| EML | H-host:E-host 40%:GD 10% | 400 |
| ETL | Liq: ETM 40% | 350 |
| EIL | Liq | 10 |
| Cathode | Al | 1000 |

The chemical structures of the device materials are shown below.

HAT-CN

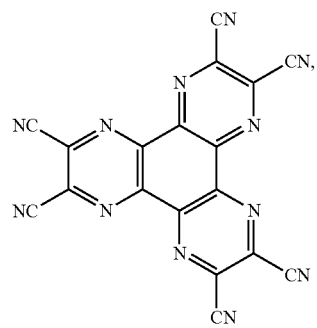

HTM

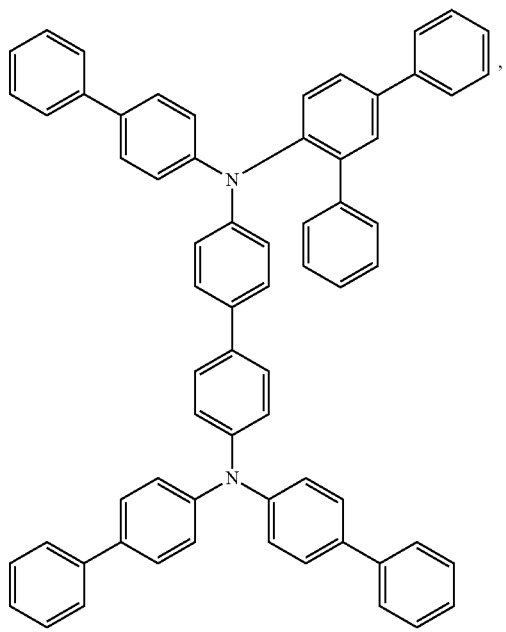

ETM

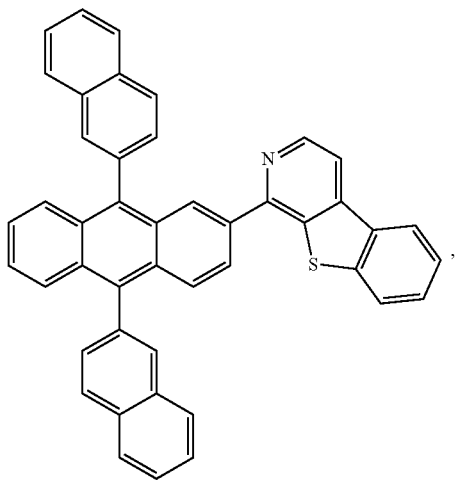

Liq

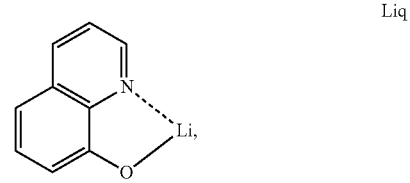

HH1

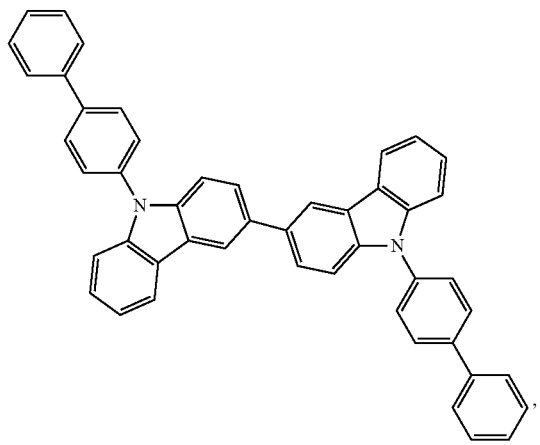

HH2

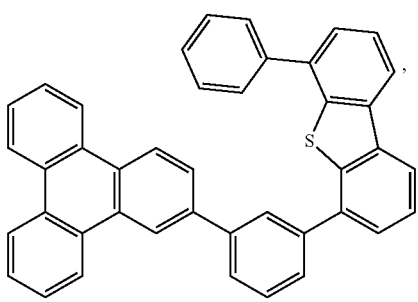

-continued

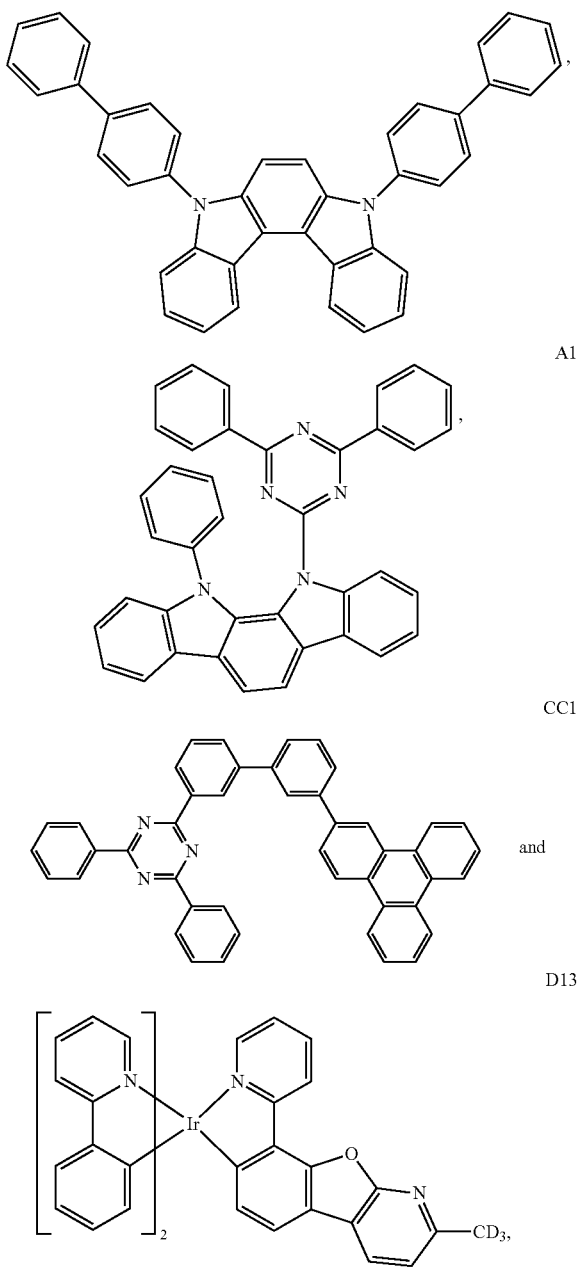

HA67

A1

CC1 and

D13

Table 2 below summarizes the device performance data at 1,000 nits. The lifetime (LT$_{95}$) was calculated from accelerated lifetest data at 40 mA/cm² assuming an acceleration factor of 1.8, and was normalized to that of device CE-1.

| Devices | H-host | E-host | Color | V [V] | PE [lm/W] | LT$_{95}$ [A.U.] |
|---|---|---|---|---|---|---|
| CD 1 | HH1 | CC-1 | Green | 3.4 | 75 | 100 |
| CD 2 | HH2 | CC-1 | Green | 4.3 | 61 | 37 |
| CD 3 | HA1 | CC-1 | Green | 3.0 | 93 | 63 |
| Device 1 | HH1 | A1 | Green | 2.8 | 110 | 218 |
| Device 2 | HH2 | A1 | Green | 3.1 | 80 | 185 |
| Device 3 | HA1 | A1 | Green | 2.7 | 117 | 85 |

The data in Table 2 show that inventive devices (Device 1, Device 2, and Device 3) have lower voltages, higher efficiency and longer lifetime than comparative devices (CD1, CD2, and CD3). The superior performance of the inventive devices is attributable to their use of compound A1 as the E-host, while the comparative devices have compound CC-1 as the E-host. It appears that combining the E-host A1 with dopant D13 has unique benefit to improve device performance, which is unexpected.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A composition comprising a mixture of a first compound and a second compound,
wherein the first compound is selected from the group consisting of:

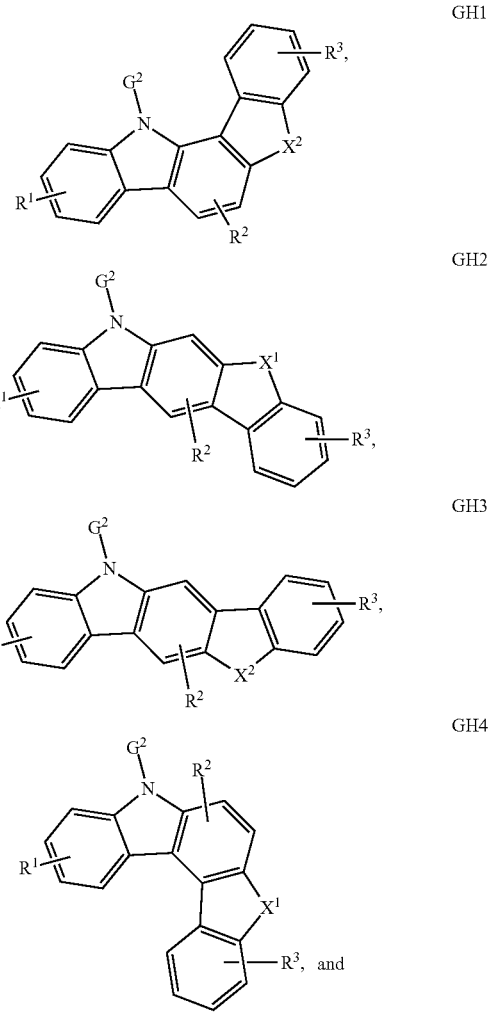

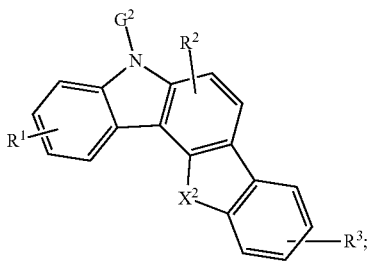

GH5

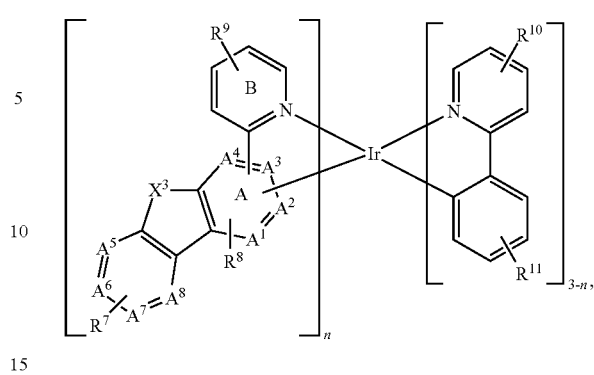

wherein each $A^1$, $A^2$, $A^3$, $A^4$, $A^5$, $A^6$, $A^7$, and $A^8$ comprise carbon or nitrogen;

wherein ring B is bonded to ring A through a C—C bond;

wherein the iridium is bonded to ring A through a Ir—C bond;

wherein $X^3$ is selected from a group consisting of O, S and Se;

wherein $R^7$ to $R^{11}$ each independently represent mono to the possible maximum number of substitution, or no substitution;

wherein $R^7$ to $R^{11}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein any two adjacent substituents can optionally join or fuse into a ring; and wherein n is an integer from 1 to 3.

2. The composition of claim 1, wherein $G^2$ is further substituted.

3. The composition of claim 1, wherein the first compound is selected from the group consisting of:

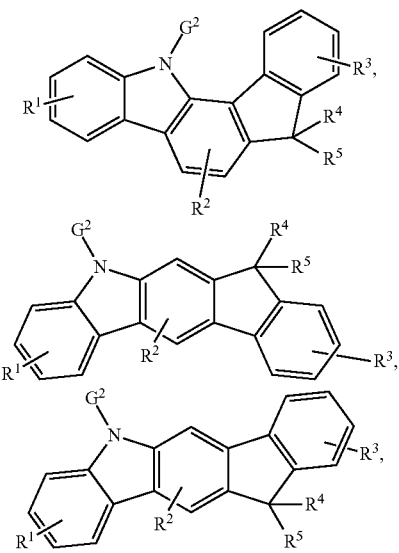

wherein $X^1$ and $X^2$ are each independently selected from the group consisting of $CR^4R^5$, O, S and Se;

wherein $R^1$ to $R^3$ each independently represent mono to the possible maximum number of substitution, or no substitution;

wherein $R^1$ to $R^3$ each independently represent mono to the possible maximum number of substitution, or no substitution;

wherein (i) $G^2$ comprises a moiety selected from the group consisting of dibenzofuran, dibenzothiophene, dibenzoselenophene, fluorene, triphenylene, and combinations thereof, or (ii) $G^2$ comprises a moiety selected from the group consisting of phenanthroline, azadibenzofuran, azadibenzothiophene, azadibenzoselenophene, azafluorene, azatriphenylene, and combinations thereof;

wherein $R^2$, $R^3$, $R^4$, and $R^5$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, acyl, carbonyl, carboxylic acid, ester, nitrile, isonitrile, sulfanyl, sulfinyl, sulfonyl, phosphino, and combinations thereof, and wherein any two adjacent substituents can optionally join or fuse into a ring;

wherein at least one of option (a) or option (b) is true:
   (a) $X^1$ or $X^2$ is present and represents Se;
   (b)(1)(i) the first compounds has the structure of GH2 or GH3, or (1)(ii) the first compound has a structure of GH1, GH4, or GH5, and two $R^2$ are not joined to form a ring, and
   (2) at least one of $R^1$ and $R^3$ is unsubstituted, and
   (3) $G^2$ is selected from the group consisting of dibenzoselenophene, phenanthroline, azadibenzofuran, azadibenzoselenophene, azafluorene, and combinations thereof;

with the proviso that none of $R^1$, $R^2$, $R^3$, $R^4$, or $R^5$ is triphenylene;

wherein the second compound has a formula $Ir(L_A)_n (L_B)_{3-n}$, and having the structure according to Formula II

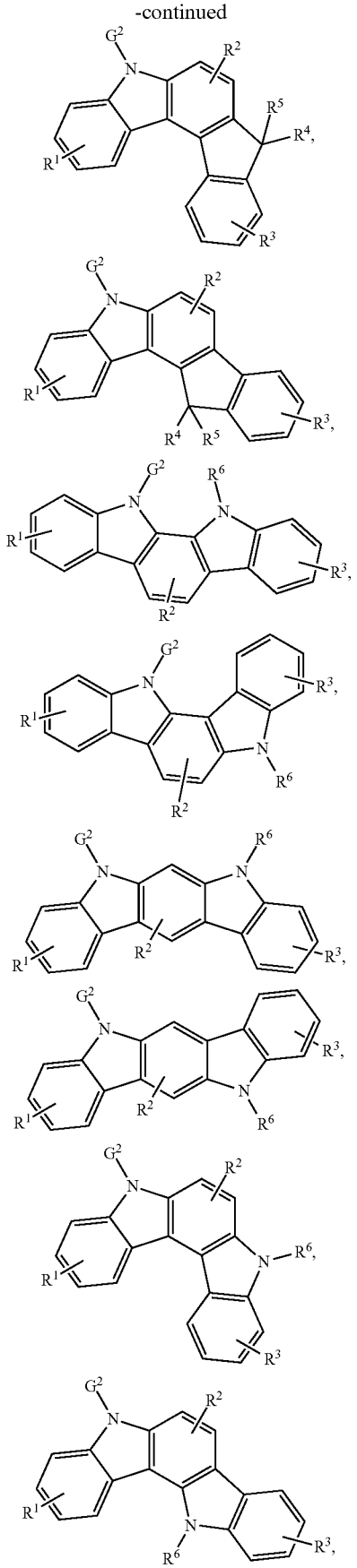
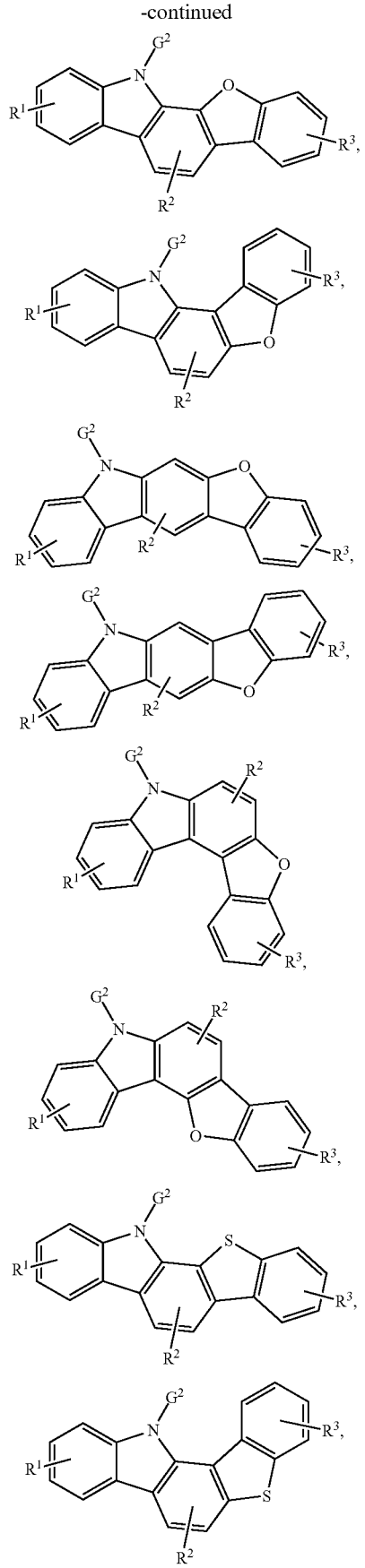

-continued
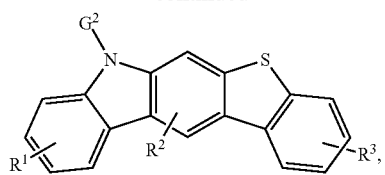
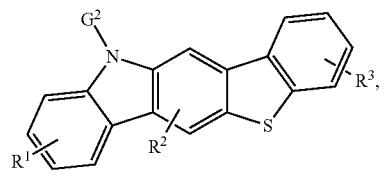
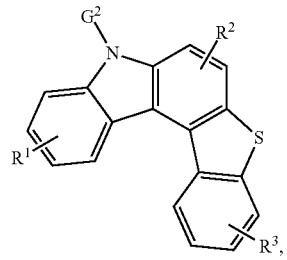
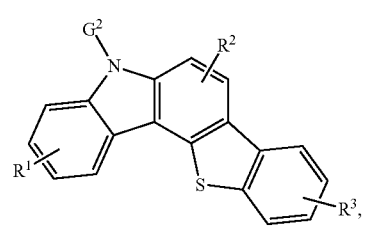
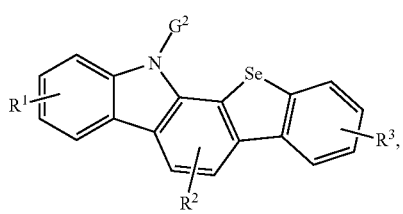
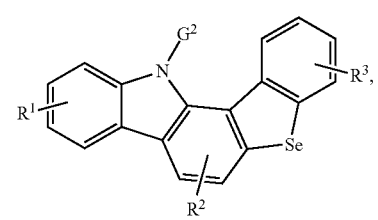
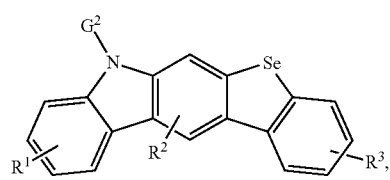
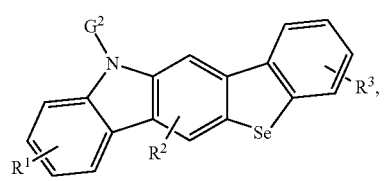
-continued
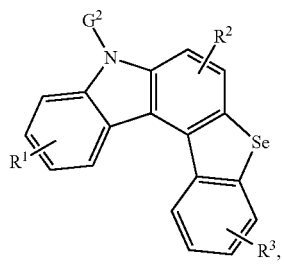
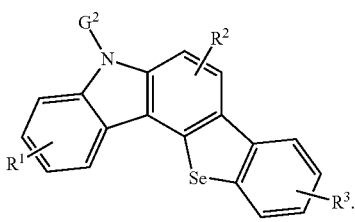
4. The composition of claim 1, wherein the second compound has the formula:
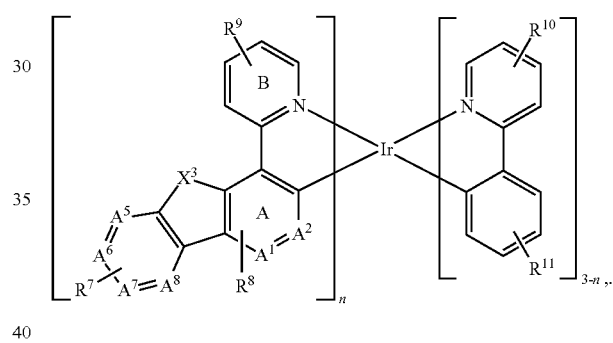
Formula III
5. The composition of claim 1, wherein $X^3$ is O.
6. The composition of claim 1, wherein $L_A$ is selected from the group consisting of:
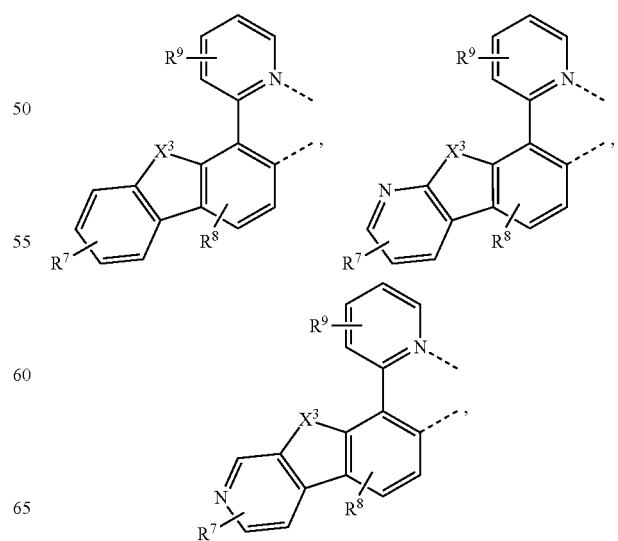

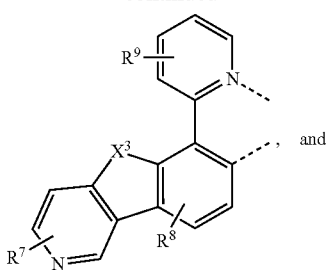
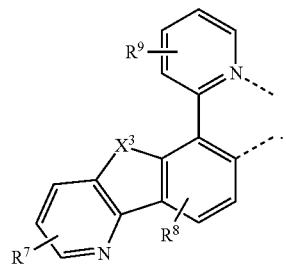
, and
7. The composition of claim 1, wherein the second compound is selected from the group consisting of:
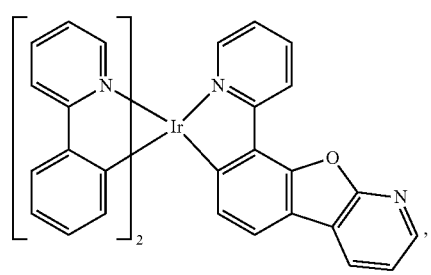
D1
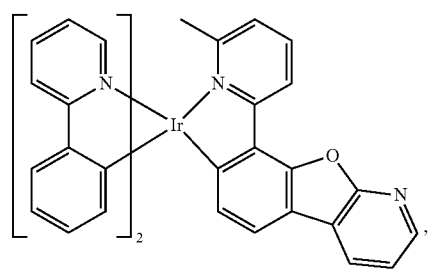
D2
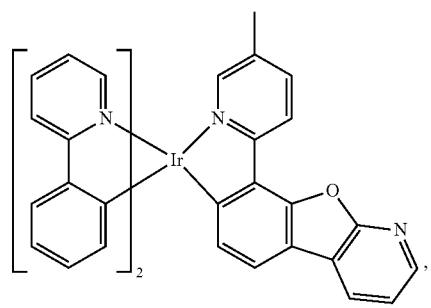
D3
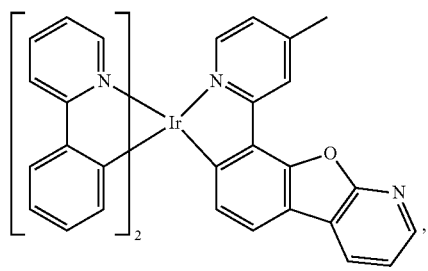
D4
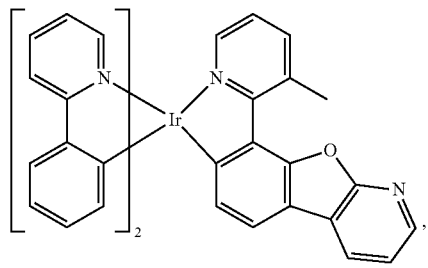
D5
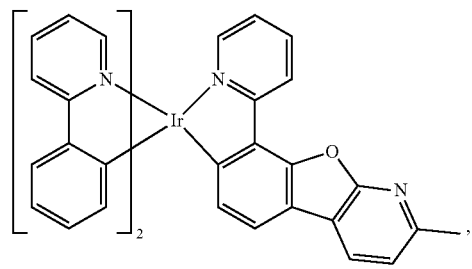
D6
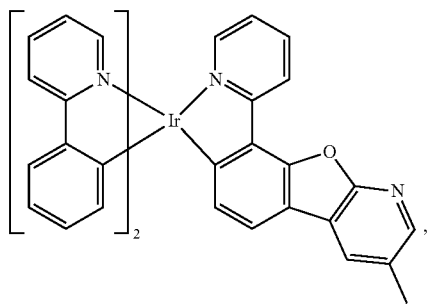
D7
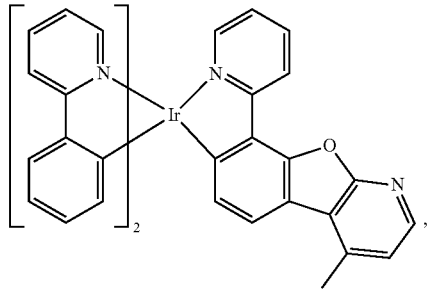
D8

D9
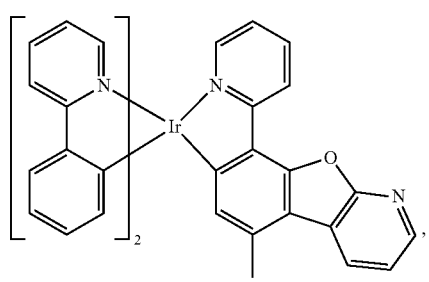
D10
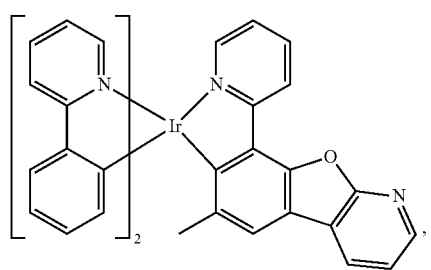
D11
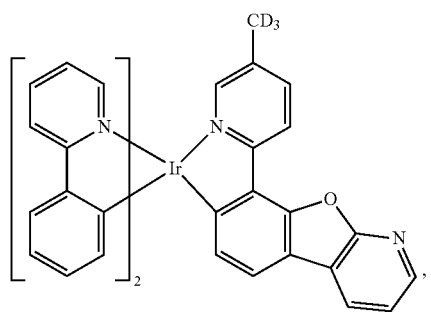
D12
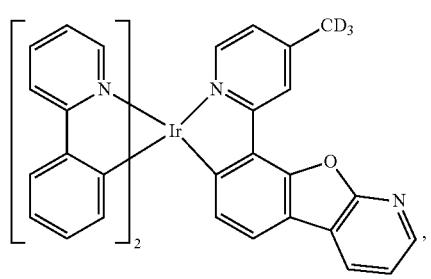
D13
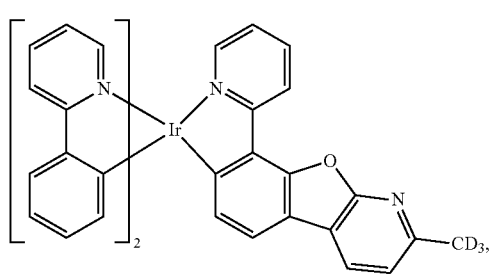
D14
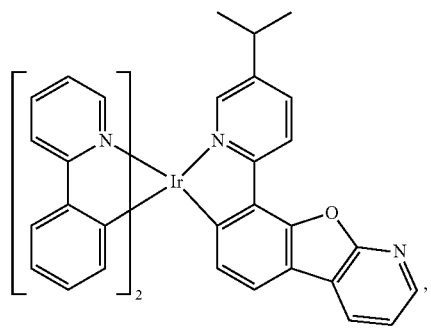
D15
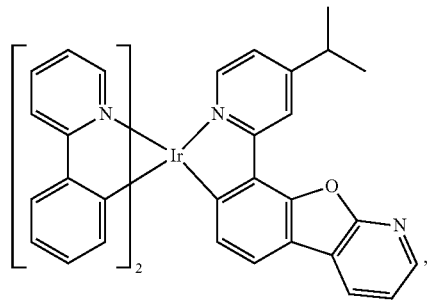
D16
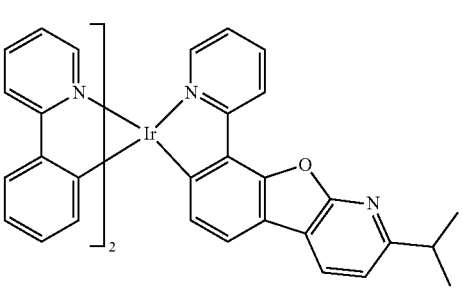
D17
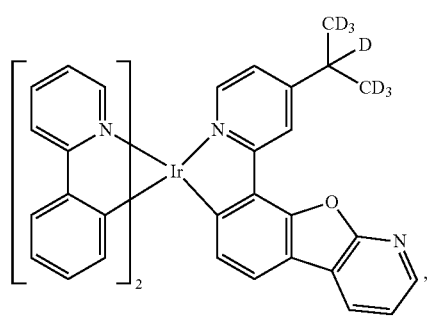
D18
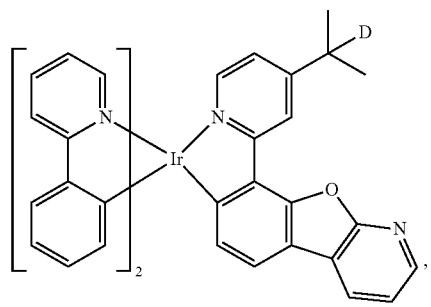

-continued
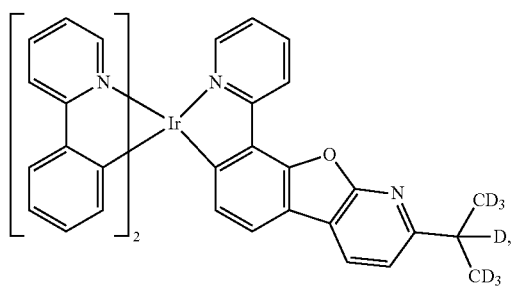
D19
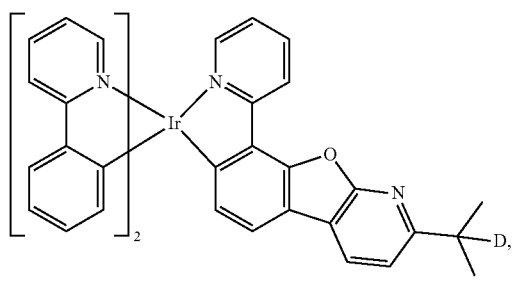
D20
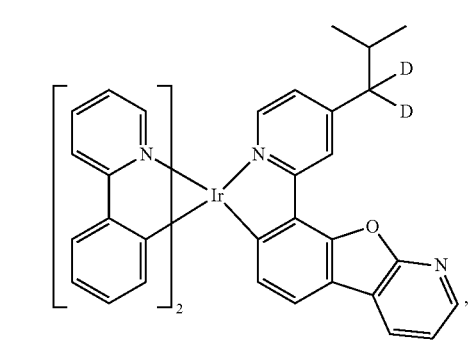
D21
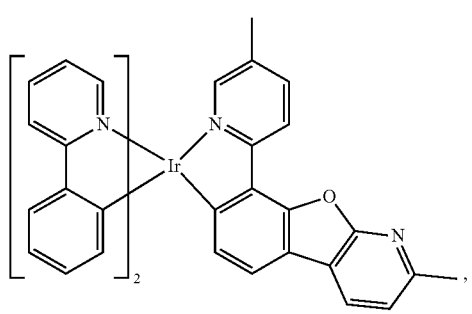
D22
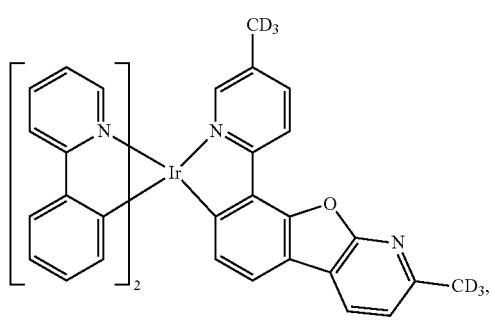
D23
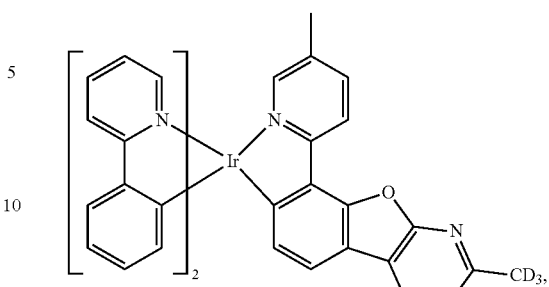
D24
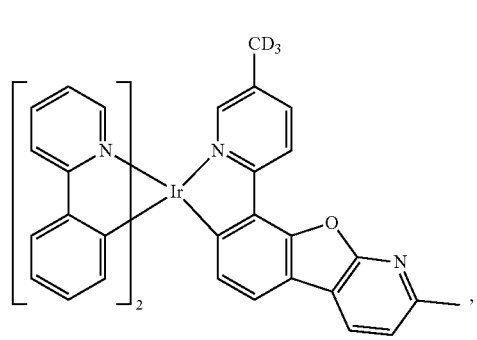
D25
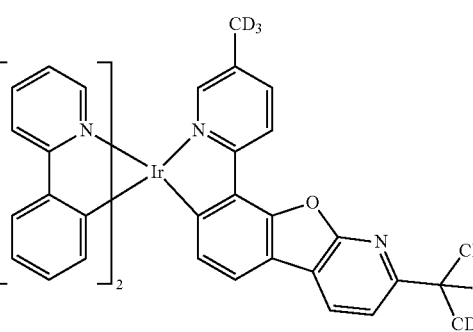
D26
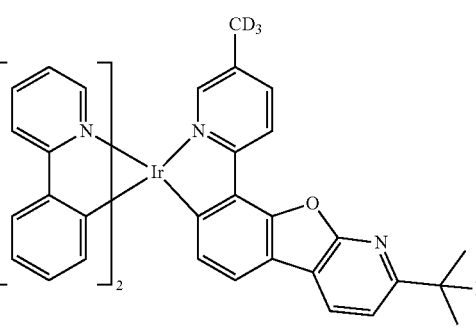
D27
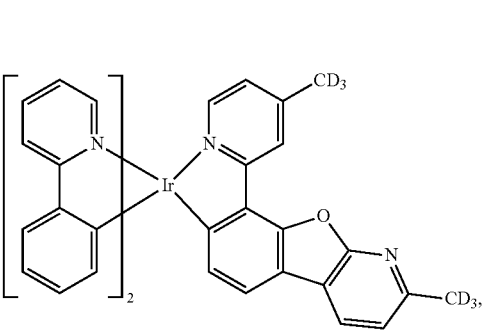
D28

259
-continued
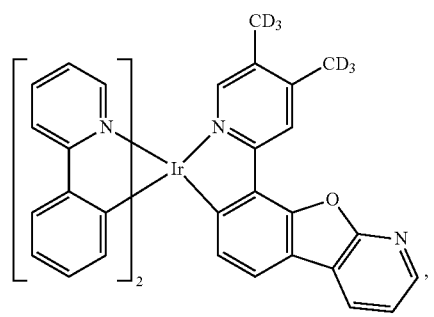
D29
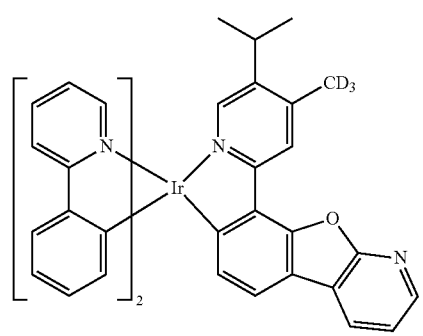
D30
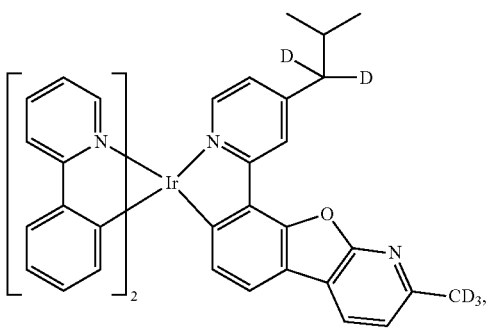
D31
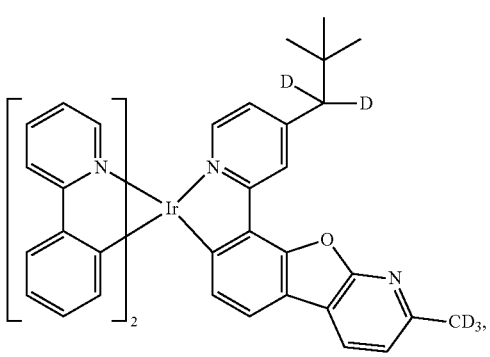
D32
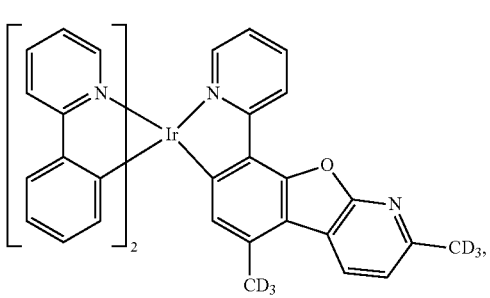
D33
260
-continued
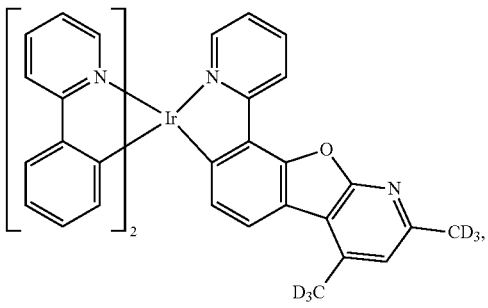
D34
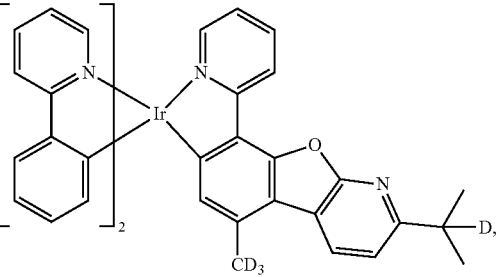
D35
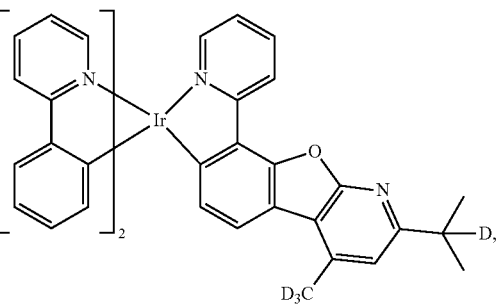
D36
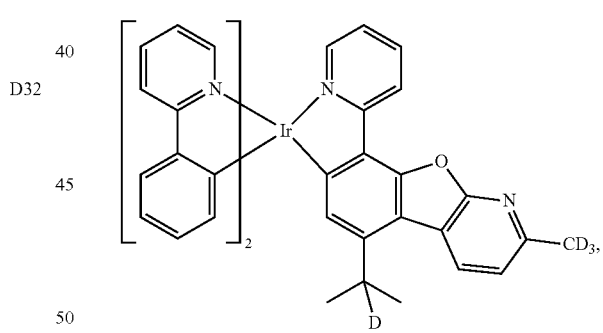
D37
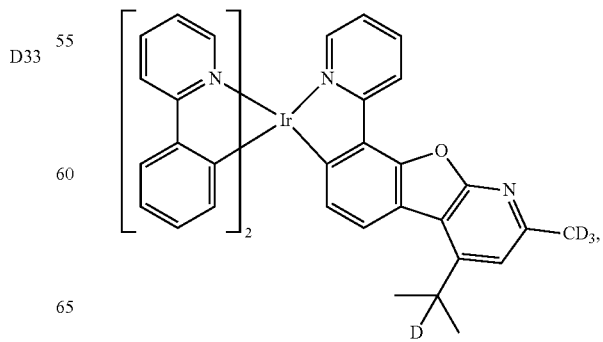
D38

D39
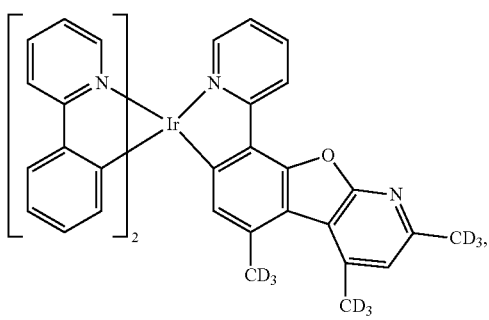
D40
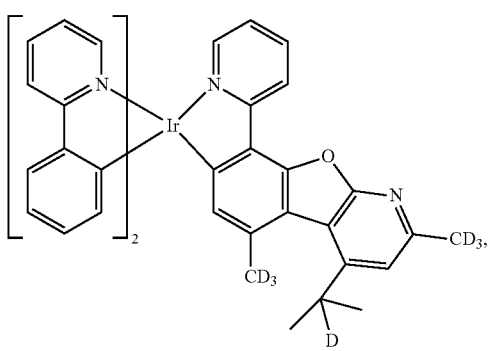
D41
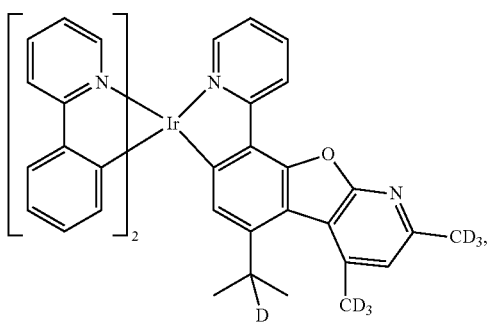
D42
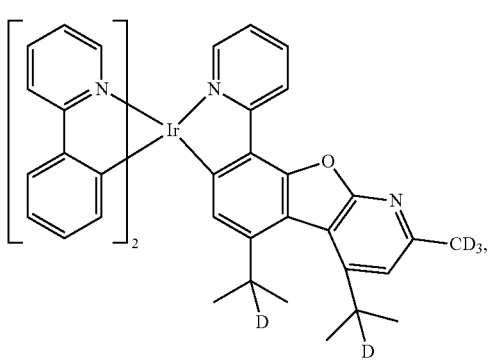
D43
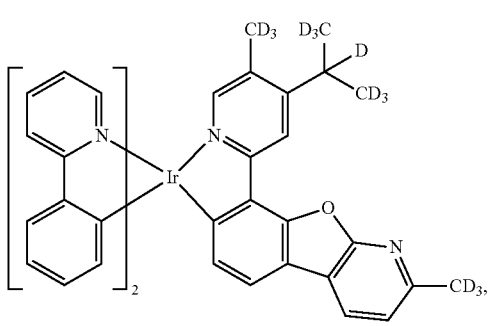
D44
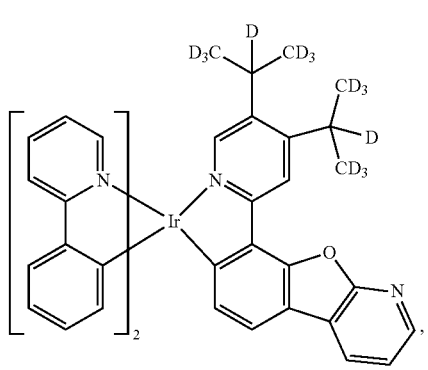
D45
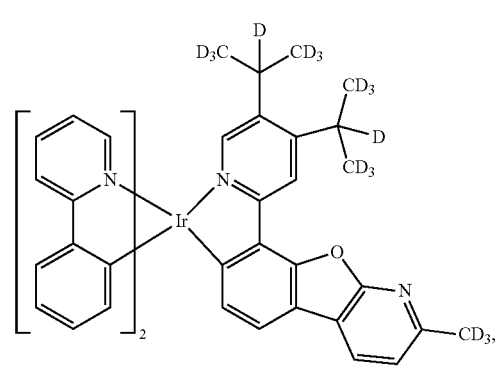
D46
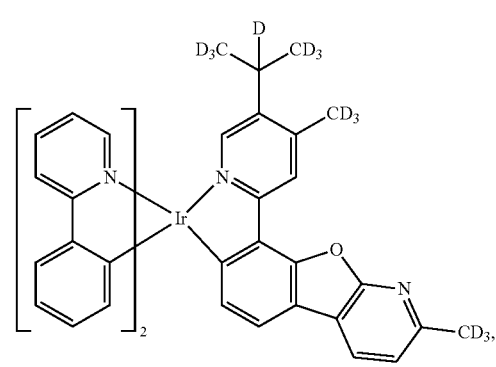
D47
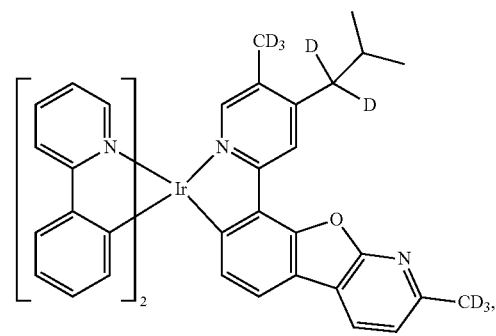

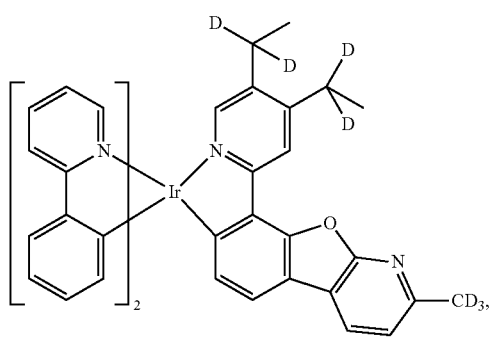 D48
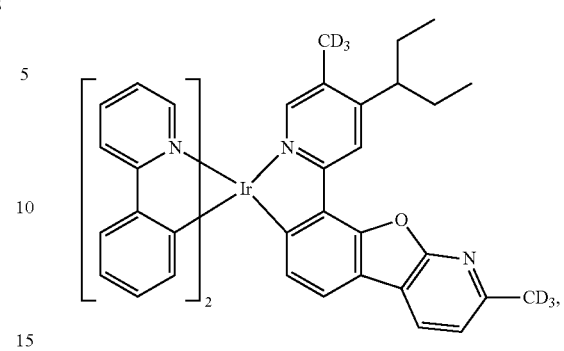 D52
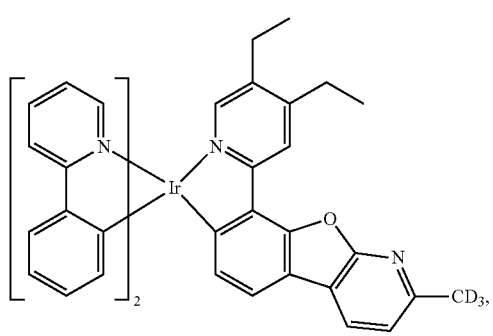 D49
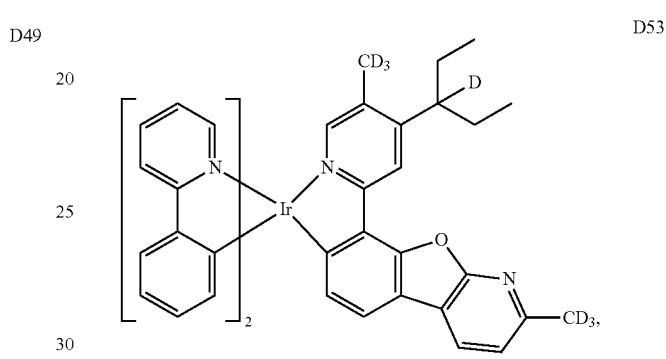 D53
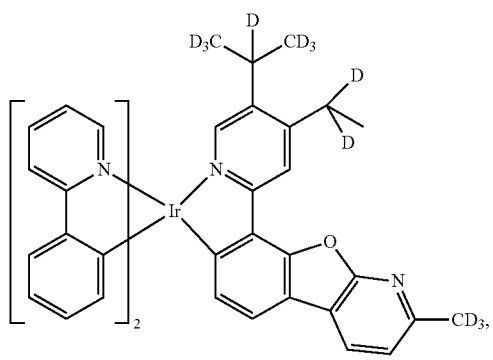 D50
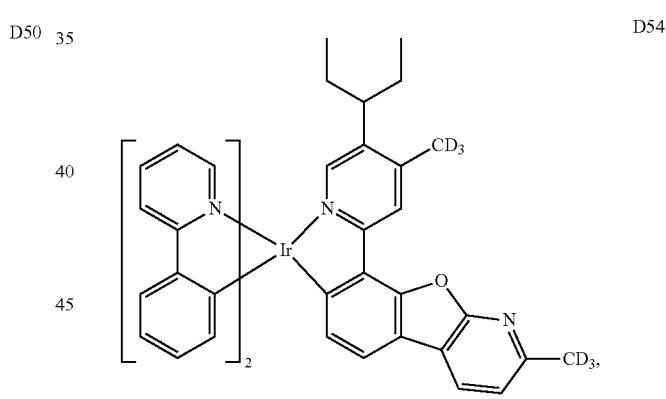 D54
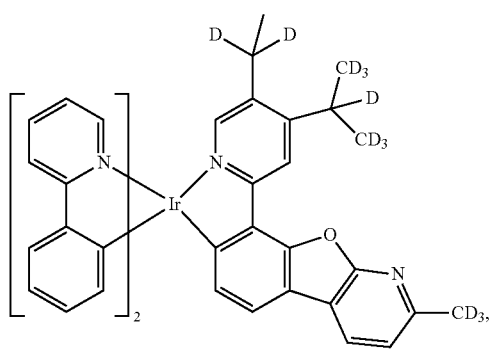 D51
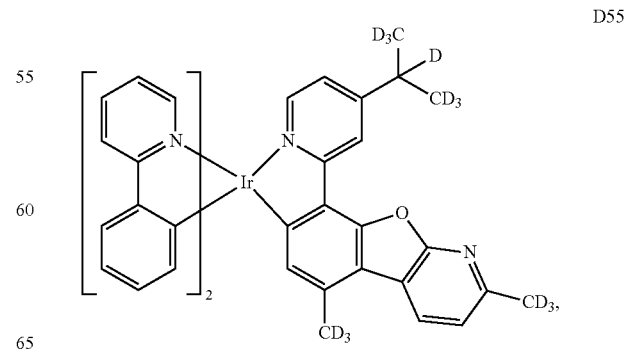 D55

-continued
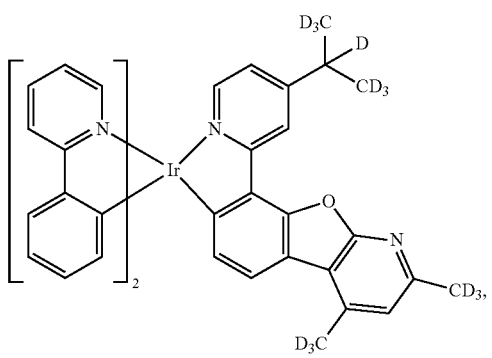
D56
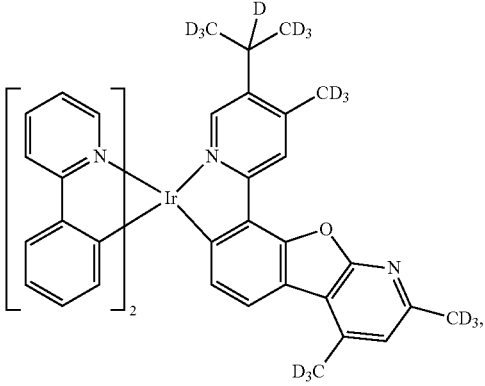
D60
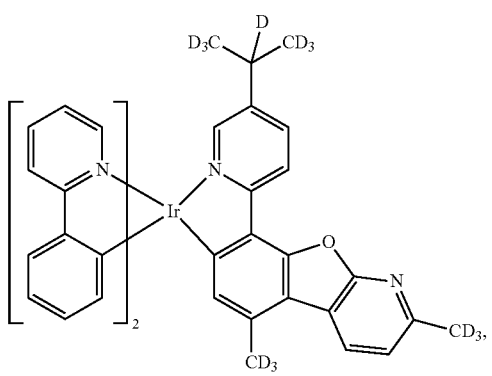
D57
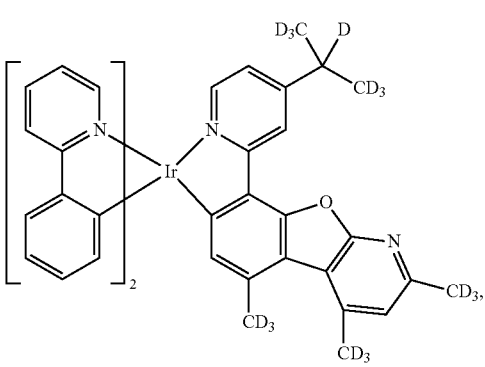
D61
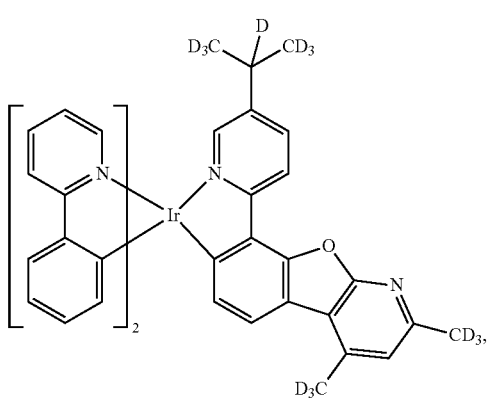
D58
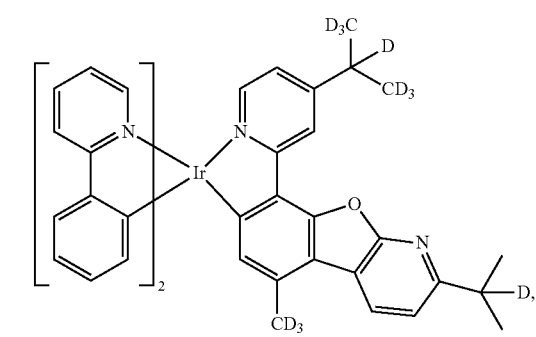
D62
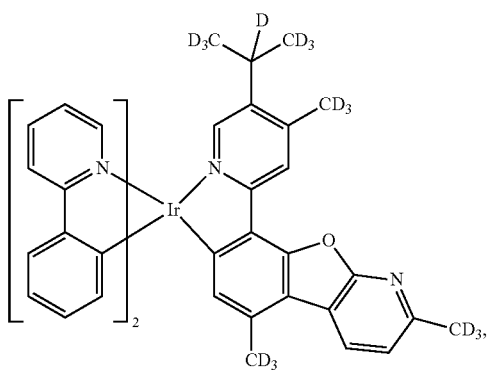
D59
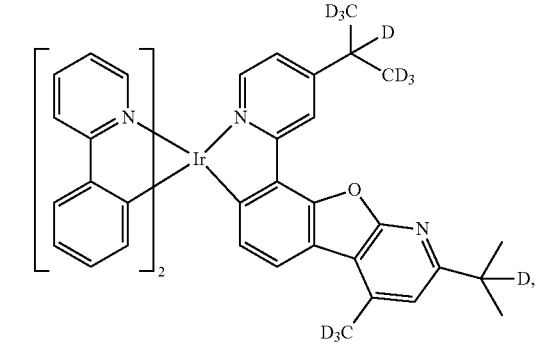
D63

-continued
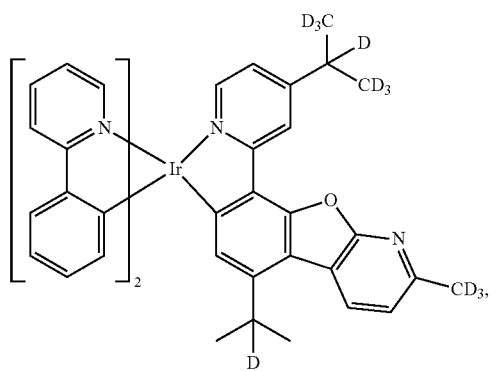
D64
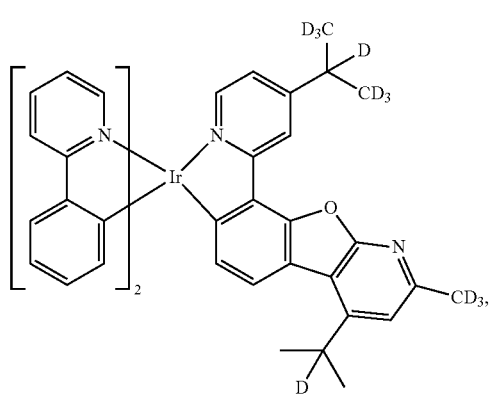
D65
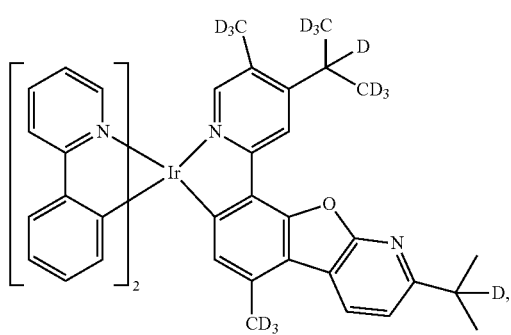
D66
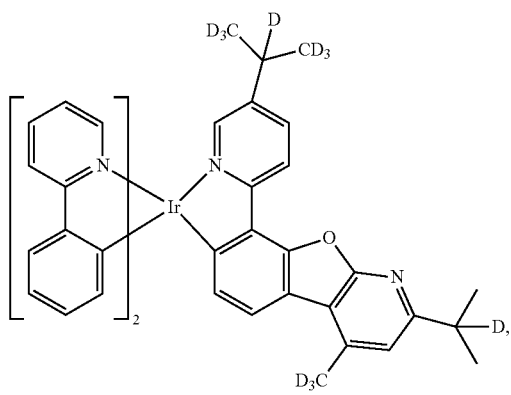
D67
-continued
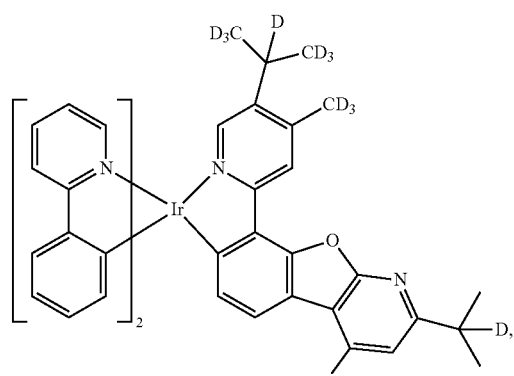
D68
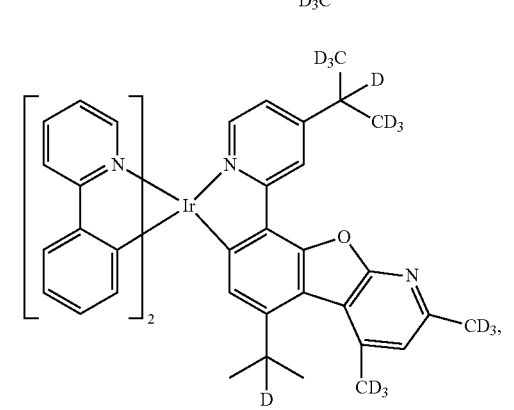
D69
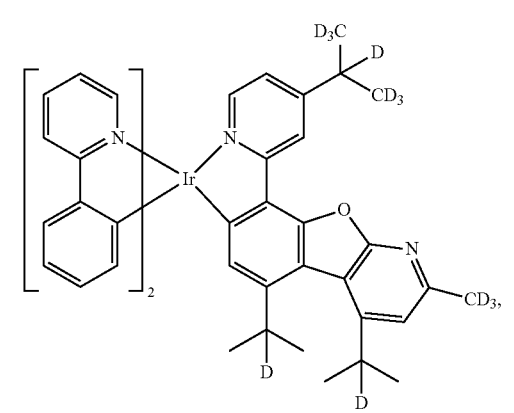
D70
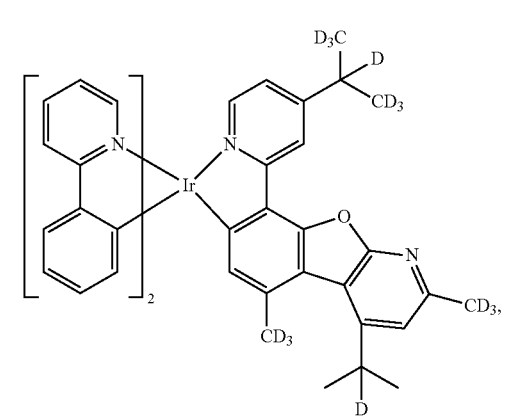
D71

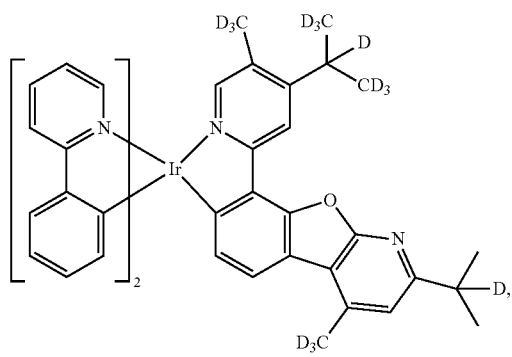
D72
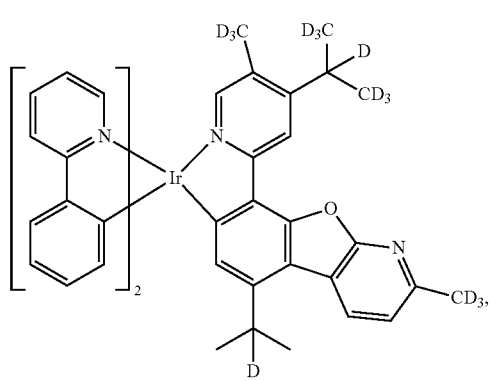
D73
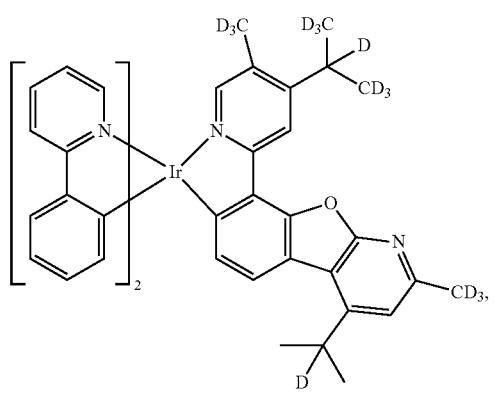
D74
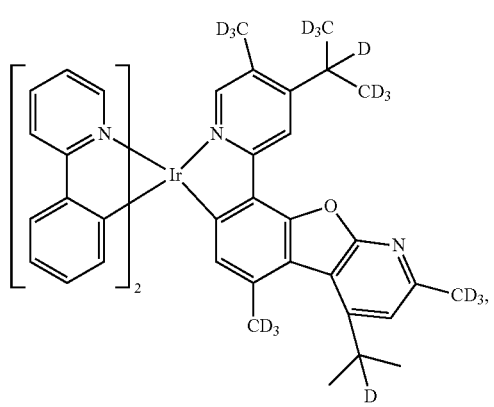
D75
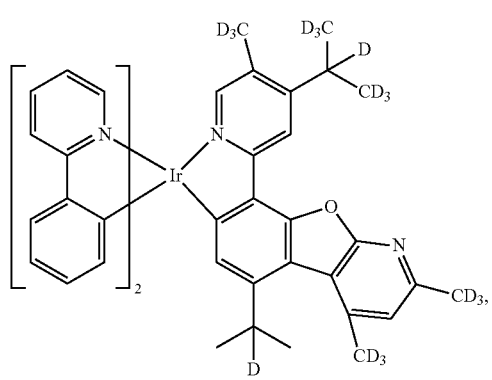
D76
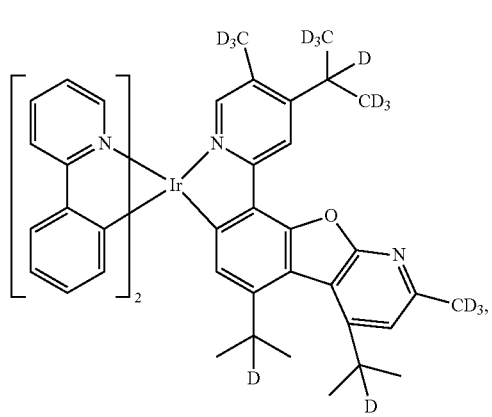
D77
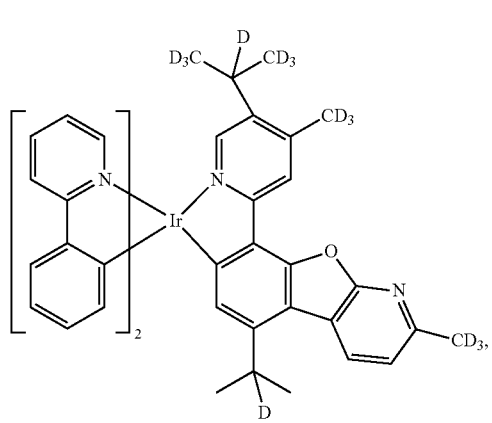
D78
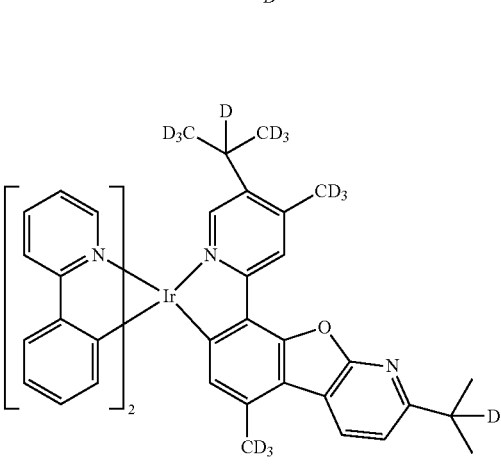
D79

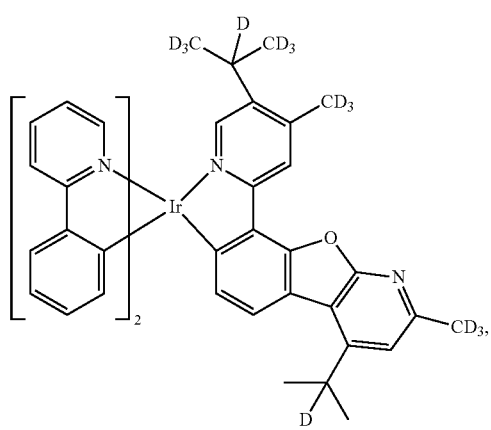
D80
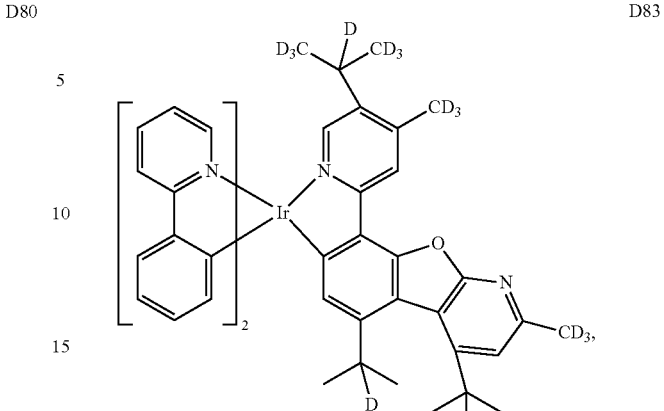
D83
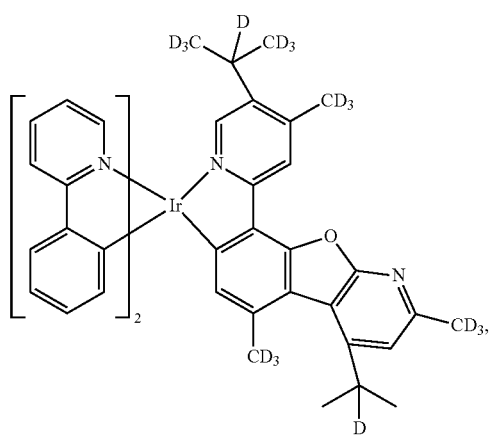
D81
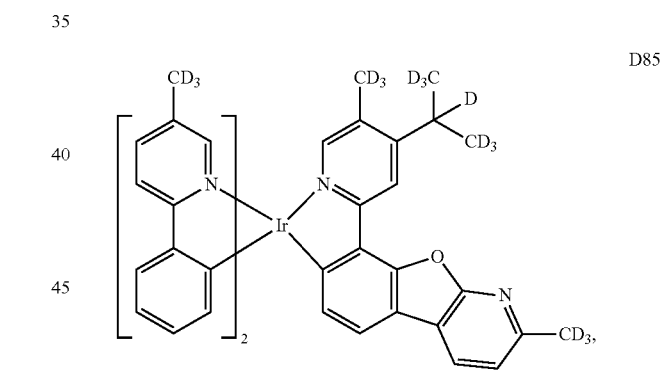
D84
D82
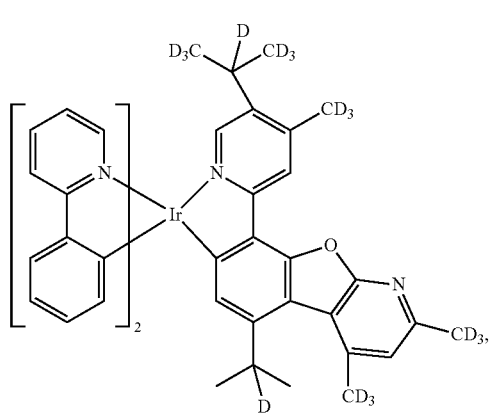
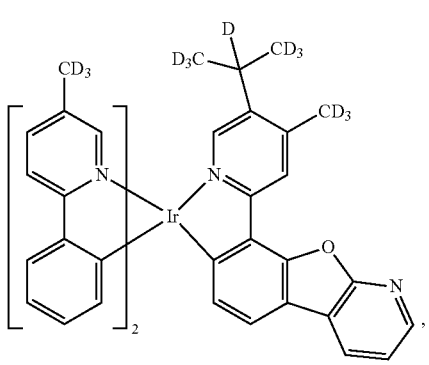
D85
D86

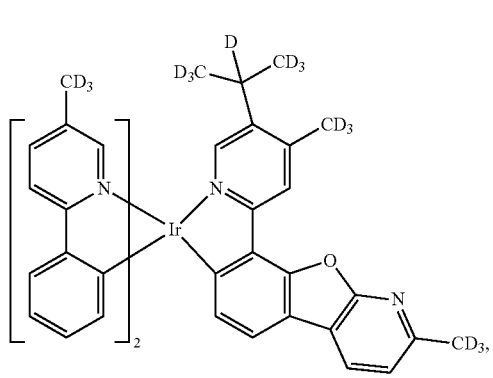
D87
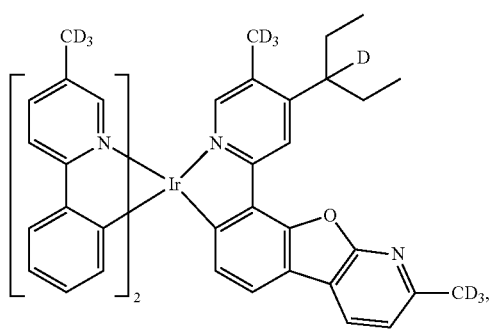
D88
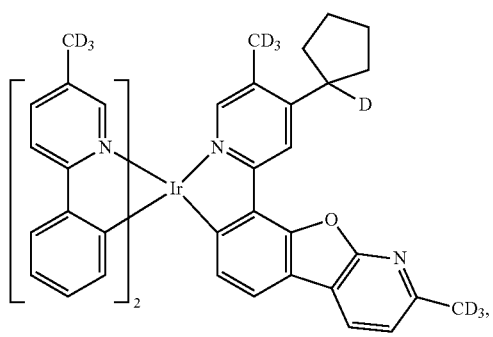
D89
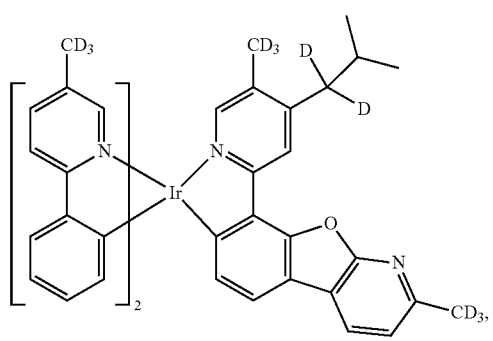
D90
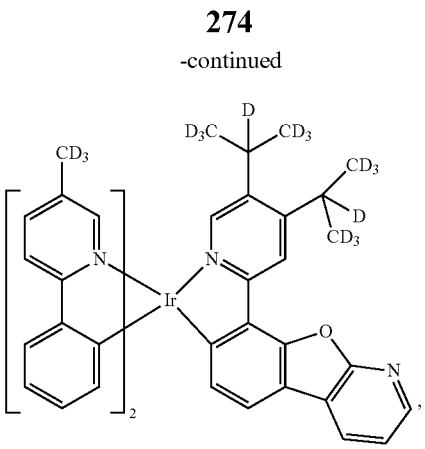
D91
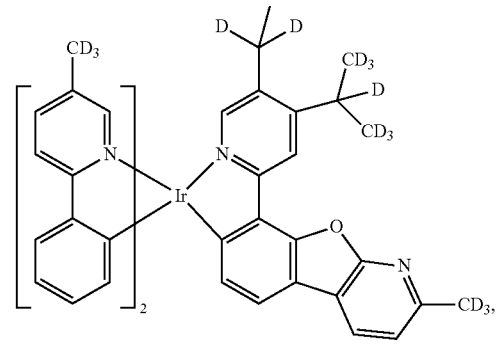
D92
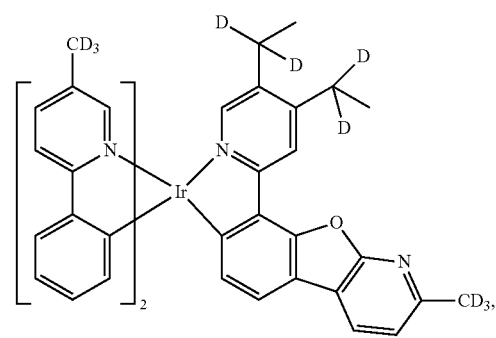
D93
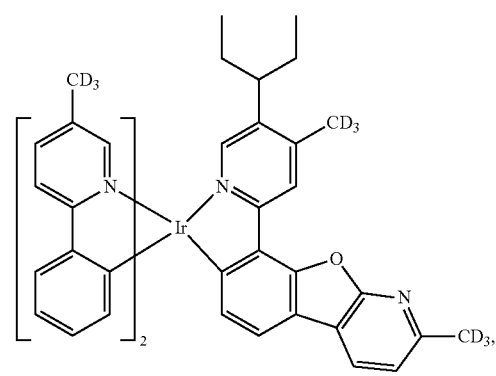
D94

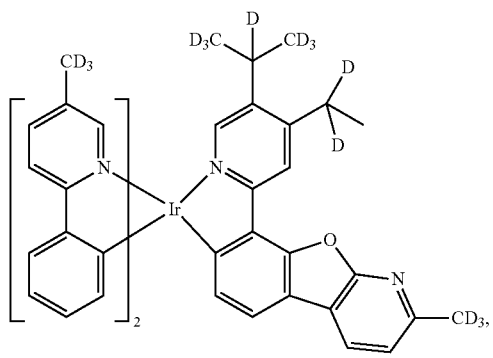 D95
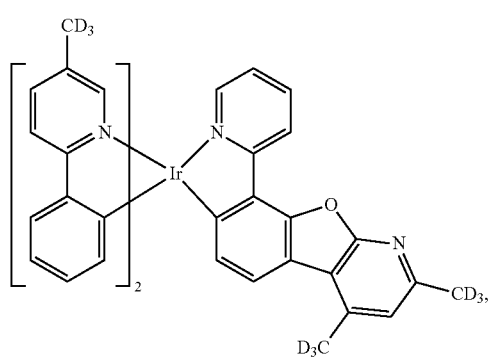 D99
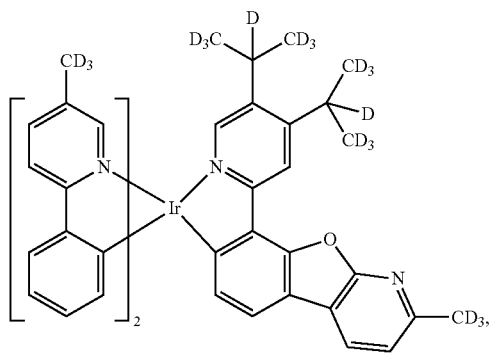 D96
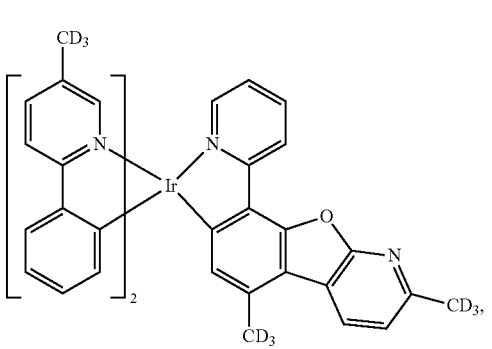 D100
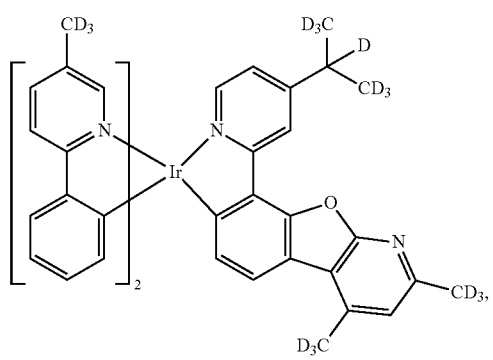 D97
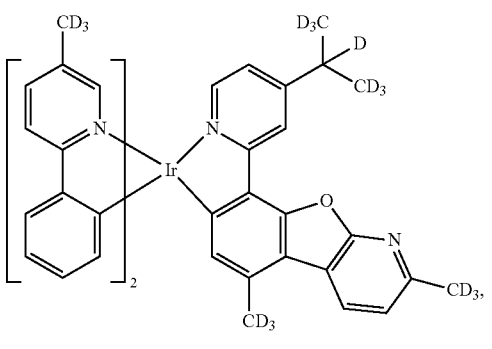 D101
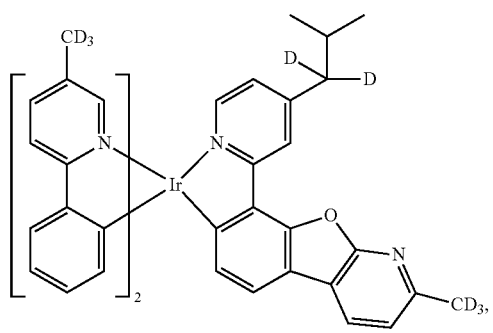 D98
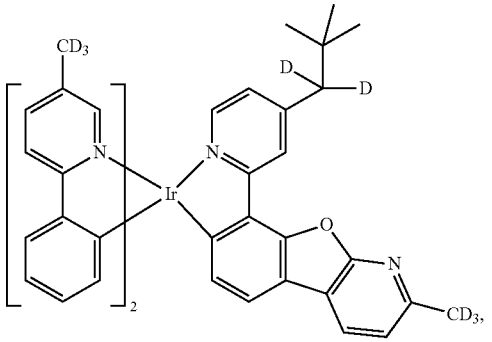 D102

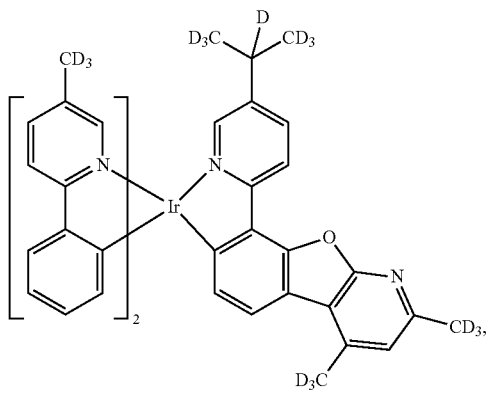 D103
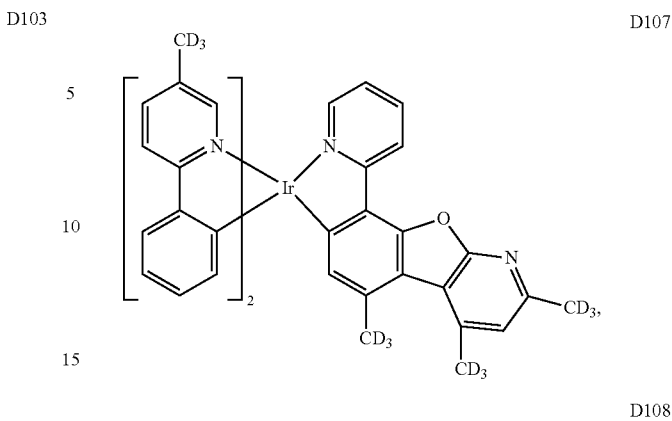 D107
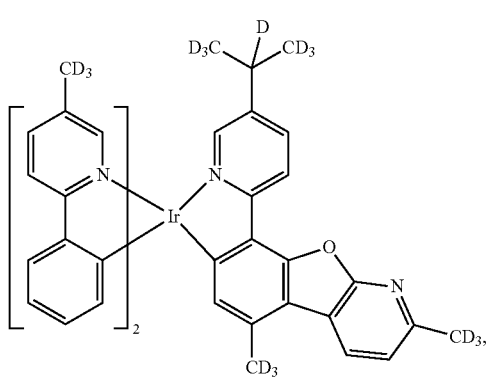 D104
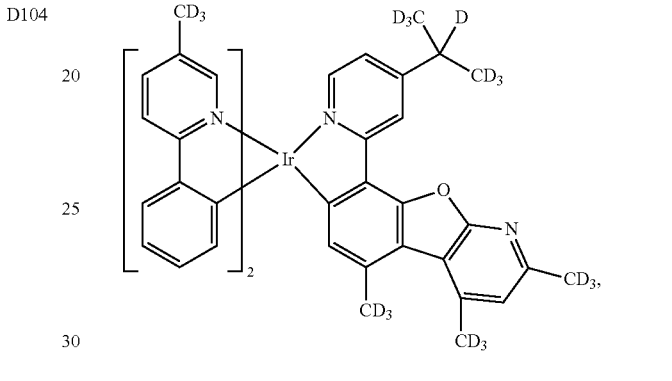 D108
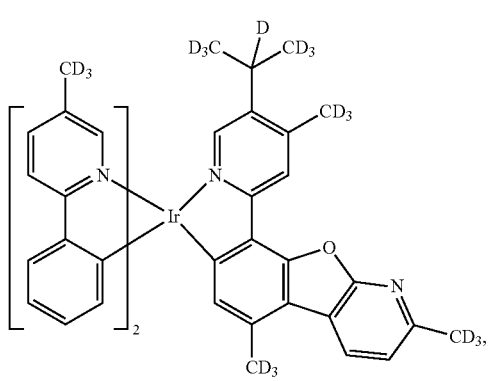 D105
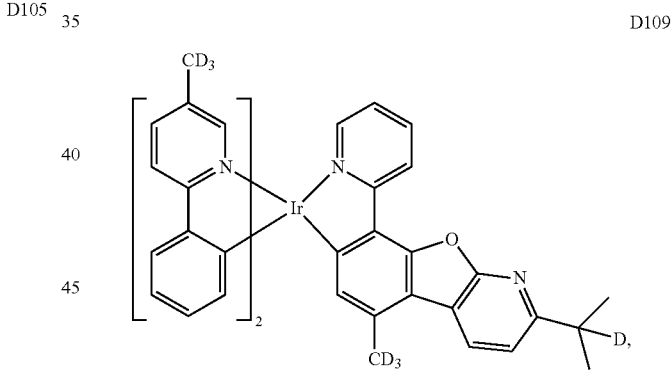 D109
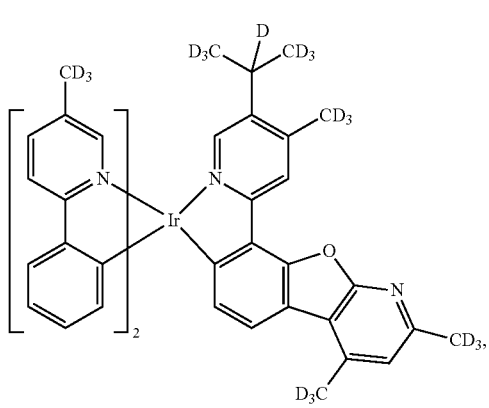 D106
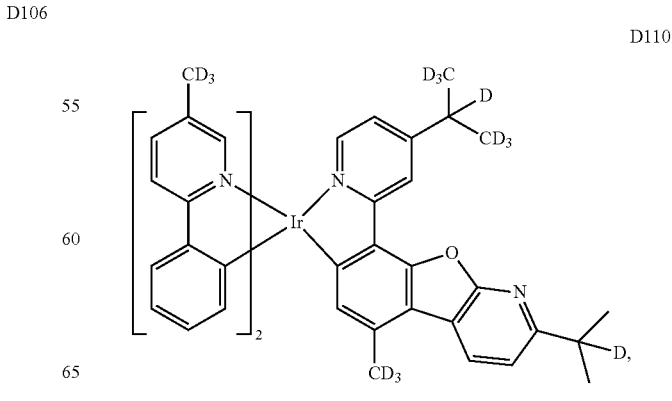 D110

D111
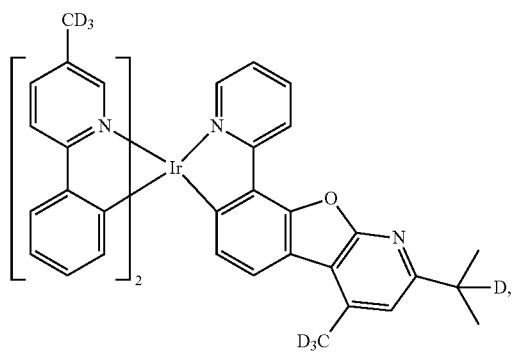
D112
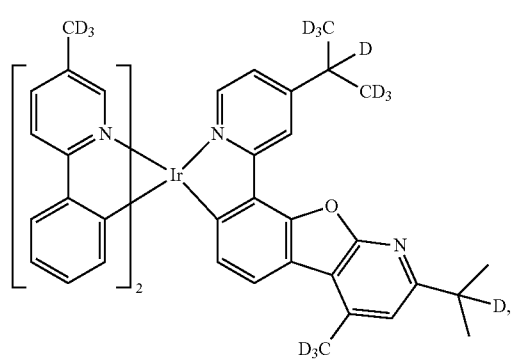
D113
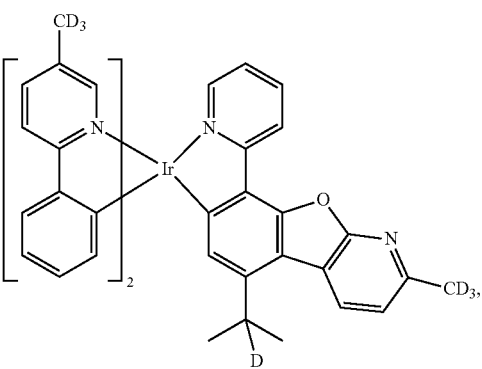
D114
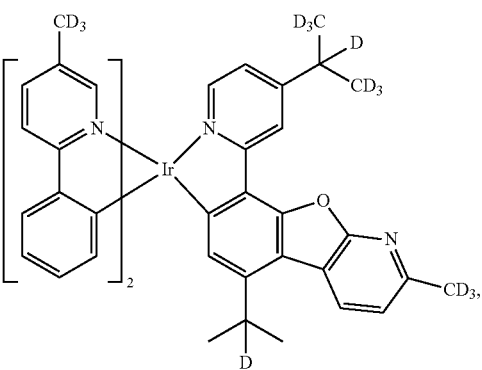
D115
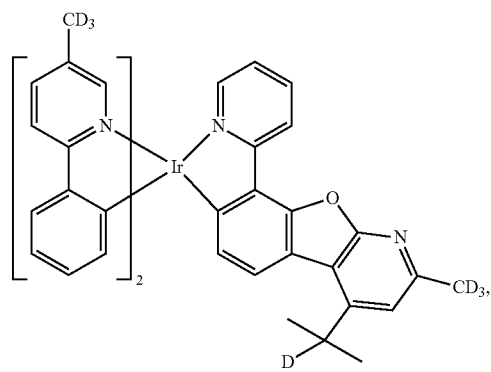
D116
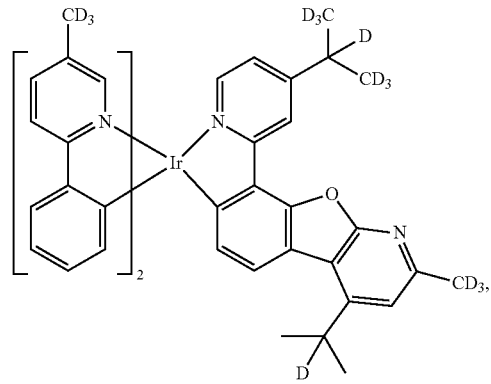
D117
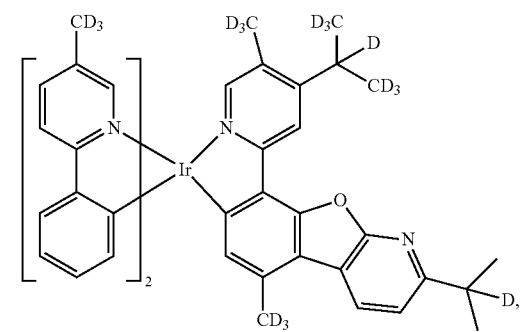
D118
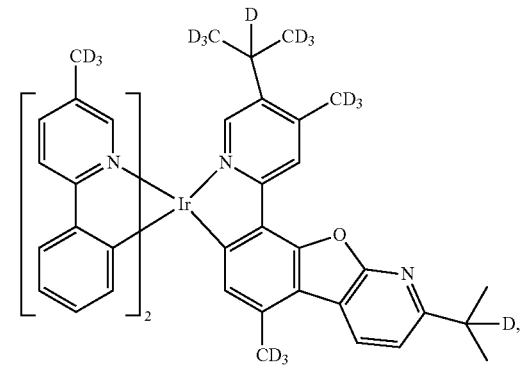

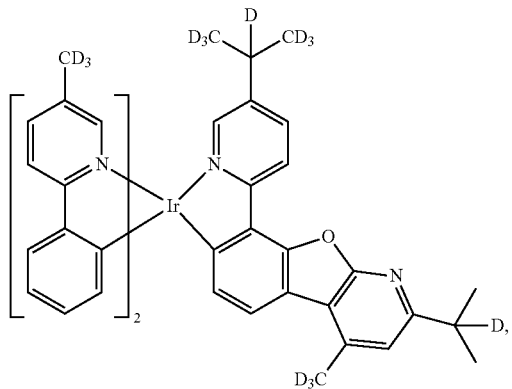
D119
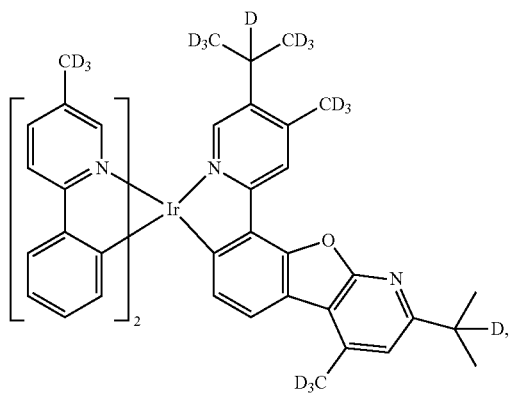
D120
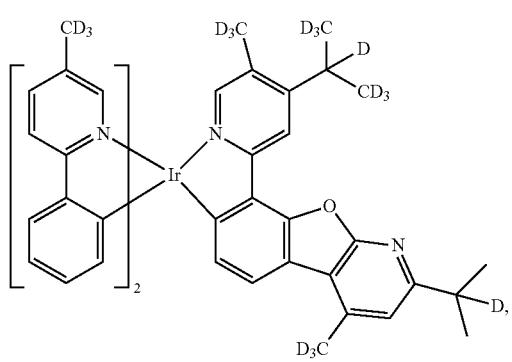
D121
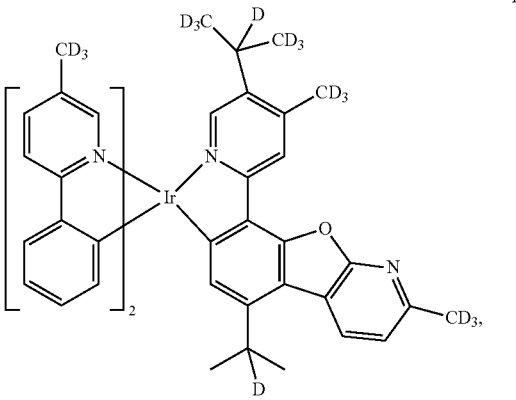
D122
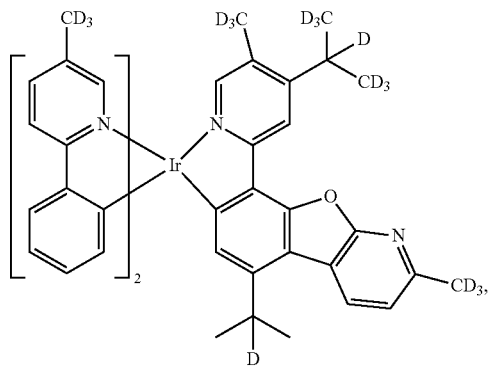
D123
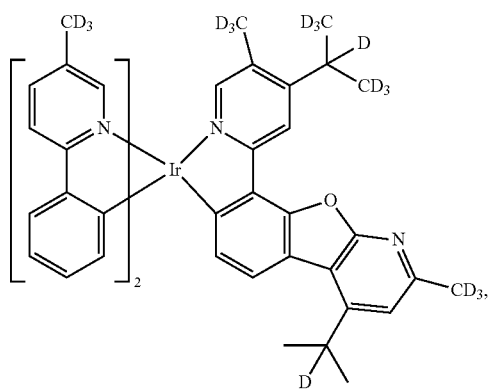
D124
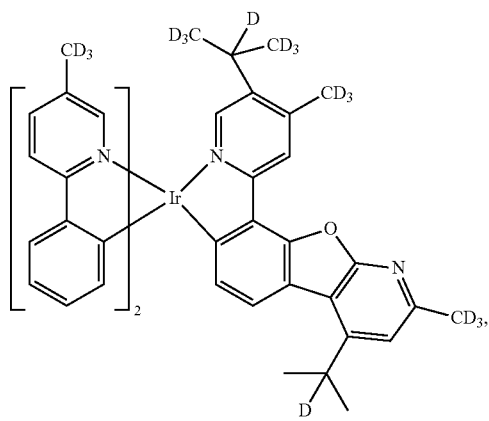
D125
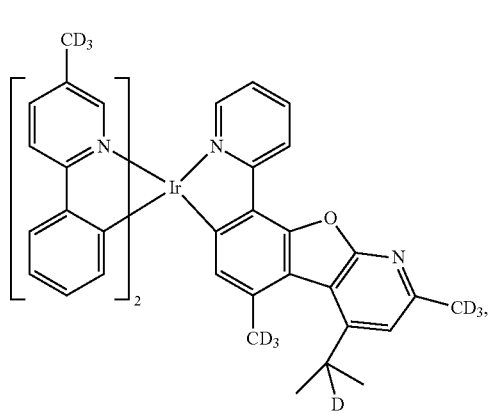
D126

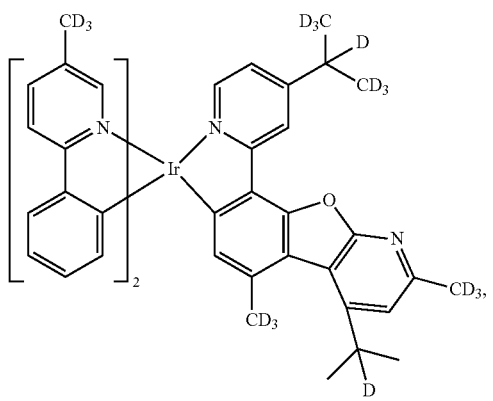
D127
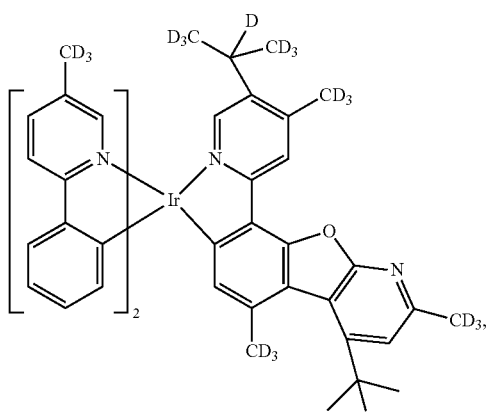
D128
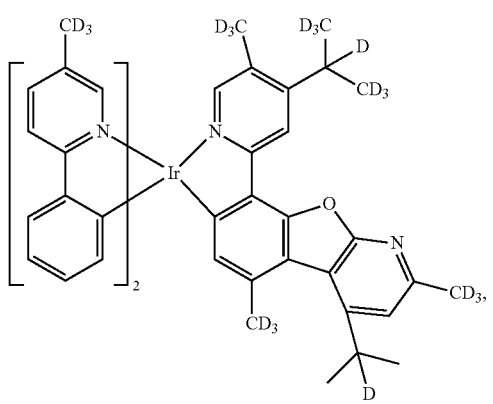
D129
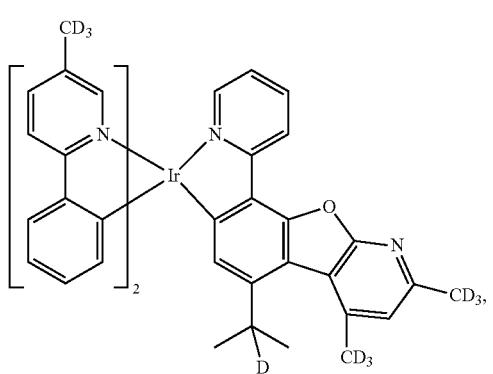
D130
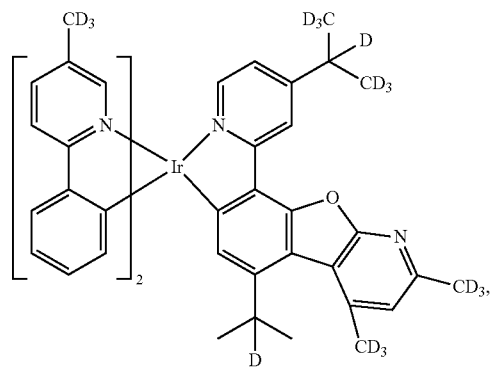
D131
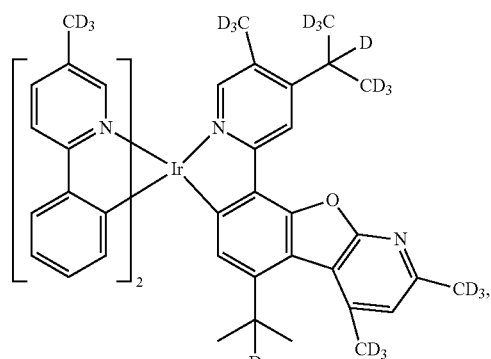
D132
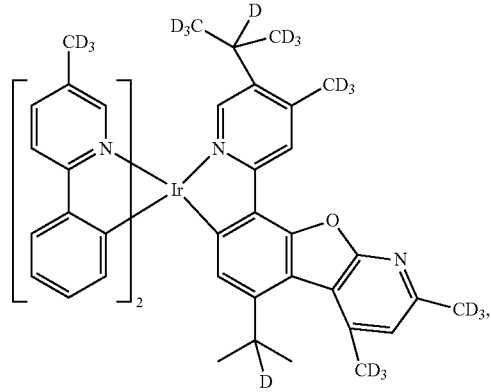
D133
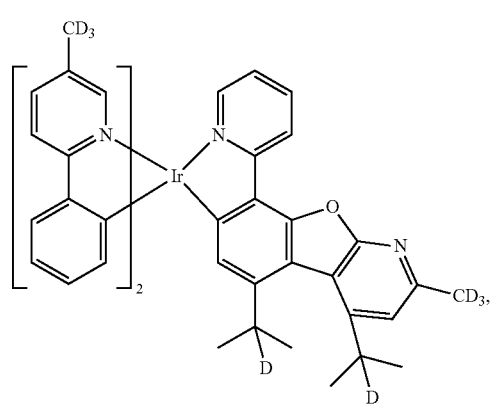
D134

D135
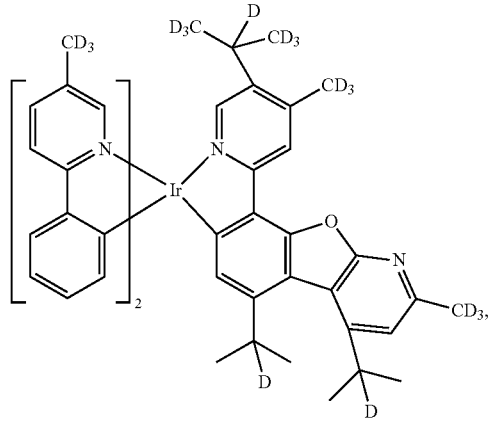
D136
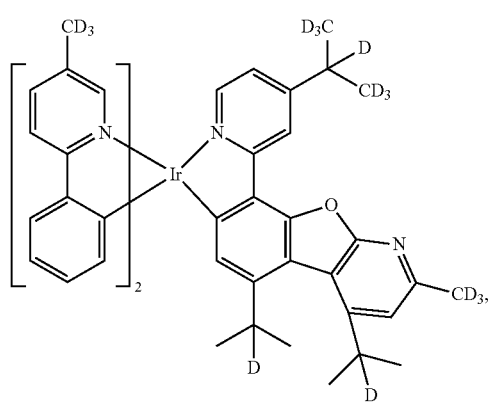
D137
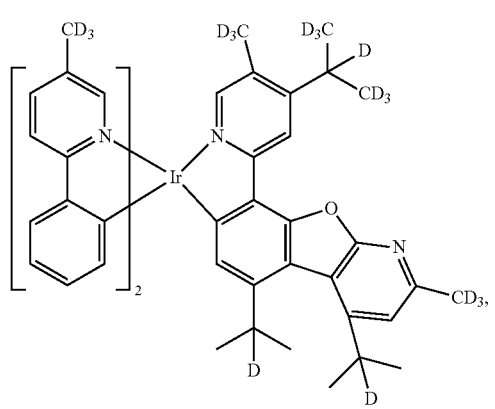
D138
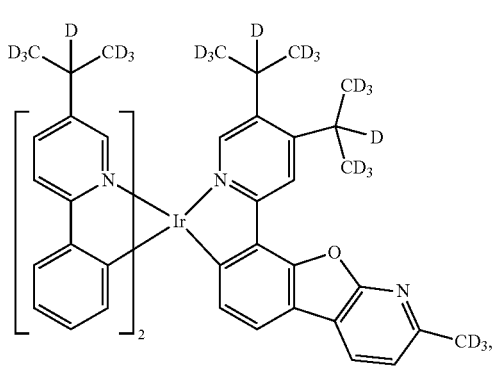
D139
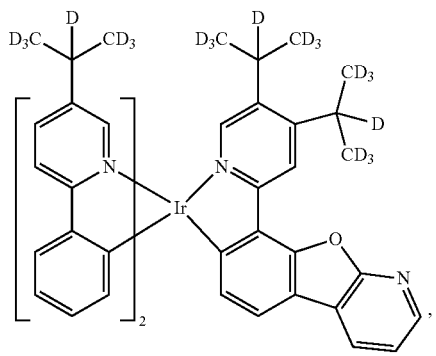
D140
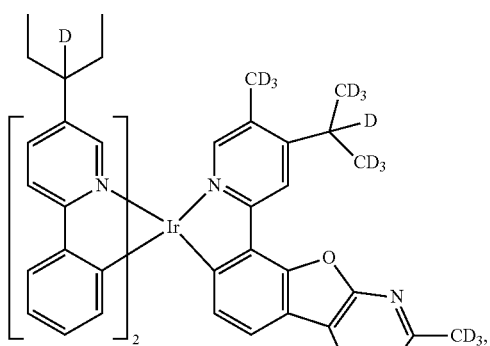
D141
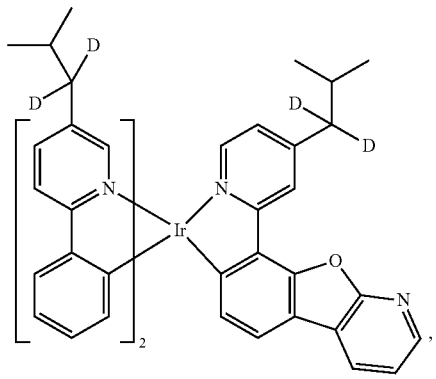
D142
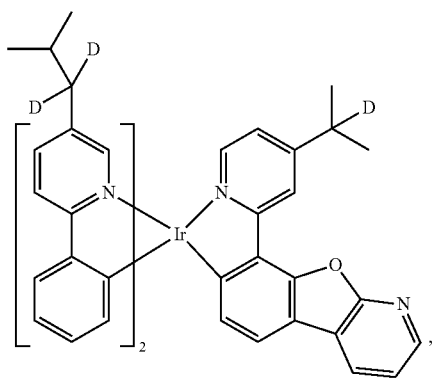

D143
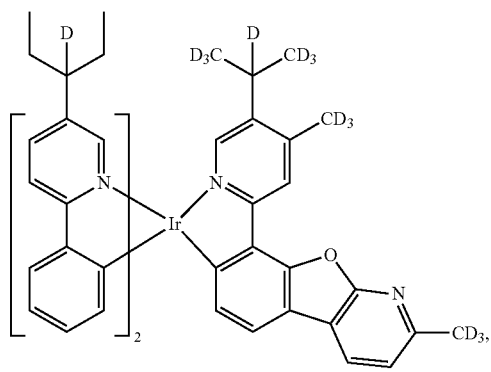
D144
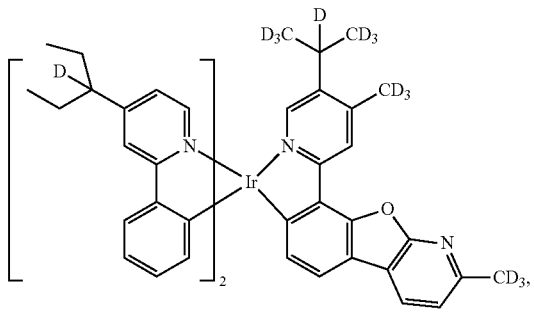
D145
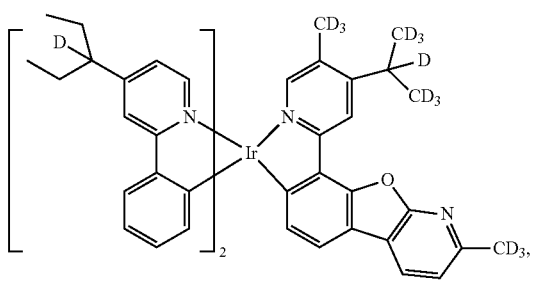
D146
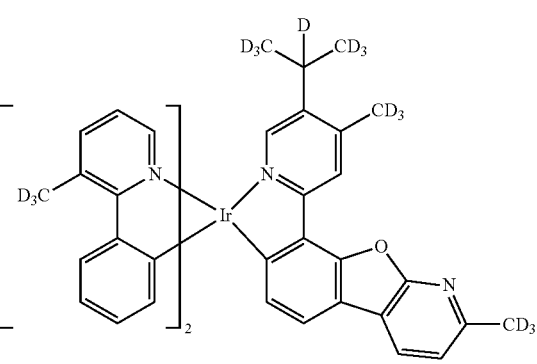
D147
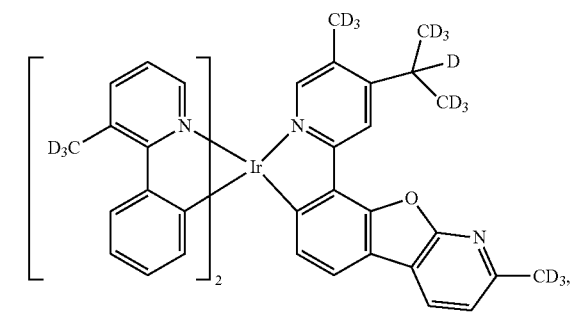
D148
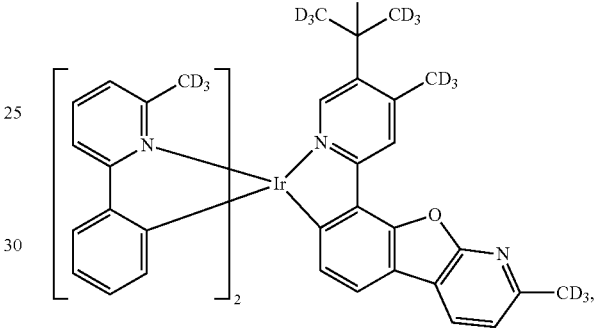
D149
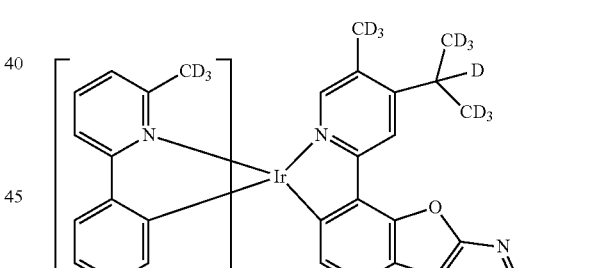
D150
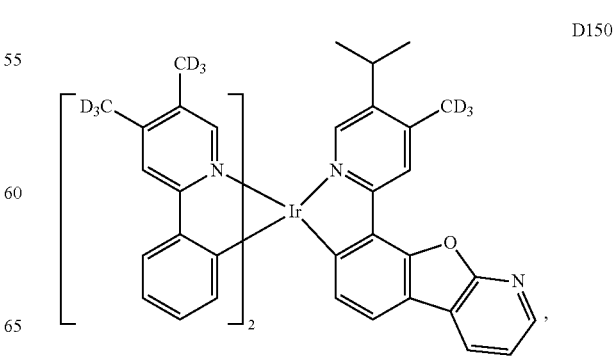

-continued
D151
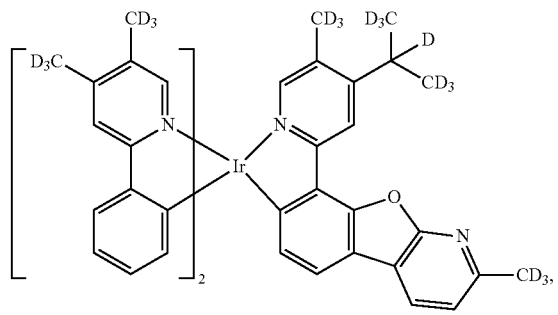
D152
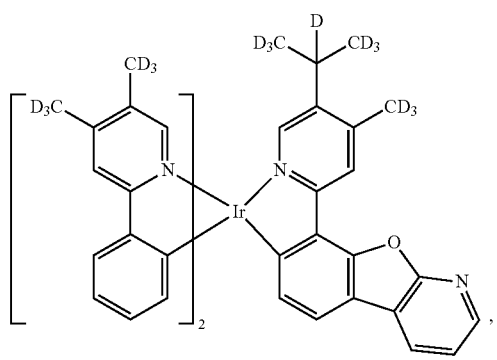
D153
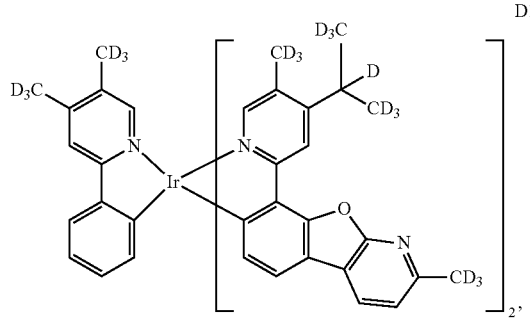
D154
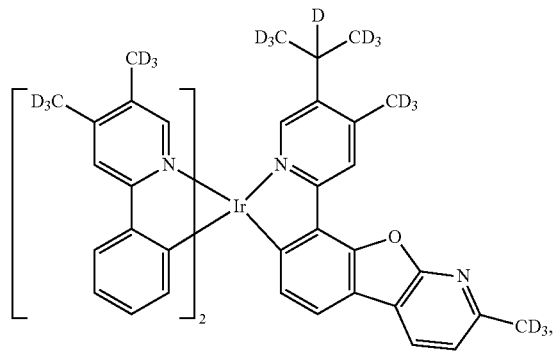
-continued
D155
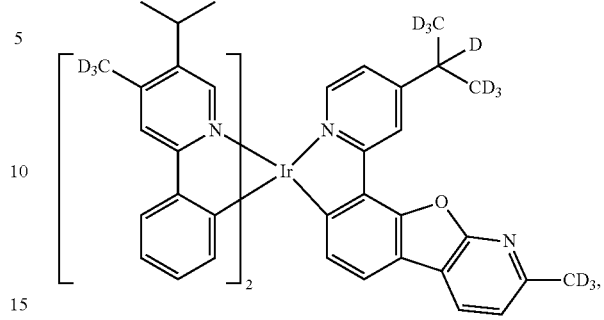
D156
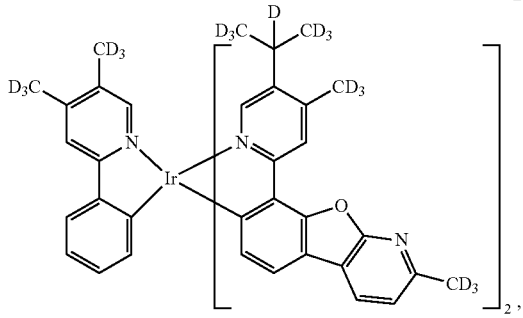
D157
D158
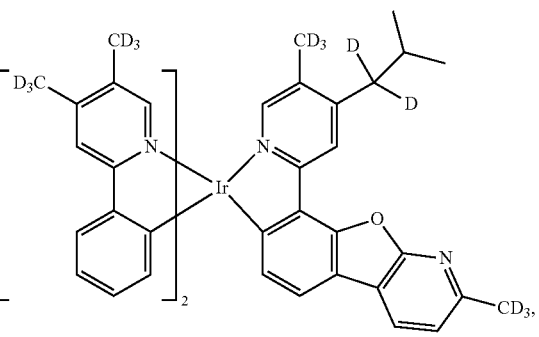

D159
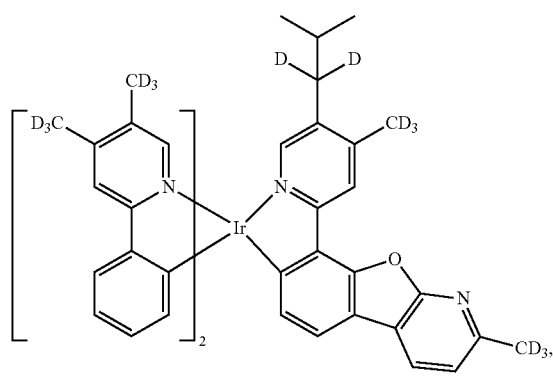
D160
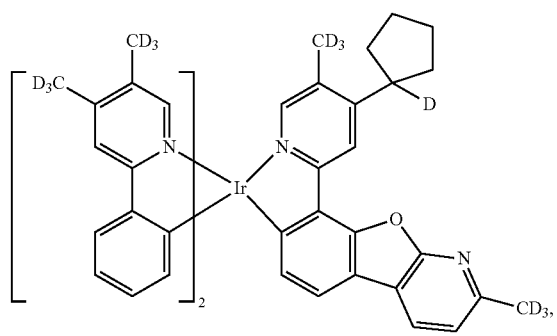
D161
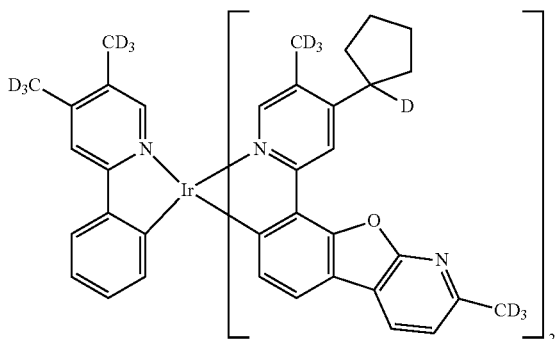
D162
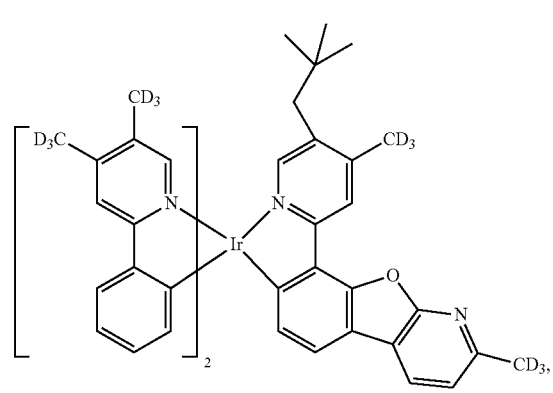
D163
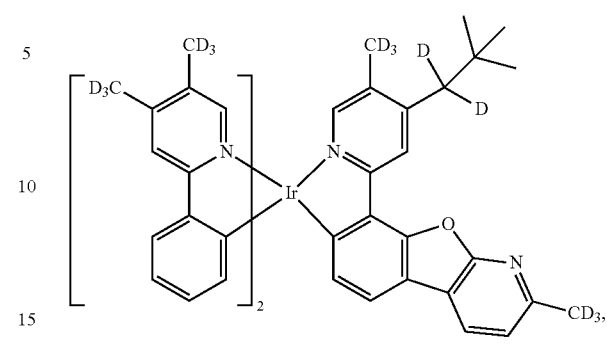
D164
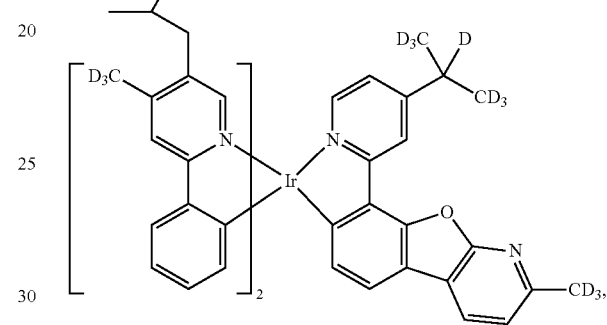
D165
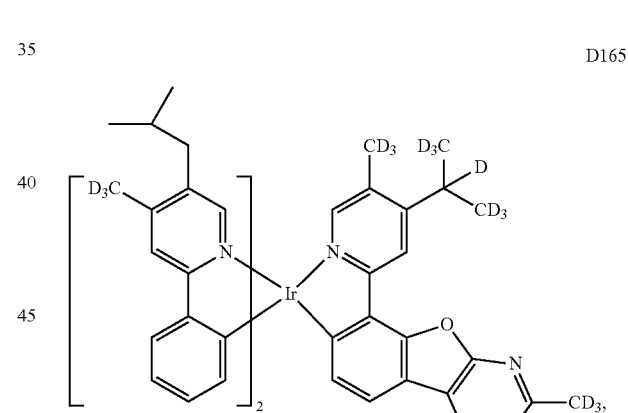
D166
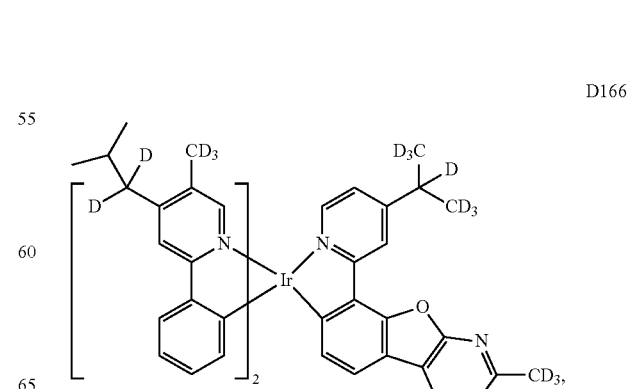

D167 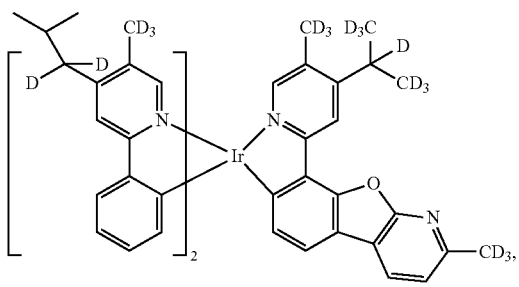
D171 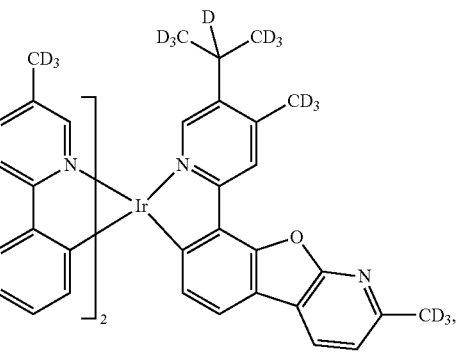
D168 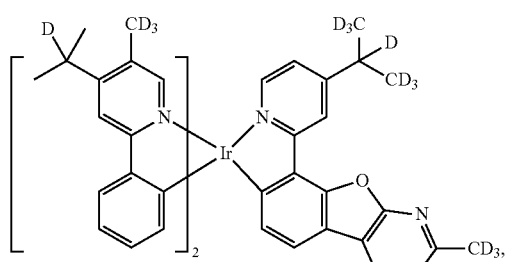
D172 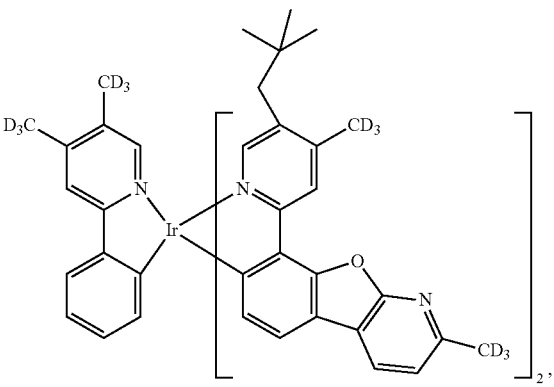
D169 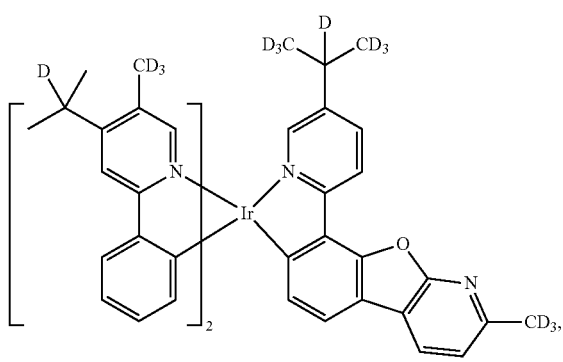
D173 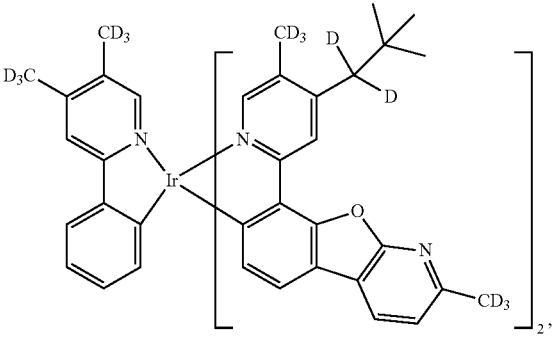
D170 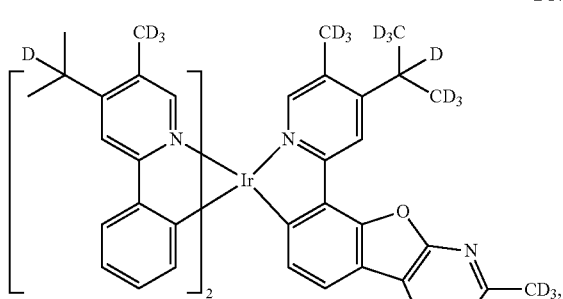
D174 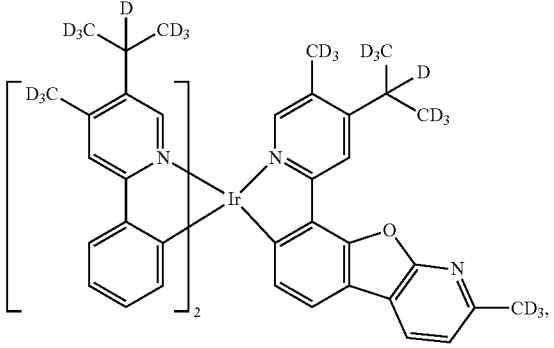

D175
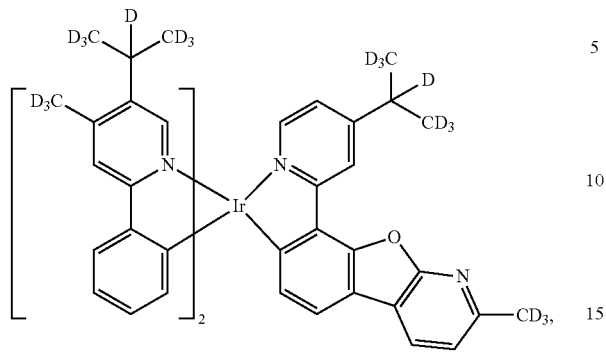
D176
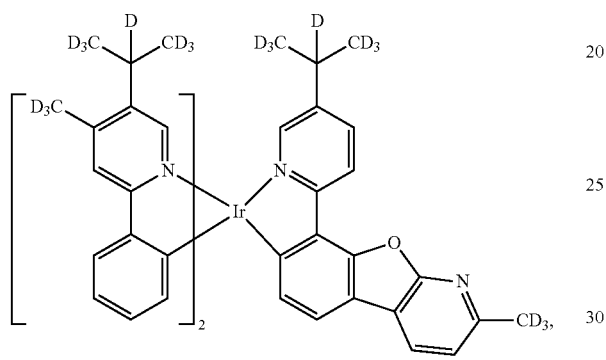
D177
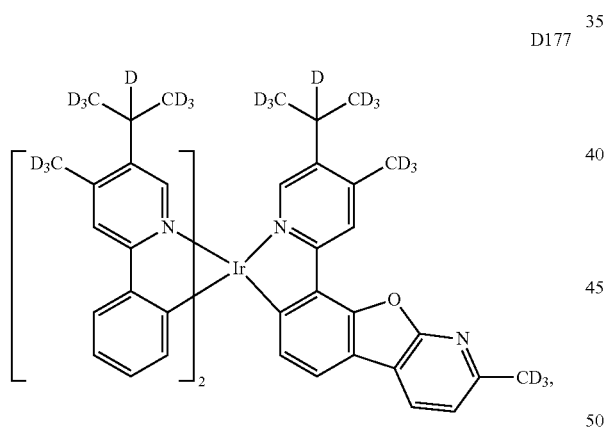
D178
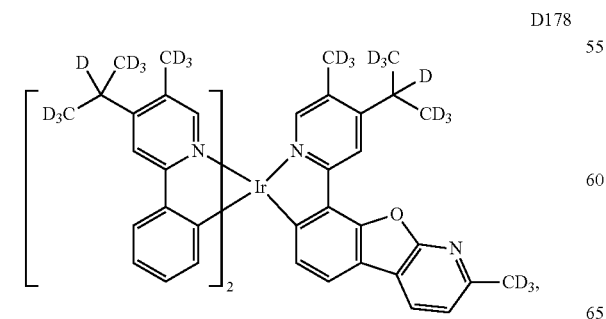
D179
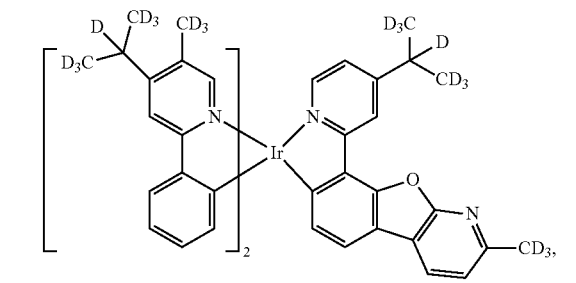
D180
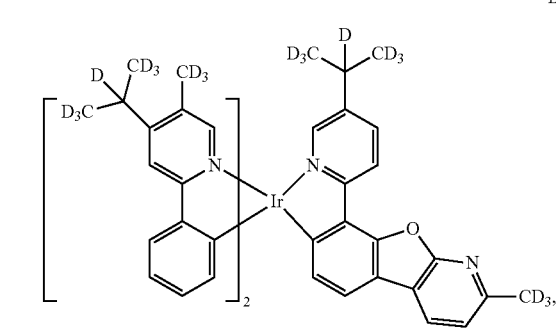
D181
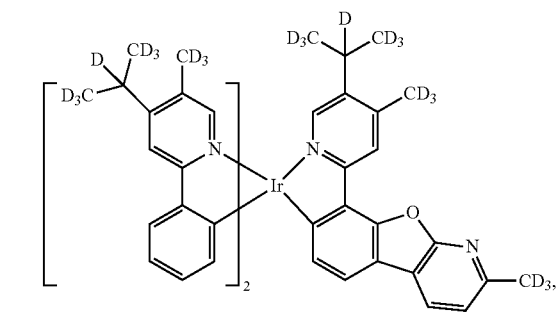
D182
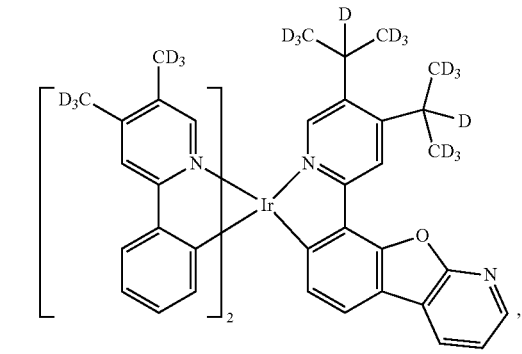

297
-continued
D183
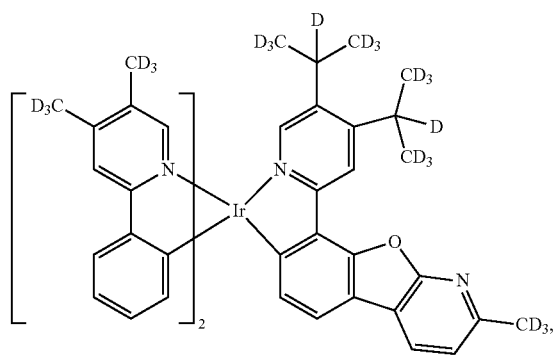
D184
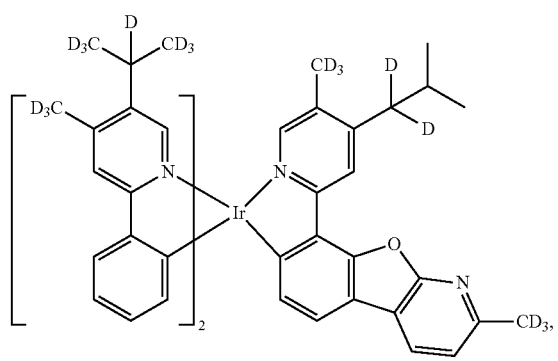
D185
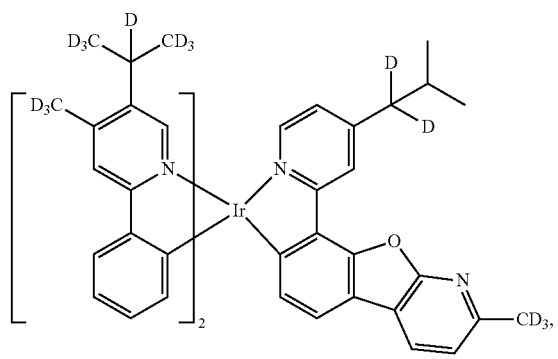
D186
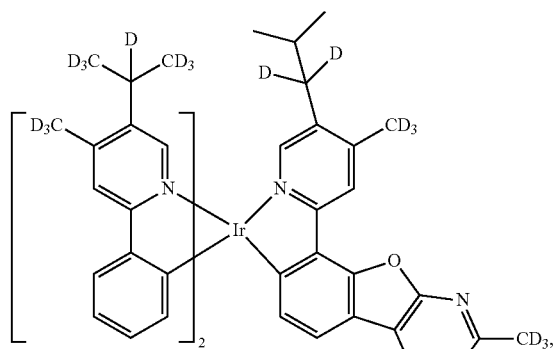
298
-continued
D187
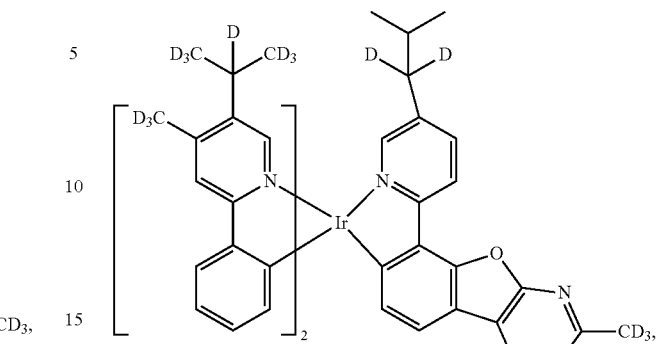
D188
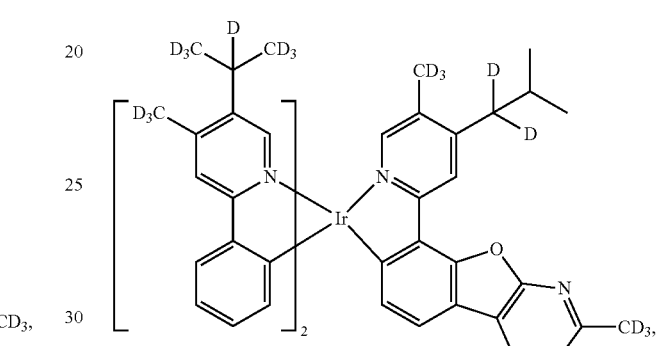
D189
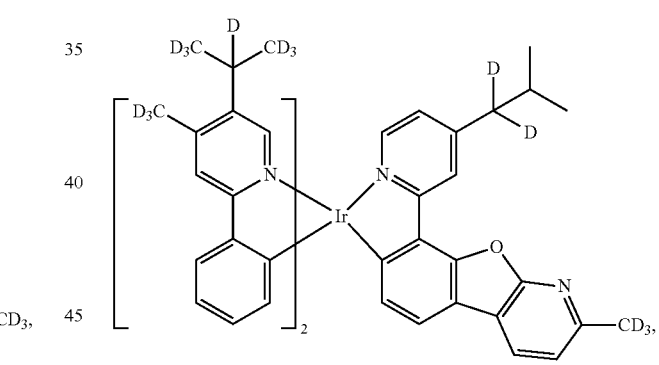
D190
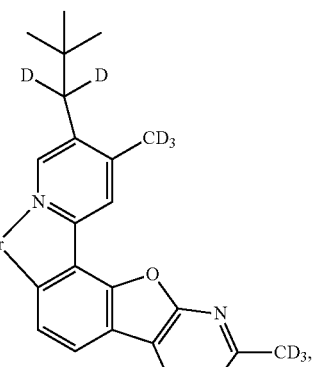

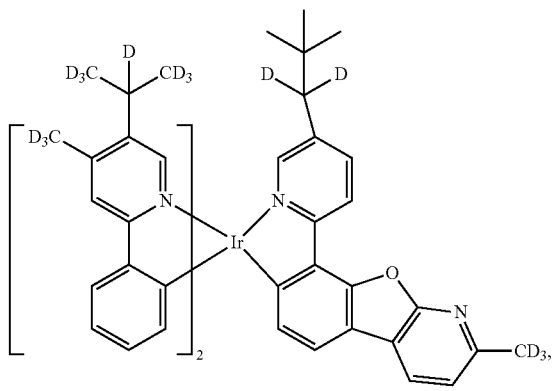
D191
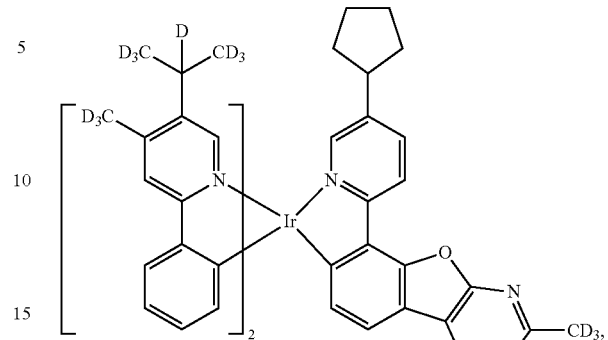
D195
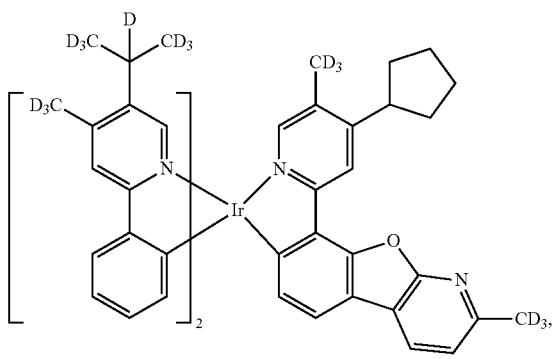
D192
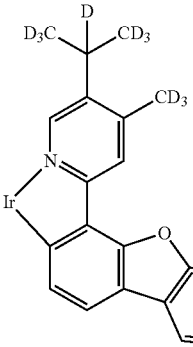
D196
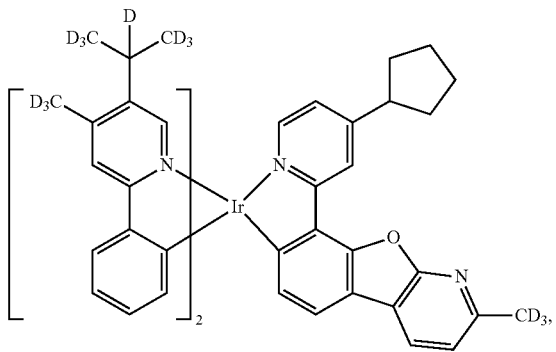
D193
D197
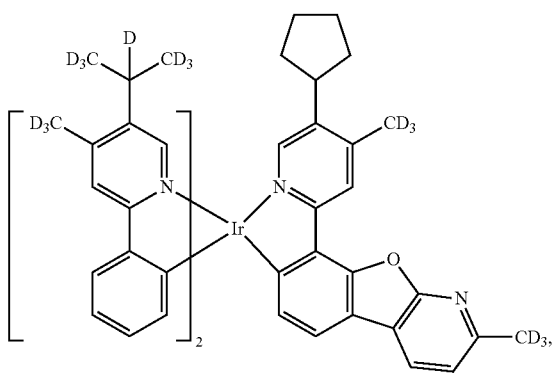
D194
D198

D199
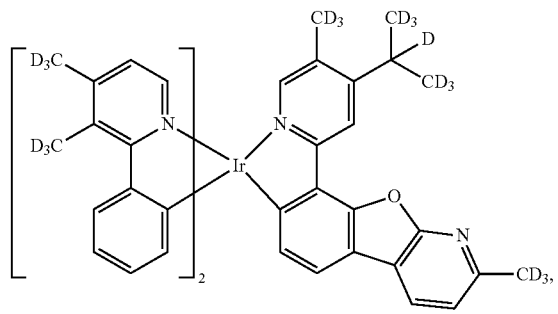
D200
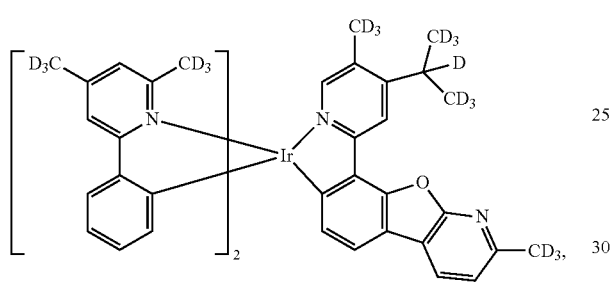
D201
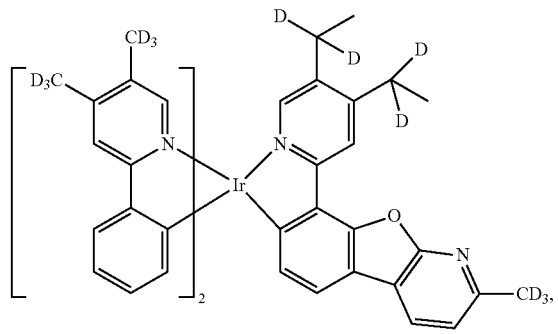
D202
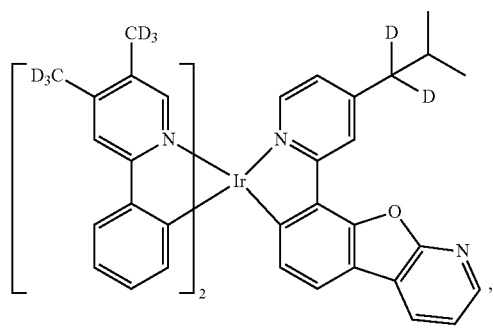
D203
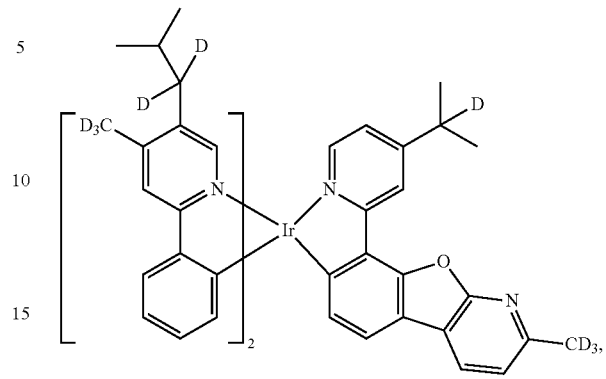
D204
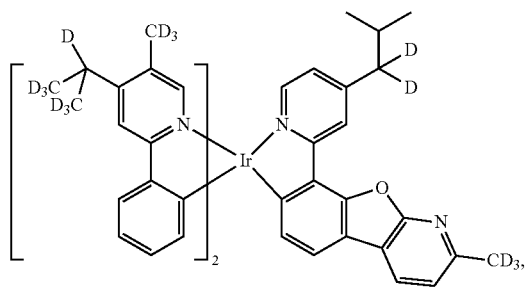
D205
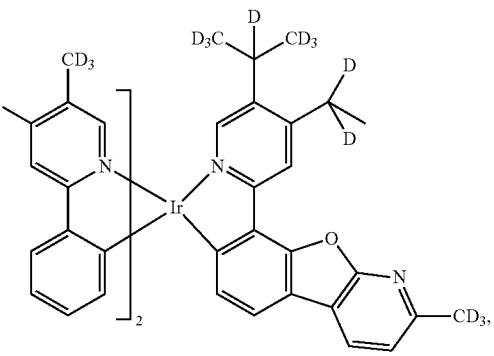
D206
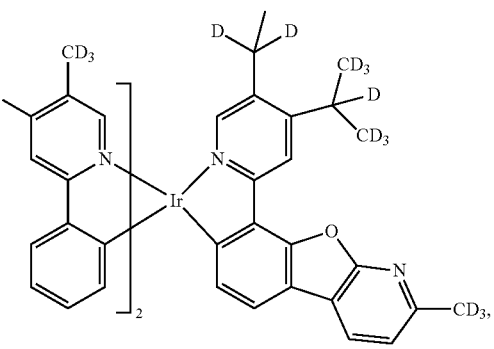

303
-continued
D207
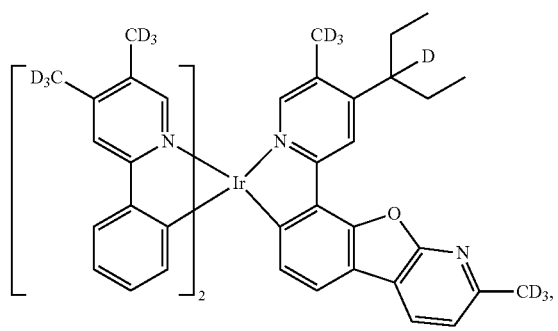
D208
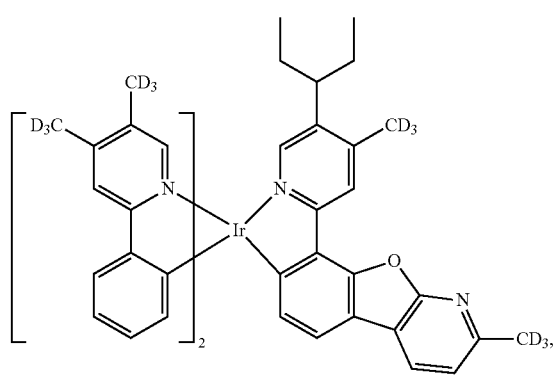
D209
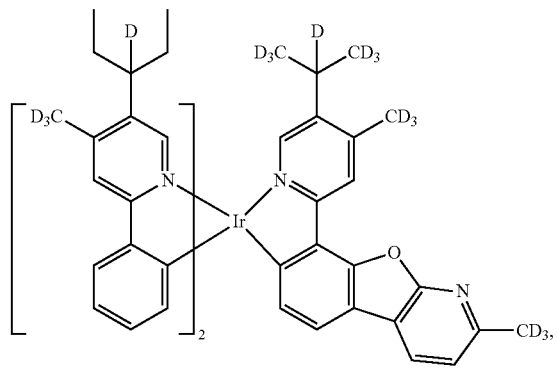
D210
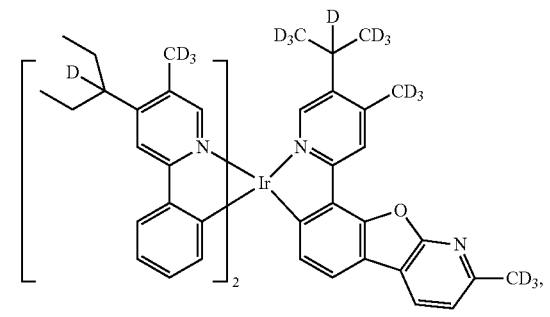
304
-continued
D211
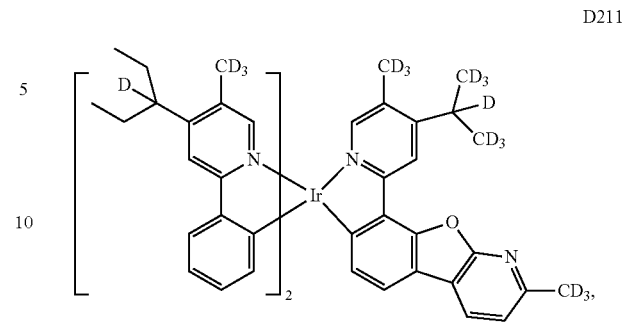
D212
D213
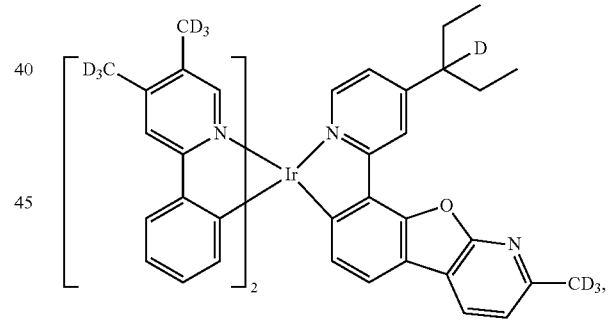
D214
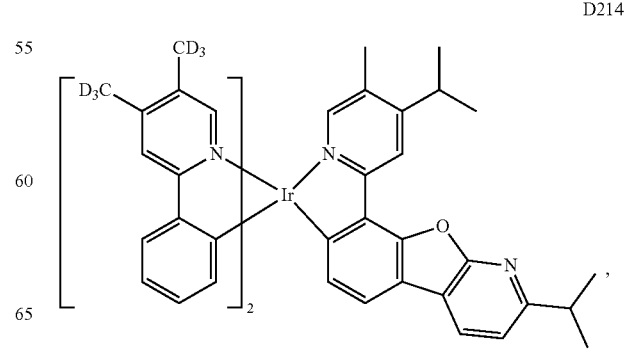

D215
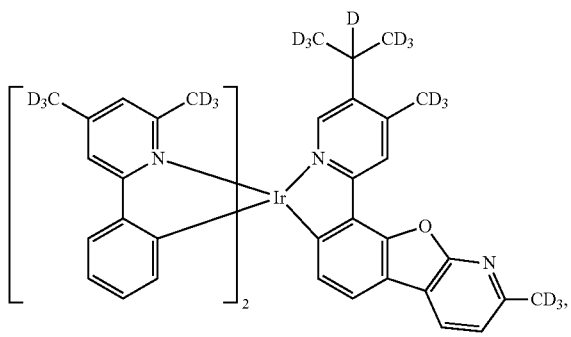
D216
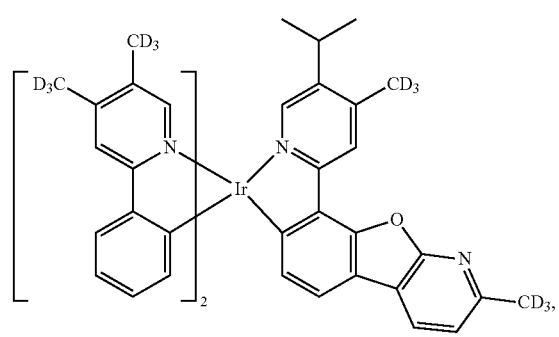
D217
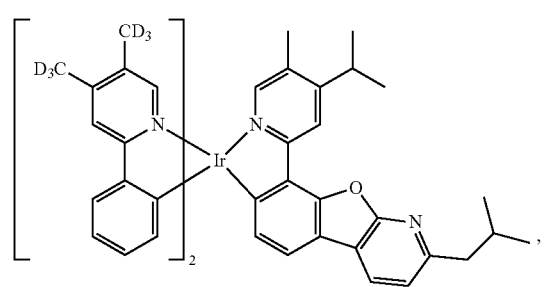
D218
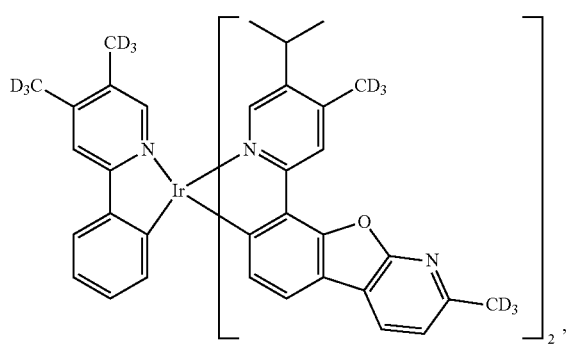
D219
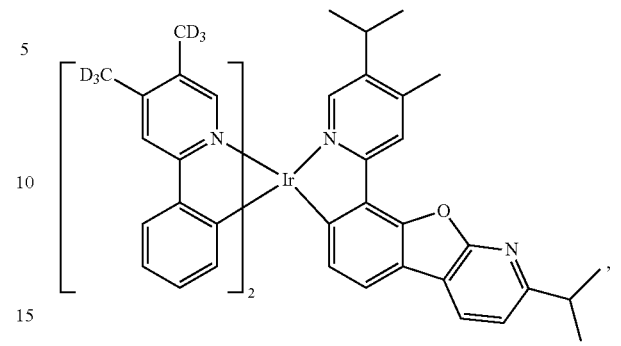
D220
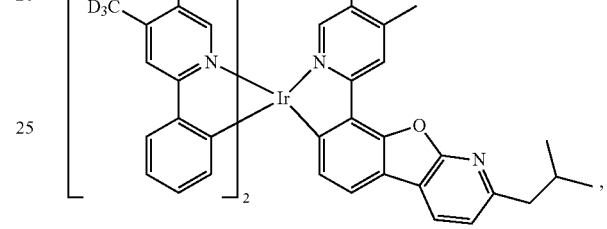
D221
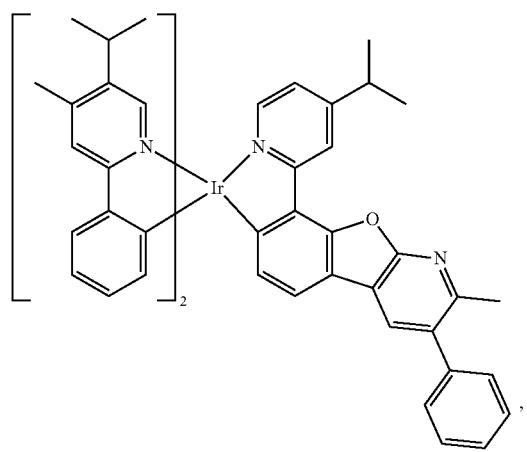
D222
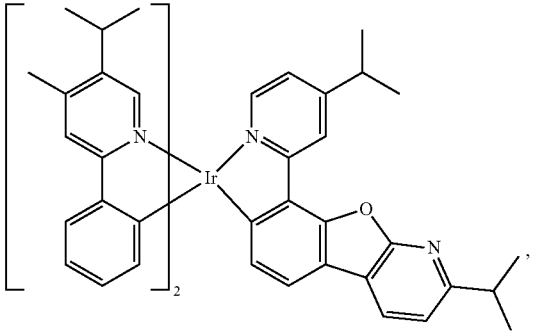

307
-continued
D223
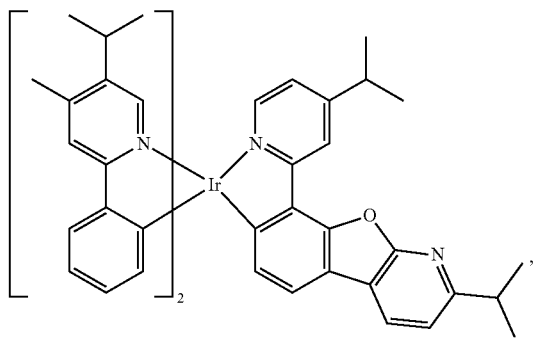
D224
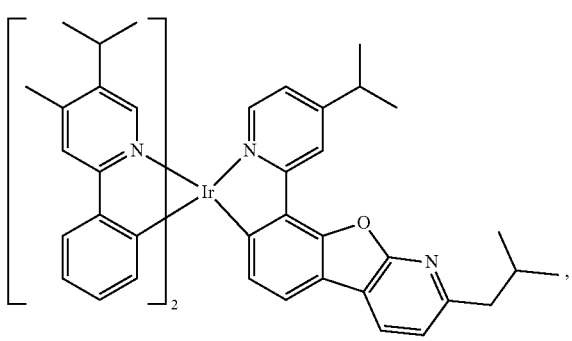
D225
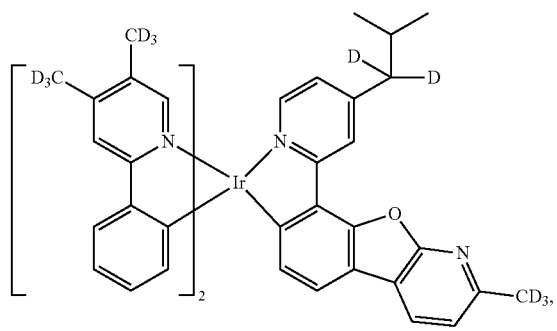
D226
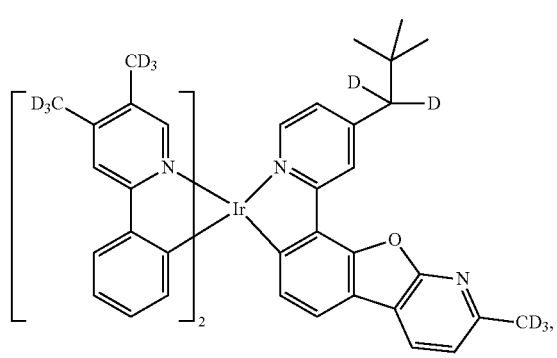
308
-continued
D227
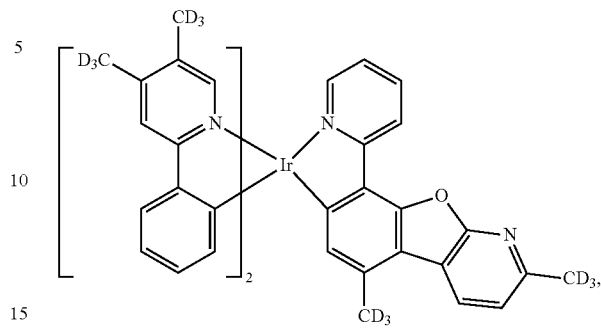
D228
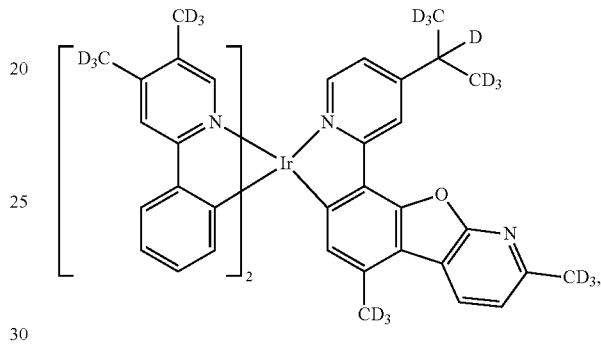
D229
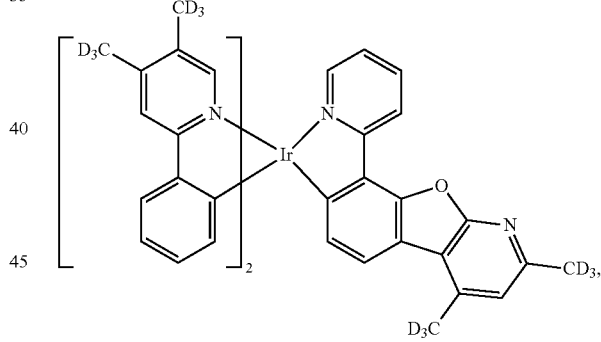
D230
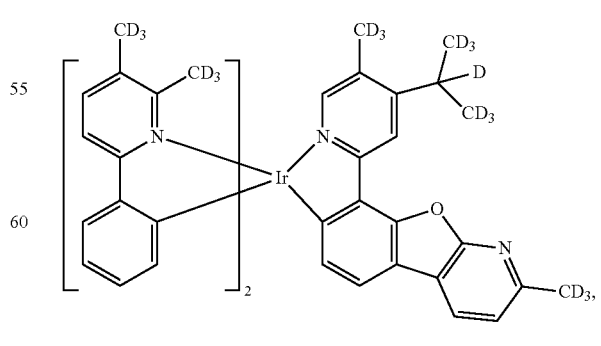

309
-continued
D231
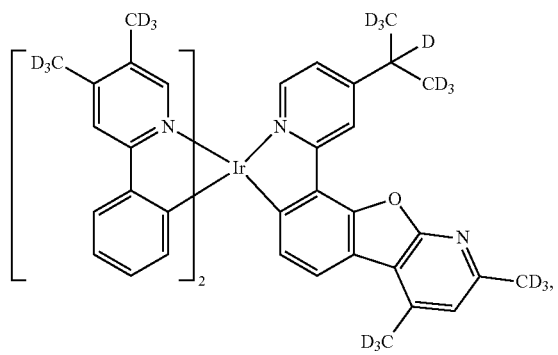
D232
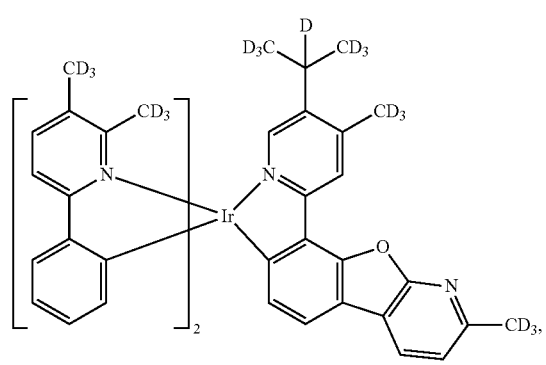
D233
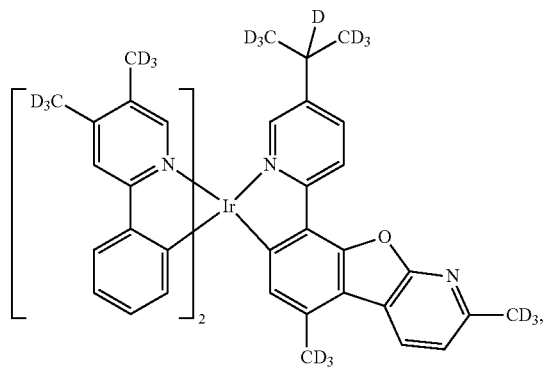
D234
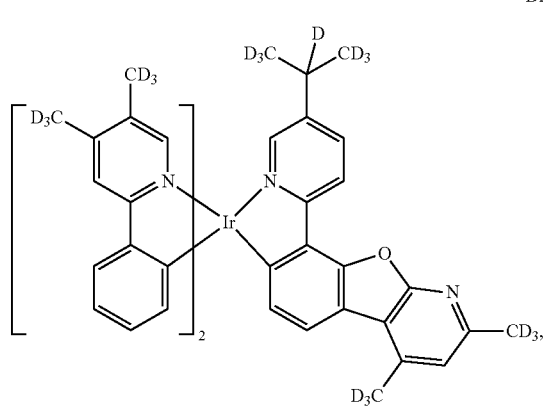
310
-continued
D235
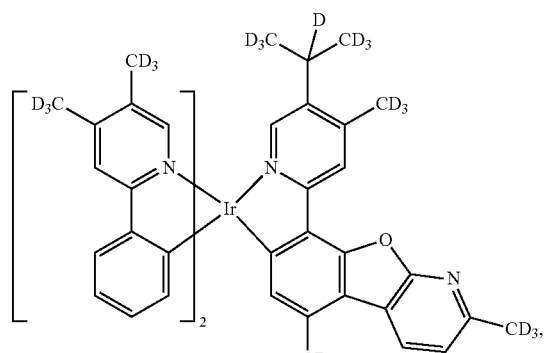
D236
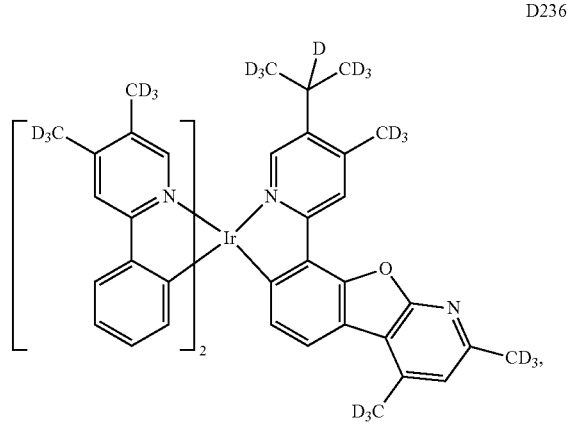
D237
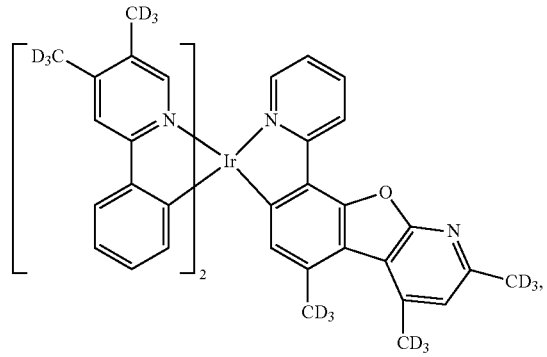
D238
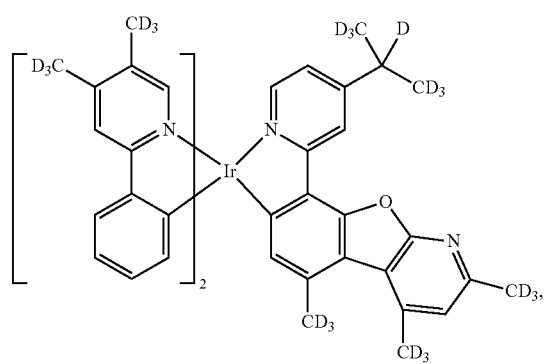

D239
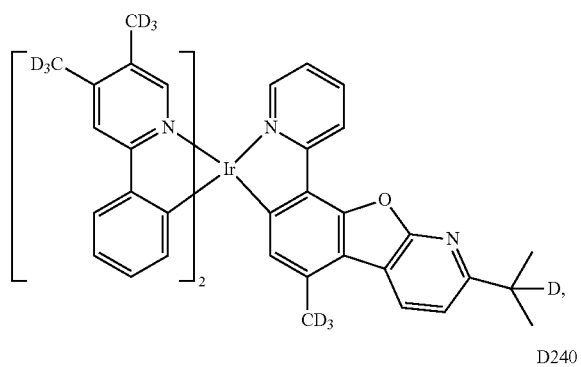
D240
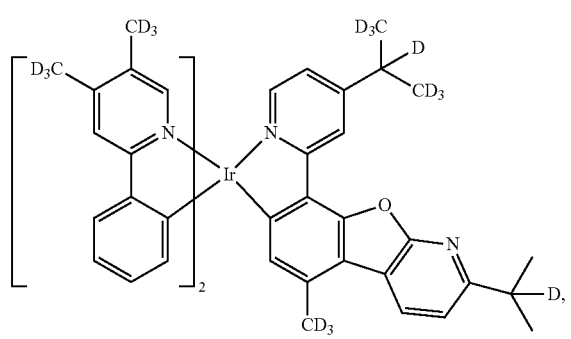
D241
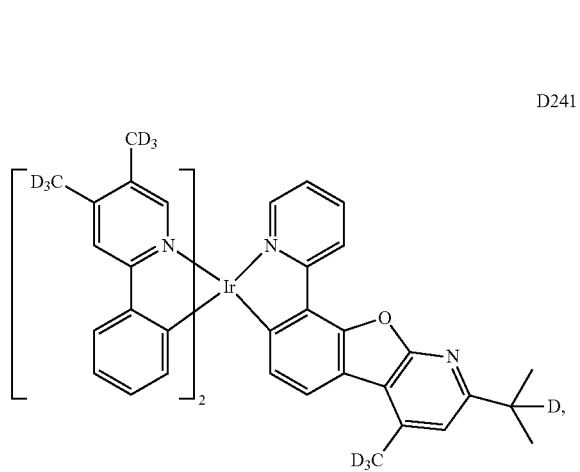
D242
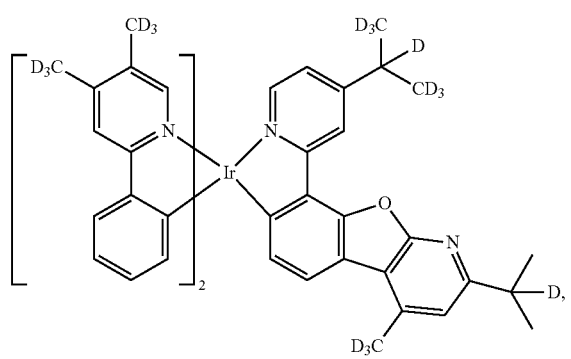
D243
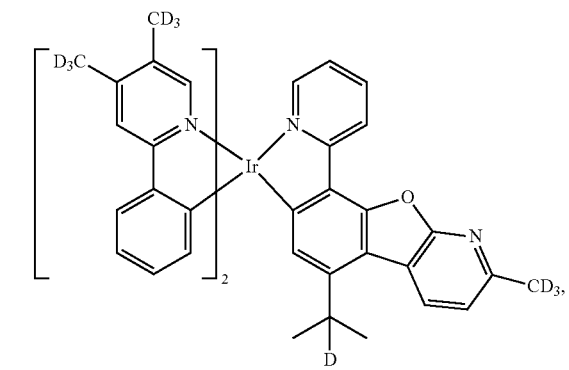
D244
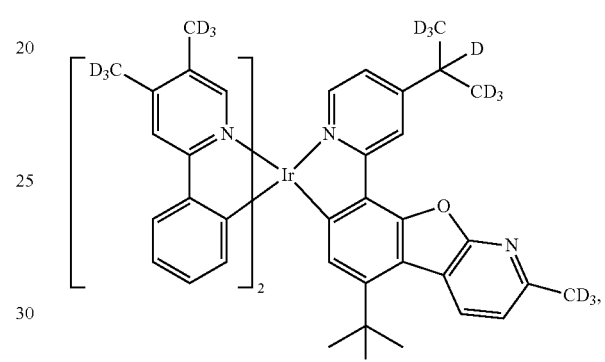
D245
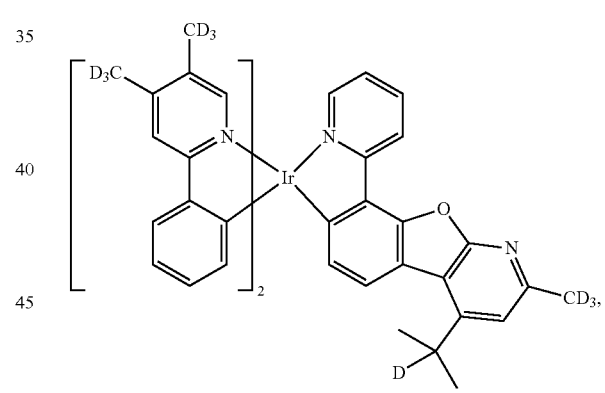
D246
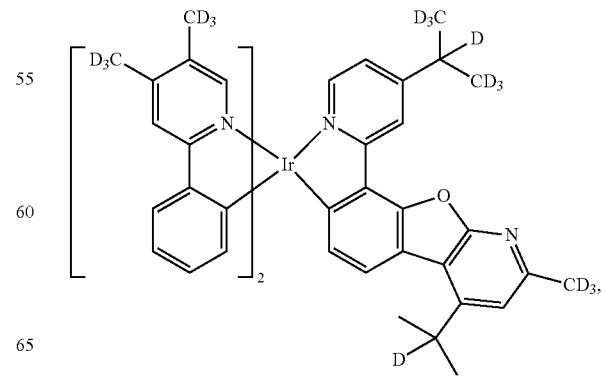

D247
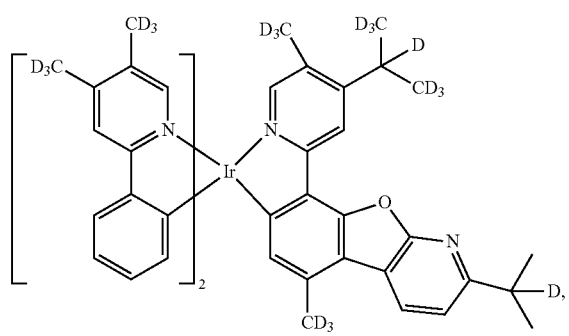
D248
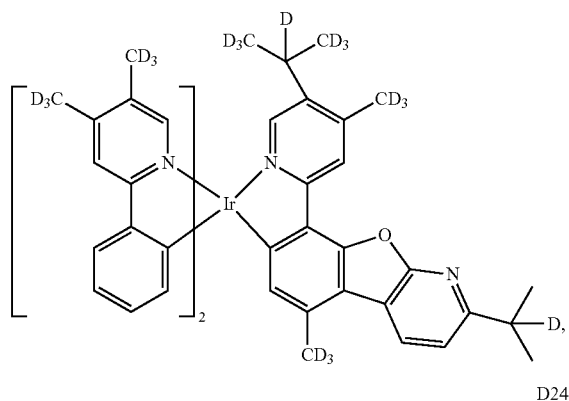
D249
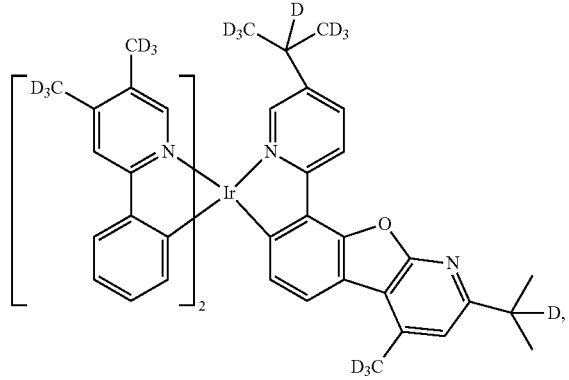
D250
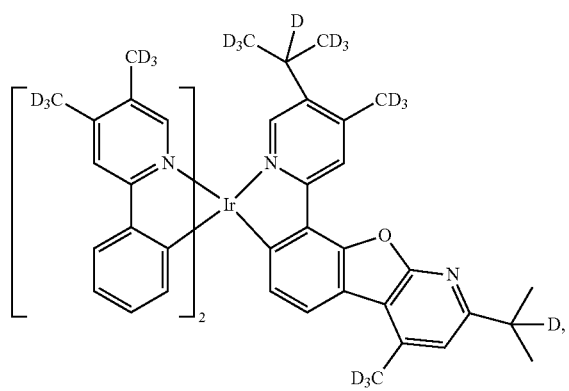
D251
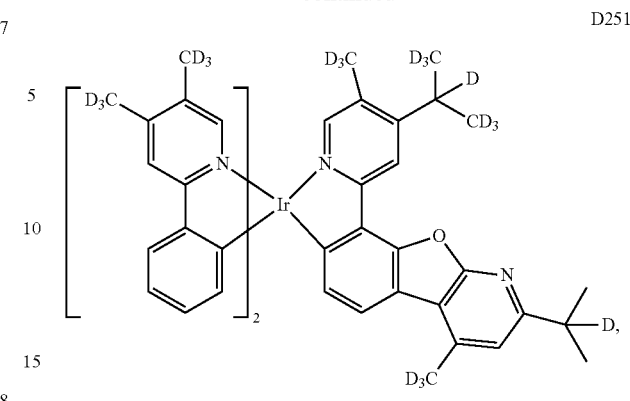
D252
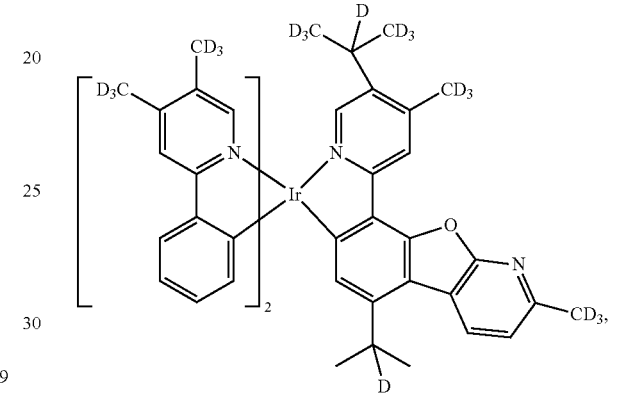
D253
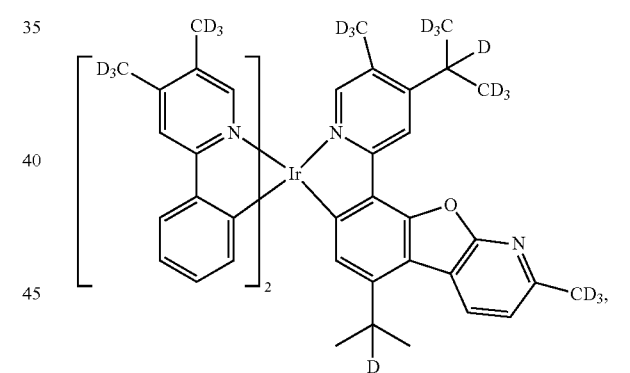
D254
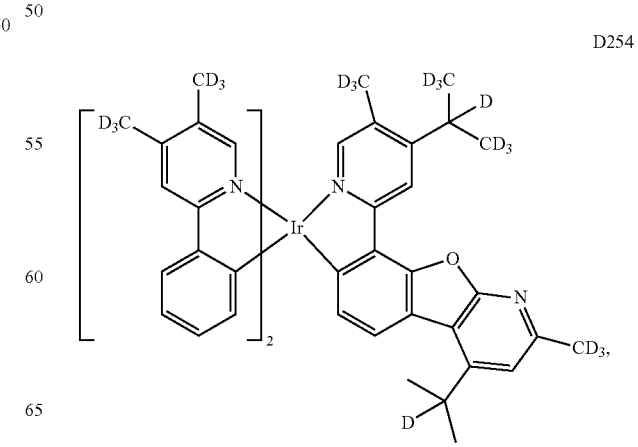

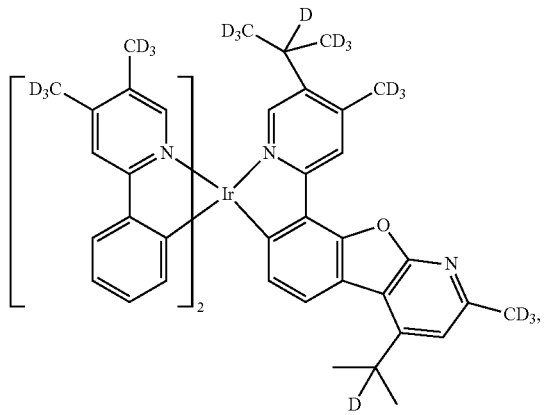
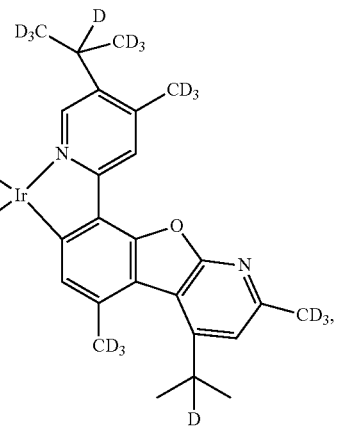
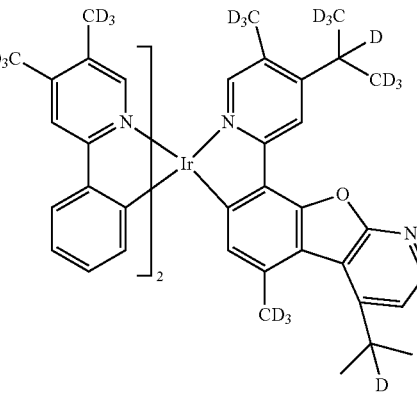
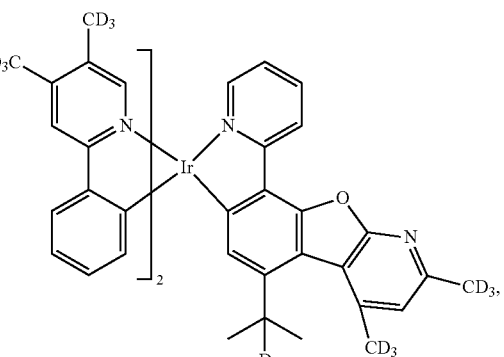
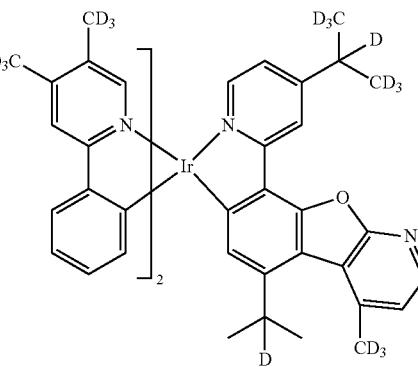

D262
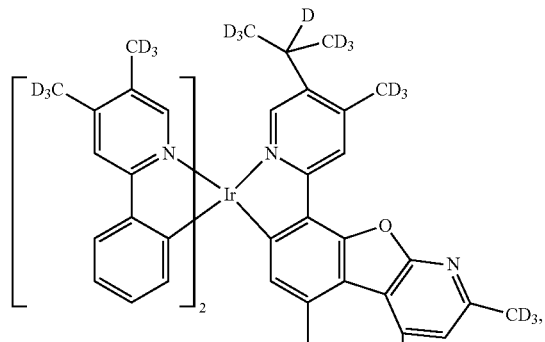
D263
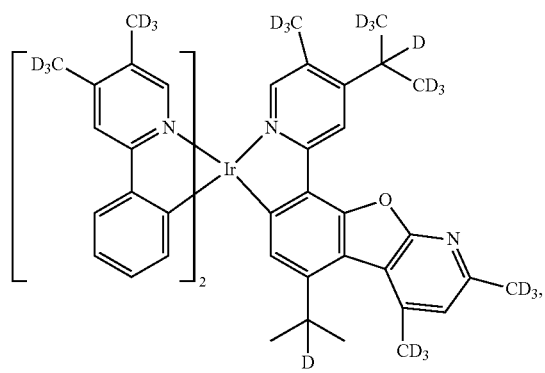
D264
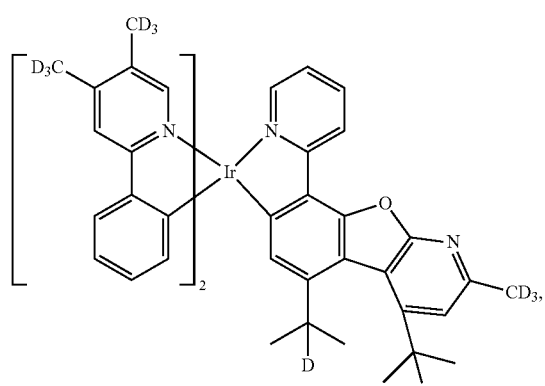
D265
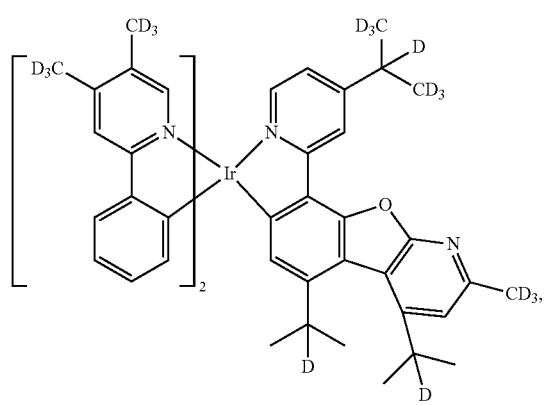
D266
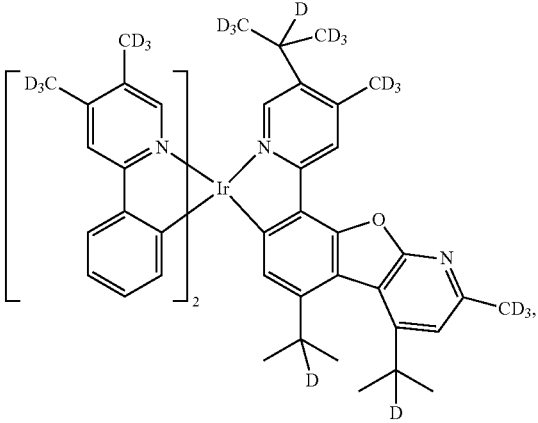
D267
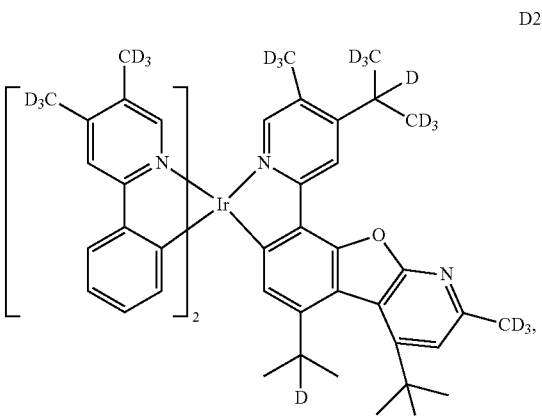
D268
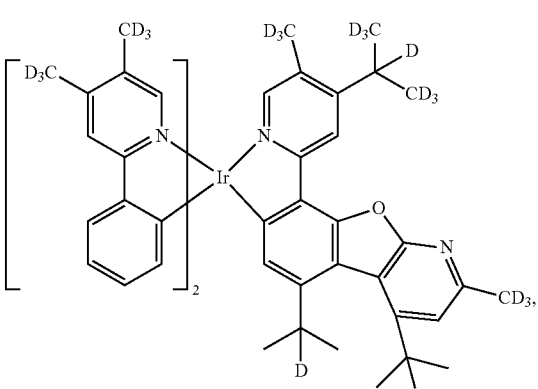
D269
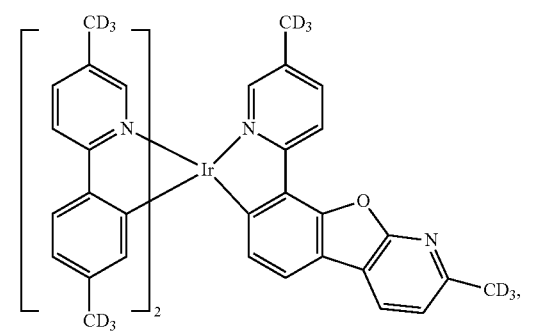

D270
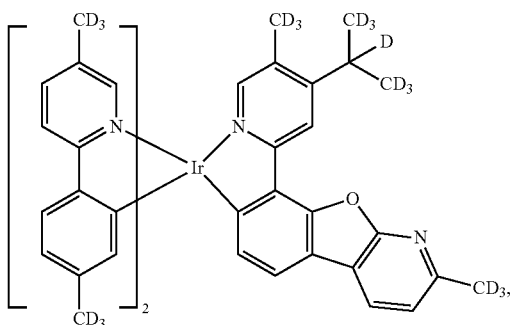
D271
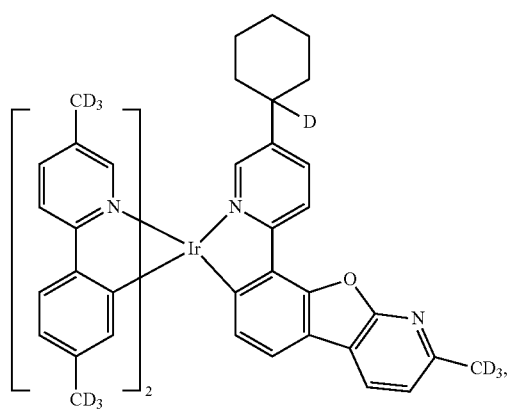
D272
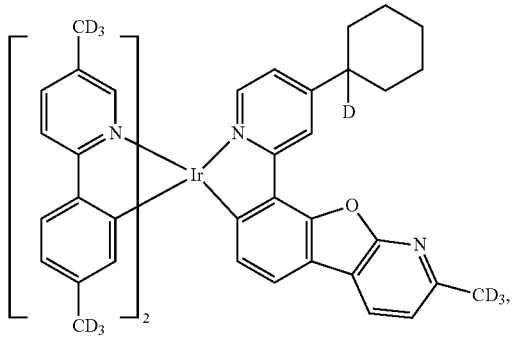
D273
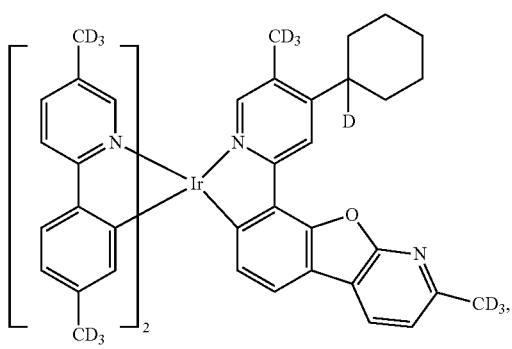
D274
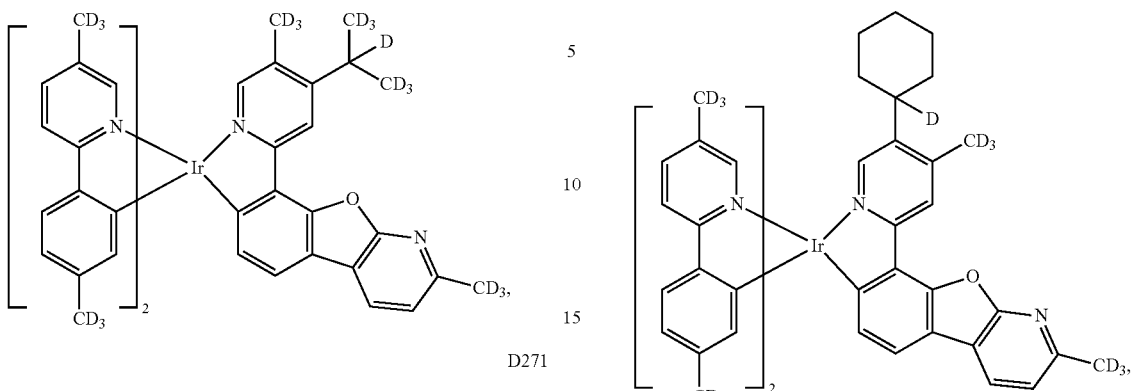
D275
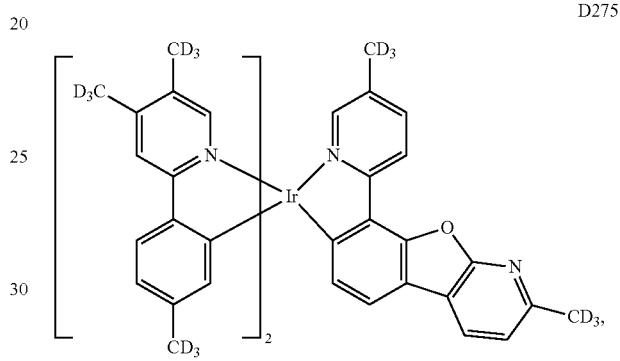
D276
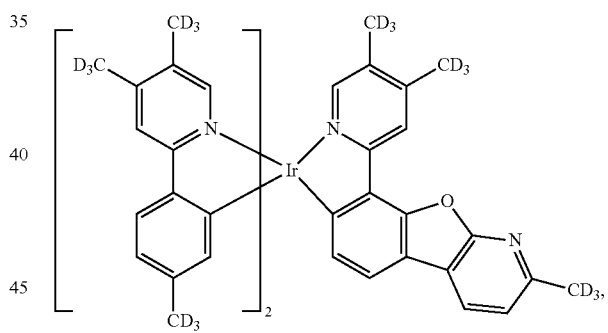
D277
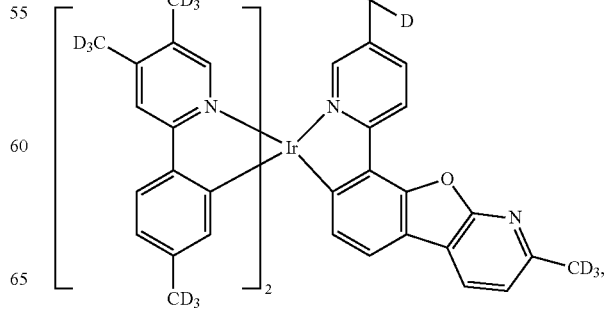

D278
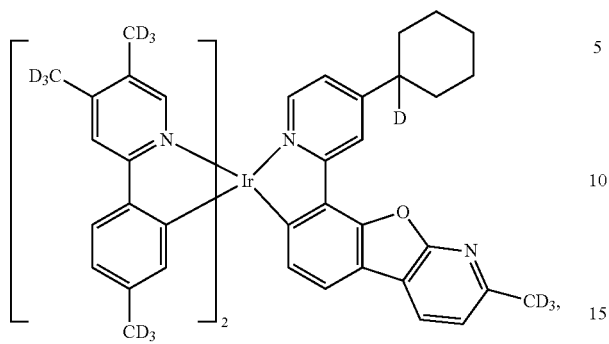
E1
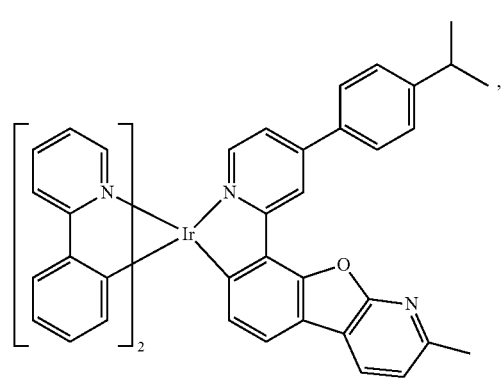
E2
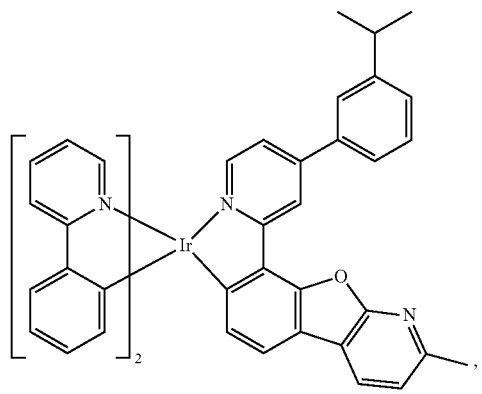
E3
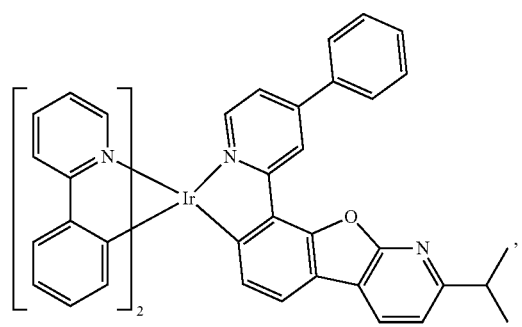
E4
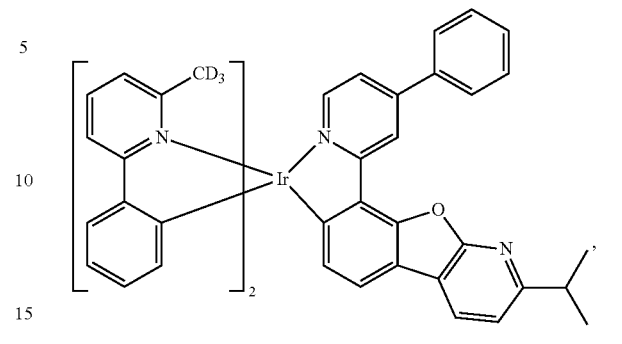
E5
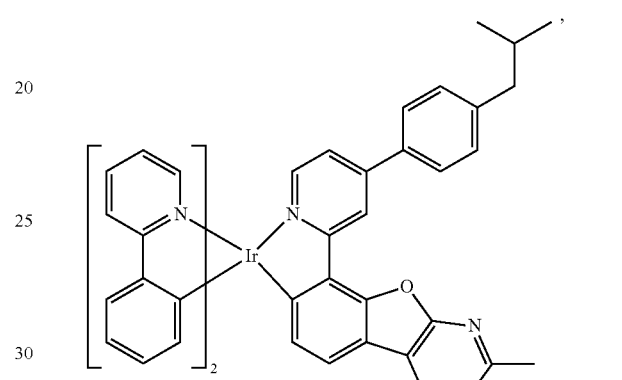
E6
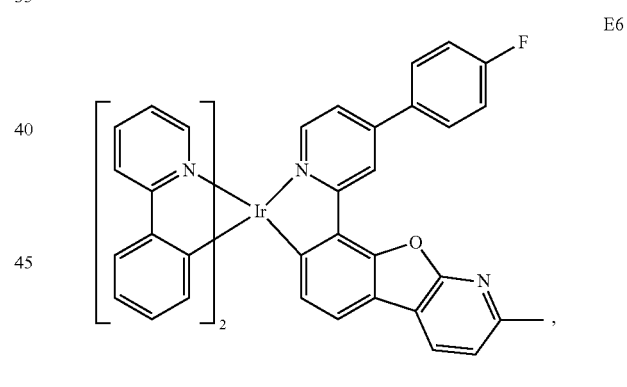
E7
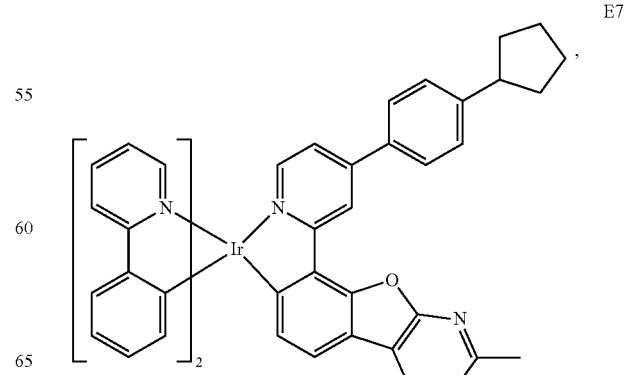

323
-continued
E8
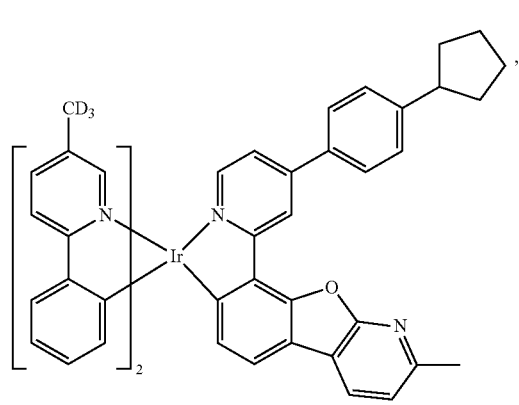
E9
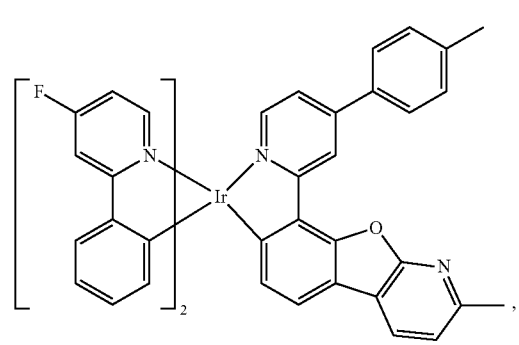
E10
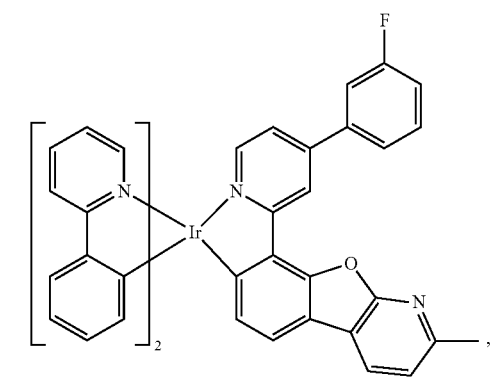
E11
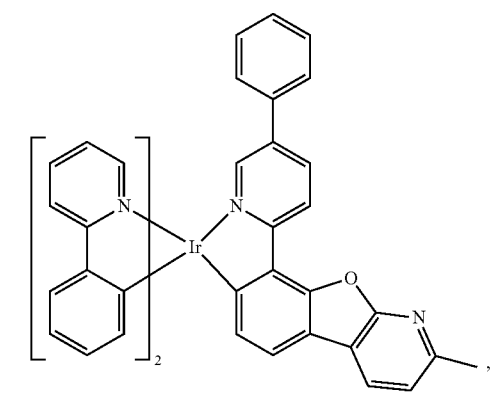
324
-continued
E12
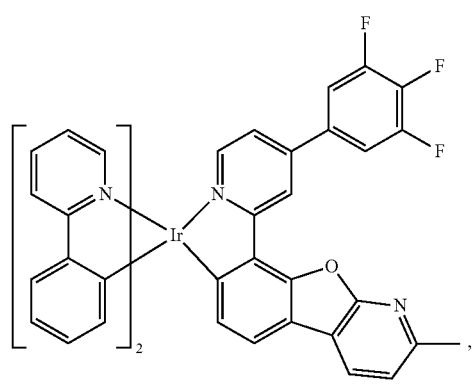
E13
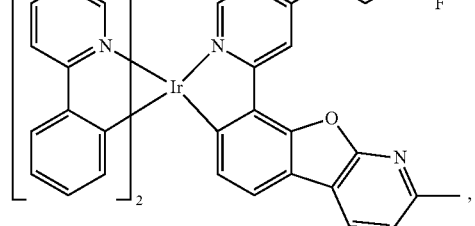
E14
E15
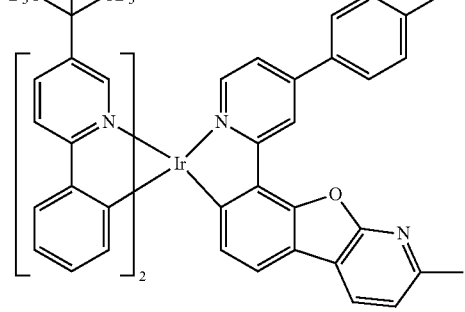

-continued
E16
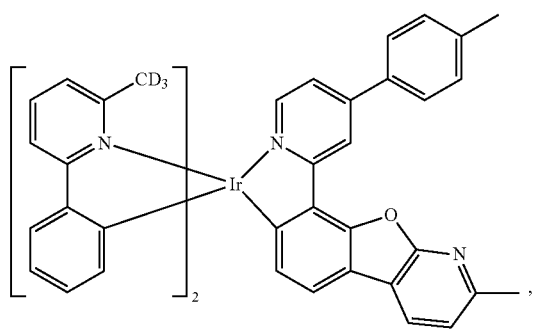
E17
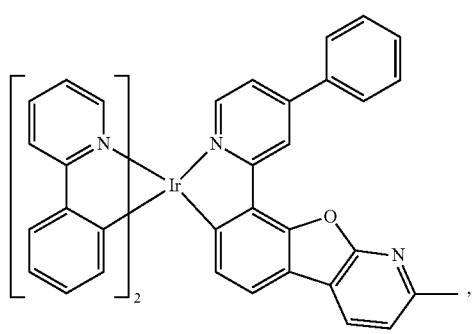
E18
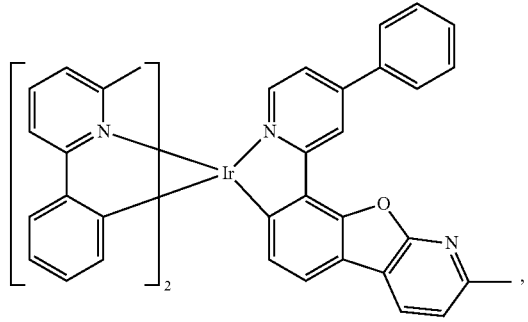
E19
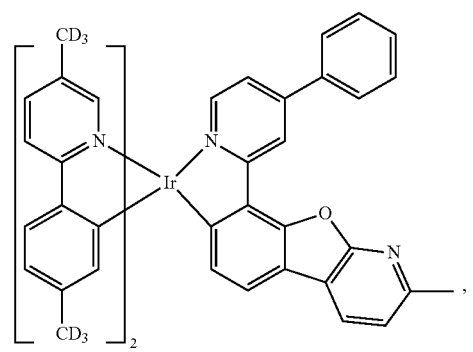
-continued
E20
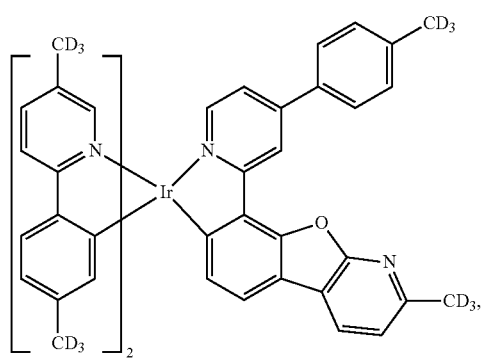
E21
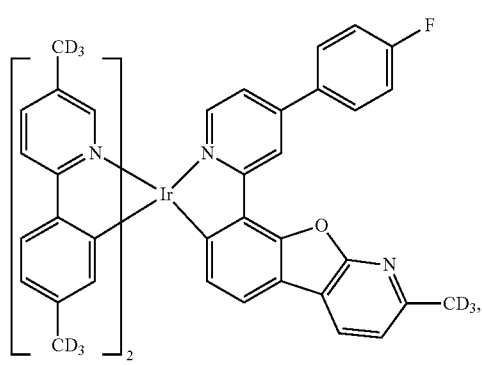
E19
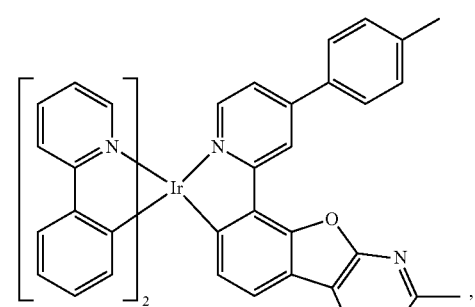
F1
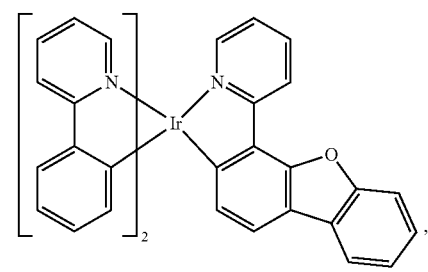
F2
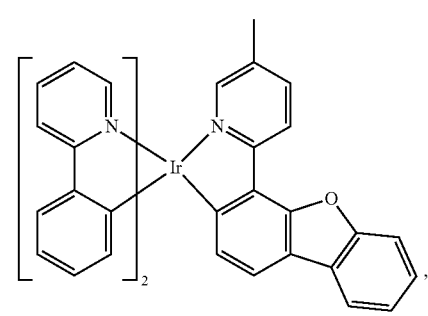

F3
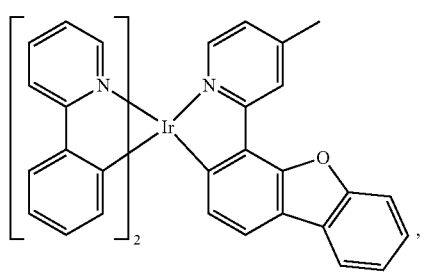
F4
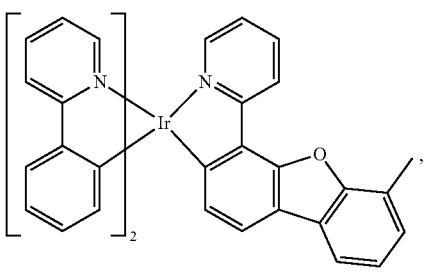
F5
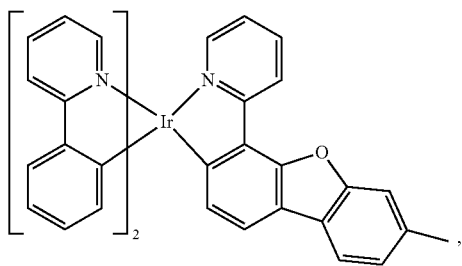
F6
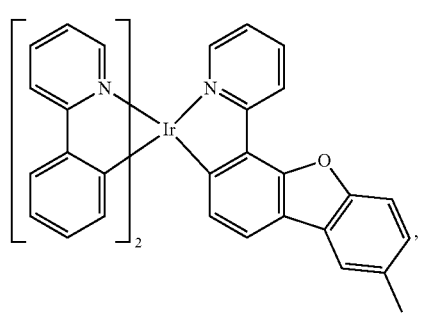
F7
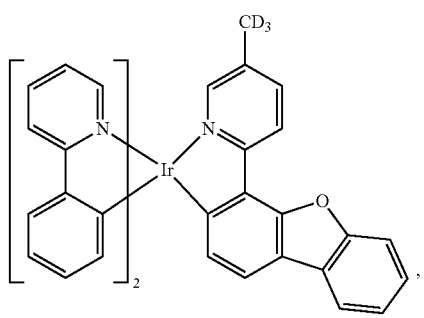
F8
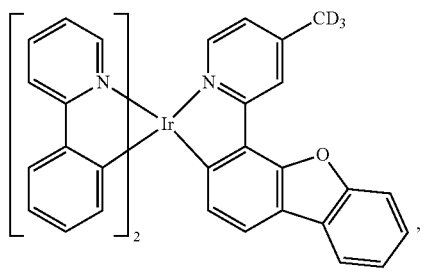
F9
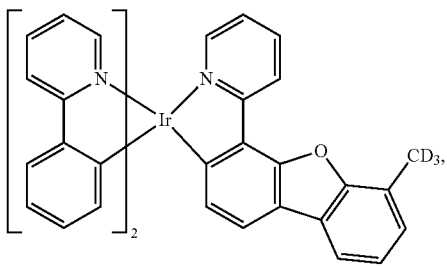
F10
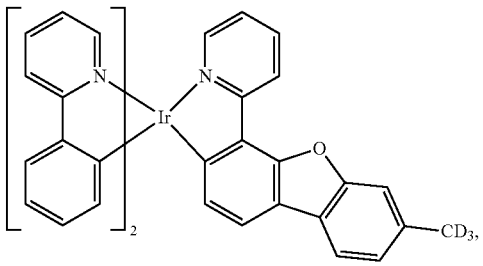
F11
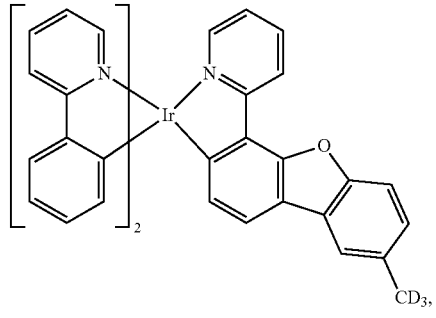
F12
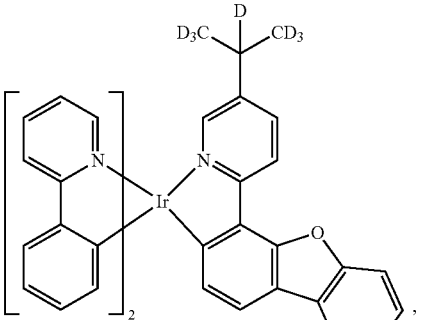

F13
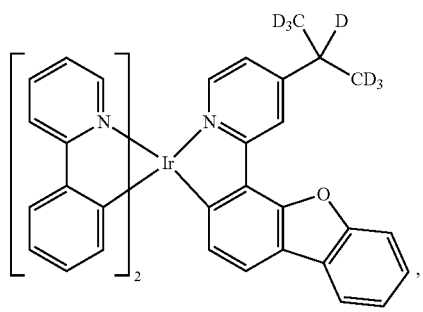
F14
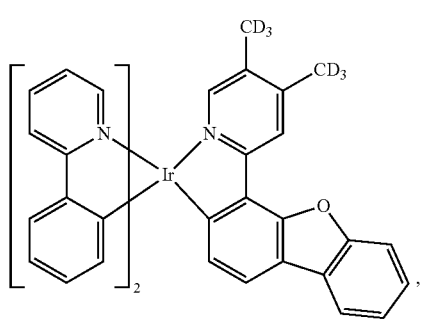
F15
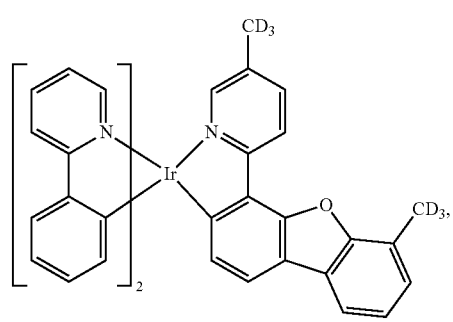
F16
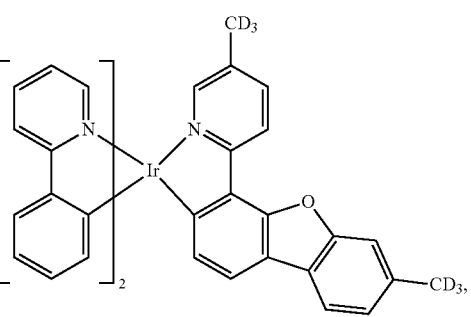
F17
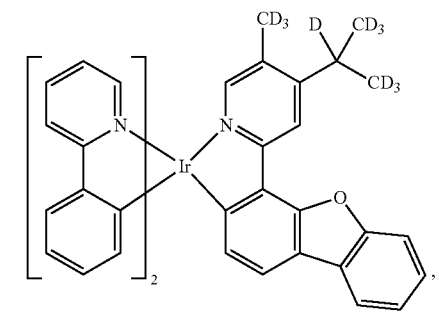
F18
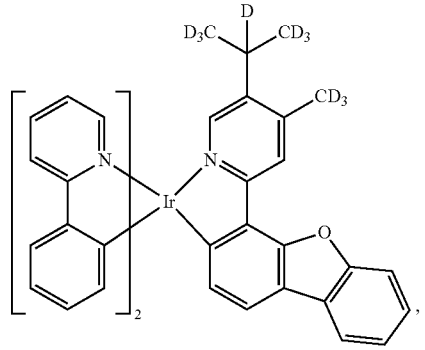
F19
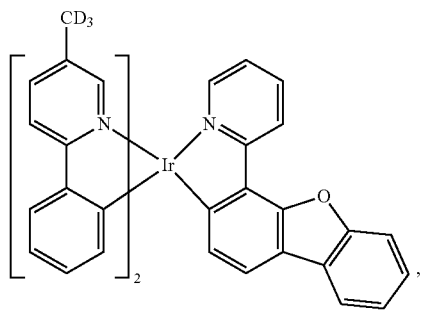
F20
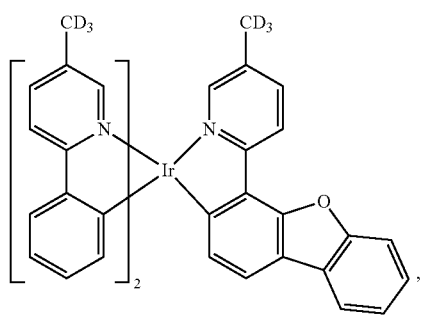
F21
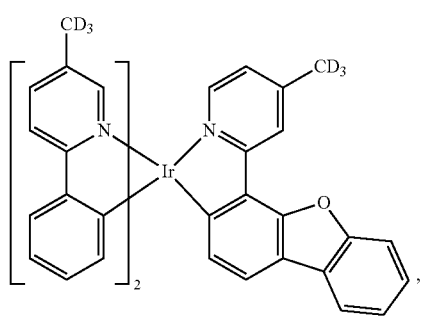
F22
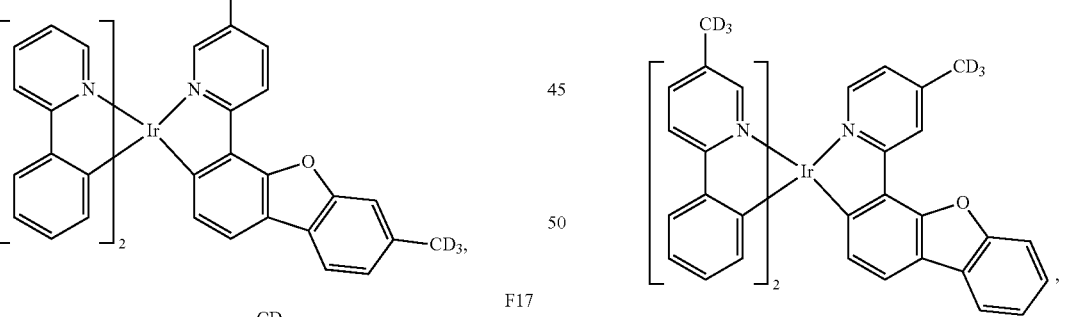

331
-continued
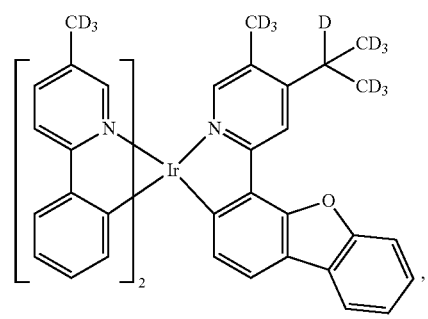
F23
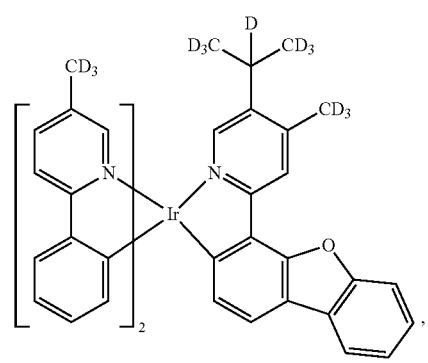
F24
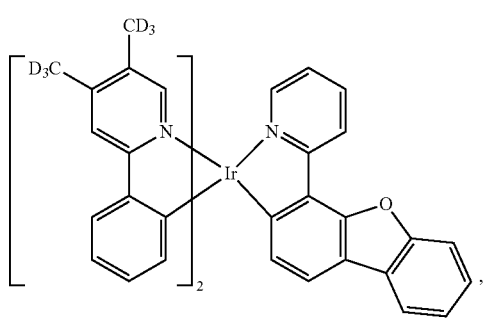
F25
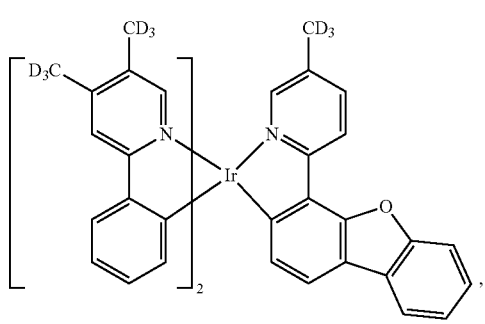
F26
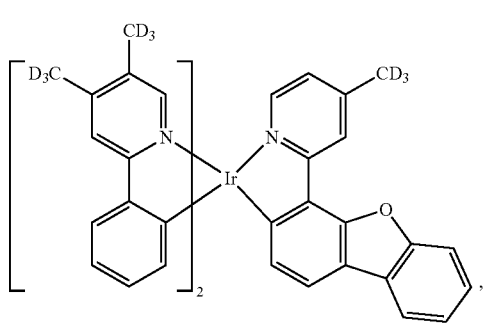
F27
332
-continued
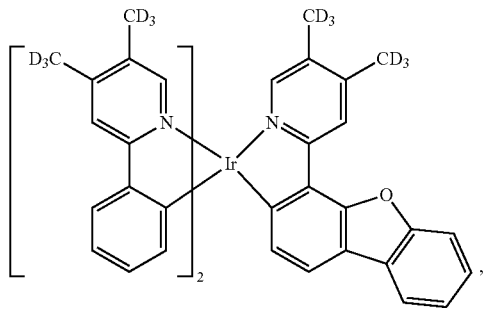
F28
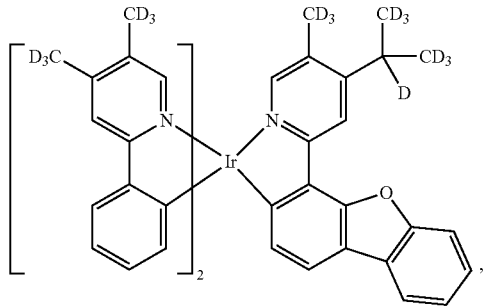
F29
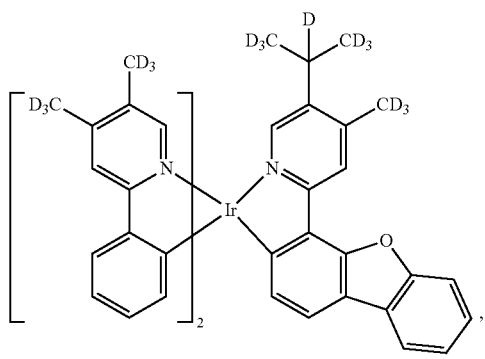
F30
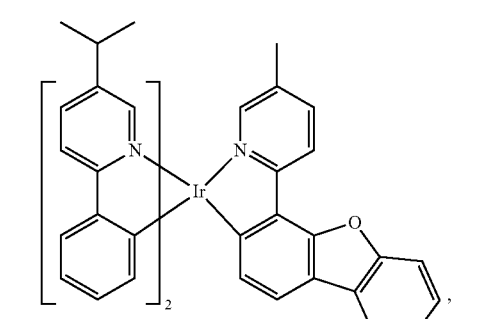
F31
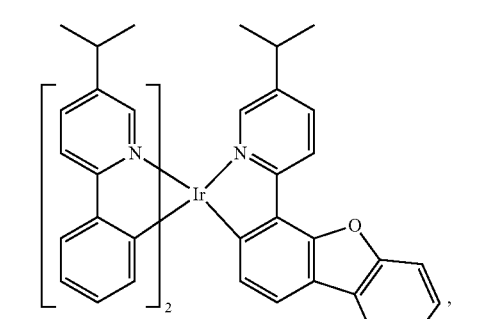
F32

-continued

F33
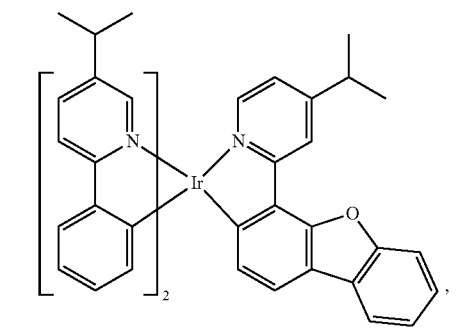

F34
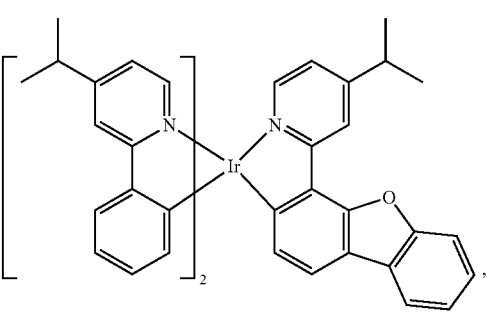

F35
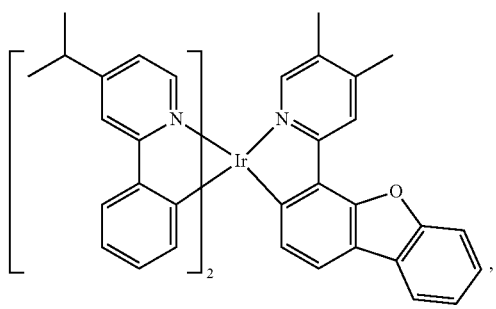
, and

F36
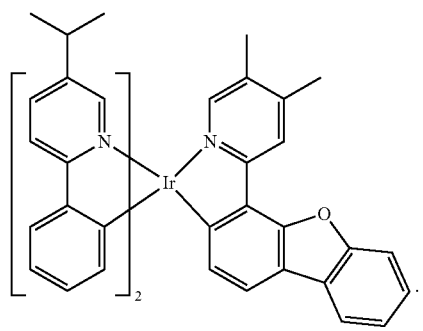
.

8. The composition comprising a mixture of a first compound and a second compound, wherein the first compound and the second compound are selected in pairs from the group consisting of (Compound HA26, Compound D151), (Compound HA30, Compound D87), (Compound HA33, Compound D13), (Compound HA34, Compound D85), (Compound HA52, Compound D85), and (Compound HA68, Compound D151), wherein the first compounds are defined as HA26
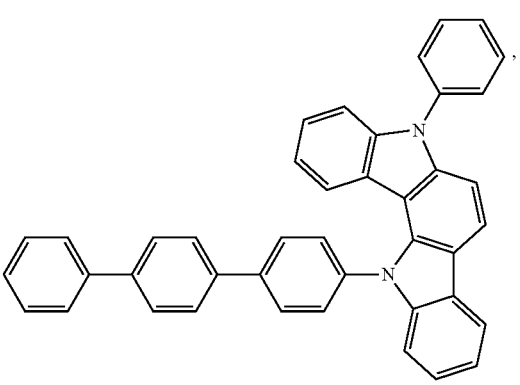
, HA30
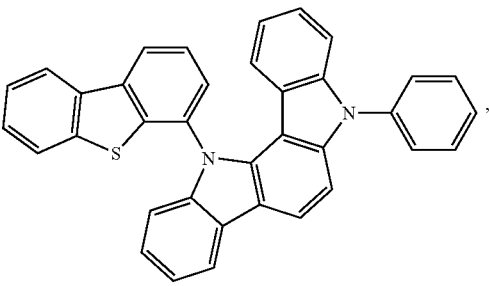
, HA33
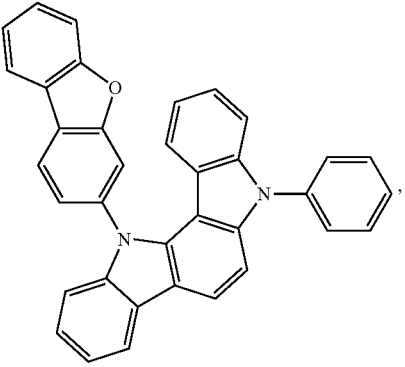
, HA34
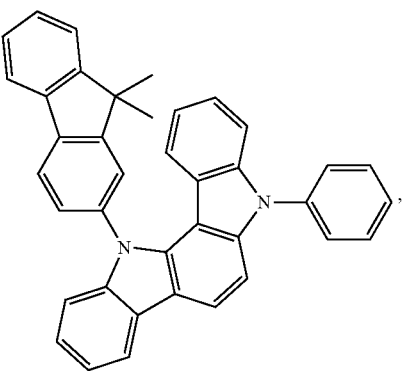
, -continued

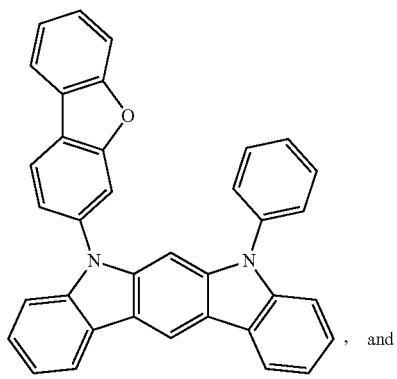, and

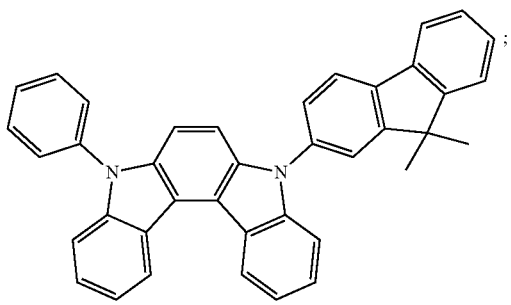;

and wherein the second compounds are defined as follows:

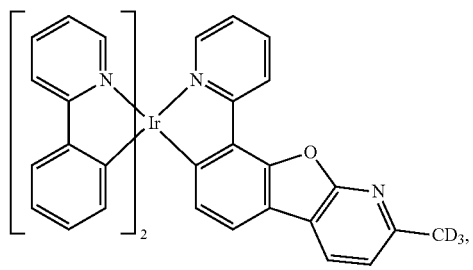

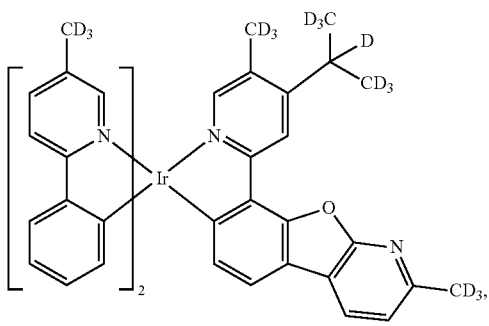

-continued

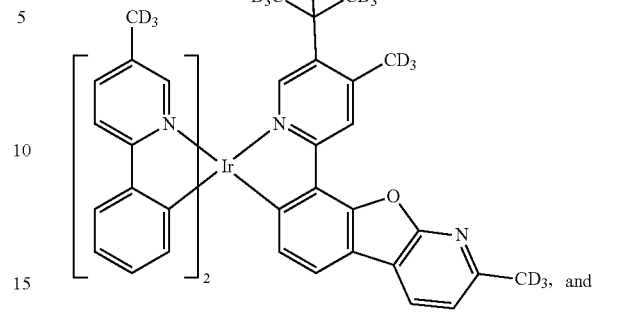, and

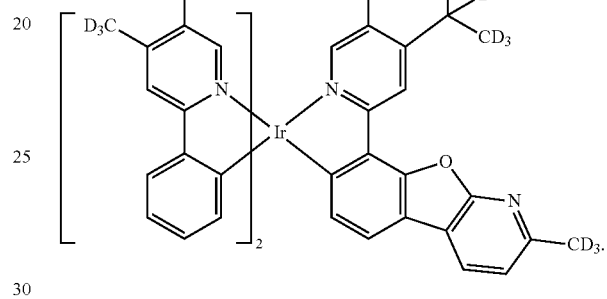.

9. The composition of claim 1, wherein the first compound has an evaporation temperature T1 of 150 to 350° C.; wherein the second compound has an evaporation temperature T2 of 150 to 350° C.;
wherein absolute value of T1-T2 is less than 20° C.;
wherein the first compound has a concentration C1 in said mixture and a concentration C2 in a film formed by evaporating the mixture in a vacuum deposition tool at a constant pressure between $1 \times 10^{-6}$ Torr to $1 \times 10^{-9}$ Torr, at a 2Å/sec deposition rate on a surface position at a predefined distance away from the mixture being evaporated; and
wherein absolute value of (C1-C2)/C1 is less than 5%.

10. The composition of claim 1, wherein the first compound has a vapor pressure of P1 at T1 at 1 atm, the second compound has a vapor pressure of P2 at T2 at 1 atm; and
wherein the ratio of P1/P2 is within the range of 0.90 to 1.10.

11. The composition of claim 1, wherein first compound has a first mass loss rate and the second compound has a second mass loss rate, wherein the ratio between the first mass loss rate and the second mass loss rate is within the range of 0.90 to 1.10.

12. A method for fabricating an organic light emitting device, the method comprising:
placing a premixed VTE evaporation source in an evaporation crucible;
providing a substrate having a first electrode disposed thereon;
depositing a first organic layer over the first electrode by evaporating the premixed VTE evaporation source from the evaporation crucible, wherein the premixed VTE evaporation source is a mixture of a first compound and a second compound in a vacuum deposition tool at a constant pressure between $1 \times 10^{-6}$ Torr to 1×10$^{-9}$ Torr, at a 2Å/sec deposition rate on a surface position at a predefined distance away from the mixture being evaporated; and depositing a second electrode over the first organic layer; wherein the first compound is selected from the group consisting of:

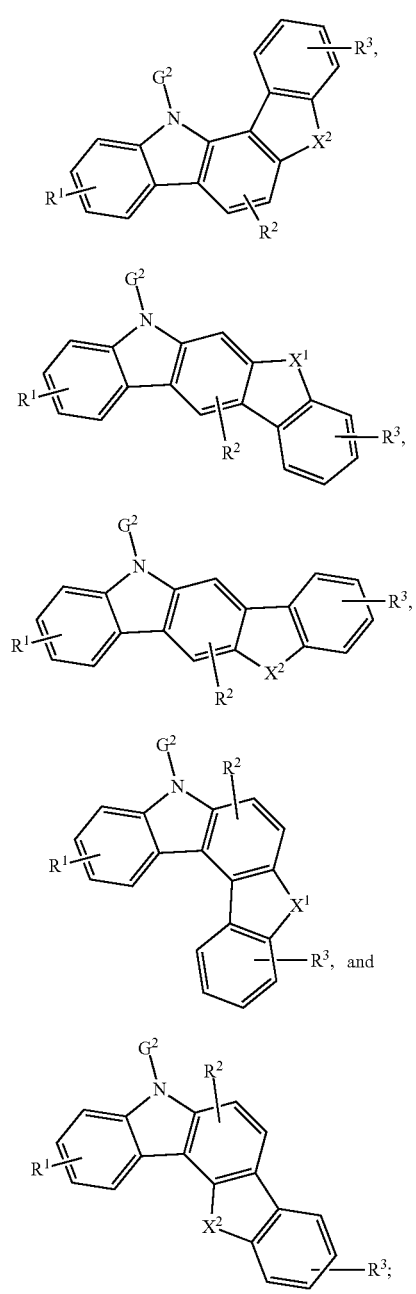

wherein X$^1$ and X$^2$ are each independently selected from the group consisting of CR$^4$R$^5$, O, S and Se;

wherein R$^1$ to R$^3$ each independently represent mono to the possible maximum number of substitution, or no substitution;

wherein R$^1$ to R$^3$ each independently represent mono to the possible maximum number of substitution, or no substitution;

wherein (i) G$^2$ comprises a moiety selected from the group consisting of dibenzofuran, dibenzothiophene, dibenzoselenophene, fluorene, triphenylene, and combinations thereof, or (ii) G$^2$ comprises a moiety selected from the group consisting of phenanthroline, azadibenzofuran, azadibenzothiophene, azadibenzoselenophene, azafluorene, azatriphenylene, and combinations thereof;

wherein R$^1$, R$^2$, R$^3$, R$^4$, and R$^5$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, acyl, carbonyl, carboxylic acid, ester, nitrile, isonitrile, sulfanyl, sulfinyl, sulfonyl, phosphino, and combinations thereof, and wherein any two adjacent substituents can optionally join or fuse into a ring;

wherein at least one of option (a) or option (b) is true:
(a) X$^1$ or X$^2$ is present and represents Se;
(b)(1)(i) the first compounds has the structure of GH2 or GH3, or (1)(ii) the first compound has a structure of GH1, GH4, or GH5, and two le are not joined to form a ring, and
(2) at least one of R$^1$ and R$^3$ is unsubstituted, and
(3) G$^2$ is selected from the group consisting of dibenzoselenophene, phenanthroline, azadibenzofuran, azadibenzoselenophene, azafluorene, and combinations thereof;

with the proviso that none of R$^1$, R$^2$, R$^3$, R$^4$, or R$^5$ is triphenylene;

wherein the second compound has a formula Ir(L$_A$)$_n$(L$_B$)$_{3-n}$, and having the structure according to Formula II

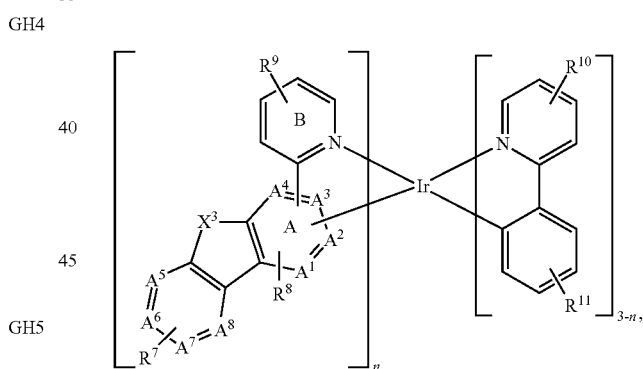

wherein each A$^1$, A$^2$, A$^3$, A$^4$, A$^5$, A$^6$, A$^7$, and A$^8$ comprise carbon or nitrogen;

wherein ring B is bonded to ring A through a C—C bond;

wherein the iridium is bonded to ring A through a Ir—C bond;

whererin X$^3$ is selected from a group consisting of O, S and Se;

wherein R$^7$ to R$^{11}$ each independently represent mono to the possible maximum number of substitution, or no substitution;

wherein R$^7$ to R$^{11}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein any two adjacent substituents can optionally join or fuse into a ring; and wherein n is an integer from 1 to 3.

13. A composition comprising a first compound and a second compound selected in pairs from the group consisting of

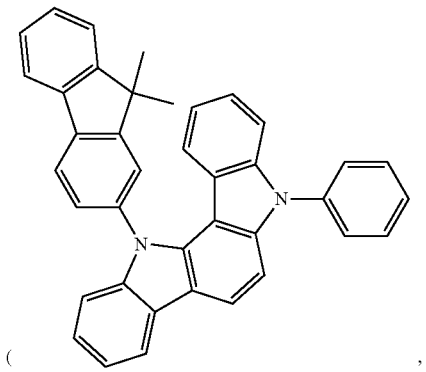
( HA34 ,

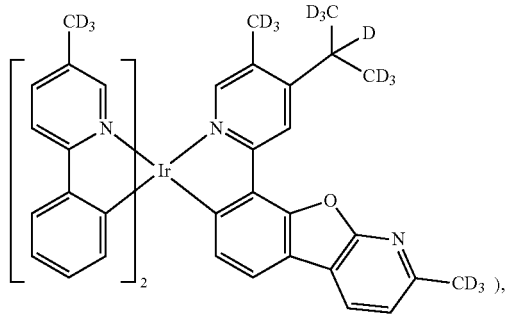
( D85 CD₃ ),

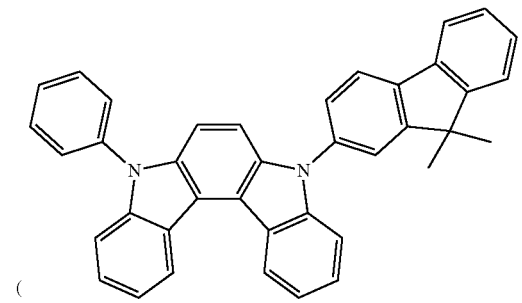
( HA68 ,

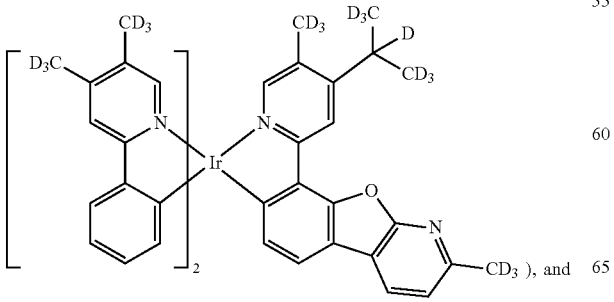
( D151 CD₃ ), and

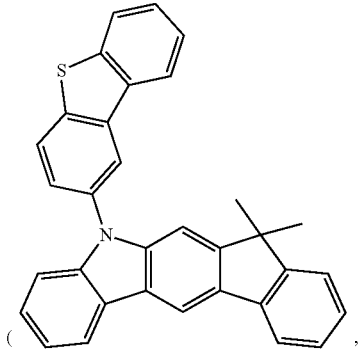
( HA92 ,

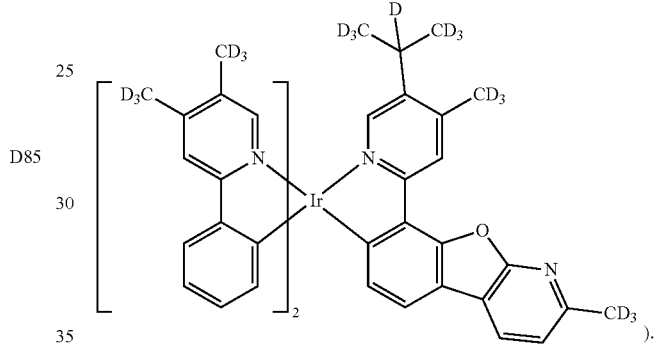
D154 CD₃ ).

14. The composition of claim 3, wherein the second compound is selected from the group consisting of:

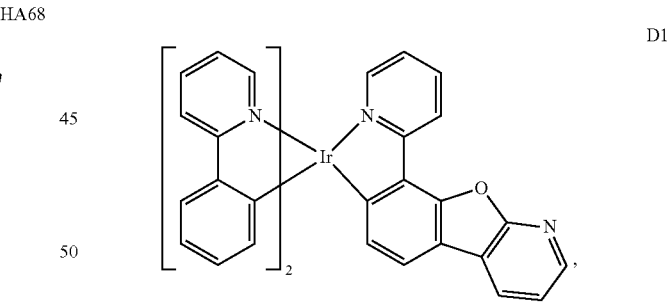
D1 ,

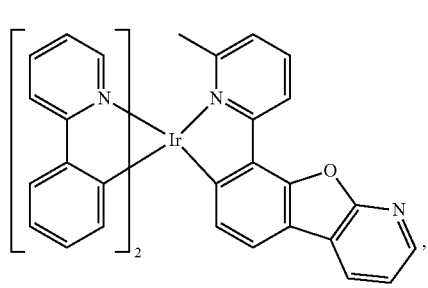
D2 ,

-continued
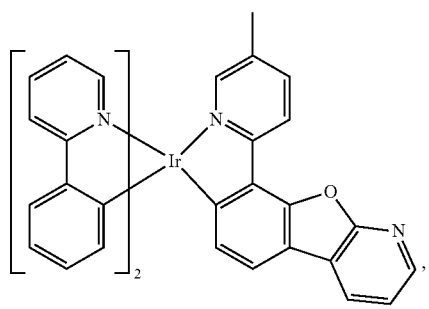
D3
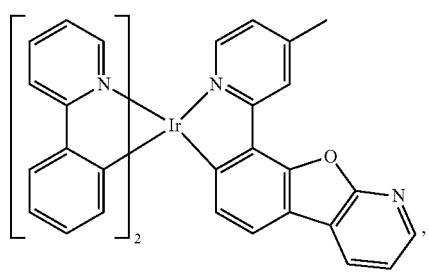
D4
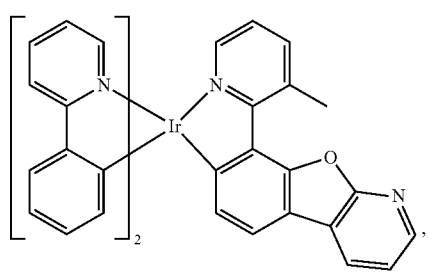
D5
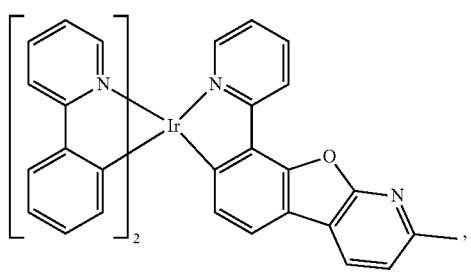
D6
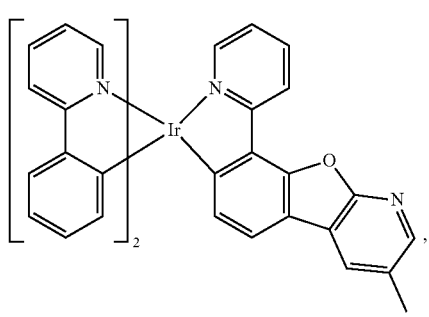
D7
-continued
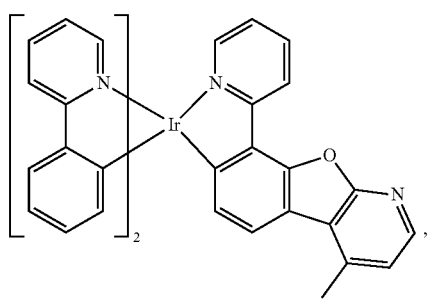
D8
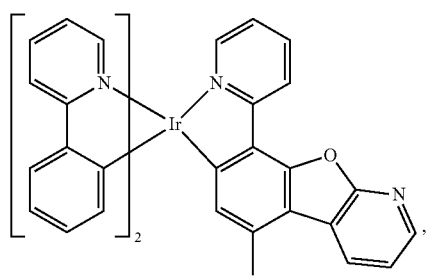
D9
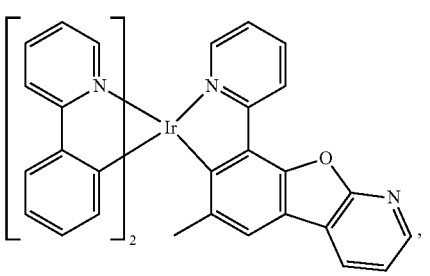
D10
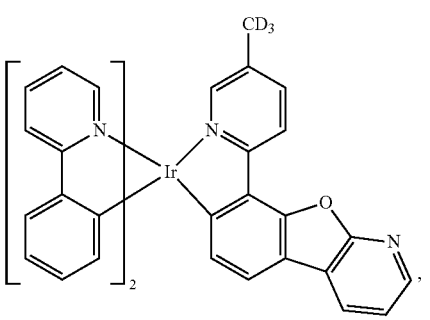
D11
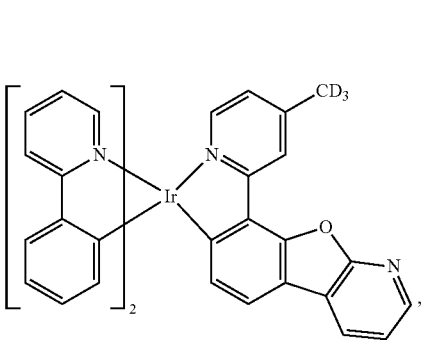
D12

-continued
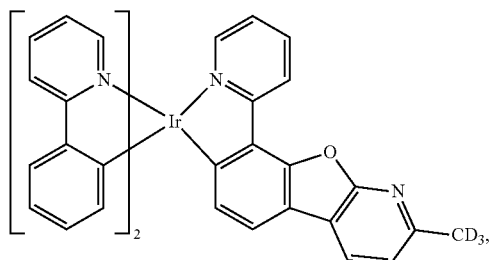
D13
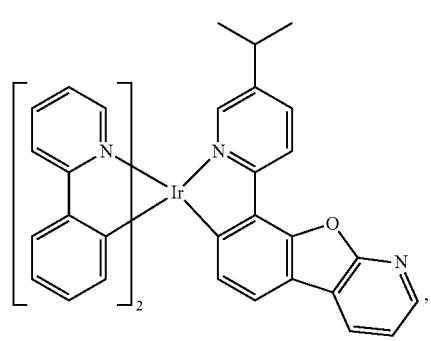
D14
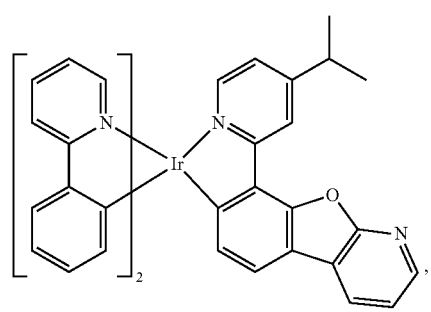
D15
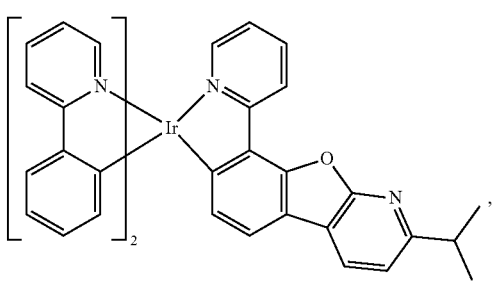
D16
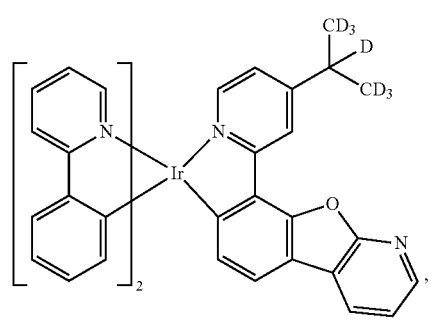
D17
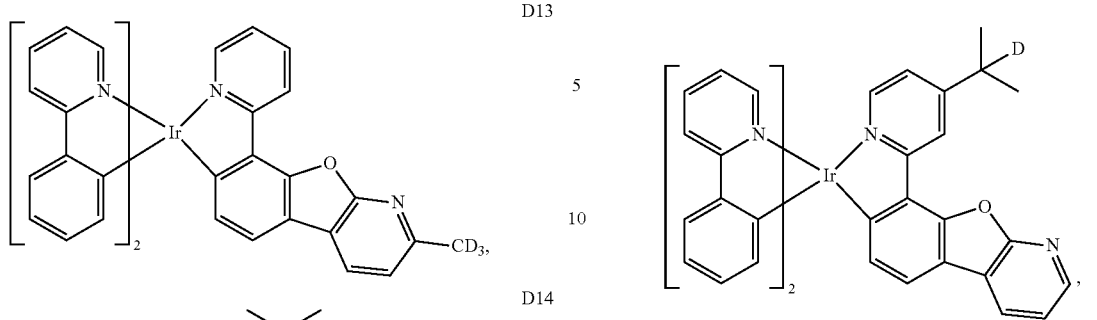
D18
D19
D20
D21
D22

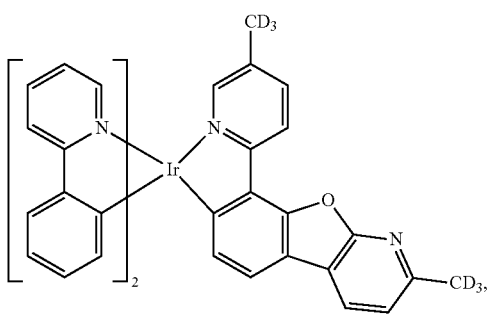
D23
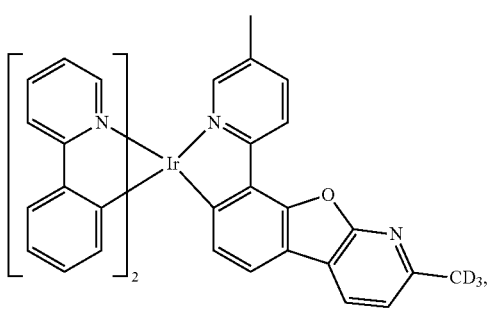
D24
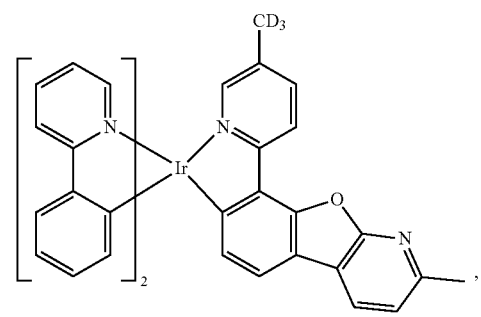
D25
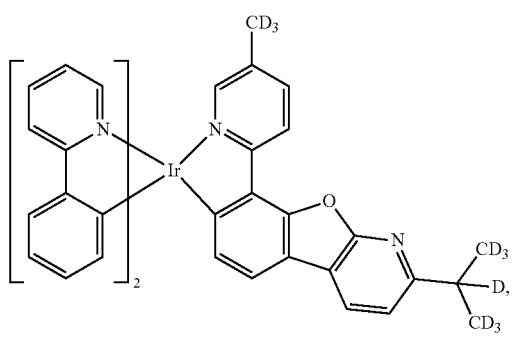
D26
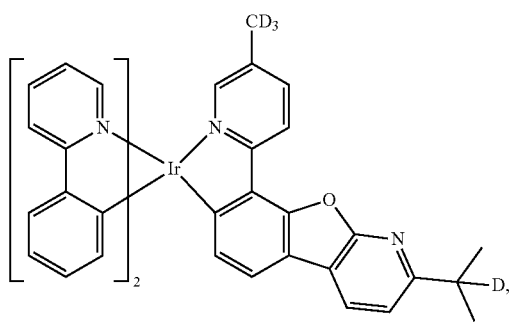
D27
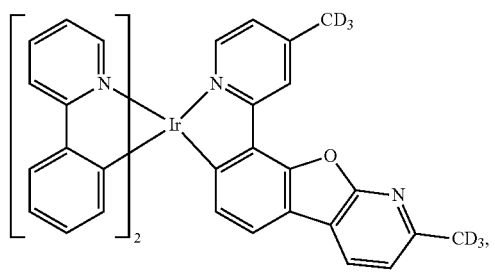
D28
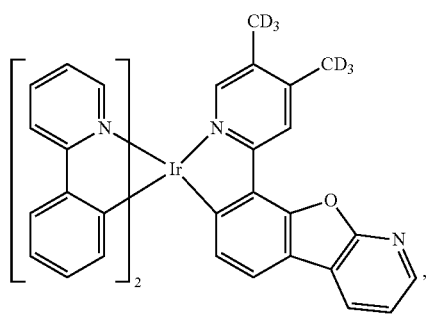
D29
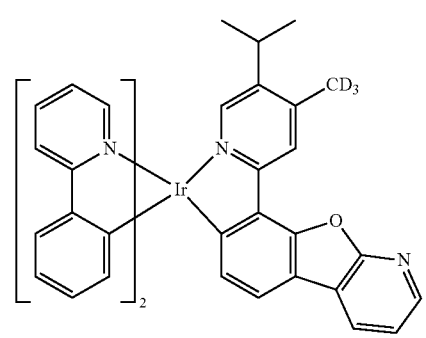
D30
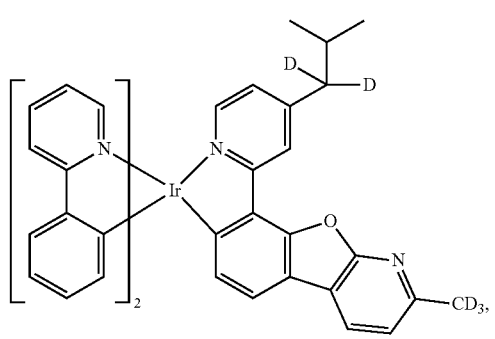
D31
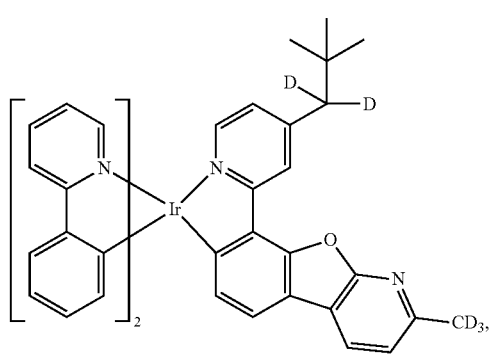
D32

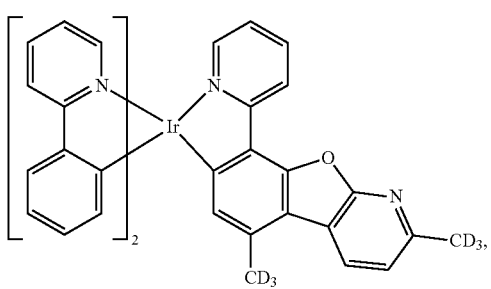 D33
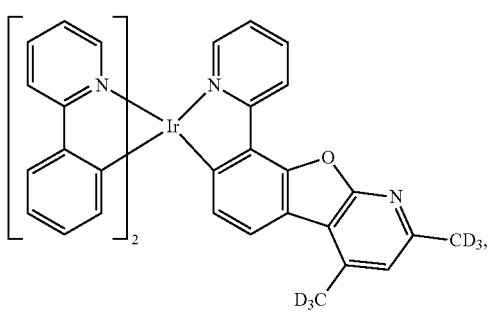 D34
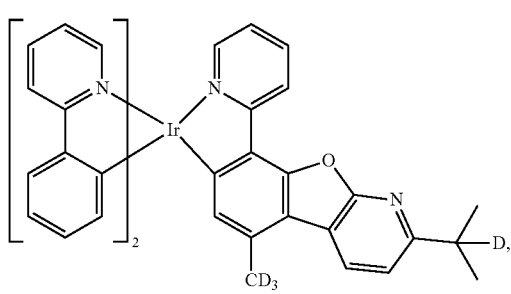 D35
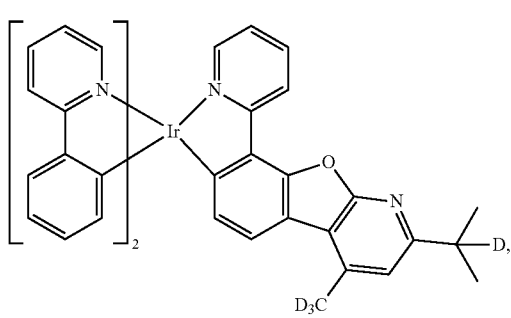 D36
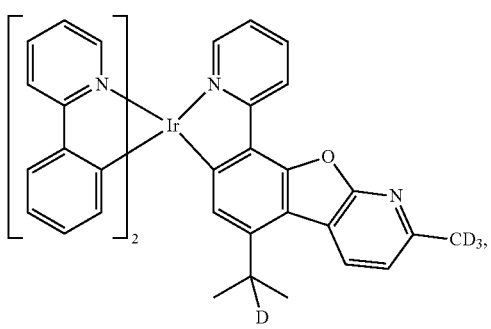 D37
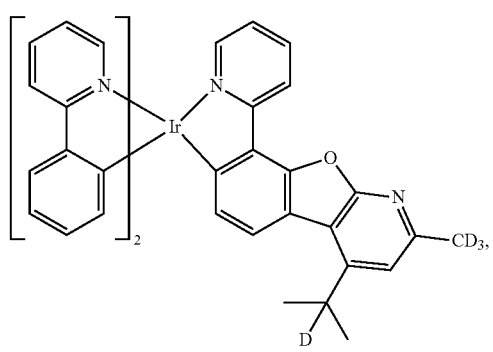 D38
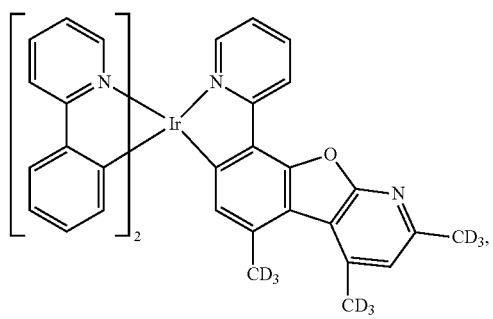 D39
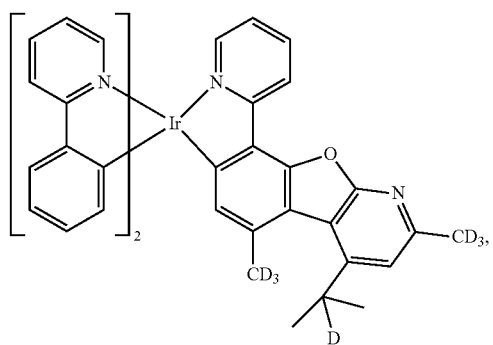 D40
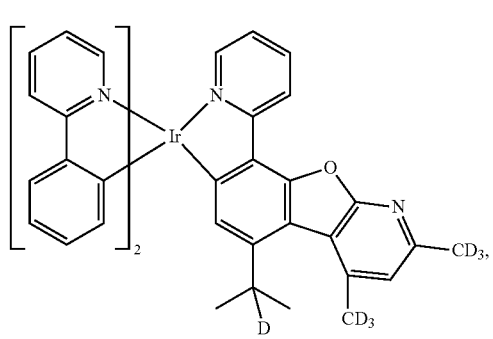 D41

-continued
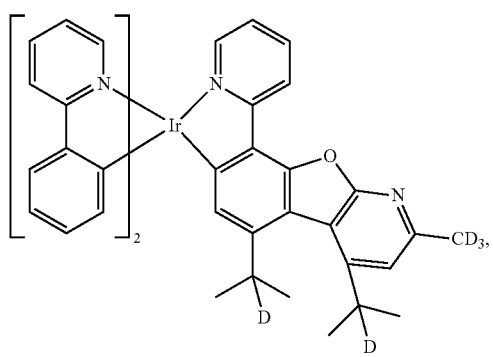
D42
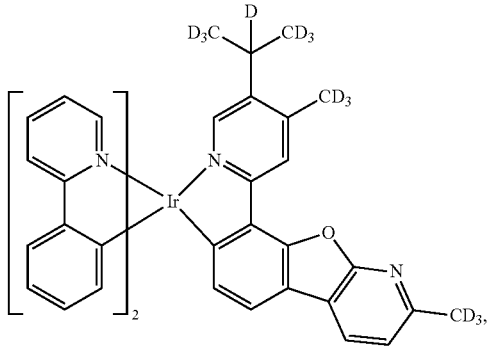
D46
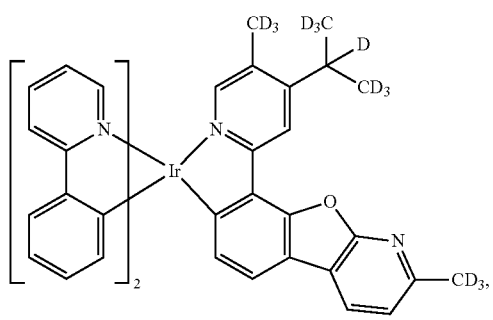
D43
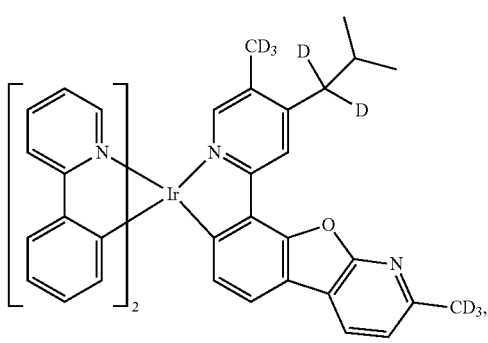
D47
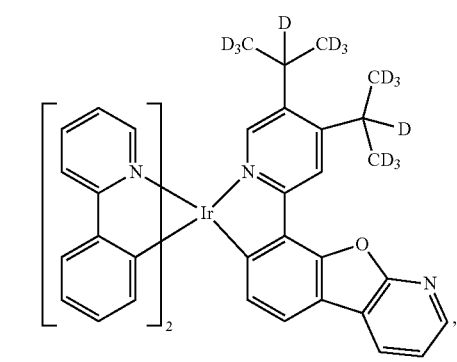
D44
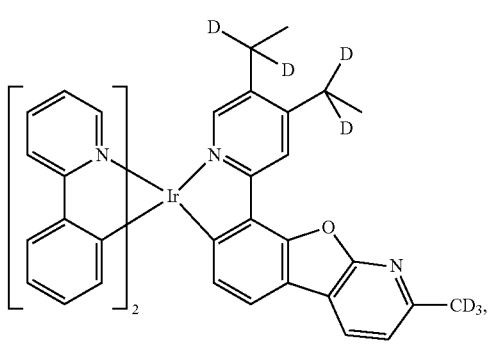
D48
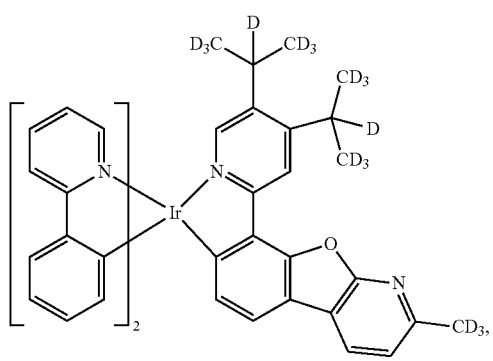
D45
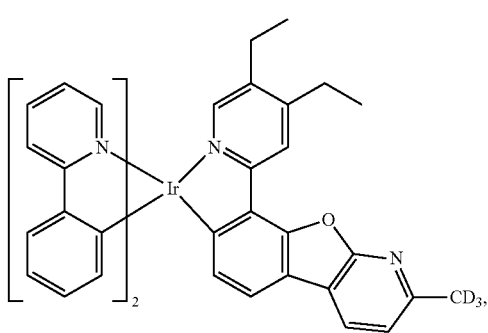
D49

351
-continued
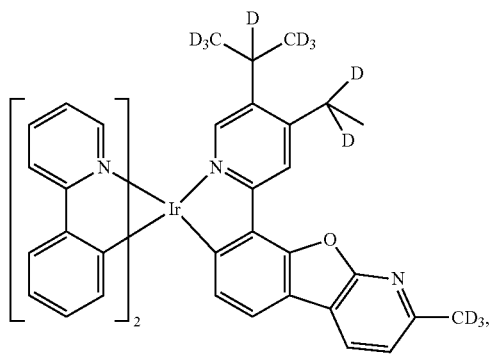
D50
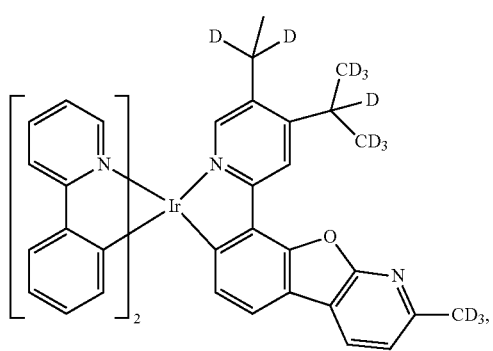
D51
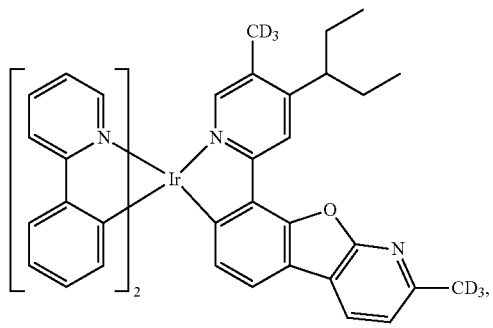
D52
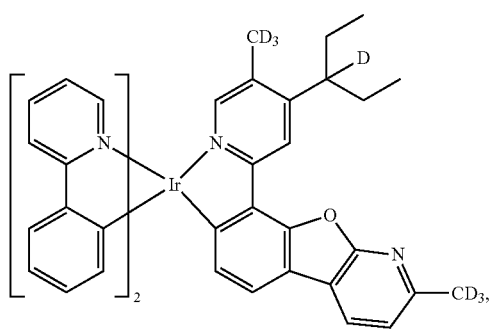
D53
352
-continued
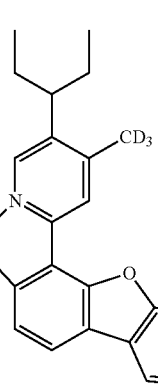
D54
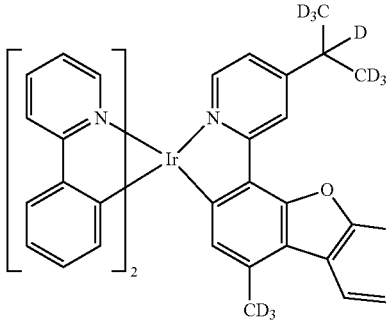
D55
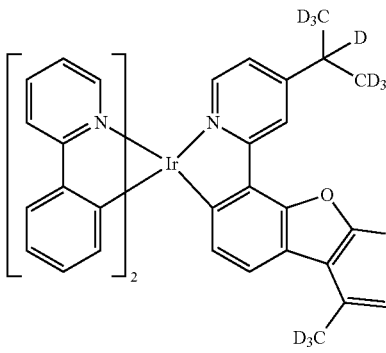
D56
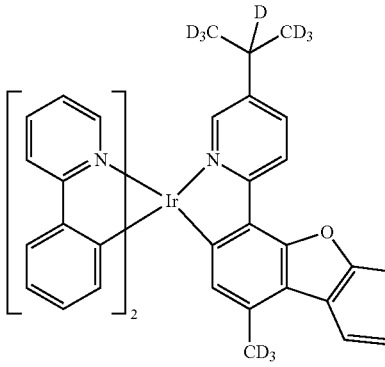
D57

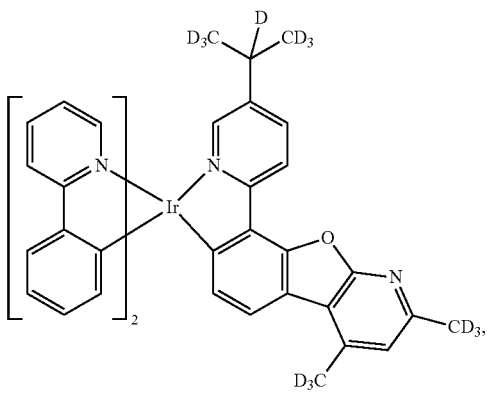 D58
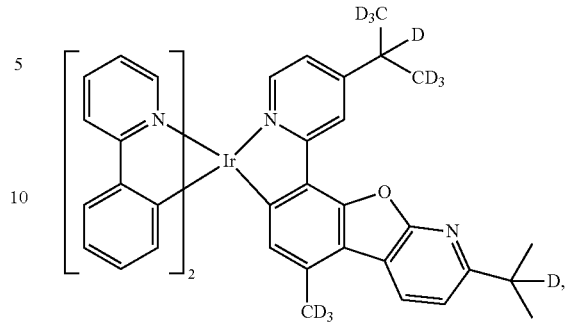 D62
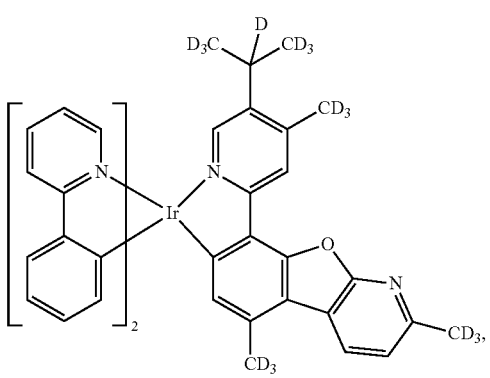 D59
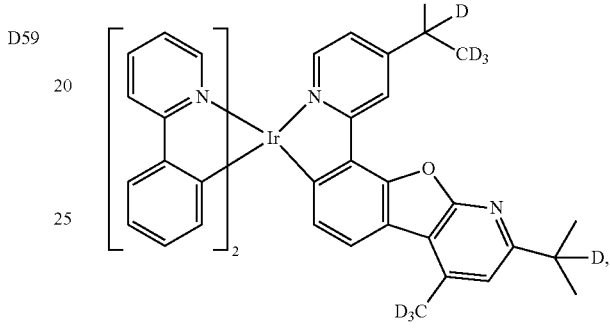 D63
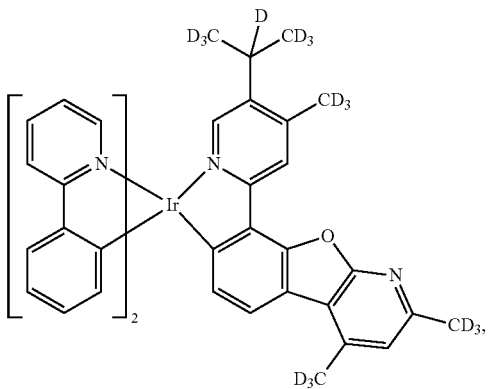 D60
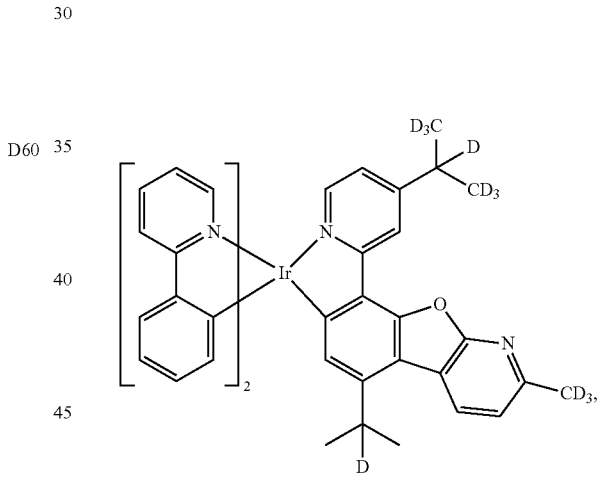 D64
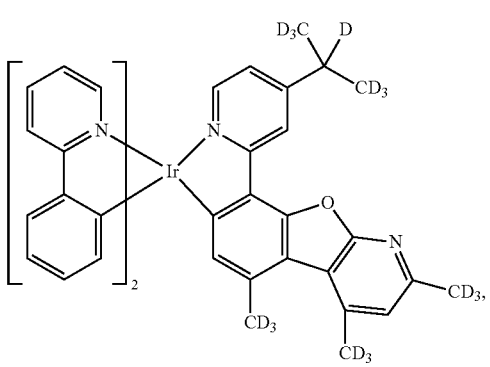 D61
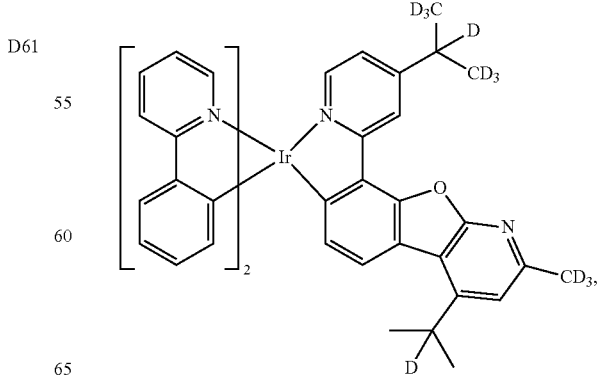 D65

D66
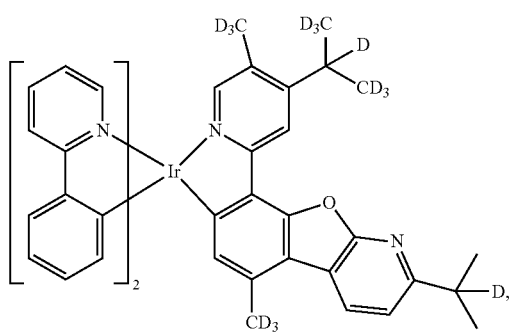
D67
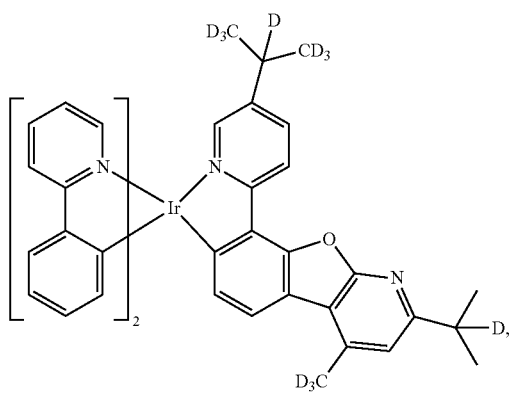
D68
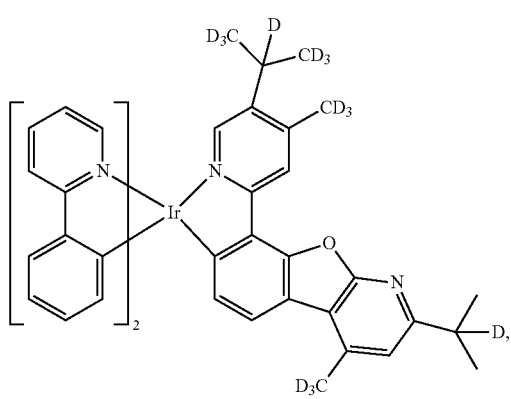
D69
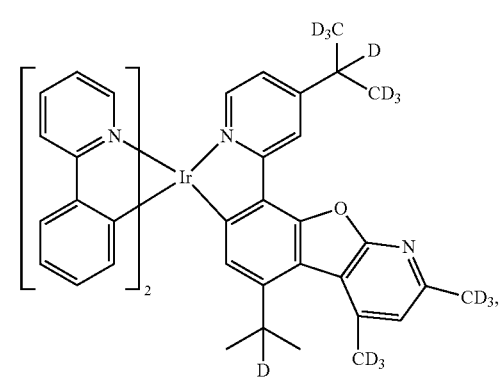
D70
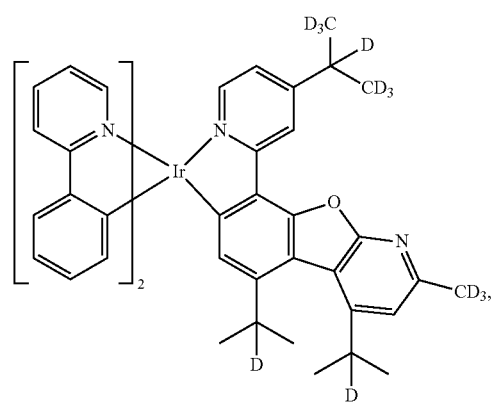
D71
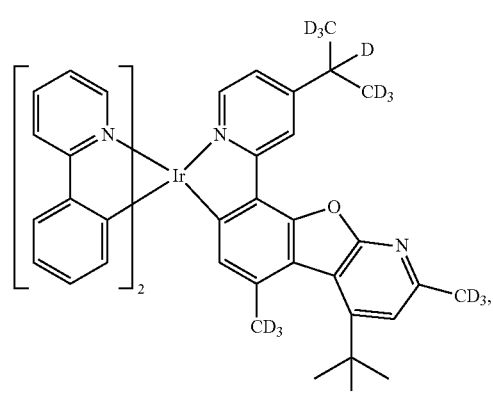
D72
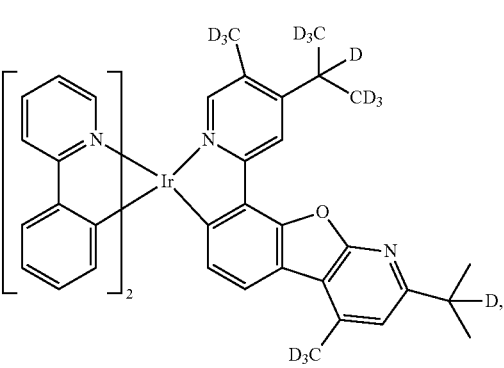
D73
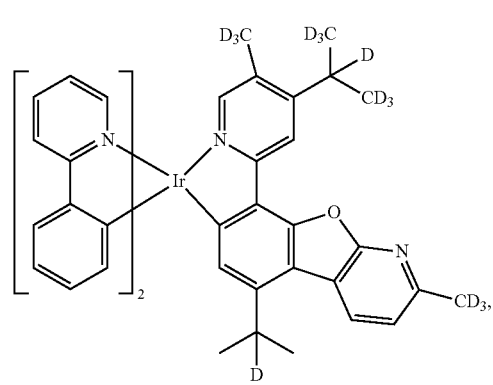

D74 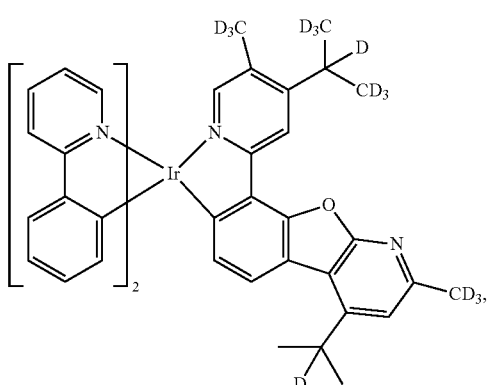
D75 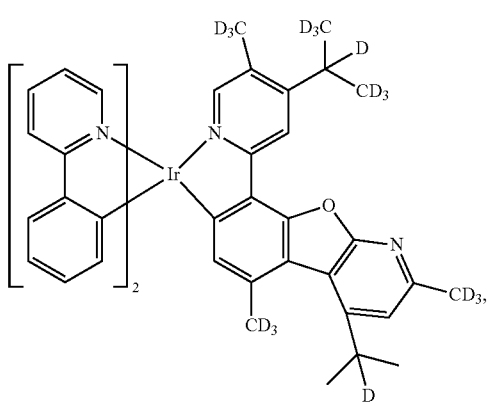
D76 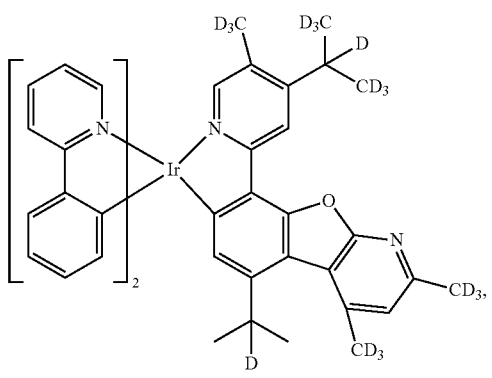
D77 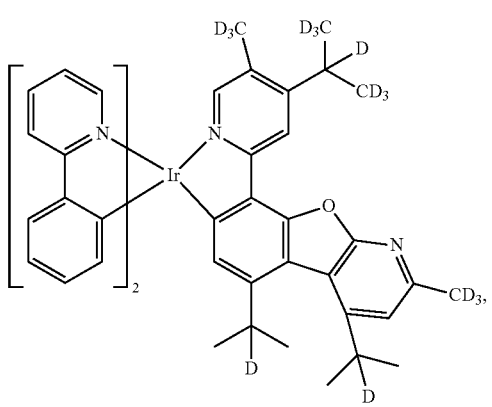
D78 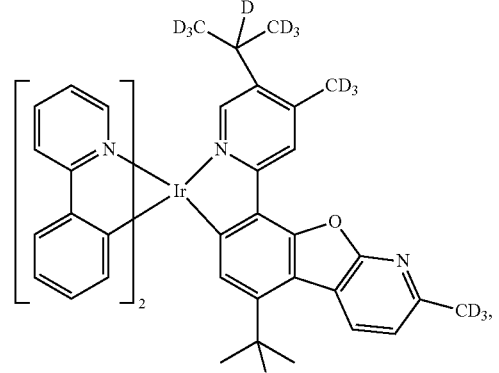
D79 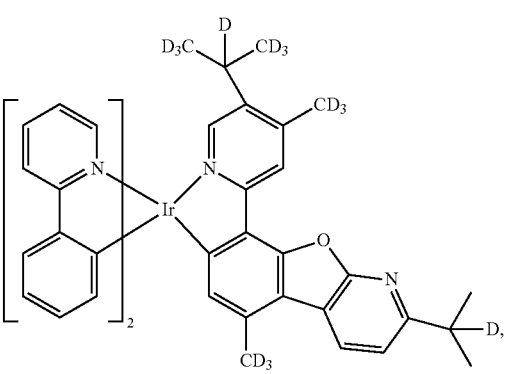
D80 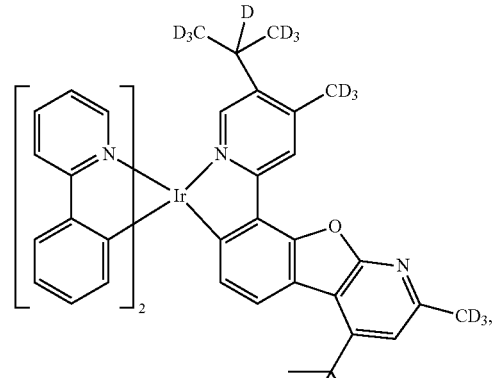
D81 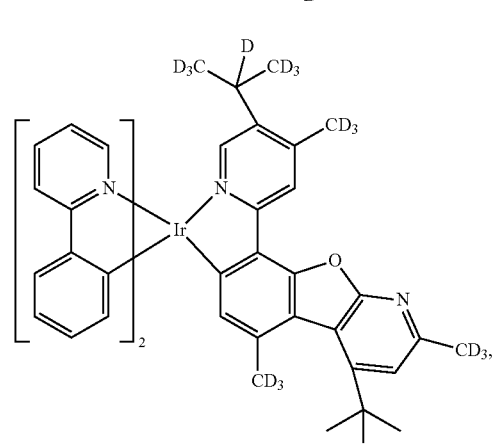

D82 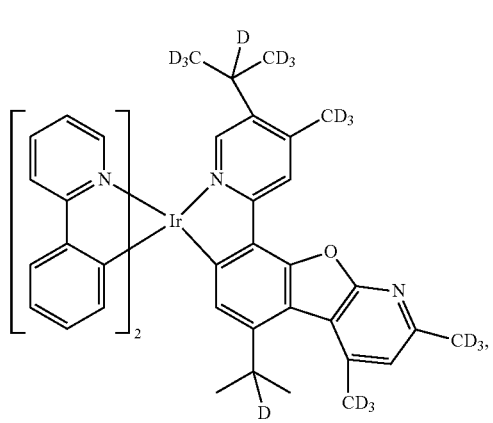
D83 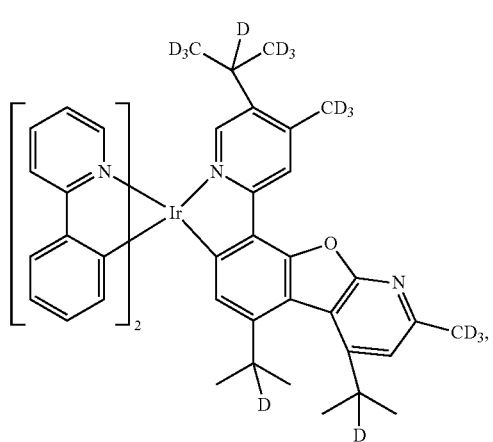
D84 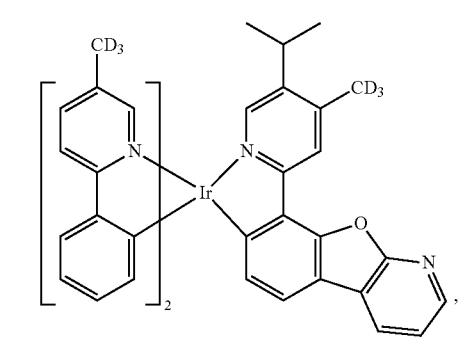
D85 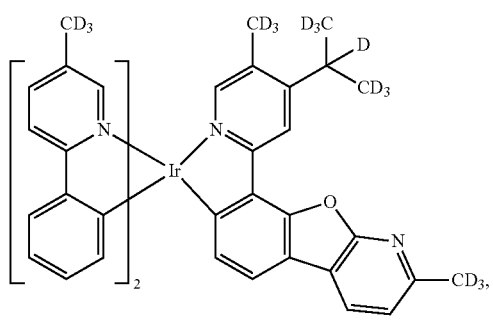
D86 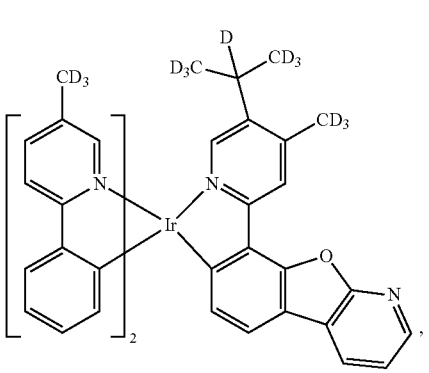
D87 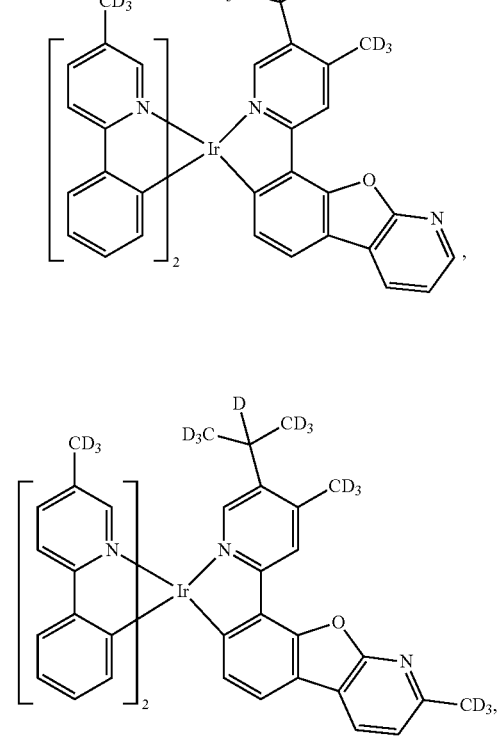
D88 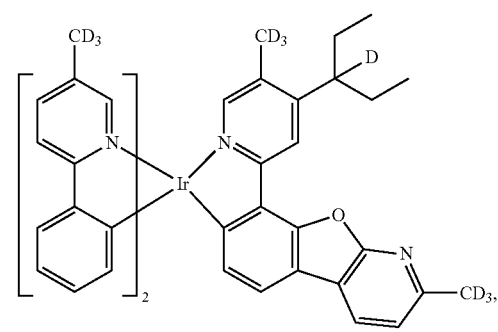
D89 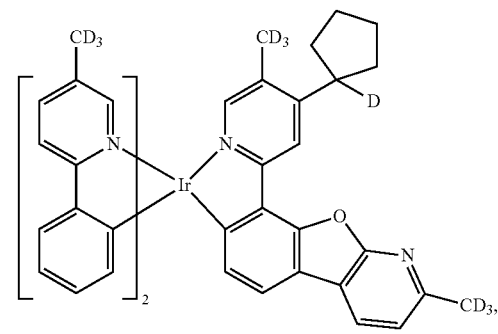

-continued
D90
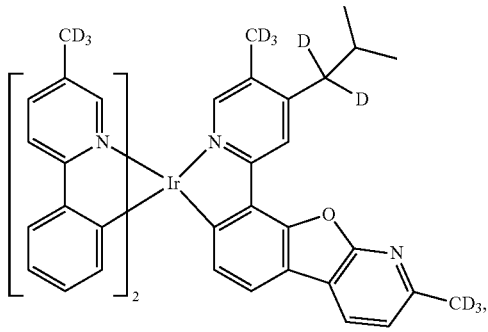
D91
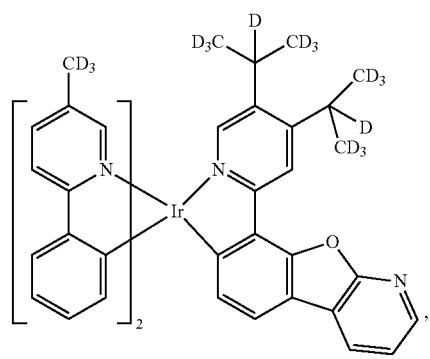
D92
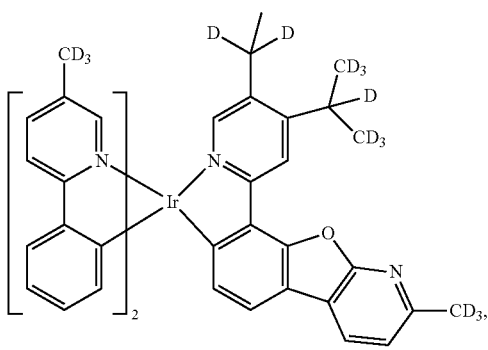
D93
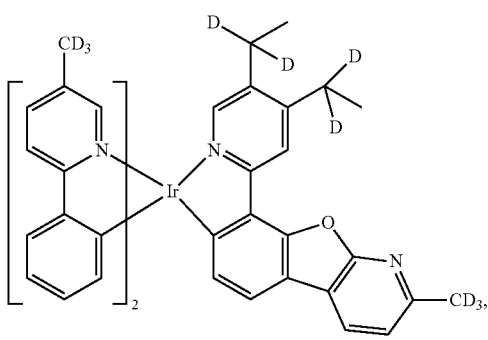
-continued
D94
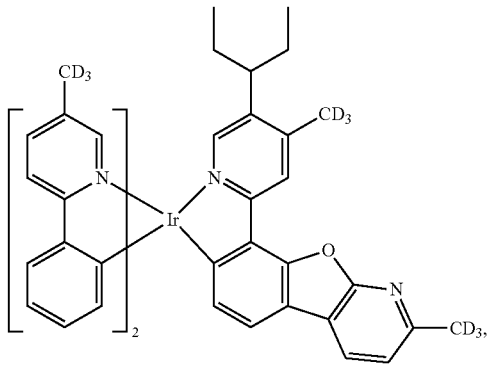
D95
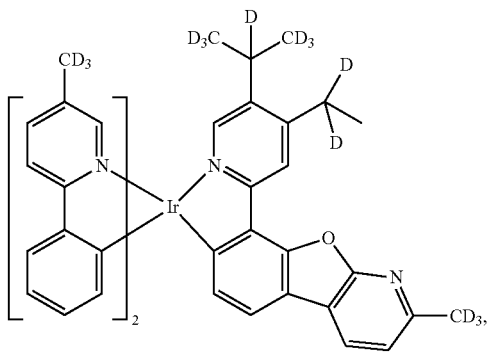
D96
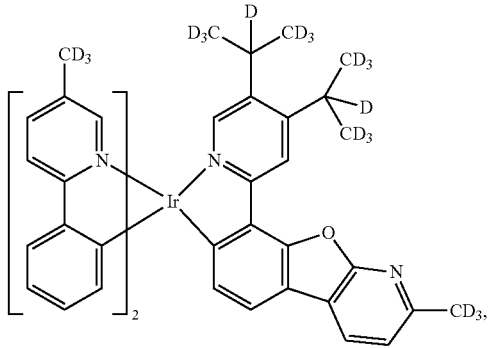
D97
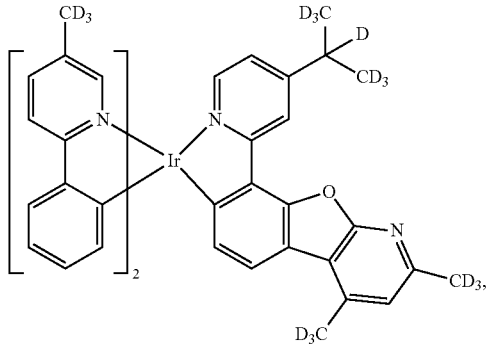

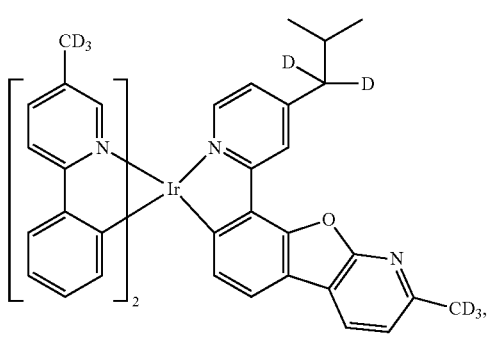
D98
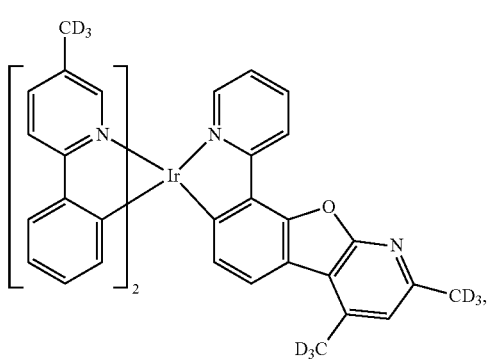
D99
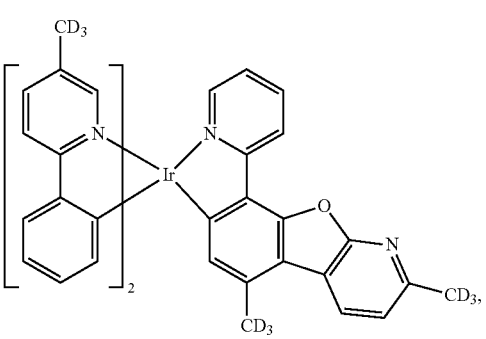
D100
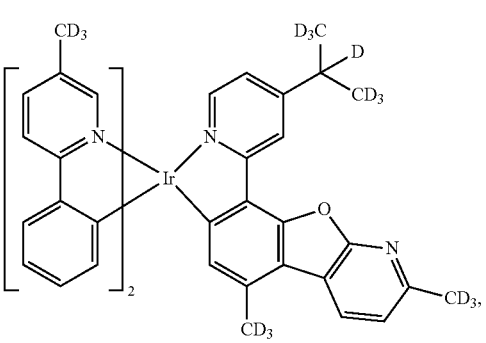
D101
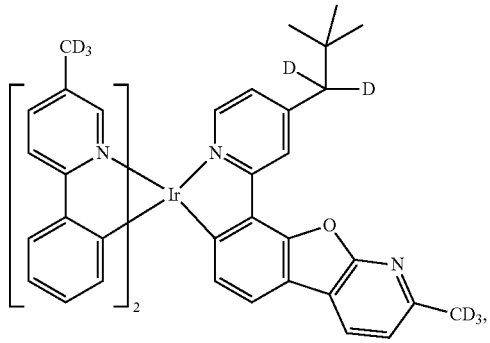
D102
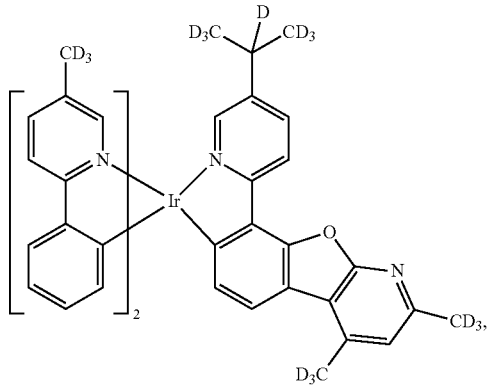
D103
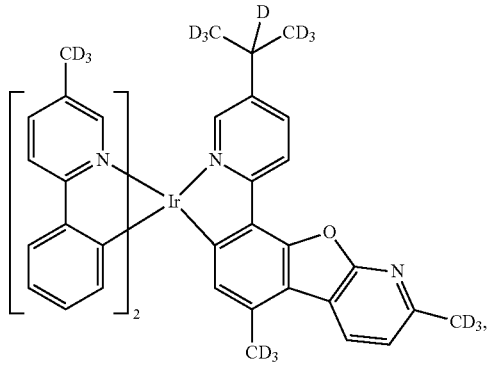
D104
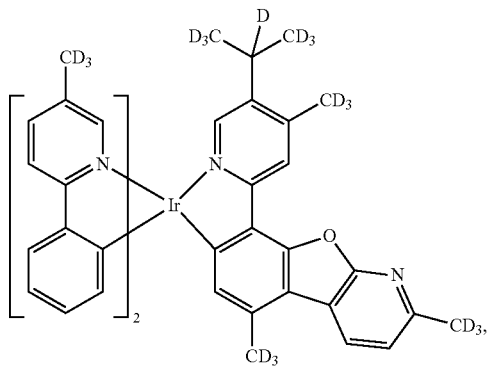
D105

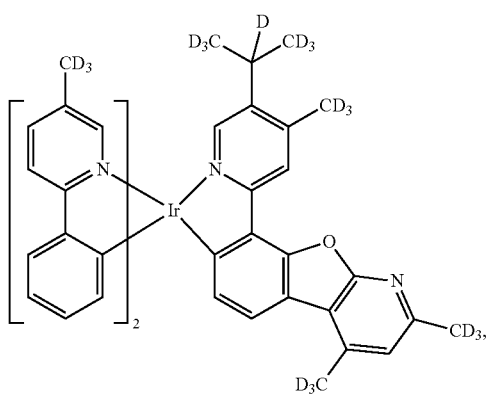
D106
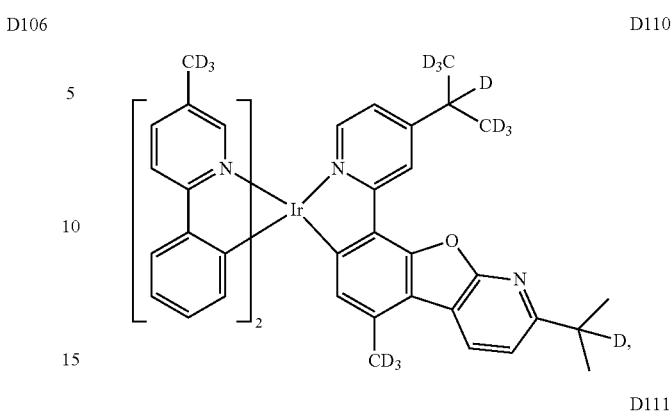
D110
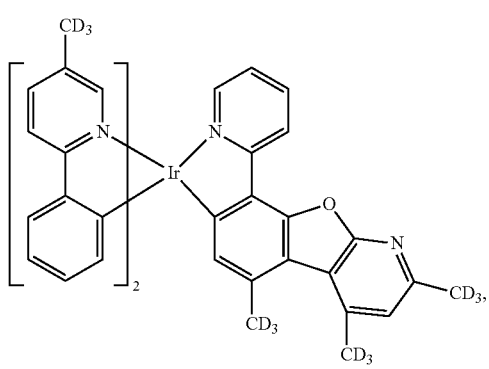
D107
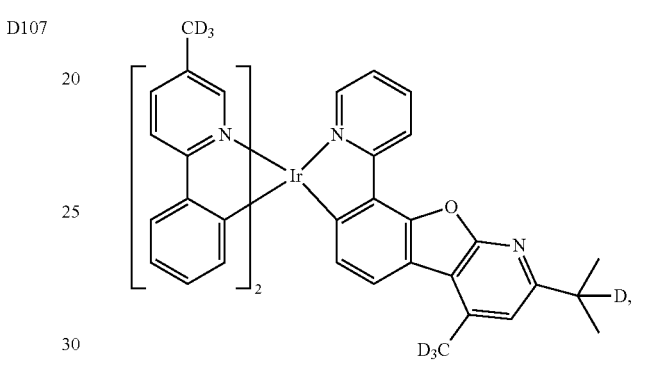
D111
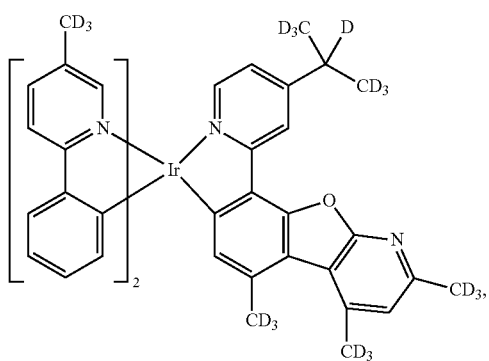
D108
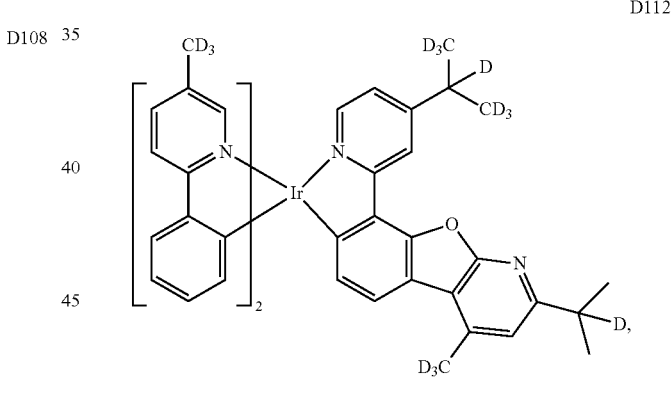
D112
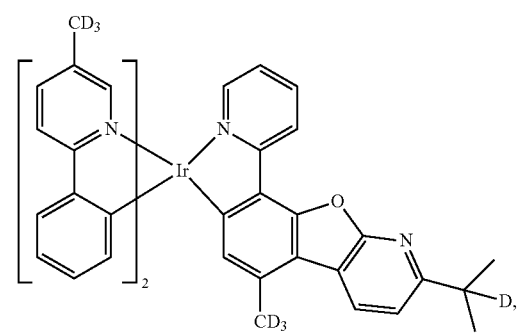
D109
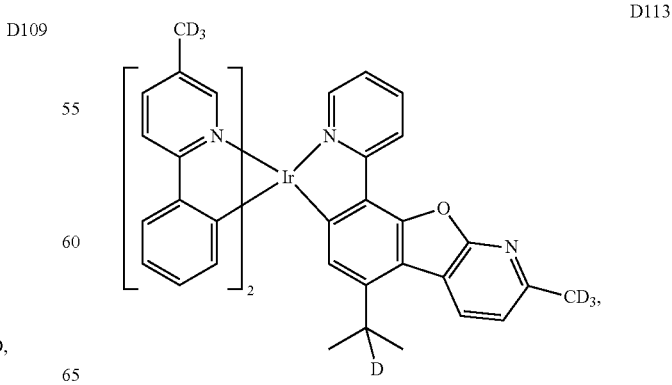
D113

D114
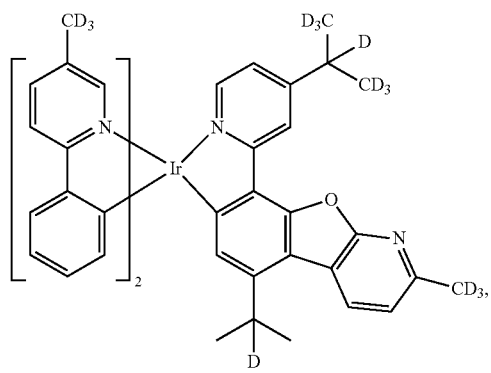
D115
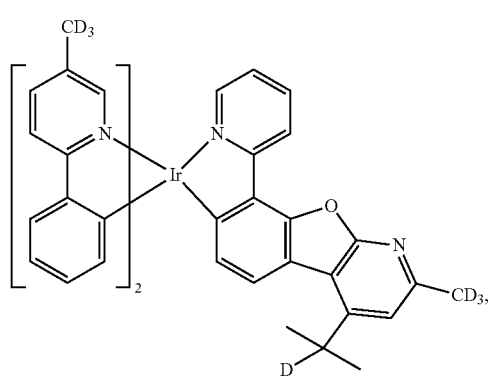
D116
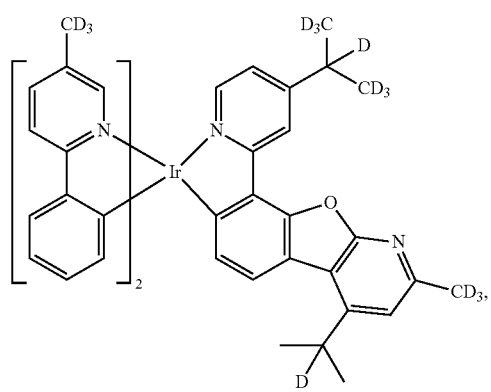
D117
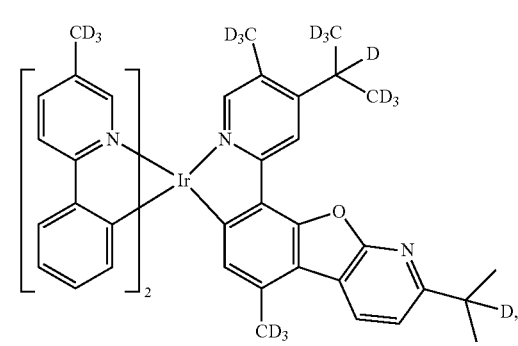
D118
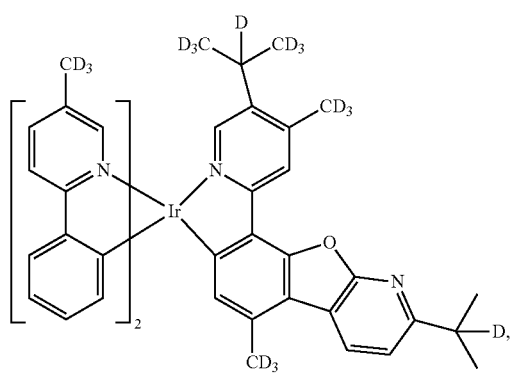
D119
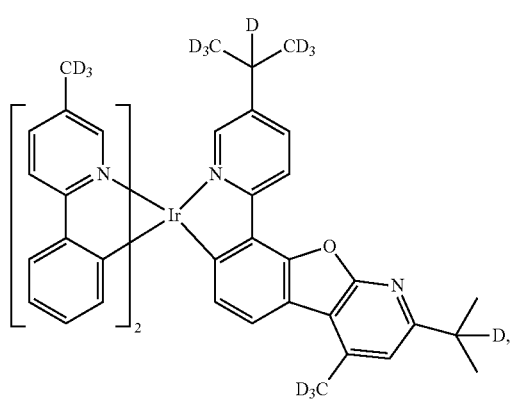
D120
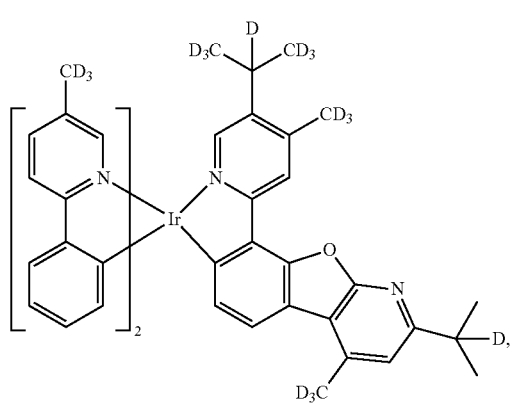
D121
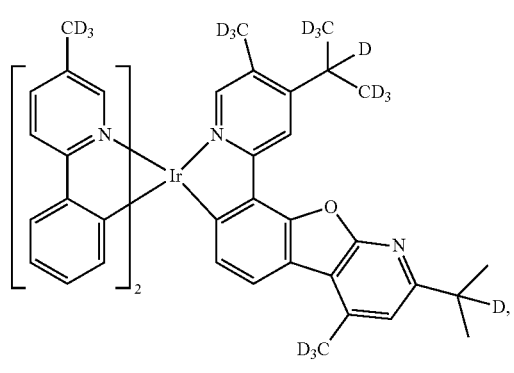

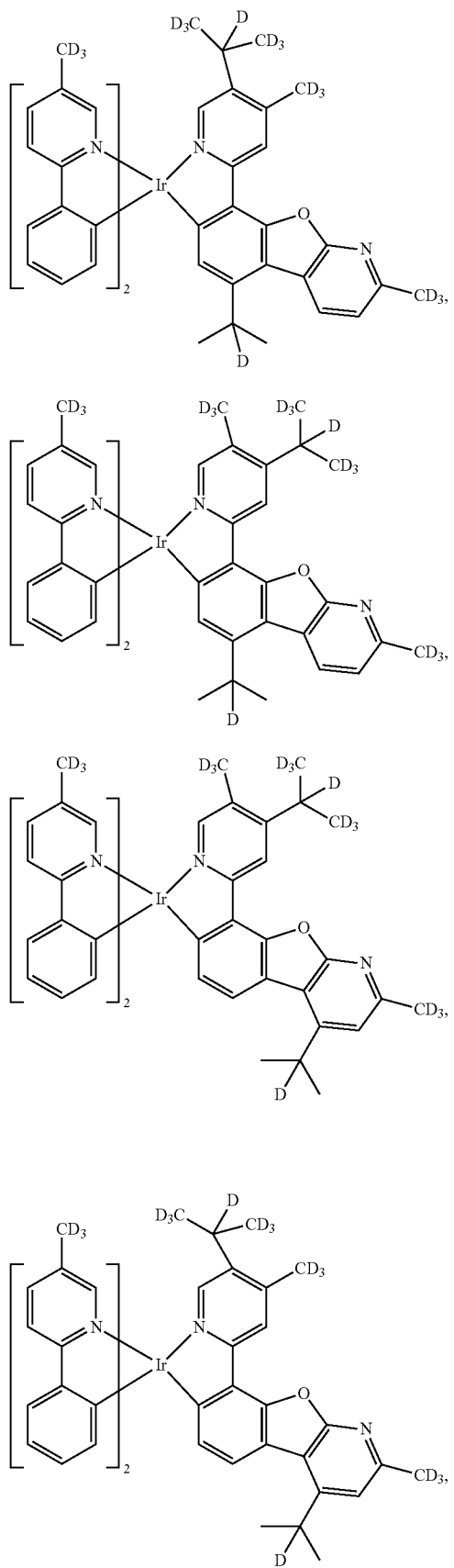
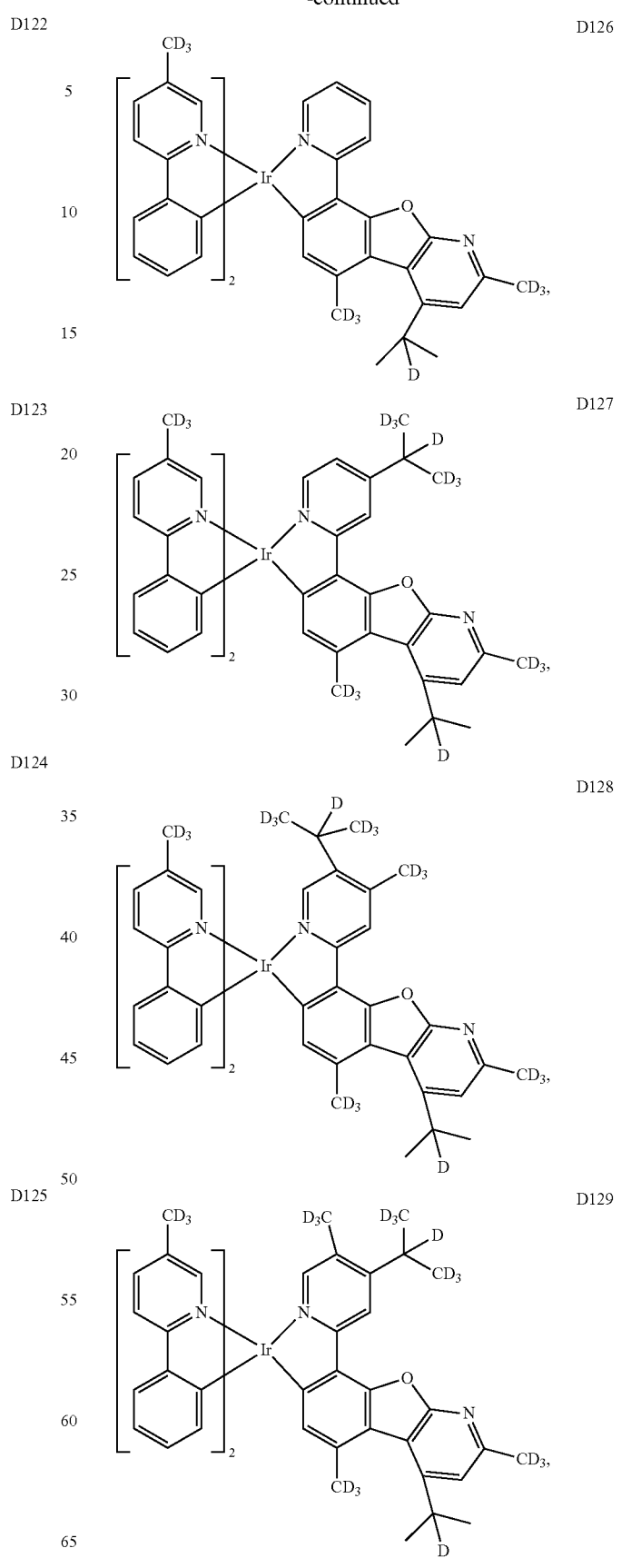

371
-continued
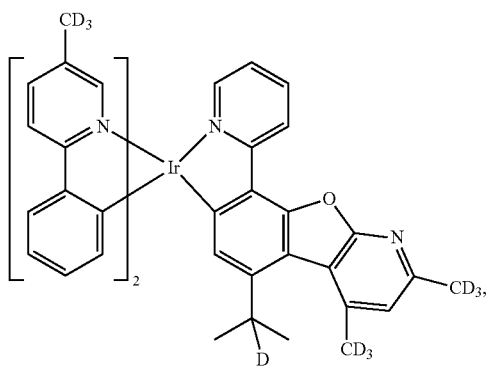
D130
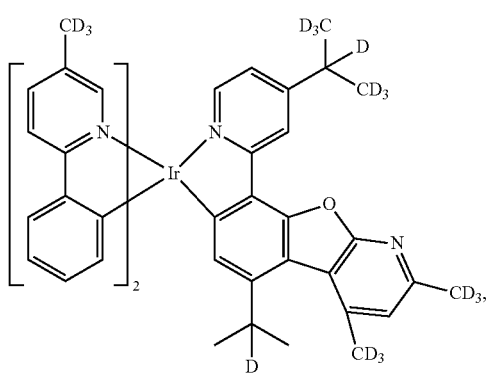
D131
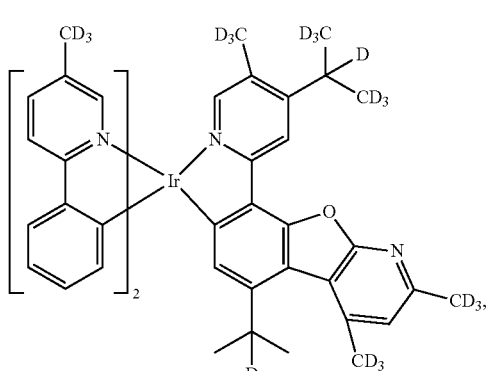
D132
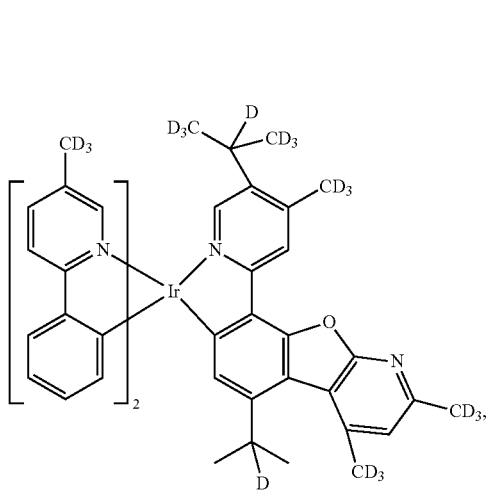
D133
372
-continued
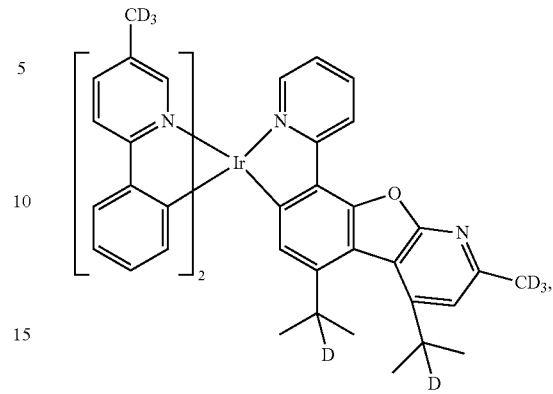
D134
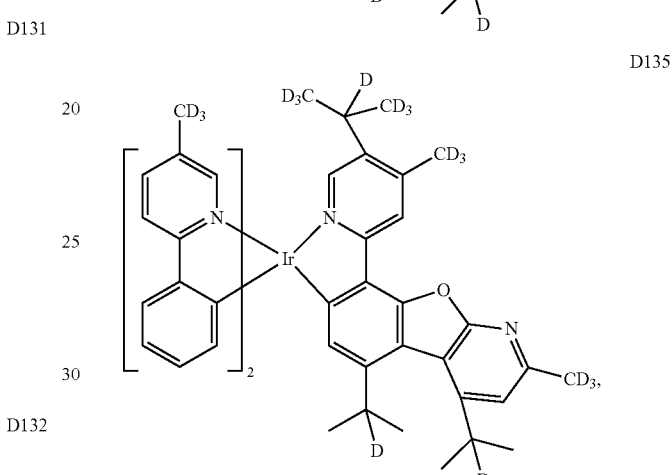
D135
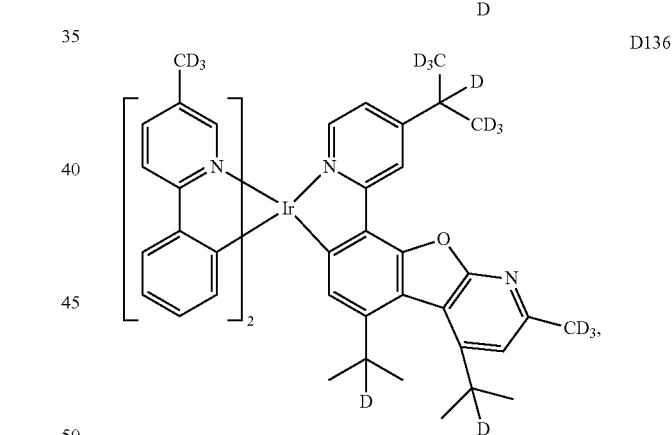
D136
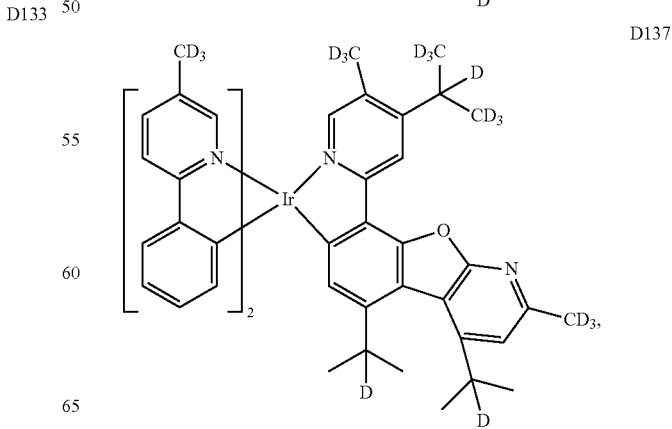
D137

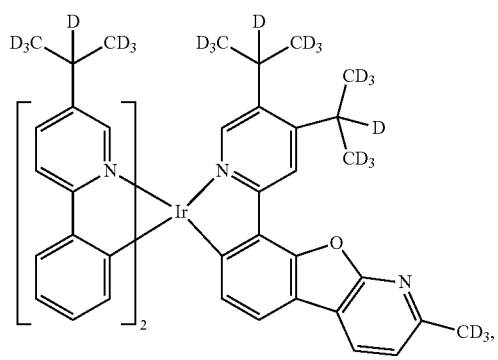 D138
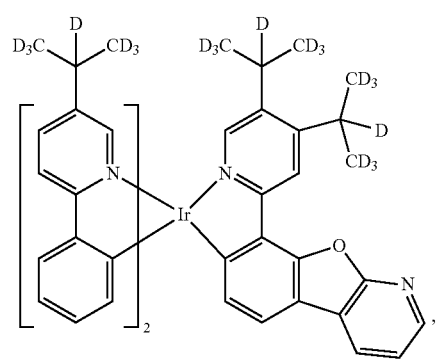 D139
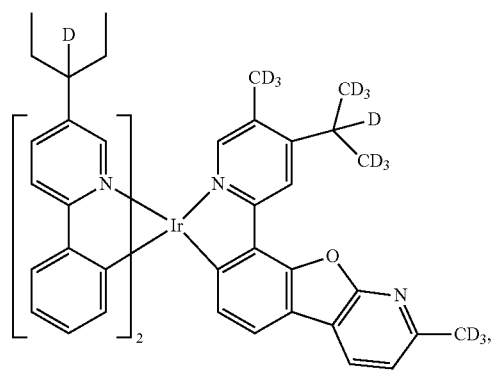 D140
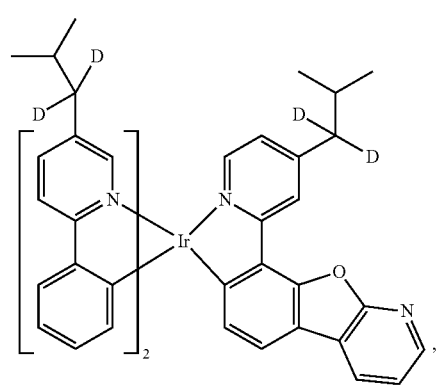 D141
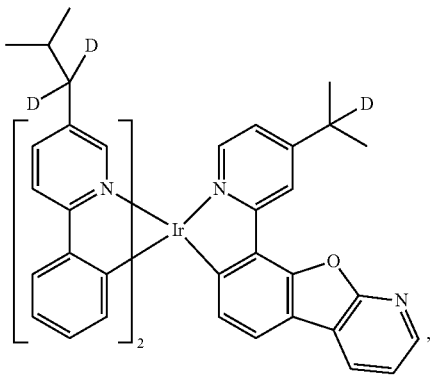 D142
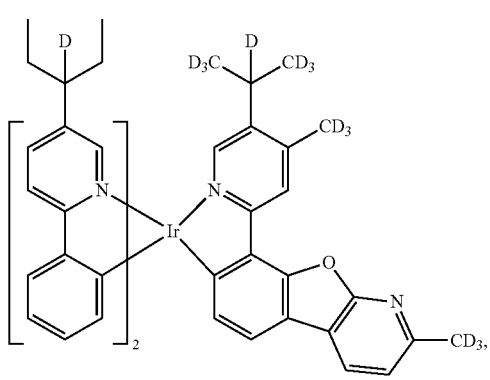 D143
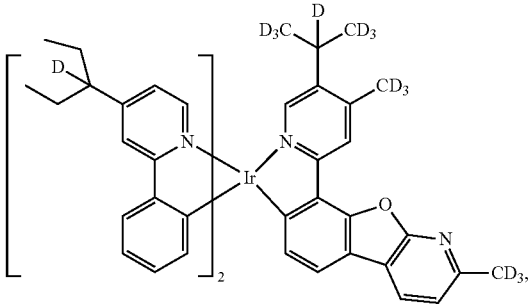 D144
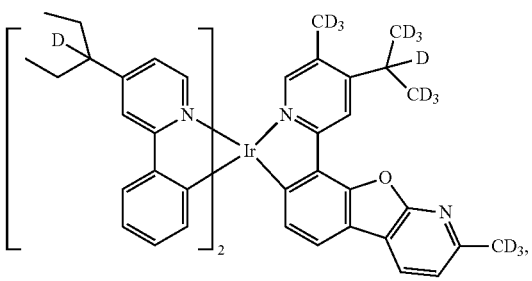 D145

D146
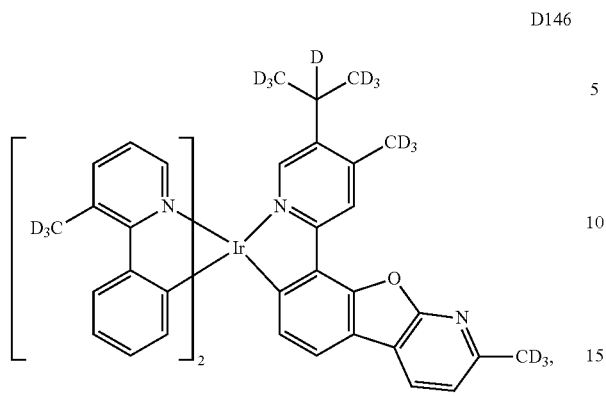
D147
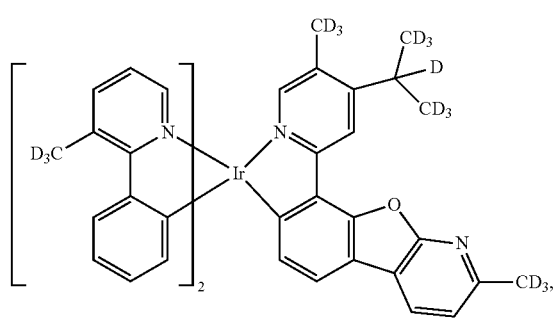
D148
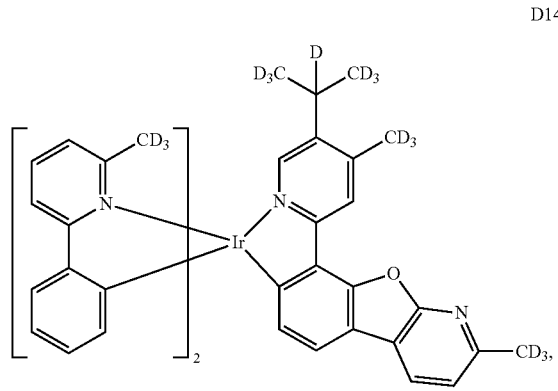
D149
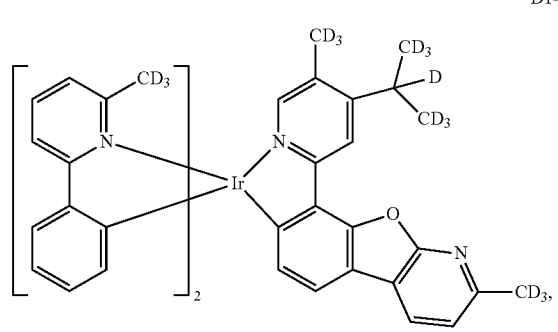
D150
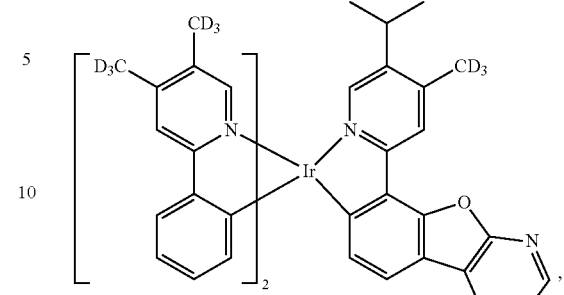
D151
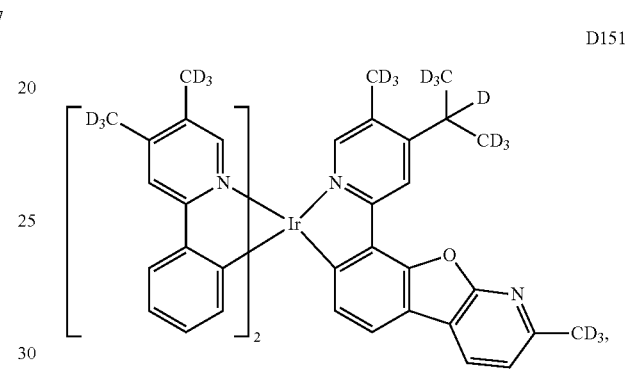
D152
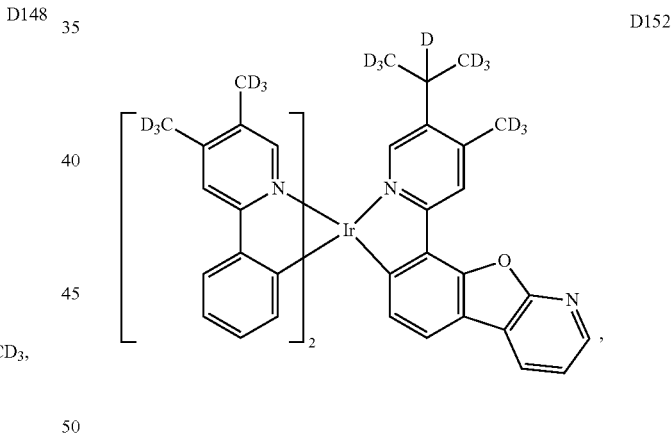
D153
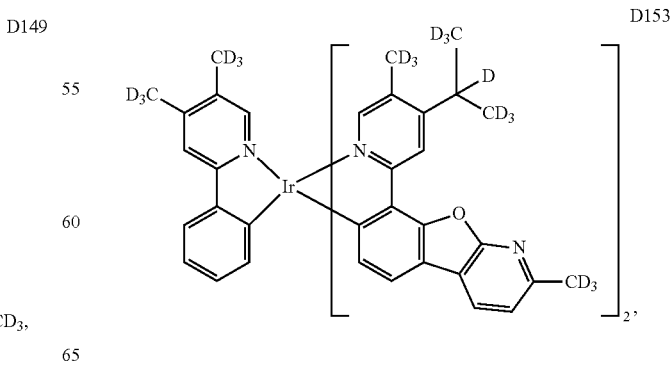

D154
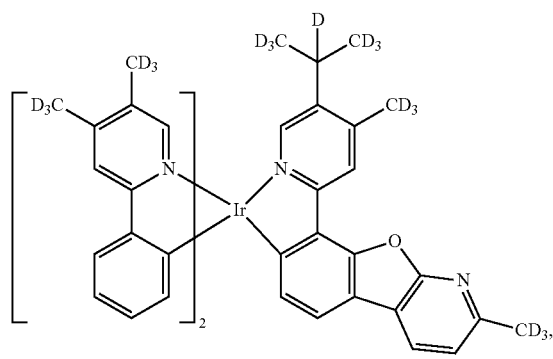
D155
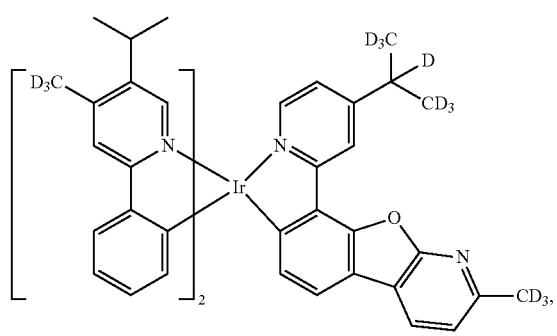
D156
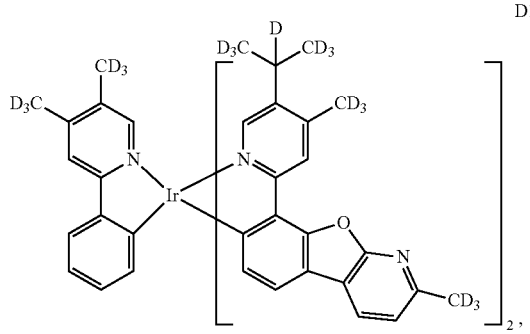
D157
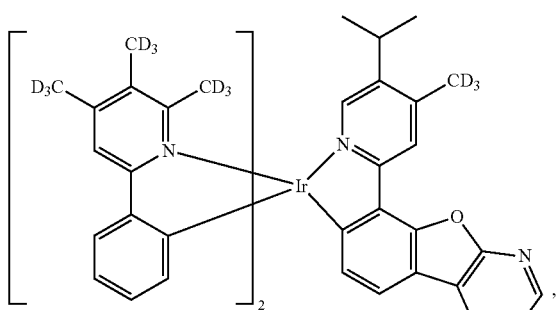
D158
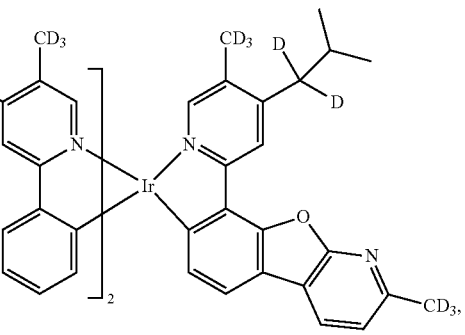
D159
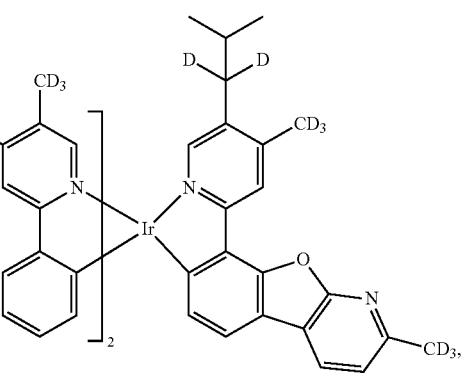
D160
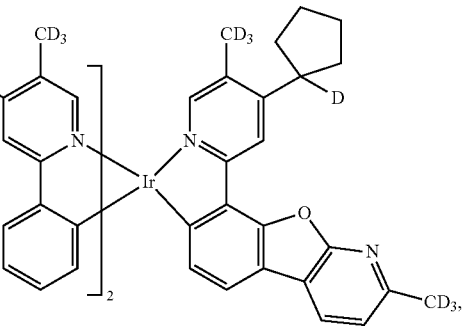
D161
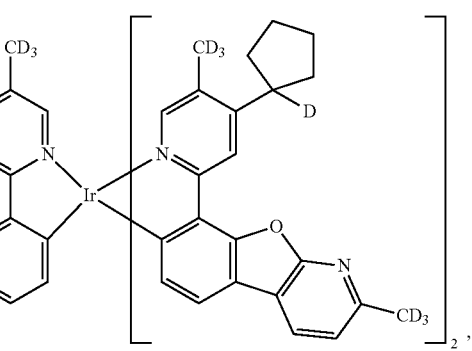

D162
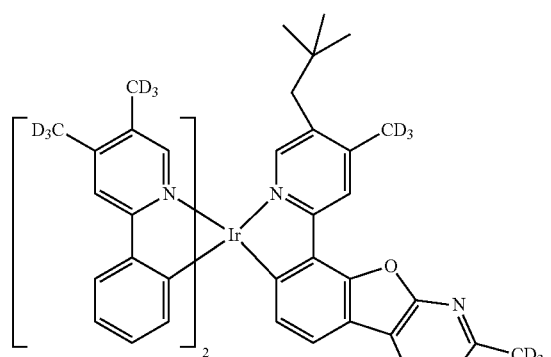
D163
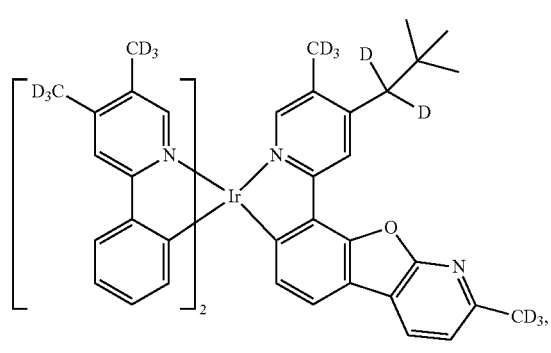
D164
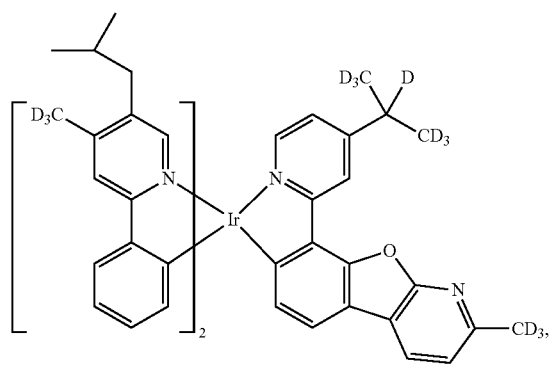
D165
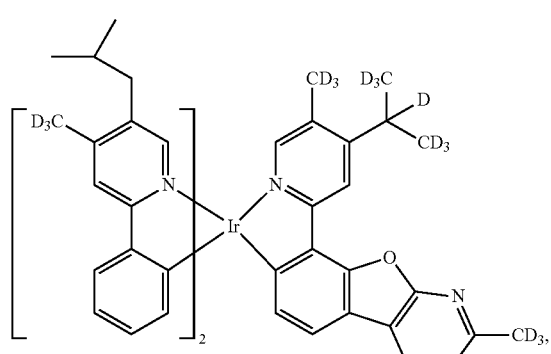
D166
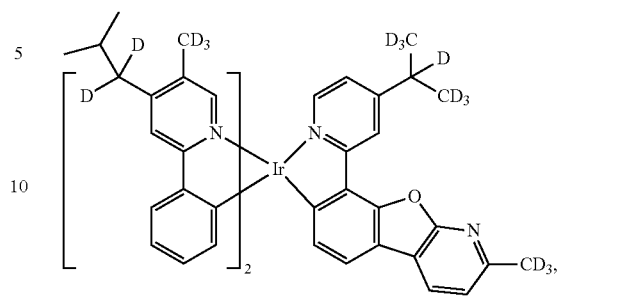
D167
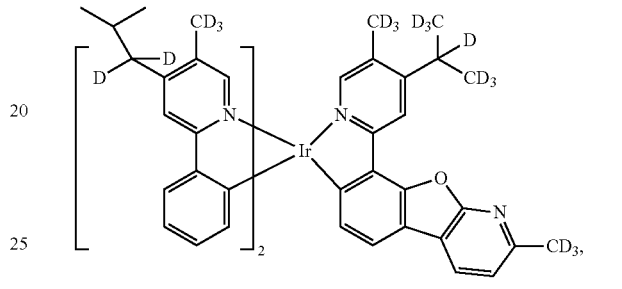
D168
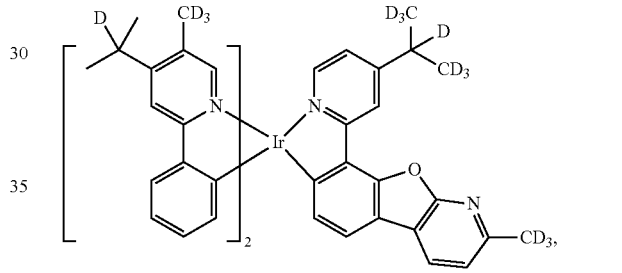
D169
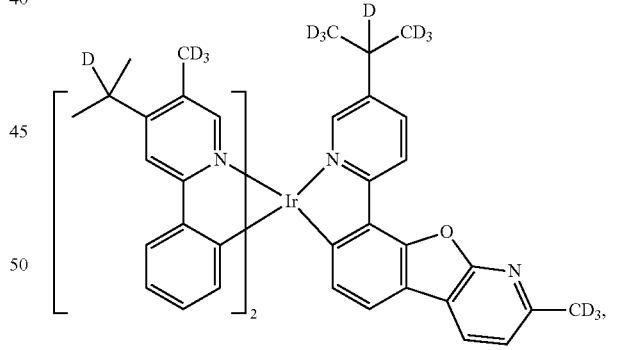
D170
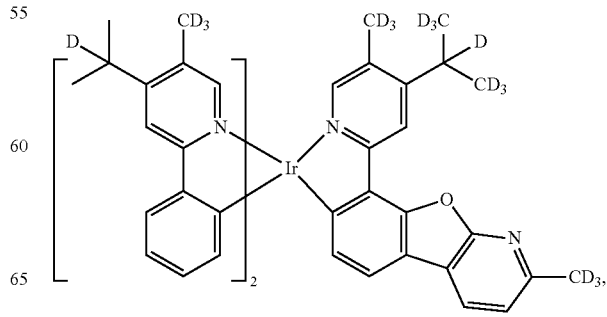

D171
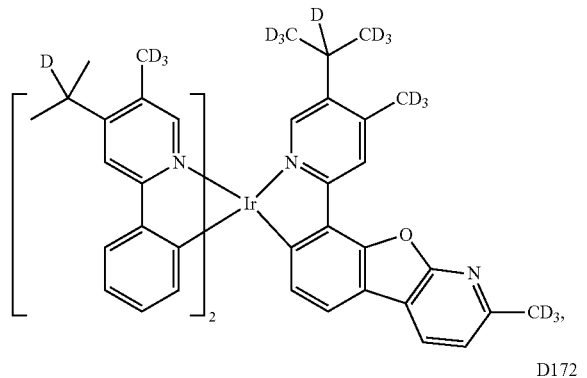
D172
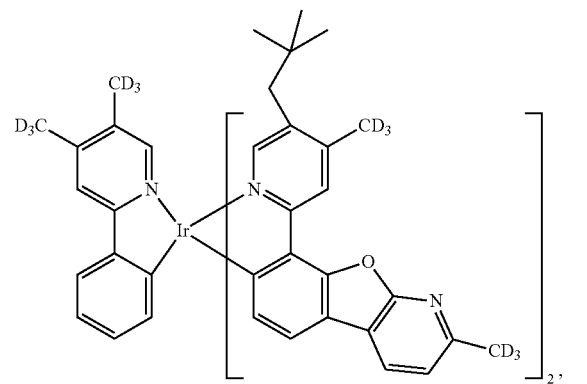
D173
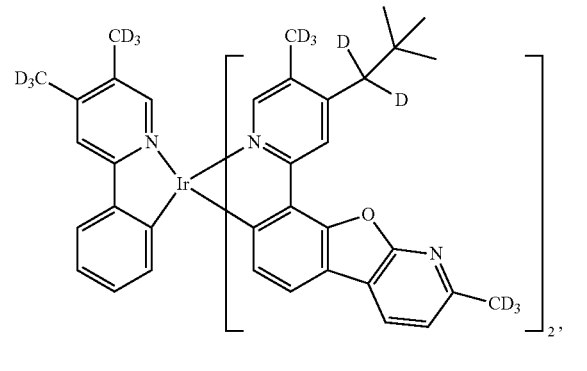
D174
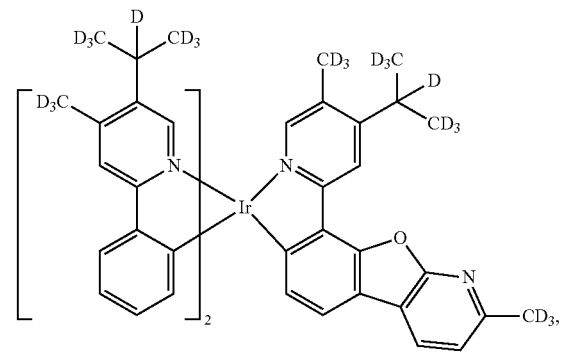
D175
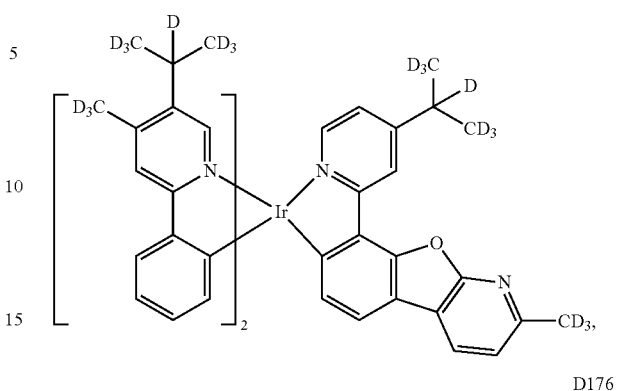
D176
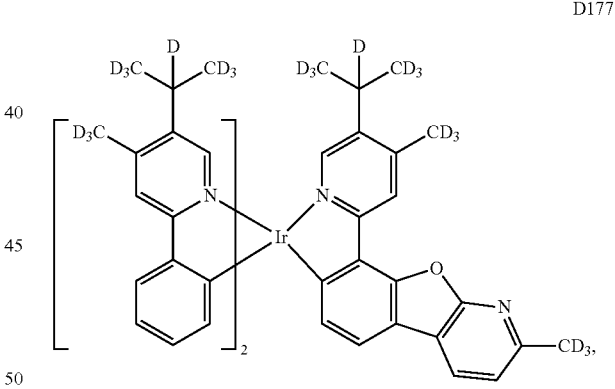
D177
D178
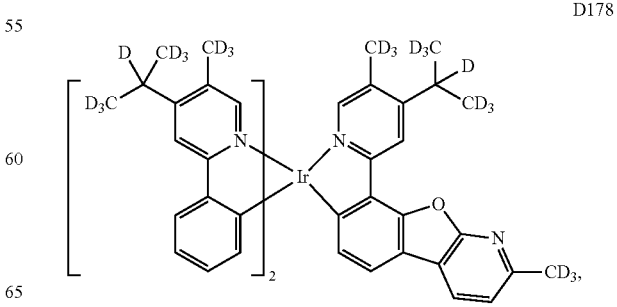

-continued
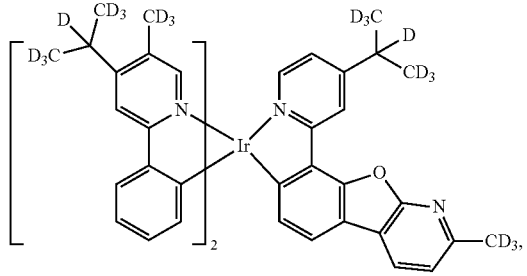
D179
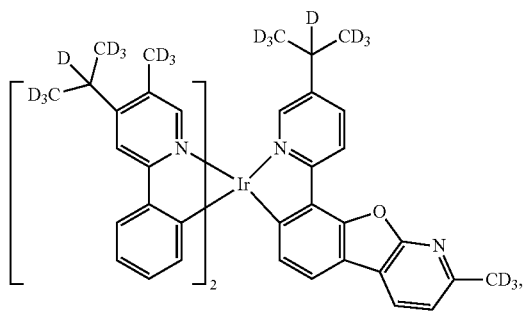
D180
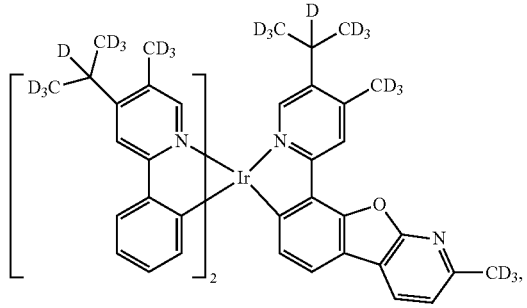
D181
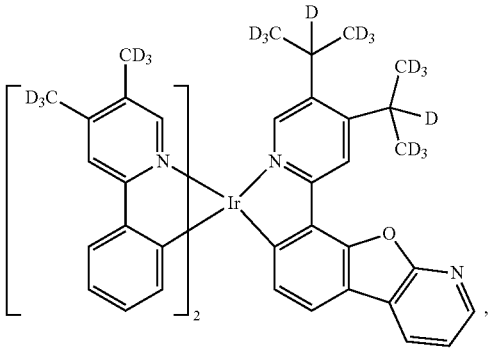
D182
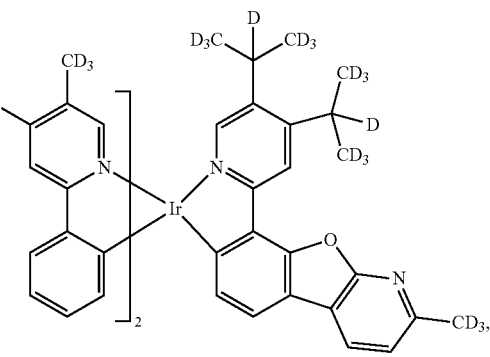
D183
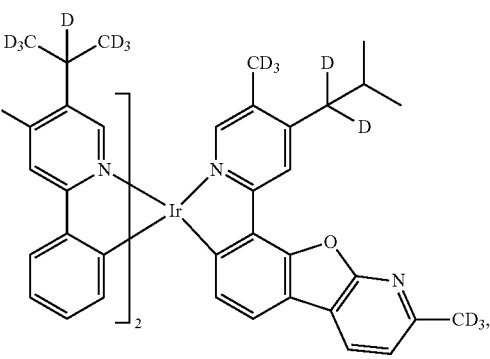
D184
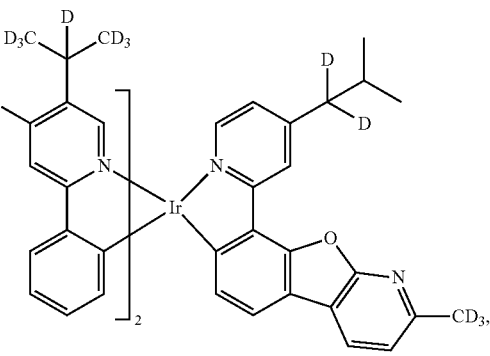
D185
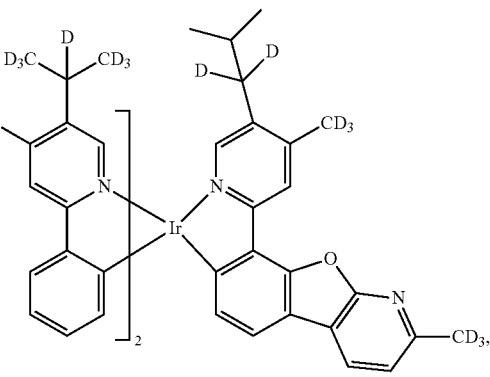
D186

-continued
D187
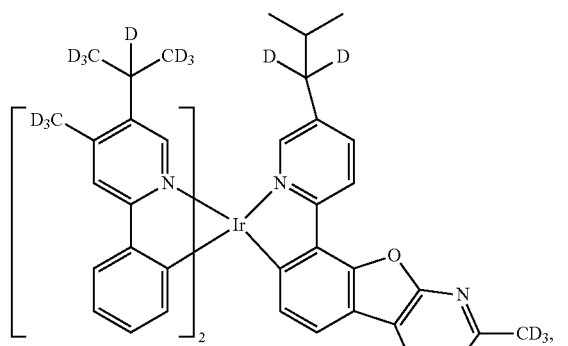
D188
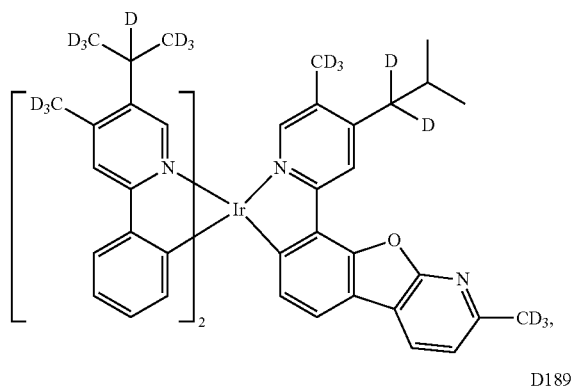
D189
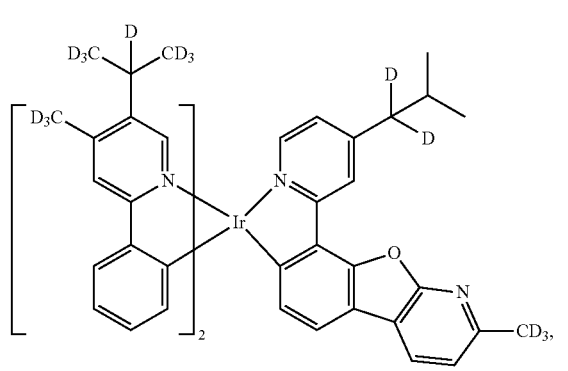
D190
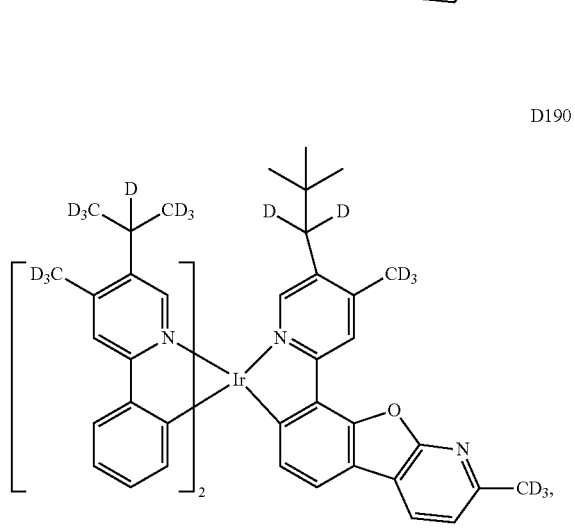
-continued
D191
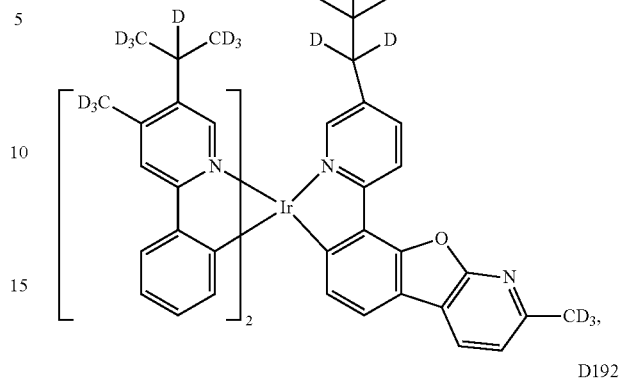
D192
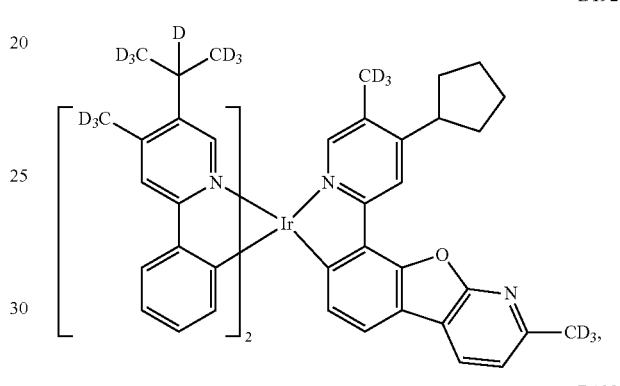
D193
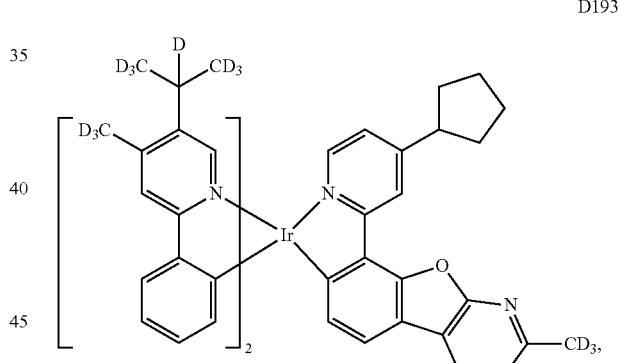
D194
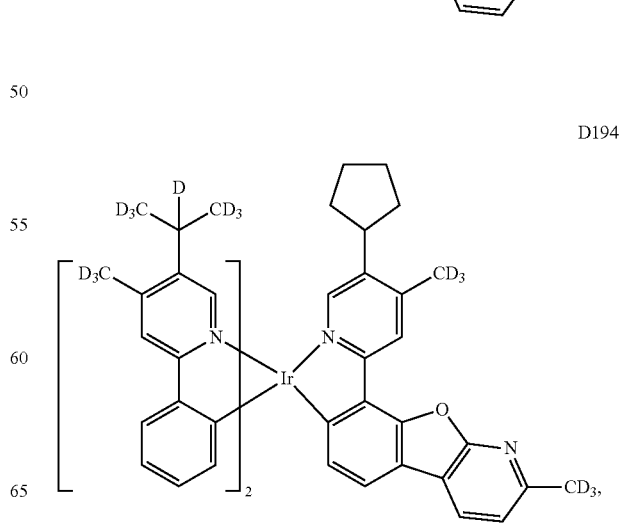

-continued
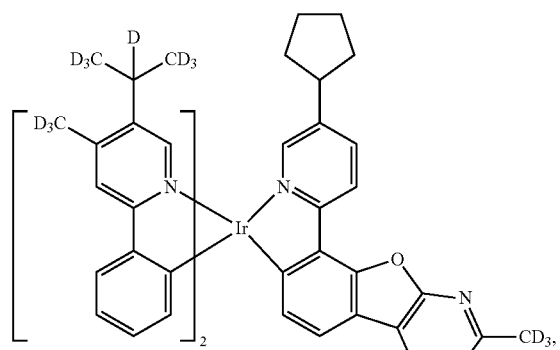
D195
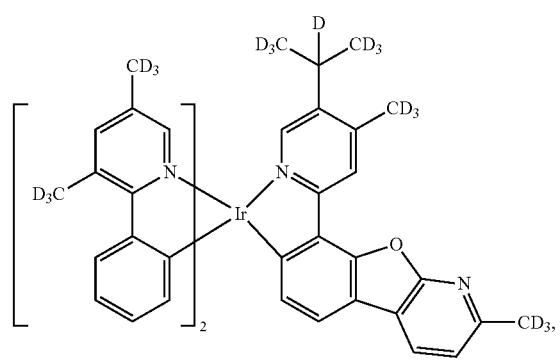
D196
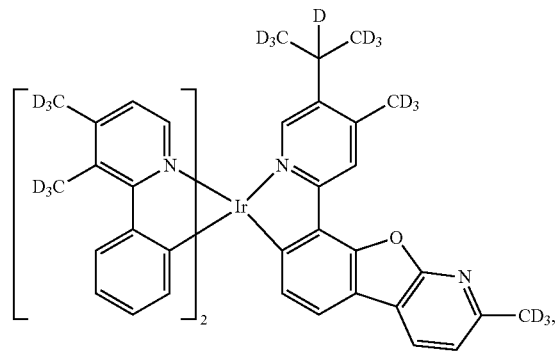
D197
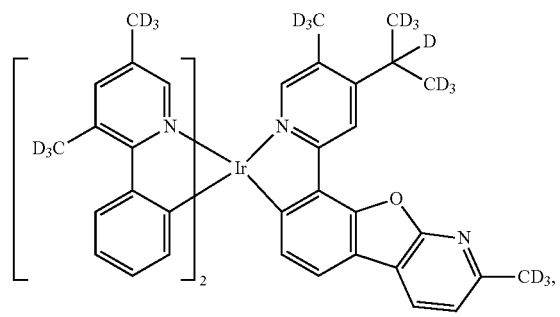
D198
-continued
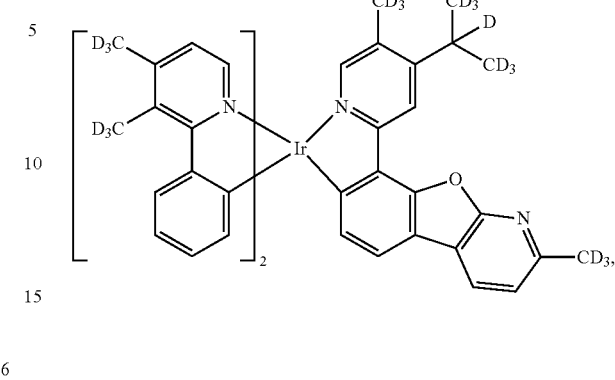
D199
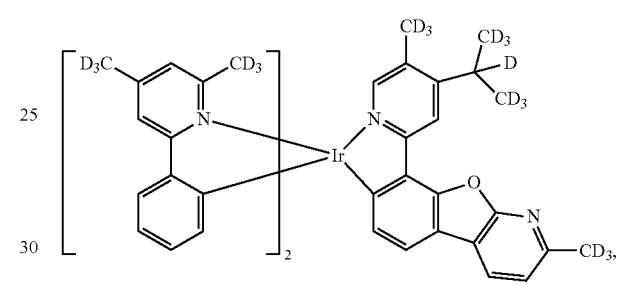
D200
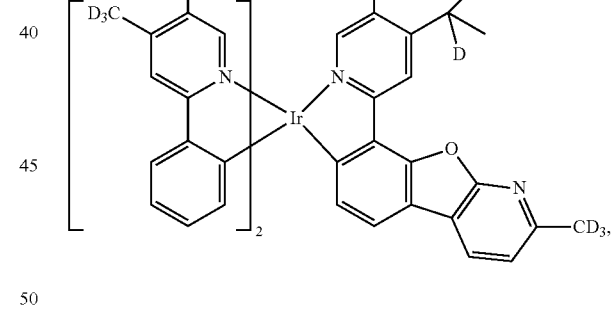
D201
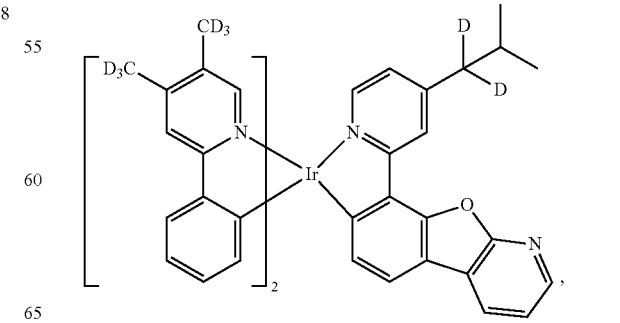
D202

D203
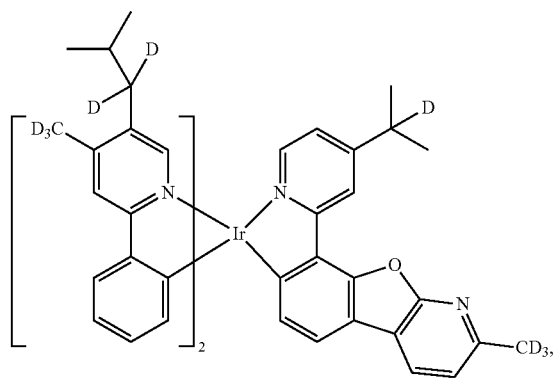
D204
D207
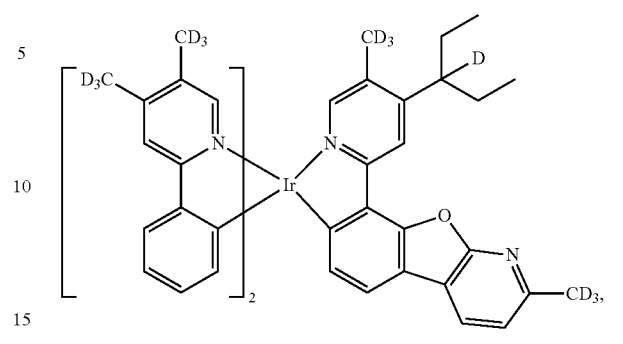
D208
D205
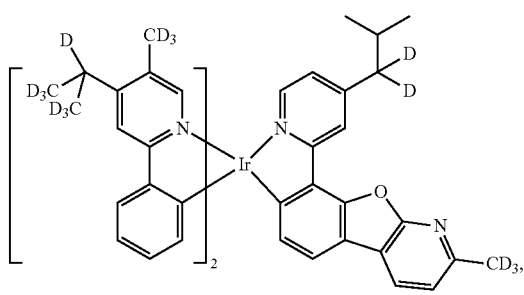
D209
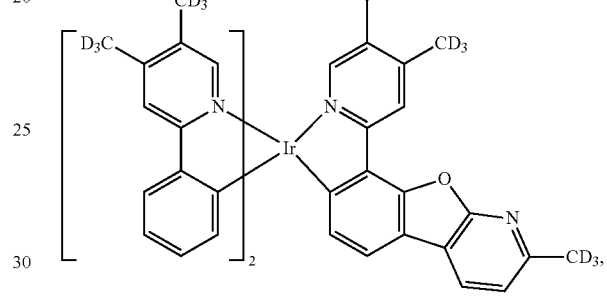
D206
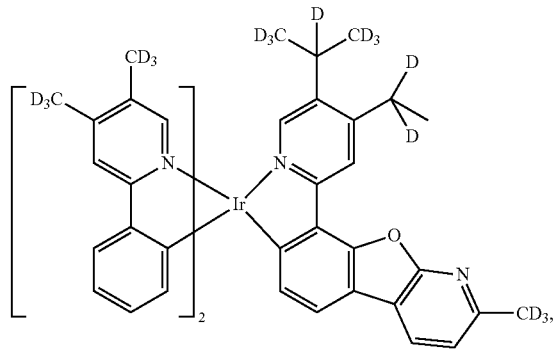
D210
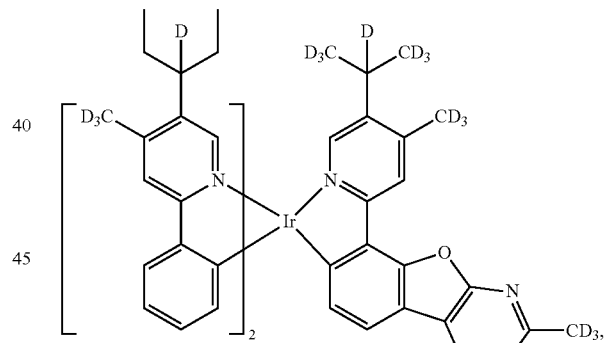
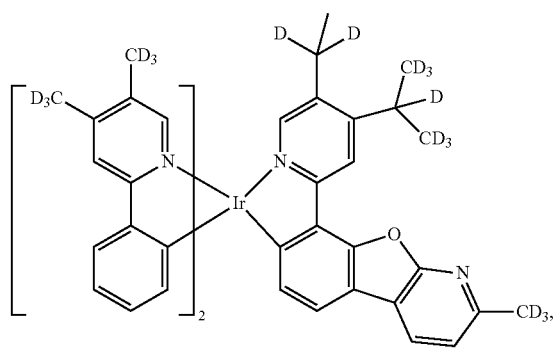
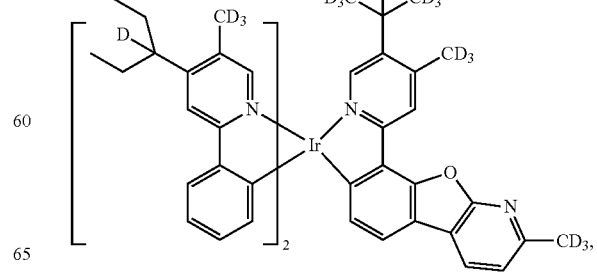

391
-continued
D211
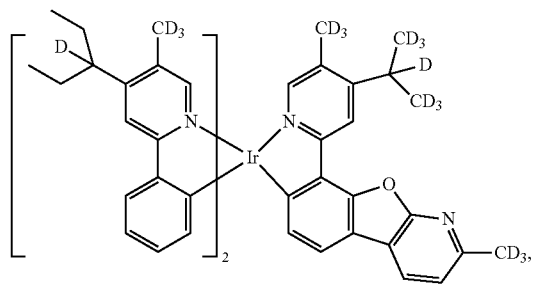
D212
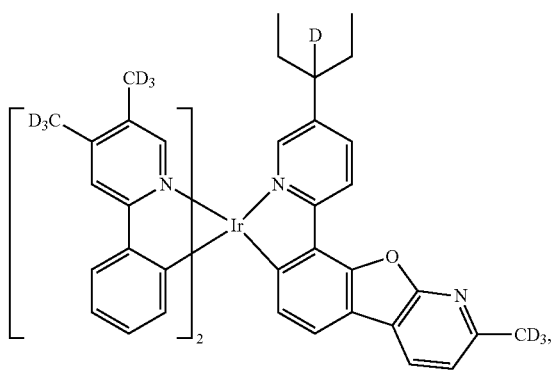
D213
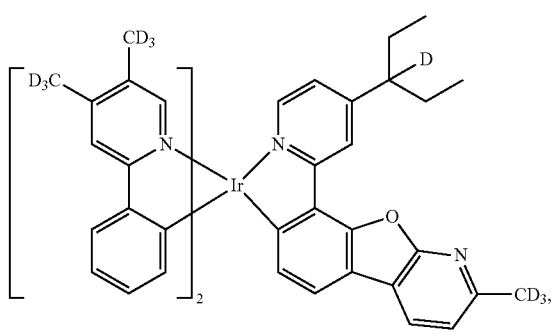
D214
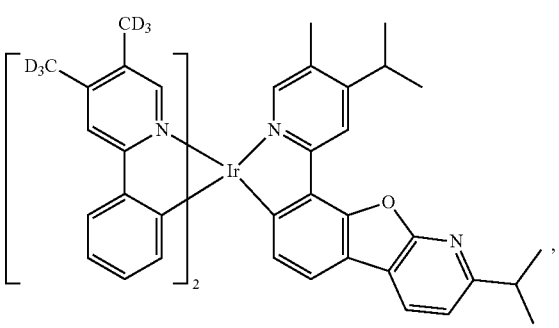
392
-continued
D215
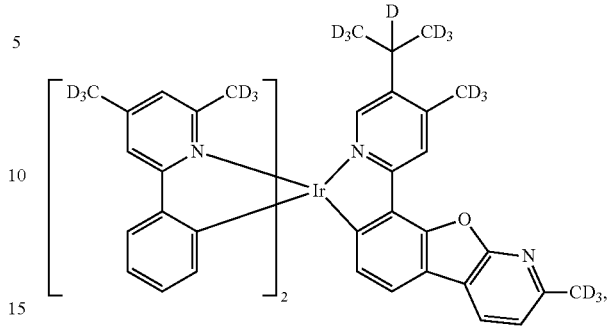
D216
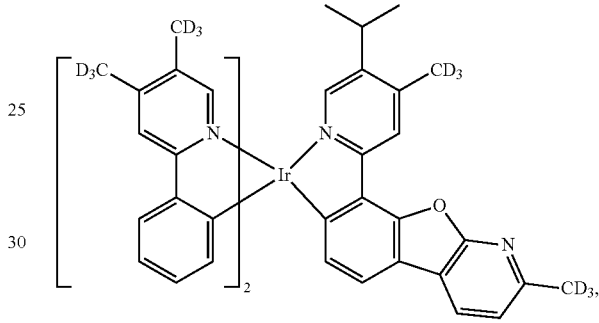
D217
D218
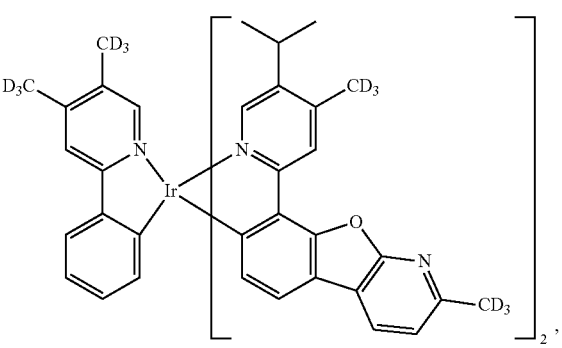

393
-continued
D219
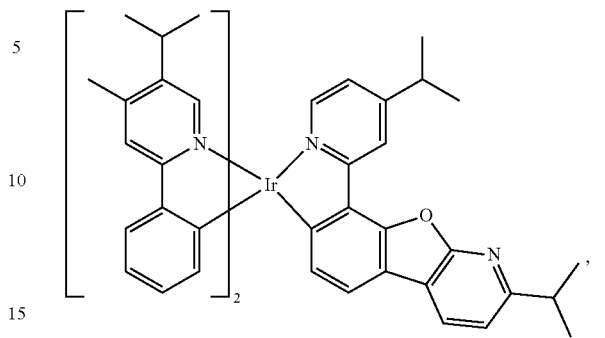
D220
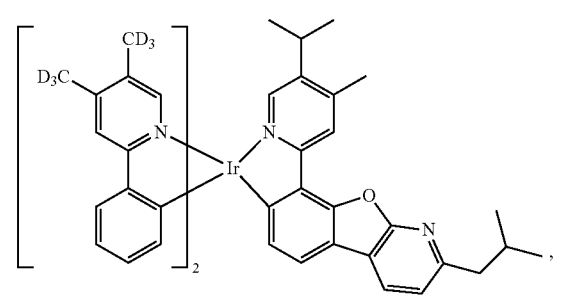
D221
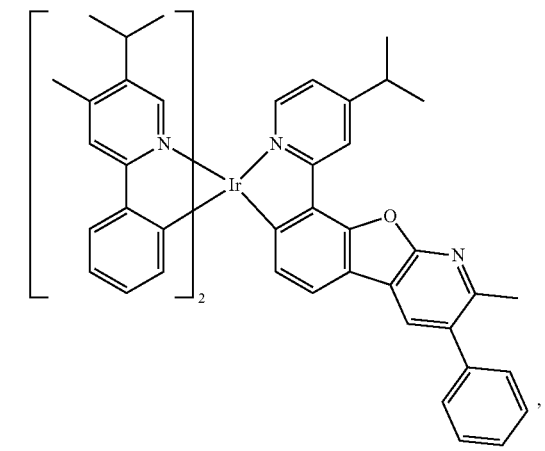
D222
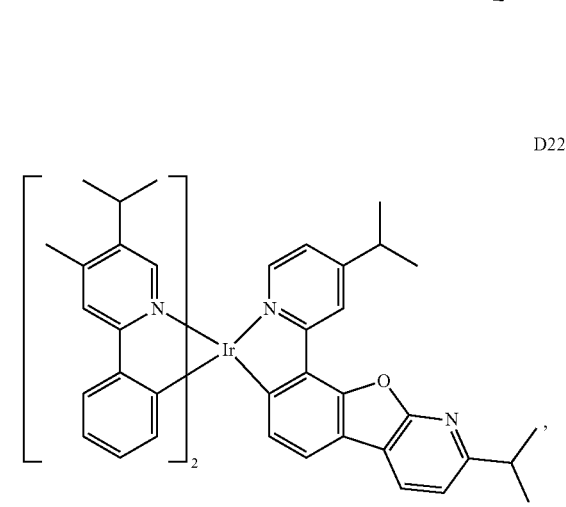
394
-continued
D223
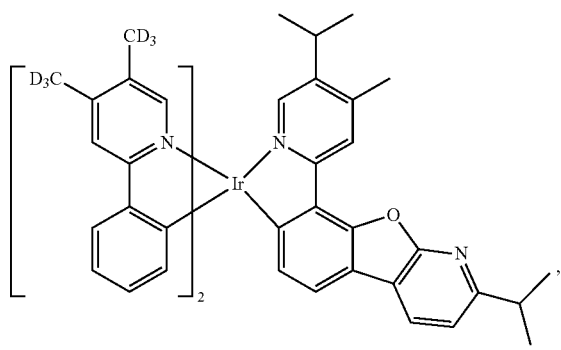
D224
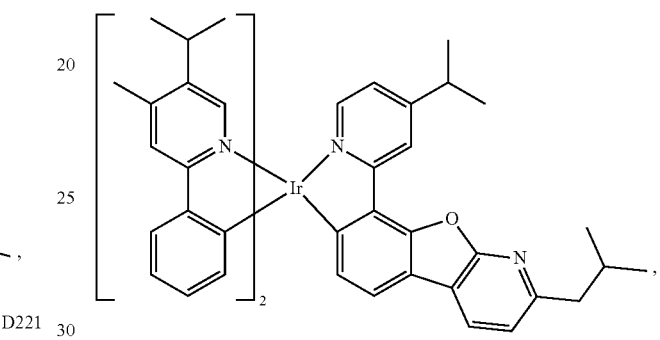
D225
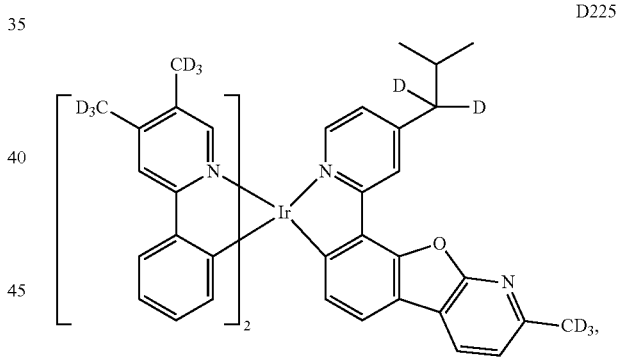
D226
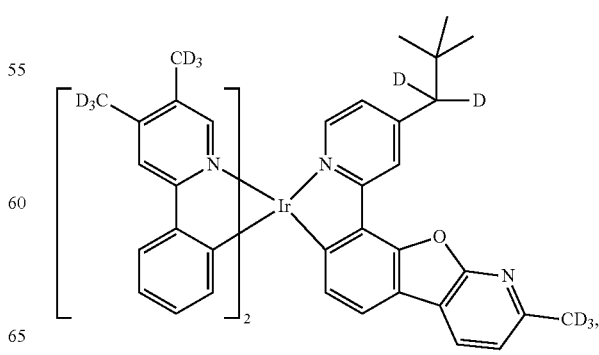

395
-continued
D227
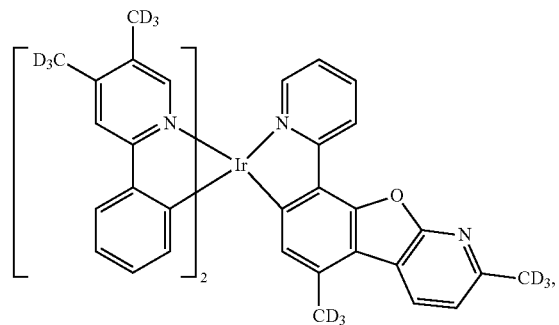
D228
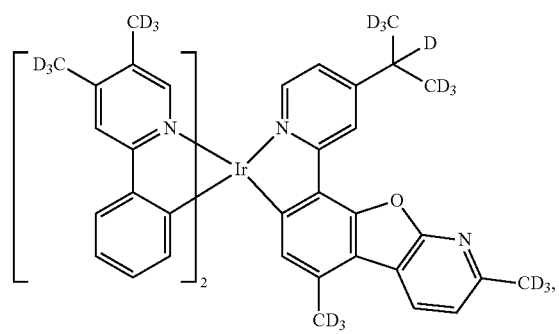
D229
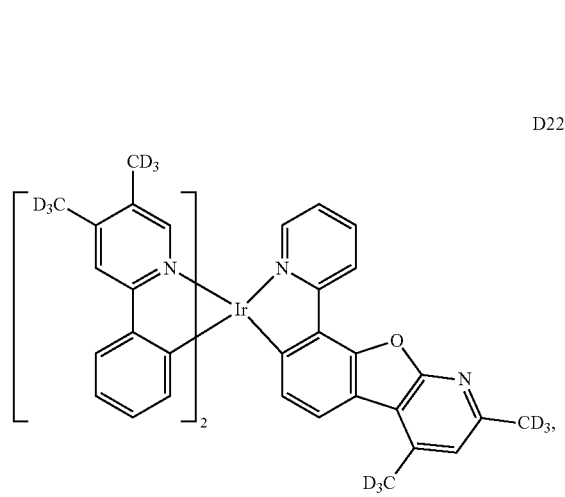
D230
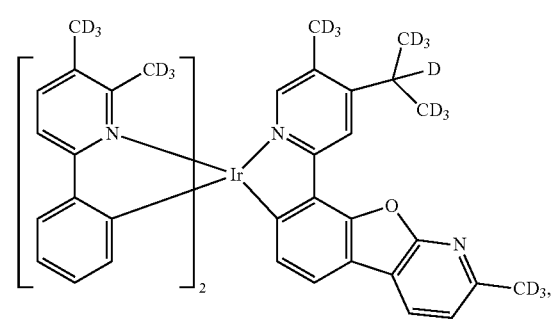
396
-continued
D231
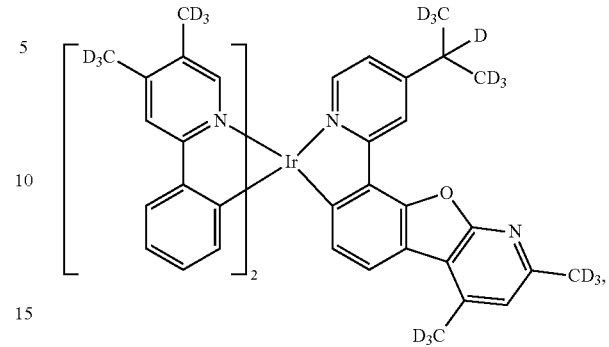
D232
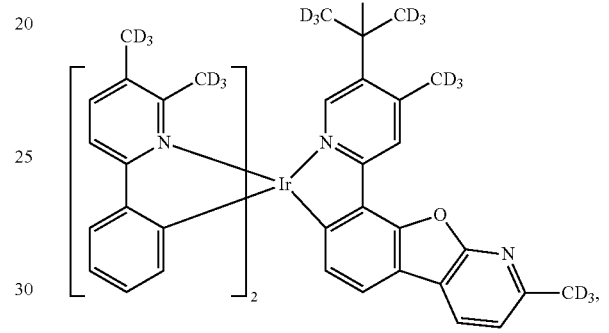
D233
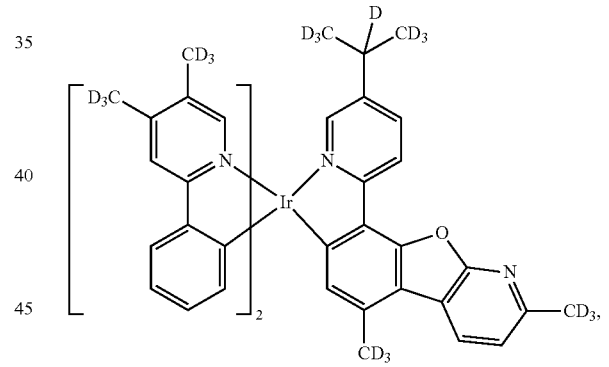
D234
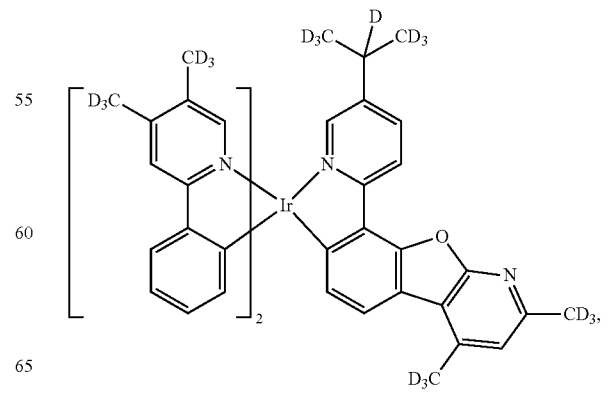

D235
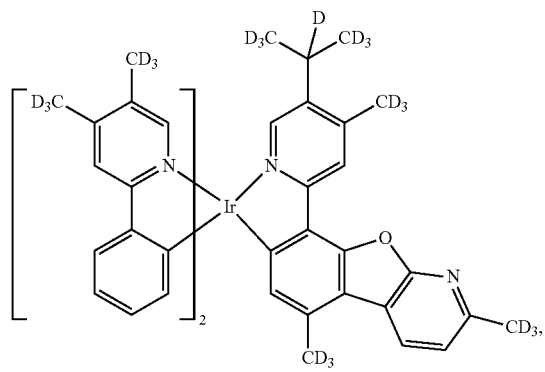
D236
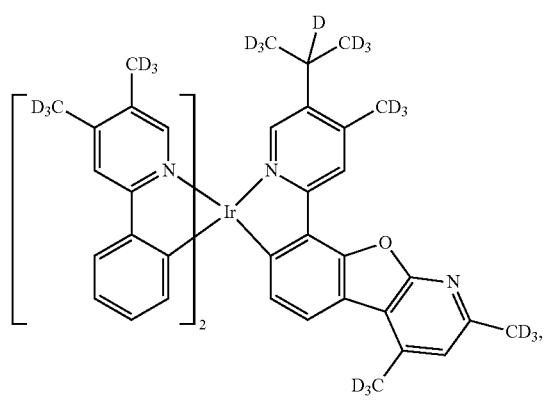
D237
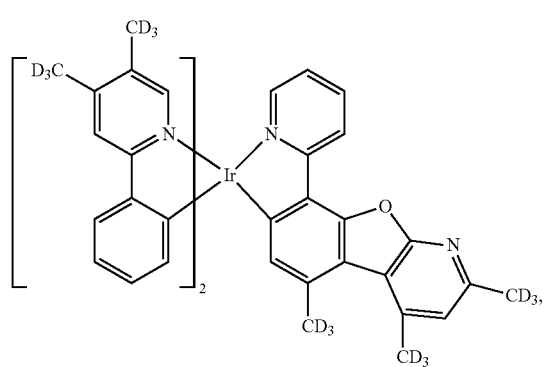
D238
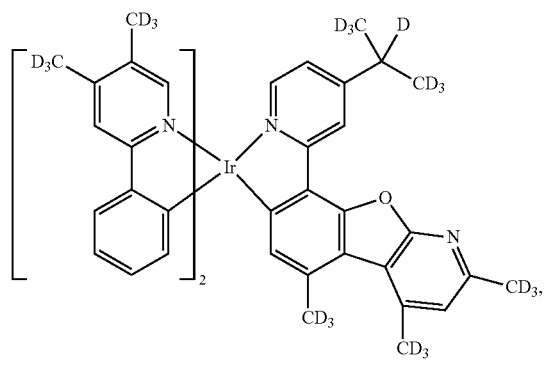
D239
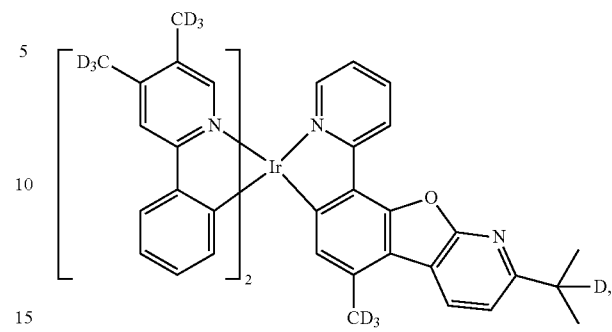
D240
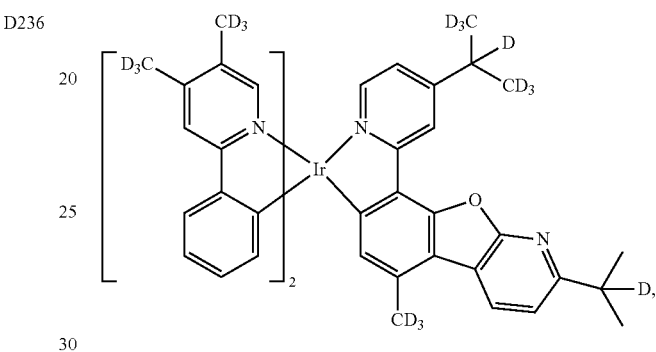
D241
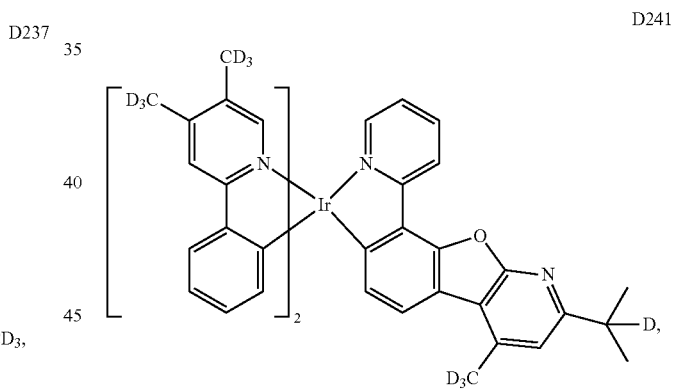
D242
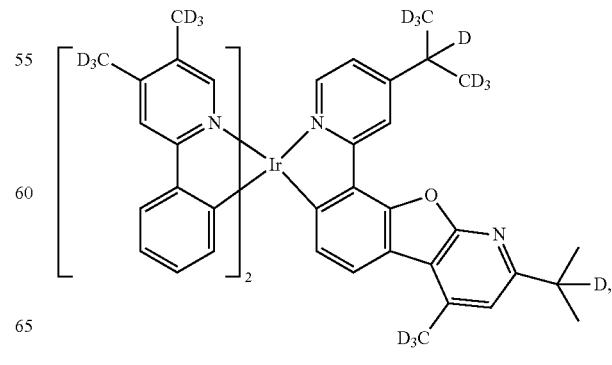

D243
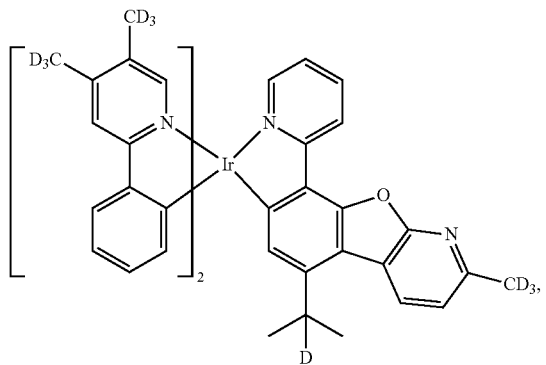
D244
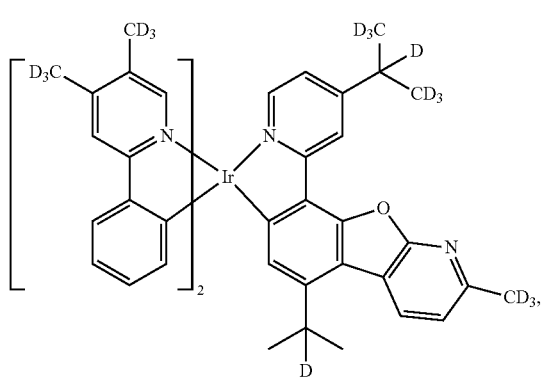
D245
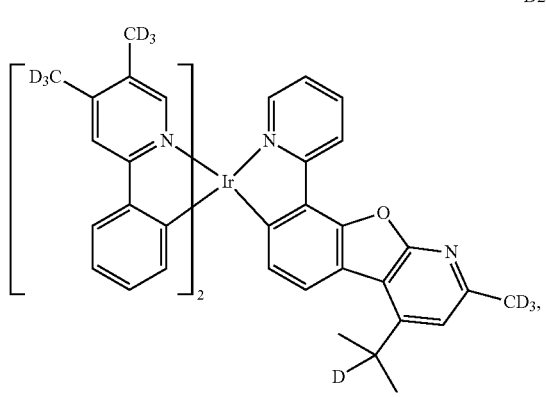
D246
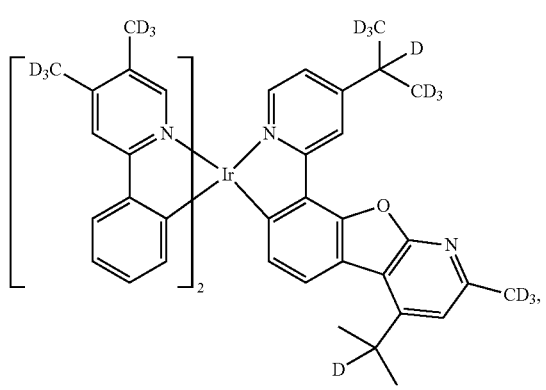
D247
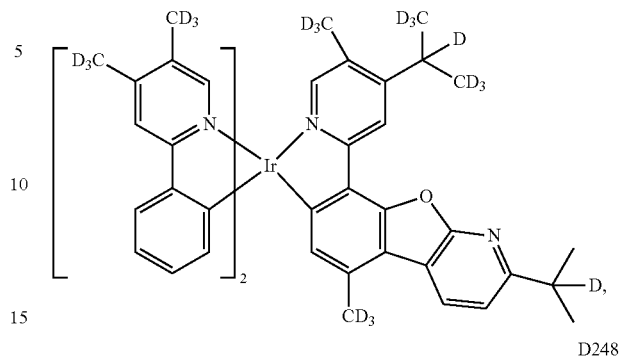
D248
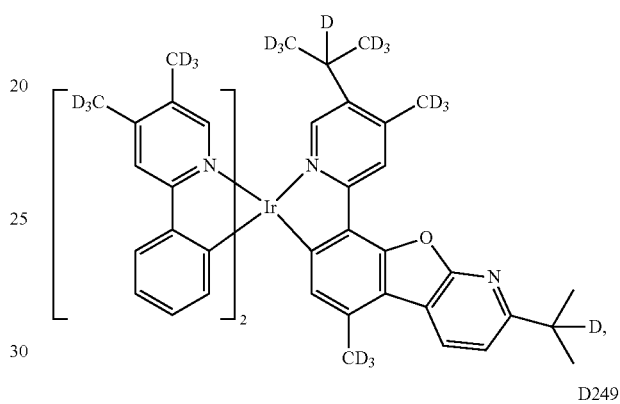
D249
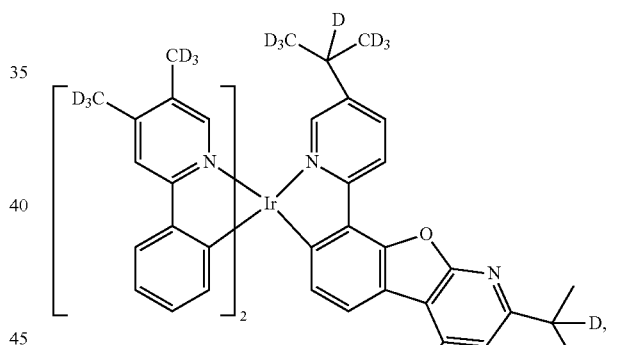
D250
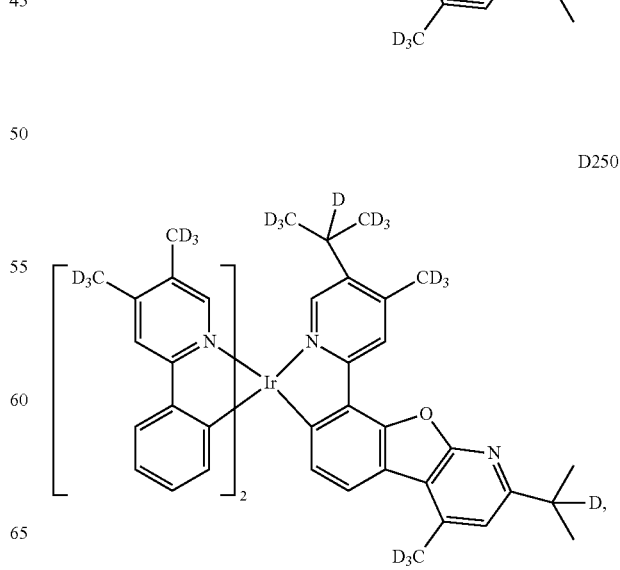

D251
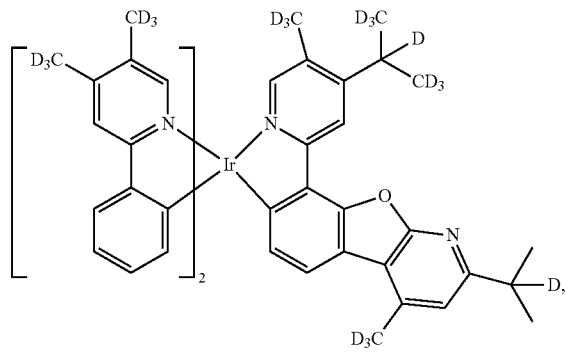
D252
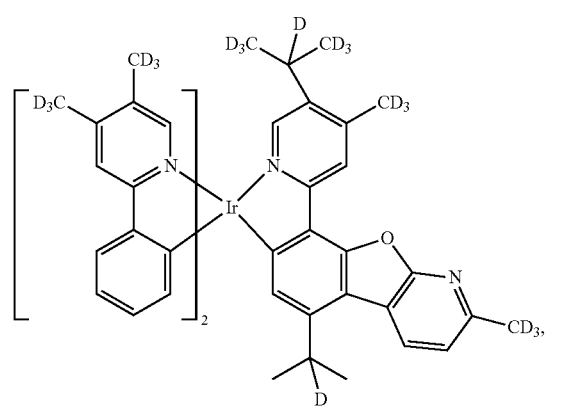
D253
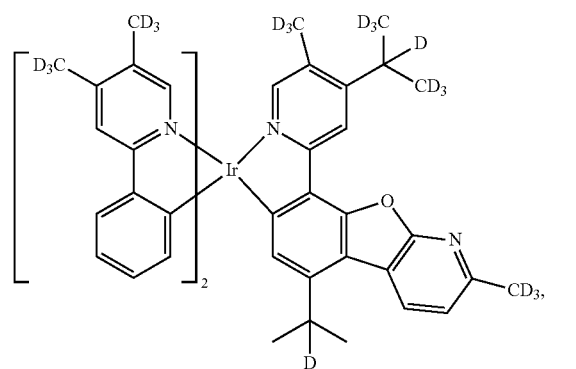
D254
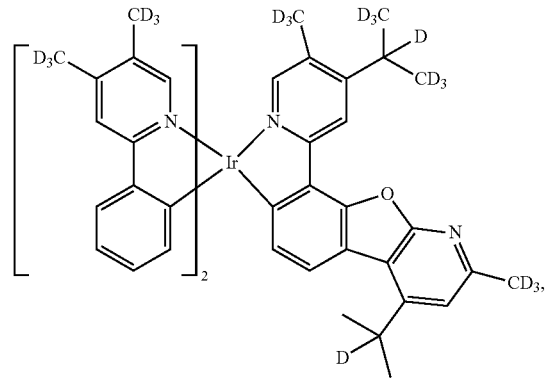
D255
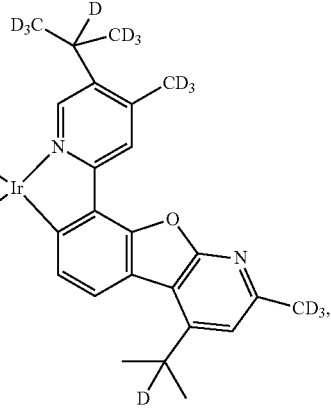
D256
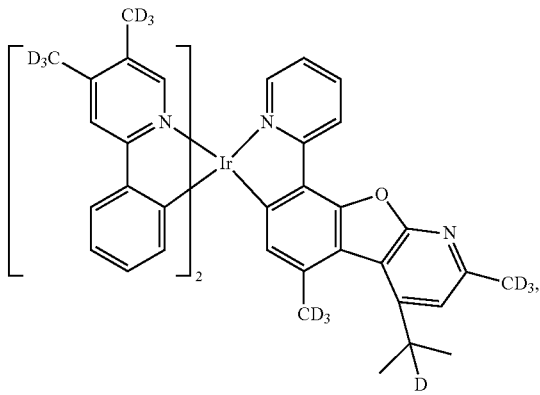
D257
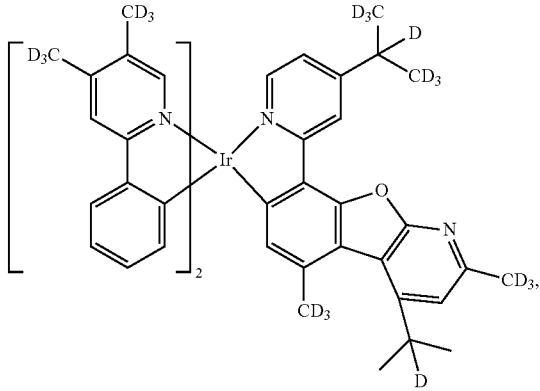

D258
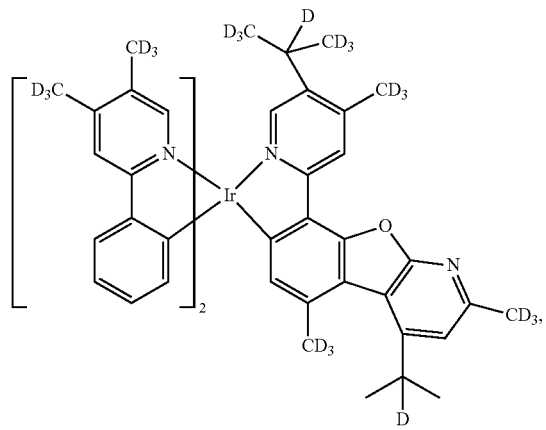
D259
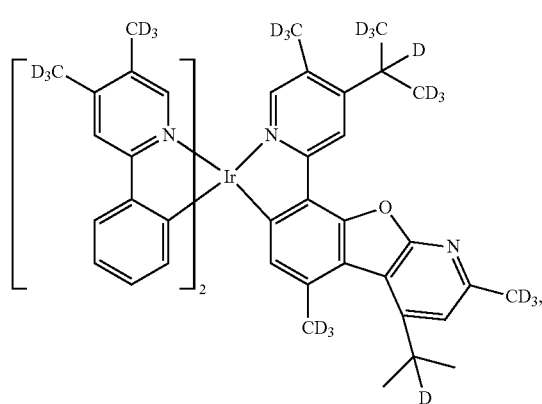
D260
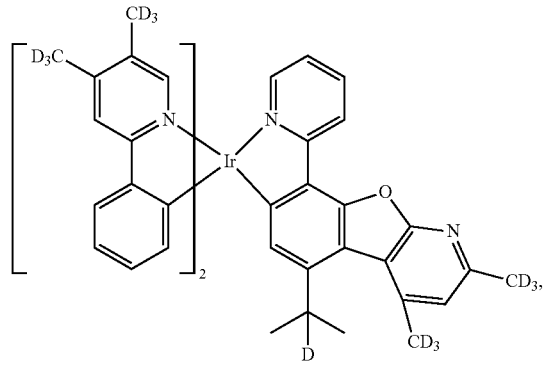
D261
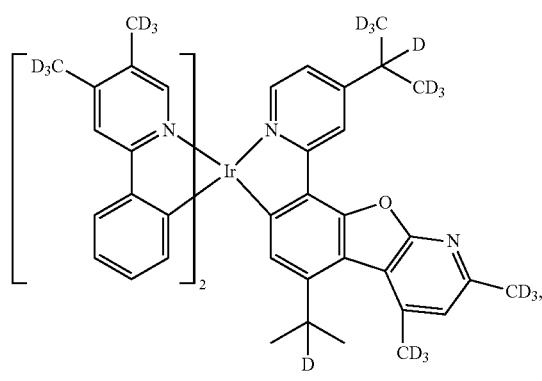
D262
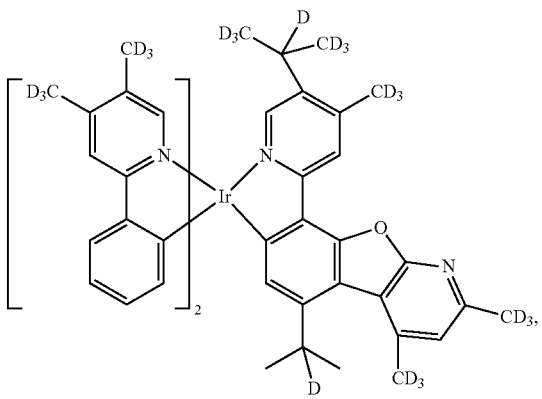
D263
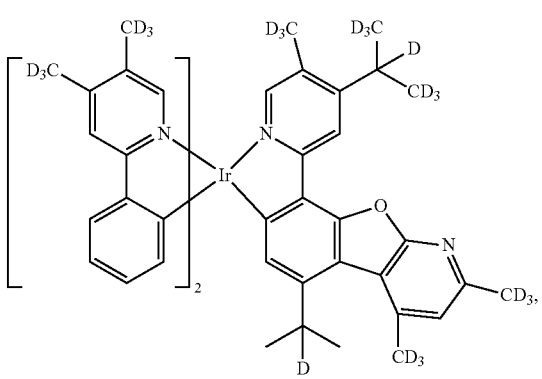
D264
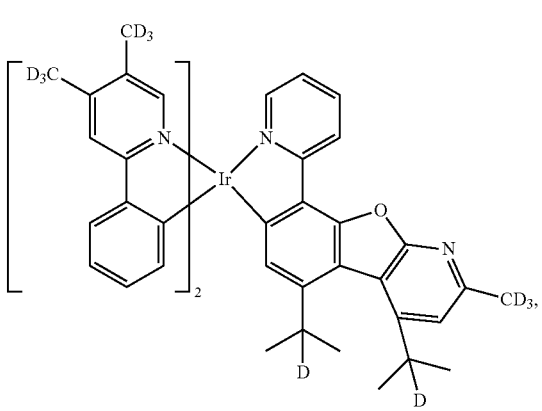
D265
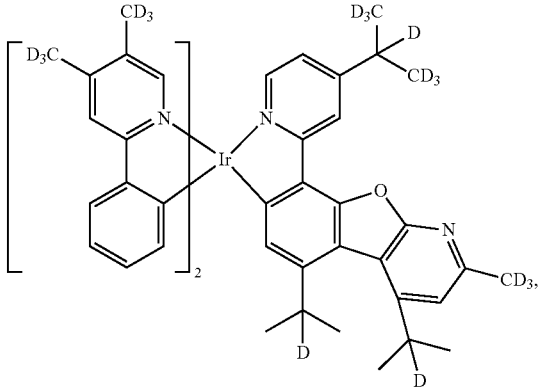

D266
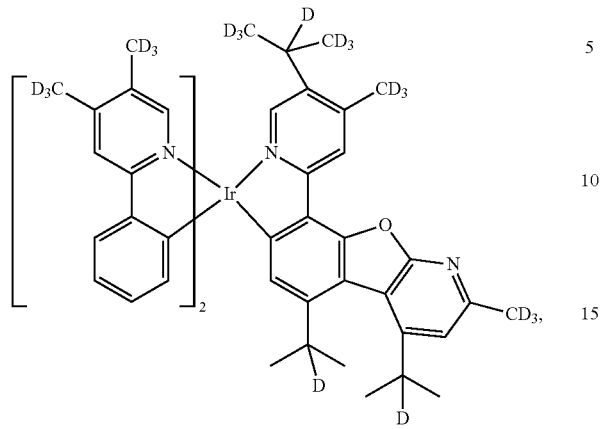
D267
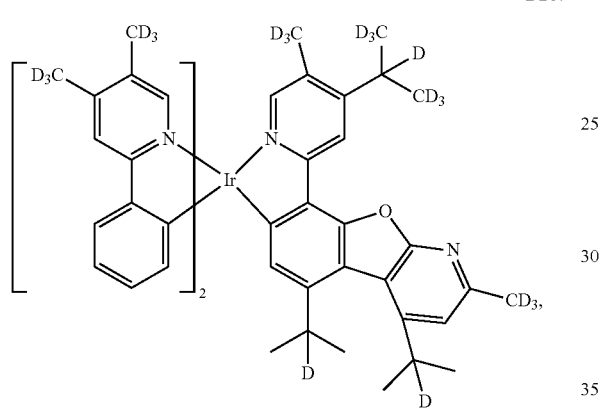
D268
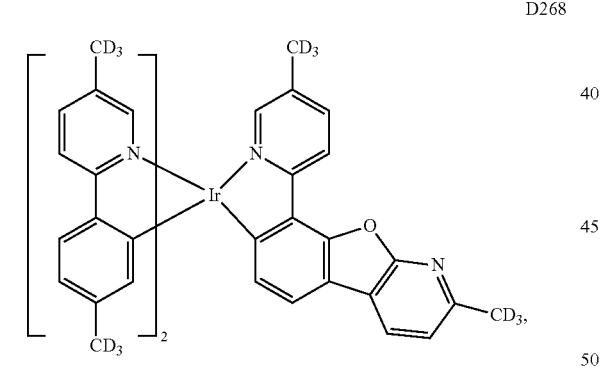
D269
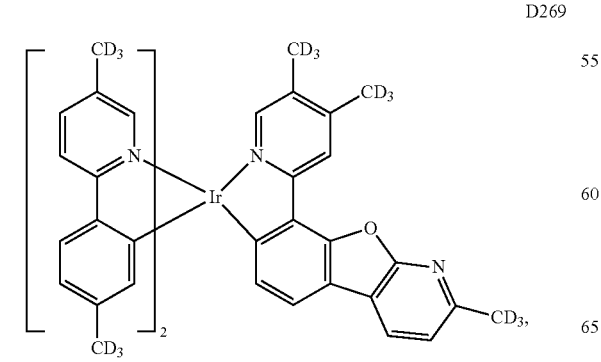
D270
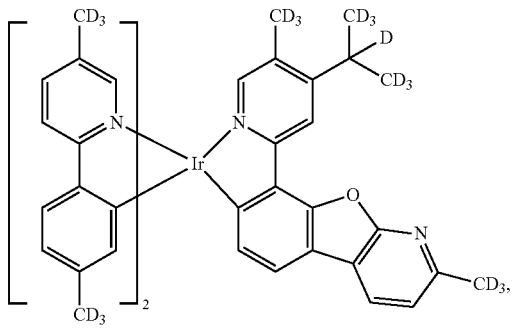
D271
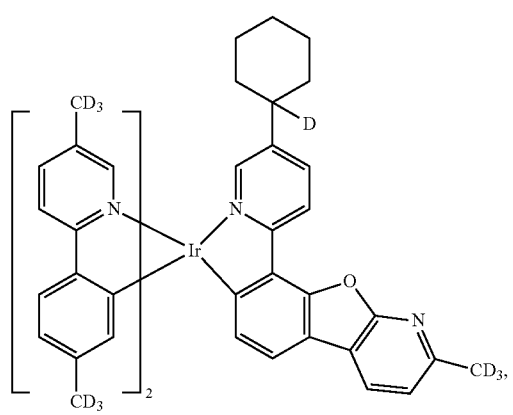
D272
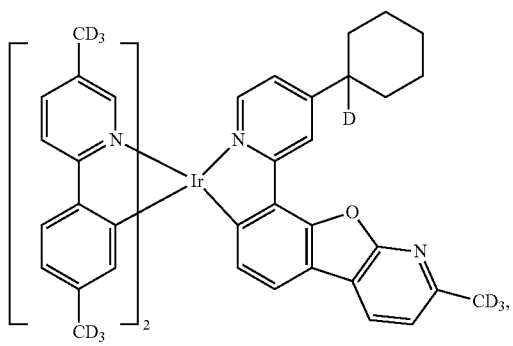
D273
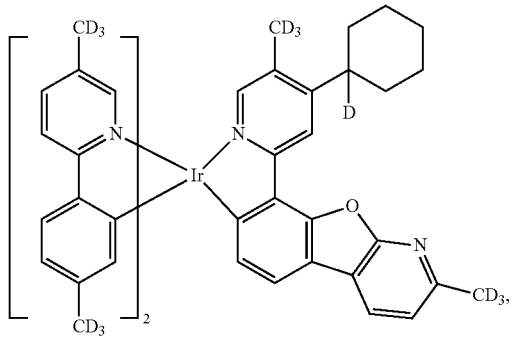

D274
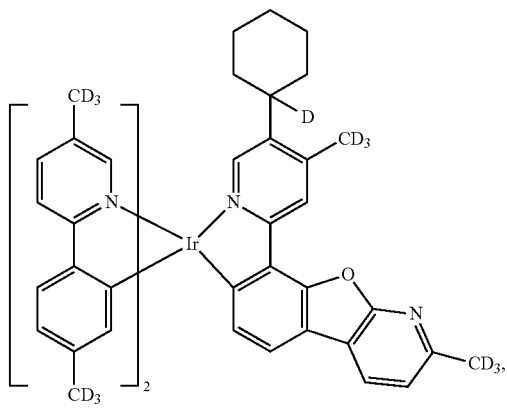
D275
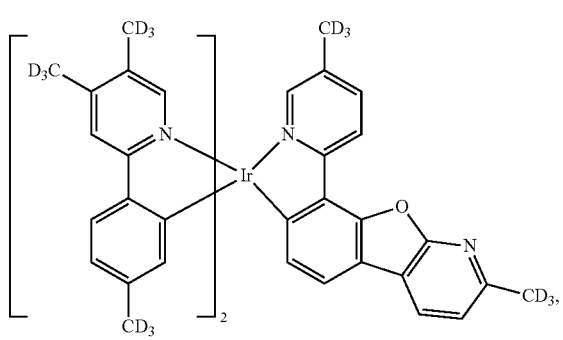
D276
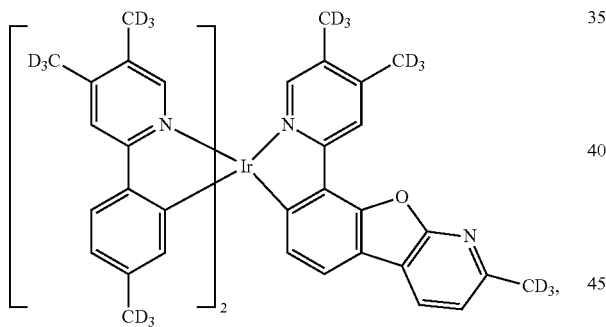
D277
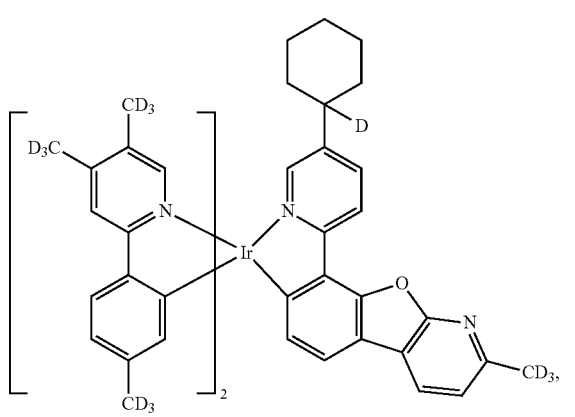
D278
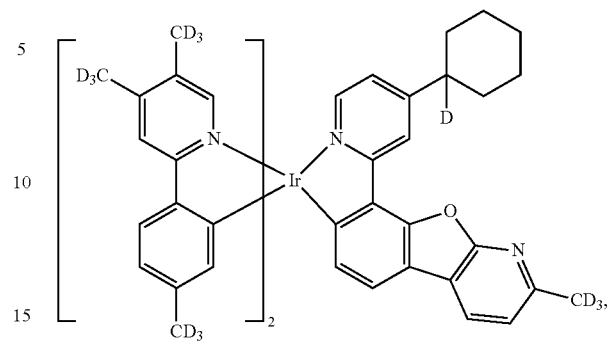
E1
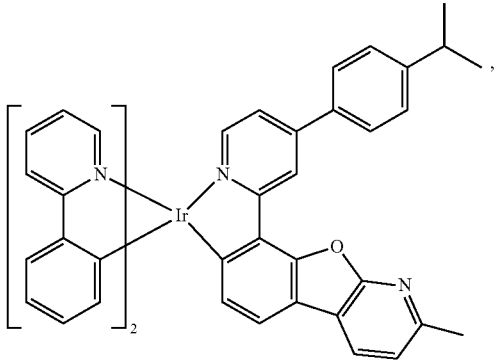
E2
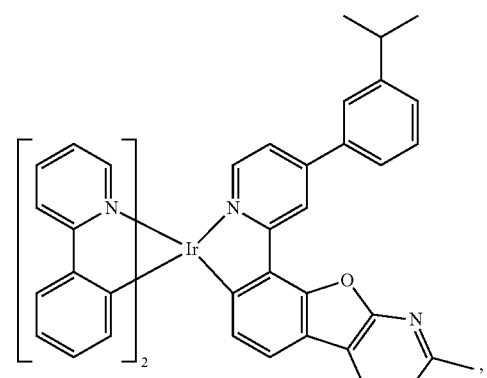
E3
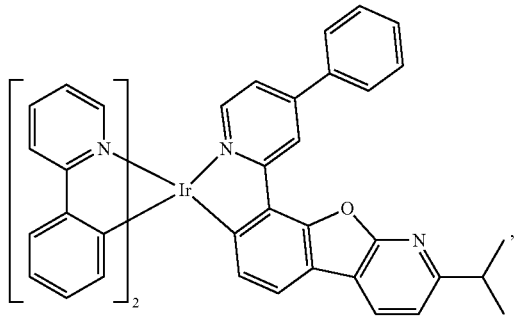

E4
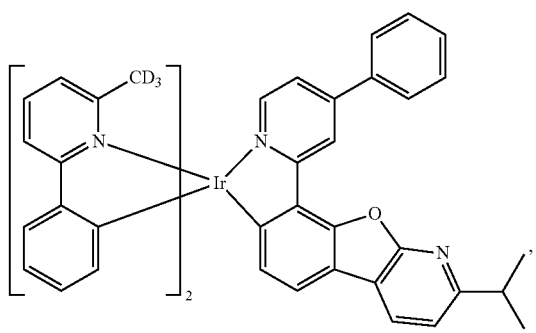
E5
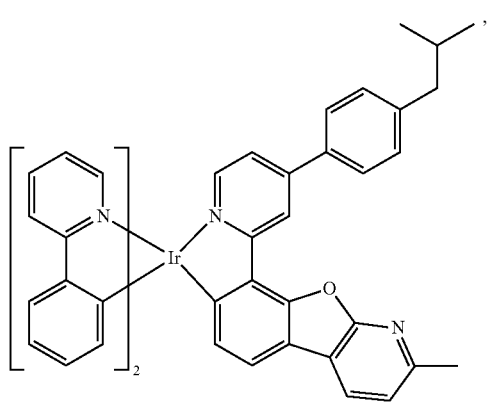
E6
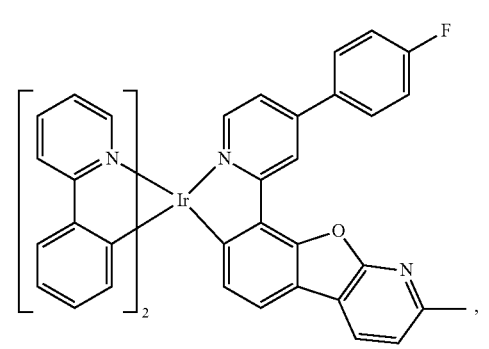
E7
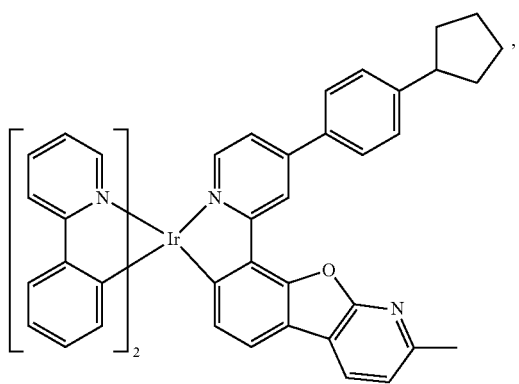
E8
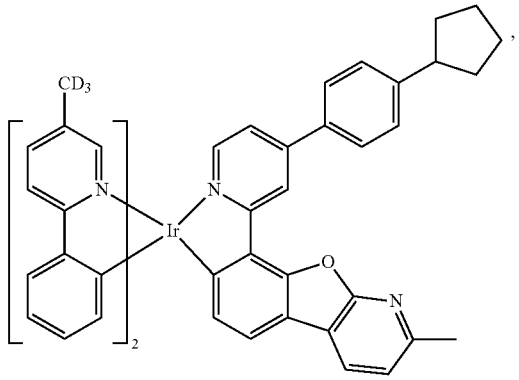
E9
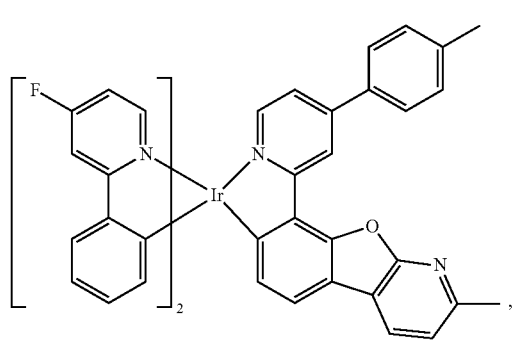
E10
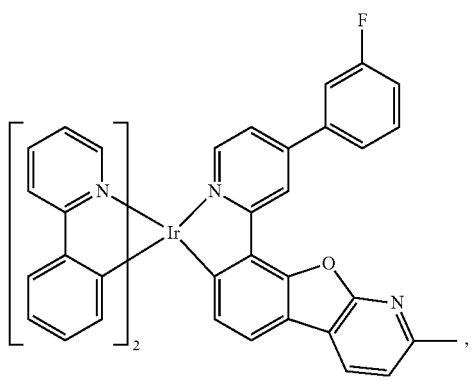
E11
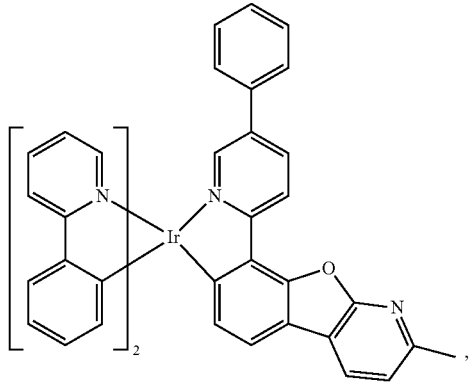

E12 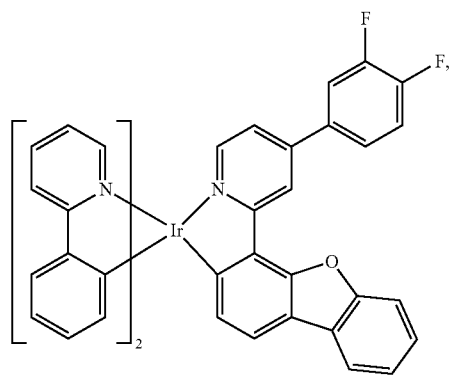
E13 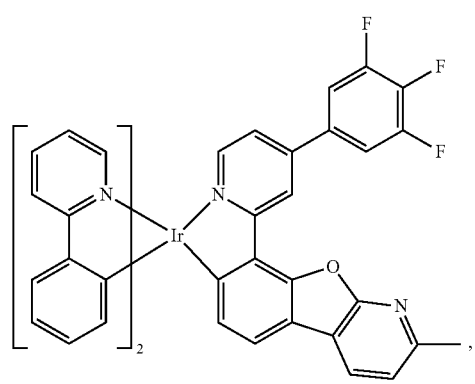
E14 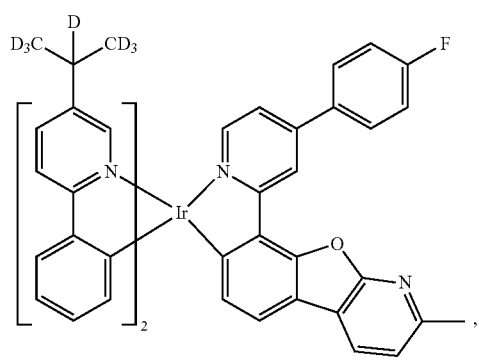
E15 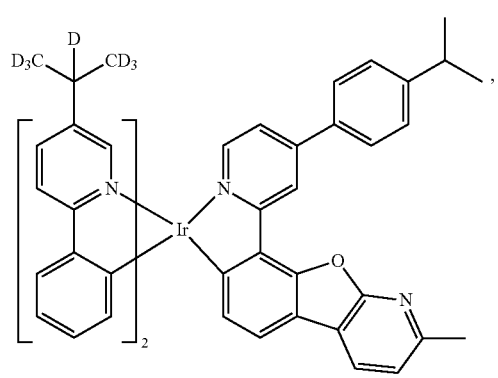
E16 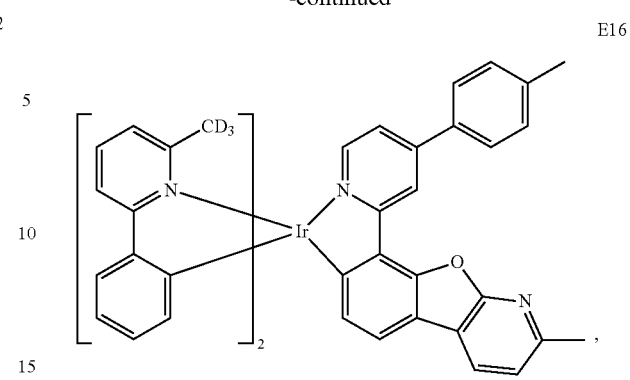
E17 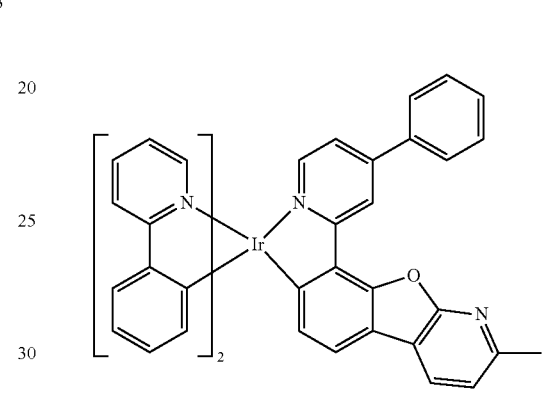
E18 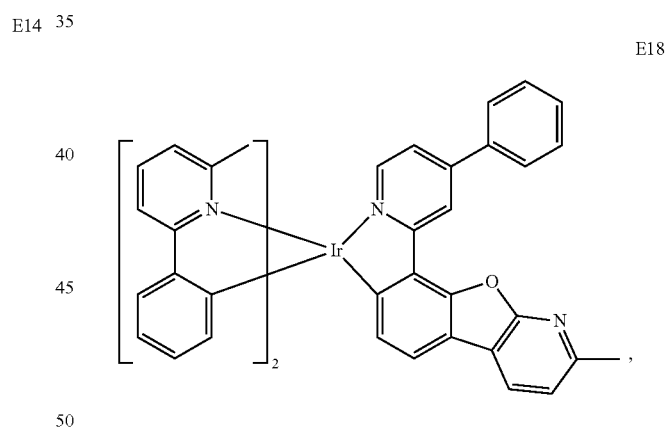
E19 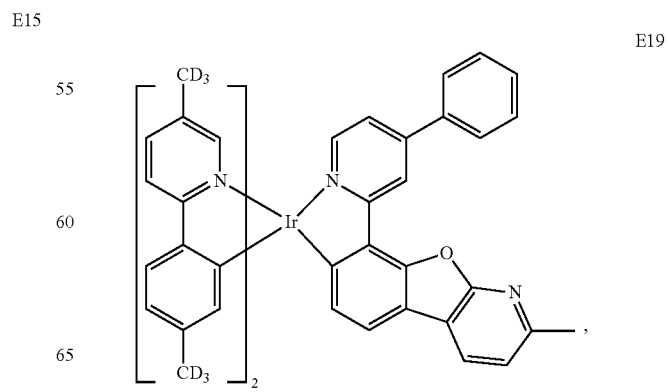

E20
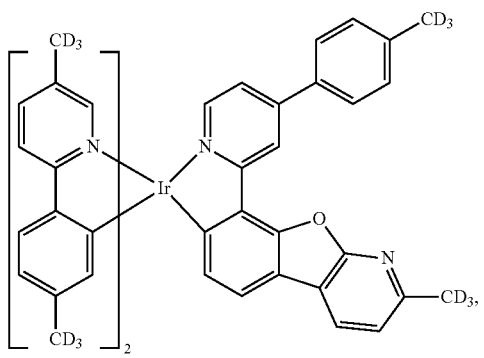
E21
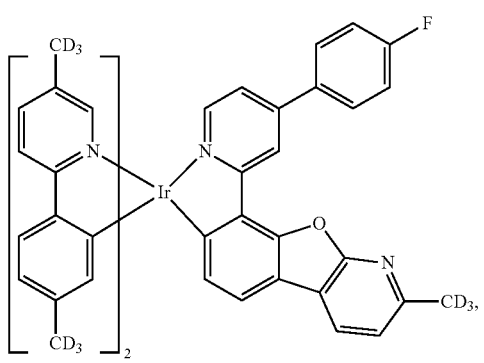
E19
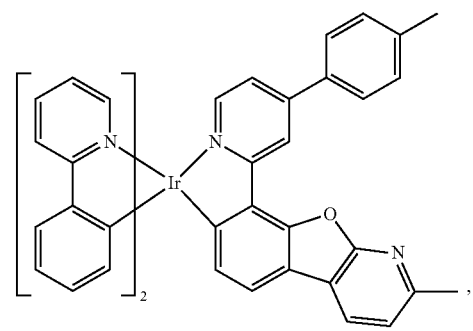
F1
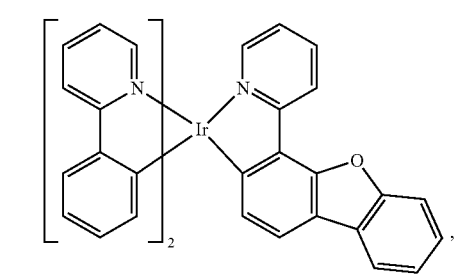
F2
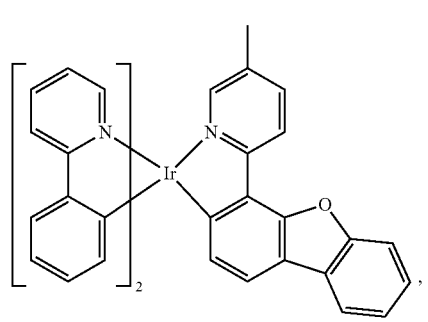
F3
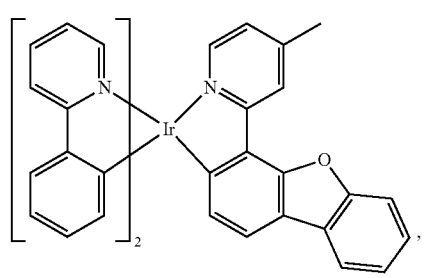
F4
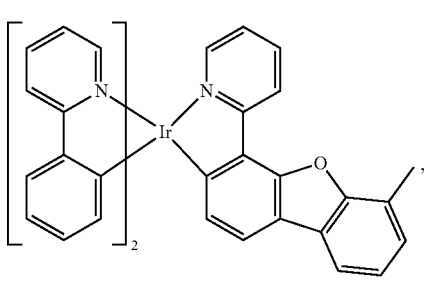
F5
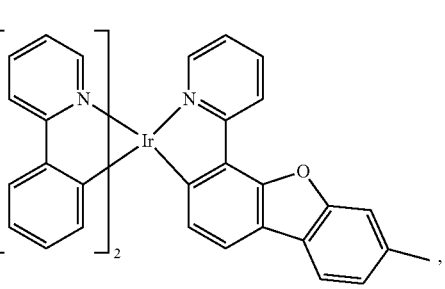
F6
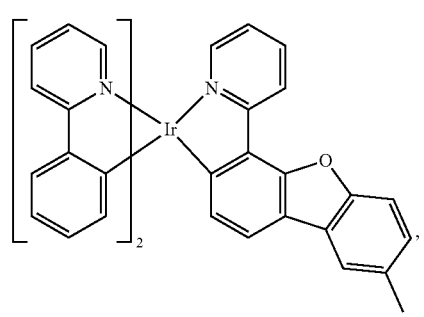
F7
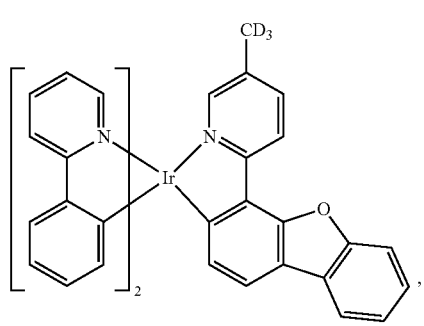

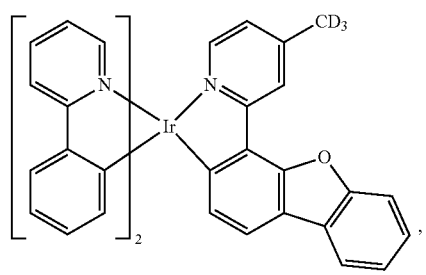 F8
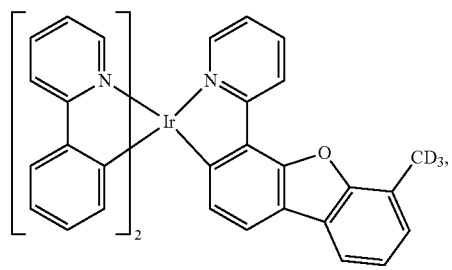 F9
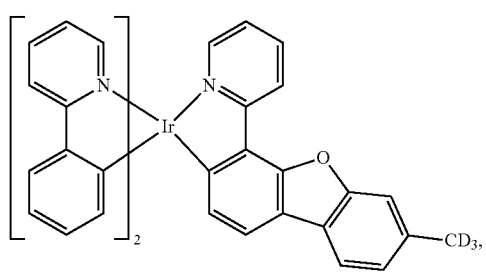 F10
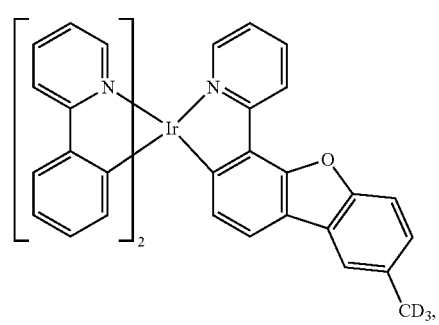 F11
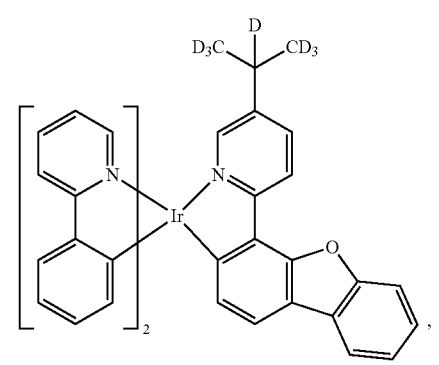 F12
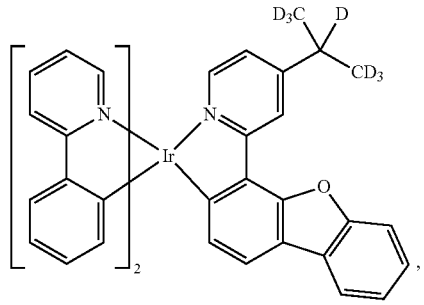 F13
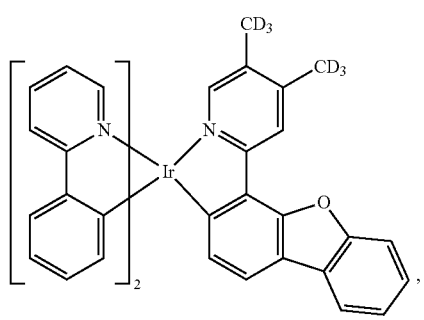 F14
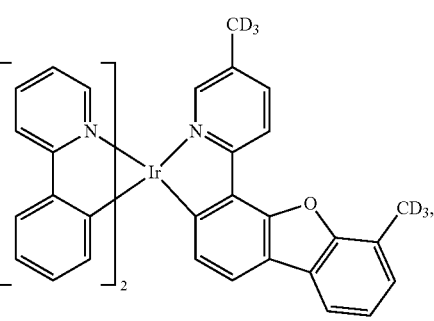 F15
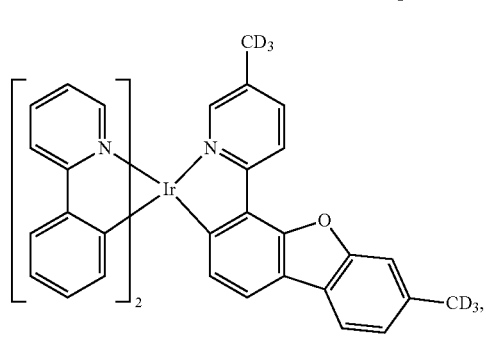 F16
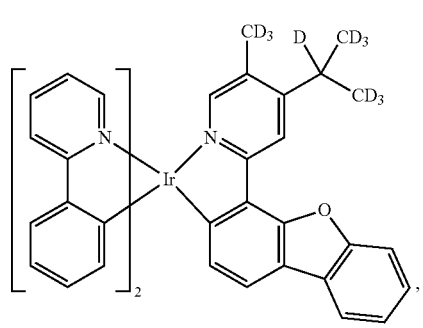 F17

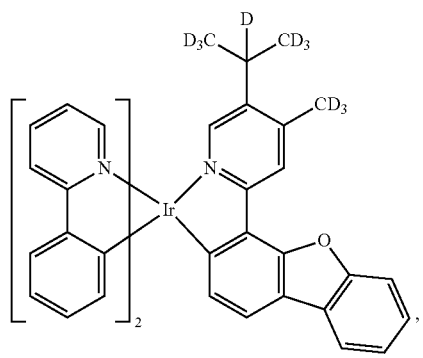
F18
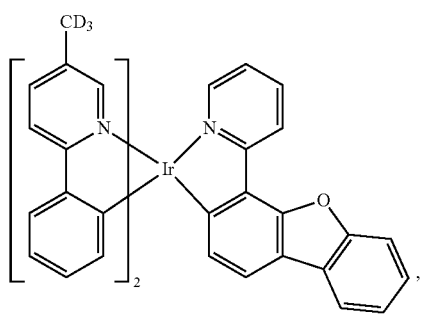
F19
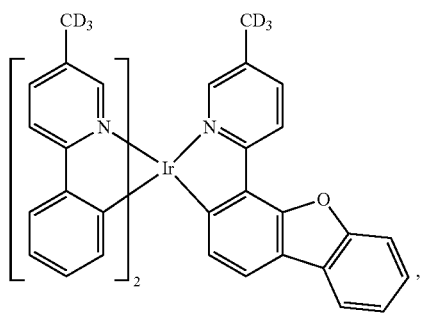
F20
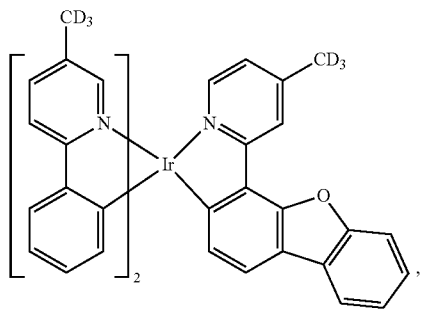
F21
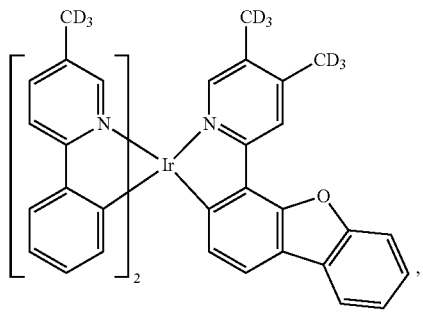
F22
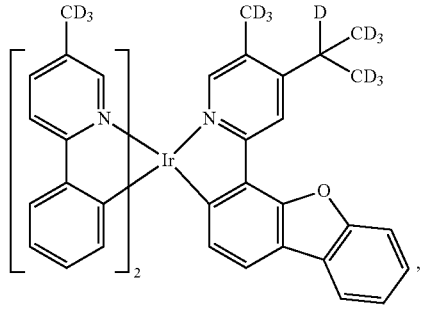
F23
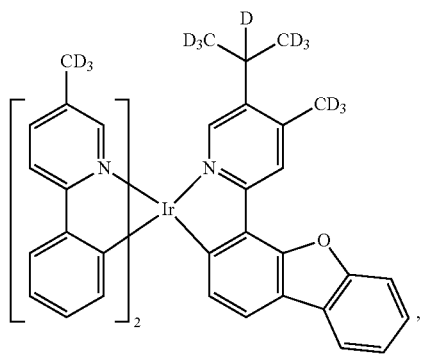
F24
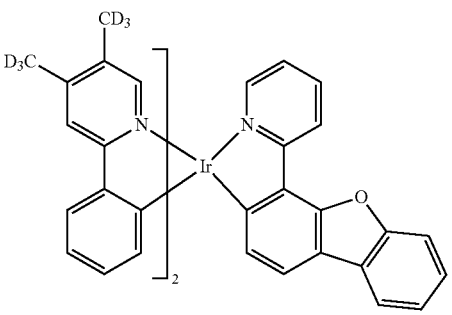
F25
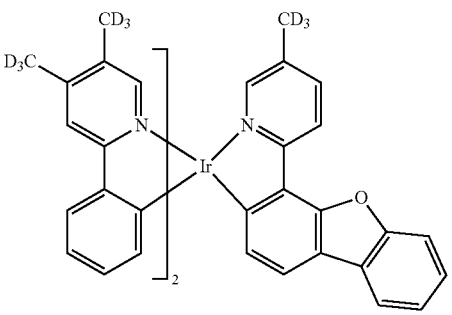
F26
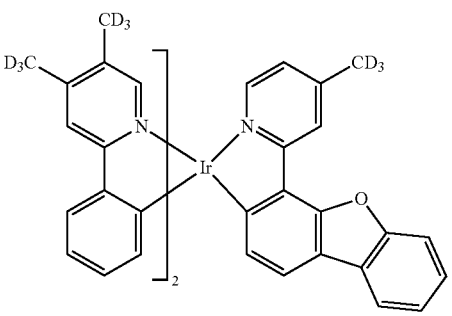
F27

419
-continued

F28 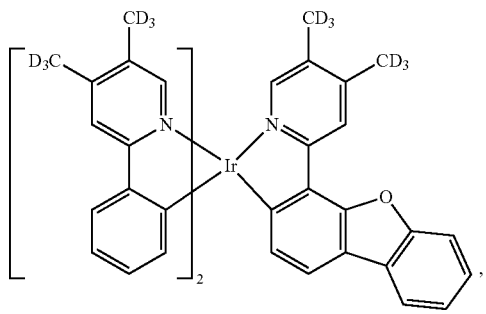

F29 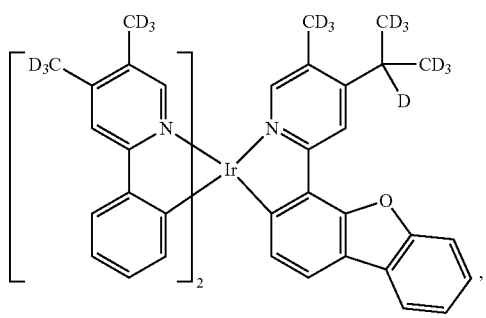

F30 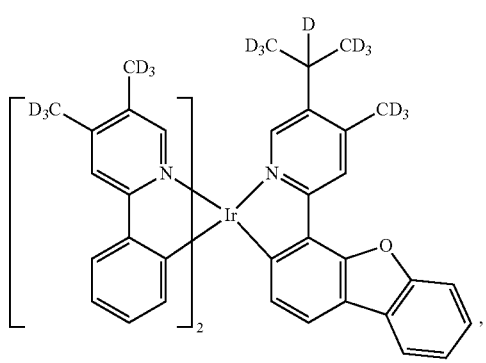

F31 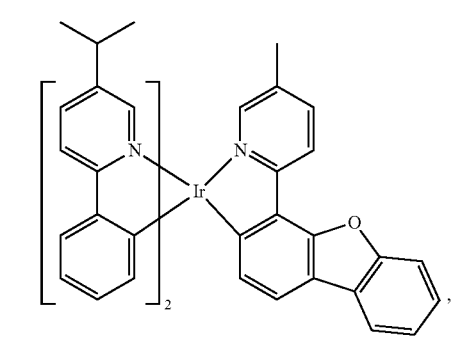

F32 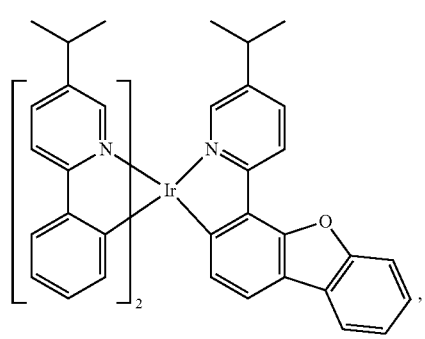

420
-continued

F33 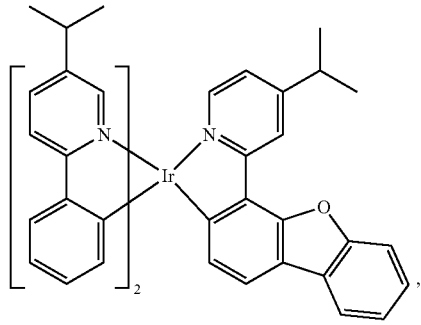

F34 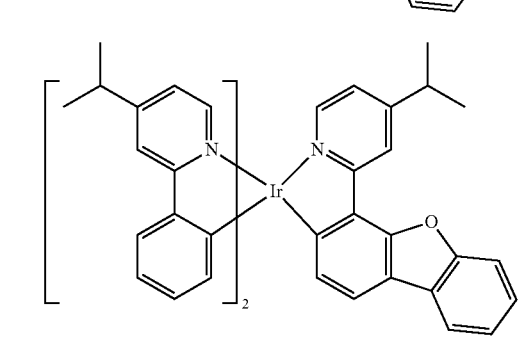

F35 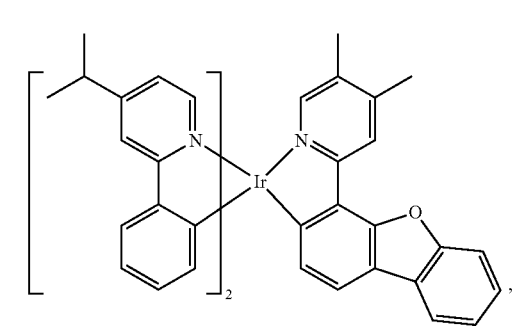

and

F36 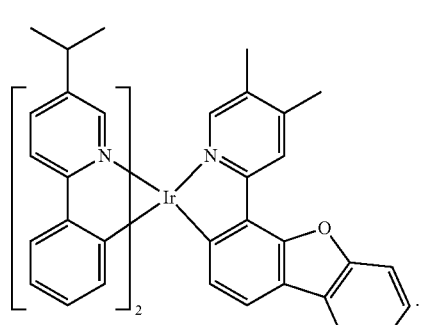

15. The composition of claim 1, wherein (a) $X^1$ or $X^2$ is present and represents Se.

16. The composition of claim 1, wherein (b)(1)(i) the first compounds has the structure of GH2 or GH3, and
   (2) at least one of $R^1$ and $R^3$ is unsubstituted, and
   (3)(i) $G^2$ is selected from the group consisting of dibenzoselenophene, phenanthroline, azadibenzofuran, azadibenzoselenophene, azafluorene, and combinations thereof.

17. The composition of claim 1, wherein (1)(ii) the first compound has a structure of GH1, GH4, or GH5, and two le are not joined to form a ring, and (2) at least one of le and $R^3$ is unsubstituted, and
(3)(i) $G^2$ is selected from the group consisting of dibenzoselenophene, phenanthroline, azadibenzofuran, azadibenzoselenophene, azafluorene, and combinations thereof.

* * * * *

UNITED STATES PATENT AND TRADEMARK OFFICE
CERTIFICATE OF CORRECTION

PATENT NO. : 11,302,872 B2  
APPLICATION NO. : 15/239877  
DATED : April 12, 2022  
INVENTOR(S) : Lichang Zeng et al.

Page 1 of 2

It is certified that error appears in the above-identified patent and that said Letters Patent is hereby corrected as shown below:

In the Claims

In Claim 3, Column 249, Lines 20-67, please delete the compounds:

"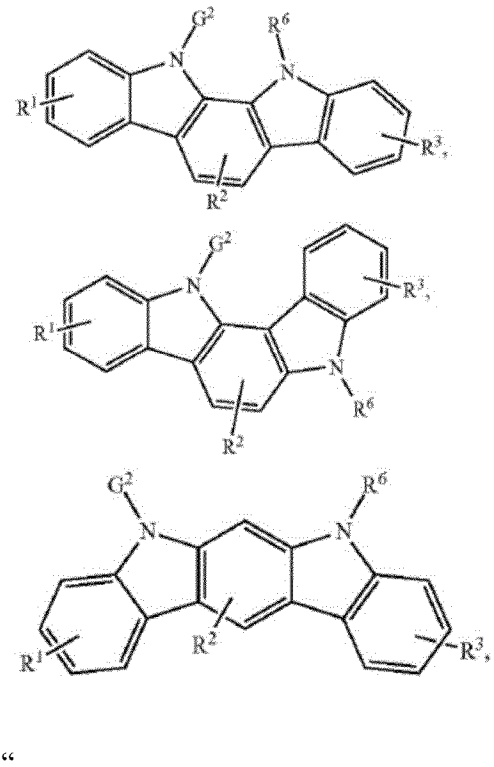 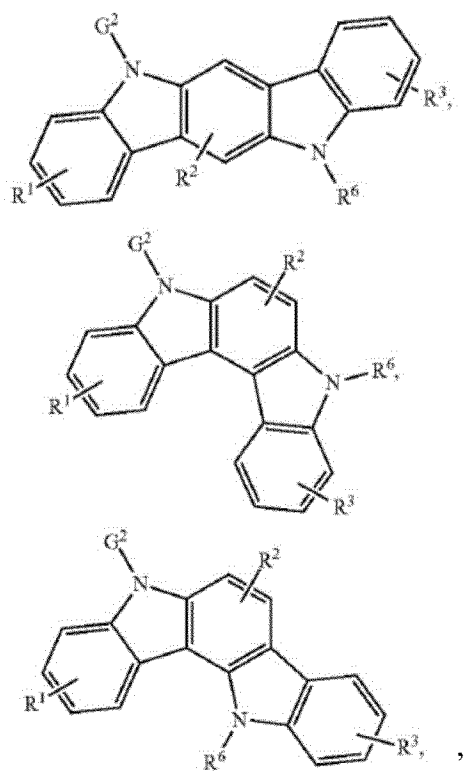"

Signed and Sealed this  
Twenty-eighth Day of June, 2022

Katherine Kelly Vidal  
*Director of the United States Patent and Trademark Office*

CERTIFICATE OF CORRECTION (continued)
U.S. Pat. No. 11,302,872 B2

In Claim 3, Column 250, Lines 1-9, please delete compound:

" 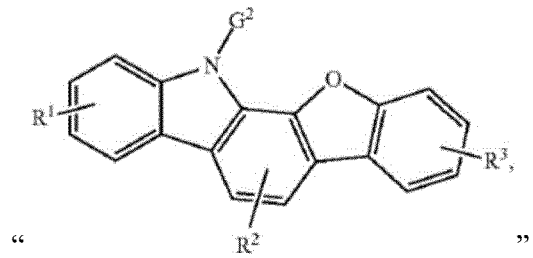 "

In Claim 3, Column 250, Lines 51-58, please delete compound:

" 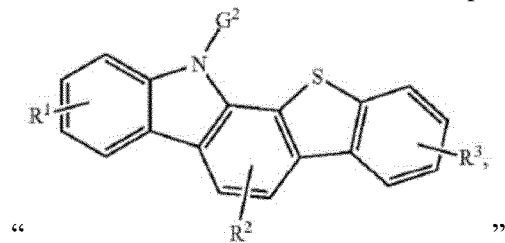 "

In Claim 3, Column 251, Lines 34-42, please delete compound:

" 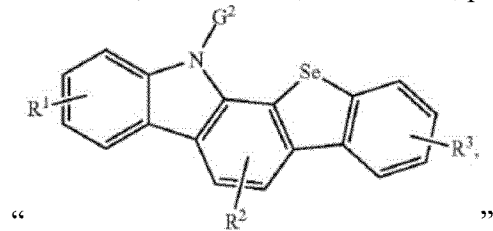 "